US008765940B2

(12) United States Patent
Brown et al.

(10) Patent No.: US 8,765,940 B2
(45) Date of Patent: Jul. 1, 2014

(54) HETEROCYCLIC COMPOUNDS AND THEIR USES

(75) Inventors: Matthew Brown, San Francisco, CA (US); Yi Chen, San Jose, CA (US); Timothy David Cushing, Pacifica, CA (US); Felix Gonzalez Lopez De Turiso, San Mateo, CA (US); Xiao He, Foster City, CA (US); Todd J. Kohn, San Mateo, CA (US); Julia Winslow Lohman, San Francisco, CA (US); Vatee Pattaropong, Burlingame, CA (US); Jennifer Seganish, Scotch Plains, NJ (US); Youngsook Shin, Emeryville, CA (US); Jillian L. Simard, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/377,210

(22) PCT Filed: Jun. 25, 2010

(86) PCT No.: PCT/US2010/039937
§ 371 (c)(1),
(2), (4) Date: Dec. 9, 2011

(87) PCT Pub. No.: WO2010/151737
PCT Pub. Date: Dec. 29, 2010

(65) Prior Publication Data
US 2012/0094972 A1     Apr. 19, 2012

Related U.S. Application Data

(60) Provisional application No. 61/220,493, filed on Jun. 25, 2009.

(51) Int. Cl.
*C07D 401/14* (2006.01)
*C07D 413/14* (2006.01)
*C07D 417/14* (2006.01)
*C07D 471/04* (2006.01)
*C07D 473/00* (2006.01)
*C07D 491/107* (2006.01)
*C07D 491/20* (2006.01)
*C07D 513/04* (2006.01)

(52) U.S. Cl.
USPC .............. 540/362; 544/48; 544/52; 544/70; 544/73; 544/277; 544/331; 546/113; 546/160

(58) Field of Classification Search
None
See application file for complete search history.

(56) References Cited

U.S. PATENT DOCUMENTS

| 6,355,636 B1 | 3/2002 | Wissner et al. |
| 6,384,051 B1 | 5/2002 | Frost et al. |
| 2010/0298290 A1* | 11/2010 | Anand et al. ............. 514/210.21 |

FOREIGN PATENT DOCUMENTS

| WO | 92/17452 | 10/1992 |
| WO | 2004/069250 A1 | 8/2004 |
| WO | 2004/108703 A1 | 12/2004 |
| WO | 2004/108704 A1 | 12/2004 |
| WO | 2004/112710 A2 | 12/2004 |
| WO | 2005/082891 A1 | 9/2005 |
| WO | 2010/061180 A1 | 6/2010 |

OTHER PUBLICATIONS

Staben et al., Structure-Based Optimization of Pyrazolo-Pyrimidine and -Pyridine Inhibitors of PI3-kinase, 20 Bioorg. & Med. Chem. Letts., 6048-6051 (2010).*
Berndt, et al., "The p110δ structure: Mechanisms for selectivity and potency of new PI(3)K inhibitors" Nature Chemical Biology, Jan. 10, 2010 pp. 1-8.
Berndt, et al., "Supplementary Methods and Results the p110δ structure: Mechanisms for selectivity and potency of new PI(3)K inhibitors" Nature Chemical Biology, Jan. 2010 pp. 1-34.
Price, "A Synthesis of Substituted 4-Aminoquinolines" J of Am Chem Soc (1946) pp. 1246-1250, vol. 68.
Boschelli, "Facile preparation of new 4-phenylamino-3-quinolinecarboritrile Src kinase inhibitors via 7-fluoro intermediates: Identification of potent 7-amino analogs", Bioorganic & Medicinal Chem (2008) pp. 405-412, vol. 16 No. 1.
Crespo, "Redesigning kinase inhibitors to enhance specificity", J of Medicinal Chem (2008) pp. 4890-4898, vol. 51, No. 16.
Domori, et al; Abstract "Aminonaphthyridines" 1972.
Flowers, et al; Abstract "Reaction of aromatic or heterocyclic amines and perfluori-2-methylpent-2-ene to give fused pyridines, ketenimines, or enamines" 1974.

* cited by examiner

*Primary Examiner* — Janet L Andres
*Assistant Examiner* — Timothy R Rozof
(74) *Attorney, Agent, or Firm* — Richard V. Person

(57) ABSTRACT

Substituted bicyclic heteroaryls and compositions containing them, for the treatment of general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, including but not restricted to autoimmune diseases such as systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions including all forms of hypersensitivity, The present invention also enables methods for treating cancers that are mediated, dependent on or associated with p110 activity, including but not restricted to leukemias, such as Acute Myeloid leukaemia (AML) Myelo-dysplastic syndrome (MDS) myelo-proliferative diseases (MPD) Chronic Myeloid Leukemia (CML) T-cell Acute Lymphoblastic leukaemia (T-ALL) B-cell Acute Lymphoblastic leukaemia (B-ALL) Non Hodgkins Lymphoma (NHL) B-cell lymphoma and solid tumors, such as breast cancer.

5 Claims, No Drawings

HETEROCYCLIC COMPOUNDS AND THEIR USES

This application claims the benefit of U.S. Provisional Application No. 61/220,493, filed Jun. 25, 2009, which is hereby incorporated by reference.

The present invention relates generally to phosphatidylinositol 3-kinase (PI3K) enzymes, and more particularly to selective inhibitors of PI3K activity and to methods of using such materials.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., J. Biol Chem, 274: 8347-8350 (1999) for a review). The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol 2:358-60 (1992)).

The levels of phosphatidylinositol-3,4,5-triphosphate (PIP3), the primary product of PI 3-kinase activation, increase upon treatment of cells with a variety of stimuli. This includes signaling through receptors for the majority of growth factors and many inflammatory stimuli, hormones, neurotransmitters and antigens, and thus the activation of PI3Ks represents one, if not the most prevalent, signal transduction events associated with mammalian cell surface receptor activation (Cantley, Science 296:1655-1657 (2002); Vanhaesebroeck et al. Annu Rev. Biochem, 70: 535-602 (2001)). PI 3-kinase activation, therefore, is involved in a wide range of cellular responses including cell growth, migration, differentiation, and apoptosis (Parker et al., Current Biology, 5:577-99 (1995); Yao et al., Science, 267:2003-05 (1995)). Though the downstream targets of phosphorylated lipids generated following PI 3-kinase activation have not been fully characterized, it is known that pleckstrin-homology (PH) domain- and FYVE-finger domain-containing proteins are activated when binding to various phosphatidylinositol lipids (Sternmark et al., J Cell Sci, 112:4175-83 (1999); Lemmon et al., Trends Cell Biol, 7:237-42 (1997)). Two groups of PH-domain containing PI3K effectors have been studied in the context of immune cell signaling, members of the tyrosine kinase TEC family and the serine/threonine kinases of the AGC family. Members of the Tec family containing PH domains with apparent selectivity for PtdIns (3,4,5)P$_3$ include Tec, Btk, Itk and Etk. Binding of PH to PIP$_3$ is critical for tyrosine kinase activity of the Tec family members (Schaeffer and Schwartzberg, Curr. Opin. Immunol. 12: 282-288 (2000)) AGC family members that are regulated by PI3K include the phosphoinositide-dependent kinase (PDK1), AKT (also termed PKB) and certain isoforms of protein kinase C (PKC) and S6 kinase. There are three isoforms of AKT and activation of AKT is strongly associated with PI3K-dependent proliferation and survival signals. Activation of AKT depends on phosphorylation by PDK1, which also has a 3-phosphoinositide-selective PH domain to recruit it to the membrane where it interacts with AKT. Other important PDK1 substrates are PKC and S6 kinase (Deane and Fruman, Annu. Rev. Immunol. 22_563-598 (2004)). In vitro, some isoforms of protein kinase C (PKC) are directly activated by PIP3. (Burgering et al., Nature, 376:599-602 (1995)).

Presently, the PI 3-kinase enzyme family has been divided into three classes based on their substrate specificities. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 subunits (Otsu et al., Cell, 65:91-104 (1991); Hiles et al., Cell, 70:419-29 (1992)). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. As described below, the patterns of expression of each of these PI3Ks in human cells and tissues are also distinct. Though a wealth of information has been accumulated in recent past on the cellular functions of PI 3-kinases in general, the roles played by the individual isoforms are not fully understood.

Cloning of bovine p110α has been described. This protein was identified as related to the *Saccharomyces cerevisiae* protein: Vps34p, a protein involved in vacuolar protein processing. The recombinant p110α product was also shown to associate with p85α, to yield a PI3K activity in transfected COS-1 cells. See Hiles et al., Cell, 70, 419-29 (1992).

The cloning of a second human p110 isoform, designated p110β, is described in Hu et al., Mol Cell Biol, 13:7677-88 (1993). This isoform is said to associate with p85 in cells, and to be ubiquitously expressed, as p110β mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that this isoform is broadly important in signaling pathways.

Identification of the p110δ isoform of PI 3-kinase is described in Chantry et al., J Biol Chem, 272:19236-41 (1997). It was observed that the human p110δ isoform is expressed in a tissue-restricted fashion. It is expressed at high levels in lymphocytes and lymphoid tissues and has been shown to play a key role in PI 3-kinase-mediated signaling in the immune system (Al-Alwan et al. JI 178: 2328-2335 (2007); Okkenhaug et al JI, 177: 5122-5128 (2006); Lee et al. PNAS, 103: 1289-1294 (2006)). P110δ has also been shown to be expressed at lower levels in breast cells, melanocytes and endothelial cells (Vogt et al. Virology, 344: 131-138 (2006) and has since been implicated in conferring selective migratory properties to breast cancer cells (Sawyer et al. Cancer Res. 63:1667-1675 (2003)). Details concerning the P110δ isoform also can be found in U.S. Pat. Nos. 5,858,753; 5,822,910; and 5,985,589. See also, Vanhaesebroeck et al., Proc Nat. Acad Sci USA, 94:4330-5 (1997), and international publication WO 97/46688.

In each of the PI3Kα, β, and δ subtypes, the p85 subunit acts to localize PI 3-kinase to the plasma membrane by the interaction of its SH2 domain with phosphorylated tyrosine residues (present in an appropriate sequence context) in target proteins (Rameh et al., Cell, 83:821-30 (1995)). Five isoforms of p85 have been identified (p85α, p85β, p55γ, p55α and p50α) encoded by three genes. Alternative transcripts of Pik3r1 gene encode the p85α, p55α and p50α proteins (Deane and Fruman, Annu Rev. Immunol. 22: 563-598

(2004)). p85α is ubiquitously expressed while p85β, is primarily found in the brain and lymphoid tissues (Volinia et al., Oncogene, 7:789-93 (1992)). Association of the p85 subunit to the PI 3-kinase p110α, β, or δ catalytic subunits appears to be required for the catalytic activity and stability of these enzymes. In addition, the binding of Ras proteins also upregulates PI 3-kinase activity.

The cloning of p110γ revealed still further complexity within the PI3K family of enzymes (Stoyanov et al., Science, 269:690-93 (1995)). The p110γ isoform is closely related to p110α and p110β (45-48% identity in the catalytic domain), but as noted does not make use of p85 as a targeting subunit. Instead, p110γ binds a p101 regulatory subunit that also binds to the βγ subunits of heterotrimeric G proteins. The p101 regulatory subunit for PI3 Kgamma was originally cloned in swine, and the human ortholog identified subsequently (Krugmann et al., J. Biol. Chem., 274:17152-8 (1999)). Interaction between the N-terminal region of p101 with the N-terminal region of p110γ is known to activate PI3Kγ through Gβγ. Recently, a p101-homologue has been identified, p84 or p87$^{PIKAP}$ (PI3Kγ adapter protein of 87 kDa) that binds p110γ (Voigt et al. J. Biol. Chem., 281: 9977-9986 (2006), Suire et al. Curr. Biol. 15: 566-570 (2005)). p87$^{PIKAP}$ is homologous to p101 in areas that bind p110γ and Gβγ and also mediates activation of p110γ downstream of G-protein-coupled receptors. Unlike p101, p87$^{PIKAP}$ is highly expressed in the heart and may be crucial to PI3Kγ cardiac function.

A constitutively active PI3K polypeptide is described in international publication WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., Mol Cell Biol, 14:2675-85 (1994)).

Thus, PI 3-kinases can be defined by their amino acid identity or by their activity. Additional members of this growing gene family include more distantly related lipid and protein kinases including Vps34 TOR1, and TOR2 of *Saccharomyces cerevisiae* (and their mammalian homologs such as FRAP and mTOR), the ataxia telangiectasia gene product (ATR) and the catalytic subunit of DNA-dependent protein kinase (DNA-PK). See generally, Hunter, Cell, 83:1-4 (1995).

PI 3-kinase is also involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., Nature, 369:327-29 (1994); Rudd, Immunity, 4:527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science, 251:313-16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the IC$_{50}$ values of wortmannin against each of the various Class I PI 3-kinases are in the range of 1-10 nM. Similarly, the IC$_{50}$ values for LY294002 against each of these PI 3-kinases is about 1 μM (Fruman et al., Ann Rev Biochem, 67:481-507 (1998)). Hence, the utility of these compounds in studying the roles of individual Class I PI 3-kinases is limited.

Based on studies using wortmannin, there is evidence that PI 3-kinase function also is required for some aspects of leukocyte signaling through G-protein coupled receptors (Thelen et al., Proc Natl Acad Sci USA, 91:4960-64 (1994)). Moreover, it has been shown that wortmannin and LY294002 block neutrophil migration and superoxide release. However, in as much as these compounds do not distinguish among the various isoforms of PI3K, it remains unclear from these studies which particular PI3K isoform or isoforms are involved in these phenomena and what functions the different Class I PI3K enzymes perform in both normal and diseased tissues in general. The co-expression of several PI3K isoforms in most tissues has confounded efforts to segregate the activities of each enzyme until recently.

The separation of the activities of the various PI3K isozymes has been advanced recently with the development of genetically manipulated mice that allowed the study of isoform-specific knock-out and kinase dead knock-in mice and the development of more selective inhibitors for some of the different isoforms. P110α and p110β knockout mice have been generated and are both embryonic lethal and little information can be obtained from these mice regarding the expression and function of p110α and β (Bi et al. Mamm. Genome, 13:169-172 (2002); Bi et al. J. Biol. Chem. 274:10963-10968 (1999)). More recently, p110α kinase dead knock in mice were generated with a single point mutation in the DFG motif of the ATP binding pocket (p110α$D^{933A}$) that impairs kinase activity but preserves mutant p110α kinase expression. In contrast to knock out mice, the knockin approach preserves signaling complex stoichiometry, scaffold functions and mimics small molecule approaches more realistically than knock out mice. Similar to the p110α KO mice, p110α$D^{933A}$ homozygous mice are embryonic lethal. However, heterozygous mice are viable and fertile but display severely blunted signaling via insulin-receptor substrate (IRS) proteins, key mediators of insulin, insulin-like growth factor-1 and leptin action. Defective responsiveness to these hormones leads to hyperinsulinemia, glucose intolerance, hyperphagia, increase adiposity and reduced overall growth in heterozygotes (Foukas, et al. Nature, 441: 366-370 (2006)). These studies revealed a defined, non-redundant role for p110α as an intermediate in IGF-1, insulin and leptin signaling that is not substituted for by other isoforms. We will have to await the description of the p110β kinase-dead knock in mice to further understand the function of this isoform (mice have been made but not yet published; Vanhaesebroeck).

P110γ knock out and kinase-dead knock in mice have both been generated and overall show similar and mild phenotypes with primary defects in migration of cells of the innate immune system and a defect in thymic development of T cells (Li et al. Science, 287: 1046-1049 (2000), Sasaki et al. Science, 287: 1040-1046 (2000), Patrucco et al. Cell, 118: 375-387 (2004)).

Similar to p110γ, PI3K delta knock out and kinase-dead knock-in mice have been made and are viable with mild and like phenotypes. The p110δ$^{D910A}$ mutant knock in mice demonstrated an important role for delta in B cell development and function, with marginal zone B cells and CD5+ B1 cells nearly undetectable, and B- and T cell antigen receptor signaling (Clayton et al. J. Exp. Med. 196:753-763 (2002); Okkenhaug et al. Science, 297: 1031-1034 (2002)). The p110δ$^{D910A}$ mice have been studied extensively and have elucidated the diverse role that delta plays in the immune system. T cell dependent and T cell independent immune responses are severely attenuated in p110δ$^{D910A}$ and secretion of TH1 (INF-γ) and TH2 cytokine (IL-4, IL-5) are impaired (Okkenhaug et al. J. Immunol. 177: 5122-5128 (2006)). A human patient with a mutation in p110δ has also recently been described. A Taiwanese boy with a primary B cell immunodeficiency and a gamma-hypoglobulinemia of previously unknown aetiology presented with a single basepair substitution, m.3256G to A in codon 1021 in exon 24 of p110δ. This mutation resulted in a mis-sense amino acid substitution (E to K) at codon 1021, which is located in the highly conserved catalytic domain of p110δ protein. The patient has no other identified mutations and his phenotype is consistent with p110δ deficiency in mice as far as studied. (Jou et al. Int. J. Immunogenet. 33: 361-369 (2006)).

Isoform-selective small molecule compounds have been developed with varying success to all Class I PI3 kinase isoforms (Ito et al. J. Pharm. Exp. Therapeut., 321:1-8 (2007)). Inhibitors to alpha are desirable because mutations in p110α have been identified in several solid tumors; for example, an amplification mutation of alpha is associated with 50% of ovarian, cervical, lung and breast cancer and an activation mutation has been described in more than 50% of bowel and 25% of breast cancers (Hennessy et al. Nature Reviews, 4: 988-1004 (2005)). Yamanouchi has developed a compound YM-024 that inhibits alpha and delta equi-potently and is 8- and 28-fold selective over beta and gamma respectively (Ito et al. J. Pharm. Exp. Therapeut., 321:1-8 (2007)).

P110β is involved in thrombus formation (Jackson et al. Nature Med. 11: 507-514 (2005)) and small molecule inhibitors specific for this isoform are thought after for indication involving clotting disorders (TGX-221: 0.007 uM on beta; 14-fold selective over delta, and more than 500-fold selective over gamma and alpha) (Ito et al. J. Pharm. Exp. Therapeut., 321:1-8 (2007)).

Selective compounds to p110γ are being developed by several groups as immunosuppressive agents for autoimmune disease (Rueckle et al. Nature Reviews, 5: 903-918 (2006)). Of note, AS 605240 has been shown to be efficacious in a mouse model of rheumatoid arthritis (Camps et al. Nature Medicine, 11: 936-943 (2005)) and to delay onset of disease in a model of systemic lupus erythematosis (Barber et al. Nature Medicine, 11: 933-935 (205)).

Delta-selective inhibitors have also been described recently. The most selective compounds include the quinazolinone purine inhibitors (PIK39 and IC87114). IC87114 inhibits p110δ in the high nanomolar range (triple digit) and has greater than 100-fold selectivity against p110α, is 52 fold selective against p110β but lacks selectivity against p110γ (approx. 8-fold). It shows no activity against any protein kinases tested (Knight et al. Cell, 125: 733-747 (2006)). Using delta-selective compounds or genetically manipulated mice (p110δ$^{D910A}$) it was shown that in addition to playing a key role in B and T cell activation, delta is also partially involved in neutrophil migration and primed neutrophil respiratory burst leads to a partial block of antigen-IgE mediated mast cell degranulation (Condliffe et al. Blood, 106: 1432-1440 (2005); Ali et al. Nature, 431: 1007-1011 (2002)). Hence p110δ is emerging as an important mediator of many key inflammatory responses that are also known to participate in aberrant inflammatory conditions, including but not limited to autoimmune disease and allergy. To support this notion, there is a growing body of p110δ target validation data derived from studies using both genetic tools and pharmacologic agents. Thus, using the delta-selective compound IC 87114 and the p110δ$^{D910A}$ mice, Ali et al. (Nature, 431: 1007-1011 (2002)) have demonstrated that delta plays a critical role in a murine model of allergic disease. In the absence of functional delta, passive cutaneous anaphylaxis (PCA) is significantly reduced and can be attributed to a reduction in allergen-IgE induced mast cell activation and degranulation. In addition, inhibition of delta with IC 87114 has been shown to significantly ameliorate inflammation and disease in a murine model of asthma using ovalbumin-induced airway inflammation (Lee et al. FASEB, 20: 455-465 (2006). These data utilizing compound were corroborated in p110δ$^{D910A}$ mutant mice using the same model of allergic airway inflammation by a different group (Nashed et al. Eur. J. Immunol. 37:416-424 (2007)).

There exists a need for further characterization of PI3Kδ function in inflammatory and autoimmune settings. Furthermore, our understanding of PI3Kδ requires further elaboration of the structural interactions of p110δ, both with its regulatory subunit and with other proteins in the cell. There also remains a need for more potent and selective or specific inhibitors of PI3K delta, in order to avoid potential toxicology associated with activity on isozymes p110α (insulin signaling) and β (platelet activation). In particular, selective or specific inhibitors of PI3Kδ are desirable for exploring the role of this isozyme further and for development of superior pharmaceuticals to modulate the activity of the isozyme.

SUMMARY

The present invention comprises a new class of compounds having the general formula

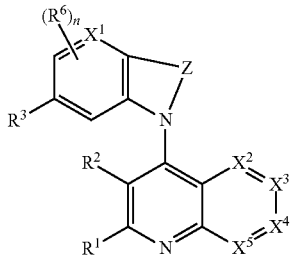

which are useful to inhibit the biological activity of human PI3Kδ. Another aspect of the invention is to provide compounds that inhibit PI3Kδ selectively while having relatively low inhibitory potency against the other PI3K isoforms. Another aspect of the invention is to provide methods of characterizing the function of human PI3Kδ. Another aspect of the invention is to provide methods of selectively modulating human PI3Kδ activity, and thereby promoting medical treatment of diseases mediated by PI3Kδ dysfunction. Other aspects and advantages of the invention will be readily apparent to the artisan having ordinary skill in the art.

DETAILED DESCRIPTION

One aspect of the invention relates to compounds having the structure:

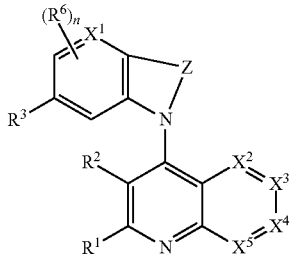

or any pharmaceutically-acceptable salt thereof, wherein:

$X^1$ is C or N;

$X^2$ is $C(R^4)$ or N;

$X^3$ is $C(R^5)$ or N;

$X^4$ is $C(R^5)$ or N;

$X^5$ is $C(R^4)$ or N; wherein no more than two of $X^2$, $X^3$, $X^4$ and $X^5$ are N;

Z is —C≡C—, —C═C—, —O—C═C—, —C═C—O—, —C═C—O—, —C═N—, —N═C—, —C—N—, —N—C—, —S(═O)$_2$—C═C—, —C═S(═O)$_2$—C—, —C═C—S(═O)$_2$—, —S(═O)$_2$—N═C—, —N═S(═O)$_2$—C—, —C═S(═O)$_2$—N—, —C═N—S(═O)$_2$—, —C═C—C(═O)— and —C(═O)—C═C—; any of which are substituted by 0, 1, 2, 3 or 4 substituents selected from halo, nitro, cyano, $C_{1-4}$alk, $CH_2OH$, $OC_{1-4}$alk, $OC_{1-4}$haloalk, $NHC_{1-4}$alk, $N(C_{1-4}$alk$)C_{1-4}$alk and $C_{1-4}$haloalk; and additionally substituted by 0 or 1 saturated or partially saturated 3-, 4-, 5- or 6-membered spiro rings containing 0, 1 or 2 heteroatoms selected from N, O and S, the spiro ring being substituted by 0, 1, 2 or 3 substituents independently selected from oxo, halo, $C_{1-6}$alk and $C_{1-4}$haloalk;

n is 0, 1, 2 or 3;

$R^1$ is selected from H, halo, $C_{1-6}$alk, $C_{1-4}$haloalk, cyano, nitro, —C(═O)$R^a$, —C(═O)O$R^a$, —C(═O)N$R^aR^a$, —C(═NR$^a$)NR$^a$R$^a$, —OR$^a$, —OC(═O)R$^a$, —OC(═O)NR$^a$R$^a$, —OC(═O)N(R$^a$)S(═O)$_2$R$^a$, —OC$_{2-6}$alkNR$^a$R$^a$, —OC$_{2-6}$alkOR$^a$, —SR$^a$, —S(═O)R$^a$, —S(═O)$_2$R$^a$, —S(═O)$_2$NR$^a$R$^a$, —S(═O)$_2$N(R$^a$)C(═O)R$^a$, —S(═O)$_2$N(R$^a$)C(═O)OR$^a$, —S(═O)$_2$N(R$^a$)C(═O)NR$^a$R$^a$, —NR$^a$R$^a$, —N(R$^a$)C(═O)R$^a$, —N(R$^a$)C(═O)OR$^a$, —N(R$^a$)C(═O)NR$^a$R$^a$, —N(R$^a$)C(═NR$^a$)NR$^a$R$^a$, —N(R$^a$)S(═O)$_2$R$^a$, —N(R$^a$)S(═O)$_2$NR$^a$R$^a$, —NR$^a$C$_{2-6}$alkNR$^a$R$^a$, —NR$^a$C$_{2-6}$alkOR$^a$, —NR$^a$C$_{2-6}$alkCO$_2$R$^a$, —NR$^a$C$_{2-6}$alkSO$_2$R$^b$, —CH$_2$C(═O)R$^a$, —CH$_2$C(═O)OR$^a$, —CH$_2$C(═O)NR$^a$R$^a$, —CH$_2$C(═NR$^a$)NR$^a$R$^a$, —CH$_2$OR$^a$, —CH$_2$OC(═O)R$^a$, —CH$_2$C(═O)NR$^a$R$^a$, —CH$_2$C(═O)N(R$^a$)S(═O)$_2$R$^a$, —CH$_2$OC$_{2-6}$alkNR$^a$R$^a$, —CH$_2$OC$_{2-6}$alkOR$^a$, —CH$_2$SR$^a$, —CH$_2$S(═O)R$^a$, —CH$_2$S(═O)$_2$R$^b$, —CH$_2$S(═O)$_2$NR$^a$R$^a$, —CH$_2$S(═O)$_2$N(R$^a$)C(═O)R$^a$, —CH$_2$S(═O)$_2$N(R$^a$)C(═O)OR$^a$, —CH$_2$S(═O)$_2$N(R$^a$)C(═O)NR$^a$R$^a$, —CH$_2$NR$^a$R$^a$, —CH$_2$N(R$^a$)C(═O)R$^a$, —CH$_2$N(R$^a$)C(═O)OR$^a$, —CH$_2$N(R$^a$)C(═O)NR$^a$R$^a$, —CH$_2$N(R$^a$)C(═NR$^a$)NR$^a$R$^a$, —CH$_2$N(R$^a$)S(═O)$_2$R$^a$, —CH$_2$N(R$^a$)S(═O)$_2$NR$^a$R$^a$, —CH$_2$NR$^a$C$_{2-6}$alkNR$^a$R$^a$, —CH$_2$NR$^a$C$_{2-6}$alkOR$^a$, —CH$_2$NR$^a$C$_{2-6}$alkCO$_2$R$^a$ and —CH$_2$NR$^a$C$_{2-6}$alkSO$_2$R$^b$; or $R^1$ is a direct-bonded, $C_{1-4}$alk-linked, $OC_{1-2}$alk-linked, $C_{1-2}$alkO-linked, $N(R^a)$-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1 or 2 substituents independently selected from halo, $C_{1-6}$alk, $C_{1-4}$haloalk, cyano, nitro, —C(═O)R$^a$, —C(═O)OR$^a$, —C(═O)NR$^a$R$^a$, —C(═NR$^a$)NR$^a$R$^a$, —OR$^a$, —OC(═O)R$^a$, —OC(═O)NR$^a$R$^a$, —OC(═O)N(R$^a$)S(═O)$_2$R$^a$, —OC$_{2-6}$alkNR$^a$R$^a$, —OC$_{2-6}$alkOR$^a$, —SR$^a$, —S(═O)R$^a$, —S(═O)$_2$R$^a$, —S(═O)$_2$NR$^a$R$^a$, —S(═O)$_2$N(R$^a$)C(═O)R$^a$, —S(═O)$_2$N(R$^a$)C(═O)OR$^a$, —S(═O)$_2$N(R$^a$)C(═O)NR$^a$R$^a$, —NR$^a$R$^a$, —N(R$^a$)C(═O)R$^a$, —N(R$^a$)C(═O)OR$^a$, —N(R$^a$)C(═O)NR$^a$R$^a$, —N(R$^a$)C(═NR$^a$)NR$^a$R$^a$, —N(R$^a$)S(═O)$_2$R$^a$, —N(R$^a$)S(═O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups, and wherein the ring is additionally substituted by 0 or 1 directly bonded, SO$_2$ linked, C(═O) linked or CH$_2$ linked group selected from phenyl, pyridyl, pyrimidyl, morpholino, piperazinyl, piperadinyl, cyclopentyl, cyclohexyl all of which are further substituted by 0, 1, 2 or 3 independent $R^b$ groups;

$R^2$ is selected from H, halo, $C_{1-6}$alk, $C_{1-4}$haloalk, cyano, nitro, —C(═O)R$^a$, —C(═O)OR$^a$, —C(═O)NR$^a$R$^a$, —C(═NR$^a$)NR$^a$R$^a$, —OR$^a$, —OC(═O)R$^a$, —OC(═O)NR$^a$R$^a$, —OC(═O)N(R$^a$)S(═O)$_2$R$^a$, —OC$_{2-6}$alkNR$^a$R$^a$, —OC$_{2-6}$alkOR$^a$, —SR$^a$, —S(═O)R$^a$, —S(═O)$_2$R$^a$, —S(═O)$_2$NR$^a$R$^a$, —S(═O)$_2$N(R$^a$)C(═O)R$^a$, —S(═O)$_2$N(R$^a$)C(═O)OR$^a$, —S(═O)$_2$N(R$^a$)C(═O)NR$^a$R$^a$, —NR$^a$R$^a$, —N(R$^a$)C(═O)R$^a$, —N(R$^a$)C(═O)OR$^a$, —N(R$^a$)C(═O)NR$^a$R$^a$, —N(R$^a$)C(═NR$^a$)NR$^a$R$^a$, —N(R$^a$)S(═O)$_2$R$^a$, —N(R$^a$)S(═O)$_2$NR$^a$R$^a$, —NR$^a$C$_{2-6}$alkNR$^a$R$^a$ and —NR$^a$C$_{2-6}$alkOR$^a$; or $R^1$ and $R^2$ together with the carbons by which they are attached form a saturated, partially-saturated or unsaturated 5-, 6- or 7-membered ring containing 0, 1 or 2 atoms selected from N, O and S, wherein the available carbon atoms of the ring are substituted by 0, 1 or 2 oxo or thioxo groups, wherein the ring is additionally substituted by 0, 1, 2 or 3 substituents selected from halo, $C_{1-6}$alk, $C_{1-4}$haloalk, cyano, nitro, —C(═O)R$^a$, —C(═O)OR$^a$, —C(═O)NR$^a$R$^a$, —C(═NR$^a$)NR$^a$R$^a$, —OR$^a$, —OC(═O)R$^a$, —OC(═O)NR$^a$R$^a$, —OC(═O)N(R$^a$)S(═O)$_2$R$^a$, —OC$_{2-6}$alkNR$^a$R$^a$, —OC$_{2-6}$alkOR$^a$, —SR$^a$, —S(═O)R$^a$, —S(═O)$_2$R$^a$, —S(═O)$_2$ R$^a$, —S(═O)$_2$NR$^a$R$^a$, —S(═O)$_2$N(R$^a$)C(═O)R$^a$, —S(═O)$_2$N(R$^a$)C(═O)OR$^a$, —S(═O)$_2$N(R$^a$)C(═O)NR$^a$R$^a$, —NR$^a$R$^a$, —N(R$^a$)C(═O)R$^a$, —N(R$^a$)C(═O)OR$^a$, —N(R$^a$)C(═O)NR$^a$R$^a$, —N(R$^a$)C(═NR$^a$)NR$^a$R$^a$, —N(R$^a$)S(═O)$_2$R$^a$, —N(R$^a$)S(═O)$_2$NR$^a$R$^a$, —NR$^a$C$_{2-6}$alkNR$^a$R$^a$, —NR$^a$C$_{2-6}$alkOR$^a$, —NR$^a$C$_{2-6}$alkCO$_2$R$^a$, —NR$^a$C$_{2-6}$alkSO$_2$R$^b$, —CH$_2$C(═O)R$^a$, —CH$_2$C(═O)OR$^a$, —CH$_2$C(═O)NR$^a$R$^a$, —CH$_2$C(═NR$^a$)NR$^a$R$^a$, —CH$_2$OR$^a$, —CH$_2$OC(═O)R$^a$, —CH$_2$OC(═O)NR$^a$R$^a$, —CH$_2$C(═O)N(R$^a$)S(═O)$_2$R$^a$, —CH$_2$OC$_{2-6}$alkNR$^a$R$^a$, —CH$_2$OC$_{2-6}$alkOR$^a$, —CH$_2$SR$^a$, —CH$_2$S(═O)R$^a$, —CH$_2$S(═O)$_2$R$^b$, —CH$_2$S(═O)$_2$NR$^a$R$^a$, —CH$_2$S(═O)$_2$N(R$^a$)C(═O)R$^a$, —CH$_2$S(═O)$_2$N(R$^a$)C(═O)OR$^a$, —CH$_2$S(═O)$_2$N(R$^a$)C(═O)NR$^a$R$^a$, —CH$_2$NR$^a$R$^a$, —CH$_2$N(R$^a$)C(═O)R$^a$, —CH$_2$N(R$^a$)C(═O)OR$^a$, —CH$_2$N(R$^a$)C(═O)NR$^a$R$^a$, —CH$_2$N(R$^a$)C(═NR$^a$)NR$^a$R$^a$, —CH$_2$N(R$^a$)S(═O)$_2$R$^a$, —CH$_2$N(R$^a$)S(═O)$_2$NR$^a$R$^a$, —CH$_2$NR$^a$C$_{2-6}$alkNR$^a$R$^a$, —CH$_2$NR$^a$C$_{2-6}$alkOR$^a$, —CH$_2$NR$^a$C$_{2-6}$alkCO$_2$R$^a$ and —CH$_2$NR$^a$C$_{2-6}$alkSO$_2$R$^b$; or the ring is substituted by a direct-bonded, $C_{1-4}$alk-linked, $OC_{1-2}$alk-linked, $C_{1-2}$alkO-linked, $N(R^a)$-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1 or 2 substituents independently selected from halo, $C_{1-6}$alk, $C_{1-4}$haloalk, cyano, nitro, —C(═O)R$^a$, —C(═O)OR$^a$, —C(═O)NR$^a$R$^a$, —C(═NR$^a$)NR$^a$R$^a$, —OR$^a$, —OC(═O)R$^a$, —OC(═O)NR$^a$R$^a$, —OC(═O)N(R$^a$)S(═O)$_2$R$^a$, —OC$_{2-6}$alkNR$^a$R$^a$, —OC$_{2-6}$alkOR$^a$, —SR$^a$, —S(═O)R$^a$, —S(═O)$_2$R$^a$, —S(═O)$_2$NR$^a$R$^a$, —S(═O)$_2$N(R$^a$)C(═O)R$^a$, —S(═O)$_2$N(R$^a$)C(═O)OR$^a$, —S(═O)$_2$N(R$^a$)C(═O)NR$^a$R$^a$, —NR$^a$R$^a$, —N(R$^a$)C(═O)R$^a$, —N(R$^a$)C(═O)OR$^a$, —N(R$^a$)C(═O)NR$^a$R$^a$, —N(R$^a$)C(═NR$^a$)NR$^a$R$^a$, —N(R$^a$)S(═O)$_2$R$^a$, —N(R$^a$)S(═O)$_2$NR$^a$R$^a$, —NR$^a$C$_{2-6}$alkNR$^a$R$^a$ and —NR$^a$C$_{2-6}$alkOR$^a$;

$R^3$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$; or $R^3$ is selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$;

$R^4$ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk, C$_{1-4}$haloalk, or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —OC$_{1-4}$alk, —NH$_2$, —NHC$_{1-4}$alk and —N(C$_{1-4}$ alk)C$_{1-4}$alk;

$R^5$ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk or C$_{1-4}$haloalk;

$R^6$ is selected from halo, cyano, OH, OC$_{1-4}$alk, C$_{1-4}$alk, C$_{1-3}$haloalk, OC$_{1-4}$alk, NH$_2$, NHC$_{1-4}$alk, N(C$_{1-4}$alk)C$_{1-4}$alk, —C(=O)O$R^a$, —C(=O)N($R^a$)$R^a$ and —N($R^a$)C(=O)$R^b$;

$R^a$ is independently, at each instance, H or $R^b$; and $R^b$ is independently, at each instance, phenyl, benzyl or $C_{1-6}$alk, the phenyl, benzyl and $C_{1-6}$alk being substituted by 0, 1, 2 or 3 substituents selected from halo, C$_{1-4}$alk, C$_{1-3}$haloalk, —OC$_{1-4}$alk, —NH$_2$, —NHC$_{1-4}$alk and —N(C$_{1-4}$alk)C$_{1-4}$alk.

Another aspect of the invention relates to compounds having the structure:

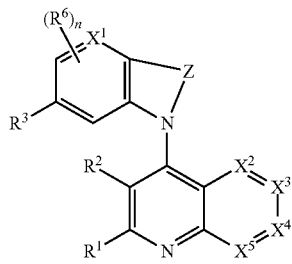

or any pharmaceutically-acceptable salt thereof, wherein:

$X^1$ is C or N;
$X^2$ is C($R^4$) or N;
$X^3$ is C($R^5$) or N;
$X^4$ is C($R^5$) or N;
$X^5$ is C($R^4$) or N; wherein no more than two of $X^2$, $X^3$, $X^4$ and $X^5$ are N;

Z is —C=C—, —C—C—, —O—C—C—, —C—O—C—, —C—C—O—, —C=N—, —N=C—, —C—N—, —N—C—, —S(=O)$_2$—C—C—, —C—S(=O)$_2$—C—, —C—C—S(=O)$_2$—, —S(=O)$_2$—N—C—, —N—S(=O)$_2$—C—, —C—N—S(=O)$_2$—, —C=C—C(=O)— and —C(=O)—C=C—; any of which are substituted by 0, 1, 2, 3 or 4 substituents selected from halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk and C$_{1-4}$haloalk; and additionally substituted by 0 or 1 saturated or partially saturated 3-, 4-, 5- or 6-membered spiro rings containing 0, 1 or 2 heteroatoms selected from N, O and S, the spiro ring being substituted by 0, 1, 2 or 3 substituents independently selected from halo, $C_{1-6}$alk and C$_{1-4}$haloalk;

n is 0, 1, 2 or 3;

$R^1$ is selected from H, halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$; or $R^1$ is a direct-bonded, C$_{1-4}$alk-linked, OC$_{1-2}$alk-linked, C$_{1-2}$alkO-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$, wherein the available carbon atoms of the ring are additionally substituted by 0, 1 or 2 oxo or thioxo groups;

$R^2$ is selected from H, halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$; or $R^1$ and $R^2$ together form a saturated or partially-saturated 2-, 3-, 4- or 5-carbon bridge substituted by 0, 1, 2 or 3 substituents selected from halo, cyano, OH, OC$_{1-4}$alk, C$_{1-4}$alk, C$_{1-3}$haloalk, OC$_{1-4}$alk, NH$_2$, NHC$_{1-4}$alk and N(C$_{1-4}$alk)C$_{1-4}$alk;

$R^3$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^3$ is selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^4$ is, independently, in each instance, H, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk, C$_{1-4}$haloalk or an unsaturated 5-, 6- or 7-membered monocyclic ring containing 0, 1, 2, 3 or 4 atoms selected from N, O and S, but containing no more than one O or S, substituted by 0, 1 or 2 substituents selected from halo, C$_{1-4}$alk, C$_{1-3}$haloalk, —OC$_{1-4}$alk, —NH$_2$, —NHC$_{1-4}$alk and —N(C$_{1-4}$alk)C$_{1-4}$alk;

R$^5$ is, independently, in each instance, H, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk or C$_{1-4}$haloalk;

R$^6$ is selected from halo, cyano, OH, OC$_{1-4}$alk, C$_{1-4}$alk, C$_{1-3}$haloalk, OC$_{1-4}$alk, NH$_2$, NHC$_{1-4}$alk and N(C$_{1-4}$alk)C$_{1-4}$alk;

R$^a$ is independently, at each instance, H or R$^b$; and

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OC$_{1-4}$alk, —NH$_2$, —NHC$_{1-4}$alk and —N(C$_{1-4}$alk)C$_{1-4}$alk.

In another embodiment, in conjunction with any of the above or below embodiments, X$^1$ is N.

In another embodiment, in conjunction with any of the above or below embodiments, X$^1$ is C.

In another embodiment, in conjunction with any of the above or below embodiments,
X$^2$ is C(R$^4$);
X$^3$ is C(R$^5$);
X$^4$ is C(R$^5$); and
X$^5$ is C(R$^4$).

In another embodiment, in conjunction with any of the above or below embodiments,
X$^2$ is N;
X$^3$ is C(R$^5$);
X$^4$ is C(R$^5$); and
X$^5$ is C(R$^4$).

In another embodiment, in conjunction with any of the above or below embodiments,
X$^2$ is C(R$^4$);
X$^3$ is N;
X$^4$ is C(R$^5$); and
X$^5$ is C(R$^4$).

In another embodiment, in conjunction with any of the above or below embodiments,
X$^2$ is C(R$^4$);
X$^3$ is C(R$^5$);
X$^4$ is N; and
X$^5$ is C(R$^4$).

In another embodiment, in conjunction with any of the above or below embodiments,
X$^2$ is C(R$^4$);
X$^3$ is C(R$^5$);
X$^4$ is C(R$^5$); and
X$^5$ is N.

In another embodiment, in conjunction with any of the above or below embodiments, R$^1$ is selected from C$_{1-6}$alk and C$_{1-4}$haloalk.

In another embodiment, in conjunction with any of the above or below embodiments, R$^1$ is a direct-bonded unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups.

In another embodiment, in conjunction with any of the above or below embodiments, R$^1$ is a direct-bonded unsaturated 5-, 6- or 7-membered monocyclic ring containing 0, 1, 2, 3 or 4 atoms selected from N, O and S, but containing no more than one O or S atom, substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups.

In another embodiment, in conjunction with any of the above or below embodiments, R$^1$ is phenyl or pyridine, both of which are substituted by 0, 1, 2 or 3 substituents independently selected from halo, C$_{1-6}$alk and C$_{1-4}$haloalk.

In another embodiment, in conjunction with any of the above or below embodiments, R$^1$ is a methylene-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups.

In another embodiment, in conjunction with any of the above or below embodiments, $R^1$ is an ethylene-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O) $R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O) $R^a$, —S(=O)$_2$N($R^a$)C(=O)O$R^a$, —S(=O)$_2$N($R^a$)C(=O) N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$) S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$, wherein the available carbon atoms of the ring are additionally substituted by 0, 1 or 2 oxo or thioxo groups.

In another embodiment, in conjunction with any of the above or below embodiments, $R^2$ is selected from halo, $C_{1-6}$alk, $C_{1-4}$haloalk, cyano, nitro, —C(=O)$R^a$, —C(=O) O$R^a$, —C(=O)N$R^aR^a$, —C(=N$R^a$)N$R^aR^a$, —O$R^a$, —OC (=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O) $R^a$, —S(=O)$_2$N($R^a$)C(=O)O$R^a$, —S(=O)$_2$N($R^a$)C(=O) N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$) S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$.

In another embodiment, in conjunction with any of the above or below embodiments, $R^2$ is selected from halo, $C_{1-6}$alk and $C_{1-4}$haloalk.

In another embodiment, in conjunction with any of the above or below embodiments, $R^2$ is H.

In another embodiment, in conjunction with any of the above or below embodiments, $R^1$ and $R^2$ together form a saturated or partially-saturated 2-, 3-, 4- or 5-carbon bridge substituted by 0, 1, 2 or 3 substituents selected from halo, cyano, OH, OC$_{1-4}$alk, $C_{1-4}$alk, $C_{1-3}$haloalk, OC$_{1-4}$alk, NH$_2$, NHC$_{1-4}$alk and N(C$_{1-4}$alk)C$_{1-4}$alk.

In another embodiment, in conjunction with any of the above or below embodiments, $R^3$ is selected from saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N ($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O) $R^a$, —N($R^a$)C(=O)O$R^a$, —N($R^a$)C(=O)N$R^aR^a$, —N($R^a$)C (=N$R^a$)N$R^aR^a$, —N($R^a$)S(=O)$_2R^a$, —N($R^a$)S(=O)$_2$ N$R^aR^a$, —N$R^a$C$_{2-6}$alkN$R^aR^a$ and —N$R^a$C$_{2-6}$alkO$R^a$.

In another embodiment, in conjunction with any of the above or below embodiments, $R^3$ is selected from saturated 5-, 6- or 7-membered monocyclic ring containing 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O) N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N ($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$) S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$.

In another embodiment, in conjunction with any of the above or below embodiments, $R^3$ is selected from saturated 5-, 6- or 7-membered monocyclic ring containing 1, 2, 3 or 4 atoms selected from N, O and S, but containing no more than one O or S, wherein the ring is substituted by 0, 1, 2 or 3 substituents independently selected from halo, $C_{1-6}$alk and $C_{1-4}$haloalk.

In another embodiment, in conjunction with any of the above or below embodiments, $R^3$ is selected from saturated 6-membered monocyclic ring containing 1 or 2 atoms selected from N, O and S, but containing no more than one O or S, wherein the ring is substituted by 0, 1, 2 or 3 substituents independently selected from halo, $C_{1-6}$alk and $C_{1-4}$haloalk.

In another embodiment, in conjunction with any of the above or below embodiments, $R^3$ is selected from saturated 6-membered monocyclic ring containing 1 or 2 atoms selected from N, O and S, but containing no more than one O or S.

In another embodiment, in conjunction with any of the above or below embodiments, $R^3$ is selected from halo, $C_{1-6}$alk, $C_{1-4}$haloalk, cyano, nitro, —C(=O)$R^a$, —C(=O) O$R^a$, —C(=O)N$R^aR^a$, —C(=N$R^a$)N$R^aR^a$, —O$R^a$, —OC (=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O) $R^a$, —S(=O)$_2$N($R^a$)C(=O)O$R^a$, —S(=O)$_2$N($R^a$)C(=O) N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$) S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$.

In another embodiment, in conjunction with any of the above or below embodiments, Z is —C=C—, —C—C—, S(=O)$_2$—C—C— and —C—C—S(=O)$_2$— any of which are substituted by 0, 1 or 2 substituents selected from halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk and C$_{1-4}$haloalk; and additionally substituted by 0 or 1 saturated or partially saturated 3-, 4-, 5- or 6-membered spiro rings containing 0, 1 or 2 heteroatoms selected from N, O and S, the spiro ring being substituted by 0, 1, 2 or 3 substituents independently selected from halo, $C_{1-6}$alk and $C_{1-4}$haloalk.

In another embodiment, in conjunction with any of the above or below embodiments, Z is —C=C—, —C—C—, S(=O)$_2$—C—C— and —C—C—S(=O)$_2$— any of which are substituted by 0, 1 or 2 substituents selected from halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk and C$_{1-4}$haloalk; and additionally substituted by a saturated 3-, 4-, 5- or 6-membered spiro ring containing 0, 1 or 2 heteroatoms selected from N, O and S;

Another aspect of the invention relates to a method of treating PI3K-mediated conditions or disorders.

In certain embodiments, the PI3K-mediated condition or disorder is selected from rheumatoid arthritis, ankylosing spondylitis, osteoarthritis, psoriatic arthritis, psoriasis, inflammatory diseases, and autoimmune diseases. In other embodiments, the PI3K-mediated condition or disorder is selected from cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from type II diabetes. In still other embodiments, the PI3K-mediated condition or disorder is selected from respiratory diseases, bronchitis, asthma, and chronic obstructive pulmonary disease. In certain embodiments, the subject is a human.

Another aspect of the invention relates to the treatment of rheumatoid arthritis, ankylosing spondylitis, osteoarthritis, psoriatic arthritis, psoriasis, inflammatory diseases or autoimmune diseases comprising the step of administering a compound according to any of the above embodiments.

Another aspect of the invention relates to the treatment of rheumatoid arthritis, ankylosing spondylitis, osteoarthritis, psoriatic arthritis, psoriasis, inflammatory diseases and autoimmune diseases, inflammatory bowel disorders, inflammatory eye disorders, inflammatory or unstable bladder disorders, skin complaints with inflammatory components, chronic inflammatory conditions, autoimmune diseases, systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions and hypersensitivity, comprising the step of administering a compound according to any of the above or below embodiments.

Another aspect of the invention relates to the treatment of cancers that are mediated, dependent on or associated with p110δ activity, comprising the step of administering a compound according to any of the above or below embodiments.

Another aspect of the invention relates to the treatment of cancers are selected from acute myeloid leukaemia, myelodysplastic syndrome, myelo-proliferative diseases, chronic myeloid leukaemia, T-cell acute lymphoblastic leukaemia, B-cell acute lymphoblastic leukaemia, non-hodgkins lymphoma, B-cell lymphoma, solid tumors and breast cancer, comprising the step of administering a compound according to any of the above or below embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of rheumatoid arthritis, ankylosing spondylitis, osteoarthritis, psoriatic arthritis, psoriasis, inflammatory diseases, and autoimmune diseases.

The compounds of this invention may have in general several asymmetric centers and are typically depicted in the form of racemic mixtures. This invention is intended to encompass racemic mixtures, partially racemic mixtures and separate enantiomers and diasteromers.

Unless otherwise specified, the following definitions apply to terms found in the specification and claims:

"$C_{\alpha-\beta}$alk" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. Examples of $C_{1-6}$alk include, but are not limited to the following:

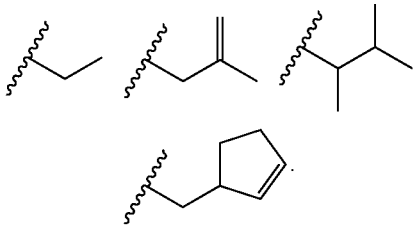

"Benzo group", alone or in combination, means the divalent radical $C_4H_4=$, one representation of which is —CH=CH—CH=CH—, that when vicinally attached to another ring forms a benzene-like ring—for example tetrahydronaphthalene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V-W}$haloalk" means an alk group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

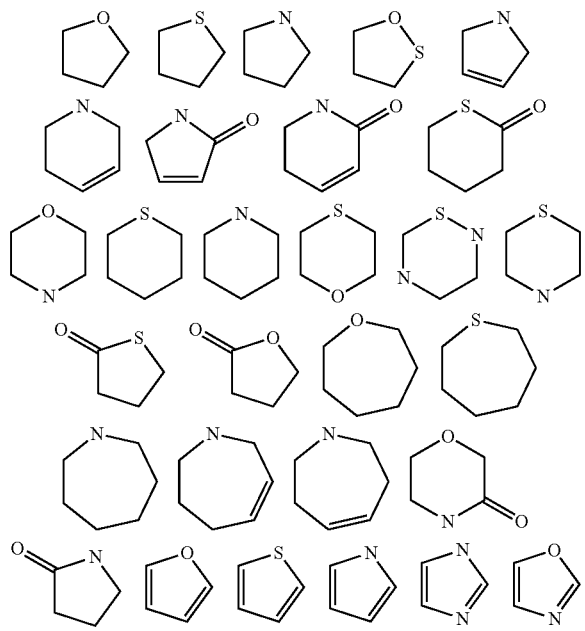

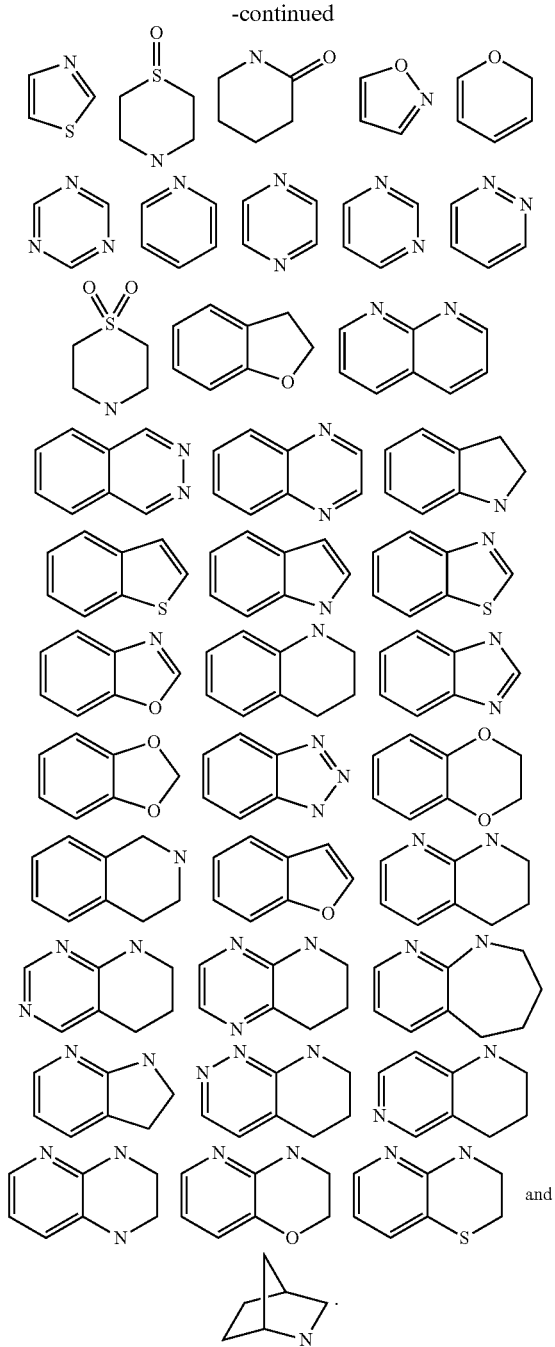

"Available nitrogen atoms" are those nitrogen atoms that are part of a heterocycle and are joined by two single bonds (e.g. piperidine), leaving an external bond available for substitution by, for example, H or $CH_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, orthomethylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl. Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyldimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

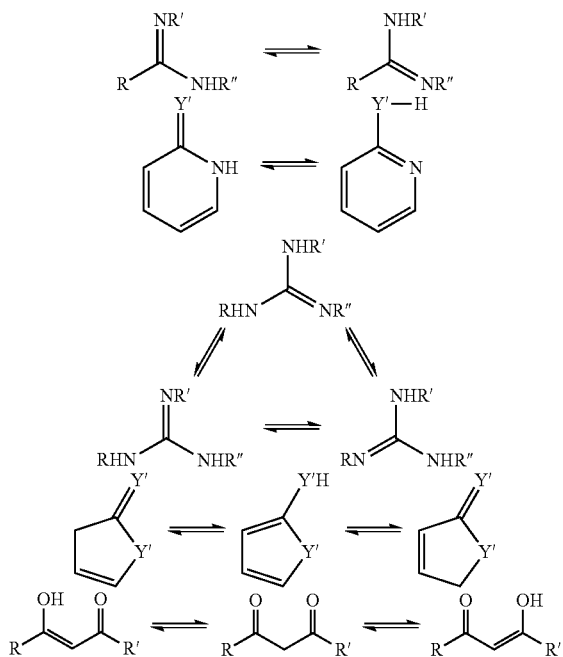

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

The following abbreviations are used:

| | |
|---|---|
| BINAP - | 2,2'-bis(diphenylphosphino)-1,1'-binaphthyl |
| Dba - | dibenzylideneacetone |
| DCM - | dichloromethane |
| DMF - | N,N-dimethylformamide |
| eq - | equivalent(s) |
| Et$_2$O - | diethyl ether |
| EtOAc - | ethyl acetate |
| EtOH - | ethyl alcohol |
| h - | hour(s) |
| HPLC - | high performance liquid chromatography |
| LCMS - | liquid chromatography-mass spectrometry |
| MeOH - | methyl alcohol |
| NMP - | N-methylpyrrolidone |
| PPA - | polyphosphoric acid |
| rt - | room temperature |
| TFA - | trifluoroacetic acid |
| THF - | tetrahydrofuran |

General

Reagents and solvents used below can be obtained from commercial sources. $^1$H-NMR spectra were recorded on a Bruker 400 MHz and 500 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Mass spectrometry results are reported as the ratio of mass over charge, followed by the relative abundance of each ion (in parentheses Electrospray ionization (ESI) mass spectrometry analysis was conducted on a Agilent 1100 series LC/MSD electrospray mass spectrometer. All compounds could be analyzed in the positive ESI mode using acetonitrile:water with 0.1% TFA as the delivery solvent. Reverse phase analytical HPLC was carried out using a Agilent 1200 series on Agilent Eclipse XDB-C18 5 μm column (4.6×150 mm) as the stationary phase and eluting with acetonitrile:water with 0.1% TFA. Reverse phase Semi-Prep HPLC was carried out using a Agilent 1100 Series on a Phenomenex Gemini 10 μm C18 column (250×21.20 mm) as the stationary phase and eluting with acetonitrile:water with 0.1% TFA.

General Procedures

Procedure A

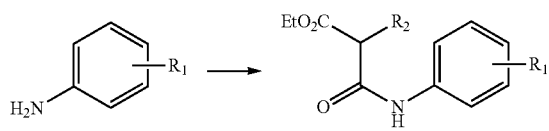

A mixture of the substituted aniline (1 eq) in pyridine (2 eq) was treated with diethyl alkylmalonate (1.5 eq) and the stirred mixture was heated at 130° C. for 24 h. After this time the reaction was treated with diethyl alkylmalonate (0.5 eq) and heated at 130° C. for an additional 12 h. After this time the reaction was cooled to rt and evaporated under reduced pressure. The crude product was taken up in DCM, washed with saturated aqueous bicarbonate and the separated organic layer was dried over MgSO$_4$, filtered and evaporated under reduced pressure. The crude product was dissolved in benzene and evaporated under reduced pressure. The crude product was purified by column chromatography on silica (using a gradient of hexanes:EtOAc, 1:0 to 3:1 as eluent) to provide ethyl substituted phenylamino-oxopropanoates.

Procedure B

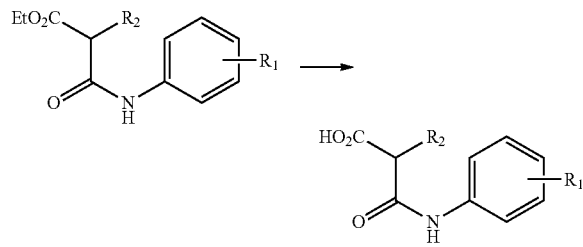

A mixture of the ethyl substituted phenylamino-oxopropanoate (1 eq) in THF-water (4:1, 0.878 M) was treated with sodium hydroxide (1.2 eq) and stirred at rt for 1 h. After this time the reaction was acidified to pH 2 with concentrated HCl and then it was extracted with EtOAc. The separated organic layer was dried over MgSO$_4$, filtered and evaporated under reduced pressure to give substituted phenylamino-oxopropanoic acids Procedure C

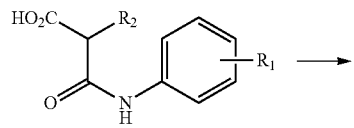

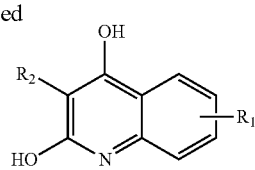

A mixture of phenylamino-oxopropanoic acid in PPA (0.6M) was stirred at 130° C. for 2 h. After this time the reaction was cooled to rt and treated with 2M aqueous sodium hydroxide until a precipitate formed. The precipitate was filtered and washed with 1M aqueous sodium hydroxide and dried under vacuum to give substituted quinoline diols.

Procedure D

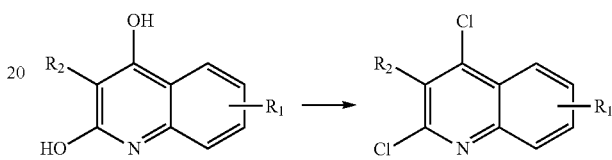

A mixture of the quinoline diol (1 eq) and phosphorus oxychloride (10 eq) was heated at 100° C. for 2 h. After this time the reaction was cooled to rt and evaporated under reduced pressure. The resulting brown residue was taken up in DCM and washed with water. The separated organic layer was dried over MgSO$_4$, filtered and evaporated under reduced pressure. The product was then purified by column chromatography (using a 9 to 1 mixture of hexanes and EtOAc as eluent) to give the substituted dichloroquinolines.

Procedure E

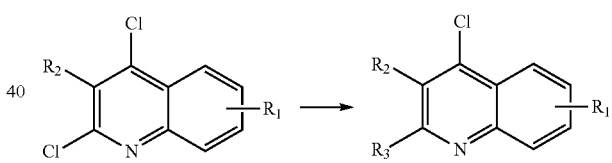

A mixture of the substituted dichloroquinoline (1 eq), the Stille reagent (1 eq) and tetrakis(triphenylphosphine)palladium (0.1 eq) in toluene (0.21M) was heated at reflux overnight. After this time the reaction was cooled to rt and treated with EtOAc and water. The separated organic layer was dried over MgSO$_4$, filtered and evaporated in vacuo. Column chromatography gave the substituted 4-chloro quinolines.

Procedure F

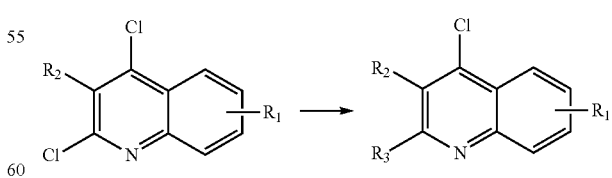

A mixture of the substituted dichloroquinoline (1 eq), the boronic acid (1 eq), sodium carbonate (2 eq) and tetrakis(triphenylphosphine)palladium (0.1 eq) in toluene-water (5:2, 0.15M) was heated at reflux overnight. After this time the reaction was cooled to rt and treated with EtOAc and water. The separated organic layer was dried over MgSO$_4$, filtered and evaporated in vacuo. Column chromatography gave the substituted 4-chloro quinolines.

Procedure G

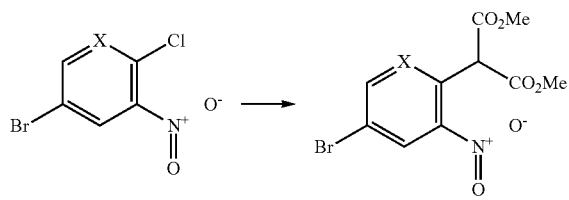

To a suspension of potassium carbonate (3 eq) in DMF (1M) at 0° C. was added dimethyl malonate (1.2 eq) via syringe over 10 min. After this time the chloro-nitro compound (1 eq) was added portionwise over 4 min. The reaction was allowed to warm to rt overnight. After this time the reaction was poured into 2.0 M aqueous HCl and diluted with EtOAc. The separated organic layer was washed with LiCl (1.0 M aqueous solution) and brine, and then dried over $MgSO_4$, filtered and evaporated in vacuo to give the dimethyl-nitromalonates.

Procedure H

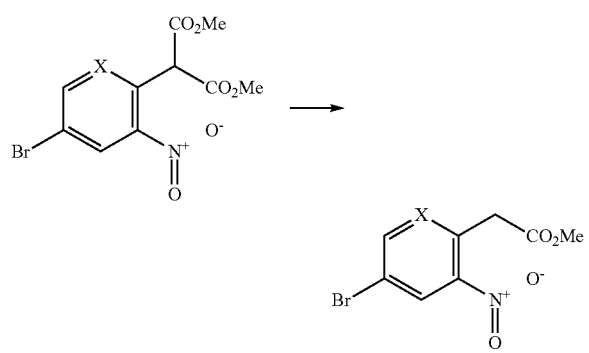

To a stirred suspension of the dimethyl-nitromalonate (1 eq) in water (2.1M) was added lithium chloride (5 eq). The reaction was heated at 150° C. for 14 h. After this time the reaction was diluted with EtOAc and water. The separated organic layer was dried over $MgSO_4$, filtered and evaporated in vacuo to give the methyl nitroacetates.

Procedure I

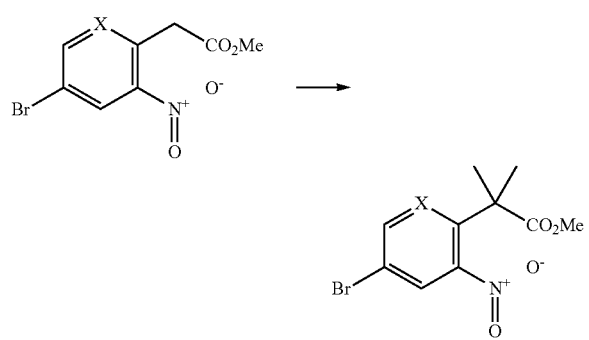

A mixture of the methyl nitroacetate (1 eq) in DMF (0.28M) at 0° C. was treated with sodium hydride (60% dispersion in oil, 1.1 eq). The reaction was stirred while warming to rt for 30 min. After this time the reaction was cooled to 0° C. and iodomethane (1.1 eq) was added dropwise over 2 min. The reaction was allowed to warm to rt for 4 h. After this time the reaction was cooled to 0° C. and then treated with sodium hydride (60% dispersion in oil, 1.1 eq). The reaction was allowed to warm to rt for 20 min and then cooled to 0° C. and treated with iodomethane (1.366 mL, 22.00 mmol). The reaction was allowed to warm to rt overnight. After this time the reaction was carefully treated with water and then diluted with EtOAc. The separated organic layer was washed with LiCl (1M aqueous solution), dried over $MgSO_4$, filtered and evaporated in vacuo to give the methyl-nitro-methyl propanoates.

Procedure J

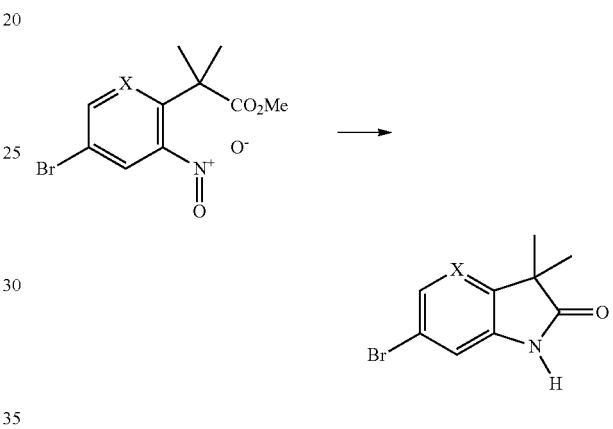

A mixture of the methyl-nitro-methylpropanoate (1 eq) in acetic acid (100 eq) was treated with iron powder (5 eq). The reaction was heated to 100° C. for 2 h. After this time the reaction was cooled to rt and filtered over Celite™. The Celite™ was washed with acetic acid and the combined filtrates were evaporated in vacuo. The resulting residue was purified by column chromatography (hexanes:EtOAc, 1:0 to 0:1) to give the bromo-dimethylpyridinone (or indolinone).

Procedure K

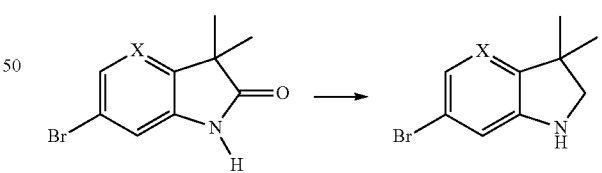

To a stirred suspension of the bromo-dimethylpyridinone (or indolinone) (1 eq) in toluene (0.4M) was added sodium bis(2-methoxyethoxy)aluminum hydride (3 eq) dropwise over 2 min (an exotherm was observed and suspension becomes a yellow solution). The reaction was stirred at rt for 1 h and then it was cooled to 0° C. The reaction was carefully quenched with water and then it was diluted with DCM and treated with saturated aqueous Rochelle's salt. The separated organic layer was washed with 1N NaOH and then dried over $MgSO_4$, filtered and evaporated in vacuo to give the bromo-dimethyl-pyrrolopyridine (or bromo-dimethylindoline).

Procedure L


To a suspension of the halo-dimethyl-pyrrolopyridine (or halo-dimethylindoline) (1 eq), substituted dichloroquinoline (1 eq) in NMP (1.4M) was added a 4.0M solution of HCl in 1,4-dioxane (1 eq). The reaction was heated in the microwave at 150° C. for 2 h. After this time the reaction was diluted with EtOAc and aqueous NaOH. The separated organic layer was dried, filtered and evaporated in vacuo. The resulting residue was purified by column chromatography (hexanes:EtOAc, 1:0 to 1:2) to give the bromoquinolines.

Procedure M

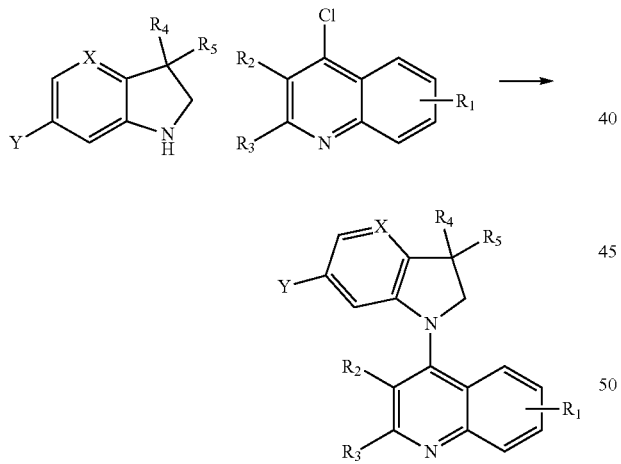

To a stirred solution of the halo-dimethyl-pyrrolopyridine (or halo-dimethylindoline) (1 eq), in DMF (0.03M) was added NaH (60% dispersion in oil, 1.5 eq). The reaction was stirred at rt for 20 min. After this time the substituted dichloroquinoline (1 eq) in DMF (0.03M) was added. The resulting mixture was heated at 130° C. for 12 h. After this time the reaction was allowed to cool to rt and quenched with $Na_2CO_3$ (10% aqueous solution). The reaction mixture was then treated with EtOAc and water. The separated organic layer was washed with LiCl (5% aqueous solution), dried over $MgSO_4$, filtered and evaporated in vacuo to give the bromoquinolines.

Procedure N

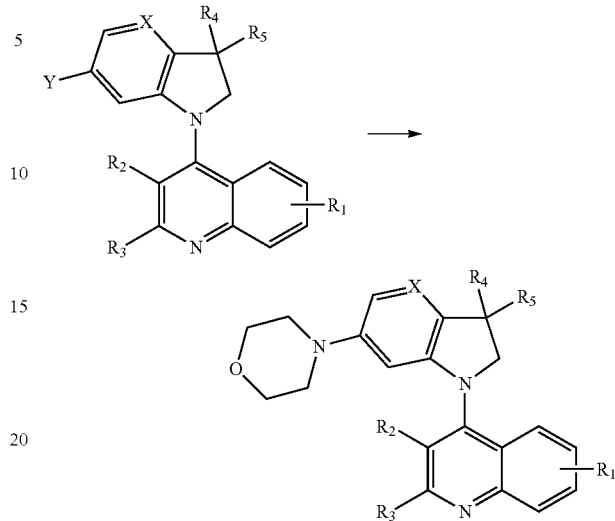

A stirred solution of the halo-quinoline (1 eq) in toluene (0.05M) was treated with $Pd_2dba_3$ (0.1 eq), XPhos (0.2 eq), morpholine (1.1 eq) and sodium tert-butoxide (2 eq). The mixture was heated at reflux overnight. After this time the reaction was diluted with EtOAc and water. The separated organic layer was dried over $MgSO_4$, filtered and evaporated in vacuo. Purification by reverse phase HPLC (10 to 60% acetonitrile in water) (or column chromatography) gave the morpholino quinolines.

Procedure O

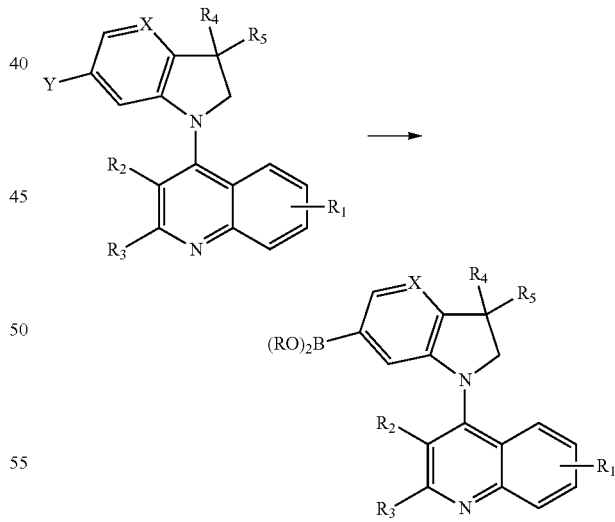

A stirred solution of the halo-quinoline (1 eq) in 1,4-dioxane (0.1M) was treated with $Pd(PCy_3)_2$ (0.1 eq), bis(pinacolato)diboron (1.1 eq), and KOAc (1.5 eq). The mixture was heated at 100° C. for 2 h in the microwave. After this time the reaction was diluted with EtOAc and water. The separated organic layer was washed with brine and then dried over $MgSO_4$, filtered and evaporated in vacuo to give the boronic acids (or esters).

Procedure P

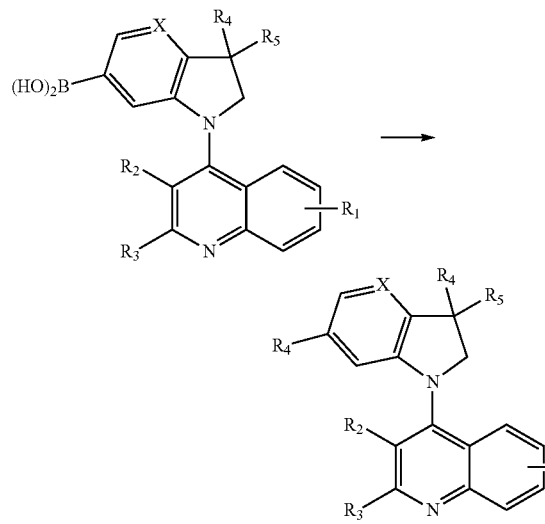

A stirred solution of the boronic acid (or ester) (1 eq) in 1,4-dioxane (0.1M) was treated with PdCl$_2$(PPh$_3$)$_2$ (0.1 eq), an aryl chloride (1 eq) and sodium carbonate (2 eq). The mixture was heated at 120° C. for 2 h in the microwave. After this time the reaction was diluted with EtOAc and water. The separated organic layer was washed with brine and then dried over MgSO$_4$, filtered and evaporated in vacuo. Purification by reverse phase HPLC (10 to 60% acetonitrile in water) (or column chromatography) gave the substituted quinoline products.

Procedure Q

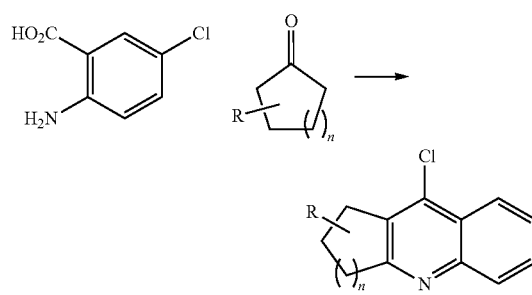

A mixture of 2-amino-5-chlorobenzoic acid (1 eq) and cyclic ketone (1 eq) was treated with POCl$_3$ (5 eq) at 0° C. The mixture was heated at reflux for 7 h and at rt for 16 h. After this time the reaction was poured into ice water and extracted with DCM. The crude residue was purified by flash column chromatography to give the desired quinoline.

Procedure R

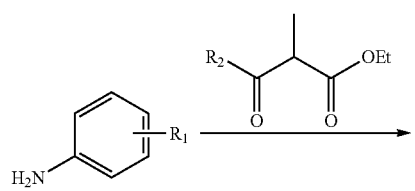

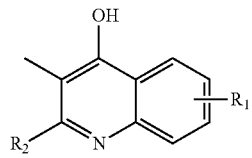

A stirred mixture of substituted aniline (1 eq) and ethyl 2-methyl-3-oxobutanoate (2 eq) in PPA was heated at 170° C. for 2 h. After 2 h, the mixture was cooled to rt, neutralized with 2N aqueous NaOH to pH 8. The resulting precipitate was collected by filtration, washed with water, and dried to give substituted 2,3-dimethylquinolin-4-ol.

Procedure S

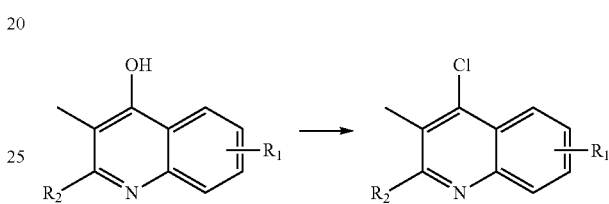

A mixture of substituted 2,3-dimethylquinolin-4-ol (1 eq) and POCl$_3$ (10 eq) was heated at reflux for 3 h. After this time the reaction mixture was concentrated under reduced pressure. The resulting residue was carefully treated with ice water and the aqueous mixture was basified with NH$_4$OH. The resulting precipitate was collected by filtration, washed with water, and dried to give substituted 4-chloro-2,3-dimethylquinoline.

Procedure T

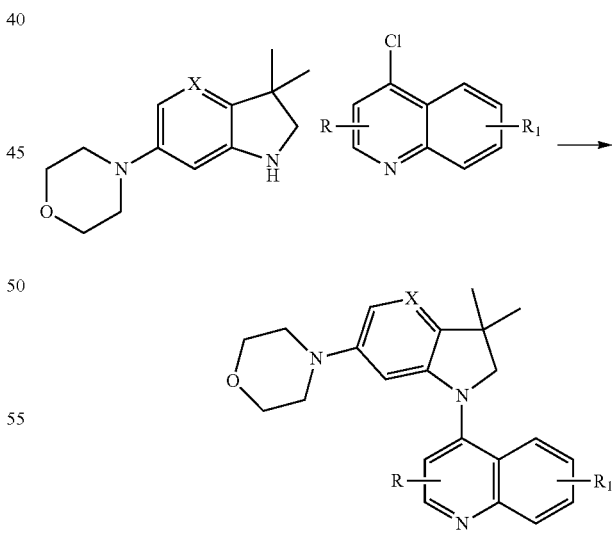

A mixture of indoline (1 eq), quinoline (2 eq), cesium carbonate (2 eq), Pd$_2$(dba)$_3$ (0.1 eq) and (±) BINAP (0.15 eq) were dissolved in 1,4-dioxane (0.4M). The resulting mixture was purged with argon and subjected to microwave heating at 140° C. for 3 h. The crude residue was purified by chromatography to give the desired morpholino-quinoline product.

Procedure U

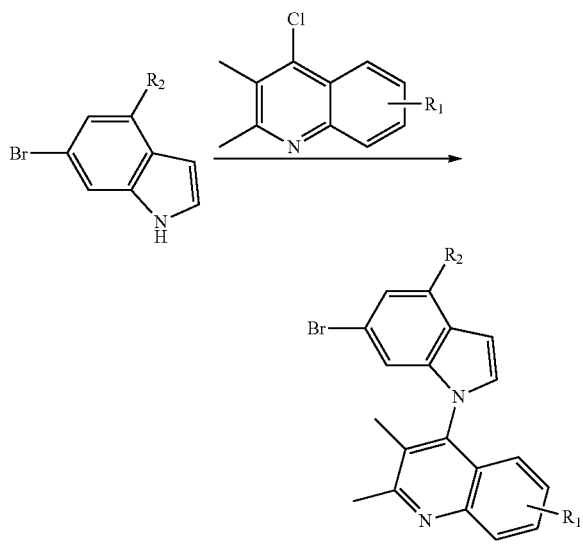

A stirred mixture of substituted indole (1 eq), substituted quinoline (1.5 eq), Cs$_2$CO$_3$ (3 eq), and DMF (0.2M) was heated at 140° C. for 5 h. After this time the mixture was concentrated under reduced pressure. The resulting residue was purified by column chromatography using 0 to 100% gradient of EtOAc in hexane as eluent to give the substituted indol-1-yl-2,3-dimethylquinoline.

Procedure V

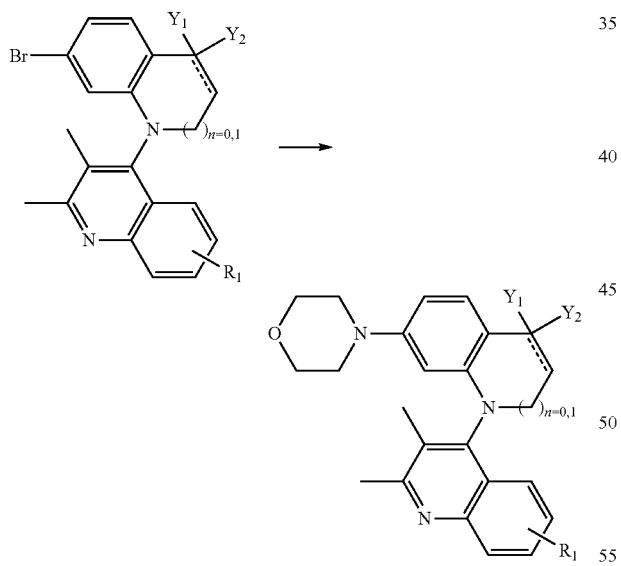

A suspension of bromoquinoline (1 eq), morpholine (2.0 eq), and DMSO (0.13M) was degassed with argon for 20 min. To the suspension was added CuI (0.2 eq), K$_2$CO$_3$ (3.0 eq), and L-proline (0.4 eq) and the mixture was stirred at 120° C. After 24 h the mixture was cooled to rt. To the mixture was added water and the mixture was extracted with DCM twice. The combined organics were dried over Na$_2$SO$_4$, filtered, and concentrated under reduced pressure. The mixture was purified by column chromatography on a silica gel column using 0% to 100% gradient of EtOAc in hexane as eluent to give the morpholino quinolines.

Procedure W

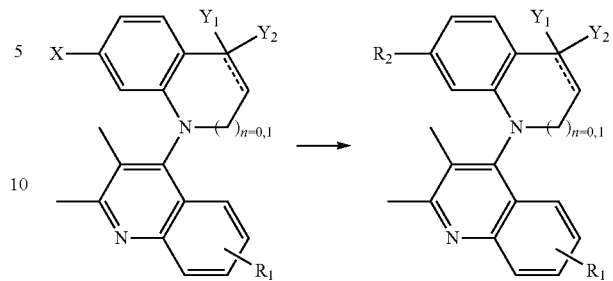

A mixture of substituted 4-(6-halo-3,3-dimethylindolin-1-yl)-2,3-dimethylquinoline (1 eq), boronic acid (2 eq), 2 M aqueous Na$_2$CO$_3$ (6 eq) solution, and tetrakis(triphenylphosphine)palladium(0) (0.1 eq) in DMF was heated at 100° C. After 3 h, the mixture was poured into water. The resulting precipitate was collected by filtration, washed with water, and dried to give a solid. The crude product was purified by column chromatography on a silica gel column using 0% to 100% gradient of DCM-MeOH-NH$_4$OH (89:9:1) in DCM as eluent to give product.

Procedure X

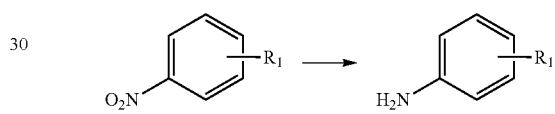

To a solution of substituted nitro benzene (1 eq) in acetic acid was added iron powder (3 eq) in portions. Upon complete addition, the mixture was carefully heated at 100° C. After 2 h, the hot mixture was carefully filtered through Celite™. The Celite™ was washed with EtOH and the filtrate was concentrated under reduced pressure. The resulting residue was purified by column chromatography to give the corresponding substituted aniline.

Procedure Y

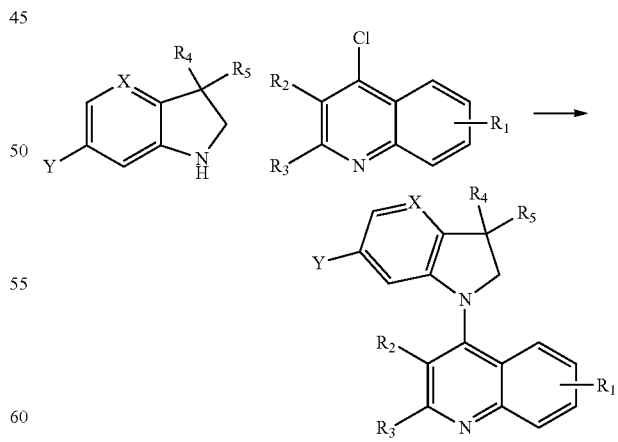

A reaction vessel was charged with chloroquinoline (1 eq), indoline (1-1.2 eq), sodium tert-butoxide (2 eq), toluene (0.1M to 0.5M), and either Pd$_2$dba$_3$ (0.1 eq) and XPhos (0.2 eq) or XPhos precatalyst (0.1 eq, CAS 1028206-56-5). The mixture was stirred at 95-110° C. under nitrogen. Upon completion (30 min-24 h), the reaction was concentrated, and the resulting residue partitioned between either EtOAc and water or DCM and water. The organic phase was dried over MgSO$_4$ and concentrated, affording a crude material that was purified either by column chromatography on silica gel or basic alumina, or by reverse-phase HPLC (acetonitrile in water) to give the desired product.
Procedure Z

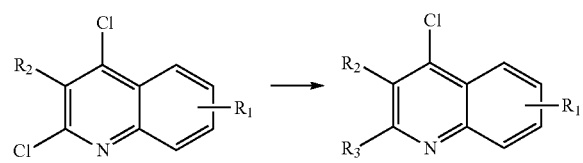

A reaction vessel was charged with chloroquinoline (1 eq) and Pd(PPh$_3$)$_4$ (0.1 eq), then dry THF (0.4 M) was added via syringe. The reaction was sparged with nitrogen for one min, then organozinc halide (1.05 eq, 0.5M in THF) was added and the reaction stirred at 50° C. under nitrogen for 2 h. The reaction was then cooled to rt, carefully quenched with saturated aqueous ammonium chloride, and the product extracted with EtOAc. The organic phase was washed with water, dried over MgSO$_4$, concentrated, and the crude material was purified either by column chromatography on silica gel or by reverse-phase HPLC to afford the desired product.
Procedure AA

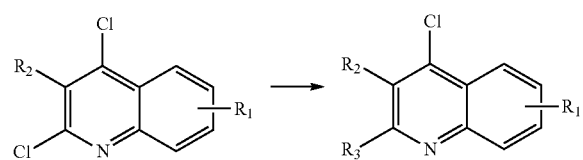

A reaction vessel was charged with chloroquinoline (1 eq), amide (1.2 eq), cesium carbonate (1.4 eq), Pd$_2$dba$_3$ (0.05 eq), XantPhos (0.15 eq), and 1,4-dioxane (0.5 M). The reaction mixture was sparged with nitrogen for 1 min and stirred at 95-100° C. for 18 h. Upon completion the reaction mixture was cooled to rt and filtered through Celite™. The filtrate was concentrated, and the crude material was purified by column chromatography on silica gel to afford the desired product.

Example 1

4-(3,3-Dimethyl-6-(4-morpholinyl)-2,3-dihydro-1H-indol-1-yl)-7-fluoro-3-methyl-2-(2-pyridinyl)quinoline Ethyl 3-(3-fluorophenylamino)-2-methyl-3-oxopropanoate

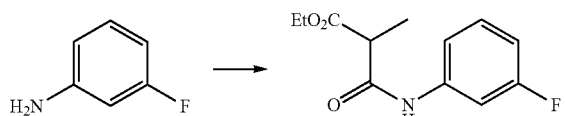

Prepared according to procedure A using 3-fluoroaniline (18 mL, 187 mmol), pyridine (31 mL, 374 mmol) and diethyl methylmalonate (48 mL, 281 mmol). The crude was purified by column chromatography on silica (using a gradient of hexane:EtOAc, 1:0 to 3:1 as eluent) to give ethyl 3-(3-fluorophenylamino)-2-methyl-3-oxopropanoate as a light brown solid. Mass Spectrum (ESI) m/e=240.1 (M+1).

3-(3-Fluorophenylamino)-2-methyl-3-oxopropanoic acid

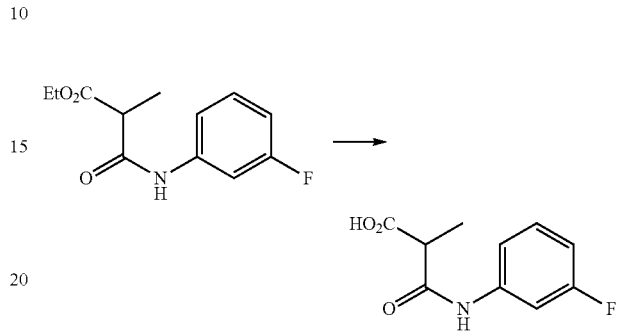

Prepared according to procedure B using ethyl 3-(3-fluorophenylamino)-2-methyl-3-oxopropanoate (21.0 g, 87.8 mmol) in THF (80 mL) to give 3-(3-fluorophenylamino)-2-methyl-3-oxopropanoic acid as a white solid. Mass Spectrum (ESI) m/e=212.1 (M+1).

7-Fluoro-3-methylquinoline-2,4-diol and 5-fluoro-3-methylquinoline-2,4-diol

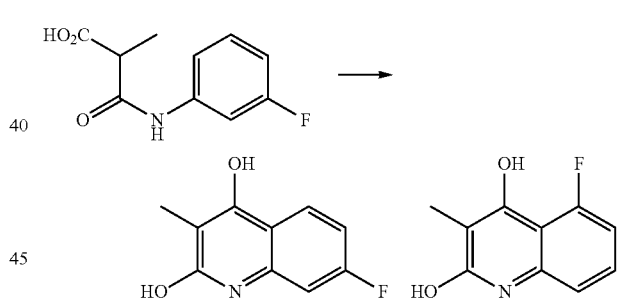

Prepared according to procedure C using 3-(3-fluorophenylamino)-2-methyl-3-oxopropanoic acid (19 g, 90 mmol) and PPA (150 mL) to give a mixture of 7-fluoro-3-methylquinoline-2,4-diol and 5-fluoro-3-methylquinoline-2,4-diol. Mass Spectrum (ESI) m/e=194.1 (M+1).

2,4-Dichloro-7-fluoro-3-methylquinoline and 2,4-dichloro-5-fluoro-3-methyl quinoline

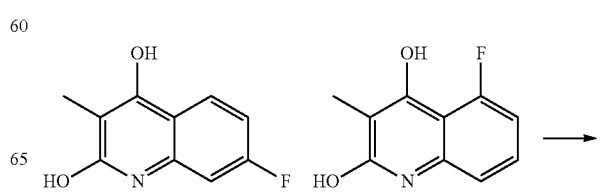

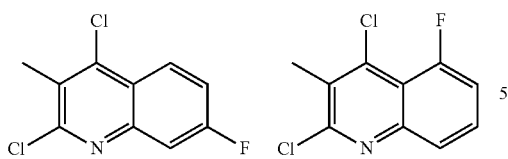

Prepared according to procedure D using 7-fluoro-3-methylquinoline-2,4-diol and 5-fluoro-3-methylquinoline-2,4-diol (14.0 g, 72 mmol) to give a mixture of 2,4-dichloro-7-fluoro-3-methylquinoline and 2,4-dichloro-5-fluoro-3-methyl quinoline as a white solid. Mass Spectrum (ESI) m/e=230 (M+1).

4-Chloro-5-fluoro-3-methyl-2-(pyridin-2-yl)quinoline and 4-chloro-7-fluoro-3-methyl-2-(pyridin-2-yl)quinoline

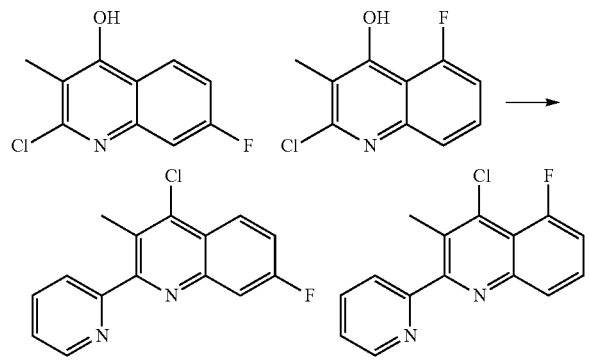

Prepared according to procedure E using 2,4-dichloro-7-fluoro-3-methylquinoline and 2,4-dichloro-5-fluoro-3-methyl quinoline (1.5 g, 6.52 mmol), Pd(PPh$_3$)$_4$ (377 mg, 0.326 mmol) in toluene (20 mL) to give a separable mixture of 4-chloro-7-fluoro-3-methyl-2-(pyridin-2-yl)quinoline (Mass Spectrum (ESI) m/e=273.0 (M+1)) and 4-chloro-5-fluoro-3-methyl-2-(pyridin-2-yl)quinoline. Mass Spectrum (ESI) m/e=273.0 (M+1)).

1-(3,3-Dimethyl-6-nitroindolin-1-yl)ethanone

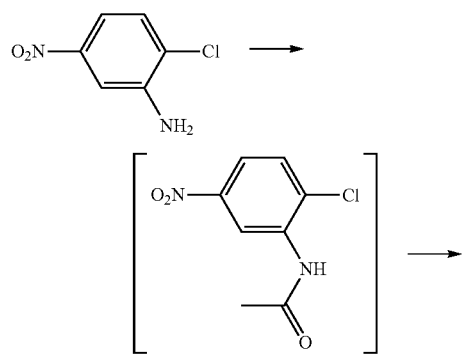

The reactor used for this process was a 12-L, 3-necked round bottom flask equipped with a mechanical stirrer, pressure equalized addition funnels, and a Claisen adapter jointed to a coiled condenser with a nitrogen gas inlet and off-gas outlet, a thermocouple temperature probe (operating range rt to 100° C.). The flask was placed under an atmosphere of nitrogen gas for 15 min prior to charging. 2-Chloro-5-nitroaniline (173 g, 1 mol) and N,N-dimethylacetamide (2 L) were charged to the 12-L flask. Stirring was initiated and a clear orange solution was obtained. Acetyl chloride (75 mL, 1.05 mol) was added through a 125-mL pressure-equalized addition funnel at such a rate that the internal temperature was maintained under 35° C. The maximum temperature reached 37-38° C. when the feeding rate was not controlled. The reaction to N-(2-chloro-5-nitrophenyl)acetamide was monitored by HPLC in 30 min intervals. NaOH (50% in water, 155 mL, 3.0 mol) was added to the mixture through a 250-mL pressure-equalized addition funnel in one portion. 3-Chloro-2-methylpropene (148 mL, 1.5 mol) was added to the mixture through a 250-mL pressure-equalized addition funnel in one portion at rt. The reaction mixture was heated to 60° C. and monitored by HPLC in 30 min intervals. The heating was stopped when the allylation to N-(2-chloro-5-nitrophenyl)-N-(2-methylallyl)acetamide was completed. Sodium formate (102 g, 1.5 mol) was added through a poly funnel and triethyl amine (140 mL, 1.0 mol) was charged through a 250-mL pressure-equalized addition funnel in one portion. Palladium (II) acetate (27 g, 0.12 mol) was added through a poly funnel. The resulting dark homogeneous solution of N-(2-chloro-5-nitrophenyl)-N-(2-methylallyl)acetamide was heated to 100° C. and the conversion to 1-(3,3-dimethyl-6-nitroindolin-1-yl) ethanone was monitored by HPLC hourly. The heating was stopped when the Heck cyclization was completed. The solution of 1-(3,3-dimethyl-6-nitroindolin-1-yl)ethanone was cooled to below 20° C. in an icy water bath. Deionized water (3 L) was added into the dark suspension through a 5-L pressure-equalized addition funnel with strong agitation. The resulting dark suspension was stirred at rt for 3 h. The solid was filtered through a fritted-filter funnel under house vacuum. The solid remaining in the flask was rinsed into the funnel with deionized water (2 L) and the filter cake was washed with deionized water (1 L×2). The solids were transferred into a 5 L round bottom flask and slurried in heptane (3 L) for 1 h. The solids were filtered through a fritted-filter funnel under house vacuum and dried under house vacuum at 70° C. for at least 17 h to give 1-(3,3-dimethyl-6-nitroindolin-1-yl)-ethanone as a brown solid: purity of 98% by HPLC.

1-(6-Amino-3,3-dimethylindolin-1-yl)ethanone

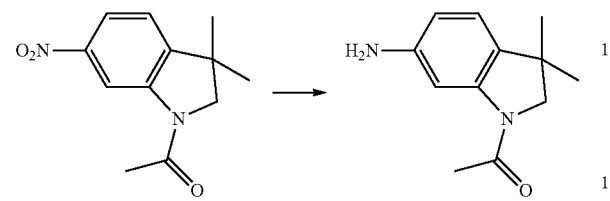

A Parr hydrogenation unit was charged with 1-(3,3-dimethyl-6-nitroindolin-1-yl)-ethanone (450 g, 1.92 mol), THF (1.8 L), and 10% Pd/C (20.3 g). The unit was purged with nitrogen twice then agitated. The unit was pressurized with 50 psi hydrogen and the agitation was continued until absorption ceased. Hydrogen absorption was exothermic. The temperature was maintained below 50° C. during the reaction. The reaction was monitored by GC. After 8 min, the unit was purged with nitrogen. The mixture was filtered through a Celite™ pad and washed the pad with THF (100 mL×1). The filtrate was concentrated under reduced pressure to ¼ total volume and cooled to 0° C. To the mixture was added heptane (800 mL×1) and the mixture was stirred at 0° C. for 45 min. The resulting precipitate was collected by filtration, washed the solid with heptane (150 mL×1), and dried at 50° C. under reduced pressure to give 1-(6-amino-3,3-dimethylindolin-1-yl)ethanone.

1-(3,3-Dimethyl-6-morpholinoindolin-1-yl)ethanone

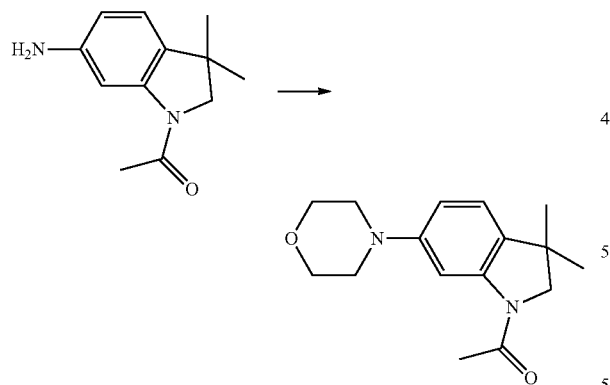

A mixture of 1-(6-amino-3,3-dimethylindolin-1-yl)ethanone (5 g, 24.5 mmol), 1-bromo-2-(2-bromoethoxy)ethane (6.25 g, 26.9 mmol), and Na$_2$CO$_3$ (5.19 g, 49 mmol) in MeOH (25 mL) was heated to 150° C. in a sealed tube. After 2.5 h, the mixture was cooled to rt. The reaction mixture was diluted with water (100 mL). The resulting solid was filtered, washed with water (300 mL), and dried in the air to give 1-(3,3-dimethyl-6-morpholinoindolin-1-yl)ethanone as a grey solid: $^1$H NMR (500 MHz, DMSO-d$_6$) δ ppm 7.74 (1H, s), 7.06 (1H, d, J=8.1 Hz), 6.61 (1H, dd, J=8.2, 2.1 Hz), 3.82 (2H, s), 3.67-3.76 (4H, m), 2.95-3.06 (4H, m), 2.13 (3H, s), 1.26 (6H, s). Mass Spectrum (ESI) m/e=275.2 (M+1).

4-(3,3-Dimethylindolin-6-yl)morpholine

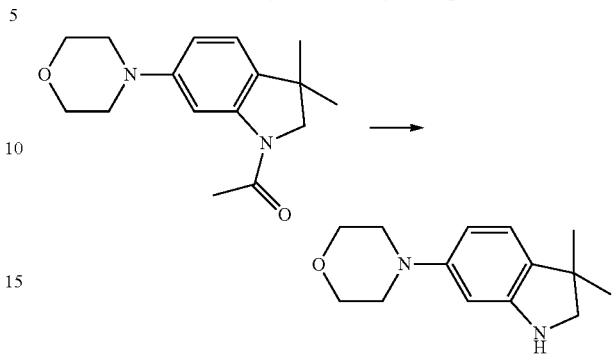

1-(3,3-Dimethyl-6-morpholinoindolin-1-yl)ethanone was dissolved in acetonitrile (100 mL) and treated with 5 N HCl (50 mL) at 95° C. After 2 h, the mixture was cooled to rt. The reaction was carefully neutralized with saturated NaHCO$_3$ solution to pH 10 and extracted with EtOAc (100 mL×4). The combined organics were washed with water, brine, dried, and concentrated under reduced pressure. The residue was purified by column chromatography on silica gel (EtOAc/hexane, 0/1 to 1/0) to give 4-(3,3-dimethylindolin-6-yl)morpholine as a white solid: $^1$H NMR (400 MHz, DMSO-d$_6$) δ ppm 6.80 (1H, d, J=7.8 Hz), 6.14 (1H, dd, J=8.0, 2.2 Hz), 6.09 (1H, d, J=2.0 Hz), 5.28 (1H, s), 3.65-3.73 (4H, m), 3.13 (2H, d, J=2.0 Hz), 2.92-2.99 (4H, m), 1.17 (6H, s). Mass Spectrum (ESI) m/e=233.2 (M+1).

4-(3,3-Dimethyl-6-(4-morpholinyl)-2,3-dihydro-1H-indol-1-yl)-7-fluoro-3-methyl-2-(2-pyridinyl)quinoline

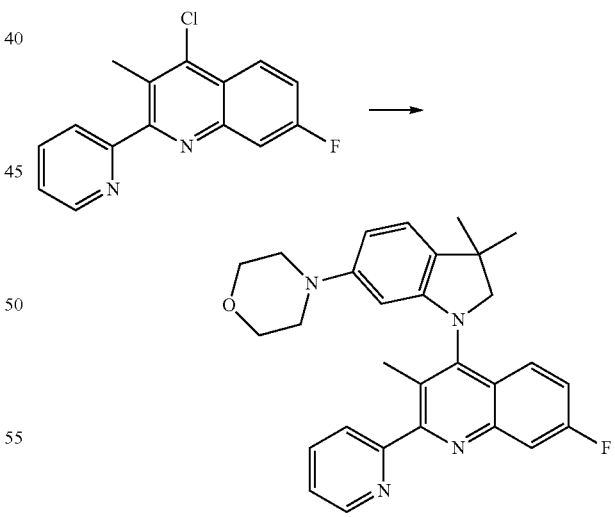

Prepared according to procedure M using 3,3-dimethyl-6-morpholinoindoline (85 mg, 0.367 mmol) in DMF (6 mL), 4-chloro-7-fluoro-3-methyl-2-(pyridin-2-yl)quinoline (100 mg, 367 μmol) and sodium hydride (18 mg, 733 μmol) and heating at 130° C. overnight. After purification 4-(3,3-dimethyl-6-(4-morpholinyl)-2,3-dihydro-1H-indol-1-yl)-7-fluoro-3-methyl-2-(2-pyridinyl)quinoline was obtained as a yellow film. 1H NMR (500 MHz, chloroform-d) δ ppm 8.73-

8.76 (1H, m), 7.80-7.94 (4H, m), 7.40 (1H, ddd, J=7.6, 4.9, 1.5 Hz), 7.20-7.27 (1H, m), 7.08 (1H, d, J=8.3 Hz), 6.31 (1H, dd, J=8.1, 2.2 Hz), 5.59 (1H, d, J=2.4 Hz), 3.69-3.81 (6H, m), 2.89-3.03 (4H, m), 2.37 (3H, s), 1.51 (3H, s), 1.46 (3H, s). Mass Spectrum (ESI) m/e=469 (M+1).

Example 2

4-(3,3-Dimethyl-6-(4-morpholinyl)-2,3-dihydro-1H-indol-1-yl)-5-fluoro-3-methyl-2-(2-pyridinyl)quinoline

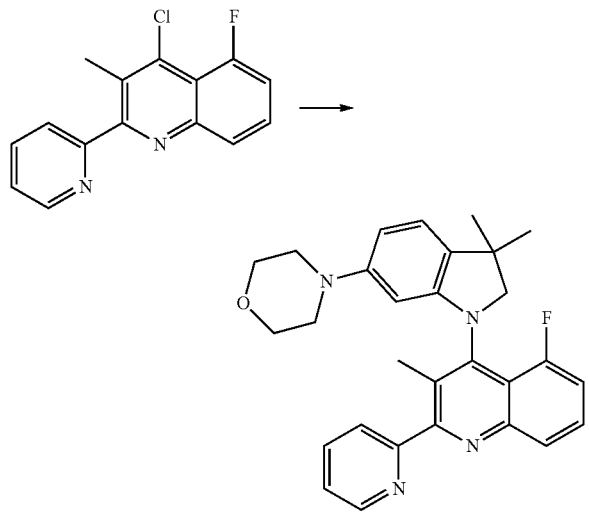

Prepared according to procedure M using 3,3-dimethyl-6-morpholinoindoline (348 mg, 1496 µmol), 4-chloro-5-fluoro-3-methyl-2-(pyridin-2-yl)quinoline (340 mg, 1247 µmol) in DMF (12 mL), and sodium hydride (72 mg, 2992 µmol) and heating at 130° C. overnight. After purification 4-(3,3-dimethyl-6-(4-morpholinyl)-2,3-dihydro-1H-indol-1-yl)-5-fluoro-3-methyl-2-(2-pyridinyl)quinoline was obtained as a yellow film. 1H NMR (400 MHz, chloroform-d) δ ppm 8.76 (1H, dd, J=3.5, 1.2 Hz), 8.02 (1H, d, J=8.2 Hz), 7.83-7.96 (2H, m), 7.60 (1H, td, J=8.1, 5.3 Hz), 7.40 (1H, ddd, J=7.0, 5.1, 2.0 Hz), 7.08-7.17 (1H, m), 7.04 (1H, d, J=8.2 Hz), 6.26 (1H, dd, J=8.0, 2.2 Hz), 5.50 (1H, d, J=2.3 Hz), 3.76-3.85 (1H, m), 3.60-3.76 (5H, m), 2.86-3.02 (4H, m), 2.42 (3H, s), 1.50 (3H, s), 1.44 (3H, s). Mass Spectrum (ESI) m/e=469 (M+1).

Example 3

1-(7-fluoro-3-methyl-2-(2-pyridinyl)-4-quinolinyl)-6-(4-morpholinyl)-1,2,2',3',5',6'-hexahydrospiro[indole-3,4'-pyran]

Dimethyl 2-(4-bromo-2-nitrophenyl)malonate

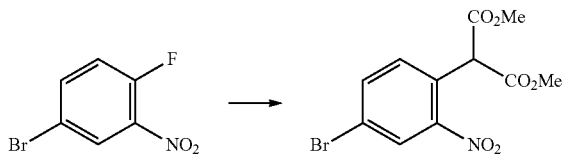 [SMILES: O=[N+]([O-])c1cc(Br)ccc1F ; COC(=O)C(C(=O)OC)c1ccc(Br)cc1[N+](=O)[O-]]

Prepared according to procedure G using potassium carbonate (94.23 g, 681.8 mmol), dimethyl malonate (39.1 mL, 340.9 mmol) and 4-bromo-1-fluoro-2-nitrobenzene (28 mL, 227.27 mmol) in DMF (227 mL). After pouring over 200 mL of 2N aqueous HCl the precipitate was collected by filtration and washed with water (4 L) to give dimethyl 2-(4-bromo-2-nitrophenyl)malonate. Mass Spectrum (ESI) m/e=332 [(M+1) ($^{79}$Br)] and 334 [(M+1) ($^{81}$Br)].

Methyl 2-(4-bromo-2-nitrophenyl)acetate

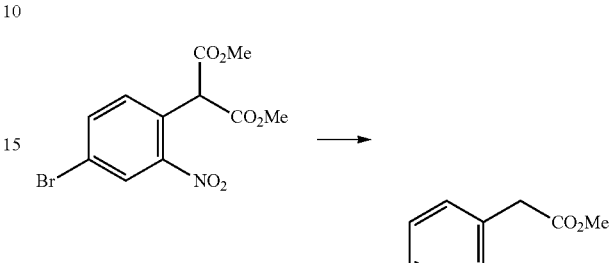

Prepared according to procedure H using dimethyl 2-(4-bromo-2-nitrophenyl)-malonate in DMSO (40 mL), LiCl (1.16 g, 27.4 mmol) and water (0.25 mL, 13.88 mmol) and heating at 100° C. for 15 h. After purification methyl 2-(4-bromo-2-nitrophenyl)acetate was obtained as an orange oil. Mass Spectrum (ESI) m/e=274 [(M+1) ($^{79}$Br)] and 276 [(M+1) ($^{81}$Br)].

Methyl 4-(4-bromo-2-nitrophenyl)tetrahydro-2H-pyran-4-carboxylate

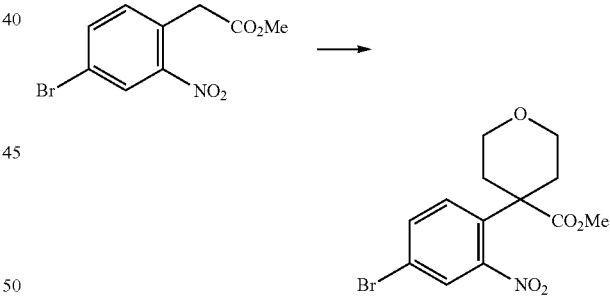

Sodium hydride (0.32 g, 8.03 mmol, 60% dispersion in oil) was added in portions at rt to a stirred solution of methyl 2-(4-bromo-2-nitrophenyl)acetate (1 g, 3.65 mmol) in DMSO (15 mL). After the mixture was stirred at rt for 30 min, sodium iodide (0.055 g, 0.365 mmol) and bis(2-bromoethyl) ether (1.27 g, 5.47 mmol) were added. The resultant mixture was stirred at 40° C. After 19 h, the mixture was poured into brine with ice (50 mL) and extracted with EtOAc (3×50 mL). The combined extracts were washed with brine (3×80 mL), dried over Na$_2$SO$_4$, filtered, and evaporated in vacuo. The residue was purified by column chromatography (0 to 50% gradient of EtOAc in n-hexane) to give methyl 4-(4-bromo2-nitrophenyl)tetrahydro-2H-pyran-4-carboxylate as an orange syrup. Mass Spectrum (ESI) m/e=344 [(M+1) ($^{79}$Br)] and 346 [(M+1) ($^{81}$Br)]. -

6-Bromo-2',3',5',6'-tetrahydrospiro[indoline-3,4'-pyran]-2-one

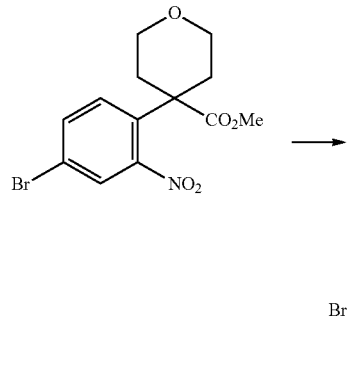

Prepared according to procedure J using methyl 4-(4-bromo-2-nitrophenyl)tetrahydro-2H-pyran-4-carboxylate (6.67 g, 19.4 mmol), AcOH (97 mL) and Fe powder (5.42 g, 96.97 mmol) and heating the mixture at 100° C. for 2 h. After purification 6-bromo-2',3',5',6'-tetrahydrospiro[indoline-3,4'-pyran]-2-one was obtained as an orange solid. Mass Spectrum (ESI) m/e=282 [(M+1) ($^{79}$Br)] and 284 [(M+1) ($^{81}$Br)].

6-Bromo-2',3',5',6'-tetrahydrospiro[indoline-3,4'-pyran]

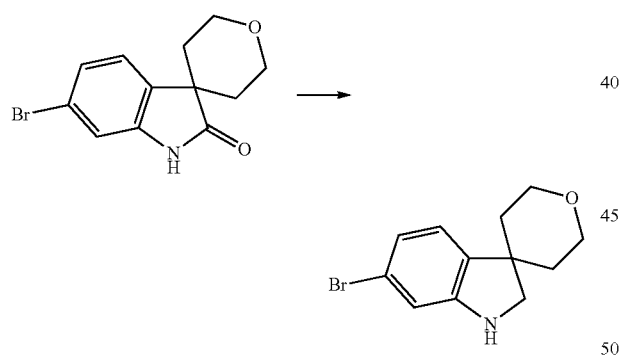

A heterogeneous mixture of 6-bromo-2',3',5',6'-tetrahydrospiro[indoline-3,4'-pyran]-2-one (3.5 g, 12.4 mmol) in toluene (25 mL) was stirred at 80° C. To the heated mixture was added a solution of Red-Al (65% in toluene, 11.6 mL, 37.2 mmol) and the mixture was stirred at 80° C. for 50 min. After this time the mixture was cooled to 0° C. and quenched with a 2 N solution of aqueous NaOH (31 mL, 62 mmol). The mixture was extracted with EtOAc (2×100 mL). The combined extracts were washed with brine (3×100 mL), dried over Na$_2$SO$_4$, filtered, and evaporated in vacuo. The resulting residue was purified by column chromatography (0 to 100% gradient of DCM-MeOH—NH$_4$OH (89:9:1) in DCM) to give 6-bromo-2',3',5',6'-tetrahydrospiro[indoline-3,4'-pyran] as a yellow solid. Mass Spectrum (ESI) m/e 268 [(M+1) ($^{79}$Br)] and 270 [(M+1) ($^{81}$Br)].

6-Bromo-1-(7-fluoro-3-methyl-2-(2-pyridinyl)-4-quinolinyl)-1,2,2',3',5',6'-hexahydrospiro[indole-3,4'-pyran]

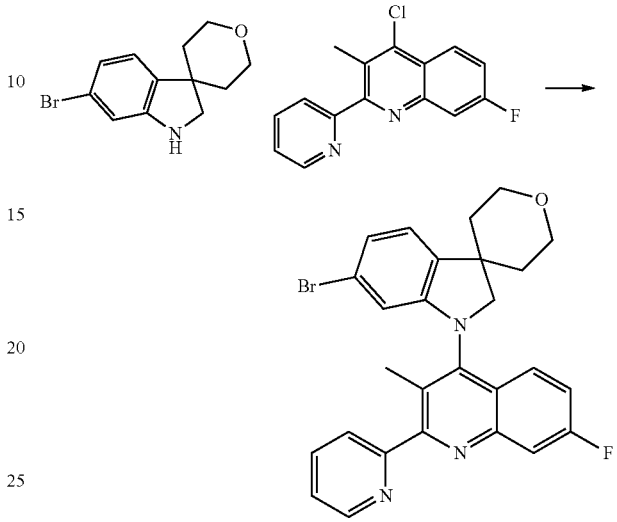

Prepared according to procedure M using 6-bromo-2',3',5',6'-tetrahydrospiro-[indoline-3,4'-pyran] (98 mg, 367 μmol), 4-chloro-7-fluoro-3-methyl-2-(pyridin-2-yl)quinoline (100 mg, 367 μmol) in DMF (4.5 mL) and sodium hydride (18 mg, 0.73 mmol) and heating the reaction mixture at 130° C. for 8 h. After purification 6-bromo-1-(7-fluoro-3-methyl-2-(pyridin-2-yl)quinolin-4-yl)-2',3',5',6'-tetrahydrospiro[indoline-3,4'-pyran] was obtained as a yellow film. 1H NMR (400 MHz, chloroform-d) δ ppm 8.74 (1H, d, J=5.1 Hz), 7.89-7.98 (2H, m), 7.85 (1H, dd, J=10.0, 2.5 Hz), 7.75 (1H, dd, J=9.2, 6.1 Hz), 7.41 (1H, ddd, J=6.7, 4.5, 2.5 Hz), 7.28-7.33 (1H, m), 7.07 (1H, d, J=7.8 Hz), 6.89 (1H, dd, J=7.8, 2.0 Hz), 6.11 (1H, d, J=2.0 Hz), 3.93-4.10 (4H, m), 3.45-3.60 (2H, m), 2.38 (3H, s), 2.08-2.25 (2H, m), 1.91 (1H, dd, J=13.9, 2.5 Hz), 1.81 (1H, dd, J=13.7, 2.3 Hz). Mass Spectrum (ESI) m/e 504 [(M+1) ($^{79}$Br)] and 506 [(M+1) ($^{81}$Br)].

1-(7-Fluoro-3-methyl-2-(2-pyridinyl)-4-quinolinyl)-6-(4-morpholinyl)-1,2,2',3',5',6'-hexahydrospiro[indole-3,4'-pyran]

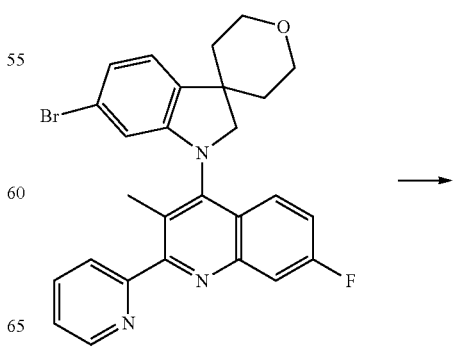

-continued

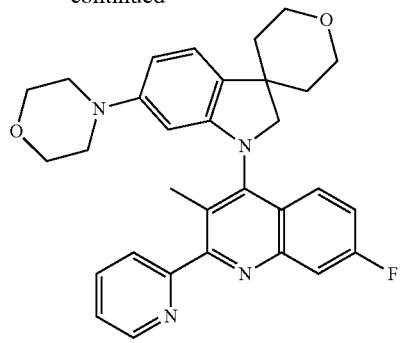

A suspension of 6-bromo-1-(7-fluoro-3-methyl-2-(pyridin-2-yl)quinolin-4-yl)-2',3',5',6'-tetrahydrospiro[indoline-3,4'-pyran] (100 mg, 0.198 mmol), morpholine and DMSO (2.5 mL) was degassed with argon for 15 min in a Schlenck tube. To the mixture was added copper (I) iodide (8 mg, 40 µmol), 1-(−)-proline (9 mg, 79 mmol) and potassium carbonate (82 mg, 595 µmol) and the mixture was heated at 120° C. overnight. After this time the reaction was cooled to rt and diluted with DCM (100 mL) and water (40 mL). The separated organic layer was dried over MgSO$_4$, filtered and evaporated in vacuo. Column chromatography (hexane:EtOAc, 1:0 to 0:1) gave the desired product as a yellow oil. The product was further purified by reverse phase HPLC to give 1-(7-fluoro-3-methyl-2-(2-pyridinyl)-4-quinolinyl)-6-(4-morpholinyl)-1,2,2',3',5',6'-hexahydrospiro[indole-3,4'-pyran]. 1H NMR (400 MHz, chloroform-d) δ ppm 8.76 (1H, dd, J=3.7, 1.0 Hz), 7.75-8.00 (4H, m), 7.41 (1H, ddd, J=7.1, 5.0, 1.6 Hz), 7.21-7.27 (1H, m), 7.13 (1H, d, J=8.2 Hz), 6.35 (1H, dd, J=8.2, 2.3 Hz), 5.61 (1H, d, J=2.3 Hz), 3.96-4.09 (3H, m), 3.89-3.96 (1H, m), 3.70-3.79 (4H, m), 3.49-3.60 (2H, m, J=12.2, 12.2, 2.9, 2.7 Hz), 2.91-3.04 (4H, m), 2.38 (3H, s), 2.09-2.22 (2H, m), 1.76-1.93 (2H, m). Mass Spectrum (ESI) m/e=511 (M+1).

Example 4

4-(3,3-dimethyl-6-(4-morpholinyl)-2,3-dihydro-1H-indol-1-yl)-7-fluoro-3-methyl-2-(3-pyridinyl)quinoline 4-Chloro-7-fluoro-3-methyl-2-(pyridin-3-yl)quinoline and 4-chloro-5-fluoro-3-methyl-2-(pyridin-3-yl)quinoline

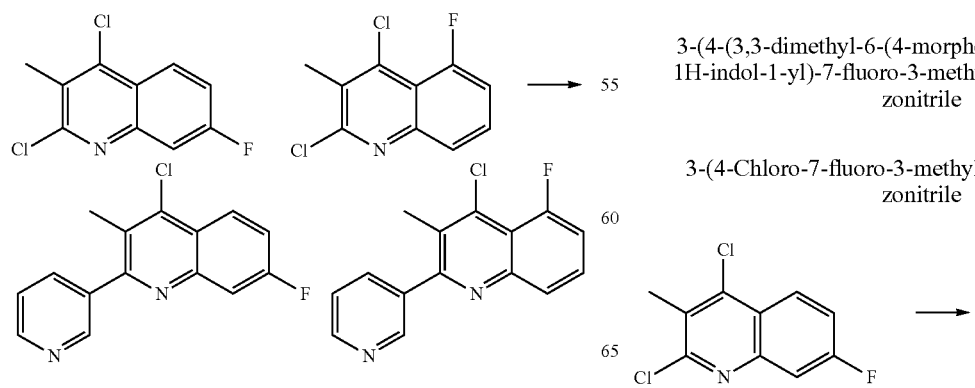

Prepared according to general procedure E using 2,4-dichloro-7-fluoro-3-methylquinoline and 2,4-dichloro-5-fluoro-3-methyl quinoline (1.0 g, 4.35 mmol), Pd(PPh$_3$)$_4$ (251 mg, 0.22 mmol) in toluene (15 mL) to give a separable mixture of 4-chloro-7-fluoro-3-methyl-2-(pyridin-3-yl)quinoline and 4-chloro-5-fluoro-3-methyl-2-(pyridin-3-yl)quinoline.

4-(3,3-Dimethyl-6-(4-morpholinyl)-2,3-dihydro-1H-indol-1-yl)-7-fluoro-3-methyl-2-(3-pyridinyl)quinoline

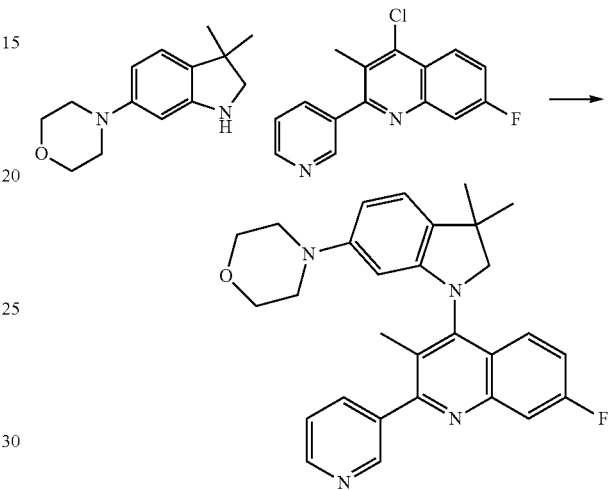

Prepared according to procedure M using 4-chloro-7-fluoro-3-methyl-2-(pyridin-3-yl)quinoline (250 mg, 0.92 mmol), 4-(3,3-dimethylindolin-6-yl)morpholine (213 mg, 0.92 mmol) and sodium hydride (44 mg, 1.833 mmol) in DMF (2.0 mL) and heating the reaction at 120° C. for 3 h. After purification 4-(3,3-dimethyl-6-(4-morpholinyl)-2,3-dihydro-1H-indol-1-yl)-7-fluoro-3-methyl-2-(3-pyridinyl)-quinoline was obtained as a yellow film. 1H NMR (400 MHz, chloroform-d) δ ppm 8.90 (1H, br. s.), 8.66-8.81 (1H, m), 8.00 (1H, dt, J=7.8, 2.0 Hz), 7.89 (1H, dd, J=9.4, 5.9 Hz), 7.81 (1H, dd, J=10.0, 2.5 Hz), 7.48 (1H, dd, J=7.8, 4.7 Hz), 7.23-7.30 (1H, m), 7.09 (1H, d, J=8.2 Hz), 6.34 (1H, dd, J=8.2, 2.3 Hz), 5.61 (1H, d, J=2.3 Hz), 3.68-3.81 (6H, m), 2.90-3.02 (4H, m), 2.30 (3H, s), 1.52 (3H, s), 1.47 (3H, s). Mass Spectrum (ESI) m/e=469 (M+1).

Example 5

3-(4-(3,3-dimethyl-6-(4-morpholinyl)-2,3-dihydro-1H-indol-1-yl)-7-fluoro-3-methyl-2-quinolinyl)benzonitrile 3-(4-Chloro-7-fluoro-3-methylquinolin-2-yl)benzonitrile

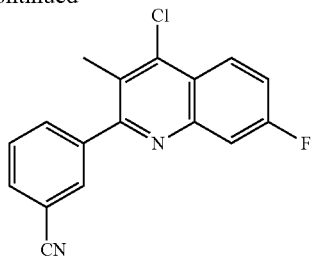

Prepared according to procedure F using 2,4-dichloro-7-fluoro-3-methylquinoline (500 mg, 2.17 mmol), 3-cyanophenylboronic acid (319 mg, 2.17 mmol), Pd(PPh₃)₄ (251 mg, 0.22 mmol) in toluene:water (10 mL:4 mL) and heating at reflux overnight. After purification, 3-(4-chloro-7-fluoro-3-methylquinolin-2-yl)benzonitrile was obtained as a white solid.

3-(4-(3,3-Dimethyl-6-(4-morpholinyl)-2,3-dihydro-1H-indol-1-yl)-7-fluoro-3-methyl-2-quinolinyl)benzonitrile

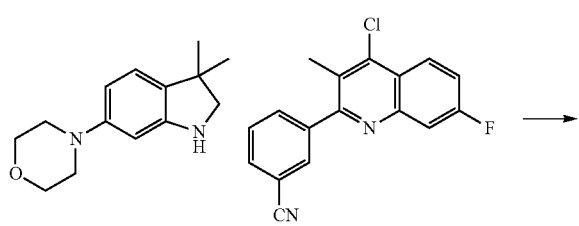

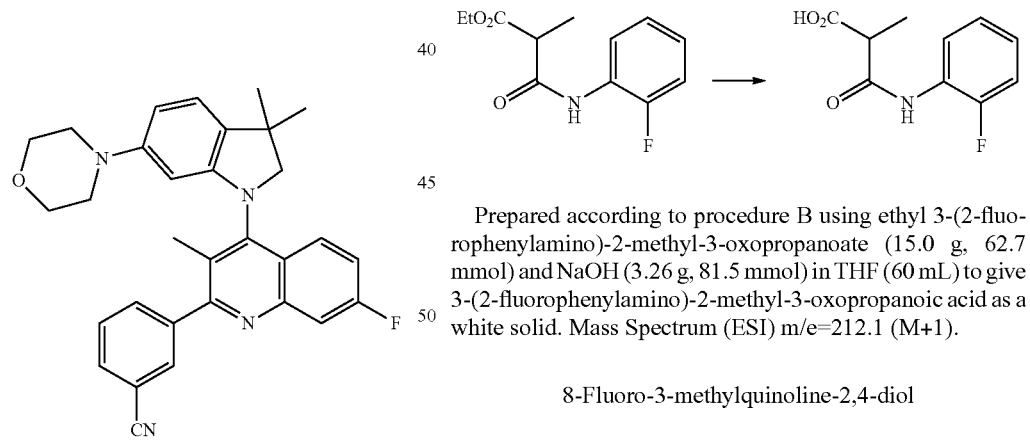

Prepared according to procedure M using 3-(4-chloro-7-fluoro-3-methylquinolin-2-yl)benzonitrile (220 mg, 0.74 mmol), 3,3-dimethyl-6-morpholinoindoline (189 mg, 0.816 mmol), sodium hydride (36 mg, 1.48 mmol) in DMF (2.0 mL) and heating at 130° C. overnight. After purification 3-(4-(3,3-dimethyl-6-(4-morpholinyl)-2,3-dihydro-1H-indol-1-yl)-7-fluoro-3-methyl-2-quinolinyl)benzonitrile was obtained as a yellow film. 1H NMR (400 MHz, chloroform-d) δ ppm 7.94-7.98 (1H, m), 7.85-7.91 (2H, m), 7.75-7.82 (2H, m), 7.64 (1H, t, J=7.8 Hz), 7.23-7.31 (1H, m), 7.10 (1H, d, J=8.2 Hz), 6.35 (1H, dd, J=8.2, 2.3 Hz), 5.55-5.63 (1H, m), 3.68-3.79 (6H, m), 2.91-3.04 (4H, m), 2.28 (3H, s), 1.50-1.54 (3H, m), 1.47 (3H, s). Mass Spectrum (ESI) m/e=493 (M+1).

Example 6

4-(3,3-Dimethyl-6-(4-morpholinyl)-2,3-dihydro-1H-indol-1-yl)-8-fluoro-3-methyl-2-(2-pyridinyl)quinoline Ethyl 3-(2-fluorophenylamino)-2-methyl-3-oxopropanoate

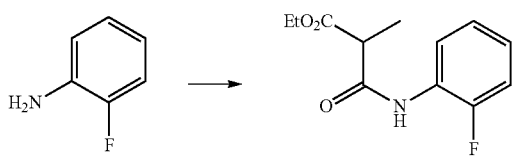 [SMILES: Nc1ccccc1F ; CCOC(=O)C(C)C(=O)Nc1ccccc1F]

Prepared according to procedure A using 2-fluoroaniline (17 mL, 180 mmol), pyridine (29 mL, 360 mmol) and diethyl methylmalonate (46 mL, 270 mmol). The crude was purified by column chromatography on silica (using a gradient of hexane:EtOAc, 1:0 to 4:1 as eluent) to give ethyl 3-(2-fluorophenylamino)-2-methyl-3-oxopropanoate as a light brown solid. Mass Spectrum (ESI) m/e=239.9 (M+1).

3-(2-Fluorophenylamino)-2-methyl-3-oxopropanoic acid

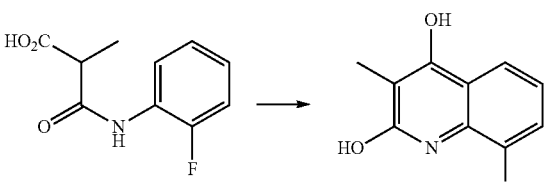

Prepared according to procedure B using ethyl 3-(2-fluorophenylamino)-2-methyl-3-oxopropanoate (15.0 g, 62.7 mmol) and NaOH (3.26 g, 81.5 mmol) in THF (60 mL) to give 3-(2-fluorophenylamino)-2-methyl-3-oxopropanoic acid as a white solid. Mass Spectrum (ESI) m/e=212.1 (M+1).

8-Fluoro-3-methylquinoline-2,4-diol

Prepared according to procedure C using 3-(2-fluorophenylamino)-2-methyl-3-oxopropanoic acid (11 g, 52 mmol)

and PPA (80 mL) to give 8-fluoro-3-methylquinoline-2,4-diol as a white solid. Mass Spectrum (ESI) m/e=193.9 (M+1).

2,4-Dichloro-8-fluoro-3-methylquinoline

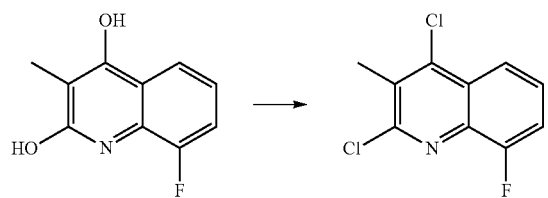

Prepared according to procedure D using 8-fluoro-3-methylquinoline-2,4-diol (2.8 g, 14 mmol) and phosphorous oxychloride (14 mL, 145 mmol) to give 2,4-dichloro-8-fluoro-3-methylquinoline as a white solid. Mass Spectrum (ESI) m/e=229.9 (M+1).

4-Chloro-8-fluoro-3-methyl-2-(pyridin-2-yl)quinoline

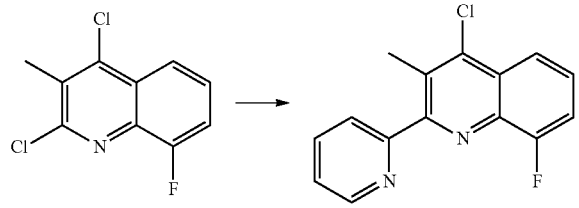 [SMILES: Cc1c(Cl)nc2c(F)cccc2c1Cl ; Cc1c(-c2ccccn2)nc2c(F)cccc2c1Cl]

Prepared according to procedure E using 2,4-dichloro-8-fluoro-3-methylquinoline (1.0 g, 4.35 mmol), Pd(PPh$_3$)$_4$ (251 mg, 0.22 mmol) and 2-tributylstannylpyridine (1.6 mL, 4.35 mmol) in toluene (15 mL) to give 4-chloro-8-fluoro-3-methyl-2-(pyridin-2-yl)quinoline as a white solid.

4-(3,3-Dimethyl-6-(4-morpholinyl)-2,3-dihydro-1H-indol-1-yl)-8-fluoro-3-methyl-2-(2-pyridinyl)quinoline

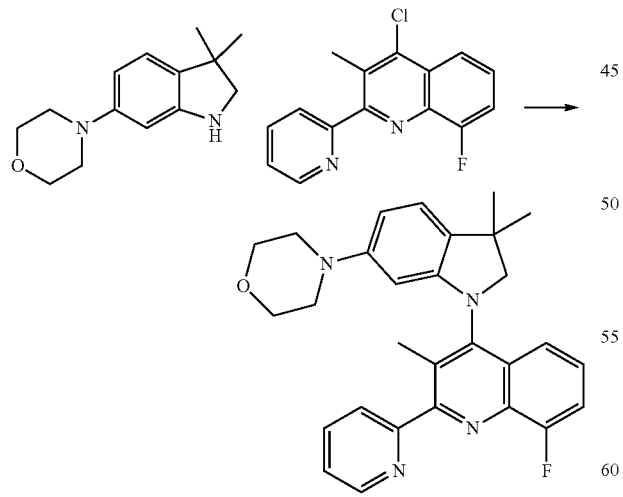

Prepared according to procedure M using 4-chloro-8-fluoro-3-methyl-2-(pyridin-2-yl)quinoline (235 mg, 0.86 mmol), 4-(3,3-dimethylindolin-6-yl)morpholine (200 mg, 0.86 mmol), sodium hydride (41 mg, 1.72 mmol) in DMF (2.0 mL) and heating at 130° C. for 4 h. After purification 4-(3,3-dimethyl-6-(4-morpholinyl)-2,3-dihydro-1H-indol-1-yl)-8-fluoro-3-methyl-2-(2-pyridinyl)quinoline was obtained as a yellow film. 1H NMR (400 MHz, chloroform-d) δ ppm 8.64-8.79 (1H, m), 7.87-7.98 (2H, m), 7.60-7.65 (1H, m), 7.32-7.42 (3H, m), 7.08 (1H, d, J=7.8 Hz), 6.31 (1H, dd, J=8.0, 2.2 Hz), 5.59 (1H, d, J=2.3 Hz), 3.63-3.83 (6H, m), 2.86-3.05 (4H, m), 2.43 (3H, s), 1.52 (3H, s), 1.47 (3H, s). Mass Spectrum (ESI) m/e=469 (M+1).

Example 7

1-(7-fluoro-3-methyl-2-(4-pyridinyl)-4-quinolinyl)-6-(4-morpholinyl)-1,2,2',3',5',6'-hexahydrospiro[indole-3,4'-pyran]

1-(6-Bromo-2',3',5',6'-tetrahydrospiro[indoline-3,4'-pyran]-1-yl)ethanone

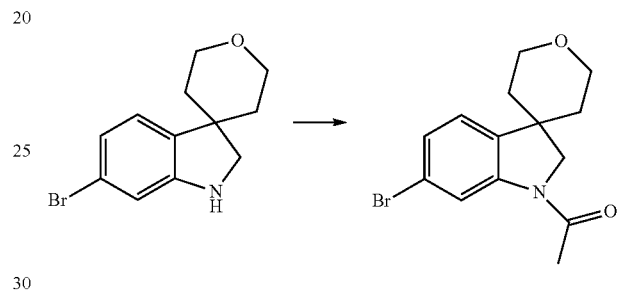

6-Bromo-2',3',5',6'-tetrahydrospiro[indoline-3,4'-pyran] (2.53 g, 9.44 mmol) was dissolved in pyridine (8.39 mL, 104 mmol) and acetic anhydride (1.34 mL, 14.2 mmol) was added followed by DMAP (0.0576 g, 0.472 mmol). The reaction was heated to 85° C. for 90 min. After this time the reaction was concentrated in vacuo and the resulting oil was partitioned between EtOAc and 0.5N HCl. The organic layer was dried over Na$_2$SO$_4$, filtered and concentrated in vacuo. The crude residue was purified by column chromatography to give 1-(6-bromo-2',3',5',6'-tetrahydrospiro[indoline-3,4'-pyran]-1-yl)ethanone.

1-(6-Morpholino-2',3',5',6'-tetrahydrospiro[indoline-3,4'-pyran]-1-yl)ethanone

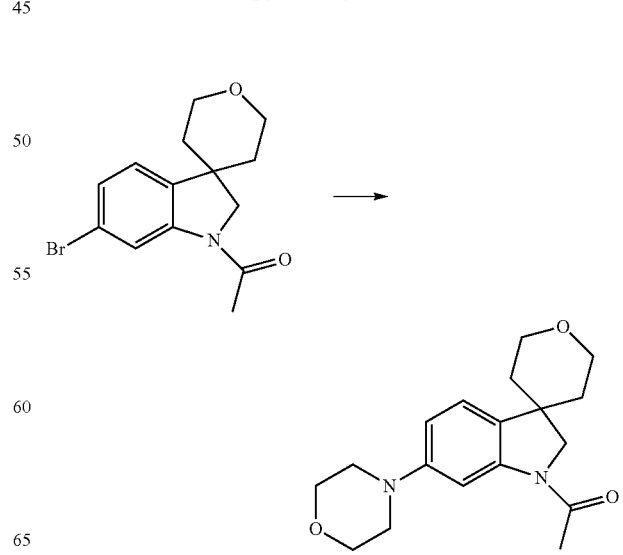

1-(6-Bromo-2',3',5',6'-tetrahydrospiro[indoline-3,4'-pyran]-1-yl)ethanone (2.56 g, 8.25 mmol) was combined with morpholine (1.08 mL, 12.4 mmol), dicyclohexyl-(2',4',6'-triisopropylbiphenyl-4-yl)phosphine (0.118 g, 0.248 mmol), Pd$_2$dba$_3$ (0.256 g, 0.248 mmol), and cesium carbonate (4.03 g, 12.4 mmol) in tert-butanol (30.0 mL, 314 mmol). The reaction was purged with N$_2$, and heated at 110° C. for 4 h. After this time the reaction was diluted with EtOAc and filtered through a Celite pad. The filtrate was concentrated in vacuo. The crude material was triturated with EtOAc/hexane to give 1-(6-morpholino-2',3',5',6'-tetrahydrospiro-[indoline-3,4'-pyran]-1-yl)ethanone. Mass Spectrum (ESI) m/e=317 (M+1).

6-Morpholino-2',3',5',6'-tetrahydrospiro[indoline-3,4'-pyran]

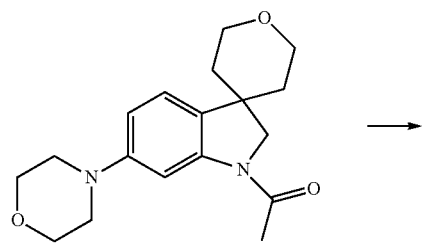

A mixture of 1-(6-morpholino-2',3',5',6'-tetrahydrospiro[indoline-3,4'-pyran]-1-yl)ethanone (1.35 g, 4.27 mmol) in acetonitrile (30 mL) was treated with 2.0M aqueous HCl (12 mL). The reaction was stirred at rt overnight and then it was heated to 120° C. for 36 h. After this time the reaction was cooled to rt and quenched with aqueous NaOH. The mixture was partitioned between EtOAc (200 mL) and water (80 mL). The separated organic layer was washed with NaHCO$_3$ (saturated aqueous solution) and then it was dried over MgSO$_4$, filtered and evaporated in vacuo to give 6-morpholino-2',3',5',6'-tetrahydrospiro[indoline-3,4'-pyran] as a pale solid. Mass Spectrum (ESI) m/e=275 (M+1).

4-Chloro-7-fluoro-3-methyl-2-(pyridin-4-yl)quinoline

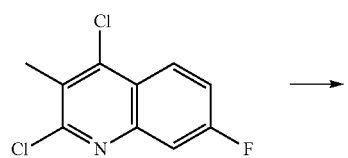

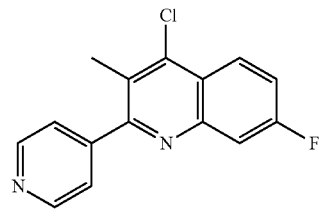

Prepared according to procedure E using 2,4-dichloro-7-fluoro-3-methylquinoline (500 mg, 2.17 mmol), palladium tetrakistriphenylphosphine (0.251 mg, 0.22 mmol) and 4-tributylstannylpyridine (800 mg, 4.35 mmol) in toluene (15 mL). After purification 4-chloro-7-fluoro-3-methyl-2-(pyridin-4-yl)quinoline was obtained as a white solid.

1-(7-Fluoro-3-methyl-2-(4-pyridinyl)-4-quinolinyl)-6-(4-morpholinyl)-1,2,2',3',5',6'-hexahydrospiro[indole-3,4'-pyran]

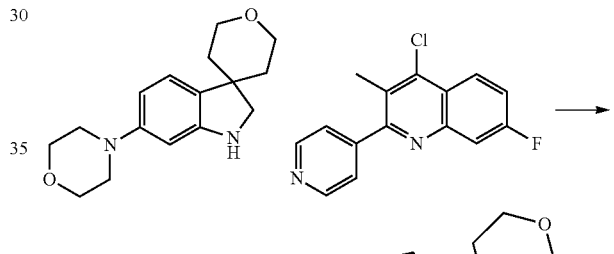

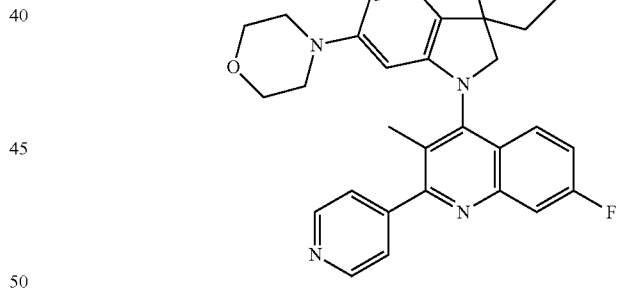

Prepare according to procedure L using 4-chloro-7-fluoro-3-methyl-2-(pyridin-4-yl)quinoline (60 mg, 220 µmol), 6-morpholino-2',3',5',6'-tetrahydrospiro[indoline-3,4'-pyran] (60 mg, 220 µmol) and a 4.0M solution of HCl in 1,4-dioxane (0.05 mL, 0.22 mmol). After purification 1-(7-fluoro-3-methyl-2-(4-pyridinyl)-4-quinolinyl)-6-(4-morpholinyl)-1,2,2',3',5',6'-hexahydrospiro[indole-3,4'-pyran] was obtained as a yellow film. 1H NMR (500 MHz, chloroform-d) δ ppm 8.80 (2H, dd, J=4.3, 1.8 Hz), 7.74-7.92 (2H, m), 7.49-7.62 (2H, m), 7.25-7.32 (1H, m), 7.15 (1H, d, J=8.1 Hz), 6.36 (1H, dd, J=8.2, 2.3 Hz), 5.60 (1H, d, J=2.2 Hz), 4.01-4.08 (2H, m), 3.95 (2H, s), 3.74 (4H, t, J=5.1 Hz), 3.49-3.63 (2H, m), 2.90-3.03 (4H, m), 2.28 (3H, s), 2.10-2.22 (2H, m, J=14.2, 14.2, 12.0, 4.6 Hz), 1.85-1.93 (1H, m), 1.74-1.82 (1H, m). Mass Spectrum (ESI) m/e=511 (M+1).

Example 8

1-(7-Fluoro-3-methyl-2-(3-pyridinyl)-4-quinolinyl)-6-(4-morpholinyl)-1,2,2',3',5',6'-hexahydrospiro[indole-3,4'-pyran]

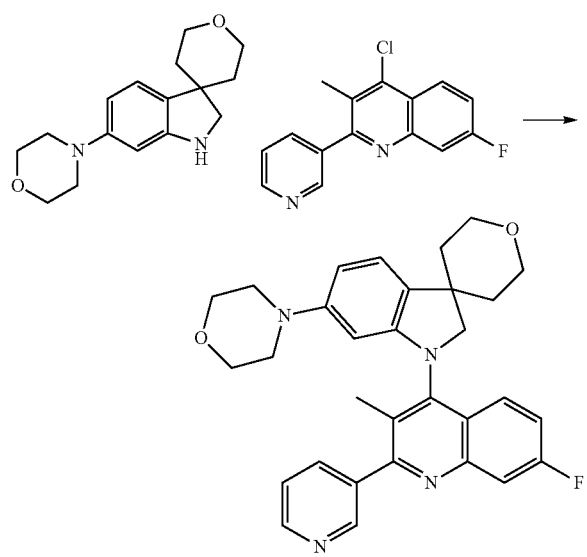

Prepare according to procedure L using 4-chloro-7-fluoro-3-methyl-2-(pyridin-3-yl)quinoline (75 mg, 0.27 μmol), 6-morpholino-2',3',5',6'-tetrahydrospiro-[indoline-3,4'-pyran] (75 mg, 0.27 mmol) and a 4.0M solution of HCl in 1,4-dioxane (0.014 mL, 0.055 mmol). After purification 1-(7-fluoro-3-methyl-2-(3-pyridinyl)-4-quinolinyl)-6-(4-morpholinyl)-1,2,2',3',5',6'-hexahydrospiro[indole-3,4'-pyran] was obtained as a yellow film. 1H NMR (400 MHz, chloroform-d) δ ppm 8.91 (1H, d, J=2.3 Hz), 8.73 (1H, dd, J=4.9, 1.8 Hz), 8.01 (1H, dt, J=7.8, 2.2 Hz), 7.76-7.89 (2H, m), 7.48 (1H, dd, J=8.0, 4.9 Hz), 7.27 (1H, dd, J=17.6, 2.7 Hz), 7.14 (1H, d, J=8.2 Hz), 6.36 (1H, dd, J=8.2, 2.3 Hz), 5.61 (1H, d, J=2.3 Hz), 4.00-4.09 (2H, m), 3.91-3.99 (2H, m), 3.70-3.79 (4H, m), 3.50-3.61 (2H, m, J=12.0, 12.0, 2.5, 2.3 Hz), 2.90-3.02 (4H, m), 2.30 (3H, s), 2.10-2.24 (2H, m), 1.89 (1H, dd, J=13.7, 2.3 Hz), 1.75-1.82 (1H, m). Mass Spectrum (ESI) m/e=511 (M+1).

Example 9

4-(3,3-Dimethyl-6-(4-morpholinyl)-2,3-dihydro-1H-pyrrolo[3,2-b]pyridin-1-yl)-7-fluoro-3-methyl-2-(2-pyridinyl)quinoline Dimethyl 2-(5-bromo-3-nitropyridin-2-yl)malonate

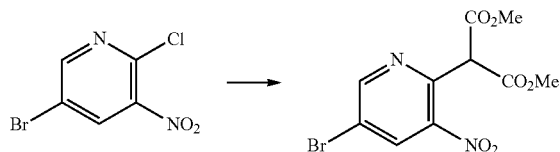

Prepared according to procedure G using 5-bromo-2-chloro-3-nitropyridine (25 g, 105 mmol) and potassium carbonate (44 g, 316 mmol), dimethyl malonate (18 mL, 158 mmol) in DMF (105 mL, 105 mmol). After purification dimethyl 2-(5-bromo-3-nitropyridin-2-yl)malonate was obtained as a dark liquid. Mass Spectrum (ESI) m/e=333 [(M+1) ($^{79}$Br)] and 335 [(M+1) ($^{81}$Br)].

Methyl 2-(5-bromo-3-nitropyridin-2-yl)acetate

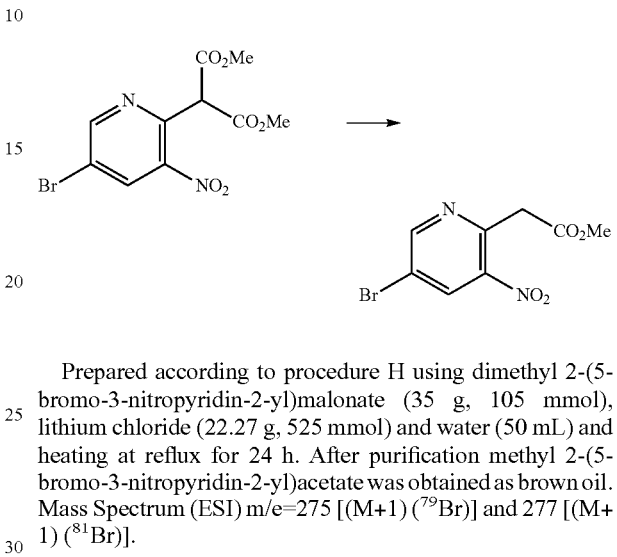

Prepared according to procedure H using dimethyl 2-(5-bromo-3-nitropyridin-2-yl)malonate (35 g, 105 mmol), lithium chloride (22.27 g, 525 mmol) and water (50 mL) and heating at reflux for 24 h. After purification methyl 2-(5-bromo-3-nitropyridin-2-yl)acetate was obtained as brown oil. Mass Spectrum (ESI) m/e=275 [(M+1) ($^{79}$Br)] and 277 [(M+1) ($^{81}$Br)].

Methyl 2-(5-bromo-3-nitropyridin-2-yl)-2-methylpropanoate

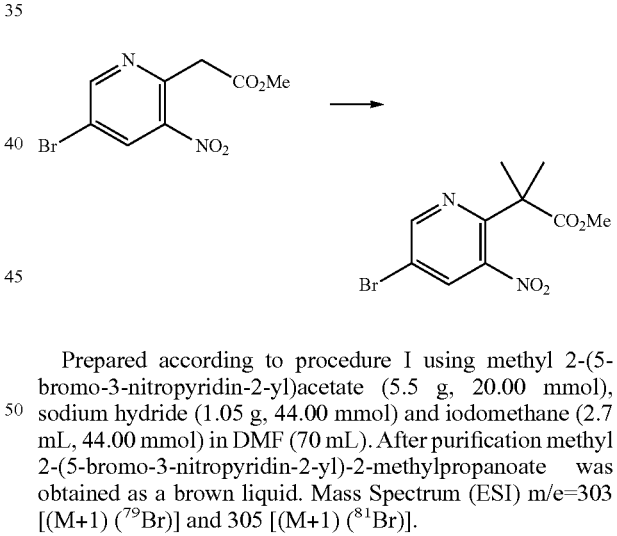

Prepared according to procedure I using methyl 2-(5-bromo-3-nitropyridin-2-yl)acetate (5.5 g, 20.00 mmol), sodium hydride (1.05 g, 44.00 mmol) and iodomethane (2.7 mL, 44.00 mmol) in DMF (70 mL). After purification methyl 2-(5-bromo-3-nitropyridin-2-yl)-2-methylpropanoate was obtained as a brown liquid. Mass Spectrum (ESI) m/e=303 [(M+1) ($^{79}$Br)] and 305 [(M+1) ($^{81}$Br)].

6-Bromo-3,3-dimethyl-1H-pyrrolo[3,2-b]pyridin-2(3H)-one

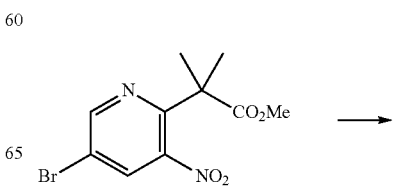

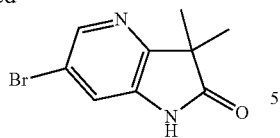

Prepared according to procedure J using methyl 2-(5-bromo-3-nitropyridin-2-yl)-2-methylpropanoate (0.780 g, 2.57 mmol), acetic acid (14.73 mL, 257 mmol) and iron powder (0.719 g, 12.87 mmol) and heating at 100° C. for 2 h. After purification 6-bromo-3,3-dimethyl-1H-pyrrolo[3,2-b]pyridin-2(3H)-one was obtained as a white solid.

6-Bromo-3,3-dimethyl-2,3-dihydro-1H-pyrrolo[3,2-b]pyridine

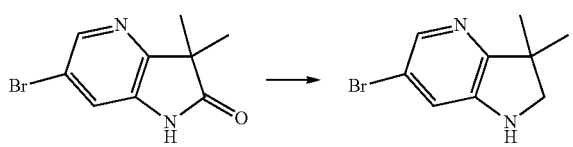

Prepared according to procedure K using 6-bromo-3,3-dimethyl-1H-pyrrolo[3,2-b]pyridin-2(3H)-one (300 mg, 1.244 mmol), sodium bis(2-methoxyethoxy)-aluminium hydride (1.131 mL, 3.73 mmol) in toluene (3 mL). After purification 6-bromo-3,3-dimethyl-2,3-dihydro-1H-pyrrolo[3,2-b]pyridine was obtained as a white solid.

4-(6-Bromo-3,3-dimethyl-2,3-dihydro-1H-pyrrolo[3,2-b]pyridin-1-yl)-7-fluoro-3-methyl-2-(pyridin-2-yl)quinoline

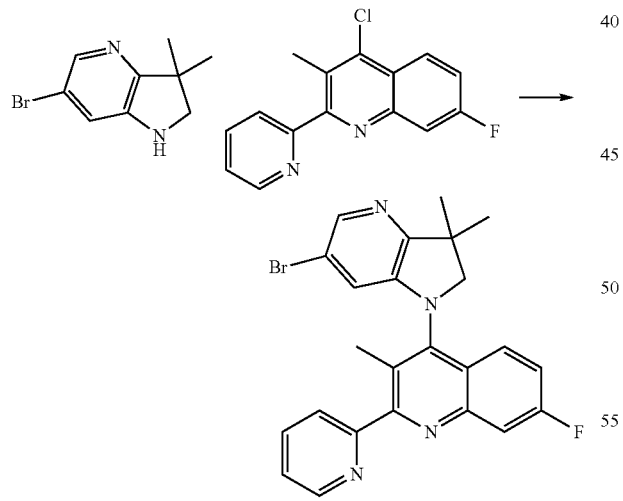

Prepared according to procedure L using 6-bromo-3,3-dimethyl-2,3-dihydro-1H-pyrrolo[3,2-b]pyridine (200 mg, 0.88 mmol), 4-chloro-7-fluoro-3-methyl-2-(pyridin-2-yl)quinoline (240 mg, 0.88 mmol) and 4.0M solution of HCl in 1,4-dioxane (0.22 mL, 0.88 mmol) in NMP (1.0 mL) and heating at 150° C. for 3 h in the microwave. After purification 4-(6-bromo-3,3-dimethyl-2,3-dihydro-1H-pyrrolo[3,2-b]pyridin-1-yl)-7-fluoro-3-methyl-2-(pyridin-2-yl)quinoline was obtained as a yellow film. Mass Spectrum (ESI) m/e=463 [(M+1) ($^{79}$Br)] and 465 [(M+1) ($^{81}$Br)].

4-(3,3-Dimethyl-6-(4-morpholinyl)-2,3-dihydro-1H-pyrrolo[3,2-b]pyridin-1-yl)-7-fluoro-3-methyl-2-(2-pyridinyl)quinoline

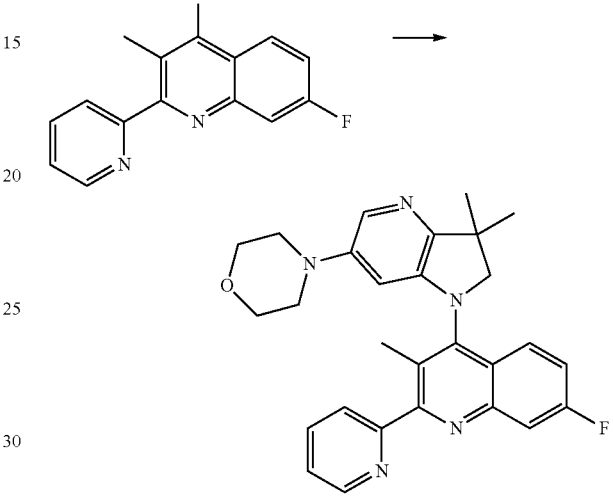

Prepared according to procedure N using 4-(6-bromo-3,3-dimethyl-2,3-dihydro-1H-pyrrolo[3,2-b]pyridin-1-yl)-7-fluoro-3-methyl-2-(pyridin-2-yl)quinoline (75 mg, 0.162 mmol), Pd$_2$dba$_3$ (3.8 mg, 0.016 mmol), XPhos (15.4 mg, 0.032 mmol), morpholine (1.6.9 mL, 0.194 mmol) and sodium tert-butoxide (31.1 mg, 0.324 mmol) in toluene (6 mL). After purification 4-(3,3-dimethyl-6-(4-morpholinyl)-2,3-dihydro-1H-pyrrolo[3,2-b]pyridin-1-yl)-7-fluoro-3-methyl-2-(2-pyridinyl)quinoline was obtained as a yellow solid. 1H NMR (400 MHz, chloroform-d) δ ppm 8.70-8.77 (1H, m), 7.75-7.96 (4H, m), 7.60 (1H, d, J=2.7 Hz), 7.41 (1H, ddd, J=7.1, 5.0, 1.6 Hz), 7.30 (1H, ddd, J=9.1, 8.1, 2.7 Hz), 5.83 (1H, d, J=2.3 Hz), 3.82 (2H, s), 3.69-3.77 (4H, m), 2.91-3.06 (4H, m), 2.38 (3H, s), 1.57-1.64 (3H, m), 1.50-1.56 (3H, m). Mass Spectrum (ESI) m/e=470 (M+1).

Example 10

4-(1-(7-Fluoro-3-methyl-2-(2-pyridinyl)-4-quinolinyl)-3,3-dimethyl-2,3-dihydro-1H-indol-6-yl)-2-pyrimidinamine 1-(6-Iodo-3,3-dimethylindolin-1-yl)ethanone

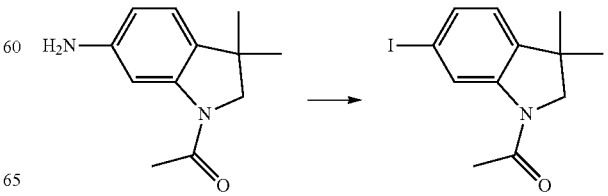

In a 500 mL three-necked round bottom flask equipped with an overhead stirrer, was combined 1-(6-amino-3,3-dimethylindolin-1-yl)ethanone (6.98 g, 34.22 mmol) with 30 mL of ice/water. The solution was cooled in an ice bath before concentrated HCl (6.8 mL, 81.60 mmol) was added. A solution of NaNO$_2$ (2.48 g, 35.93 mmol) dissolved in 30 mL of water was added drop wise over a period of 10 min. After 30 min a solution of KI (11.36 g, 68.44 mmol) dissolved in 70 mL of CHCl$_3$ was added via an addition funnel over a period of 0.5 h. Then the brownish solution was stirred at rt until gas evolution ceased. Partitioned the solution in a separation funnel, and washed the organic layer with saturated NaHCO$_3$, followed by 5% Na$_2$S$_2$O$_3$. The organics were dried over MgSO$_4$ before being concentrated under vacuum to $\frac{1}{10}^{th}$ the volume. This was purified by column chromatography on silica eluting with 20% hexane/DCM. The fractions containing the product were combined and concentrated under vacuum to give 1-(6-iodo-3,3-dimethylindolin-1-yl)ethanone as a tan colored solid. Mass Spectrum (ESI) m/e=316.0 (M+1).

6-Iodo-3,3-dimethylindoline

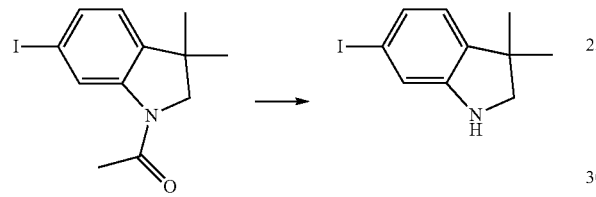

1-(6-Iodo-3,3-dimethylindolin-1-yl)ethanone (6.95 g, 22.08 mmol) was combined with MeOH and concentrated HCl (25 mL, 300 mmol). The solution was heated at a gentle reflux for 1 h before it was cooled to rt. After cooling the solution to 0° C. a white solid was filtered off to give 6-iodo-3,3-dimethylindoline hydrochloride. The HCl salt was neutralized to give 6-iodo-3,3-dimethylindoline hydrochloride. Mass Spectrum (ESI) m/e=274.0 (M+1).

7-Fluoro-4-(6-iodo-3,3-dimethylindolin-1-yl)-3-methyl-2-(pyridin-2-yl)quinoline

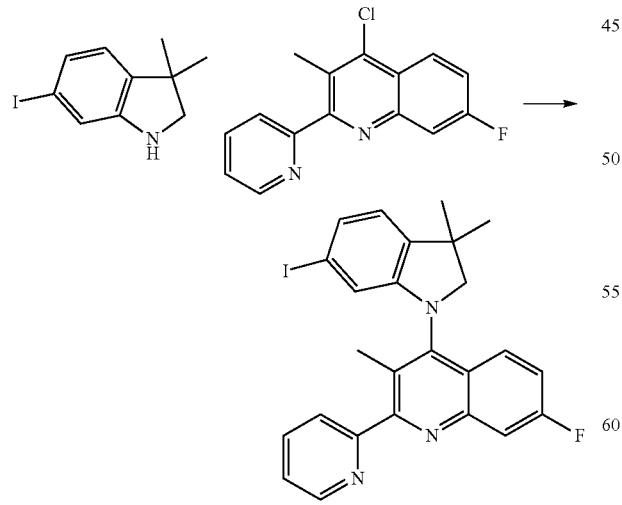

Prepared according to procedure L using 4-chloro-7-fluoro-3-methyl-2-(pyridin-2-yl)quinoline (250 mg, 0.92 mmol), 6-iodo-3,3-dimethylindoline (250 mg, 0.92 mmol) and 4.0M solution of HCl in 1,4-dioxane (0.22 mL, 0.92 mmol) in NMP (1.0 mL) and heating at 150° C. for 3 h in the microwave. After purification 7-fluoro-4-(6-iodo-3,3-dimethylindolin-1-yl)-3-methyl-2-(pyridin-2-yl)quinoline was obtained as a foam. Mass Spectrum (ESI) m/e=510 (M+1).

4-(3,3-Dimethyl-6-(4,4,5,5-tetramethyl-1,3,2-dioxaborolan-2-yl)indolin-1-yl)-7-fluoro-3-methyl-2-(pyridin-2-yl)quinoline

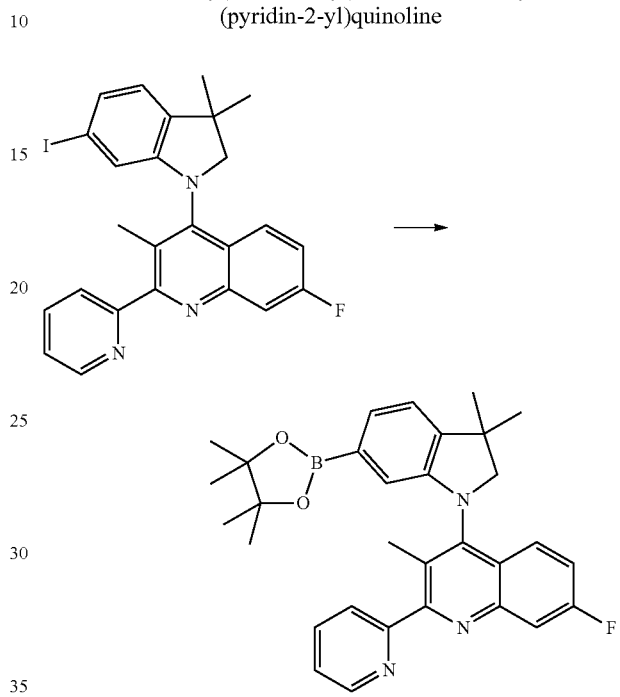

Prepared according to procedure O using 7-fluoro-4-(6-iodo-3,3-dimethylindolin-1-yl)-3-methyl-2-(pyridin-2-yl)quinoline (180 mg, 0.353 mmol), Pd(PCy$_3$)$_2$ (11.8 mg, 0.018 mmol), bis(pinacolato)diboron (99 mg, 0.389 mmol) and potassium acetate (52 mg, 0.530 mmol) in 1,4-dioxane (5229 µL, 61.1 mmol) and heating at 100° C. overnight. After purification 4-(3,3-dimethyl-6-(4,4,5,5-tetramethyl-1,3,2-dioxaborolan-2-yl)indolin-1-yl)-7-fluoro-3-methyl-2-(pyridin-2-yl)quinoline was obtained as a colorless film. Mass Spectrum (ESI) m/e=510 (M+1).

4-(1-(7-Fluoro-3-methyl-2-(2-pyridinyl)-4-quinolinyl)-3,3-dimethyl-2,3-dihydro-1H-indol-6-yl)-2-pyrimidinamine

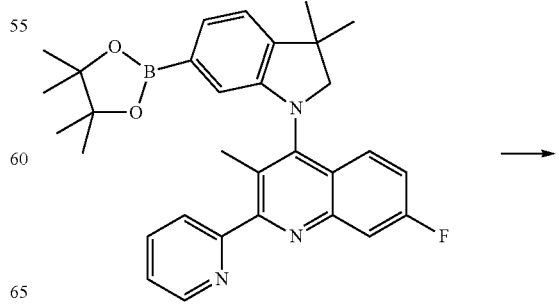

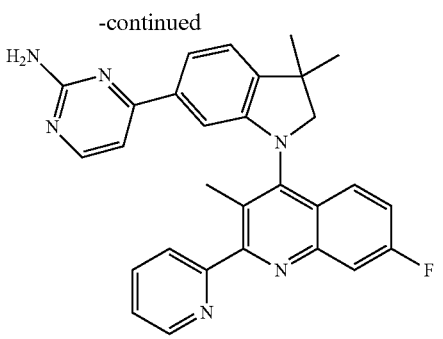

Prepared according to procedure P using 4-(3,3-dimethyl-6-(4,4,5,5-tetramethyl-1,3,2-dioxaborolan-2-yl)indolin-1-yl)-7-fluoro-3-methyl-2-(pyridin-2-yl)quinoline (75 mg, 0.147 mmol), PdCl$_2$(PPh$_3$)$_2$ (10.33 mg, 0.015 mmol), 2-amine-4-chloropyrimidine (21.0 mg, 0.162 mmol) and sodium carbonate (26.5 mg, 0.442 mmol) in 1,4-dioxane (2.0 mL) and water (0.7 mL) and heating in the microwave for 1 h at 120° C. After purification 4-(1-(7-fluoro-3-methyl-2-(2-pyridinyl)-4-quinolinyl)-3,3-dimethyl-2,3-dihydro-1H-indol-6-yl)-2-pyrimidinamine was obtained as a yellow film. 1H NMR (400 MHz, chloroform-d) δ ppm 8.66-8.83 (1H, m), 8.17 (1H, d, J=5.5 Hz), 7.79-7.99 (4H, m), 7.36-7.48 (2H, m), 7.26-7.29 (2H, m), 6.87 (1H, d, J=5.5 Hz), 6.62 (1H, d, J=1.6 Hz), 5.43 (2H, br. s.), 3.82 (2H, s), 2.29-2.44 (3H, m), 1.58 (3H, s), 1.52 (3H, s). Mass Spectrum (ESI) m/e=477 (M+1).

Example 11

4-(1-(7-Fluoro-3-methyl-2-(2-pyridinyl)-4-quinolinyl)-3,3-dimethyl-2,3-dihydro-1H-pyrrolo[3,2-b]pyridin-6-yl)-2-pyrimidinamine 1-(7-Fluoro-3-methyl-2-(pyridin-2-yl)quinolin-4-yl)-3,3-dimethyl-2,3-dihydro-1H-pyrrolo[3,2-b]pyridin-6-ylboronic acid

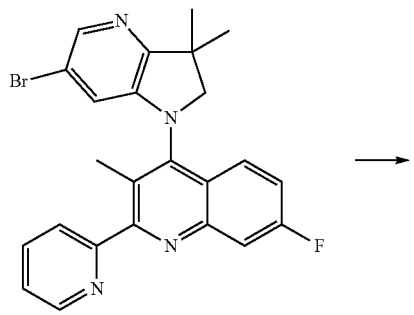

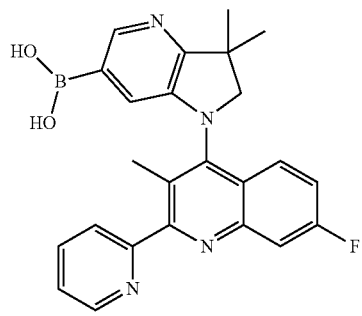

Prepared according to procedure O using 4-(6-bromo-3,3-dimethyl-2,3-dihydro-1H-pyrrolo[3,2-b]pyridin-1-yl)-7-fluoro-3-methyl-2-(pyridin-2-yl)quinoline (100 mg, 0.22 mmol), Pd(PCy$_3$)$_2$ (14.4 mg, 0.022 mmol), bis(pinacolato) diboron (60 mg, 0.24 mmol) and potassium acetate (35 mg, 0.32 mmol) in 1,4-dioxane (4.0 mL) and heating at 120° C. in the microwave for 1 h. After aqueous work up 1-(7-fluoro-3-methyl-2-(pyridin-2-yl)quinolin-4-yl)-3,3-dimethyl-2,3-dihydro-1H-pyrrolo[3,2-b]pyridin-6-ylboronic acid was obtained as a colorless film. Mass Spectrum (ESI) m/e=429 (M+1).

4-(1-(7-Fluoro-3-methyl-2-(2-pyridinyl)-4-quinolinyl)-3,3-dimethyl-2,3-dihydro-1H-pyrrolo[3,2-b]pyridin-6-yl)-2-pyrimidinamine

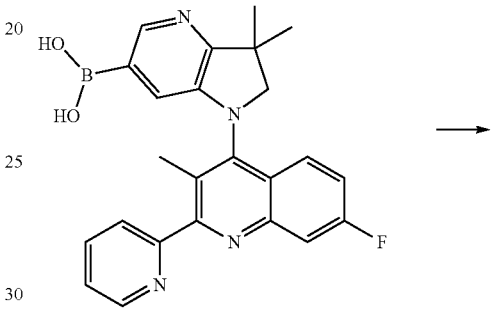

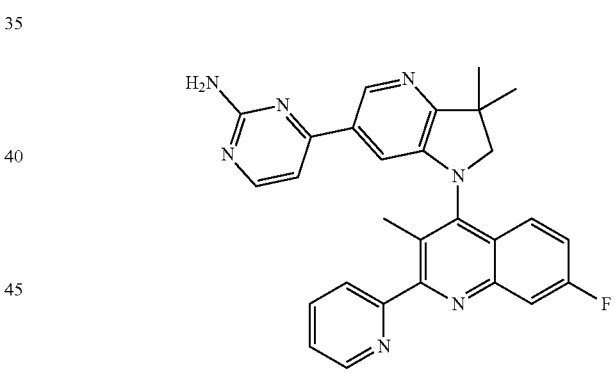

Prepared according to procedure P using 1-(7-fluoro-3-methyl-2-(pyridin-2-yl)quinolin-4-yl)-3,3-dimethyl-2,3-dihydro-1H-pyrrolo[3,2-b]pyridin-6-ylboronic acid (92 mg, 0.215 mmol), PdCl$_2$(PPh$_3$)$_2$ (15.12 mg, 0.021 mmol), 2-amine-4-chloropyrimidine (30.6 mg, 0.236 mmol) and sodium carbonate (68.3 mg, 0.644 mmol) in 1,4-dioxane (2.5 mL) and water (0.5 mL) and heating in the microwave for 1 h at 120° C. After purification 4-(1-(7-fluoro-3-methyl-2-(2-pyridinyl)-4-quinolinyl)-3,3-dimethyl-2,3-dihydro-1H-pyrrolo[3,2-b]pyridin-6-yl)-2-pyrimidinamine was obtained as a yellow solid. 1H NMR (400 MHz, chloroform-d) δ ppm 8.68-8.80 (1H, m), 8.49 (1H, d, J=2.0 Hz), 8.26 (1H, d, J=5.5 Hz), 7.72-7.99 (4H, m), 7.41 (1H, ddd, J=7.0, 5.1, 2.0 Hz), 7.29-7.34 (1H, m), 6.93 (1H, d, J=5.1 Hz), 6.77-6.86 (1H, m), 5.16 (2H, br. s.), 3.77-3.95 (2H, m), 2.27-2.44 (3H, m), 1.61-1.68 (3H, m), 1.51-1.60 (3H, m). Mass Spectrum (ESI) m/e=478 (M+1).

Example 12

4-(3,3-Dimethyl-6-(4-morpholinyl)-2,3-dihydro-1H-pyrrolo[3,2-b]pyridin-1-yl)-7-fluoro-3-(1-methylethyl)-2-(2-pyridinyl)quinoline

Ethyl 2-(3-fluorophenylcarbamoyl)-3-methylbutanoate

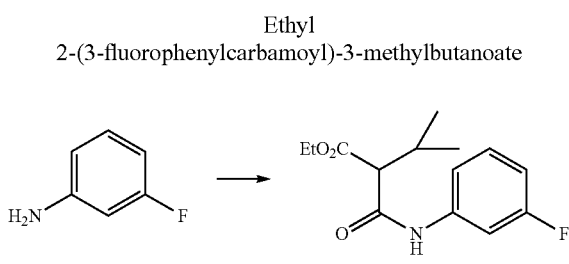

Prepared according to procedure A using 3-fluoroaniline (8.70 mL, 90 mmol), pyridine (10.92 mL, 135 mmol) and diethyl isopropylmalonate (20.02 mL, 99 mmol). The crude was purified by column chromatography (hexane:EtOAc, 1:0 to 4:1) to give ethyl 2-(3-fluorophenylcarbamoyl)-3-methylbutanoate.

2-(3-Fluorophenylcarbamoyl)-3-methylbutanoic acid

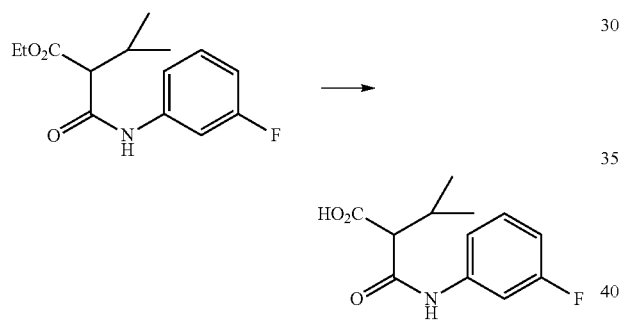

Prepared according to procedure B using ethyl 2-(3-fluorophenylcarbamoyl)-3-methylbutanoate (5.2 g, 19.45 mmol) in THF (20 mL) to give 2-(3-fluorophenylcarbamoyl)-3-methylbutanoic acid as a white solid.

7-Fluoro-3-isopropylquinoline-2,4-diol and 5-fluoro-3-isopropylquinoline-2,4-diol

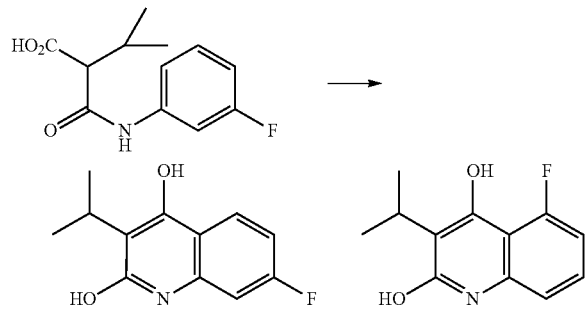

Prepared according to procedure C using 2-(3-fluorophenylcarbamoyl)-3-methylbutanoic acid (2.4 g, 10.03 mmol) and PPA (15 mL) to give a mixture of 7-fluoro-3-isopropylquinoline-2,4-diol and 5-fluoro-3-isopropylquinoline-2,4-diol as a white solid.

2,4-Dichloro-7-fluoro-3-isopropylquinoline and 2,4-dichloro-5-fluoro-3-isopropylquinoline

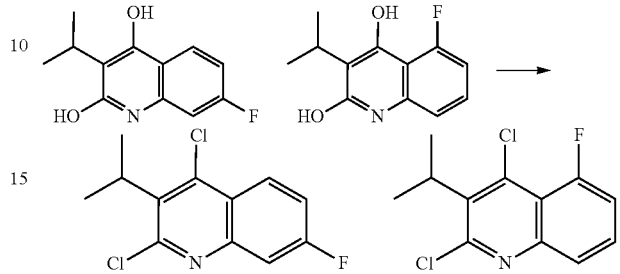

Prepared according to procedure D using 7-fluoro-3-isopropylquinoline-2,4-diol and 5-fluoro-3-isopropylquinoline-2,4-diol (1.0 g, 4.5 mmol) to give a mixture of 2,4-dichloro-7-fluoro-3-isopropylquinoline and 2,4-dichloro-5-fluoro-3-isopropylquinoline as a white solid. Mass Spectrum (ESI) m/e=258 (M+1).

4-Chloro-7-fluoro-3-isopropyl-2-(pyridin-2-yl)quinoline and 4-chloro-5-fluoro-3-isopropyl-2-(pyridin-2-yl)quinoline

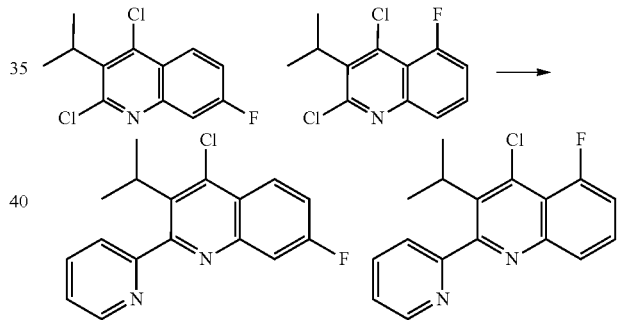

Prepared according to procedure E using 2,4-dichloro-7-fluoro-3-isopropylquinoline and 2,4-dichloro-5-fluoro-3-isopropylquinoline (700 mg, 2.71 mmol), palladium tetrakistriphenylphosphine (157 mg, 0.136 mmol) in toluene (10 mL) to give a separable mixture of 4-chloro-7-fluoro-3-isopropyl-2-(pyridin-2-yl)-quinoline and 4-chloro-5-fluoro-3-isopropyl-2-(pyridin-2-yl)quinoline.

4-(6-Bromo-3,3-dimethyl-2,3-dihydro-1H-pyrrolo[3,2-b]pyridin-1-yl)-7-fluoro-3-isopropyl-2-(pyridin-2-yl)quinoline

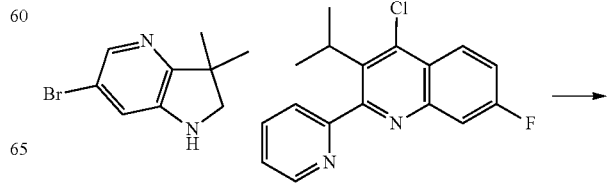

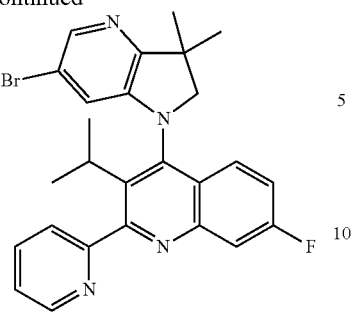

Prepared according to procedure L using 6-bromo-3,3-dimethyl-2,3-dihydro-1H-pyrrolo[3,2-b]pyridine (94 mg, 0.416 mmol), 4-chloro-7-fluoro-3-isopropyl-2-(pyridin-2-yl)quinoline (125 mg, 0.416 mmol) and 4.0M solution of HCl in 1,4-dioxane (0.10 mL, 0.416 mmol) in NMP (0.6 mL) and heating in the microwave for 5 h at 150° C. After purification 4-(6-bromo-3,3-dimethyl-2,3-dihydro-1H-pyrrolo[3,2-b]pyridin-1-yl)-7-fluoro-3-isopropyl-2-(pyridin-2-yl)quinoline was obtained as a colorless film. Mass Spectrum (ESI) m/e=491 [(M+1) ($^{79}$Br)] and 493 [(M+1) ($^{81}$Br)].

4-(3,3-Dimethyl-6-(4-morpholinyl)-2,3-dihydro-1H-pyrrolo[3,2-b]pyridin-1-yl)-7-fluoro-3-(1-methylethyl)-2-(2-pyridinyl)quinoline

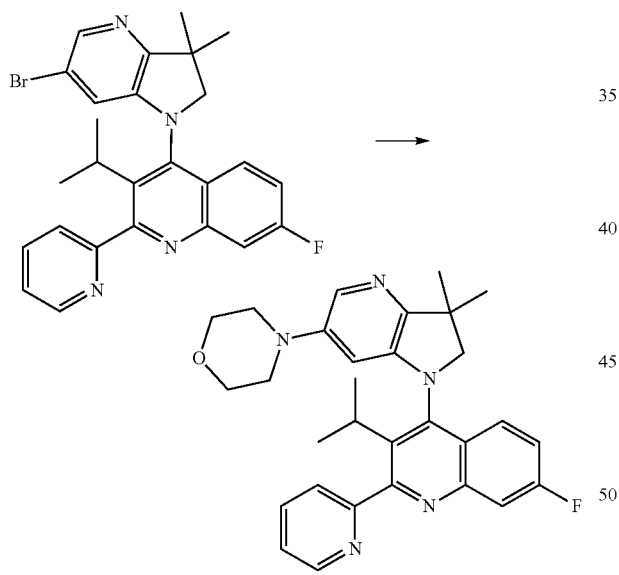

Prepared according to procedure N using 4-(6-bromo-3,3-dimethyl-2,3-dihydro-1H-pyrrolo[3,2-b]pyridin-1-yl)-7-fluoro-3-isopropyl-2-(pyridin-2-yl)quinoline (30 mg, 0.061 mmol), sodium tert-butoxide (11.73 mg, 0.122 mmol), morpholine (5.85 μL, 0.067 mmol), XPhos (5.82 mg, 0.012 mmol) and Pd$_2$(dba)$_3$ (5.6 mg, 6.11 μmol) in toluene (2.0 mL) and heating at 120° C. in the microwave for 90 min. After purification 4-(3,3-dimethyl-6-(4-morpholinyl)-2,3-dihydro-1H-pyrrolo[3,2-b]pyridin-1-yl)-7-fluoro-3-(1-methylethyl)-2-(2-pyridinyl)quinoline was obtained as a yellow oil. 1H NMR (400 MHz, chloroform-d) δ ppm 8.74 (1H, dd, J=4.9, 2.2 Hz), 7.86-7.93 (1H, m), 7.82 (1H, dd, J=9.8, 2.7 Hz), 7.66 (1H, d, J=7.4 Hz), 7.62 (1H, d, J=2.3 Hz), 7.53 (1H, dd, J=9.4, 5.9 Hz), 7.42 (1H, dd, J=7.4, 3.9 Hz), 7.17-7.25 (1H, m), 5.75 (1H, d, J=2.3 Hz), 3.80-3.93 (2H, m), 3.70-3.78 (4H, m), 3.34-3.48 (1H, m), 2.88-3.04 (4H, m), 1.62 (3H, s), 1.51 (3H, s), 1.29 (3H, d, J=7.0 Hz), 1.23 (3H, d, J=7.0 Hz). Mass Spectrum (ESI) m/e=498 (M+1).

Example 13

1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]

Ethyl 4-(5-bromo-3-nitropyridin-2-yl)tetrahydro-2H-pyran-4-carboxylate

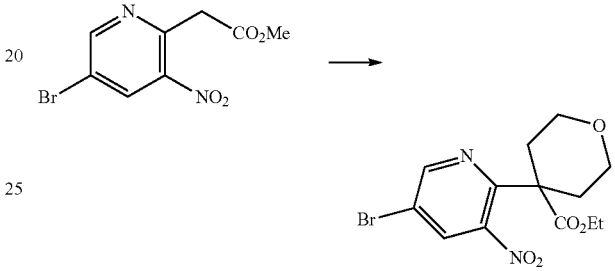

To a stirred solution of methyl 2-(5-bromo-3-nitropyridin-2-yl)acetate (2.0 g, 7.27 mmol) in DMF (15 mL) was added sodium hydride (0.384 g, 16.00 mmol) portionwise over 5 min (solution turns dark blue). The reaction was stirred at rt for 15 min and then 2-bromoethyl ether (1.69 mL, 7.27 mmol) was added via syringe over 1 min. The reaction was stirred at rt for 16 h. After this time 0.2 g of NaH was added and the reaction was stirred at rt for 14 h. The reaction was treated with saturated aqueous NH$_4$Cl (60 mL) and EtOAc (300 mL). The separated organic layer was washed with 1.0M aqueous LiCl (60 mL) and then dried over MgSO$_4$, filtered and evaporated in vacuo. Column chromatography (hexane:EtOAc, 1:0 to 1:1) gave ethyl 4-(5-bromo-3-nitropyridin-2-yl)tetrahydro-2H-pyran-4-carboxylate as a dark brown oil.

6'-Bromo-2,3,5,6-tetrahydrospiro[pyran-4,3'-pyrrolo[3,2-b]pyridin]-2'(1'H)-one

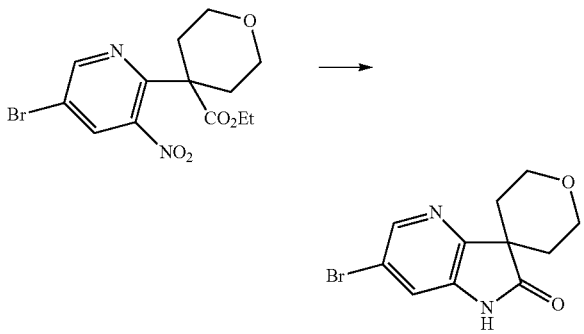

Prepared according to procedure J using ethyl 4-(5-bromo-3-nitropyridin-2-yl)tetrahydro-2H-pyran-4-carboxylate (250 mg, 0.724 mmol), AcOH (4 mL) and Fe powder (202 mg, 3.62 mmol) and heating the mixture at 100° C. for 2 h. After purification 6'-bromo-2,3,5,6-tetrahydrospiro[pyran-4,3'-pyrrolo[3,2-b]pyridin]-2'(1'H)-one was obtained.

6'-Bromo-1',2,2',3,5,6-hexahydrospiro[pyran-4,3'-pyrrolo[3,2-b]pyridine]

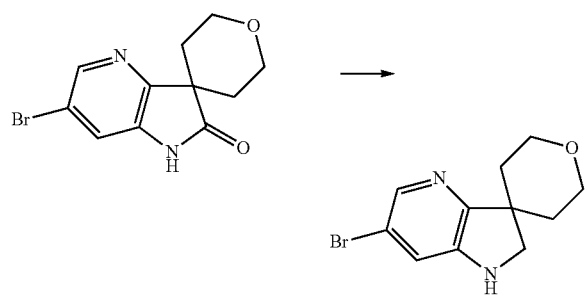

Prepared according to procedure K using 6'-bromo-2,3,5,6-tetrahydrospiro[pyran-4,3'-pyrrolo[3,2-b]pyridin]-2'(1'H)-one (138 mg, 0.487 mmol) and sodium bis(2-methoxyethoxy)aluminium hydride (304 μL, 1.560 mmol) in toluene (3 mL). After purification 6'-bromo-1',2,2',3,5,6-hexahydrospiro[pyran-4,3'-pyrrolo[3,2-b]pyridine] was obtained as a white solid.

6'-Bromo-1'-(7-fluoro-3-methyl-2-(pyridin-2-yl)quinolin-4-yl)-1',2,2',3,5,6-hexahydrospiro[pyran-4,3'-pyrrolo[3,2-b]pyridine]

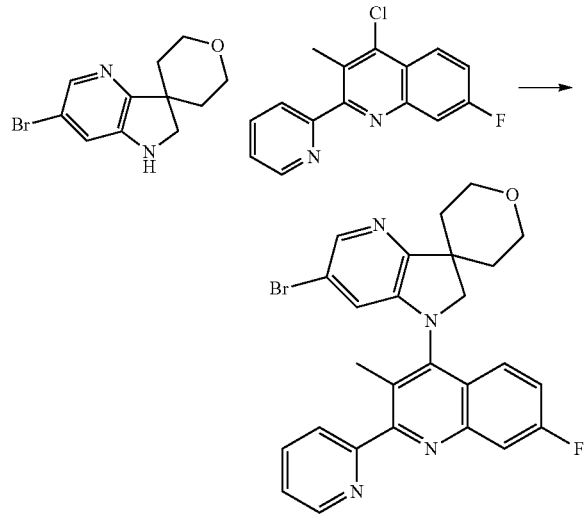

Prepared according to procedure L using 6'-bromo-1',2,2',3,5,6-hexahydrospiro-[pyran-4,3'-pyrrolo[3,2-b]pyridine] (89 mg, 0.33 mmol), 4-chloro-7-fluoro-3-methyl-2-(pyridin-2-yl)quinoline (90 mg, 0.33 mmol) and hydrochloric acid in 1,4-dioxane (83 μL, 0.330 mmol) in NMP (2.0 mL) and heating in the microwave at 150° C. for 2 h. After purification 6'-bromo-1'-(7-fluoro-3-methyl-2-(pyridin-2-yl)quinolin-4-yl)-1',2,2',3,5,6-hexahydrospiro[pyran-4,3'-pyrrolo[3,2-b]pyridine] was obtained as a yellow film. Mass Spectrum (ESI) m/e=505 [(M+1) ($^{79}$Br)] and 507 [(M+1) ($^{81}$Br)].

1'-(7-Fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]

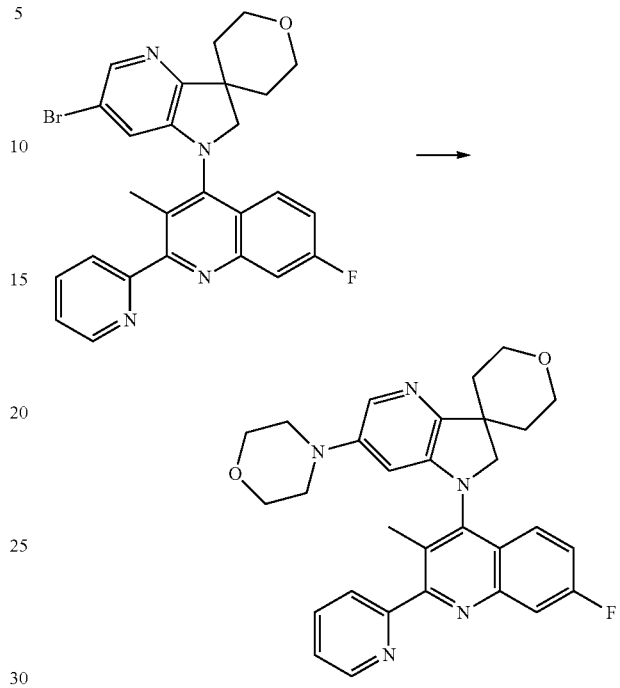

Prepared according to procedure N using 6'-bromo-1'-(7-fluoro-3-methyl-2-(pyridin-2-yl)quinolin-4-yl)-1',2,2',3,5,6-hexahydrospiro[pyran-4,3'-pyrrolo[3,2-b]pyridine] (30 mg, 0.059 mmol), Pd$_2$dba$_3$ (5.4 mg, 5.94 μmol), morpholine (5.69 μL, 0.065 mmol), sodium tert-butoxide (11.4 mg, 0.119 mmol) and XPhos (5.66 mg, 0.012 mmol) in toluene (1.5 mL) and heating in the microwave for 1 h at 120° C. After purification 1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] was obtained as a yellow film. 1H NMR (400 MHz, chloroform-d) δ ppm 8.75 (1H, dd, J=3.3, 1.0 Hz), 7.83-7.97 (3H, m), 7.75 (1H, dd, J=9.2, 6.1 Hz), 7.62 (1H, d, J=2.3 Hz), 7.41 (1H, ddd, J=7.0, 5.1, 2.0 Hz), 7.28-7.34 (1H, m), 5.83 (1H, d, J=2.3 Hz), 4.09-4.23 (2H, m), 3.95-4.04 (2H, m), 3.71-3.80 (4H, m), 3.52-3.62 (2H, m), 3.01 (4H, q, J=4.4 Hz), 2.32-2.46 (5H, m), 1.74-1.91 (2H, m). Mass Spectrum (ESI) m/e=512 (M+1).

Example 14

1-(7-Fluoro-3-methyl-2-(2-methyl-3-pyridinyl)-4-quinolinyl)-6-(4-morpholinyl)-1,2,2',3',5',6'-hexahydrospiro[indole-3,4'-pyran]

4-Chloro-7-fluoro-3-methyl-2-(2-methylpyridin-3-yl)quinoline

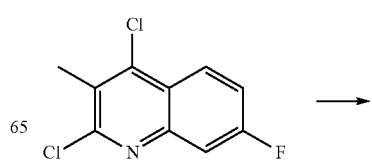

-continued

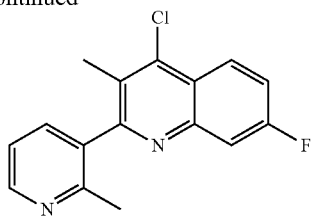

To a stirred solution of 2,4-dichloro-7-fluoro-3-methylquinoline (400 mg, 1.74 mmol) in 1,4-dioxane:water (5 mL:1 mL) was added $PdCl_2(PPh_3)_2$ (122 mg, 0.17 mmol), sodium carbonate (553 mg, 5.22 mmol) and 2-methyl-3-(4,4,5,5-tetramethyl-1,3,2-dioxaborolan-2-yl)pyridine. The reaction was heated at reflux overnight. After this time the reaction was diluted with EtOAc (100 mL) and water (50 mL). The separated organic layer was dried over $MgSO_4$, filtered and evaporated in vacuo. Column chromatography (hexane:EtOAc, 1:0 to 1:1) gave 4-chloro-7-fluoro-3-methyl-2-(2-methylpyridin-3-yl)quinoline.

1-(7-fluoro-3-methyl-2-(2-methyl-3-pyridinyl)-4-quinolinyl)-6-(4-morpholinyl)-1,2,2',3',5',6'-hexahydrospiro[indole-3,4'-pyran]

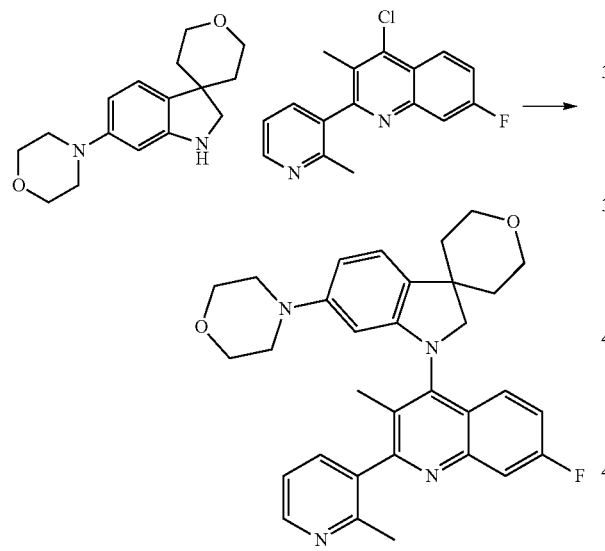

To a stirred solution of 6-morpholino-2',3',5',6'-tetrahydrospiro[indoline-3,4'-pyran] (86 mg, 0.31 mmol), 4-chloro-7-fluoro-3-methyl-2-(2-methylpyridin-3-yl)quinoline (90 mg, 0.31 mmol) in toluene (1.7 mL) was added $Pd_2dba_3$ (43 mg, 0.047 mmol), XPhos (45 mg, 0.09 mmol) and sodium tert-butoxide (90 mg, 0.94 mmol) and the reaction was heated in the microwave for 1 h at 100° C. After this time the reaction was cooled to rt and treated with EtOAc (100 mL) and water (40 mL). The separated organic layer was washed with NaCl (saturated aqueous solution, 40 mL), dried over $MgSO_4$, filtered and evaporated in vacuo. Purification by reverse phase HPLC (10 to 60% acetonitrile in water) gave 1-(7-fluoro-3-methyl-2-(2-methyl-3-pyridinyl)-4-quinolinyl)-6-(4-morpholinyl)-1,2,2',3',5',6'-hexahydrospiro[indole-3,4'-pyran].
1H NMR (400 MHz, chloroform-d) δ ppm 8.59-8.67 (1H, m), 7.84-7.94 (1H, m), 7.76-7.83 (1H, m), 7.59-7.69 (1H, m), 7.27-7.34 (2H, m), 7.11-7.18 (1H, m), 6.28-6.47 (1H, m), 5.48-5.70 (1H, m), 3.97-4.09 (2H, m), 3.85-3.94 (1H, m), 3.68-3.80 (4H, m), 3.48-3.63 (2H, m), 2.89-3.05 (4H, m), 2.36-2.44 (3H, m), 2.09-2.25 (2H, m), 2.05 (4H, dd, J=4.5, 2.3 Hz), 1.90 (1H, dt, J=13.7, 1.2 Hz), 1.72-1.81 (1H, m). Mass Spectrum (ESI) m/e=525 (M+1).

Example 15

4-(3,3-Dimethyl-6-(4-morpholinyl)-2,3-dihydro-1H-pyrrolo[3,2-b]pyridin-1-yl)-7-fluoro-3-methyl-2-(2-methyl-3-pyridinyl)quinoline 4-(6-Bromo-3,3-dimethyl-2,3-dihydro-1H-pyrrolo[3,2-b]pyridin-1-yl)-7-fluoro-3-methyl-2-(2-methylpyridin-3-yl)quinoline

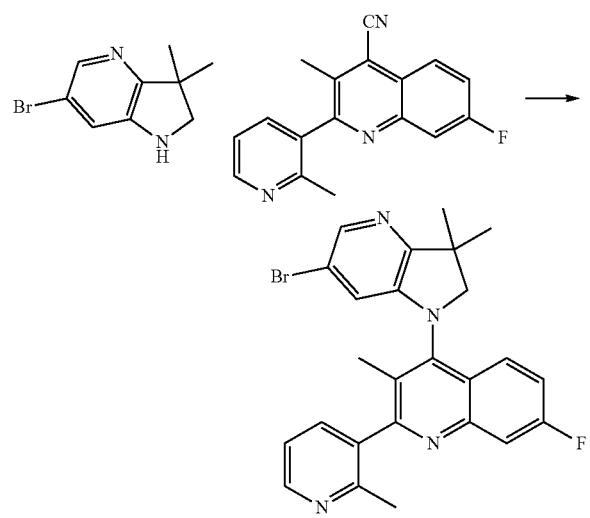

Prepared according to procedure L using 6-bromo-3,3-dimethyl-2,3-dihydro-1H-pyrrolo[3,2-b]pyridine (100 mg, 0.44 mmol), 4-chloro-7-fluoro-3-methyl-2-(2-methylpyridin-3-yl)quinoline (126 mg, 0.44 mmol) and hydrochloric acid in 1,4-dioxane (0.11 mL, 0.44 mmol) in NMP (2.0 mL) and heating in the microwave at 150° C. for 2 h. After purification 4-(6-bromo-3,3-dimethyl-2,3-dihydro-1H-pyrrolo[3,2-b]pyridin-1-yl)-7-fluoro-3-methyl-2-(2-methylpyridin-3-yl)quinoline was obtained as a yellow film. Mass Spectrum (ESI) m/e=477 [(M+1) ($^{79}$Br)] and 479 [(M+1) ($^{81}$Br)].

4-(3,3-Dimethyl-6-(4-morpholinyl)-2,3-dihydro-1H-pyrrolo[3,2-b]pyridin-1-yl)-7-fluoro-3-methyl-2-(2-methyl-3-pyridinyl)quinoline

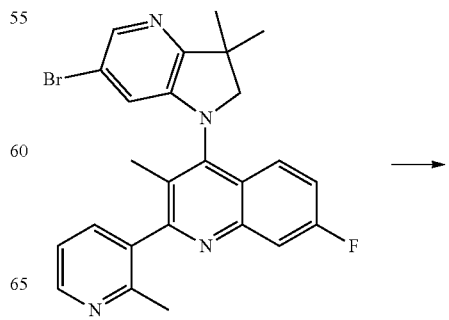

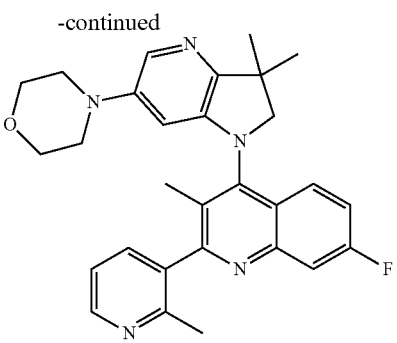

Prepared according to procedure N using 4-(6-bromo-3,3-dimethyl-2,3-dihydro-1H-pyrrolo[3,2-b]pyridin-1-yl)-7-fluoro-3-methyl-2-(2-methylpyridin-3-yl)-quinoline (41 mg, 0.086 mmol), Pd$_2$dba$_3$ (7.86 mg, 8.59 μmol), morpholine (8.23 μL, 0.094 mmol), sodium tert-butoxide (16.5 mg, 0.172 mmol) and XPhos (8.19 mg, 0.017 mmol) in toluene (1.5 mL) and heating in the microwave for 1 h at 120° C. After purification 4-(3,3-dimethyl-6-(4-morpholinyl)-2,3-dihydro-1H-pyrrolo[3,2-b]pyridin-1-yl)-7-fluoro-3-methyl-2-(2-methyl-3-pyridinyl)quino line was obtained as a yellow film. 1H NMR (400 MHz, chloroform-d) δ ppm 8.66 (1H, dt, J=4.9, 1.7 Hz), 7.78-7.88 (2H, m), 7.67 (1H, d, J=7.6 Hz), 7.57-7.63 (1H, m), 7.30-7.40 (2H, m), 5.84 (1H, d, J=2.0 Hz), 3.70-3.92 (6H, m), 2.93-3.12 (4H, m), 2.42 (3H, s), 2.08 (3H, s), 1.66 (3H, m), 1.59 (3H, s). Mass Spectrum (ESI) m/e=484 (M+1).

Example 16

1-(7-Fluoro-3-methyl-2-(2-pyridinyl)-4-quinolinyl)-N-(2-methoxyethyl)-N,3,3-trimethyl-2,3-dihydro-1H-pyrrolo[3,2-b]pyridin-6-amine

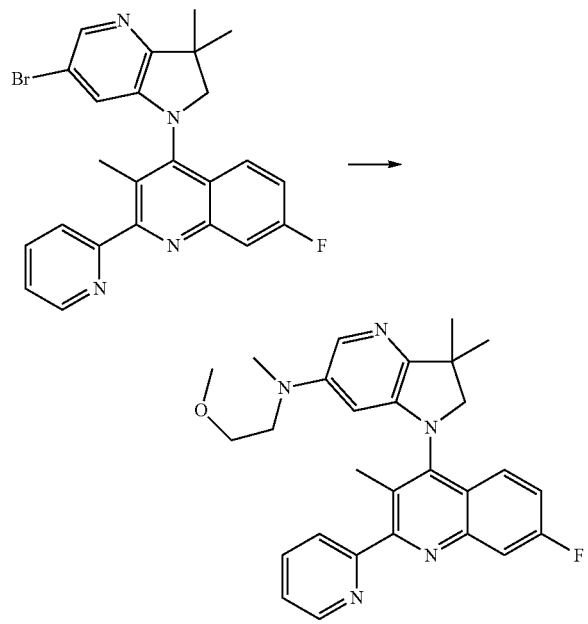

Prepared according to procedure N using 4-(6-bromo-3,3-dimethyl-2,3-dihydro-1H-pyrrolo[3,2-b]pyridin-1-yl)-7-fluoro-3-methyl-2-(pyridin-2-yl)quinoline (80 mg, 0.17 mmol), Pd$_2$dba$_3$ (15.8 mg, 0.017 mmol), N-(2-methoxyethyl)methylamine (15.4 mg, 0.17 mmol), sodium tert-butoxide (33.2 mg, 0.34 mmol) and XPhos (16.5 mg, 0.035 mmol) and heating in the microwave for 2 h at 120° C. After purification 1-(7-fluoro-3-methyl-2-(2-pyridinyl)-4-quinolinyl)-N-(2-methoxyethyl)-N,3,3-trimethyl-2,3-dihydro-1H-pyrrolo[3,2-b]pyridin-6-amine was obtained as a yellow film. 1H NMR (400 MHz, chloroform-d) δ ppm 8.69-8.79 (1H, m), 7.75-7.98 (4H, m), 7.45 (1H, dd, J=2.1, 1.7 Hz), 7.37-7.43 (1H, m, J=7.4, 4.8, 1.5, 1.5 Hz), 7.28-7.33 (1H, m), 5.62-5.75 (1H, m), 3.73-3.87 (2H, m), 3.38-3.45 (2H, m), 3.29-3.35 (2H, m), 3.24 (3H, d, J=1.4 Hz), 2.84 (3H, d, J=1.4 Hz), 2.38 (3H, s), 1.61 (3H, s), 1.55 (3H, s). Mass Spectrum (ESI) m/e=472 (M+1).

Example 17

4-(3,3-dimethyl-6-(1H-pyrazol-4-yl)-2,3-dihydro-1H-pyrrolo-[3,2-b]pyridin-1-yl)-7-fluoro-3-methyl-2-(2-pyridinyl)quinoline

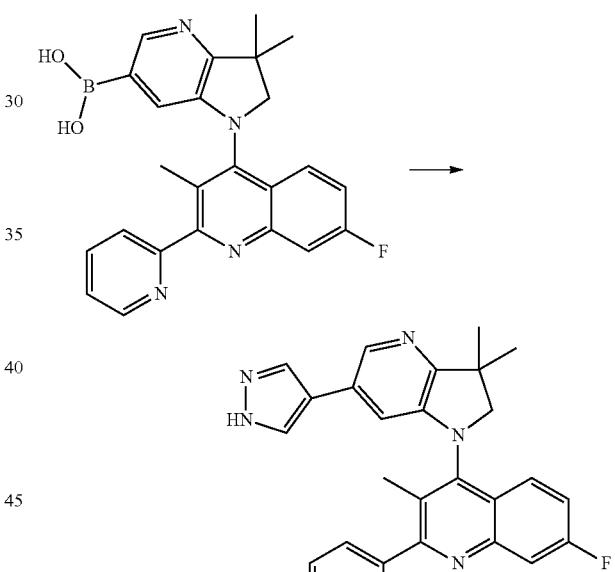

Prepared according to procedure P using 1-(7-fluoro-3-methyl-2-(pyridin-2-yl)-quinolin-4-yl)-3,3-dimethyl-2,3-dihydro-1H-pyrrolo[3,2-b]pyridin-6-ylboronic acid (60 mg, 0.14 mmol), 4-bromopyrazole (21 mg, 0.14 mmol), PdCl$_2$(PPh$_3$)$_2$ (9.8 mg, 0.014 mmol), sodium carbonate (29.7 mg, 0.28 mmol) and heating in the microwave for 1 h at 120° C. After purification 4-(3,3-dimethyl-6-(1H-pyrazol-4-yl)-2,3-dihydro-1H-pyrrolo[3,2-b]pyridin-1-yl)-7-fluoro-3-methyl-2-(2-pyridinyl)quinoline was obtained as a yellow film. 1H NMR (400 MHz, chloroform-d) δ ppm 8.71-8.79 (1H, m), 8.10-8.17 (1H, m), 7.78-7.97 (4H, m), 7.69-7.75 (2H, m), 7.38-7.45 (1H, m), 7.30-7.37 (1H, m), 6.34 (1H, quin, J=2.2 Hz), 3.83-3.93 (2H, m), 2.33-2.46 (3H, m), 1.63-1.70 (3H, m), 1.56-1.62 (3H, m). Mass Spectrum (ESI) m/e=451 (M+1).

Example 18

4-(3,3-Dimethyl-6-(9H-purin-6-yl)-2,3-dihydro-1H-pyrrolo[3,2-b]pyridin-1-yl)-7-fluoro-3-methyl-2-(2-pyridinyl)quinoline

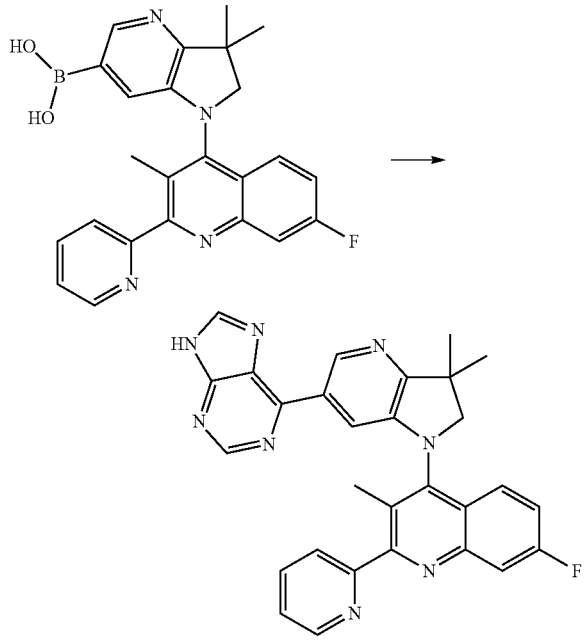

Prepared according to procedure P using 1-(7-fluoro-3-methyl-2-(pyridin-2-yl)-quinolin-4-yl)-3,3-dimethyl-2,3-dihydro-1H-pyrrolo[3,2-b]pyridin-6-ylboronic acid (25 mg, 0.058 mmol), 6-chloropurine (9 mg, 0.058 mmol), PdCl$_2$(PPh$_3$)$_2$ (4.1 mg, 0.0058 mmol), sodium carbonate (12.3 mg, 0.117 mmol) and heating in the microwave for 1 h at 120° C. After purification 4-(3,3-dimethyl-6-(9H-purin-6-yl)-2,3-dihydro-1H-pyrrolo[3,2-b]pyridin-1-yl)-7-fluoro-3-methyl-2-(2-pyridinyl)quinoline was obtained as a yellow film. 1H NMR (400 MHz, MeOH) δ ppm 9.27 (1H, br. s.), 8.83 (1H, s), 8.67-8.73 (1H, m), 8.41 (1H, br. s.), 8.01-8.12 (2H, m), 7.92 (1H, d, J=7.8 Hz), 7.83 (1H, dd, J=10.0, 2.5 Hz), 7.52-7.60 (2H, m), 7.48 (1H, ddd, J=9.3, 8.3, 2.5 Hz), 4.06-4.12 (1H, m), 3.95-4.03 (1H, m), 2.33 (3H, s), 1.70 (3H, s), 1.62 (3H, s). Mass Spectrum (ESI) m/e=503 (M+1).

Example 19

1-(7-Fluoro-3-methyl-2-(2-pyridinyl)-4-quinolinyl)-3,3-dimethyl-2,3-dihydro-1H-pyrrolo[3,2-b]pyridine-6-carboxamide

1-(7-Fluoro-3-methyl-2-(2-pyridinyl)-4-quinolinyl)-3,3-dimethyl-2,3-dihydro-1H-pyrrolo[3,2-b]pyridine-6-carbonitrile

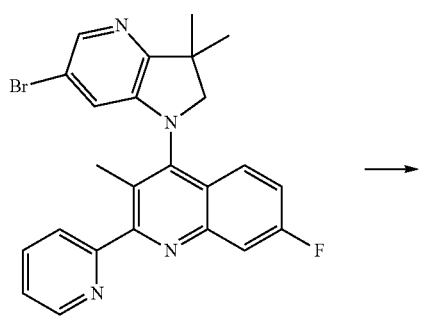

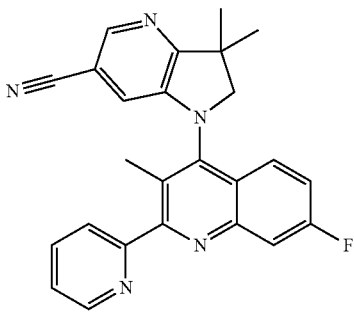

A stirred solution of 4-(6-bromo-3,3-dimethyl-2,3-dihydro-1H-pyrrolo[3,2-b]-pyridin-1-yl)-7-fluoro-3-methyl-2-(pyridin-2-yl)quinoline (95 mg, 0.20 mmol), Pd$_2$dba$_3$ (56 mg, 0.06 mmol), XPhos (58 mg, 0.6 mmol) and cyanotributyltin (65 mg, 0.20 mmol) in dicyclohexylmethylamine (1.5 mL) and NMP (1.0 mL) was heated in the microwave at 150° C. After this time the reaction was treated with EtOAc (100 mL) and water (50 mL). The separated organic layer was dried over MgSO$_4$, filtered and evaporated in vacuo. Reverse phase HPLC (10% to 60% acetonitrile in water) gave 1-(7-fluoro-3-methyl-2-(2-pyridinyl)-4-quinolinyl)-3,3-dimethyl-2,3-dihydro-1H-pyrrolo[3,2-b]pyridine-6-carbonitrile. Mass Spectrum (ESI) m/e=410 (M+1).

1-(7-Fluoro-3-methyl-2-(2-pyridinyl)-4-quinolinyl)-3,3-dimethyl-2,3-dihydro-1H-pyrrolo[3,2-b]pyridine-6-carboxamide

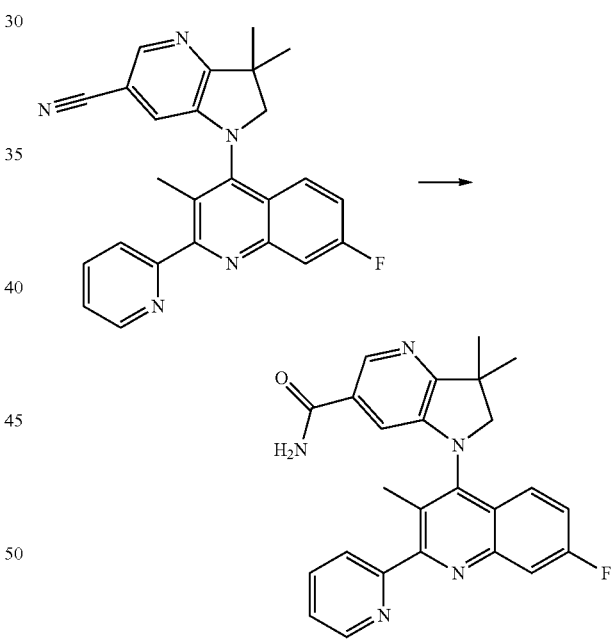

1-(7-Fluoro-3-methyl-2-(pyridin-2-yl)quinolin-4-yl)-3,3-dimethyl-2,3-dihydro-1H-pyrrolo[3,2-b]pyridine-6-carbonitrile (80 mg, 0.195 mmol) in EtOH (3 mL) was treated with sodium hydroxide (156 mg, 3.91 mmol) in water (1.0 mL). The reaction was heated at reflux for 3 h. After this time the reaction was evaporated in vacuo. Reverse phase HPLC (10% to 60% acetonitrile in water) gave 1-(7-fluoro-3-methyl-2-(2-pyridinyl)-4-quinolinyl)-3,3-dimethyl-2,3-dihydro-1H-pyrrolo[3,2-b]pyridine-6-carboxamide. 1H NMR (400 MHz, DMSO-d$_6$) δ ppm 8.72 (1H, ddd, J=4.8, 1.8, 1.1 Hz), 8.34 (1H, d, J=1.8 Hz), 7.99-8.06 (1H, m), 7.80-7.96 (4H, m), 7.48-7.61 (2H, m), 7.31 (1H, br. s.), 6.61 (1H, d, J=1.8 Hz), 3.90-3.99 (1H, m), 3.85 (1H, d, J=9.4 Hz), 2.27 (3H, s), 1.53 (3H, s), 1.45 (3H, s). Mass Spectrum (ESI) m/e=428 (M+1).

Example 20

4-(3,3-Dimethyl-6-(4-morpholinyl)-2,3-dihydro-1H-pyrrolo[3,2-b]pyridin-1-yl)-2-(3,5-dimethylphenyl)-7-fluoro-3-methylquinoline

4-Chloro-2-(3,5-dimethylphenyl)-7-fluoro-3-methylquinoline

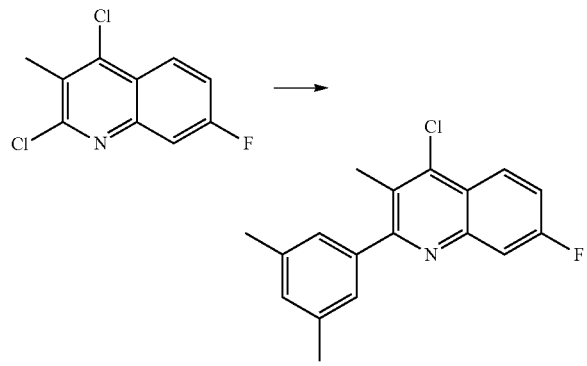

Prepared according to procedure F using 2,4-dichloro-7-fluoro-3-methylquinoline (500 mg, 2.173 mmol), 3,5-dimethylbenzeneboronic acid (326 mg, 2.173 mmol), sodium carbonate (1.15 g, 10.87 mmol) and Pd(PPh$_3$)$_4$ (251 mg, 0.217 mmol) in toluene/water (4 mL:1 mL) and heating in the microwave for 90 min at 120° C. After purification 4-chloro-2-(3,5-dimethylphenyl)-7-fluoro-3-methylquinoline was obtained as a white solid. Mass Spectrum (ESI) m/e=300 (M+1).

Methyl 2-methyl-2-(5-morpholino-3-nitropyridin-2-yl)propanoate

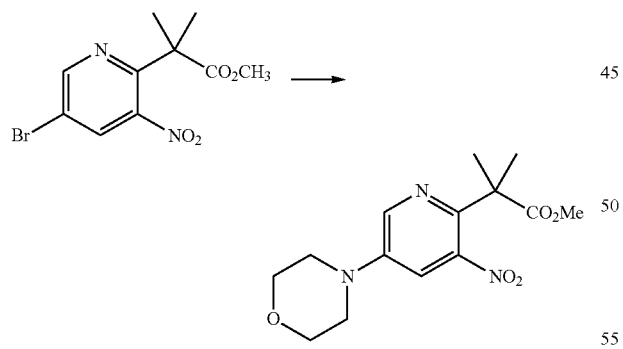

A stirred mixture of methyl 2-(5-bromo-3-nitropyridin-2-yl)-2-methylpropanoate (1.2 g, 3.96 mmol), morpholine (0.34 mL, 3.96 mmol), Pd$_2$dba$_3$ (181 mg, 0.20 mmol), XPhos (189 mg, 0.40 mmol) and sodium tert-butoxide (1.1 g, 11.88 mmol) in toluene (30 mL) was heated at reflux for two h. After this time the reaction was cooled to rt and partitioned between EtOAc (300 mL) and water (100 mL). The separated organic layer was dried over MgSO$_4$, filtered and evaporated in vacuo. Column chromatography gave methyl 2-methyl-2-(5-morpholino-3-nitropyridin-2-yl)propanoate as a yellow oil.

3,3-Dimethyl-6-morpholino-1H-pyrrolo[3,2-b]pyridin-2(3H)-one

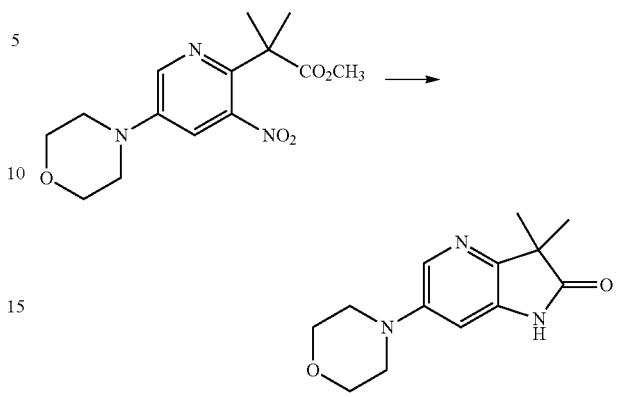

To a stirred solution of methyl 2-methyl-2-(5-morpholino-3-nitropyridin-2-yl)-propanoate (1.2 g, 3.88 mmol) in acetic acid (22.2 mL, 388 mmol) was added iron powder (1.08 g, 19.40 mmol). The reaction was heated at 80° C. for 2 h. After this time the reaction was cooled to rt and filtered over Celite™. The Celite™ was washed with acetic acid and the combined filtrates were evaporated in vacuo. Purification by column chromatography (hexane:EtOAc, 1:0 to 0:1) gave 3,3-dimethyl-6-morpholino-1H-pyrrolo[3,2-b]pyridin-2(3H)-one. Mass Spectrum (ESI) m/e=248 (M+1).

4-(3,3-Dimethyl-2,3-dihydro-1H-pyrrolo[3,2-b]pyridin-6-yl)morpholine

To a stirred suspension of 3,3-dimethyl-6-morpholino-1H-pyrrolo[3,2-b]pyridin-2(3H)-one (425 mg, 1.719 mmol) in toluene (14 mL) at 0° C. was added sodium bis(2-methoxyethoxy)aluminum hydride (3.3 M solution in toluene, 1.56 mL, 5.16 mmol). The reaction was stirred while warming to rt for 4 h. After this time the reaction was carefully quenched with water (5 mL) and then diluted with DCM (50 mL) and treated with saturated aqueous solution Na$_2$S$_2$O$_3$ (20 mL). The separated aqueous layer was then extracted with DCM (20 mL) and the combined organic layers were washed with brine (20 mL) and then dried over MgSO$_4$, filtered and evaporated in vacuo to give 4-(3,3-dimethyl-2,3-dihydro-1H-pyrrolo[3,2-b]pyridin-6-yl)morpholine. Mass Spectrum (ESI) m/e=234.2 (M+1).

4-(3,3-Dimethyl-6-(4-morpholinyl)-2,3-dihydro-1H-pyrrolo[3,2-b]pyridin-1-yl)-2-(3,5-dimethylphenyl)-7-fluoro-3-methylquinoline

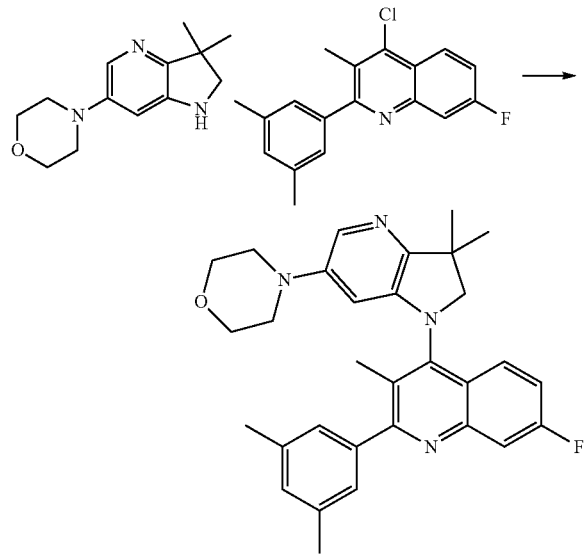

To a stirred solution of 4-chloro-2-(3,5-dimethylphenyl)-7-fluoro-3-methylquinoline (39 mg, 0.13 mmol), 4-(3,3-dimethyl-2,3-dihydro-1H-pyrrolo[3,2-b]pyridin-6-yl)morpholine (30 mg, 0.13 mmol) in toluene (1.5 mL) was added Pd$_2$dba$_3$ (12 mg, 0.013 mmol), XPhos (12 mg, 0.026 mmol) and sodium tert-butoxide (25 mg, 0.26 mmol) and the reaction was heated in the microwave for 1 h at 100° C. After this time the reaction was cooled to rt and treated with EtOAc (100 mL) and water (40 mL). The separated organic layer was washed with NaCl (saturated aqueous solution, 40 mL), dried over MgSO$_4$, filtered and evaporated in vacuo. Purification by reverse phase HPLC (10 to 60% acetonitrile in water) gave 4-(3,3-dimethyl-6-(4-morpholinyl)-2,3-dihydro-1H-pyrrolo[3,2-b]pyridin-1-yl)-2-(3,5-dimethylphenyl)-7-fluoro-3-methylquinoline as a white solid. 1H NMR (400 MHz, chloroform-d) δ ppm 7.84 (1H, dd, J=10.0, 2.5 Hz), 7.77 (1H, dd, J=9.3, 6.0 Hz), 7.60 (1H, d, J=2.3 Hz), 7.23-7.29 (1H, m), 7.17-7.21 (2H, m), 7.11 (1H, d, J=1.8 Hz), 5.79 (1H, d, J=2.3 Hz), 3.82 (2H, s), 3.73-3.78 (4H, m), 2.93-3.04 (4H, m), 2.39-2.44 (6H, m), 2.27 (3H, s), 1.58 (3H, s), 1.52 (3H, s). Mass Spectrum (ESI) m/e=497 (M+1).

Example 21

4-(1-(7-Fluoro-3-methyl-2-(2-pyridinyl)-4-quinolinyl)-3,3-dimethyl-2,3-dihydro-1H-indol-6-yl)-6-methyl-2-pyrimidinamine

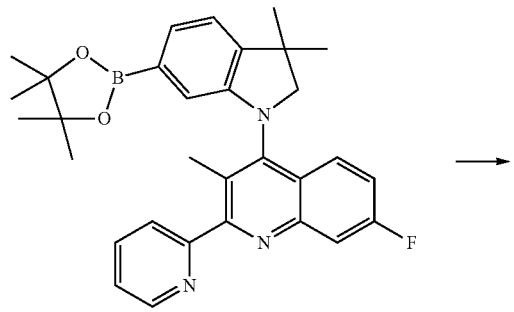

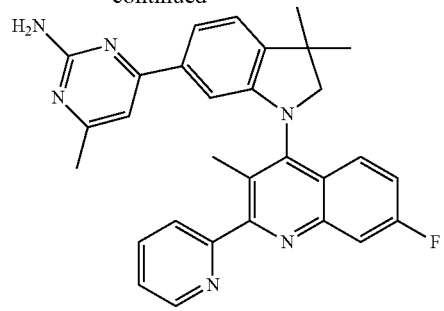

Prepared according to procedure P using 4-(3,3-dimethyl-6-(4,4,5,5-tetramethyl-1,3,2-dioxaborolan-2-yl)indolin-1-yl)-7-fluoro-3-methyl-2-(pyridin-2-yl)quinoline (70 mg, 0.14 mmol) (described herein), 4-chloro-6-methylpyrimidin-2-amine (21.7 mg, 0.15 mmol), bis(triphenylphosphine)palladium(ii) chloride (9.6 mg, 0.014 mmol), and sodium carbonate (43.7 mg, 0.41 mmol) in 1,4-dioxane (3.1 mL) and water (0.79 mL), and heating in a microwave at 120° C. for 60 min. After purification 4-(1-(7-fluoro-3-methyl-2-(2-pyridinyl)-4-quinolinyl)-3,3-dimethyl-2,3-dihydro-1H-indol-6-yl)-6-methyl-2-pyrimidinamine was obtained as a yellow solid. 1H NMR (400 MHz, chloroform-d) δ ppm 8.75 (1H, d, J=4.3 Hz), 7.76-7.96 (4H, m), 7.34-7.46 (2H, m), 7.28 (1H, br. s.), 7.21-7.26 (1H, m), 6.66-6.76 (1H, m), 6.58 (1H, d, J=1.2 Hz), 5.19 (2H, br. s.), 3.74-3.90 (2H, m), 2.35-2.41 (3H, m), 2.28-2.35 (3H, m), 1.55-1.61 (3H, m), 1.49-1.55 (3H, m). Mass Spectrum (ESI) m/e=491 (M+1).

Example 22

5-chloro-4-(1-(7-fluoro-3-methyl-2-(2-pyridinyl)-4-quinolinyl)-3,3-dimethyl-2,3-dihydro-1H-indol-6-yl)-2-pyrimidinamine

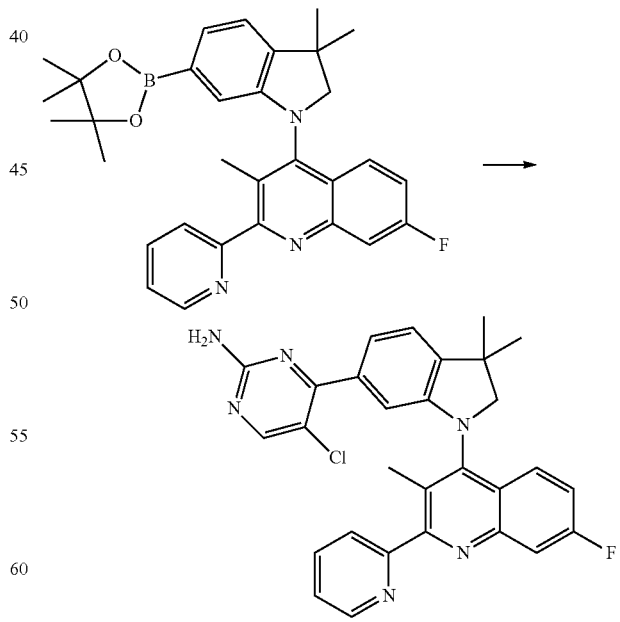

Prepared according to procedure P using 4-(3,3-dimethyl-6-(4,4,5,5-tetramethyl-1,3,2-dioxaborolan-2-yl)indolin-1-yl)-7-fluoro-3-methyl-2-(pyridin-2-yl)quinoline (68.7 mg, 0.14 mmol) (described herein), 4,5-dichloropyrimidin-2- amine (22.1 mg, 0.14 mmol), bis(triphenylphosphine)palladium(ii) chloride (9.5 mg, 0.013 mmol), and sodium carbonate (42.9 mg, 0.41 mmol) in 1,4-dioxane (2.9 mL) and water (0.73 mL), and heating in a microwave at 120° C. for 60 min. After purification 5-chloro-4-(1-(7-fluoro-3-methyl-2-(2-pyridinyl)-4-quinolinyl)-3,3-dimethyl-2,3-dihydro-1H-indol-6-yl)-2-pyrimidinamine was obtained as a yellow solid. 1H NMR (400 MHz, chloroform-d) δ ppm 8.74 (1H, dd, J=3.9, 1.2 Hz), 8.19 (1H, s), 7.76-7.99 (4H, m), 7.35-7.42 (1H, m), 7.28-7.30 (1H, m), 7.23-7.27 (1H, m), 7.16 (1H, dd, J=7.4, 1.2 Hz), 6.36 (1H, s), 4.94-5.21 (2H, br. s.), 3.76-3.88 (2H, m), 2.37 (3H, s), 1.58 (3H, s), 1.52 (3H, s). Mass Spectrum (ESI) m/e=511 (M+1).

Example 23

1-(7-Fluoro-3-methyl-2-(2-(methylsulfonyl)phenyl)-4-quinolinyl)-6-(4-morpholinyl)-1,2,2',3',5',6'-hexahydrospiro[indole-3,4'-pyran]

4-Chloro-7-fluoro-3-methyl-2-(2-(methylthio)phenyl)quinoline

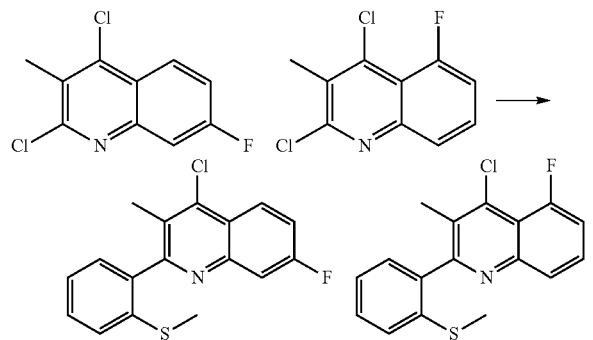

A mixture of 2,4-dichloro-7-fluoro-3-methylquinoline (100 mg, 0.44 mmol), 2-(methylthio)phenylboronic acid (95 mg, 0.57 mmol) (in a mixture with the 5-F regioisomer; described herein), tetrakis(triphenylphosphine)palladium(o) (25.1 mg, 0.022 mmol), sodium carbonate (230 mg, 2.17 mmol), acetonitrile (3 mL), and water (1.5 mL) was heated in a microwave at 100° C. for 60 min, then partitioned between EtOAc and water. The organic layer was washed with brine, dried (MgSO$_4$), and concentrated. Column chromatography afforded (in order of elution) 4-chloro-7-fluoro-3-methyl-2-(2-(methylthio)phenyl)quinoline and 4-chloro-5-fluoro-3-methyl-2-(2-(methylthio)phenyl) as white solids. Mass Spectrum (ESI) m/e=318 (M+1).

4-Chloro-7-fluoro-3-methyl-2-(2-(methylsulfonyl)phenyl)quinoline

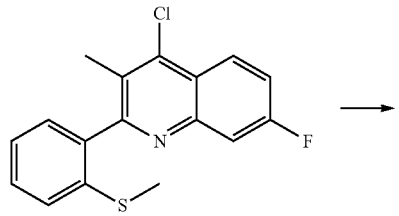

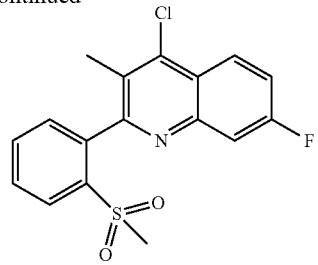

To a solution of 4-chloro-7-fluoro-3-methyl-2-(2-(methylthio)phenyl)quinoline (95 mg, 0.30 mmol) (described herein) in acetone (3.5 mL) and water (0.88 mL) was sequentially added NMO (105 mg, 0.90 mmol) and osmium tetroxide (4.7 μL, 0.015 mmol). The reaction mixture was stirred at rt for 35 h, then quenched with 15 mL 10% aqueous sodium thiosulfate solution, concentrated to remove the acetone, and partitioned between EtOAc and 10% aqueous sodium thiosulfate solution. The organic layer was washed with brine, dried (MgSO$_4$), and concentrated, affording 4-chloro-7-fluoro-3-methyl-2-(2-(methylsulfonyl)-phenyl)quinoline. Mass Spectrum (ESI) m/e=350 (M+1).

1-(7-Fluoro-3-methyl-2-(2-(methylsulfonyl)phenyl)-4-quinolinyl)-6-(4-morpholinyl)-1,2,2',3',5',6'-hexahydrospiro[indole-3,4'-pyran]

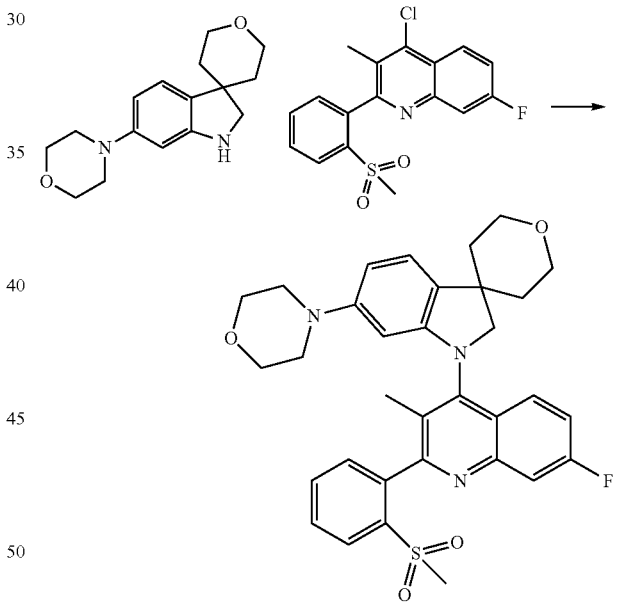

Prepared according to procedure L using 6-morpholino-2',3',5',6'-tetrahydrospiro-[indoline-3,4'-pyran] (76 mg, 0.28 mmol) (described herein), 4-chloro-7-fluoro-3-methyl-2-(2-(methylsulfonyl)phenyl)quinoline (97 mg, 0.28 mmol) (described herein), 4.0 M hydrochloric acid in 1,4-dioxane (0.07 mL, 0.28 mmol), and NMP (0.476 mL). After purification 1-(7-fluoro-3-methyl-2-(2-(methylsulfonyl)phenyl)-4-quinolinyl)-6-(4-morpholinyl)-1,2,2',3',5',6'-hexahydrospiro[indole-3,4'-pyran] was obtained as an orange solid. Compound is rotameric. 1H NMR (400 MHz, chloroform-d) δ ppm 8.16-8.30 (1H, m), 7.90 and 8.00 (1H, m), 7.75-7.85 (1H, m), 7.63-7.75 (2H, m), 7.42-7.53 (1H, m), 7.28-7.39 (1H, m), 7.06-7.18 (1H, m), 6.25-6.40 (1H, m), 5.65 and 5.81 (1H, m), 4.21 (1H, m), 3.85-4.09 (3H, m), 3.69-3.83 (5H, m), 3.63 (1H, m), 3.46-3.59 (1H, m), 3.16 (1H, s), 2.91-3.13 (6H, m), 2.09-2.24 (2H, m), 1.95 (2H, m), 1.89 (1H, m), 1.66-1.79 (1H, m). Mass Spectrum (ESI) m/e=588 (M+1).

Example 24

4-(3,3-Dimethyl-6-(4-morpholinyl)-2,3-dihydro-1H-indol-1-yl)-7-fluoro-3-methyl-2-(2-(methylsulfonyl)phenyl)quinoline 7-Fluoro-4-(6-iodo-3,3-dimethylindolin-1-yl)-3-methyl-2-(2-(methylsulfonyl)phenyl)quinoline

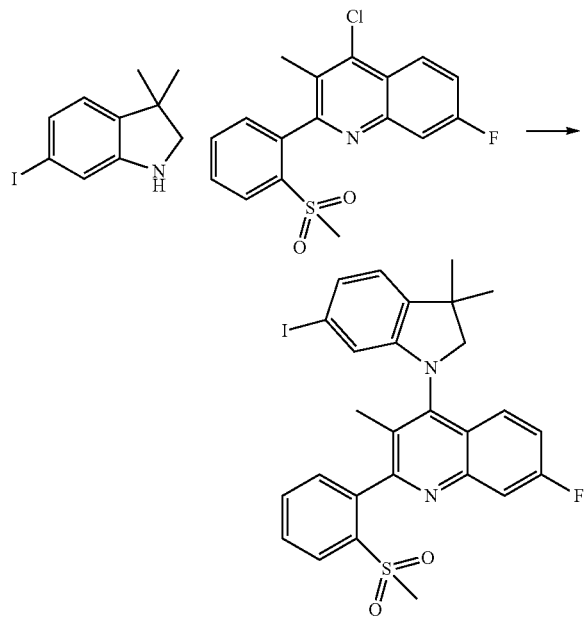

Prepared according to procedure L using 4-chloro-7-fluoro-3-methyl-2-(2-(methylsulfonyl)phenyl)quinoline (102 mg, 0.29 mmol) (described herein), 6-iodo-3,3-dimethylindoline (80 mg, 0.29 mmol) (described herein), hydrochloric acid (70 µL, 0.29 mmol), and NMP (0.490 mL). The reaction mixture was heated in a microwave at 150° C. for 150 min. Purification afforded 7-fluoro-4-(6-iodo-3,3-dimethylindolin-1-yl)-3-methyl-2-(2-(methylsulfonyl)phenyl)quinoline as a yellow solid. Mass Spectrum (ESI) m/e=587 (M+1).

4-(3,3-Dimethyl-6-(4-morpholinyl)-2,3-dihydro-1H-indol-1-yl)-7-fluoro-3-methyl-2-(2-(methylsulfonyl)phenyl)quinoline

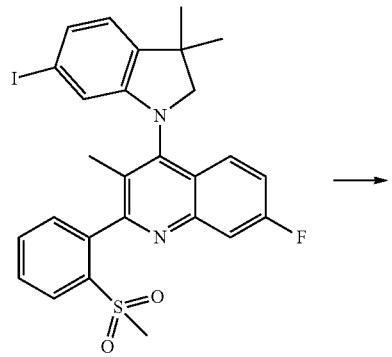

-continued

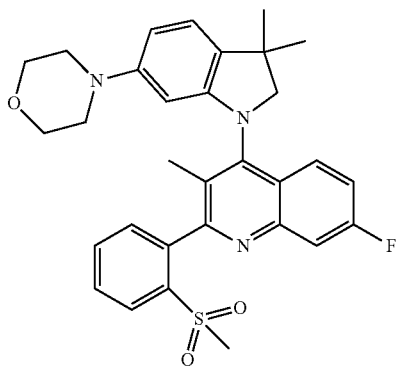

Prepared according to procedure N using 7-fluoro-4-(6-iodo-3,3-dimethylindolin-1-yl)-3-methyl-2-(2-(methylsulfonyl)phenyl)quinoline (68 mg, 0.12 mmol) (described herein), morpholine (20 µL, 0.23 mmol), Pd$_2$dba$_3$ (7.4 mg, 8.1 µmol), 2-dicyclohexylphosphino-2,4,6-triisopropylbiphenyl (8.2 mg, 0.017 mmol), and sodium tert-butoxide (22.1 mg, 0.23 mmol) in toluene (2.2 mL), and heated at 95° C. for 15 h. After purification 4-(3,3-dimethyl-6-(4-morpholinyl)-2,3-dihydro-1H-indol-1-yl)-7-fluoro-3-methyl-2-(2-(methylsulfonyl)phenyl)quinoline was obtained as a yellow glass. 1H NMR (400 MHz, chloroform-d) δ ppm 8.17-8.28 (1H, m), 7.94 and 8.08 (1H, m), 7.74-7.84 (1H, m), 7.63-7.74 (2H, m), 7.42-7.53 (1H, m), 7.29-7.40 (1H, m), 6.98-7.13 (1H, m), 6.21-6.39 (1H, m), 5.65 and 5.82 (1H, m), 3.94 and 3.66 (1H, m), 3.69-3.82 (5H, m), 3.15 (1H, m), 3.05-3.12 (3H, m), 2.84-3.05 (4H, m), 1.94 (2H, s), 1.47-1.55 (3H, m), 1.40-1.47 (3H, m). Mass Spectrum (ESI) m/e=546 (M+1).

Example 25

4-(1-(7-Fluoro-3-methyl-2-(2-(methylsulfonyl)phenyl)-4-quinolinyl)-3,3-dimethyl-2,3-dihydro-1H-pyrrolo[3,2-b]pyridin-6-yl)-2-pyrimidinamine 4-(6-Bromo-3,3-dimethyl-2,3-dihydro-1H-pyrrolo[3,2-b]pyridin-1-yl)-7-fluoro-3-methyl-2-(2-(methylsulfonyl)phenyl)quinoline

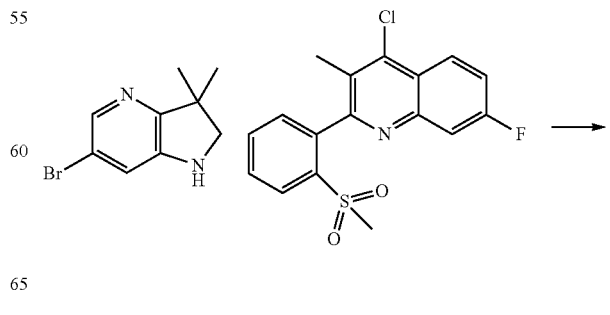

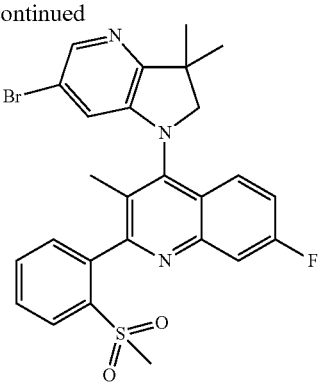

Prepared according to procedure L using 4-chloro-7-fluoro-3-methyl-2-(2-(methylsulfonyl)phenyl)quinoline (242 mg, 0.69 mmol) (described herein), 6-bromo-3,3-dimethyl-2,3-dihydro-1H-pyrrolo[3,2-b]pyridine (157 mg, 0.69 mmol) (described herein), 4.0 M hydrochloric acid in 1,4-dioxane (0.17 mL, 0.69 mmol), and NMP (1.2 mL). The reaction mixture was stirred and heated in a microwave at 150° C. for 120 min. Chromatography afforded 4-(6-bromo-3,3-dimethyl-2,3-dihydro-1H-pyrrolo[3,2-b]pyridin-1-yl)-7-fluoro-3-methyl-2-(2-(methylsulfonyl)-phenyl)quinoline as a dark oil. Mass Spectrum (ESI) m/e=541 (M+1).

1-(7-fluoro-3-methyl-2-(2-(methylsulfonyl)phenyl)quinolin-4-yl)-3,3-dimethyl-2,3-dihydro-1H-pyrrolo[3,2-b]pyridin-6-ylboronic acid

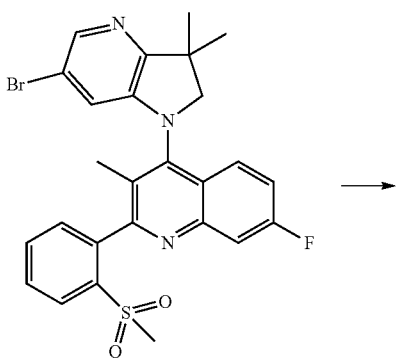

A stirred solution of 4-(6-bromo-3,3-dihydro-1H-pyrrolo[3,2-b]-pyridin-1-yl)-7-fluoro-3-methyl-2-(2-(methylsulfonyl)phenyl)quinoline (93 mg, 0.17 mmol) (described herein) in 1,4-dioxane (2.5 mL) was sparged with N₂ for 10 min. After this time bis(pinacolato)diboron (48.1 mg, 0.19 mmol), potassium acetate (25.3 mg, 0.26 mmol), and bis(tricyclohexylphosphine)palladium(o) (11.5 mg, 0.017 mmol) were added and the reaction heated at 100° C. for 16 h. The reaction was cooled to rt and partitioned between EtOAc and water. The organic layer was dried (MgSO₄) and concentrated, affording crude 1-(7-fluoro-3-methyl-2-(2-(methylsulfonyl)phenyl)quinolin-4-yl)-3,3-dimethyl-2,3-dihydro-1H-pyrrolo[3,2-b]pyridin-6-ylboronic acid. No further purification was attempted. Mass Spectrum (ESI) m/e=506 (M+1).

4-(1-(7-Fluoro-3-methyl-2-(2-(methylsulfonyl)phenyl)-4-quinolinyl)-3,3-dimethyl-2,3-dihydro-1H-pyrrolo[3,2-b]pyridin-6-yl)-2-pyrimidinamine

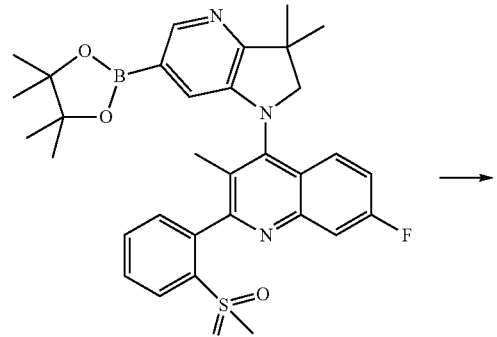

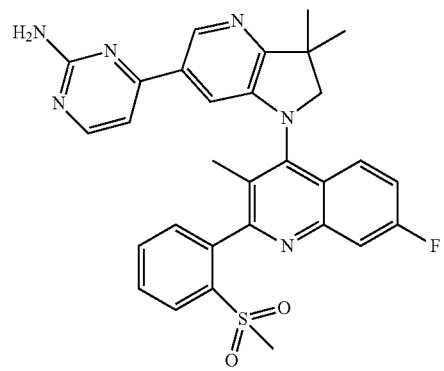

Prepared according to procedure P using 4-(3,3-dimethyl-6-(4,4,5,5-tetramethyl-1,3,2-dioxaborolan-2-yl)-2,3-dihydro-1H-pyrrolo[3,2-b]pyridin-1-yl)-7-fluoro-3-methyl-2-(2-(methylsulfonyl)phenyl)quinoline (131 mg, 0.22 mmol) (described herein), 2-amino-4-chloropyrimidine (28.9 mg, 0.22 mmol), bis(triphenylphosphine)palladium(ii) chloride (15.7 mg, 0.022 mmol), and sodium carbonate (70.9 mg, 0.67 mmol) in 1,4-dioxane (4.8 mL) and water (1.2 mL). The reaction mixture was heated in a microwave at 120° C. for 60 min. Purification afforded 4-(1-(7-fluoro-3-methyl-2-(2-(methylsulfonyl)phenyl)-4-quinolinyl)-3,3-dimethyl-2,3-dihydro-1H-pyrrolo[3,2-b]pyridin-6-yl)-2-pyrimidinamine as a yellow solid. 1H NMR (400 MHz, chloroform-d) δ ppm 8.55 (1H, m), 8.11-8.35 (2H, m), 8.04 (1H, m), 7.64-7.91 (3H, m), 7.44-7.57 (1H, m), 7.20-7.44 (2H, m), 6.70-7.05 (1H, m), 4.9-5.35 (2H, m), 3.35-3.96 (2H, m), 2.97-3.22 (3H, m), 1.87-2.05 (3H, m), 1.44-1.73 (6H, m). Mass Spectrum (ESI) m/e=555 (M+1).

Example 26

6-(7-Fluoro-3-methyl-4-(6-(4-morpholinyl)-2',3',5',6'-tetrahydrospiro[indole-3,4'-pyran]-1(2H)-yl)-2-quinolinyl)-2-pyridinol 4-Chloro-7-fluoro-2-(6-methoxypyridin-2-yl)-3-methylquinoline

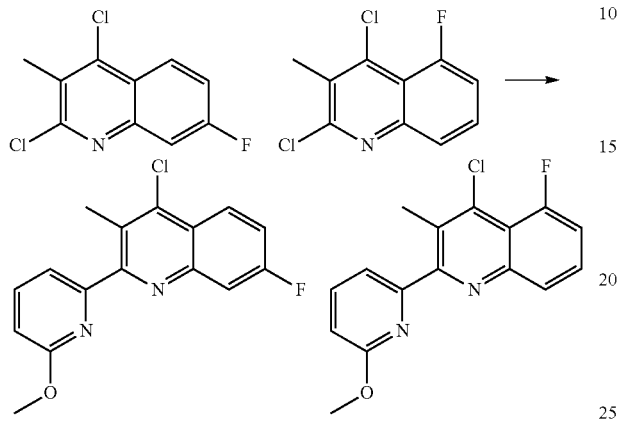

A solution of 2,4-dichloro-7-fluoro-3-methylquinoline (800 mg, 3.5 mmol) (in a mixture with the 5-F regioisomer; described herein), 2-methoxy-6-(tributylstannyl)pyridine (2.077 g, 5.2 mmol), tetrakis(triphenylphosphine)palladium (o) (402 mg, 0.35 mmol), and toluene (18.1 mL) was stirred at 97° C. for 16 h, then concentrated. Column chromatography afforded (in order of elution) 4-chloro-7-fluoro-2-(6-methoxypyridin-2-yl)-3-methylquinoline and 4-chloro-5-fluoro-2-(6-methoxypyridin-2-yl)-3-methylquinoline as white powders. Mass Spectrum (ESI) m/e=303 (M+1).

6-(7-Fluoro-3-methyl-4-(6-(4-morpholinyl)-2',3',5',6'-tetrahydrospiro[indole-3,4'-pyran]-1(2H)-yl)-2-quinolinyl)-2-pyridinol

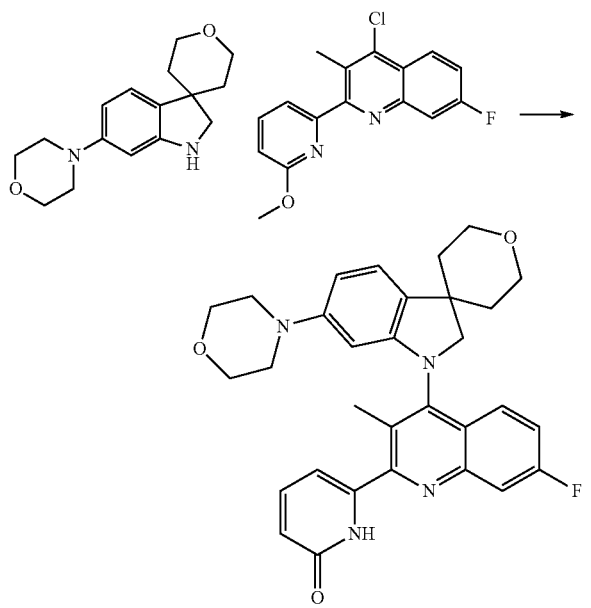

Prepared according to procedure L using 6-morpholino-2',3',5',6'-tetrahydrospiro-[indoline-3,4'-pyran] (87 mg, 0.32 mmol), 4.0M hydrochloric acid in 1,4-dioxane (66 µL, 0.25 mmol), 4-chloro-7-fluoro-2-(6-methoxypyridin-2-yl)-3-methylquinoline (80 mg, 0.25 mmol) (described herein), and NMP (440 µL), and heating in a microwave at 150° C. for 180 min. Purification afforded 6-(7-fluoro-3-methyl-4-(6-(4-morpholinyl)-2',3',5',6'-tetrahydrospiro[indole-3,4'-pyran]-1(2H)-yl)-2-quinolinyl)-2-pyridinol as a yellow solid. 1H NMR (400 MHz, chloroform-d) δ ppm 7.65-7.85 (2H, m), 7.48-7.61 (1H, m), 7.27-7.32 (1H, m), 7.15 (1H, d, J=8.2 Hz), 6.78 (1H, d, J=6.7 Hz), 6.73 (1H, d, J=9.4 Hz), 6.37 (1H, dd, J=8.2, 2.3 Hz), 5.56 (1H, d, J=2.3 Hz), 3.98-4.09 (2H, m), 3.88-3.98 (2H, m), 3.62-3.78 (4H, m), 3.47-3.61 (2H, m), 2.84-3.03 (4H, m), 2.51 (3H, s), 2.09-2.24 (2H, m), 1.83-1.93 (1H, m), 1.71-1.83 (1H, m). Mass Spectrum (ESI) m/e=527 (M+1).

Example 27

4-(3,3-Dimethyl-6-(4-morpholinyl)-2,3-dihydro-1H-pyrrolo[3,2-b]pyridin-1-yl)-7-fluoro-3-methyl-2-(2-(methylsulfonyl)phenyl)quinoline

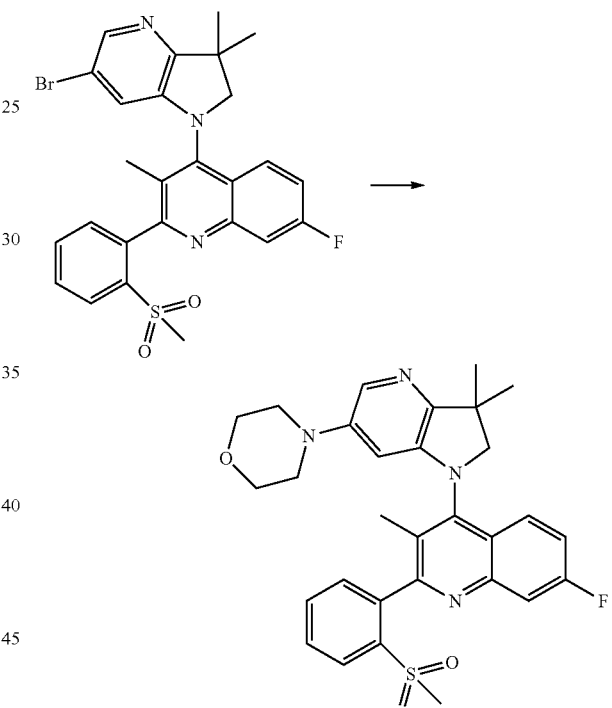

Prepared according to procedure N using 4-(6-bromo-3,3-dimethyl-2,3-dihydro-1H-pyrrolo[3,2-b]pyridin-1-yl)-7-fluoro-3-methyl-2-(2-(methylsulfonyl)phenyl)-quinoline (42 mg, 0.078 mmol) (described herein), morpholine (14 µL, 0.16 mmol), Pd$_2$dba$_3$ (5.0 mg, 5.4 µmol), 2-(dicyclohexylphosphino)-2,4,6-tri-1-propyl-1,1-biphenyl (5.6 mg, 0.012 mmol), and sodium tert-butoxide (15 mg, 0.155 mmol) in toluene (1.3 mL), and heating at 105° C. for 18 h. Purification afforded 4-(3,3-dimethyl-6-(4-morpholinyl)-2,3-dihydro-1H-pyrrolo[3,2-b]pyridin-1-yl)-7-fluoro-3-methyl-2-(2-(methylsulfonyl)phenyl)quinoline as a yellow powder. Compound is rotameric. 1H NMR (400 MHz, chloroform-d) δ ppm 8.15-8.29 (1H, m), 7.84-8.09 (1H, m), 7.77-7.83 (1H, m), 7.69-7.77 (2H, m), 7.55-7.69 (1H, m), 7.43-7.54 (1H, m), 7.31-7.43 (1H, m), 5.86 and 6.10 (1H, m), 4.05 (1H, m), 3.67-3.87 (5H, m), 3.14 (1H, m), 2.90-3.12 (6H, m), 2.00-2.16 (1H, m), 1.92 (2H, s), 1.46-1.68 (6H, m). Mass Spectrum (ESI) m/e=547 (M+1).

Example 28

6-(4-(3,3-Dimethyl-6-(4-morpholinyl)-2,3-dihydro-1H-pyrrolo-[3,2-b]pyridin-1-yl)-7-fluoro-3-methyl-2-quinolinyl)-2(1H)-pyridinone

6-(4-(6-Bromo-3,3-dimethyl-2,3-dihydro-1H-pyrrolo[3,2-b]pyridin-1-yl)-7-fluoro-3-methylquinolin-2-yl)pyridin-2(1H)-one

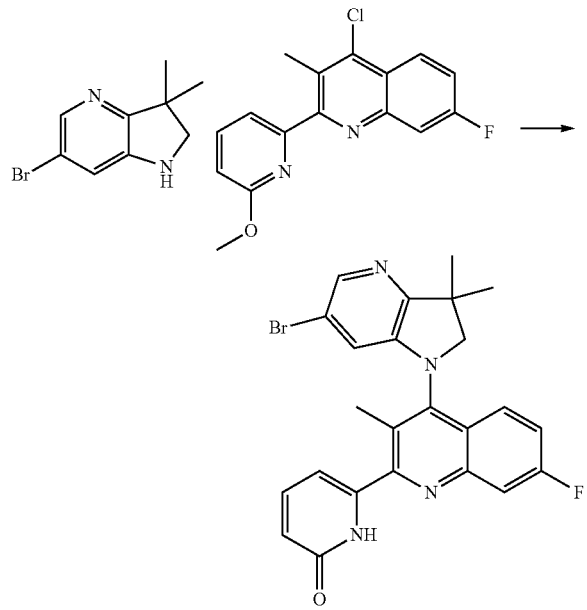

Prepared according to procedure L using 6-bromo-3,3-dimethyl-2,3-dihydro-1H-pyrrolo[3,2-b]pyridine (108 mg, 0.48 mmol) (described herein), 4.0M hydrochloric acid in 1,4-dioxane (100 µL, 0.40 mmol), 4-chloro-7-fluoro-2-(6-methoxypyridin-2-yl)-3-methylquinoline (120 mg, 0.40 mmol) (described herein), and NMP (660 µL). The reaction mixture was stirred and heated in a microwave at 150° C. for 180 min. Purification afforded 6-(4-(6-bromo-3,3-dimethyl-2,3-dihydro-1H-pyrrolo[3,2-b]pyridin-1-yl)-7-fluoro-3-methylquinolin-2-yl)pyridin-2(1H)-one as a yellow solid. Mass Spectrum (ESI) m/e=479 (M+1).

6-(4-(3,3-Dimethyl-6-(4-morpholinyl)-2,3-dihydro-1H-pyrrolo[3,2-b]pyridin-1-yl)-7-fluoro-3-methyl-2-quinolinyl)-2(1H)-pyridinone

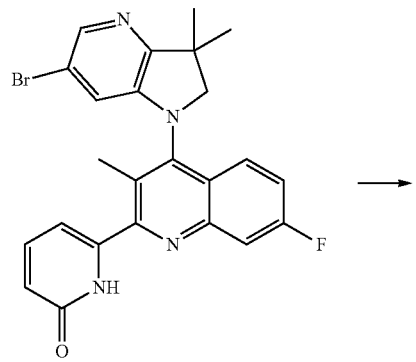

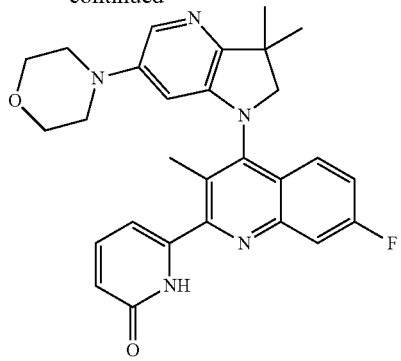

Prepared according to procedure N using 6-(4-(6-bromo-3,3-dimethyl-2,3-dihydro-1H-pyrrolo[3,2-b]pyridin-1-yl)-7-fluoro-3-methylquinolin-2-yl)pyridin-2(1H)-one (43.6 mg, 0.091 mmol), morpholine (0.016 mL, 0.18 mmol), Pd$_2$dba$_3$ (12.5 mg, 0.014 mmol), 2-(dicyclohexylphosphino)-2,4,6-tri-i-propyl-1,1-biphenyl (13.0 mg, 0.027 mmol), and sodium tert-butoxide (17.5 mg, 0.18 mmol) in toluene (1.5 mL). The reaction mixture was stirred 100° C. for 18 h. Purification afforded 6-(4-(3,3-dimethyl-6-(4-morpholinyl)-2,3-dihydro-1H-pyrrolo[3,2-b]pyridin-1-yl)-7-fluoro-3-methyl-2-quinolinyl)-2(1H)-pyridinone as a yellow solid. 1H NMR (400 MHz, chloroform-d) δ ppm 7.72-7.83 (2H, m), 7.65 (1H, d, J=2.7 Hz), 7.50-7.63 (1H, m), 7.29-7.36 (1H, m), 6.80 (2H, d, J=7.0 Hz), 5.68-5.82 (1H, m), 3.82 (2H, s), 3.64-3.78 (4H, m), 2.89-3.05 (4H, m), 2.51 (3H, s), 1.59 (3H, s), 1.55 (3H, s). Mass Spectrum (ESI) m/e=486 (M+1).

Example 29

1-(7-Fluoro-2-(6-methoxy-2-pyridinyl)-3-methyl-4-quinolinyl)-6-(4-morpholinyl)-1,2,2',3',5',6'-hexahydrospiro[indole-3,4'-pyran]

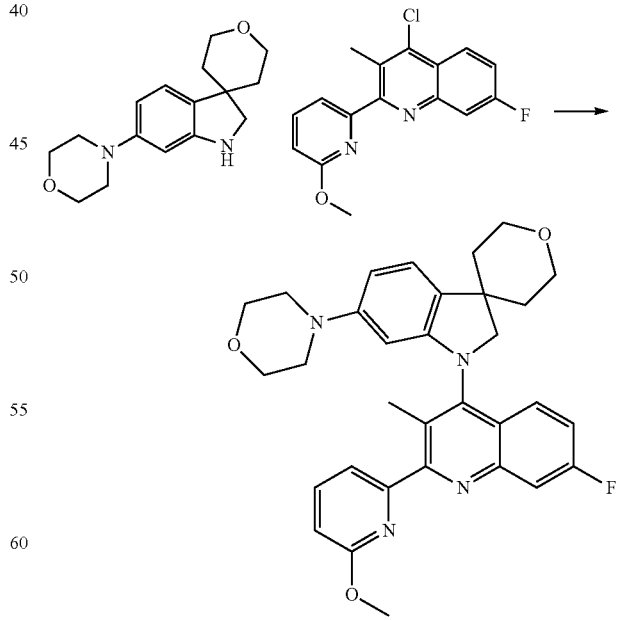

A mixture of 2-(dicyclohexylphosphino)-2',4',6'-tri-i-propyl-1,1'-biphenyl (26.9 mg, 0.056 mmol), Pd$_2$dba$_3$ (25.9 mg, 0.028 mmol), sodium tert-butoxide (45.4 mg, 0.47 mmol), 6-morpholino-2',3',5',6'-tetrahydrospiro[indoline-3,4'-pyran] (50 mg, 0.18 mmol) (described herein), and 4-chloro-7-fluoro-2-(6-methoxypyridin-2-yl)-3-methylquinoline (57 mg, 0.19 mmol) (described herein) in toluene (2 mL) was stirred at 100° C. for 18 h, then cooled to rt and concentrated. The resulting residue was taken up in EtOAc, washed with saturated aqueous sodium bicarbonate solution, 1 M NaOH, and brine, and the organic layer dried (MgSO$_4$) and concentrated. Column chromatography afforded 1-(7-fluoro-2-(6-methoxy-2-pyridinyl)-3-methyl-4-quinolinyl)-6-(4-morpholinyl)-1,2,2',3',5',6'-hexahydrospiro[indole-3,4'-pyran] as a yellow solid. 1H NMR (400 MHz, chloroform-d) δ ppm 7.75-7.90 (3H, m), 7.55 (1H, dd, J=7.2, 0.8 Hz), 7.22-7.27 (1H, m), 7.11-7.19 (1H, m), 6.85 (1H, dd, J=8.3, 0.9 Hz), 6.30-6.39 (1H, m), 5.64 (1H, d, J=2.2 Hz), 3.93-4.09 (7H, m), 3.67-3.79 (4H, m), 3.48-3.64 (2H, m), 2.91-3.05 (4H, m), 2.39-2.48 (3H, m), 2.09-2.24 (2H, m), 1.90 (1H, dt, J=13.8, 1.1 Hz), 1.76-1.86 (1H, m). Mass Spectrum (ESI) m/e=541 (M+1).

Example 30

1-(7-Fluoro-3-methyl-2-(3-(methylsulfonyl)phenyl)-4-quinolin-yl)-6-(4-morpholinyl)-1,2,2',3',5',6'-hexahydrospiro[indole-3,4'-pyran]

4-Chloro-7-fluoro-3-methyl-2-(3-(methylthio)phenyl)quinoline

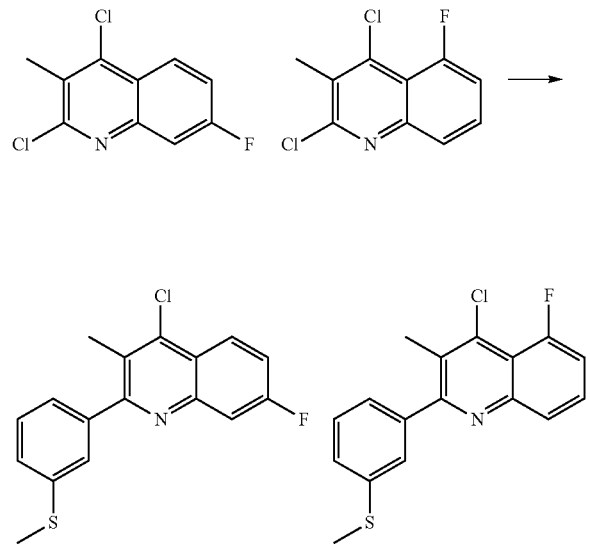

2,4-Dichloro-7-fluoro-3-methylquinoline (in a mixture with the 5-F regioisomer) (390 mg, 1.7 mmol) (described herein), 3-(methylthio)phenylboronic acid (370 mg, 2.2 mmol), tetrakis(triphenylphosphine)palladium(o) (98 mg, 0.085 mmol), and sodium carbonate (539 mg, 5.1 mmol) in acetonitrile (4.0 mL) and water (1.0 mL) were stirred and heated in a microwave at 100° C. for 60 min. The reaction mixture was then partitioned between EtOAc and water and washed with brine. The organic layer was dried (MgSO$_4$), concentrated, and purified by column chromatography to afford (in order of elution) 4-chloro-7-fluoro-3-methyl-2-(3-(methylthio)phenyl)quinoline and 4-chloro-5-fluoro-3-methyl-2-(3-(methylthio)-phenyl)quinoline as white powders. Mass Spectrum (ESI) m/e=318 (M+1).

4-Chloro-7-fluoro-3-methyl-2-(3-(methylsulfonyl)phenyl)quinoline

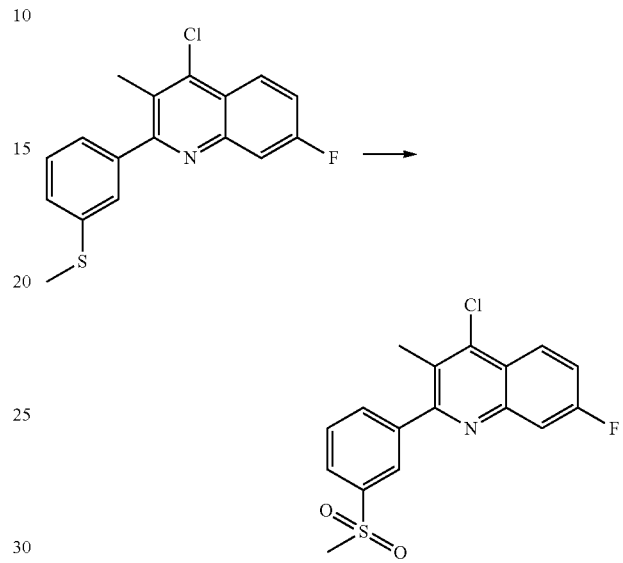

To a stirring solution of 4-chloro-7-fluoro-3-methyl-2-(3-(methylthio)phenyl)-quinoline (130 mg, 0.41 mmol) (described herein) in THF (5.0 mL) and water (1.0 mL) were sequentially added 4-methylmorpholine n-oxide (144 mg, 1.2 mmol) and osmium tetroxide (1.1 μL, 0.020 mmol). The reaction was stirred at rt for 6 h, then an additional 0.05 eq. osmium tetroxide was added and the reaction stirred for 18 more h. The reaction was then quenched with 10% aqueous sodium thiosulfate solution, concentrated, and partitioned between EtOAc and 10% aqueous sodium thiosulfate solution. The organic layer was washed with brine, dried (MgSO$_4$), and concentrated, affording 4-chloro-7-fluoro-3-methyl-2-(3-(methylsulfonyl)phenyl)quinoline. Mass Spectrum (ESI) m/e=350 (M+1).

1-(7-Fluoro-3-methyl-2-(3-(methylsulfonyl)phenyl)-4-quinolinyl)-6-(4-morpholinyl)-1,2,2',3',5',6'-hexahydrospiro[indole-3,4'-pyran]

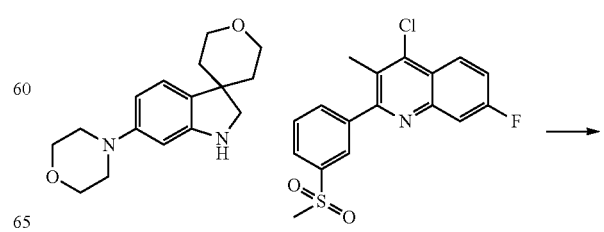

-continued

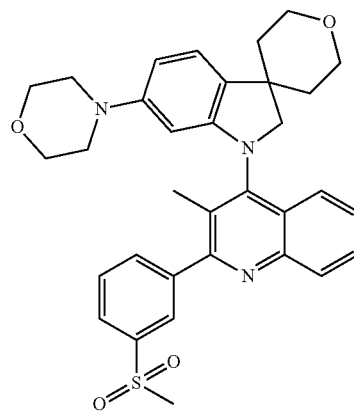

A mixture of 2-(dicyclohexylphosphino)-2,4,6-tri-i-propyl-1,1-biphenyl (24.5 mg, 0.051 mmol), Pd$_2$dba$_3$ (23.6 mg, 0.026 mmol), sodium tert-butoxide (49.5 mg, 0.52 mmol), 6-morpholino-2',3',5',6'-tetrahydrospiro[indoline-3,4'-pyran] (47.1 mg, 0.17 mmol) (described herein), and 4-chloro-7-fluoro-3-methyl-2-(3-(methylsulfonyl)phenyl)quinoline (60 mg, 0.17 mmol) (described herein) in toluene (1.7 mL) was stirred at 100° C. for 60 min, then cooled to rt and concentrated. The resulting residue was taken up in EtOAc, washed with saturated aqueous sodium bicarbonate solution, 1M NaOH, and brine, then the organic layer dried (MgSO$_4$) and concentrated. Column chromatography afforded 1-(7-fluoro-3-methyl-2-(3-(methylsulfonyl)phenyl)-4-quinolinyl)-6-(4-morpholinyl)-1,2,2',3',5',6'-hexahydrospiro[indole-3,4'-pyran] as a yellow solid. 1H NMR (400 MHz, chloroform-d) δ ppm 8.24 (1H, d, J=2.0 Hz), 8.07 (1H, d), 7.96 (1H, d), 7.76 (3H, m), 7.31 (1H, m), 7.15 (1H, d, J=8.2 Hz), 6.36 (1H, d), 5.59 (1H, s), 4.01-4.10 (2H, m), 3.91-4.01 (2H, m), 3.69-3.82 (4H, m), 3.51-3.63 (2H, m), 3.11-3.19 (3H, m), 2.97 (4H, d, J=4.7 Hz), 2.25-2.33 (3H, m), 2.10-2.24 (2H, m), 1.89 (1H, d), 1.80 (1H, d). Mass Spectrum (ESI) m/e=588 (M+1).

Example 31

1-(5,7-Difluoro-3-methyl-2-(2-pyridinyl)-4-quinolinyl)-6-(4-morpholinyl)-1,2,2',3',5',6'-hexahydrospiro[indole-3,4'-pyran]

Ethyl 3-(3,5-difluorophenylamino)-2-methyl-3-oxopropanoate

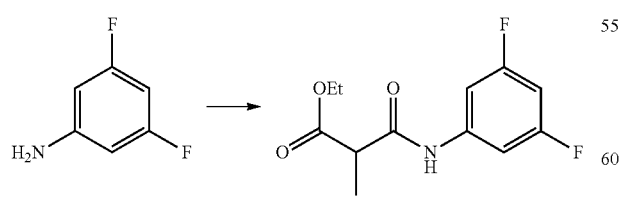

Prepared according to procedure A using diethyl 2-methylmalonate (34.5 mL, 205 mmol), pyridine (15.6 mL, 190 mmol), and 3,5-difluorobenzenamine (12.4 g, 96 mmol). The reaction was heated to 130° C. for 2 days. Purification afforded ethyl 3-(3,5-difluorophenylamino)-2-methyl-3-oxopropanoate. Mass Spectrum (ESI) m/e=258 (M+1).

3-(3,5-Difluorophenylamino)-2-methyl-3-oxopropanoic acid

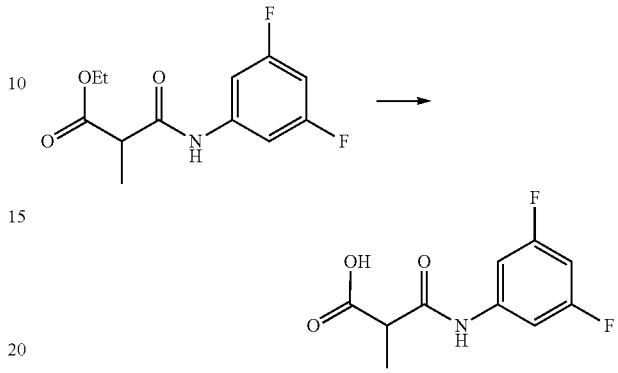

Prepared according to procedure B using ethyl 3-(3,5-difluorophenylamino)-2-methyl-3-oxopropanoate (11.4 g, 44.3 mmol) (described herein) in THF (40 mL), and sodium hydroxide (1.22 g, 53.2 mmol) in water (10 mL). The reaction was stirred at rt for 2 h, affording 3-(3,5-difluorophenylamino)-2-methyl-3-oxopropanoic acid. Mass Spectrum (ESI) m/e=230 (M+1).

5,7-Difluoro-3-methylquinoline-2,4(1H,3H)-dione

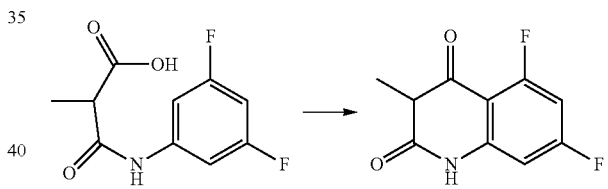

Prepared according to procedure C using 3-(3,5-difluorophenylamino)-2-methyl-3-oxopropanoic acid (6.70 g, 29.2 mmol) (described herein) in PPA (40 mL), affording 5,7-difluoro-3-methylquinoline-2,4(1H,3H)-dione. Mass Spectrum (ESI) m/e=212 (M+1).

2,4-Dichloro-5,7-difluoro-3-methylquinoline

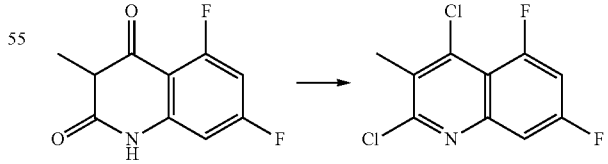

5,7-Difluoro-3-methylquinoline-2,4(1H,3H)-dione (5.20 g, 24.6 mmol) (described herein) was stirred in phosphoryl chloride (23.0 mL, 246 mmol) and heated at 100° C. for 6 h. The reaction was then quenched over ice and the product extracted with EtOAc, washed with brine, dried (MgSO$_4$), filtered, and concentrated. The resulting crude residue was

87 trituated with MeOH and dried, affording 2,4-dichloro-5,7-difluoro-3-methylquinoline. Mass Spectrum (ESI) m/e=248 (M+1).

4-Chloro-5,7-difluoro-3-methyl-2-(pyridin-2-yl)quinoline

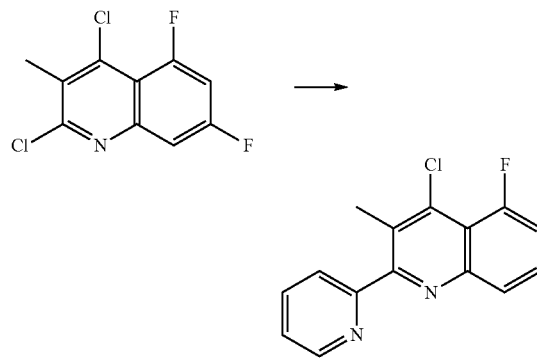

Prepared according to procedure E using 2,4-dichloro-5,7-difluoro-3-methylquinoline (1.94 g, 7.8 mmol) (described herein), 2-(tributylstannyl)pyridine (2.9 mL, 7.8 mmol), and tetrakis(triphenylphosphine)palladium(o) (0.69 g, 0.59 mmol) in toluene. The reaction was stirred at 100° C. for 18 h, then cooled to rt, concentrated, and the resulting residue triturated with hexanes. Column chromatography afforded 4-chloro-5,7-difluoro-3-methyl-2-(pyridin-2-yl)-quinoline as a white solid. Mass Spectrum (ESI) m/e=291 (M+1).

1-(5,7-Difluoro-3-methyl-2-(2-pyridinyl)-4-quinolinyl)-6-(4-morpholinyl)-1,2,2',3',5',6'-hexahydrospiro[indole-3,4'-pyran]

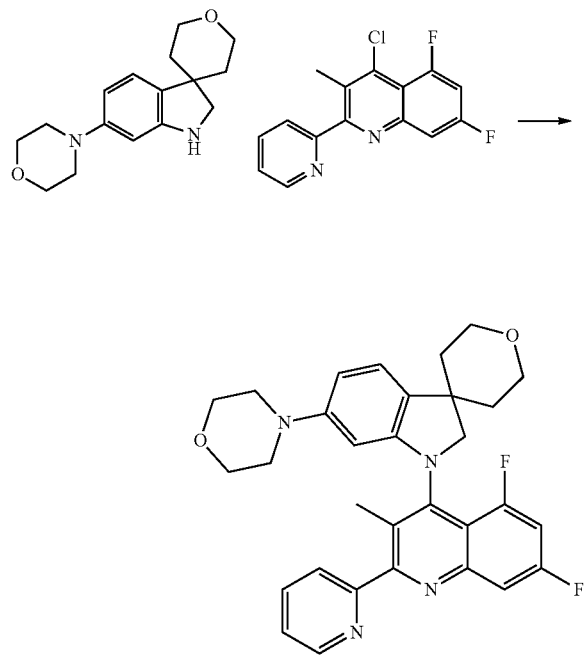

A mixture of 4-chloro-5,7-difluoro-3-methyl-2-(pyridin-2-yl)quinoline (60.7 mg, 0.21 mmol) (described herein),

88

6-morpholino-2',3',5',6'-tetrahydrospiro[indoline-3,4'-pyran] (68.7 mg, 0.25 mmol) (described herein), Pd$_2$dba$_3$ (28.7 mg, 0.031 mmol), 2-(dicyclohexylphosphino)-2,4,6-tri-i-propyl-1,1-biphenyl (29.9 mg, 0.063 mmol), and sodium tert-butoxide (60.2 mg, 0.626 mmol) in toluene (3 mL) was stirred at 100° C. for 22 h, then cooled to rt and concentrated. The resulting residue was taken up in EtOAc, washed with saturated aqueous sodium bicarbonate solution, 1 M NaOH, and brine, and the organic layer dried (MgSO$_4$) and concentrated. Chromatography afforded 1-(5,7-difluoro-3-methyl-2-(2-pyridinyl)-4-quinolinyl)-6-(4-morpholinyl)-1,2,2',3',5',6'-hexahydrospiro[indole-3,4'-pyran] as a yellow solid. 1H NMR (400 MHz, chloroform-d) δ ppm 8.71-8.79 (1H, m), 7.85-7.97 (2H, m), 7.65-7.74 (1H, m), 7.42 (1H, ddd, J=7.0, 5.0, 1.7 Hz), 7.09 (1H, d, J=8.2 Hz), 6.97 (1H, ddd, J=11.6, 8.9, 2.5 Hz), 6.25-6.34 (1H, m), 5.45-5.57 (1H, m), 3.98-4.09 (2H, m), 3.86-3.96 (2H, m), 3.69-3.82 (4H, m), 3.46-3.62 (2H, m), 2.91-3.05 (4H, m), 2.39 (3H, s), 2.06-2.24 (2H, m), 1.83-1.93 (1H, m), 1.72-1.83 (1H, m). Mass Spectrum (ESI) m/e=529 (M+1).

Example 32

4-(3,3-Dimethyl-6-(4-morpholinyl)-2,3-dihydro-1H-pyrrolo[3,2-b]pyridin-1-yl)-5-fluoro-3-methyl-2-(2-pyridinyl)quinoline 4-(6-Bromo-3,3-dimethyl-2,3-dihydro-1H-pyrrolo[3,2-b]pyridin-1-yl)-5-fluoro-3-methyl-2-(pyridin-2-yl)quinoline

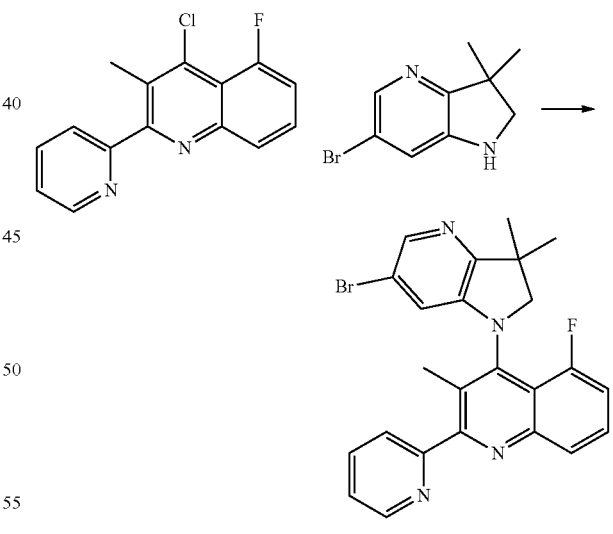

Prepared according to procedure M using 4-chloro-5-fluoro-3-methyl-2-(pyridin-2-yl)quinoline (86 mg, 0.32 mmol) (described herein), 6-bromo-3,3-dimethyl-2,3-dihydro-1H-pyrrolo[3,2-b]pyridine (86 mg, 0.38 mmol) (described herein), and sodium hydride (25 mg, 0.63 mmol) in DMF (10 mL). Reaction was heated at 60° C. for 18 h, affording 4-(6-bromo-3,3-dimethyl-2,3-dihydro-1H-pyrrolo[3,2-b]-pyridin-1-yl)-5-fluoro-3-methyl-2-(pyridin-2-yl)quinoline as an orange solid. Mass Spectrum (ESI) m/e=463 (M+1).

4-(3,3-Dimethyl-6-(4-morpholinyl)-2,3-dihydro-1H-pyrrolo[3,2-b]pyridin-1-yl)-5-fluoro-3-methyl-2-(2-pyridinyl)quinoline

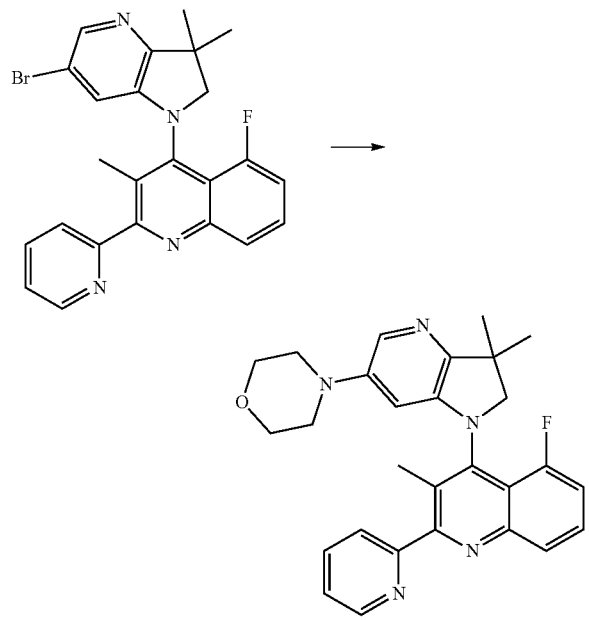

Prepared according to procedure N using 4-(6-bromo-3,3-dimethyl-2,3-dihydro-1H-pyrrolo[3,2-b]pyridin-1-yl)-5-fluoro-3-methyl-2-(pyridin-2-yl)quinoline (98.2 mg, 0.21 mmol) (described herein), morpholine (37 mg, 0.42 mmol), Pd$_2$dba$_3$ (29.1 mg, 0.032 mmol), 2-(dicyclohexylphosphino)-2,4,6-tri-i-propyl-1,1-biphenyl (30.3 mg, 0.064 mmol), and sodium tert-butoxide (50.9 mg, 0.53 mmol) in toluene (2.1 mL). The reaction mixture was stirred at 100° C. for 14 h. Purification afforded 4-(3,3-dimethyl-6-(4-morpholinyl)-2,3-dihydro-1H-pyrrolo[3,2-b]pyridin-1-yl)-5-fluoro-3-methyl-2-(2-pyridinyl)quinoline as a yellow solid. 1H NMR (400 MHz, chloroform-d) δ ppm 8.75 (1H, dt, J=4.8, 1.5 Hz), 8.03 (1H, dd, J=8.5, 1.3 Hz), 7.85-7.97 (2H, m), 7.58-7.68 (1H, m), 7.50-7.57 (1H, m), 7.36-7.45 (1H, m), 7.10-7.22 (1H, m), 5.70-5.80 (1H, m), 3.86 (1H, dd, J=8.8, 1.6 Hz), 3.66-3.78 (5H, m), 2.92-3.05 (4H, m), 2.40-2.50 (3H, m), 1.54-1.65 (3H, m), 1.45-1.54 (3H, m). Mass Spectrum (ESI) m/e=470 (M+1).

Example 33

2-(2,5-Difluorophenyl)-4-(3,3-dimethyl-6-(4-morpholinyl)-2,3-dihydro-1H-indol-1-yl)-7-fluoro-3-methylquinoline

4-Chloro-2-(2,5-difluorophenyl)-7-fluoro-3-methylquinoline

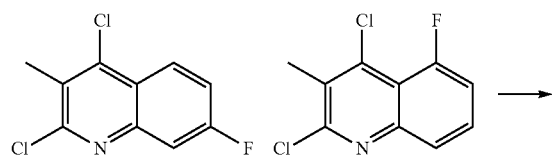

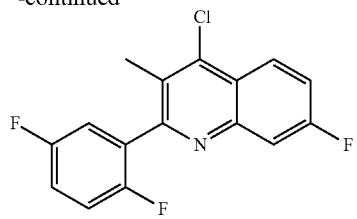

A solution of 2,4-dichloro-7-fluoro-3-methylquinoline (300 mg, 1.30 mmol) (in a mixture with the 5-F regioisomer; described herein), 2,5-difluorophenylboronic acid (268 mg, 1.70 mmol), tetrakis(triphenylphosphine)palladium(o) (151 mg, 0.130 mmol), and sodium carbonate (69 mg, 6.52 mmol) in acetonitrile (9.7 mL) and water (4.9 mL) was stirred and heated in a microwave at 100° C. for 120 min. The reaction mixture was then partitioned between EtOAc and water, and the organic layer was washed with brine, dried (MgSO$_4$), and concentrated. Column chromatography of the crude product afforded 4-chloro-2-(2,5-difluorophenyl)-7-fluoro-3-methylquinoline) as a white solid. Mass Spectrum (ESI) m/e=308 (M+1).

2-(2,5-Difluorophenyl)-7-fluoro-4-(6-iodo-3,3-dimethylindolin-1-yl)-3-methylquinoline

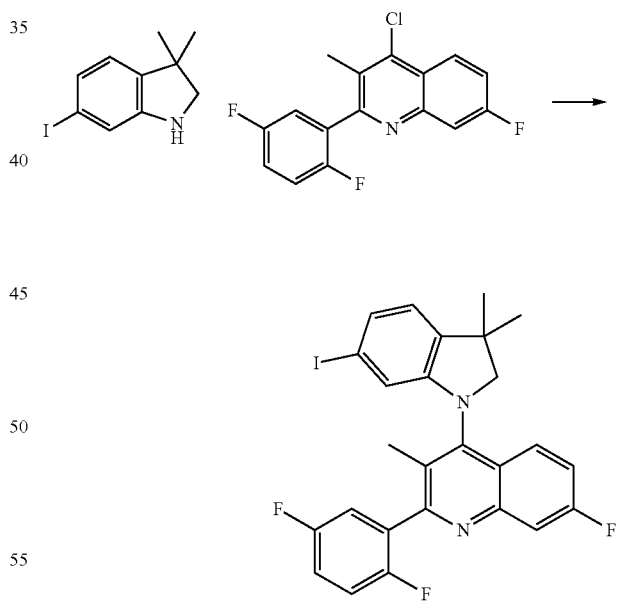

Prepared according to procedure L using 4-chloro-2-(2,5-difluorophenyl)-7-fluoro-3-methylquinoline (150 mg, 0.49 mmol) (described herein), 6-iodo-3,3-dimethylindoline (160 mg, 0.59 mmol) (described herein), and 4.0 hydrochloric acid in 1,4-dioxane (120 μL, 0.49 mmol) in NMP (810 μL). The reaction mixture was stirred and heated at 150° C. for 3 h. Purification afforded 2-(2,5-difluorophenyl)-7-fluoro-4-(6-iodo-3,3-dimethylindolin-1-yl)-3-methylquinoline as a yellow solid. Mass Spectrum (ESI) m/e=545 (M+1).

2-(2,5-Difluorophenyl)-4-(3,3-dimethyl-6-(4-morpholinyl)-2,3-dihydro-1H-indol-1-yl)-7-fluoro-3-methylquinoline

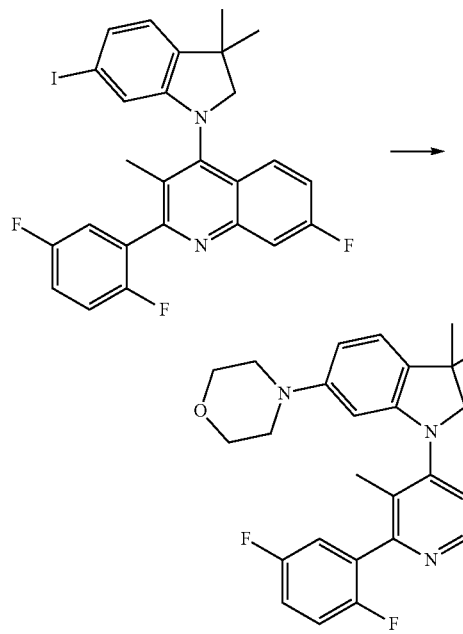

Prepared according to procedure N using 2-(2,5-difluorophenyl)-7-fluoro-4-(6-iodo-3,3-dimethylindolin-1-yl)-3-methylquinoline (166 mg, 0.31 mmol) (described herein), morpholine (53.1 μL, 0.61 mmol), Pd₂dba₃ (41.9 mg, 0.046 mmol), dicyclohexyl(2',4',6'-triisopropylbiphenyl-2-yl)phosphine (43.6 mg, 0.091 mmol), and sodium 2-methylpropan-2-olate (88 mg, 0.915 mmol) in toluene (3.0 mL). The reaction mixture was stirred at 105° C. for 1 h. Purification afforded 2-(2,5-difluorophenyl)-4-(3,3-dimethyl-6-(4-morpholinyl)-2,3-dihydro-1H-indol-1-yl)-7-fluoro-3-methylquinoline as a yellow oil. 1H NMR (500 MHz, chloroform-d) δ ppm 7.88-7.99 (1H, m), 7.76-7.84 (1H, m), 7.27-7.35 (2H, m), 7.16 (2H, m), 7.09 (1H, d, J=8.1 Hz), 6.30-6.38 (1H, d), 5.57-5.69 (1H, s), 3.75 (6H, m), 2.98 (4H, d, J=2.4 Hz), 2.18 (3H, s), 1.52 (3H, s), 1.46 (3H, s). Mass Spectrum (ESI) m/e=504 (M+1).

Example 34

2-(3,5-Bis(trifluoromethyl)phenyl)-4-(3,3-dimethyl-6-(4-morpholinyl)-2,3-dihydro-1H-indol-1-yl)-7-fluoro-3-methylquinoline

2-(3,5-bis(Trifluoromethyl)phenyl)-4-chloro-7-fluoro-3-methylquinoline and 2-(3,5-bis(Trifluoromethyl)phenyl)-4-chloro-5-fluoro-3-methylquinoline

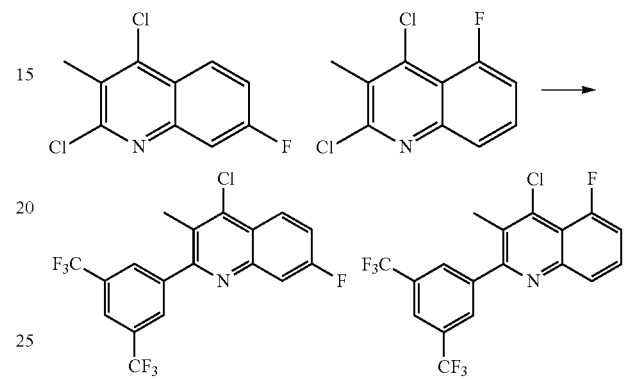

A solution of 2,4-dichloro-7-fluoro-3-methylquinoline (300 mg, 1.30 mmol) (in a mixture with the 5-F regioisomer; described herein), 3,5-bis(trifluoromethyl)phenylboronic acid (437 mg, 1.70 mmol), tetrakis(triphenylphosphine)palladium(o) (151 mg, 0.13 mmol), and sodium carbonate (415 mg, 3.91 mmol) in toluene (4.7 mL) and water (1.9 mL) was stirred at 95° C. for 4 h. After purification a mixture of 2-(3,5-bis(trifluoromethyl)phenyl)-4-chloro-7-fluoro-3-methylquinoline and 2-(3,5-bis(trifluoromethyl)phenyl)-4-chloro-5-fluoro-3-methylquinoline was obtained as a white solid. Mass Spectrum (ESI) m/e=408 (M+1).

2-(3,5-bis(Trifluoromethyl)phenyl)-7-fluoro-4-(6-iodo-3,3-dimethylindolin-1-yl)-3-methylquinoline and 2-(3,5-bis(trifluoromethyl)phenyl)-5-fluoro-4-(6-iodo-3,3-dimethylindolin-1-yl)-3-methylquinoline

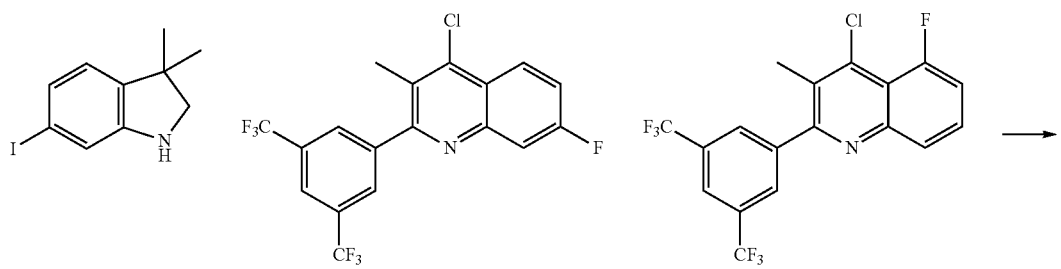

-continued

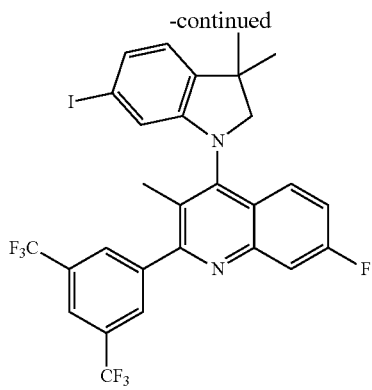

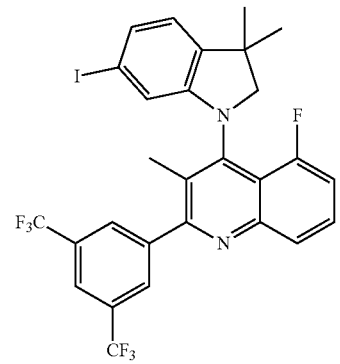

Prepared according to procedure L using a mixture of 2-(3,5-bis(trifluoromethyl)-phenyl)-4-chloro-7-fluoro-3-methylquinoline and 2-(3,5-bis(trifluoromethyl)-phenyl)-4-chloro-5-fluoro-3-methylquinoline (199 mg, 0.49 mmol) (described herein), 6-iodo-3,3-dimethylindoline (160 mg, 0.59 mmol) (described herein), 4.0M hydrochloric acid in 1,4-dioxane (120 µL, 0.49 mmol), and NMP (0.813 mL). The reaction mixture was heated in a microwave at 150° C. for 4 h, and subsequent purification afforded a mixture of 2-(3,5-bis(trifluoromethyl)phenyl)-7-fluoro-4-(6-iodo-3,3-dimethylindolin-1-yl)-3-methylquinoline and 2-(3,5-bis(trifluoromethyl)phenyl)-5-fluoro-4-(6-iodo-3,3-dimethylindolin-1-yl)-3-methylquinoline as a yellow solid. Mass Spectrum (ESI) m/e=645 (M+1).

2-(3,5-bis(Trifluoromethyl)phenyl)-4-(3,3-dimethyl-6-(4-morpholinyl)-2,3-dihydro-1H-indol-1-yl)-7-fluoro-3-methylquinoline Prepared according to procedure N using 2-(3,5-bis(trifluoromethyl)phenyl)-7-fluoro-4-(6-iodo-3,3-dimethylindolin-1-yl)-3-methylquinoline (in a mixture with the 5-F regioisomer; described herein) (160 mg, 0.25 mmol), morpholine (43 µL, 0.50 mmol), Pd$_2$dba$_3$ (34.1 mg, 0.037 mmol), 2-(dicyclohexylphosphino)-2,4,6-tri-i-propyl-1,1-biphenyl (35.5 mg, 0.074 mmol), and sodium tert-butoxide (71.6 mg, 0.745 mmol) in toluene (2.5 mL). The reaction was stirred at 105° C. for 1 h. Purification afforded 2-(3,5-bis(trifluoromethyl)phenyl)-4-(3,3-dimethyl-6-(4-morpholinyl)-2,3-dihydro-1H-indol-1-yl)-7-fluoro-3-methylquinoline as a yellow oil. 1H NMR (400 MHz, chloroform-d) δ ppm 8.12 (2H, s), 8.00 (1H, s), 7.84-7.92 (1H, m), 7.80 (1H, ddd, J=9.5, 2.1, 1.0 Hz), 7.28-7.31 (1H, m), 7.10 (1H, dd, J=8.1, 1.1 Hz), 6.31-6.39 (1H, m), 5.57-5.64 (1H, m), 3.69-3.84 (6H, m), 2.93-3.00 (4H, m), 2.30 (3H, s), 1.53 (3H, s), 1.47 (3H, s). Mass Spectrum (ESI) m/e=604 (M+1).

Example 35

2-(3,5-bis(Trifluoromethyl)phenyl)-4-(3,3-dimethyl-6-(4-morpholinyl)-2,3-dihydro-1H-indol-1-yl)-5-fluoro-3-methylquinoline

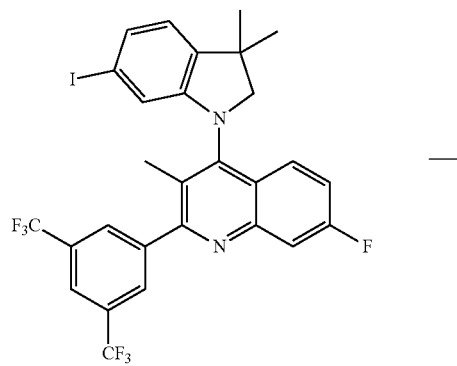

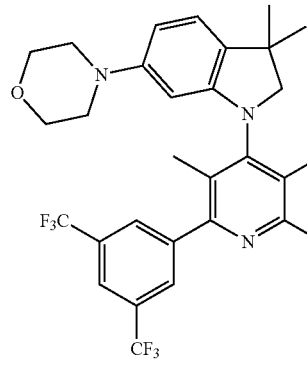

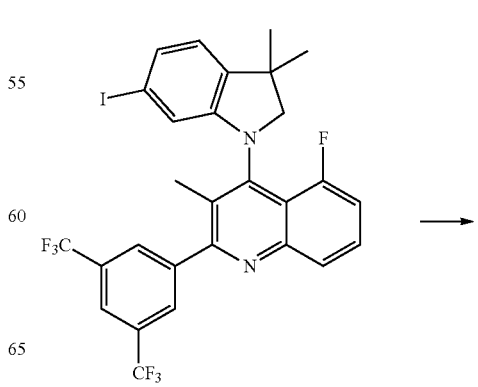

-continued

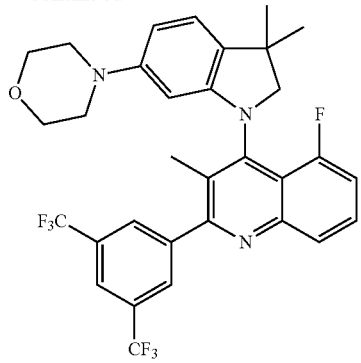

Prepared according to procedure N using 2-(3,5-bis(trifluoromethyl)phenyl)-5-fluoro-4-(6-iodo-3,3-dimethylindolin-1-yl)-3-methylquinoline (in a mixture with the 7-F regioisomer; described herein) (160 mg, 0.25 mmol), morpholine (43 μL, 0.50 mmol), $Pd_2dba_3$ (34.1 mg, 0.037 mmol), 2-(dicyclohexylphosphino)-2,4,6-tri-i-propyl-1,1-biphenyl (35.5 mg, 0.074 mmol), and sodium tert-butoxide (71.6 mg, 0.745 mmol) in toluene (2.5 mL). The reaction was stirred at 105° C. for 1 h. Purification afforded 2-(3,5-bis(trifluoromethyl)phenyl)-4-(3,3-dimethyl-6-(4-morpholinyl)-2,3-dihydro-1H-indol-1-yl)-5-fluoro-3-methylquinoline as a yellow oil. 1H NMR (400 MHz, chloroform-d) δ ppm 8.15 (2H, s), 8.00 (2H, t), 7.65 (1H, m), 7.28 (1H, m), 7.24 (1H, m), 7.17 (1H, m), 7.07 (1H, m), 3.62-3.95 (6H, m), 2.81-2.31 (4H, m), 2.35 (3H, s), 1.51 (3H, s), 1.45 (3H, s). Mass Spectrum (ESI) m/e=604 (M+1).

Example 36

5-Chloro-4-(3,3-dimethyl-6-(4-morpholinyl)-2,3-dihydro-1H-indol-1-yl)-2-(2-fluorophenyl)-3-methylquinoline 5-Chloro-2-(2-fluorophenyl)-4-(6-iodo-3,3-dimethylindolin-1-yl)-3-methylquinoline

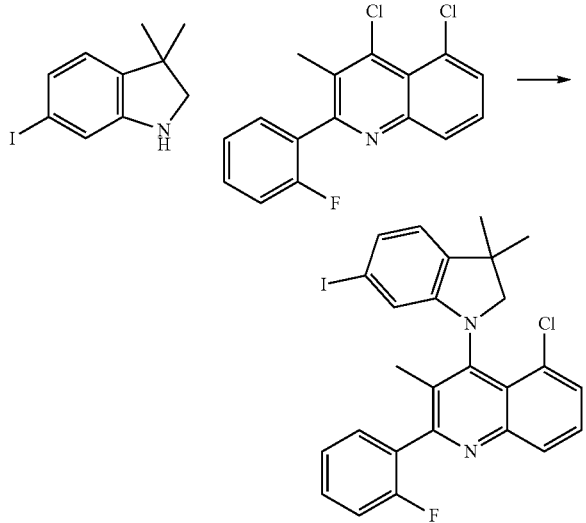

To a stirring solution of 6-iodo-3,3-dimethylindoline (64.2 mg, 0.24 mmol) (described herein) in dry DMF (4.9 mL) at 0° C. was added sodium hydride (12 mg, 0.29 mmol). The mixture was stirred for 5 min as it warmed to rt, then 4,5-dichloro-2-(2-fluorophenyl)-3-methylquinoline (60 mg, 0.20 mmol) (described herein) was added and the reaction slowly heated to 50° C. The reaction was stirred at 50° C. for 2 h, then heated further to 80° C. and stirred for 18 more h. The reaction was quenched with 10% aqueous sodium carbonate solution and partitioned between EtOAc and water. The organic layer was washed with 5% LiCl, dried ($MgSO_4$), and concentrated. Column chromatography afforded 5-chloro-4-(3,3-dimethyl-6-(4-morpholinyl)-2,3-dihydro-1H-indol-1-yl)-2-(2-fluorophenyl)-3-methylquinoline as a yellow glass. Mass Spectrum (ESI) m/e=453 (M+1).

5-Chloro-4-(3,3-dimethyl-6-(4-morpholinyl)-2,3-dihydro-1H-indol-1-yl)-2-(2-fluorophenyl)-3-methylquinoline

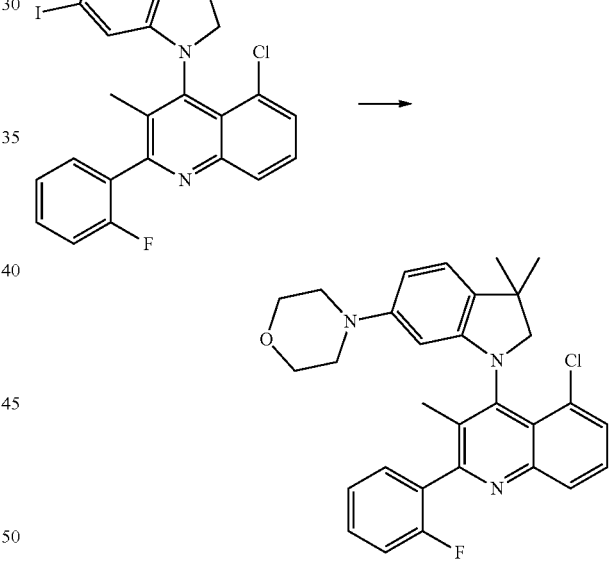

Prepared according to procedure N using 5-chloro-2-(2-fluorophenyl)-4-(6-iodo-3,3-dimethylindolin-1-yl)-3-methylquinoline (14.4 mg, 0.027 mmol) (described herein), morpholine (5 μL, 0.05 mmol), $Pd_2dba_3$ (3.64 mg, 4.0 μmol), 2-(dicyclohexylphosphino)-2',4',6'-tri-i-propyl-1,1'-biphenyl (3.79 mg, 8.0 μmol), and sodium tert-butoxide (7.65 mg, 0.080 mmol) in toluene (1.0 mL). The reaction mixture was stirred at 100° C. for 1 h. Purification afforded 5-chloro-4-(3,3-dimethyl-6-(4-morpholinyl)-2,3-dihydro-1H-indol-1-yl)-2-(2-fluorophenyl)-3-methylquinoline as a yellow solid. 1H NMR (400 MHz, chloroform-d) δ ppm 8.12 (1H, dd, J=6.5, 3.1 Hz), 7.55-7.69 (3H, m), 7.41-7.52 (1H, m), 7.30-7.38 (1H, m), 7.14-7.23 (1H, m), 7.04 (1H, d, J=8.0 Hz), 6.25 (1H, d), 5.59 (1H, d), 3.98-4.08 (1H, m), 3.76 (4H, br. s.), 3.54 (1H, d, J=1.8 Hz), 3.01 (4H, br. s.), 2.12-2.25 (3H, m), 1.47-1.55 (3H, m), 1.42 (3H, s). Mass Spectrum (ESI) m/e=502 (M+1).

Example 37

4-(3,3-Dimethyl-6-(4-morpholinyl)-2,3-dihydro-1H-pyrrolo[3,2-b]pyridin-1-yl)-5-fluoro-3,8-dimethyl-2-(2-pyridinyl)quinoline Ethyl 3-(5-fluoro-2-methylphenylamino)-2-methyl-3-oxopropanoate

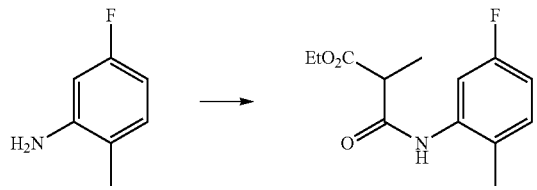

The ester was prepared according to procedure A using diethyl 2-methylmalonate (6.18 mL, 36.0 mmol), pyridine (3.88 mL, 47.9 mmol) and 5-fluoro-2-methyl aniline (3.00 g, 23.97 mmol). Heating continued for 4 days. The residue was purified by column chromatography on silica gel (0-30% EtOAc/hexanes) to give ethyl 3-(5-fluoro-2-methylphenylamino)-2-methyl-3-oxopropanoate as a tan solid. Mass Spectrum (ESI) m/e=254.2, (M+1).

3-(5-Fluoro-2-methylphenylamino)-2-methyl-3-oxopropanoic acid

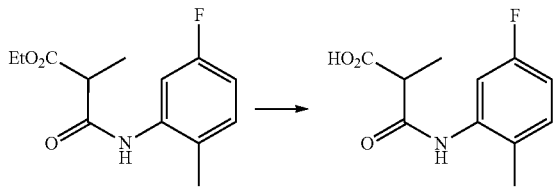 [SMILES: CCOC(=O)C(C)C(=O)Nc1cc(F)ccc1C ; Cc1ccc(F)cc1NC(=O)C(C)C(=O)O]

The acid was prepared according to procedure B using ethyl 3-(5-fluoro-2-methylphenylamino)-2-methyl-3-oxopropanoate (2.45 g, 9.67 mmol) in THF (9.67 mL). The crude product was used without further purification. Mass Spectrum (ESI) m/e=226.0, (M+1).

5-Fluoro-3,8-dimethylquinoline-2,4-diol

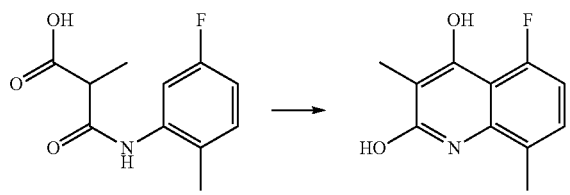 [SMILES: Cc1ccc(F)cc1NC(=O)C(C)C(=O)O ; Cc1c(O)nc2c(C)ccc(F)c2c1O]

The diol was prepared according to procedure C using (5-fluoro-2-methylphenylamino)-2-methyl-3-oxopropanoic acid (2.08 g, 9.24 mmol) and PPA (10 mL, 9.24 mmol) to give 5-fluoro-3,8-dimethylquinoline-2,4-diol. Mass Spectrum (ESI) m/e=208.1, (M+1).

2,4-Dichloro-5-fluoro-3,8-dimethylquinoline

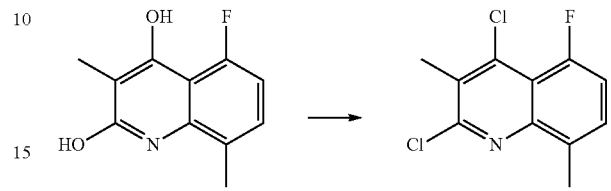

The dichloride was prepared according to procedure D using 5-fluoro-3,8-dimethylquinoline-2,4-diol (1.9 g, 9.17 mmol) and phosphorus oxychloride (8.55 mL, 92 mmol) to give 2,4-dichloro-5-fluoro-3,8-dimethylquinoline. Mass Spectrum (ESI) m/e=244.1, (M+1).

4-Chloro-5-fluoro-3,8-dimethyl-2-(pyridin-2-yl)quinoline

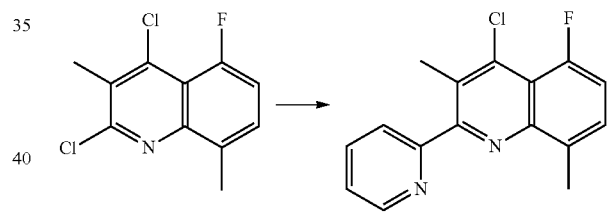

The chloride was prepared according to procedure E using 2,4,6-trichloro-7-fluoro-3-methylquinoline (0.500 g, 1.9 mmol), 2-(tributylstannyl)pyridine (0.765 mL, 2.079 mmol), palladium tetrakistriphenylphosphine (0.22 g, 0.19 mmol) in toluene (1.9 mL) to give 4-chloro-5-fluoro-3,8-dimethyl-2-(pyridin-2-yl)quinoline as a white solid. Mass Spectrum (ESI) m/e=307.0, (M+1).

4-(3,3-Dimethyl-6-(4-morpholinyl)-2,3-dihydro-1H-pyrrolo[3,2-b]pyridin-1-yl)-5-fluoro-3,8-dimethyl-2-(2-pyridinyl)quinoline

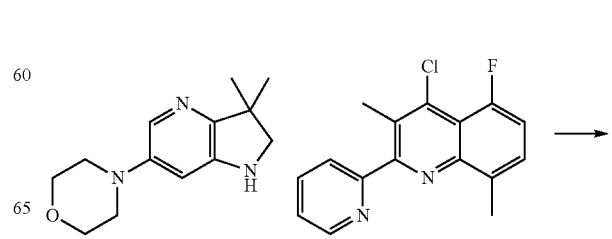

-continued

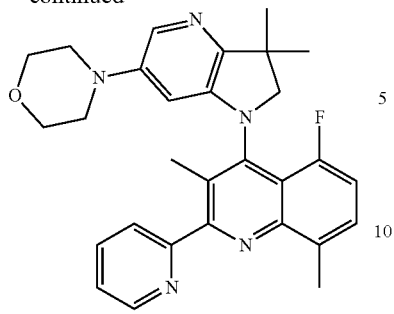

A mixture of 4-chloro-5-fluoro-3,8-dimethyl-2-(pyridin-2-yl)quinoline (30 mg, 0.11 mmol) (described herein), 4-(3,3-dimethyl-2,3-dihydro-1H-pyrrolo[3,2-b]-pyridin-6-yl)morpholine (29.3 mg, 0.13 mmol) (described herein), Pd$_2$dba$_3$ (9.58 mg, 10.5 µmol), 2-(dicyclohexylphosphino)-2',4',6'-tri-i-propyl-1,1'-biphenyl (9.98 mg, 0.021 mmol), sodium tert-butoxide (30.2 mg, 0.314 mmol), and toluene (1.0 mL) was stirred at 100° C. for 18 h, then cooled to rt and concentrated. The resulting residue was taken up in EtOAc, washed with saturated aqueous sodium bicarbonate solution, 1M NaOH, and brine, and the organic layer dried (MgSO$_4$) and concentrated. Chromatography afforded 4-(3,3-dimethyl-6-(4-morpholinyl)-2,3-dihydro-1H-pyrrolo[3,2-b]pyridin-1-yl)-5-fluoro-3,8-dimethyl-2-(2-pyridin-yl)quinoline as a yellow solid. 1H NMR (400 MHz, chloroform-d) δ ppm 8.69-8.76 (1H, m), 8.02-8.07 (1H, m), 7.92 (1H, td, J=7.7, 1.9 Hz), 7.50-7.56 (1H, m), 7.43-7.50 (1H, m), 7.34-7.43 (1H, m), 7.05 (1H, dd, J=12.2, 7.9 Hz), 5.70-5.75 (1H, m), 3.86 (1H, dt, J=8.9, 0.7 Hz), 3.68-3.79 (5H, m), 2.93-3.05 (4H, m), 2.79 (3H, s), 2.50 (3H, s), 1.56 (3H, s), 1.50 (3H, s). Mass Spectrum (ESI) m/e=484 (M+1).

Example 38

4-(3,3-Dimethyl-6-(4-morpholinyl)-2,3-dihydro-1H-pyrrolo[3,2-b]pyridin-1-yl)-7-fluoro-2-(2-pyridinyl)-3-quinolinecarbonitrile 7-Fluoro-4-hydroxy-2-oxo-1,2-dihydroquinoline-3-carbonitrile

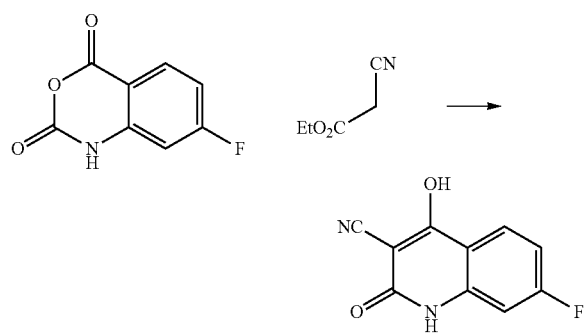

A mixture of 7-fluoro-1H-benzo[d][1,3]oxazine-2,4-dione (515 mg, 2.8 mmol) (commercially available through AstaT-ech™, Inc.), ethyl 2-cyanoacetate (303 µL, 2.8 mmol), and triethylamine (793 µL, 5.7 mmol) in DMF (1.4 mL) was stirred at 120° C. for 6 h. The reaction mixture was then concentrated. Upon addition of 1M HCl a precipitate formed, which was isolated by filtration and dried under vacuum, affording 7-fluoro-4-hydroxy-2-oxo-1,2-dihydroquinoline-3-carbonitrile. Mass Spectrum (ESI) m/e=205 (M+1).

2,4-Dichloro-7-fluoroquinoline-3-carbonitrile

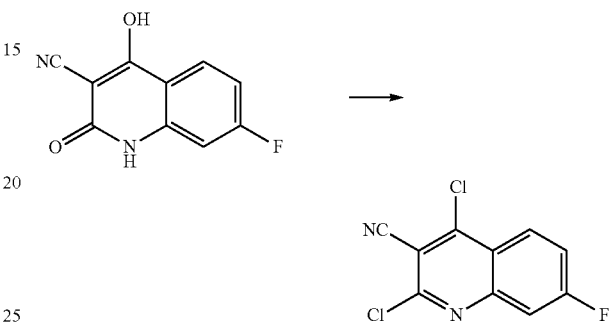

A suspension of 7-fluoro-4-hydroxy-2-oxo-1,2-dihydroquinoline-3-carbonitrile (250 mg, 1.2 mmol) (described herein), phosphorus oxychloride (1.1 mL, 12.3 mmol), and acetonitrile (1.75 mL) was stirred at 75° C. for 18 h, then quenched over ice, diluted with water, and extracted with EtOAc. The organic layer was dried (MgSO$_4$) and concentrated, affording 2,4-dichloro-7-fluoroquinoline-3-carbonitrile. Mass Spectrum (ESI) m/e=241 (M+1).

4-Chloro-7-fluoro-2-(pyridin-2-yl)quinoline-3-carbonitrile

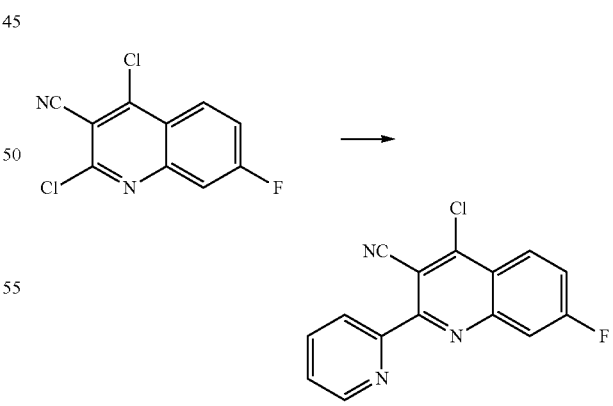

Prepared according to procedure E using 2,4-dichloro-7-fluoroquinoline-3-carbonitrile (230 mg, 0.95 mmol) (described herein), 2-(tributylstannyl)pyridine (0.42 mL, 1.15 mmol), tetrakis(triphenylphosphine)palladium(o) (110 mg, 0.095 mmol), and toluene (4.1 mL). The reaction mixture was stirred at 100° C. for 18 h, and subsequent purification afforded 4-chloro-7-fluoro-2-(pyridin-2-yl)quinoline-3-carbonitrile as an off-white solid. Mass Spectrum (ESI) m/e=284 (M+1).

4-(3,3-Dimethyl-6-(4-morpholinyl)-2,3-dihydro-1H-pyrrolo[3,2-b]pyridin-1-yl)-7-fluoro-2-(2-pyridinyl)-3-quinolinecarbonitrile

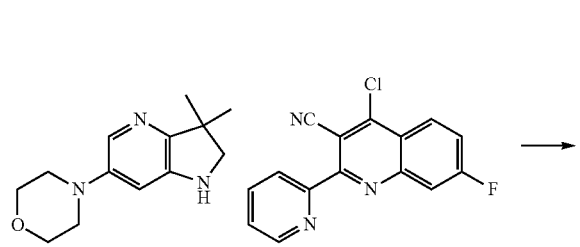

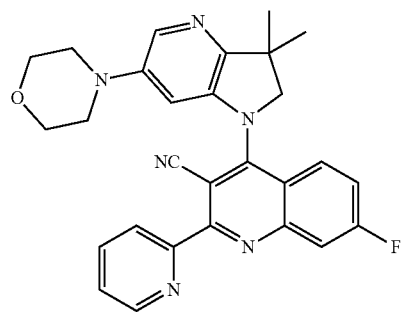

A mixture of 4-chloro-7-fluoro-2-(pyridin-2-yl)quinoline-3-carbonitrile (30 mg, 0.11 mmol) (described herein), 4-(3,3-dimethyl-2,3-dihydro-1H-pyrrolo[3,2-b]-pyridin-6-yl)morpholine (30 mg, 0.13 mmol) (described herein), sodium tert-butoxide (30.5 mg, 0.32 mmol), 2-(dicyclohexylphosphino)-2',4',6'-tri-i-propyl-1,1'-biphenyl (15.12 mg, 0.032 mmol), Pd$_2$dba$_3$ (14.53 mg, 0.016 mmol), and toluene (1.0 mL) was stirred at 105° C. for 3 h, then cooled to rt and concentrated. The resulting residue was taken up in EtOAc, washed with saturated aqueous sodium bicarbonate solution, 1M NaOH, and brine, and the organic layer dried (MgSO$_4$) and concentrated. Chromatography afforded 4-(3,3-dimethyl-6-morpholino-2,3-dihydro-1H-pyrrolo[3,2-b]pyridin-1-yl)-7-fluoro-2-(pyridin-2-yl)quinoline-3-carbonitrile as a yellow solid. 1H NMR (400 MHz, chloroform-d) δ ppm 8.83 (1H, ddd, J=4.8, 1.7, 0.9 Hz), 8.19-8.31 (1H, m), 7.82-8.01 (3H, m), 7.72-7.82 (1H, m), 7.42-7.57 (1H, m), 7.28-7.37 (1H, m), 6.05-6.21 (1H, m), 4.60-4.72 (1H, m), 3.83-3.94 (1H, m), 3.70-3.83 (4H, m), 2.90-3.11 (4H, m), 1.55-1.62 (3H, m), 1.48-1.55 (3H, m). Mass Spectrum (ESI) m/e=481 (M+1).

Example 39

4-(3,3-Dimethyl-6-(4-morpholinyl)-2,3-dihydro-1H-indol-1-yl)-5,7-difluoro-3-methyl-2-(1-piperidinyl)quinoline 4-(3,3-Dimethylindolin-6-yl)morpholine

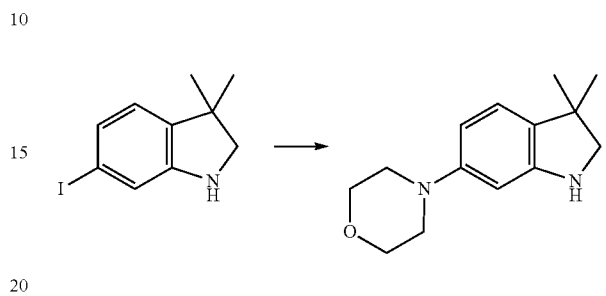

The 6-iodo-3,3-dimethylindoline (250 mg, 0.915 mmol), morpholine (0.399 mL, 4.58 mmol), Pd$_2$(dba)$_3$ (33.5 mg, 0.037 mmol), and 2-(dicyclohexylphosphino)-2,4,6-tri-i-propyl-1,1-biphenyl (34.9 mg, 0.073 mmol) were dissolved in THF (2.0 mL) and 1M lithium bis(trimethylsilyl)amide (5.03 mL, 5.03 mmol) solution in THF was added to a sealed tube and heated to 65° C. for 1 h. The reaction was cooled to rt and then poured into water (30 mL) and extracted with EtOAc (1×150 mL) and DCM (1×150 mL). The combined organic layers were dried over magnesium sulfate and the crude product was purified by medium pressure chromatography (silica, 50 to 100% EtOAc:DCM) to give 4-(3,3-dimethylindolin-6-yl)morpholine. Mass Spectrum (ESI) m/e=233.2 (M+1).

4-Chloro-5,7-difluoro-3-methyl-2-(piperidin-1-yl)quinoline

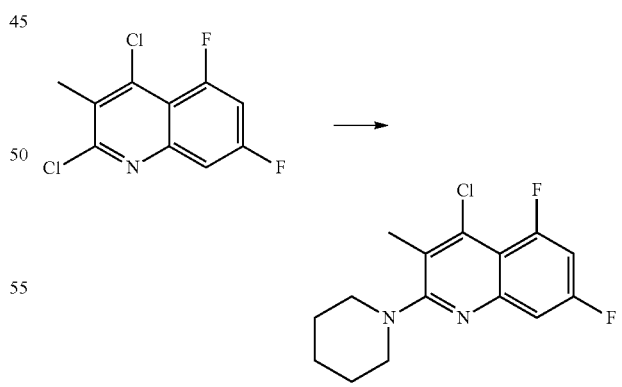

The 2,4-dichloro-5,7-difluoro-3-methylquinoline (300 mg, 1.21 mmol) was dissolved in isopropanol (3 mL) and piperidine (0.120 mL, 1.21 mmol) was added to the sealed tube. The mixture was heated to 85° C. and stirred overnight. The reaction was then cooled and concentrated to dryness. The residue was then purified by medium pressure chromatography (silica, 0 to 40% DCM:hexane) to give 4-chloro-5, 7-difluoro-3-methyl-2-(piperidin-1-yl)quinoline. Mass Spectrum (ESI) m/e=297.1 (M+1).

4-(3,3-Dimethyl-6-(4-morpholinyl)-2,3-dihydro-1H-indol-1-yl)-5,7-difluoro-3-methyl-2-(1-piperidinyl)quinoline

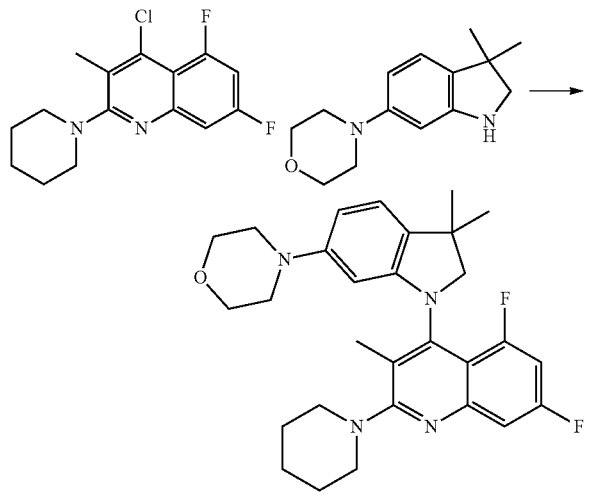

The 2-(dicyclohexylphosphino)-2,4,6-tri-i-propyl-1,1-biphenyl (9.85 mg, 0.021 mmol), 4-chloro-5,7-difluoro-3-methyl-2-(piperidin-1-yl)quinoline (38.3 mg, 0.129 mmol), 4-(3,3-dimethylindolin-6-yl)morpholine (30.0 mg, 0.129 mmol), sodium tert-butoxide (31.0 mg, 0.323 mmol) and Pd$_2$(dba)$_3$ (4.73 mg, 5.17 µmol) were slurried in toluene (1.00 mL) in a sealed tube and heated to 110° C. for 45 minutes. The reaction was cooled to rt and diluted with water (~20 mL). This mixture was extracted with EtOAc (1×50 mL) and DCM (1×50 mL). The combined organic layers were dried over magnesium sulfate and the crude product was purified by medium pressure chromatography (silica, 0 to 100% EtOAc: hexane) to give 4-(3,3-dimethyl-6-(4-morpholinyl)-2,3-dihydro-1H-indol-1-yl)-5,7-difluoro-3-methyl-2-(1-piperidinyl)quinoline. $^1$H NMR (CDCl$_3$) δ ppm 7.31 (1H, br. s.), 7.02 (1H, d, J=8.1 Hz), 6.68 (1H, ddd, J=11.7, 9.1, 2.4 Hz), 6.26 (1H, d, J=7.3 Hz), 5.46 (1H, br. s.), 3.67-3.80 (5H, m), 3.59 (1H, d, J=8.8 Hz), 3.32 (4H, br. s.), 2.94 (4H, d, J=3.7 Hz), 2.24 (3H, s), 1.65-1.86 (6H, m), 1.45 (3H, s), 1.42 (3H, s). Mass Spectrum (ESI) m/e=493.3 (M+1).

Example 40

6-Chloro-4-(3,3-dimethyl-6-(4-morpholinyl)-2,3-dihydro-1H-indol-1-yl)-7-methoxy-2,3-dimethylquinoline

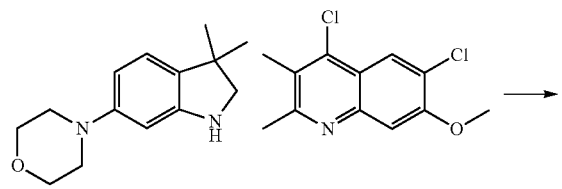

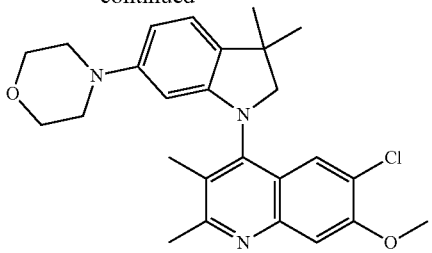

A dry, microwave vial containing 4-(3,3-dimethylindolin-6-yl)morpholine (71.3 mg, 0.31 mmol), 4,6-dichloro-7-methoxy-2,3-dimethylquinoline (139.2 mg, 0.54 mmol), cesium carbonate (150.6 mg, 0.46 mmol), Pd$_2$(dba)$_3$ (56.0 mg, 0.06 mmol), rac-BINAP (39.0 mg, 0.06 mmol), and dry 1,4-dioxane (2 mL) was evacuated and backfilled with argon. The mixture was heated in the microwave at 140° C. After 3 h, the reaction was filtered then concentrated under reduced pressure. The residue was purified on silica gel (0-100% EtOAc in hexane) to afford an impure film that was further purified with reverse-phase HPLC using 10-90% of 0.1% TFA in acetonitrile in 0.1% TFA in water to afford 6-chloro-4-(3,3-dimethyl-6-(4-morpholinyl)-2,3-dihydro-1H-indol-1-yl)-7-methoxy-2,3-dimethylquinoline as a TFA salt. $^1$H NMR (500 MHz, DMSO-d$_6$) δ ppm 7.90 (1H, s), 7.54 (1H, s), 7.06 (1H, d, J=8.3 Hz), 6.39 (1H, dd, J=8.1, 1.7 Hz), 5.76 (1H, s), 3.99 (3H, s), 3.91 (1H, d, J=9.0 Hz), 3.72 (1H, d, J=9.0 Hz), 3.58 (4H, m), 2.84 (4H, dd, J=5.9, 3.7 Hz), 2.70 (3H, s), 2.09 (3H, s), 1.35 (3H, s), 1.29 (3H, s). Mass Spectrum (ESI) m/e=452 (M+1).

Example 41

4-(3,3-Dimethyl-6-(4-morpholinyl)-2,3-dihydro-1H-indol-1-yl)-7-methoxy-2,3,6-trimethylquinoline 3-Methoxy-4-methylaniline Prepared according to procedure X using 2-methoxy-1-methyl-4-nitrobenzene (1.66 g, 9.9 mmol), iron powder (1.66 g, 29.8 mmol), and acetic acid (15.0 mL) to give 3-methoxy-4-methylaniline. $^1$H NMR (500 MHz, DMSO-d$_6$) δ ppm 6.72

(1H, d, J=7.8 Hz), 6.18 (1H, d, J=2.0 Hz), 6.04 (1H, dd, J=7.8, 2.0 Hz), 4.81 (2H, s), 3.67 (3H, s), 1.96 (3H, s).

7-Methoxy-2,3,6-trimethylquinolin-4-ol

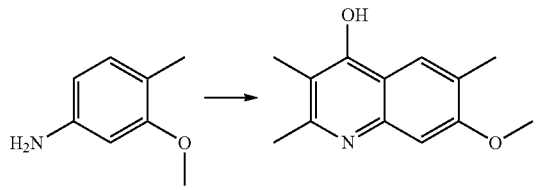

Prepared according to procedure R using 3-methoxy-4-methylaniline (617.8 mg, 4.5 mmol), ethyl-2-methyl-acetoacetate (1.3 mL, 9.1 mmol), and PPA (1.87 g, 18.7 mmol) to give 7-methoxy-2,3,6-trimethylquinolin-4-ol.

4-Chloro-7-methoxy-2,3,6-trimethylquinoline

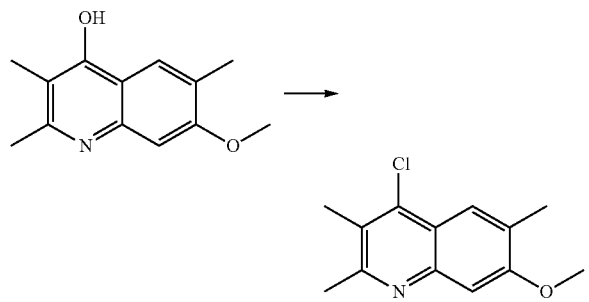

Prepared according to procedure S using 7-methoxy-2,3,6-trimethylquinolin-4-ol (444.7 mg, 2.0 mmol) and $POCl_3$ (2.0 mL, 21.5 mmol) to give 4-chloro-7-methoxy-2,3,6-trimethylquinoline. Mass Spectrum (ESI), m/e=236.1 (M+1).

4-(3,3-Dimethyl-6-(4-morpholinyl)-2,3-dihydro-1H-indol-1-yl)-7-methoxy-2,3,6-trimethylquinoline

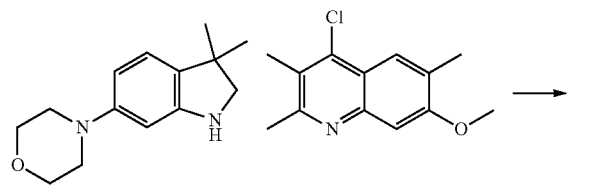

A dry, microwave vial containing 4-(3,3-dimethylindolin-6-yl)morpholine (100.7 mg, 0.43 mmol), 4-chloro-7-methoxy-2,3,6-trimethylquinoline (205.1 mg, 0.87 mmol), cesium carbonate (212.6 mg, 0.65 mmol), $Pd_2(dba)_3$ (79.8 mg, 0.087 mmol), rac-BINAP (54.4 mg, 0.087 mmol), and dry 1,4-dioxane (2.5 mL) was evacuated and backfilled with argon. The mixture was heated in the microwave at 140° C. After 8 h, the reaction was filtered then concentrated under reduced pressure. The residue was purified on silica gel (0-100% EtOAc in hexane) to afford an impure film that was further purified with reverse-phase HPLC using 20-90% of 0.1% TFA in acetonitrile in 0.1% TFA in water to afford 4-(3,3-dimethyl-6-(4-morpholinyl)-2,3-dihydro-1H-indol-1-yl)-7-methoxy-2,3,6-trimethylquinoline as a TFA salt. $^1$H NMR (500 MHz, DMSO-$d_6$) δ ppm 7.88 (1H, s), 7.44 (1H, s), 7.14 (1H, d, J=8.1 Hz), 6.49 (1H, m), 5.89 (1H, s), 4.20 (1H, d, J=9.0 Hz), 4.02 (3H, s), 3.76 (1H, d, J=9.3 Hz), 3.64 (1H, s), 3.62 (3H, d, J=3.7 Hz), 2.91 (4H, d, J=3.7 Hz), 2.80 (3H, s), 2.31 (3H, s), 2.12 (3H, s), 1.45 (3H, s), 1.33 (3H, s). Mass Spectrum (ESI) m/e=432.2 (M+1).

Example 42

8-Chloro-4-(3,3-dimethyl-6-(4-morpholinyl)-2,3-dihydro-1H-indol-1-yl)-2,3,6-trimethylquinoline

8-Chloro-2,3,6-trimethylquinolin-4-ol

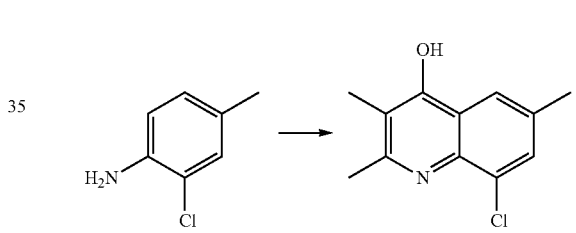

Prepared according to procedure R using 2-chloro-4-methyl-aniline (2.0 mL, 16.3 mmol), ethyl-2-methyl-acetoacetate (4.6 mL, 32.5 mmol), and PPA (8.12 g, 81.2 mmol) to afford 8-chloro-2,3,6-trimethylquinolin-4-ol.

4,8-Dichloro-2,3,6-trimethylquinoline

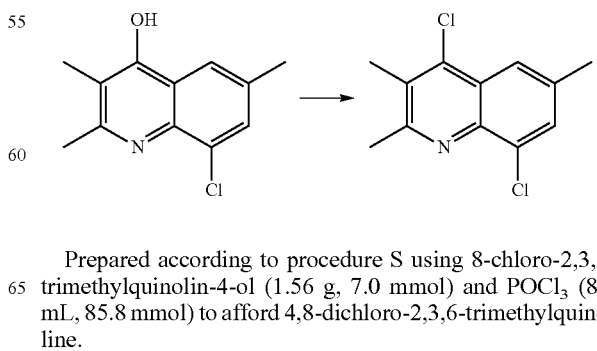

Prepared according to procedure S using 8-chloro-2,3,6-trimethylquinolin-4-ol (1.56 g, 7.0 mmol) and $POCl_3$ (8.0 mL, 85.8 mmol) to afford 4,8-dichloro-2,3,6-trimethylquinoline.

8-Chloro-4-(3,3-dimethyl-6-(4-morpholinyl)-2,3-dihydro-1H-indol-1-yl)-2,3,6-trimethylquinoline

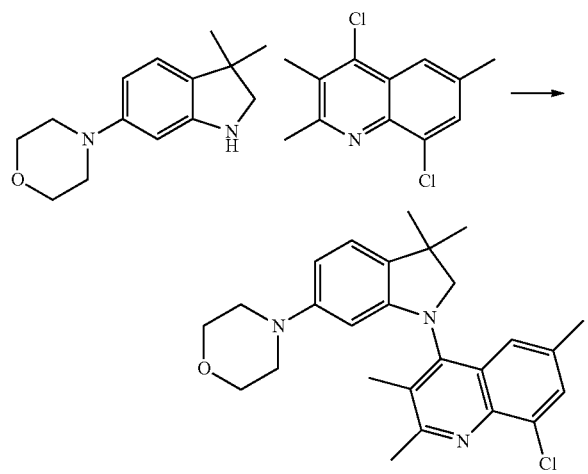

A dry, microwave vial containing 4-(3,3-dimethylindolin-6-yl)morpholine (150.7 mg, 0.65 mmol), 4,8-dichloro-2,3,6-trimethylquinoline (233.8 mg, 0.97 mmol), cesium carbonate (317.0 mg, 0.97 mmol), $Pd_2(dba)_3$ (119 mg, 0.13 mmol), rac-BINAP (81.6 mg, 0.13 mmol), and dry 1,4-dioxane (2.2 mL) was evacuated and backfilled with argon. The mixture was heated in the microwave at 140° C. After 2 h, the reaction was filtered then concentrated under reduced pressure. The residue was purified on silica gel (0-100% EtOAc in hexane) to afford an impure film that was triturated with isopropanol to afford 8-chloro-4-(3,3-dimethyl-6-(4-morpholinyl)-2,3-dihydro-1H-indol-1-yl)-2,3,6-trimethylquinoline. $^1$H NMR (500 MHz, DMSO-$d_6$) δ ppm 7.71 (1H, d, J=1.5 Hz), 7.52 (1H, s), 7.03 (1H, d, J=8.1 Hz), 6.23 (1H, s), 5.44 (1H, s), 3.72 (1H, d, J=9.0 Hz), 3.59 (4H, m), 3.53 (1H, s), 3.33 (2H, s), 2.83 (4H, s), 2.69 (3H, s), 2.40 (3H, s), 2.18 (3H, s), 1.44 (3H, s), 1.39 (3H, s). Mass Spectrum (ESI) m/e=436.1 (M+1).

Example 43

4-(3,3-Dimethyl-6-(4-morpholinyl)-2,3-dihydro-1H-indol-1-yl)-6,8-dimethoxy-2,3-dimethylquinoline

6,8-Dimethoxy-2,3-dimethylquinolin-4-ol

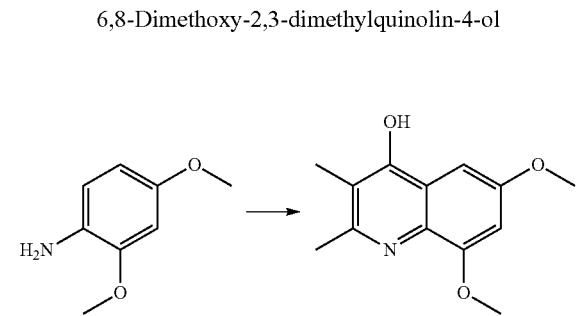

Prepared according to procedure R using 2,4-dimethoxy aniline (1.99 g, 13.0 mmol), ethyl-2-methyl-acetoacetate (3.7 mL, 26.2 mmol), and PPA (6.78 g, 67.8 mmol) to afford 6,8-dimethoxy-2,3-dimethylquinolin-4-ol. Mass Spectrum (ESI) m/e=234.1 (M+1).

4-Chloro-6,8-dimethoxy-2,3-dimethylquinoline

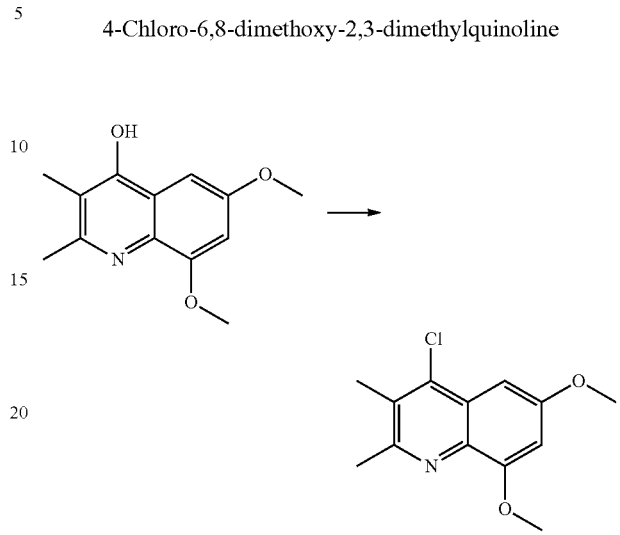

Prepared according to procedure S using 6,8-dimethoxy-2,3-dimethylquinolin-4-ol (1.0 g, 7.0 mmol) and $POCl_3$ (5.0 mL, 53.6 mmol) to afford 4-chloro-6,8-dimethoxy-2,3-dimethylquinoline. Mass Spectrum (ESI) m/e=252.1 (M+1).

4-(3,3-Dimethyl-6-(4-morpholinyl)-2,3-dihydro-1H-indol-1-yl)-6,8-dimethoxy-2,3-dimethylquinoline

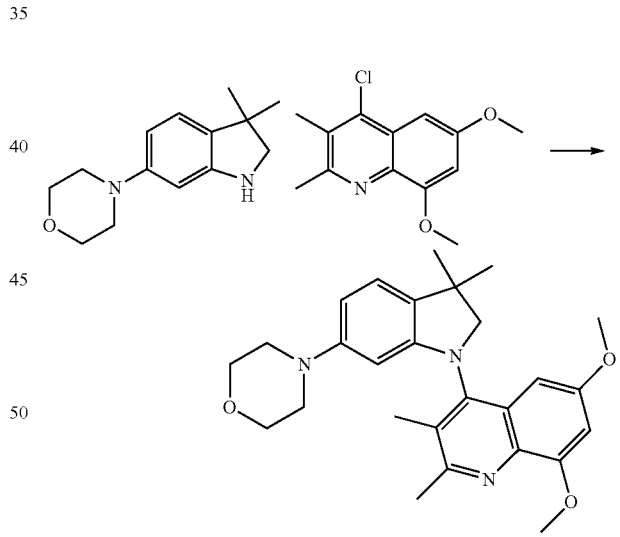

Prepared according to procedure T using 4-(3,3-dimethylindolin-6-yl)morpholine (134.7 mg, 0.58 mmol), 4-chloro-6,8-dimethoxy-2,3-dimethylquinoline (219.7 mg, 0.87 mmol), cesium carbonate (284.6 mg, 0.87 mmol), $Pd_2(dba)_3$ (106.3 mg, 0.12 mmol), rac-BINAP (73.0 mg, 0.12 mmol), and dry 1,4-dioxane (3 mL) to afford 4-(3,3-dimethyl-6-(4-morpholinyl)-2,3-dihydro-1H-indol-1-yl)-6,8-dimethoxy-2,3-dimethylquinoline as a TFA salt. $^1$H NMR (500 MHz, DMSO-$d_6$) δ ppm 7.18 (2H, m), 6.81 (1H, s), 6.49 (1H, m), 5.88 (1H, d, J=4.2 Hz), 4.13 (3H, s), 3.96 (1H, dd, J=9.0, 2.9 Hz), 3.80 (4H, m), 3.63 (4H, d, J=3.4 Hz), 2.93 (4H, s), 2.88

(3H, d, J=3.2 Hz), 2.22 (3H, d, J=2.4 Hz), 1.42 (6H, m). Mass Spectrum (ESI) m/e=448.3 (M+1).

Example 44

6-Chloro-4-(3,3-dimethyl-6-(4-morpholinyl)-2,3-dihydro-1H-indol-1-yl)-2-(2-methoxyphenyl)quinoline 6-Chloro-2-(2-methoxyphenyl)quinolin-4-ol

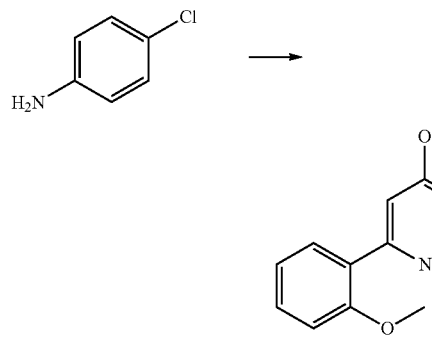

Prepared according to procedure R using 4-chloroaniline (774.0 mg, 6.1 mmol), ethyl (2-methoxybenzoyl)acetate (2.0 mL, 10.3 mmol), and PPA (4.70 g, 47.0 mmol) to afford 6-chloro-2-(2-methoxyphenyl)quinolin-4-ol. Mass Spectrum (ESI) m/e=286.0 (M+1).

4,6-Dichloro-2-(2-methoxyphenyl)quinoline

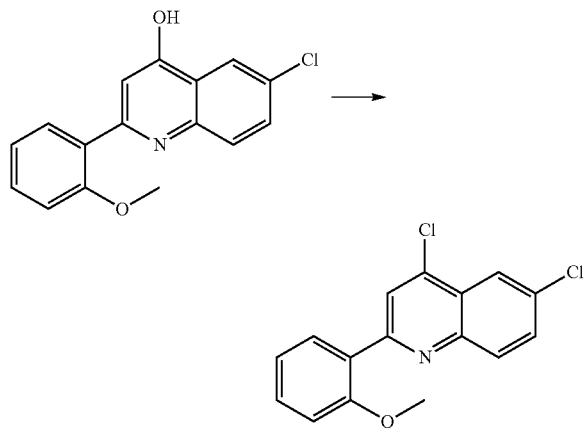

Prepared according to procedure S using 6-chloro-2-(2-methoxyphenyl)quinolin-4-ol (550.6 mg, 1.93 mmol) and POCl$_3$ (3.5 mL, 37.5 mmol) to afford 4,6-dichloro-2-(2-methoxyphenyl)quinoline. Mass Spectrum (ESI) m/e=304.0 (M+1).

6-Chloro-4-(3,3-dimethyl-6-(4-morpholinyl)-2,3-dihydro-1H-indol-1-yl)-2-(2-methoxyphenyl)quinoline

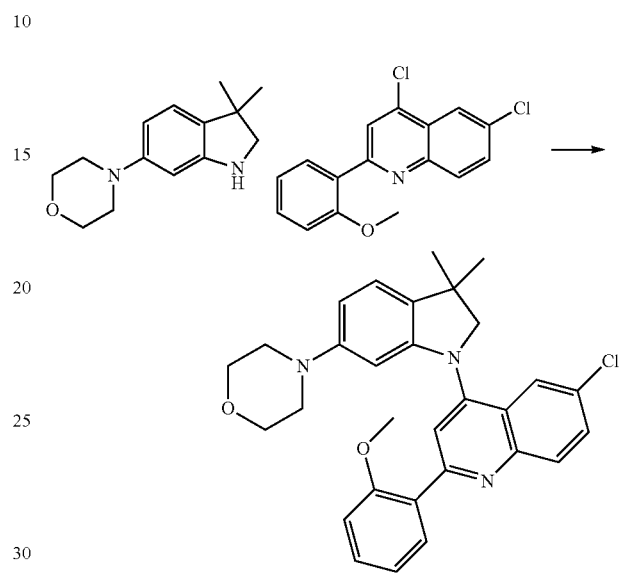

Prepared according to procedure T using 4-(3,3-dimethylindolin-6-yl)morpholine (76.8 mg, 0.33 mmol) 4,6-dichloro-2-(2-methoxyphenyl)quinoline (130 mg, 0.43 mmol), cesium carbonate (162 mg, 0.5 mmol), Pd$_2$(dba)$_3$ (61.2 mg, 0.068 mmol), rac-BINAP (41.8 mg, 0.067 mmol), and dry 1,4-dioxane (2.5 mL) to afford 6-chloro-4-(3,3-dimethyl-6-(4-morpholinyl)-2,3-dihydro-1H-indol-1-yl)-2-(2-methoxyphenyl)quinoline as a TFA salt. Mass Spectrum (ESI) m/e=500.2 (M+1)

Example 45

6-Chloro-4-(3,3-dimethyl-6-(4-pyridinyl)-2,3-dihydro-1H-indol-1-yl)-2,3-dimethylquinoline 6-Chloro-2,3-dimethylquinolin-4-ol

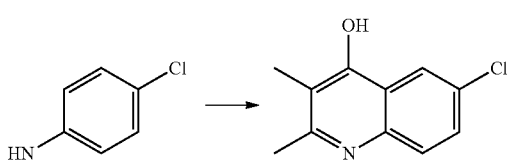

Prepared according to procedure R using 4-chloroaniline (2 g, 15.68 mmol) and ethyl 2-methyl-3-oxobutanoate (4.53 mL, 31.36 mol) to give 6-chloro-2,3-dimethylquinolin-4-ol as a white solid: Mass Spectrum (ESI) m/e=208.0 (M+1).

4,6-Dichloro-2,3-dimethylquinoline

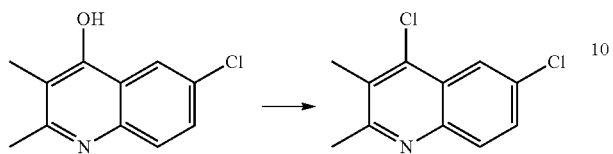

Prepared according to procedure S using 6-chloro-2,3-dimethylquinolin-4-ol (1 g, 4.82 mmol) to give 4,6-dichloro-2,3-dimethylquinoline as a white solid: Mass Spectrum (ESI) m/e=226.0 (M+1).

6-Chloro-4-(6-iodo-3,3-dimethylindolin-1-yl)-2,3-dimethylquinoline

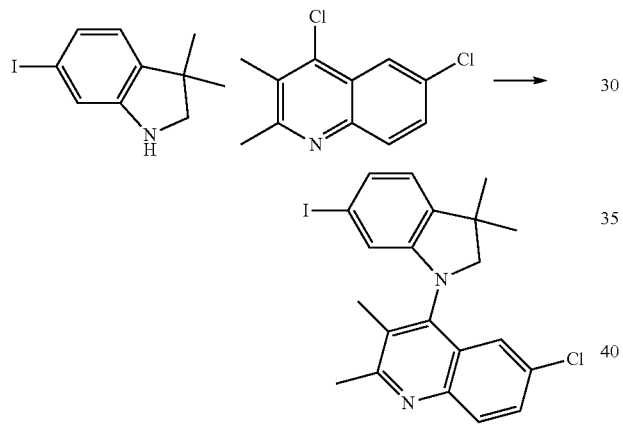

Prepared according to procedure M using 6-iodo-3,3-dimethylindoline (0.604 g, 2.21 mmol) and 4,6-dichloro-2,3-dimethylquinoline (0.5 g, 2.21 mmol) to give 6-chloro-4-(6-iodo-3,3-dimethylindolin-1-yl)-2,3-dimethylquinoline as a brown solid: Mass Spectrum (ESI) m/e=463.0 (M+1).

6-Chloro-4-(3,3-dimethyl-6-(4-pyridinyl)-2,3-dihydro-1H-indol-1-yl)-2,3-dimethylquinoline

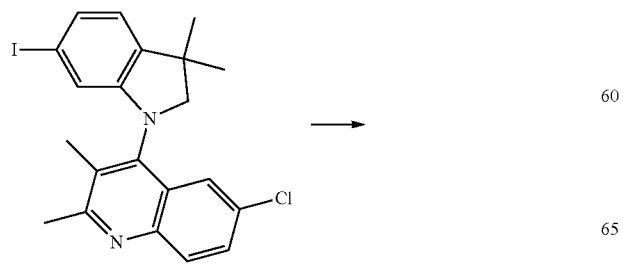

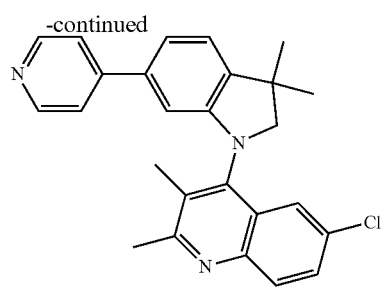

Prepared according to procedure W using 6-chloro-4-(6-iodo-3,3-dimethylindolin-1-yl)-2,3-dimethylquinoline (0.15 g, 0.32 mmol) and pyridine-4-boronic acid pinacol (0.1329 g, 0.65 mmol) to give 6-chloro-4-(3,3-dimethyl-6-(4-pyridinyl)-2,3-dihydro-1H-indol-1-yl)-2,3-dimethylquinoline as a brown solid: $^1$H NMR (400 MHz, DMSO-d$_6$) δ ppm 8.53 (2H, d, J=4.3 Hz), 8.02 (1H, d, J=9.0 Hz), 7.82 (1H, d, J=2.3 Hz), 7.60 (1H, dd, J=9.0, 2.3 Hz), 7.28-7.35 (3H, m), 7.04 (1H, dd, J=7.6, 1.4 Hz), 6.12 (1H, d, J=1.2 Hz), 3.63-3.88 (2H, m), 2.75 (3H, s), 2.27 (3H, s), 1.60 (3H, s), 1.54 (3H, s); Mass Spectrum (ESI) m/e=414.1 (M+1).

Example 46

6-Chloro-4-(3,3-dimethyl-6-(1H-pyrazol-4-yl)-2,3-dihydro-1H-indol-1-yl)-2,3-dimethylquinoline Prepared according to procedure W using 6-chloro-4-(6-iodo-3,3-dimethylindolin-1-yl)-2,3-dimethylquinoline (0.15 g, 0.32 mmol) and 4-(4,4,5,5-tetramethyl-1,3,2-dioxaborolan-2-yl)-1H-pyrazole (0.084 g, 0.432 mmol) to give 6-chloro-4-(3,3-dimethyl-6-(1H-pyrazol-4-yl)-2,3-dihydro-1H-indol-1-yl)-2,3-dimethylquinoline as a yellow solid: $^1$H NMR (500 MHz, DMSO-d$_6$) δ ppm 12.73 (1H, br. s.), 8.01 (1H, d, J=9.0 Hz), 7.91 (1H, br. s.), 7.75 (1H, d, J=2.4 Hz), 7.62-7.71 (2H, m), 7.19 (1H, d, J=7.6 Hz), 6.94 (1H, d, J=7.6

Hz), 6.07 (1H, s), 3.56-3.78 (2H, m), 2.68 (3H, s), 2.21 (3H, s), 1.48 (3H, s), 1.43 (3H, s); Mass Spectrum (ESI) m/e=403.1 (M+1).

Example 47

6-Chloro-4-(3,3-dimethyl-6-(4-morpholinyl)-2,3-dihydro-1H-indol-1-yl)-2,3-dimethylquinoline

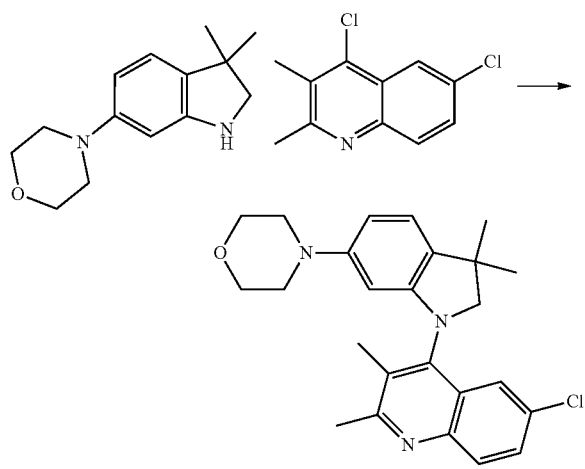

Prepared according to procedure T using 4-(3,3-dimethylindolin-6-yl)morpholine (0.15 g, 0.646 mmol) and 4,6-dichloro-2,3-dimethylquinoline (0.292 g, 1.29 mmol) to give 6-chloro-4-(3,3-dimethyl-6-(4-morpholinyl)-2,3-dihydro-1H-indol-1-yl)-2,3-dimethylquinoline as a TFA salt. $^1$H NMR (500 MHz, DMSO-$d_6$) δ ppm 8.09 (1H, d, J=9.0 Hz), 7.84-7.97 (2H, m), 7.15 (1H, d, J=8.1 Hz), 6.48 (1H, d, J=8.1 Hz), 5.84 (1H, s), 3.98 (1H, d, J=9.0 Hz), 3.78 (1H, d, J=9.0 Hz), 3.57-3.67 (4H, m), 2.87-2.98 (4H, m), 2.79 (3H, s), 2.20 (3H, s), 1.43 (3H, s), 1.37 (3H, s); Mass Spectrum (ESI) m/e=422.2 (M+1)

Example 48

4-(6-chloro-2,3-dimethyl-4-quinolinyl)-6-(4-morpholinyl)-3,4-dihydro-2H-1,4-benzoxazine 6-Nitro-2H-benzo[b][1,4]oxazin-3(4H)-one

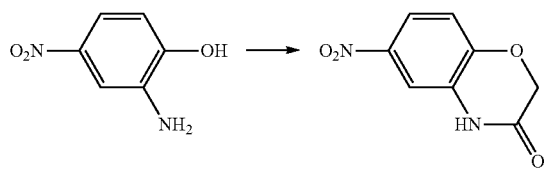 [SMILES: Nc1cc([N+](=O)[O-])ccc1O ; O=C1COc2ccc([N+](=O)[O-])cc2N1]

To a stirred suspension of KF (4.9 g, 84.35 mmol) in DMF (25 mL) was added ethyl bromoacetate and the mixture was stirred at rt. After 25 minutes, to the mixture was added 2-amino-4-nitrophenol (5 g, 32.44 mmol) and the mixture was stirred at 60° C. After 25 h, the mixture was cooled to rt, poured into cold brine (200 mL), extracted with EtOAc (100 mL×3). The combined organics were washed with brine (200 mL×1), dried over $Na_2SO_4$, filtered, and concentrated under reduced pressure. The residue was suspended in MeOH, filtered, and washed the solid with MeOH to give 6-nitro-2H-benzo[b][1,4]oxazin-3(4H)-one as a brown solid: Spectrum (ESI) m/e=193.0 (M+1).

6-Nitro-3,4-dihydro-2H-benzo[b][1,4]oxazine

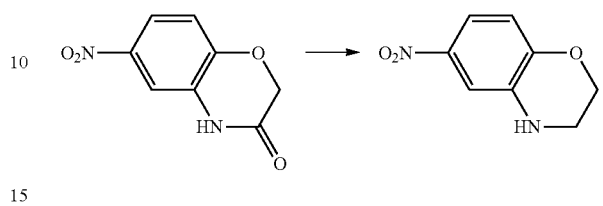

To a suspension of 6-nitro-2H-benzo[b][1,4]oxazin-3 (4H)-one (1.45 g, 7.47 mmol) in THF (11 mL) was added $BH_3$.THF (1 M solution in THF, 60 mL) at rt and the mixture was stirred at 75° C. After 3.5 h, the mixture was cooled to rt. To the cooled mixture was added MeOH (30 mL) and mixture was stirred at rt. After 30 minutes, the mixture was treated with concentrated HCl (6 mL, 72 mmol) and concentrated under reduced pressure. The residue was dissolved in EtOAc (50 mL×4), washed with brine (100 mL×2), dried over $Na_2SO_4$, filtered, and concentrated under reduced pressure. The residue was purified by column chromatography on a silica gel column using 0 to 100% gradient of EtOAc in hexane as eluent to give 6-nitro-3,4-dihydro-2H-benzo[b][1, 4]oxazine as a reddish-orange solid: Mass Spectrum (ESI) m/e=181.0 (M+1).

1-(6-Nitro-2H-benzo[b][1,4]oxazin-4(3H)-yl)ethanone

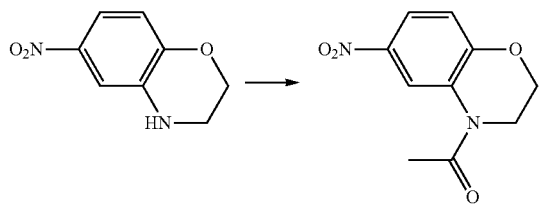 [SMILES: O=[N+]([O-])c1ccc2c(c1)NCCO2 ; CC(=O)N1CCOc2ccc([N+](=O)[O-])cc21]

A solution of 6-nitro-3,4-dihydro-2H-benzo[b][1,4]oxazine (0.7 g, 3.89 mmol) in acetic anhydride (1.9 mL) and EtOAc (7 mL) was heater under reflux with stirring. After 15 h, the mixture was concentrated under reduced pressure to give 1-(6-nitro-2H-benzo[b][1,4]oxazin-4(3H)-yl)ethanone as a yellow solid, which was carried on crude without purification: Mass Spectrum (ESI) m/e=223.0 (M+1).

1-(6-Amino-2H-benzo[b][1,4]oxazin-4(3H)-yl)ethanone

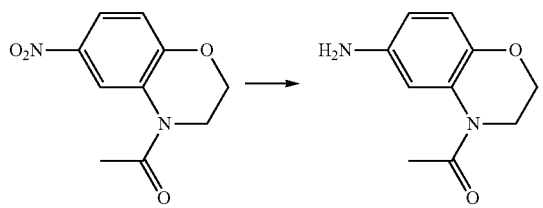 [SMILES: CC(=O)N1CCOc2ccc([N+](=O)[O-])cc21 ; CC(=O)N1CCOc2ccc(N)cc21]

To a solution of the crude 1-(6-nitro-2H-benzo[b][1,4]ox-azin-4(3H)-yl)ethanone (0.86 g, 3.89 mmol) in EtOAc (8 mL) was added SnCl$_2$.2H$_2$O (4.3834 g, 19.4 mmol) and the mixture was heated under reflux with stirring. After 1.5 h, the mixture was cooled to rt. To the mixture was added 2 M aqueous Na$_2$CO$_3$ (20 mL) followed by EtOAc (50 mL). The resulting white precipitate was filtered off and washed the white solid with EtOAc (50 mL). The filtrated was separated in a reparatory funnel. The aqueous layer was extracted with EtOAc (30 mL×1). The combined organics were washed with brine (50 mL×2), dried over Na$_2$SO$_4$, filtered, and concentrated under reduced pressure to give dark syrup. The dark syrup was purified by column chromatography on a silica gel column using 0 to 100% gradient of DCM-MeOH—NH4OH (89:9:1) in DCM as eluent to give 1-(6-amino-2H-benzo[b][1,4]oxazin-4(3H)-yl)ethanone as a red syrup: Mass Spectrum (ESI) m/e=193.1 (M+1).

6-Morpholino-3,4-dihydro-2H-benzo[b][1,4]oxazine

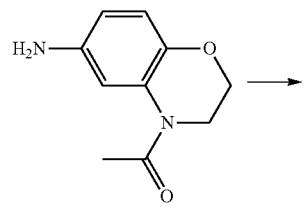

A mixture of 1-(6-amino-2H-benzo[b][1,4]oxazin-4(3H)-yl)ethanone (0.5832 g, 3.03 mmol), 1-bromo-2-(2-bromoethoxy)ethane (0.774 g, 3.34 mmol), MeOH (3 mL), and Na$_2$CO$_3$ (0.6432 g, 6.07 mmol) in a pressure vessel was stirred at 150° C. After 1.5 h, the mixture was cooled to rt. To the cooled mixture was added a solution of KOH (1.1066 g, 19.72 mmol) in water (2 mL) and the mixture was stirred at 55° C. After 1 h, the mixture was cooled to rt, poured into ice water (50 mL), and extracted with EtOAc (50 mL×2). The combined organics were washed with brine (50 mL×2), dried over Na$_2$SO$_4$, filtered, and concentrated under reduced pressure to give a violet solid. The violet solid was purified by column chromatography on a silica gel column using 0 to 100% gradient of EtOAc in hexane as eluent to give 6-morpholino-3,4-dihydro-2H-benzo[b][1,4]-oxazine as a white solid: Mass Spectrum (ESI) m/e=221.2 (M+1).

4-(6-Chloro-2,3-dimethyl-4-quinolinyl)-6-(4-morpholinyl)-3,4-dihydro-2H-1,4-benzoxazine

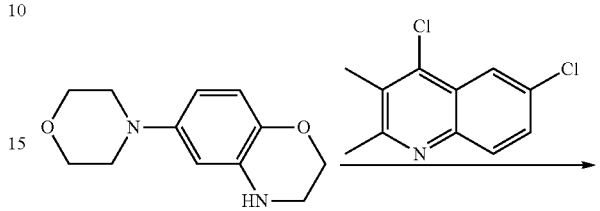

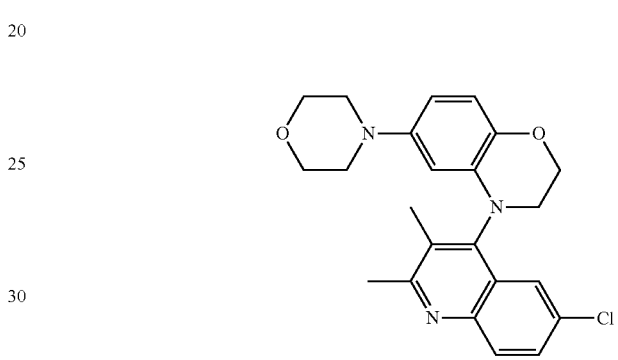

Prepared according to procedure T using 6-morpholino-3,4-dihydro-2H-benzo-[b][1,4]oxazine (0.1 g, 0.454 mmol) and 4,6-dichloro-2,3-dimethylquinoline (0.2053 g, 0.908 mmol) to give 4-(6-chloro-2,3-dimethyl-4-quinolinyl)-6-(4-morpholinyl)-3,4-dihydro-2H-1,4-benzoxazine as a yellow solid: $^1$H NMR (500 MHz, DMSO-d$_6$) δ ppm 8.01 (1H, d, J=9.5 Hz), 7.64-7.73 (2H, m), 6.77 (1H, d, J=8.6 Hz), 6.22 (1H, dd, J=8.7, 2.6 Hz), 5.41 (1H, d, J=2.7 Hz), 4.26-4.47 (2H, m), 3.57-3.67 (2H, m), 3.47-3.55 (4H, m), 2.69 (3H, s), 2.60-2.66 (4H, m), 2.22 (3H, s); Mass Spectrum (ESI) m/e=410.2 (M+1).

Example 49

6-Chloro-4-(4-methoxy-6-(4-pyridinyl)-1H-indol-1-yl)-2,3-dimethylquinoline 4-(6-Bromo-4-methoxy-1H-indol-1-yl)-6-chloro-2,3-dimethylquinoline

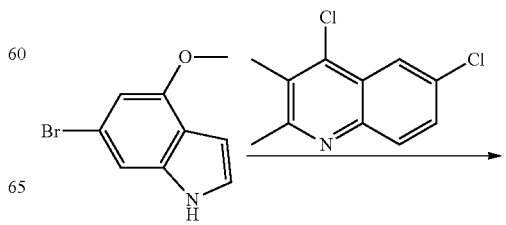

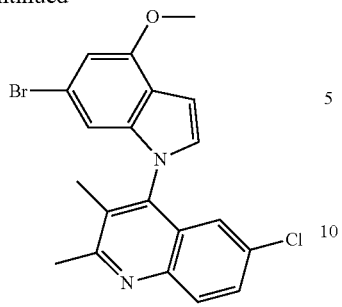

Prepared according to procedure U using 6-bromo-4-methoxy-1H-indole (0.05 g, 0.22 mmol) and 4,6-dichloro-2,3-dimethylquinoline (0.075 g, 0.33 mmol) to give 4-(6-bromo-4-methoxy-1H-indol-1-yl)-6-chloro-2,3-dimethylquinoline as a yellow solid: Mass Spectrum (ESI) m/e=415.0 [M+1 ($^{79}$Br)] and 417.0 [M+1 ($^{81}$Br)].

6-Chloro-4-(4-methoxy-6-(4-pyridinyl)-1H-indol-1-yl)-2,3-dimethylquinoline

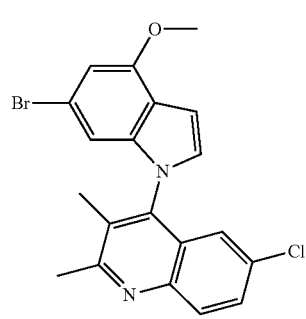

Prepared according to procedure W using 4-(6-bromo-4-methoxy-1H-indol-1-yl)-6-chloro-2,3-dimethylquinoline (0.4 g, 0.962 mmol) and 4-(4,4,5,5-tetramethyl-1,3,2-dioxaborolan-2-yl)pyridine (0.3946 g, 1.92 mmol) to give 6-chloro-4-(4-methoxy-6-(4-pyridinyl)-1H-indol-1-yl)-2,3-dimethylquinoline as a white solid: $^1$H NMR (500 MHz, DMSO-d$_6$) δ ppm 8.50 (2H, dd, J=4.6, 1.5 Hz), 8.09 (1H, d, J=8.8 Hz), 7.74 (1H, dd, J=8.9, 2.3 Hz), 7.64 (2H, dd, J=4.5, 1.6 Hz), 7.57 (1H, d, J=3.2 Hz), 7.07 (1H, s), 6.86-6.93 (3H, m), 4.07 (3H, s), 2.77 (3H, s), 2.05 (3H, s); Mass Spectrum (ESI) m/e=414.1 (M+1).

Example 50

6-Chloro-4-(4-methoxy-6-(1H-pyrazol-4-yl)-1H-indol-1-yl)-2,3-dimethylquinoline

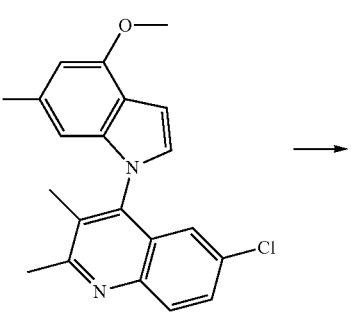

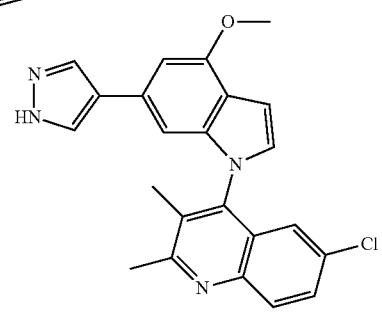

Prepared according to procedure W using 4-(6-bromo-4-methoxy-1H-indol-1-yl)-6-chloro-2,3-dimethylquinoline (0.4 g, 0.962 mmol) and 4-(4,4,5,5-tetramethyl-1,3,2-dioxaborolan-2-yl)-1H-pyrazole (0.3734 g, 1.92 mmol) to give 6-chloro-4-(4-methoxy-6-(1H-pyrazol-4-yl)-1H-indol-1-yl)-2,3-dimethylquinoline as a white solid: $^1$H NMR (500 MHz, DMSO-d$_6$) δ ppm 8.09 (2H, d, J=9.0 Hz), 7.81 (1H, s), 7.73 (1H, dd, J=8.9, 2.3 Hz), 7.39 (1H, d, J=3.2 Hz), 6.90-6.94 (2H, m), 6.80 (1H, dd, J=3.2, 0.5 Hz), 6.63 (1H, s), 4.00-4.06 (4H, m), 2.77 (3H, s), 2.06 (3H, s); Mass Spectrum (ESI) m/e=403.0 (M+1).

Example 51

1-(6-Chloro-2,3-dimethyl-4-quinolinyl)-6-(1H-pyrazol-4-yl)-1H-indol-4-ol

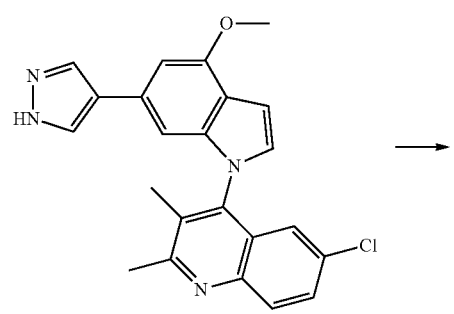

-continued

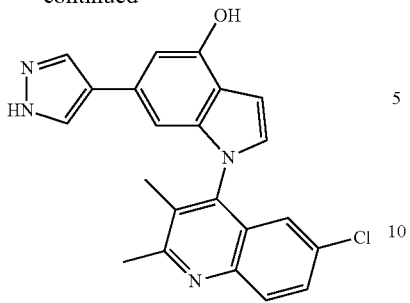

To a solution of 6-chloro-4-(4-methoxy-6-(1H-pyrazol-4-yl)-1H-indol-1-yl)-2,3-dimethylquinoline (0.1059 g, 0.272 mmol) in DCM (2.7 mL) in ice bath was added 1M BBr$_3$ in DCM (0.82 mL, 0.815 mmol) dropwise. The mixture was stirred at 0° C. for 1 h and at rt. After 26 h, to the mixture was added ice water and the mixture was neutralized with 10N NaOH to pH 9.0. The resulting solid was filtered to give a brown solid. The brown solid was purified by column chromatography on a silica gel column using 0 to 100% gradient of EtOAc in hexane as eluent to give 1-(6-chloro-2,3-dimethyl-4-quinolinyl)-6-(1H-pyrazol-4-yl)-1H-indol-4-ol as a yellow solid: 1H NMR (500 MHz, DMSO-d$_6$) δ ppm 12.74 (1H, br. s.), 9.74 (1H, s), 8.08 (1H, d, J=8.8 Hz), 7.94 (1H, br. s.), 7.73 (1H, dd, J=8.9, 2.3 Hz), 7.68 (1H, br. s.), 7.33 (1H, d, J=3.4 Hz), 6.94 (1H, d, J=2.2 Hz), 6.87 (1H, d, J=3.2 Hz), 6.76 (1H, s), 6.47 (1H, s), 2.77 (3H, s), 2.06 (3H, s); Mass Spectrum (ESI) m/e=389.0 (M+1).

Example 52

1-(6-Chloro-2,3-dimethyl-4-quinolinyl)-6-(4-pyridinyl)-1H-indole-4-carbonitrile

6-Bromo-1-(6-chloro-2,3-dimethylquinolin-4-yl)-1H-indole-4-carbonitrile

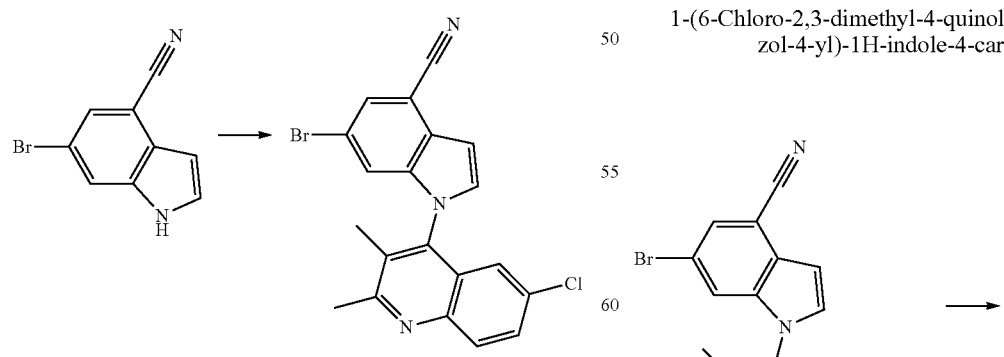

Prepared according to procedure U using 6-bromo-1H-indole-4-carbonitrile (0.5 g, 2.26 mmol) and 4,6-dichloro-2,3-dimethylquinoline (0.5626 g, 2.49 mmol) to give 6-bromo-1-(6-chloro-2,3-dimethylquinolin-4-yl)-1H-indole-4-carbonitrile as a yellow solid: Mass Spectrum (ESI) m/e=410.0 [M+1 ($^{79}$Br)] and 412.0 [M+1 ($^{81}$Br)].

1-(6-Chloro-2,3-dimethyl-4-quinolinyl)-6-(4-pyridinyl)-1H-indole-4-carbonitrile

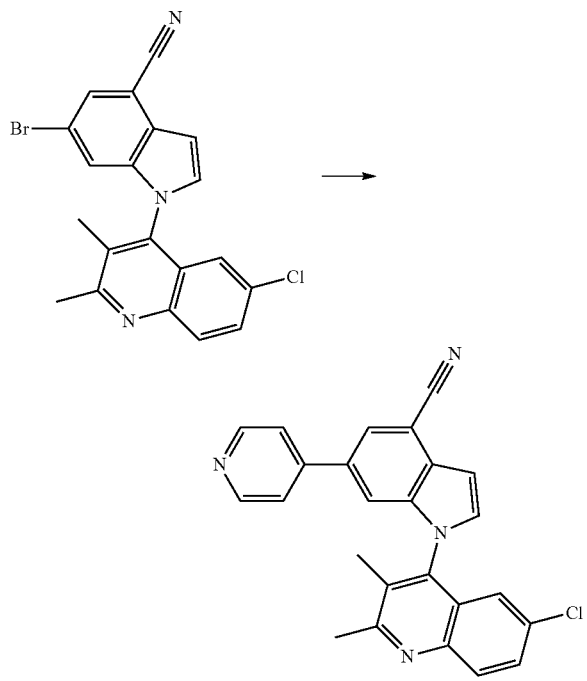

Prepared according to procedure W using 6-bromo-1-(6-chloro-2,3-dimethylquinolin-4-yl)-1H-indole-4-carbonitrile (0.2 g, 0.243 mmol) and 4-(4,4,5,5-tetramethyl-1,3,2-dioxaborolan-2-yl)pyridine (0.06 g, 0.292 mmol) to give 1-(6-chloro-2,3-dimethyl-4-quinolinyl)-6-(4-pyridinyl)-1H-indole-4-carbonitrile as a: $^1$H NMR (400 MHz, DMSO-d$_6$) δ ppm 8.55 (2H, d, J=5.9 Hz), 8.22 (1H, d, J=1.2 Hz), 8.12 (1H, d, J=9.0 Hz), 8.01 (1H, d, J=3.1 Hz), 7.70-7.79 (4H, m), 7.11 (1H, d, J=3.1 Hz), 6.91 (1H, d, J=2.3 Hz), 2.78 (3H, s), 2.02 (3H, s); Mass Spectrum (ESI) m/e=409.1 (M+1).

Example 53

1-(6-Chloro-2,3-dimethyl-4-quinolinyl)-6-(1H-pyrazol-4-yl)-1H-indole-4-carbonitrile

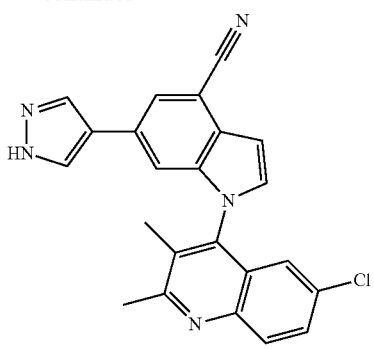

Prepared according to procedure W using 6-bromo-1-(6-chloro-2,3-dimethylquinolin-4-yl)-1H-indole-4-carbonitrile (0.2 g, 0.487 mmol) and 4-(4,4,5,5-tetramethyl-1,3,2-dioxaborolan-2-yl)-1H-pyrazole (0.1134 g, 0.584 mmol) to give 1-(6-chloro-2,3-dimethyl-4-quinolinyl)-6-(1H-pyrazol-4-yl)-1H-indole-4-carbonitrile as a white solid: $^1$H NMR (500 MHz, DMSO-$d_6$) δ ppm 12.89 (1H, br. s.), 8.23 (1H, br. s.), 8.11 (1H, d, J=9.0 Hz), 8.04 (1H, s), 7.95 (1H, br. s.), 7.83 (1H, d, J=3.2 Hz), 7.75 (1H, dd, J=8.9, 2.3 Hz), 7.45 (1H, s), 6.99 (1H, d, J=3.2 Hz), 6.91 (1H, d, J=2.2 Hz), 2.78 (3H, s), 2.02 (3H, s); Mass Spectrum (ESI) m/e=398.1 (M+1).

Example 54

6-Chloro-4-(3,3-dimethyl-6-(4-morpholinyl)-2,3-dihydro-1H-indol-1-yl)-3-methyl-2-(trifluoromethyl)quinoline 6-Chloro-3-methyl-2-(trifluoromethyl)quinolin-4-ol

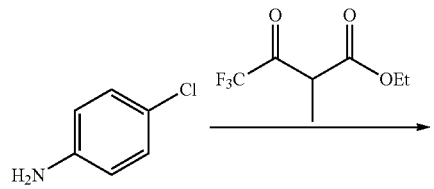

Prepared according to procedure R using 4-chloroaniline (6.44 g, 50.47 mmol) and ethyl 4,4,4-trifluoro-2-methyl-3-oxobutanoate (10 g, 50.47 mmol) to give 6-chloro-3-methyl-2-(trifluoromethyl)quinolin-4-ol as an off-white solid: Mass Spectrum (ESI) m/e=262.0 (M+1).

4,6-Dichloro-3-methyl-2-(trifluoromethyl)quinoline

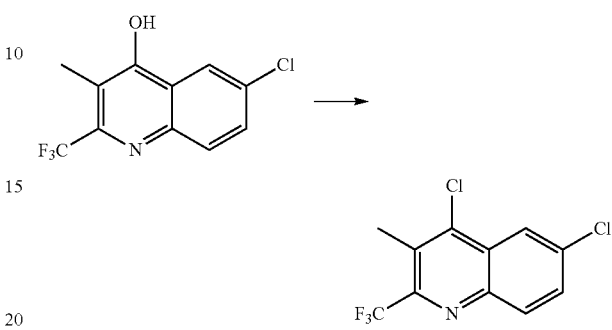

Prepared according to procedure S using 6,6-chloro-3-methyl-2-(trifluoromethyl)-quinolin-4-ol (3 g, 11.47 mmol) to give 4,6-dichloro-3-methyl-2-(trifluoromethyl)quinoline as an off-white solid: Mass Spectrum (ESI) m/e=280.0 (M+1).

6-Chloro-4-(3,3-dimethyl-6-(4-morpholinyl)-2,3-dihydro-1H-indol-1-yl)-3-methyl-2-(trifluoromethyl)quinoline

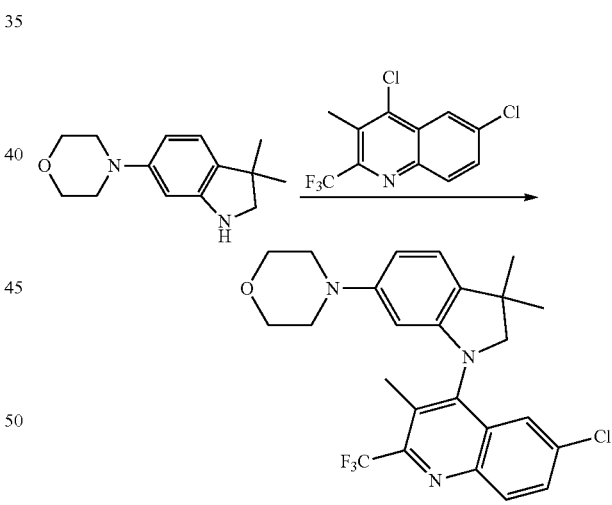

Prepared according to procedure T using 4-(3,3-dimethylindolin-6-yl)morpholine (0.2 g, 0.86 mmol) and 4,6-dichloro-3-methyl-2-(trifluoromethyl)quinoline (0.48 g, 1.72 mmol) to give an orange syrup (0.0473 g). It was purified by reverse phase HPLC using 10 to 90% gradient of acetonitrile with 0.1% TFA in water with 0.1% TFA over 60 minutes as eluent to give 6-chloro-4-(3,3-dimethyl-6-(4-morpholinyl)-2,3-dihydro-1H-indol-1-yl)-3-methyl-2-(trifluoromethyl)quinoline as a TFA salt as a yellow solid: $^1$H NMR (500 MHz, DMSO-$d_6$) δ ppm 8.23 (1H, d, J=9.0 Hz), 7.88 (1H, dd, J=8.9, 2.3 Hz), 7.83 (1H, d, J=2.4 Hz), 7.10 (1H, d, J=8.1 Hz), 6.35 (1H, dd, J=7.9, 1.3 Hz), 5.67 (1H, s), 3.66-3.80 (2H, m), 3.59

(4H, dd, J=5.5, 4.0 Hz), 2.81-2.92 (4H, m), 2.36 (3H, d, J=1.7 Hz), 1.44 (3H, s), 1.40 (3H, s); Mass Spectrum (ESI) m/e=476.1 (M+1).

Example 55

6-Chloro-4-(4-methoxy-6-(4-morpholinyl)-1H-indol-1-yl)-2,3-dimethylquinoline

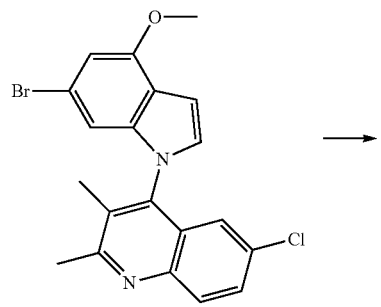

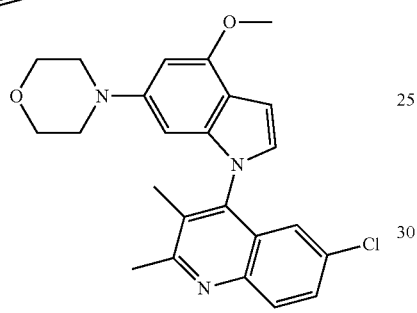

Prepared according to procedure V using 4-(6-bromo-4-methoxy-1H-indol-1-yl)-6-chloro-2,3-dimethylquinoline (0.1647 g, 0.396 mmol) and purified by reverse phase HPLC using 20 to 80% gradient of acetonitrile with 0.1% TFA in water with 0.1% TFA over 60 minutes as eluent to give 6-chloro-4-(4-methoxy-6-(4-morpholinyl)-1H-indol-1-yl)-2,3-dimethylquinoline as a yellow syrup: $^1$H NMR (500 MHz, chloroform-d) δ ppm 8.45 (1H, d, J=9.0 Hz), 7.92 (1H, dd, J=9.2, 2.1 Hz), 7.31 (1H, d, J=2.0 Hz), 7.24 (1H, d, J=3.4 Hz), 7.12 (1H, d, J=3.2 Hz), 6.86 (1H, d, J=1.0 Hz), 6.72 (1H, s), 4.00-4.15 (7H, m), 3.56 (4H, q, J=4.6 Hz), 3.07 (3H, s), 2.18 (3H, s); Mass Spectrum (ESI) m/e=422.2 (M+1).

Example 56

1-(6-Chloro-2,3-dimethyl-4-quinolinyl)-6-(4-morpholinyl)-1H-indole-4-carbonitrile

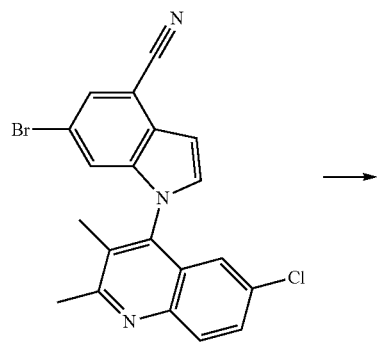

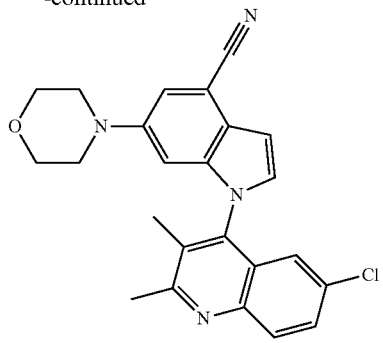

Prepared according to procedure V using 6-bromo-1-(6-chloro-2,3-dimethylquinolin-4-yl)-1H-indole-4-carbonitrile (0.0867 g, 0.211 mmol) to give 1-(6-chloro-2,3-dimethyl-4-quinolinyl)-6-(4-morpholinyl)-1H-indole-4-carbonitrile as a light yellow solid: $^1$H NMR (500 MHz, chloroform-d) δ ppm 8.07 (1H, d, J=9.0 Hz), 7.64 (1H, dd, J=9.0, 2.2 Hz), 7.26 (1H, d, J=2.0 Hz), 7.19 (1H, d, J=3.4 Hz), 7.06 (1H, d, J=2.4 Hz), 6.96 (1H, dd, J=3.2, 0.7 Hz), 6.39-6.41 (1H, m), 3.78-3.82 (4H, m), 3.00-3.05 (4H, m), 2.82 (3H, s), 2.06 (3H, s); Mass Spectrum (ESI) m/e=417.1 (M+1).

Example 57

1-(6-Chloro-2,3-dimethyl-4-quinolinyl)-6-(4-morpholinyl)-1,2,2',3',5',6'-hexahydrospiro[indole-3,4'-pyran]

6-Bromo-1-(6-chloro-2,3-dimethylquinolin-4-yl)-2',3',5',6'-tetrahydrospiro[indoline-3,4'-pyran]

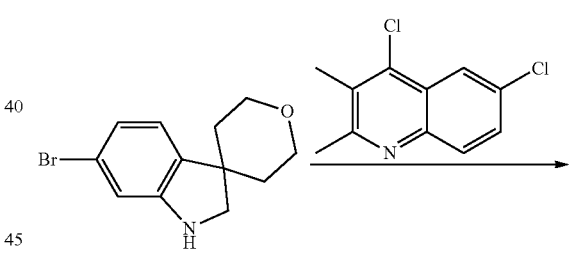

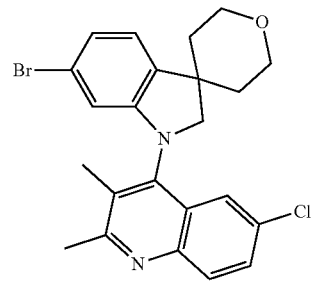

Prepared according to procedure M using 6-bromo-2',3',5',6'-tetrahydrospiro-[indoline-3,4'-pyran] (0.3 g, 1.12 mmol) and 4,6-dichloro-2,3-dimethylquinoline (0.2783 g, 1.23 mmol) to give 6-bromo-1-(6-chloro-2,3-dimethylquinolin-4-yl)-2',3',5',6'-tetrahydrospiro[indoline-3,4'-pyran] as a brown solid: $^1$H NMR (500 MHz, DMSO-d$_6$) δ ppm 8.03 (1H, d, J=9.0 Hz), 7.71 (1H, dd, J=8.9, 2.3 Hz), 7.65 (1H, d, J=2.2 Hz), 7.22 (1H, d, J=7.8 Hz), 6.83 (1H, dd, J=7.8, 1.5 Hz), 5.94 (1H, d, J=1.5 Hz), 4.04 (1H, d, J=9.8 Hz), 3.80-3.93 (3H, m), 3.39-3.54 (2H, m), 2.68 (3H, s), 2.22 (3H, s), 1.94-2.06 (2H, m), 1.85 (1H, d, J=13.4 Hz), 1.73 (1H, dd, J=13.4, 1.5 Hz); Mass Spectrum (ESI) m/e=457.1 [M+1 ($^{79}$Br)] and 459.1 [M+1 ($^{81}$Br)].

1-(6-Chloro-2,3-dimethyl-4-quinolinyl)-6-(4-morpholinyl)-1,2,2',3',5',6'-hexahydrospiro[indole-3,4'-pyran]

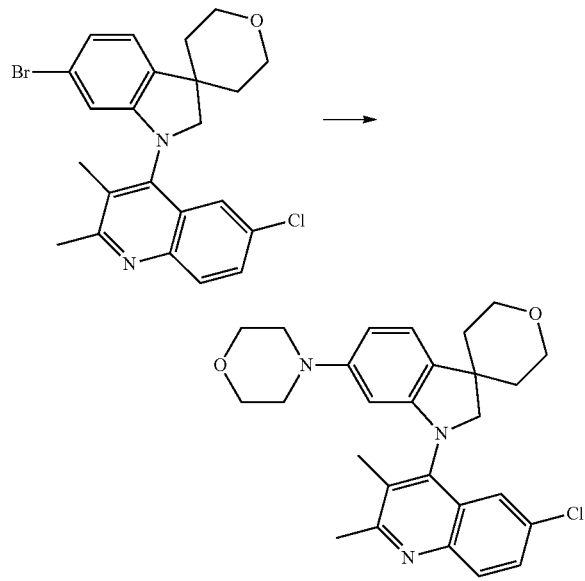

Prepared according to procedure V using 6-bromo-1-(6-chloro-2,3-dimethylquinolin-4-yl)-2',3',5',6'-tetrahydrospiro[indoline-3,4'-pyran] (0.2305 g, 0.503 mmol) to give 1-(6-chloro-2,3-dimethyl-4-quinolinyl)-6-(4-morpholinyl)-1,2,2',3',5',6'-hexahydrospiro[indole-3,4'-pyran] as a yellow solid: $^1$H NMR (500 MHz, DMSO-d$_6$) δ ppm 7.97-8.03 (1H, m), 7.67 (2H, dd, J=4.5, 2.1 Hz), 7.10 (1H, d, J=8.1 Hz), 6.26 (1H, dd, J=8.1, 1.5 Hz), 5.46 (1H, d, J=1.5 Hz), 3.94 (1H, d, J=9.5 Hz), 3.82-3.91 (2H, m), 3.78 (1H, d, J=9.8 Hz), 3.54-3.59 (4H, m), 3.40-3.52 (2H, m), 2.80-2.87 (4H, m), 2.68 (3H, s), 2.21 (3H, s), 1.92-2.02 (2H,m), 1.78 (1H, d, J=13.2 Hz), 1.68 (1H, d, J=12.5 Hz); Mass Spectrum (ESI) m/e=464.2 (M+1).

Example 58

1-(2,3-Dimethyl-4-quinolinyl)-6-(4-morpholinyl)-1,2,2',3',5',6'-hexahydrospiro[indole-3,4'-pyran]

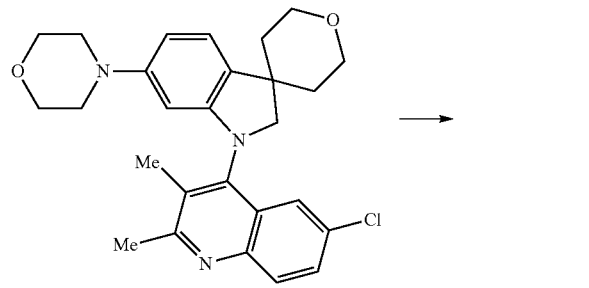

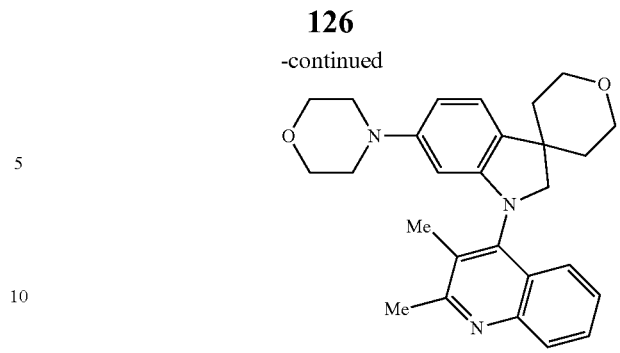

A mixture of 1-(6-chloro-2,3-dimethylquinolin-4-yl)-6-morpholino-2',3',5',6'-tetrahydrospiro[indoline-3,4'-pyran] (0.027 g, 0.058 mmol), triethylamine (0.008 mL, 0.058 mmol), and 10% Pd/C (0.02 g, 0.0188 mmol) in MeOH-EtOAc (2:1, 3 mL) was stirred under hydrogen at rt. After 3 h, the mixture was filtered through a Celite™ pad and the pad was washed with MeOH and EtOAc to give a tan solid. The tan solid was purified by column chromatography on a silica gel column using 0 to 100% gradient of EtOAc in hexane as eluent to give 1-(2,3-dimethyl-4-quinolinyl)-6-(4-morpholinyl)-1,2,2',3',5',6'-hexahydrospiro[indole-3,4'-pyran] as a yellow solid: $^1$H NMR (500 MHz, DMSO-d$_6$) δ ppm 7.97 (1H, d, J=8.3 Hz), 7.71 (1H, d, J=8.1 Hz), 7.62-7.68 (1H, m), 7.42-7.49 (1H, m), 7.08 (1H, d, J=8.3 Hz), 6.23 (1H, dd, J=8.2, 2.1 Hz), 5.41 (1H, d, J=2.2 Hz), 3.77-3.96 (4H, m), 3.52-3.59 (4H, m), 3.41-3.51 (2H, m), 2.81 (4H, dd, J=5.4, 2.9 Hz), 2.68 (3H, s), 2.22 (3H, s), 1.91-2.03 (2H, m), 1.78-1.85 (1H, m), 1.65-1.72 (1H, m); Mass Spectrum (ESI) m/e=430.2 (M+1).

Example 59

6-Bromo-1-(6-chloro-7-methoxy-2,3-dimethyl-4-quinolinyl)-1,2,2',3',5',6'-hexahydrospiro[indole-3,4'-pyran]

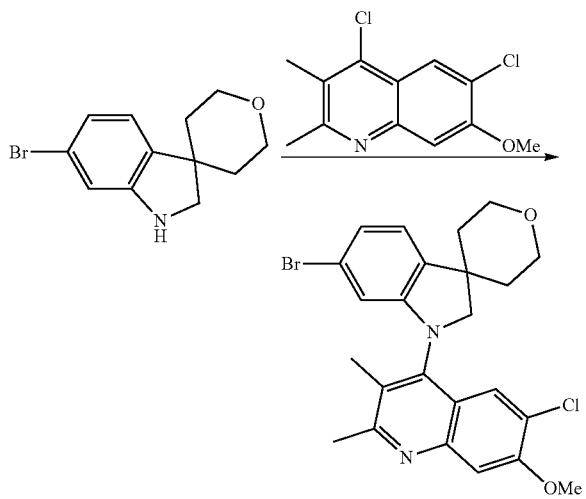

Prepared according to procedure M using 6-bromo-2',3',5',6'-tetrahydrospiro-[indoline-3,4'-pyran] (0.3 g, 1.12 mmol) and 4,6-dichloro-7-methoxy-2,3-dimethylquinoline (0.3152 g, 1.23 mmol) to give 6-bromo-1-(6-chloro-7-methoxy-2,3-dimethyl-4-quinolinyl)-1,2,2',3',5',6'-hexahydrospiro[indole-3,4'-pyran] as a: $^1$H NMR (500 MHz, DMSO-d$_6$) δ ppm 7.65 (1H, s), 7.58 (1H, s), 7.21 (1H, d, J=8.1 Hz), 6.82 (1H, dd, J=7.8, 1.7 Hz), 5.90 (1H, d, J=1.7 Hz), 3.96-4.05 (4H, m), 3.82-3.92 (3H, m), 3.41-3.53 (2H, m), 2.66 (3H, s), 2.17 (3H, s), 1.95-2.06 (2H, m), 1.85 (1H, dd, J=13.4, 1.7 Hz), 1.72 (1H, dd, J=13.3, 1.8 Hz); Mass Spectrum (ESI) m/e=487.0 [M+1 ($^{79}$Br)] and 489.1 [M+1 ($^{81}$Br)].

Example 60

1-(6-Chloro-7-methoxy-2,3-dimethyl-4-quinolinyl)-1,2,2',3',5',6'-hexahydrospiro[indole-3,4'-pyran]-6-carbonitrile

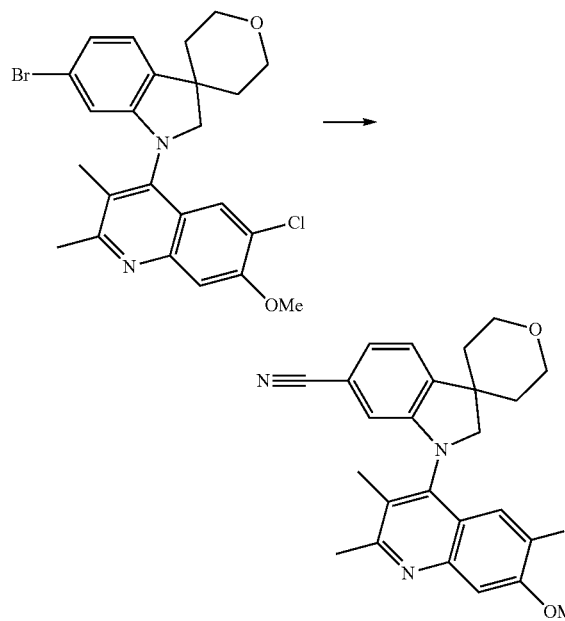

A mixture of 6-bromo-1-(6-chloro-7-methoxy-2,3-dimethylquinolin-4-yl)-2',3',5',6'-tetrahydrospiro[indoline-3,4'-pyran] (0.1 g, 0.205 mmol) and CuCN (0.0367 g, 0.41 mmol) in DMF (1 mL) was stirred at 150° C. After 48 h, the mixture was concentrated under reduced pressure. The residue was purified by column chromatography on a silica gel column using 0 to 100% gradient of EtOAc in hexane as eluent to give 1-(6-chloro-7-methoxy-2,3-dimethyl-4-quinolinyl)-1,2,2',3',5',6'-hexahydrospiro[indole-3,4'-pyran]-6-carbonitrile. $^1$H NMR (400 MHz, DMSO-d$_6$) δ ppm 7.67 (1H, s), 7.59 (1H, s), 7.47 (1H, d, J=7.4 Hz), 7.12 (1H, dd, J=7.6, 1.4 Hz), 6.16 (1H, d, J=1.6 Hz), 4.10 (1H, d, J=9.8 Hz), 4.00 (3H, s), 3.82-3.94 (3H, m), 3.42-3.56 (2H, m), 2.66 (3H, s), 2.15 (3H, s), 1.98-2.11 (2H, m), 1.89 (1H, dd, J=13.7, 1.6 Hz), 1.74 (1H, dd, J=13.5, 1.0 Hz); Mass Spectrum (ESI) m/e=434.2 (M+1).

Example 61

6-(4-Morpholinyl)-1-(2,3,8-trimethyl-4-quinolinyl)-1,2,2',3',5',6'-hexahydrospiro[indole-3,4'-pyran]

6-Bromo-1-(2,3,8-trimethylquinolin-4-yl)-2',3',5',6'-tetrahydrospiro[indoline-3,4'-pyran]

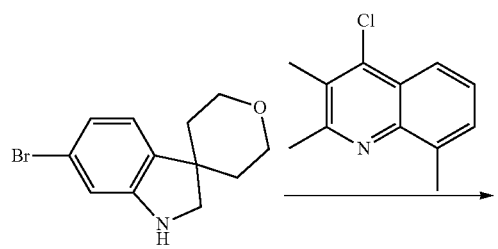

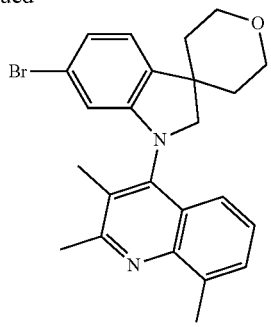

Prepared according to procedure M using 6-bromo-2',3',5',6'-tetrahydrospiro-[indoline-3,4'-pyran] (0.5 g, 1.86 mmol) and 4-chloro-2,3,8-trimethylquinoline (0.4219 g, 2.05 mmol) to give 6-bromo-1-(2,3,8-trimethylquinolin-4-yl)-2',3',5',6'-tetrahydrospiro[indoline-3,4'-pyran]: $^1$H NMR (400 MHz, DMSO-d$_6$) δ ppm 7.52 (2H, dd, J=17.2, 7.4 Hz), 7.37 (1H, dd, J=8.2, 7.0 Hz), 7.20 (1H, d, J=7.8 Hz), 6.78 (1H, dd, J=7.8, 1.6 Hz), 5.82 (1H, d, J=2.0 Hz), 3.83-4.00 (4H, m), 3.39-3.54 (2H, m), 2.73 (3H, s), 2.71 (3H, s), 2.24 (3H, s), 1.92-2.10 (2H, m), 1.66-1.90 (2H, m); Mass Spectrum (ESI) m/e=437.0 [M+1 ($^{79}$Br)] and 439.1 [M+1 ($^{81}$Br)].

6-(4-Morpholinyl)-1-(2,3,8-trimethyl-4-quinolinyl)-1,2,2',3',5',6'-hexahydrospiro[indole-3,4'-pyran]

Prepared according to procedure V using 6-bromo-1-(2,3,8-trimethylquinolin-4-yl)-2',3',5',6'-tetrahydrospiro[indoline-3,4'-pyran] (0.2 g, 0.457 mmol) and purified by reverse phase HPLC using 10 to 90% gradient of acetonitrile with 0.1% TFA in water with 0.1% TFA over 60 minutes as eluent to give 6-(4-morpholinyl)-1-(2,3,8-trimethyl-4-quinolinyl)-1,2,2',3',5',6'-hexahydrospiro[indole-3,4'-pyran] as a TFA salt. $^1$H NMR (400 MHz, DMSO-d$_6$) δ ppm 7.62-7.77 (2H, m), 7.47 (1H, t, J=7.6 Hz), 7.17 (1H, d, J=8.2 Hz), 6.40 (1H, d, J=8.6 Hz), 5.67 (1H, s), 4.09 (1H, d, J=9.0 Hz), 3.93 (1H, d, J=9.8 Hz), 3.81-3.90 (2H, m), 3.56-3.64 (4H, m), 3.39-3.50

(2H, m), 2.87-2.96 (4H, m), 2.82 (3H, s), 2.77 (3H, s), 2.22 (3H, s), 1.89-2.05 (2H, m), 1.64-1.84 (2H, m, J=46.6, 12.9 Hz); Mass Spectrum (ESI) m/e=444.2 (M+1).

Example 62

6-Chloro-7-methoxy-2,3-dimethyl-4-(3,3,7-trimethyl-6-(4-morpholinyl)-2,3-dihydro-1H-indol-1-yl)quinoline N'-(3-Bromo-2-methylphenyl)isobutyrohydrazide

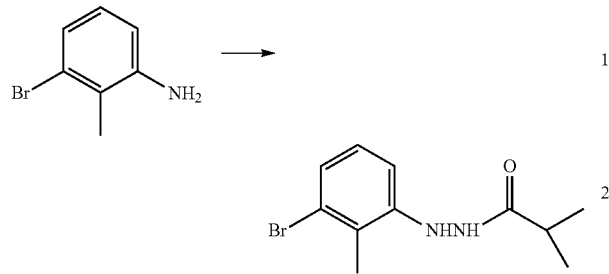

To 3-bromo-2-methylaniline (2.5 g, 13.4 mmol) in 3N HCl (16 mL) at −10° C. NaNO₂ (1.02 g, 14.78 mmol) in water (3 mL) was added dropwise. The resultant mixture was stirred for 30 minutes. SnCl₂.2H₂O (7.58 g, 33.6 mmol) in conc. HCl (6 mL) was added slowly to the mixture. At −10° C. the mixture was stirred for 1 h. The mixture was filtered. The solid was rinsed with cold brine, 2N HCl, and EtOAc respectively, and then dried under vacuum for 20 minutes. To the dried solid in MeOH (20 mL) was added NEt₃ (1.67 mL, 11.97 mmol) and isobutyryl chloride (0.67 mL, 6.3 mmol) dropwise at 0° C. The mixture was stirred at 0° C. for 30 minutes. The mixture was concentrated and the residue was purified by flash chromatography over silica gel, using 50% EtOAc in hexane, gave N'-(3-bromo-2-methylphenyl)isobutyrohydrazide. ¹H-NMR (DMSO-d⁶) δ 9.70 (1H, s), 7.37 (1H, s), 6.96-6.90 (2H, m), 6.62-6.59 (1H, m), 2.52-2.40 (1H, m), 2.23 (3H, s), 1.08 (6H, d, J=4.0 Hz). Mass Spectrum (ESI) m/e=270.1 (M+1).

6-Bromo-3,3,7-trimethylindolin-2-one

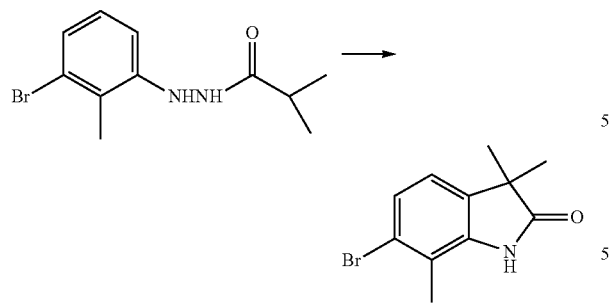

A mixture of N'-(3-bromo-2-methylphenyl)isobutyrohydrazide (1.14 g, 4.23 mmol) and CaH (0.356 g, 8.46 mmol) in 1,2,3,4-tetrahydronaphthalene (10 mL) was heated to 200° C., and stirred at 200° C. for 17 h. The mixture was cooled to 0° C. and to the mixture was added water (1.63 mL) and MeOH (1.63 mL) slowly. At 0° C. the PH of the mixture was adjusted to PH1 by adding conc. HCl. The mixture then was heated to reflux for 1 h. The reaction mixture was cooled to rt, and NaOH (3N) was added to the mixture, adjusting to pH 5. The resultant mixture was diluted with EtOAc, washed with water and brine, dried and concentrated. Purification of the residue by flash chromatography over silica gel, using 30% EtOAc in hexane, gave 6-bromo-3,3,7-trimethylindolin-2-one. ¹H-NMR (DMSO-d⁶) δ 10.58 (1H, s), 7.21 (1H, d, J=8.0 Hz), 7.07 (1H, d, J=8.0 Hz), 2.27 (3H, s), 1.24 (6H, s). Mass Spectrum (ESI) m/e=254.0 (M+1).

3,3,7-Trimethyl-6-morpholinoindolin-2-one

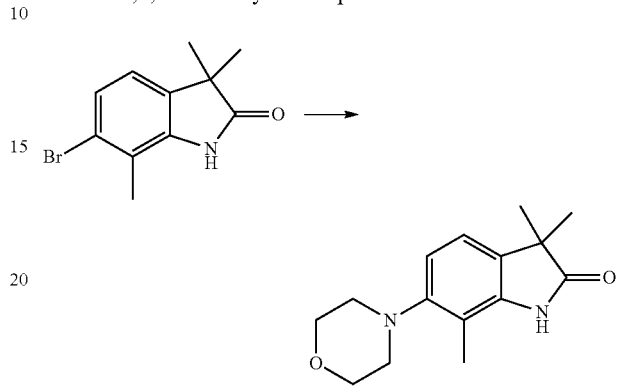

A mixture of 6-bromo-3,3,7-trimethylindolin-2-one (0.63 g, 2.44 mmol), NaOt-Bu (0.33 g, 3.42 mmol), Pd₂(dba)₃ (0.11 g, 0.12 mmol), morpholine (0.51 mL, 5.86 mmol), and 2,8,9-triisobutyl-2,5,8,9-tetraaza-1-phosphabicyclo[3.3.3]undecane (0.11 mL, 0.29 mmol) in Toluene (2.5 mL) was flushed with N₂ for 10 minutes and then heated in a microwave at 120° C. for 80 minutes. The mixture was cooled to rt and concentrated. Purification of the residue by flash chromatography over silica gel, using 40% EtOAc in hexane, gave 3,3,7-trimethyl-6-morpholinoindolin-2-one. ¹H-NMR (DMSO-d⁶) δ 10.27 (1H, s), 7.04 (1H, d, J=8.0 Hz), 6.64 (1H, d, J=8.0 Hz), 3.72 (4H, s), 2.78 (4H, s), 2.13 (3H, s), 1.21 (6H, s). Mass Spectrum (ESI) m/e=261.1 (M+1).

4-(3,3,7-Trimethylindolin-6-yl)morpholine

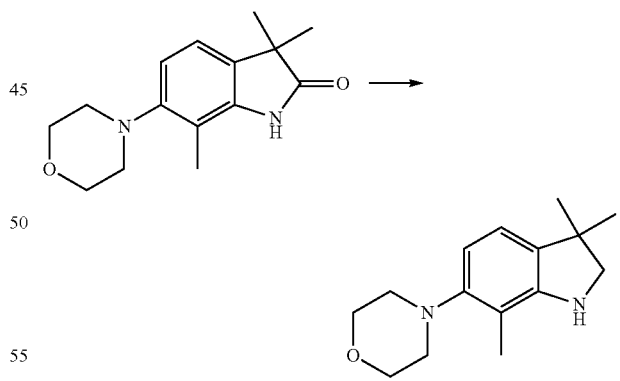

To a solution of 3,3,7-trimethyl-6-morpholinoindolin-2-one (45.7 mg, 0.176 mmol) in toluene (10 mL) at 80° C. under N₂, Red-Al (0.18 mL, 3M, 0.53 mmol) was added dropwise. The resultant mixture was stirred at 80° C. for 2 h. The mixture was cooled to rt and quenched with NaOH (2 mL, 3N). The mixture was diluted with EtOAc and washed with water and brine, dried and concentrated. Purification of the residue by flash chromatography over silica gel, using 40% EtOAc in hexane, gave 4-(3,3,7-trimethylindolin-6-yl)morpholine (33.1 mg, 76%): ¹H-NMR (DMSO-d⁶) δ 6.74 (1H, d, J=8.0 Hz), 6.29 (1H, d, J=8.0 Hz), 5.11 (1H, s), 3.69 (4H, s), 3.16 (2H, s), 2.72 (4H, s), 1.96 (3H, s), 1.18 (6H, s). Mass Spectrum (ESI) m/e=247.1 (M+1).

6-Chloro-7-methoxy-2,3-dimethyl-4-(3,3,7-trimethyl-6-(4-morpholinyl)-2,3-dihydro-1H-indol-1-yl)quinoline

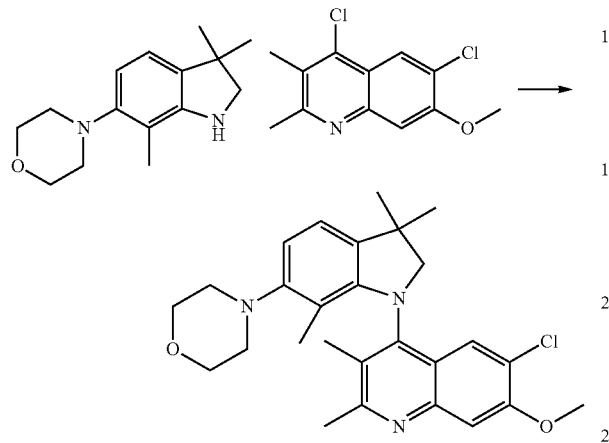

A mixture of 4-(3,3,7-trimethylindolin-6-yl)morpholine (37.9 mg, 0.154 mmol), 4,6-dichloro-7-methoxy-2,3-dimethylquinoline (made by procedures A-D, 59.1 mg, 0.231 mmol), cesium carbonate (75.3 mg, 0.231 mmol), Pd$_2$(dba)$_3$ (28.4 mg, 0.031 mmol), and Xantphos (26.7 mg, 0.046 mmol) in toluene (2 mL) under N$_2$ was heated at 100° C. for 21 h. The mixture was cooled to rt and diluted with DCM-MeOH (8:2). The mixture was filtered and the filtrates were concentrated. Purification of the residue by flash chromatography over silica gel, using 40% EtOAc in hexane, and following the second purification by flash chromatography over silica gel, using 10% MeOH in DCM, gave 6-chloro-7-methoxy-2,3-dimethyl-4-(3,3,7-trimethyl-6-(4-morpholinyl)-2,3-dihydro-1H-indol-1-yl)quinoline. $^1$H-NMR (DMSO-d$^6$) δ 7.40 (1H, s), 7.09 (1H, s), 7.07 (1H, d, J=8.0 Hz), 6.72 (1H, d, J=8.0 Hz), 4.01 (3H, s), 3.93 (1H, d, J=8.0 Hz), 3.80-3.62 (4H, m), 3.53 (1H, d, J=8.0 Hz), 3.00-2.90 (2H, m), 2.75-2.69 (2H, m), 2.61 (3H, s), 2.42 (3H, s), 1.70 (3H, s), 1.33 (3H, s), 1.09 (3H, s). Mass Spectrum (ESI) m/e=466.1 (M+1).

Example 63

7-Chloro-9-(3,3-dimethyl-6-(4-morpholinyl)-2,3-dihydro-1H-indol-1-yl)-2,3-dihydro-1H-cyclopenta[b]quinoline 7,9-Dichloro-2,3-dihydro-1H-cyclopenta[b]quinoline

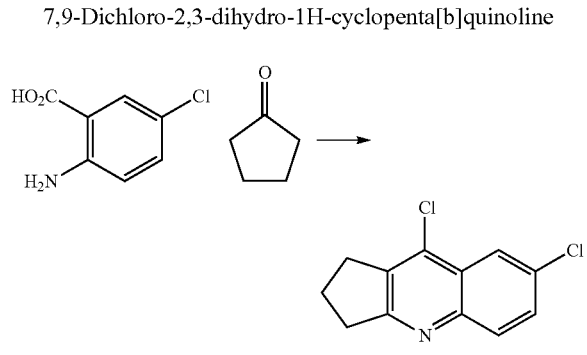

Prepared according to procedure Q using 2-amino-5-chlorobenzoic acid (5.15 g, 30 mmol) and propane (2.7 mL, 30 mmol) in POCl$_3$ (25 mL). The crude product was purified by column chromatography on silica (using a gradient of DCM:MeOH:NH$_4$OH, 90:9:1 as eluent) to give 7,9-dichloro-2,3-dihydro-1H-cyclopenta[b]quinoline. Mass Spectrum (ESI) m/e=239 (M+1).

7-Chloro-9-(3,3-dimethyl-6-(4-morpholinyl)-2,3-dihydro-1H-indol-1-yl)-2,3-dihydro-1H-cyclopenta[b]quinoline

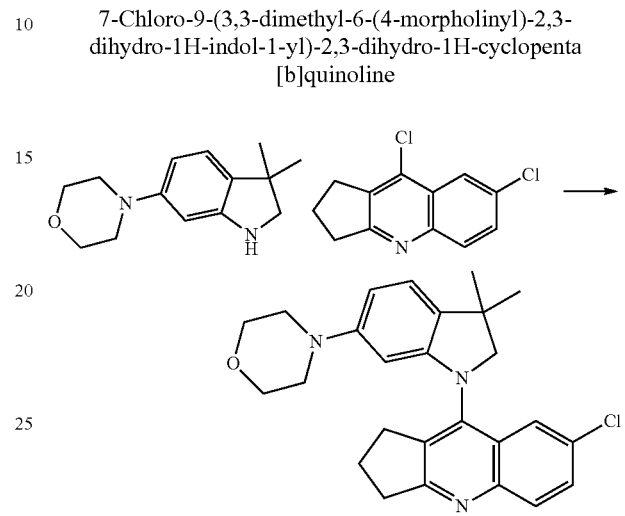

Prepared according to procedure T using 4-(3,3-dimethylindolin-6-yl)morpholine (0.2 g, 0.86 mmol), 7,9-dichloro-2,3-dihydro-1H-cyclopenta[b]quinoline (0.41 g, 1.72 mmol), cesium carbonate (0.561 g, 1.72 mmol), Pd$_2$(dba)$_3$ (0.079 g, 0.086 mmol) and (±) BINAP (0.084 g, 0.129 mmol) were added 1,4-dioxane (2 mL). The resulting mixture was purged with Argon and subjected to microwave heating at 140° C. for 3 h. The crude residue was purified by HPLC to give 7-chloro-9-(3,3-dimethyl-6-(4-morpholinyl)-2,3-dihydro-1H-indol-1-yl)-2,3-dihydro-1H-cyclopenta[b]quinoline. 1H NMR (500 MHz, DMSO-d$_6$) δ ppm 8.07 (1H, d, J=2.0 Hz), 8.0 (1H, m), 7.94 (1H, dd, J=8.9, 2.1 Hz), 7.17 (1H, d, J=8.3 Hz), 6.64 (1H, dd, J=8.3, 2.0 Hz), 6.17 (1H, s), 4.33 (1H, d, J=9.3 Hz), 3.98 (1H, m), 3.66 (4H, dd, J=5.6, 3.9 Hz), 3.24 (2H, m), 2.97 (4H, dd, J=5.9, 3.7 Hz), 2.90 (1H, m), 2.61 (1H, m), 2.18 (2H, m), 1.30 (3H, s) 1.29 (3H, s). Mass Spectrum (ESI) m/e=434 (M+1).

Example 64

7-chloro-9-(3,3-dimethyl-6-(4-morpholinyl)-2,3-dihydro-1H-indol-1-yl)-1,2,3,4-tetrahydroacridine

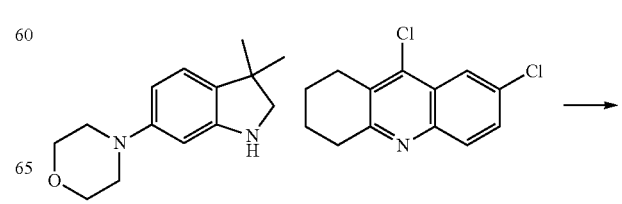

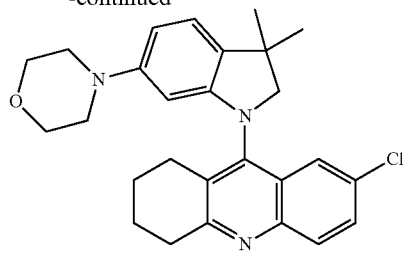

Prepared according to procedure T using 4-(3,3-dimethylindolin-6-yl)morpholine (0.2 g, 0.86 mmol), 7,9-dichloro-1,2,3,4-tetrahydroacridine (0.434 g, 1.72 mmol), cesium carbonate (0.561 g, 1.72 mmol), Pd$_2$(dba)$_3$ (0.079 g, 0.086 mmol) and (±) BINAP (0.084 g, 0.129 mmol) in 1,4-dioxane (2 mL). The crude residue was purified by HPLC to give 7-chloro-9-(3,3-dimethyl-6-(4-morpholinyl)-2,3-dihydro-1H-indol-1-yl)-1,2,3,4-tetrahydroacridine. 1H NMR (500 MHz, DMSO-d$_6$) δ ppm 8.04 (1H, d, J=9.5 Hz), 7.85 (2H, m), 7.14 (1H, d, J=8.3 Hz), 6.47 (1H, d, J=8.3 Hz), 5.84 (1H, s), 3.90 (2H, m), 3.60 (4H, m), 3.17 (2H, t, J=6.4 Hz), 2.89 (4H, m), 2.59 (2H, m), 1.79 (4H, m) 1.41 (3H, s), 1.37 (3H, s). Mass Spectrum (ESI) m/e=449 (M+1).

Example 65

7-Chloro-9-(3,3-dimethyl-6-(4-morpholinyl)-2,3-dihydro-1H-indol-1-yl)-3,3-dimethyl-2,3-dihydro-1H-cyclopenta[b]quinoline

7,9-Dichloro-3,3-dimethyl-2,3-dihydro-1H-cyclopenta[b]quinoline

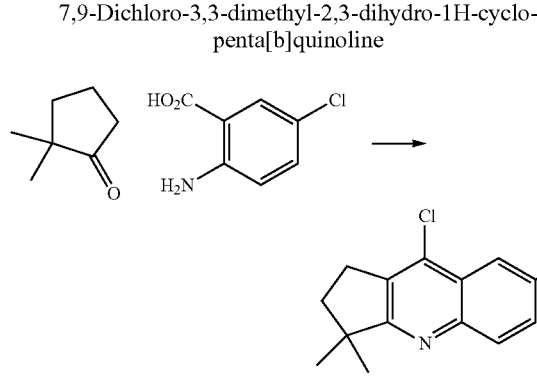

2,2-Dimethylcyclopentanone (1.12 g, 10 mmol) and 2-amino-5-chlorobenzoic acid (1.72 g, 10 mmol) were stirred at rt for 10 minutes followed by the addition of POCl$_3$ (10 mL). The resulting mixture was heated to 100° C. for 5 h and overnight at rt. After this time the reaction mixture was poured into ice water and extracted with EtOAc. The solvent was evaporated in vacuo and flash column chromatography on silica (using a gradient of EtOAc/hexane, 0-100% eluent) gave 7,9-dichloro-3,3-dimethyl-2,3-dihydro-1H-cyclopenta[b]quinoline. Mass Spectrum (ESI) m/e=267 (M+1).

7-Chloro-9-(3,3-dimethyl-6-(4-morpholinyl)-2,3-dihydro-1H-indol-1-yl)-3,3-dimethyl-2,3-dihydro-1H-cyclopenta[b]quinoline

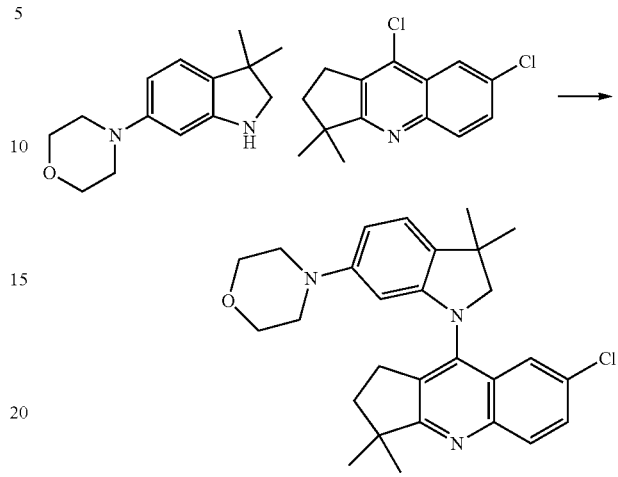

Prepared according to procedure T using 4-(3,3-dimethylindolin-6-yl)morpholine (0.2 g, 0.86 mmol), 7,9-dichloro-3,3-dimethyl-2,3-dihydro-1H-cyclopenta[b]-quinoline (0.434 g, 1.72 mmol), cesium carbonate (0.561 g, 1.72 mmol), Pd$_2$(dba)$_3$ (0.079 g, 0.086 mmol) and (±) BINAP (0.084 g, 0.129 mmol) in 1,4-dioxane (2 mL). After HPLC purification 7-chloro-9-(3,3-dimethyl-6-(4-morpholinyl)-2,3-dihydro-1H-indol-1-yl)-3,3-dimethyl-2,3-dihydro-1H-cyclopenta[b]-quinoline was obtained. 1H NMR (500 MHz, DMSO-d$_6$) δ ppm 8.02 (1H, d, J=9.0 Hz), 7.86 (1H, m), 7.68 (1H, m), 7.06 (1H, m), 6.38 (1H, m), 5.73 (1H, s), 3.86 (2H, d, J=0.5 Hz), 3.73 (2H, s), 3.62 (4H, dd, J=5.4, 4.4 Hz), 3.06 (1H, m), 2.84-2.94 (4H, m), 1.96 (1H, m), 1.33 (12H, m). Mass Spectrum (ESI) m/e=463 (M+1).

Example 66

4-(3,3-Dimethyl-6-(4-morpholinyl)-2,3-dihydro-1H-indol-1-yl)-3-methylquinoline

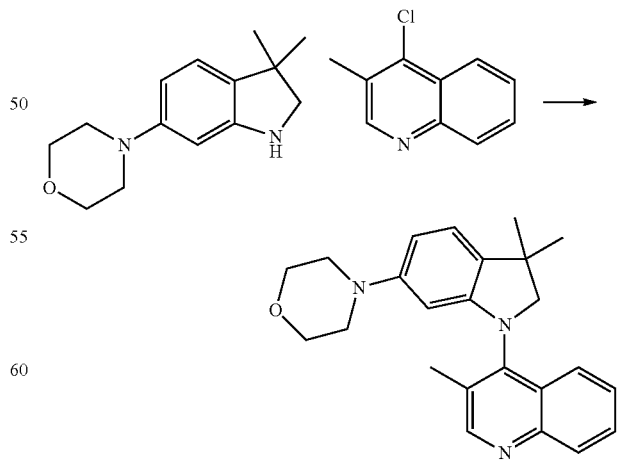

Prepared according to procedure T using 4-(3,3-dimethylindolin-6-yl)morpholine (0.175 g, 0.754 mmol), 4-chloro- 3-methylquinoline (0.134 g, 0.754 mmol), cesium carbonate (0.492 g, 1.5 mmol), Pd₂(dba)₃ (0.069 g, 0.075 mmol) and (±) BINAP (0.070 g, 0.113 mmol) in toluene (3 mL). After purification by HPLC 4-(3,3-dimethyl-6-(4-morpholinyl)-2,3-dihydro-1H-indol-1-yl)-3-methylquinoline was obtained. 1H NMR (400 MHz, MeOH) δ ppm 8.82 (1H, s), 8.07 (1H, d, J=8.2 Hz), 7.94 (1H, d, J=8.2 Hz), 7.73 (1H, m), 7.55 (1H, t, J=7.6 Hz), 7.10 (1H, d, J=8.2 Hz), 6.39 (1H, dd, J=8.2, 2.0 Hz), 5.59 (1H, s), 3.79 (1H, m), 3.76 (1H, m), 3.68 (4H, m), 2.89 (4H, m), 2.37 (3H, s), 1.50 (3H, s), 1.46 (3H, s). Mass Spectrum (ESI) m/e=375 (M+1).

Example 67

4-(3,3-Dimethyl-6-(4-pyridinyl)-2,3-dihydro-1H-indol-1-yl)-7-fluoro-3-methyl-2-(2-pyridinyl)quinoline

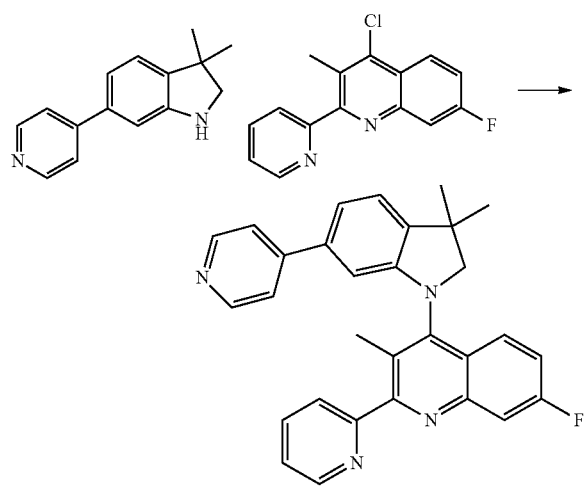

Prepared according to procedure T using 3,3-dimethyl-6-(pyridin-4-yl)indoline (0.026 g, 0.116 mmol), 4-chloro-7-fluoro-3-methyl-2-(pyridin-2-yl)quinoline (0.032 g, 0.116 mmol), cesium carbonate (0.076 g, 0.232 mmol), Pd₂(dba)₃ (0.011 g, 0.012 mmol) and (±) BINAP (0.011 g, 0.017 mmol) in toluene (3 mL). After purification by HPLC 4-(3,3-dimethyl-6-(4-pyridinyl)-2,3-dihydro-1H-indol-1-yl)-7-fluoro-3-methyl-2-(2-pyridinyl)quinoline was obtained. 1H NMR (400 MHz, MeOH) δ ppm 8.75 (1H, d, J=4.7 Hz), 8.68 (2H, m), 8.12-8.23 (3H, m), 8.07 (1H, dd, J=9.4, 5.9 Hz), 7.96 (1H, d, J=7.8 Hz), 7.83 (1H, dd, J=9.8, 2.7 Hz), 7.65 (1H, dd, J=7.6, 4.9 Hz), 7.50 (2H, m), 7.42 (1H, m), 6.62 (1H, s), 4.05 (1H, d, J=9.0 Hz), 3.90 (1H, d, J=9.4 Hz), 2.28 (3H, s), 1.65 (3H, s), 1.57 (3H, s). Mass Spectrum (ESI) m/e=462 (M+1).

Example 68

6-Chloro-4-(3,3-dimethyl-6-(4-morpholinyl)-2,3-dihydro-1H-indol-1-yl)-2,3,8-trimethylquinoline 6-Chloro-2,3,8-trimethylquinolin-4-ol

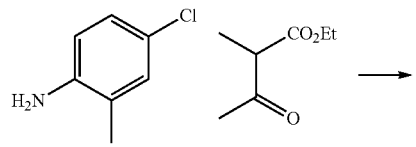

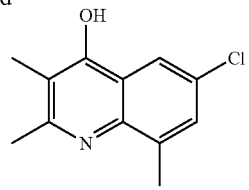

Prepared according to procedure R using 4-chloro-2-methylaniline (2.22 g, 15.7 mmol), ethyl 2-methyl-3-oxobutanoate (4.08 g, 31.4 mmol) in PPA (6.3 g, 62.8 mmol) and heating at 170° C. for 2 h and at rt overnight. The crude mixture was neutralized to pH 7-8 and the precipitated was filtered. The solid was then dried under high vacuum to give 6-chloro-2,3,8-trimethylquinolin-4-ol as white solid. Mass Spectrum (ESI) m/e=222 (M+1).

4,6-Dichloro-2,3,8-trimethylquinoline

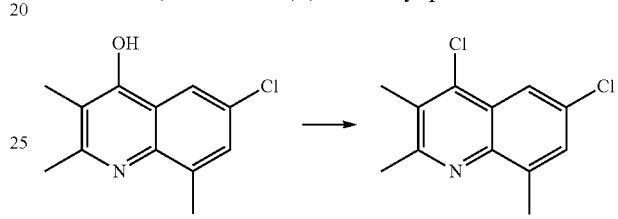

Prepared according to procedure S using 6-chloro-2,3,8-trimethylquinolin-4-ol (3.25 g, 1.65 mmol) in POCl₃ (20 mL) and heating at reflux for 3 h. After this time the reaction mixture was cooled to rt and poured into ice water. The resulting solid was filtered and washed with water. The product was then dried under vacuum and 4,6-dichloro-2,3,8-trimethylquinoline was obtained as a white solid. Mass Spectrum (ESI) m/e=241 (M+1).

6-Chloro-4-(3,3-dimethyl-6-(4-morpholinyl)-2,3-dihydro-1H-indol-1-yl)-2,3,8-trimethylquinoline

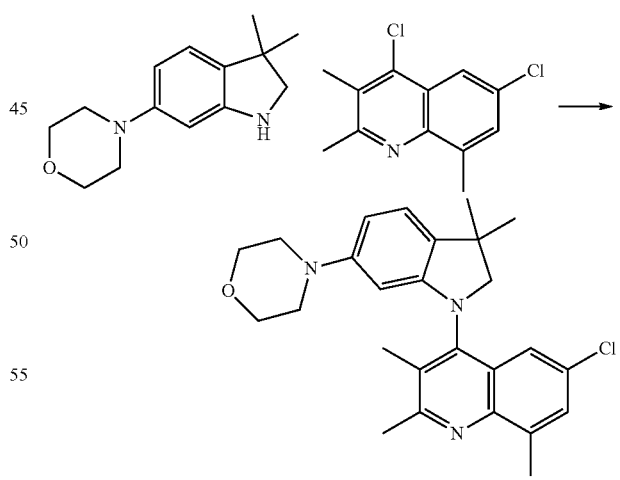

Prepared according to procedure T using 4-(3,3-dimethylindolin-6-yl)morpholine (0.2 g, 0.86 mmol), 4,6-dichloro-2,3,8-trimethylquinoline (0.413 g, 1.72 mmol), cesium carbonate (0.561 g, 1.72 mmol), Pd₂(dba)₃ (0.079 g, 0.086 mmol) and (±) BINAP (0.084 g, 0.129 mmol) in 1,4-dioxane (2 mL). After purification by HPLC 6-chloro-4-(3,3-dimethyl-6-(4-morpholinyl)-2,3-dihydro-1H-indol-1-yl)-2,3,8- trimethylquinoline was obtained. 1H NMR (500 MHz, DMSO-$d_6$) δ ppm 7.56-7.60 (2H, m), 7.05 (1H, d, J=8.3 Hz), 6.25 (1H, dd, J=8.1, 2.2 Hz), 5.44 (1H, d, J=2.2 Hz), 3.68 (1H, m), 3.58 (4H, m), 2.85 (5H, d, J=4.9 Hz), 2.71 (6H, d, J=13.2 Hz), 2.20 (3H, s), 1.42 (6H, d, J=17.9 Hz). Mass Spectrum (ESI) m/e=436 (M+1).

Example 69

4-(3,3-Dimethyl-6-(4-morpholinyl)-2,3-dihydro-1H-indol-1-yl)-2-(2-fluorophenyl)-3-methylquinoline Ethyl 3-(2-fluorophenyl)-2-methyl-3-oxopropanoate

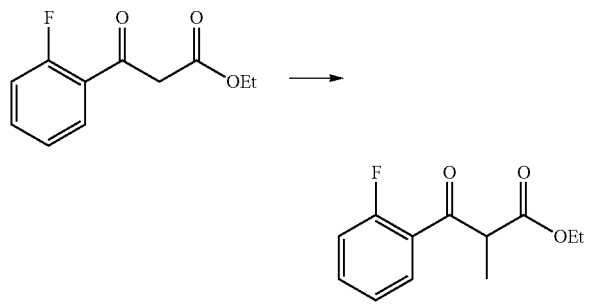

To a solution of ethyl 3-(2-fluorophenyl)-3-oxopropanoate (4.2 g, 20 mmol) in DMF (30 mL) at 0° C. was added $K_2CO_3$ (3.87 g, 28 mmol) portionwise and the mixture was stirred for 30 minutes. After this time iodomethane (1.49 mL, 24 mmol) was added and the reaction mixture was allowed to warm to rt for 2 h. After this time the reaction was treated with 50 mL AcOH/water (5 mL AcOH/45 mL water). The mixture was extracted with EtOAc and the organic layer was washed with brine, dried over $Mg_2SO_4$, filtered and evaporated in vacuo to give ethyl 3-(2-fluorophenyl)-2-methyl-3-oxopropanoate. Observed some dimethyl product. Used as crude for the next step. Mass Spectrum (ESI) m/e=225 (M+1).

2-(2-Fluorophenyl)-3-methylquinolin-4-ol

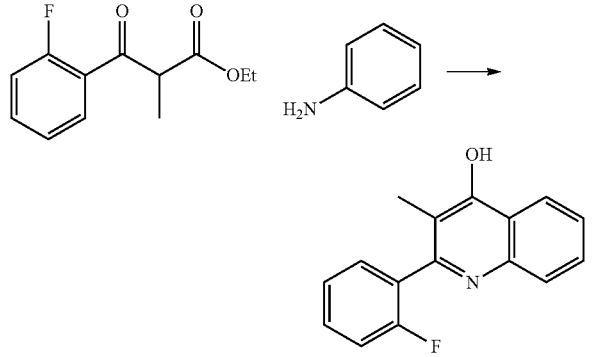

Prepared according to procedure R using aniline (0.91 mL, 10 mmol) and ethyl 3-(2-fluorophenyl)-2-methyl-3-oxopropanoate (4 g, 20 mmol) in PPA (4 g, 40 mmol). The resulting precipitate was collected by filtration, washed with water, and dried to give 2-(2-fluorophenyl)-3-methylquinolin-4-ol. Mass Spectrum (ESI) m/e=254 (M+1).

4-Chloro-2-(2-fluorophenyl)-3-methylquinoline

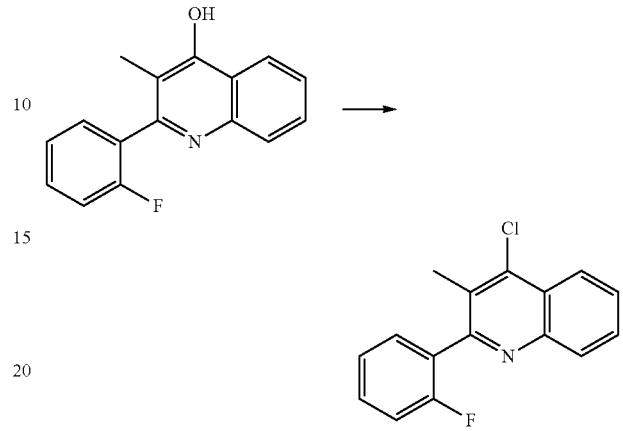

Prepared according to procedure S using 2-(2-fluorophenyl)-3-methylquinolin-4-ol (0.13 g, 0.51 mmol) in $POCl_3$ (1 mL, 10 mmol). The resulting precipitate was collected by filtration to have 4-chloro-2-(2-fluorophenyl)-3-methylquinoline. Mass Spectrum (ESI) m/e=272 (M+1).

4-(3,3-Dimethyl-6-(4-morpholinyl)-2,3-dihydro-1H-indol-1-yl)-2-(2-fluorophenyl)-3-methylquinoline

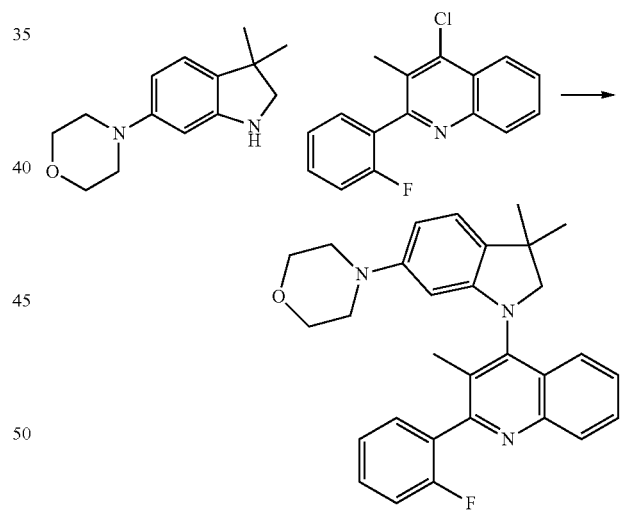

Prepared according to procedure T using 4-(3,3-dimethylindolin-6-yl)morpholine (0.043 g, 0.184 mmol), 4-chloro-2-(2-fluorophenyl)-3-methylquinoline (0.050 g, 0.184 mmol), cesium carbonate (0.12 g, 0.368 mmol), $Pd_2(dba)_3$ (0.017 g, 0.018 mmol) and (±) BINAP (0.0174 g, 0.028 mmol) in 1,4-dioxane (1 mL). After purification by HPLC 4-(3,3-dimethyl-6-(4-morpholinyl)-2,3-dihydro-1H-indol-1-yl)-2-(2-fluorophenyl)-3-methylquinoline was obtained. 1H NMR (400 MHz, DMSO-$d_6$) δ ppm 8.00 (1H, d, J=7.8 Hz), 7.82 (1H, d, J=8.2 Hz), 7.69 (1H, t, J=7.6 Hz), 7.52 (3H, m), 7.30 (2H, m), 6.98 (1H, d, J=8.2 Hz), 6.20 (1H, dd, J=8.2, 2.0 Hz), 5.46 (1H, d, J=2.0 Hz), 3.75 (1H, d, J=9.0 Hz), 3.60

(1H, d, J=9.4 Hz), 3.51 (4H, m), 2.77 (4H, m), 1.99 (3H, s), 1.39 (3H, s), 1.30 (3H, s). Mass Spectrum (ESI) m/e=468 (M+1).

Example 70

4-(3,3-Dimethyl-6-(4-morpholinyl)-2,3-dihydro-1H-indol-1-yl)-2,3,8-trimethylquinoline 2,3,8-Trimethylquinolin-4-ol

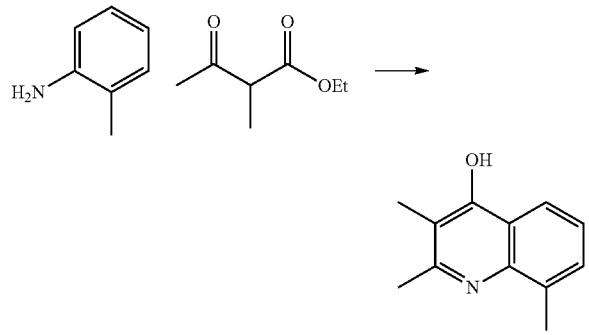

Prepared according to procedure R using 2-methylroaniline (1.07 mL, 10 mmol) and ethyl 2-methyl-3-oxobutanoate (2.89 g, 20 mmol) in PPA (4 g, 40 mmol). The resulting precipitate was collected by filtration, washed with water, and dried to give 2,3,8-trimethylquinolin-4-ol. Mass Spectrum (ESI) m/e=188 (M+1).

4-Chloro-2,3,8-trimethylquinoline

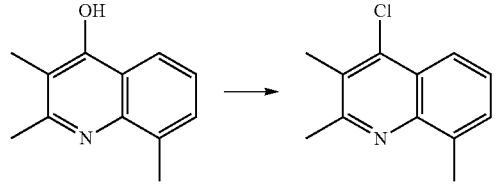

Prepared according to procedure S using 2,3,8-trimethylquinolin-4-ol (1.7 g, 9.1 mmol) in POCl₃ (12.5 mL, 136 mmol). The resulting precipitate was collected by filtration to give 4-chloro-2,3,8-trimethylquinoline. Mass Spectrum (ESI) m/e=206 (M+1).

4-(3,3-Dimethyl-6-(4-morpholinyl)-2,3-dihydro-1H-indol-1-yl)-2,3,8-trimethylquinoline

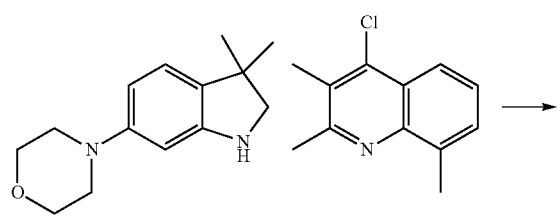

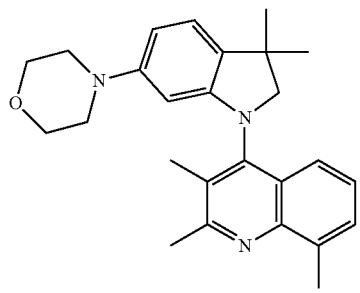

Prepared according to procedure T using 4-(3,3-dimethylindolin-6-yl)morpholine (0.151 g, 0.65 mmol), 4-chloro-2,3,8-trimethylquinoline (0.267 g, 1.3 mmol), cesium carbonate (0.424 g, 1.3 mmol), Pd₂(dba)₃ (0.060 g, 0.065 mmol) and (±) BINAP (0.061 g, 0.098 mmol) were added together in 1,4-dioxane (2 mL). Crude residue was purified via HPLC to give 4-(3,3-dimethyl-6-(4-morpholinyl)-2,3-dihydro-1H-indol-1-yl)-2,3,8-trimethylquinoline. 1H NMR (400 MHz, DMSO-d₆) δ ppm 7.40 (1H, d, J=7.8 Hz), 7.34 (1H, d, J=7.0 Hz), 7.17 (1H, m), 6.85 (1H, d, J=8.2 Hz), 6.04 (1H, dd, J=8.0, 2.2 Hz), 5.20 (1H, d, J=2.3 Hz), 3.50 (1H, d, J=9.0 Hz), 3.39 (5H, m), 2.63 (4H, dd, J=5.9, 3.9 Hz), 2.54 (3H, s), 2.52 (3H, s), 2.04 (3H, s), 1.26 (3H, s), 1.21 (3H, s). Mass Spectrum (ESI) m/e=407 (M+1).

Example 71

8-Chloro-4-(3,3-dimethyl-6-(4-morpholinyl)-2,3-dihydro-1H-indol-1-yl)-2,3-dimethylquinoline 8-Chloro-2,3-dimethylquinolin-4-ol

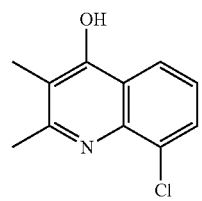

Prepared according to R using 2-chloroaniline (1.28 mL, 10 mmol) and ethyl 2-methyl-3-oxobutanoate (2.89 g, 20 mmol) in PPA (4 g, 40 mmol). The resulting precipitate was collected by filtration, washed with water, and dried to give 8-chloro-2,3-dimethylquinolin-4-ol as an off white solid. Mass Spectrum (ESI) m/e=208 (M+1).

4,8-Dichloro-2,3-dimethylquinoline

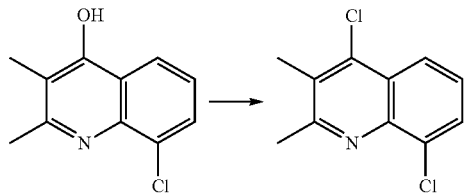

Prepared according to procedure S using 8-chloro-2,3-dimethylquinolin-4-ol (1.14 g, 5.49 mmol) in POCl₃ (7 mL). The resulting precipitate was collected by filtration to have 4,8-dichloro-2,3-dimethylquinoline. Mass Spectrum (ESI) m/e=227 (M+1).

8-Chloro-4-(3,3-dimethyl-6-(4-morpholinyl)-2,3-dihydro-1H-indol-1-yl)-2,3-dimethylquinoline and 4-(1-(4-chloro-2,3-dimethylquinolin-8-yl)-3,3-dimethylindolin-6-yl)morpholine

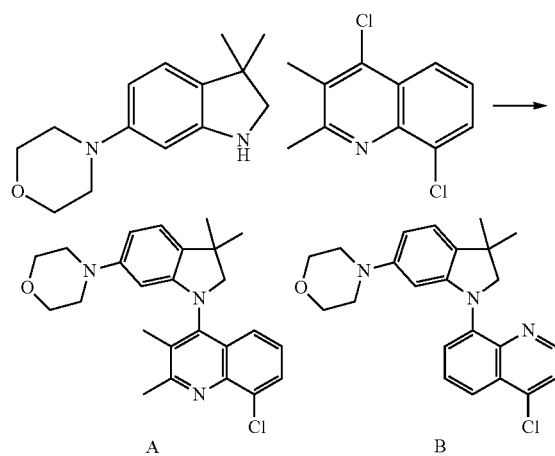

Prepared according to procedure T using 4-(3,3-dimethylindolin-6-yl)morpholine (0.116 g, 0.5 mmol), 4,8-dichloro-2,3-dimethylquinoline (0.226 g, 1 mmol), cesium carbonate (0.326 g, 1 mmol), Pd₂(dba)₃ (0.046 g, 0.05 mmol) and (±) BINAP (0.047 g, 0.075 mmol) in 1,4-dioxane (1 mL). The crude reaction mixture was purified by HPLC to give A and B.

A: 8-Chloro-4-(3,3-dimethyl-6-(4-morpholinyl)-2,3-dihydro-1H-indol-1-yl)-2,3-dimethylquinoline: 1H NMR (500 MHz, DMSO-d₆) δ ppm 7.83 (1H, dd, J=8.3, 1.2 Hz), 7.75 (1H, dd, J=7.6, 1.2 Hz), 7.58 (1H, t, J=7.9 Hz), 7.03 (1H, d, J=8.1 Hz), 6.36 (1H, dd, J=8.1, 2.2 Hz), 6.30 (1H, s), 4.01 (1H, s), 3.64-3.71 (4H, m), 3.29 (1H, s), 2.91-2.97 (4H, m), 2.67 (3H, s), 2.54 (3H, s), 1.32 (6H, s). Mass Spectrum (ESI) m/e=422 (M+1).

B: 4-(1-(4-Chloro-2,3-dimethylquinolin-8-yl)-3,3-dimethylindolin-6-yl)-morpholine: 1H NMR (500 MHz, DMSO-d₆) δ ppm 7.85 (1H, d, J=7.3 Hz), 7.72 (1H, d, J=8.3 Hz), 7.46 (1H, t, J=7.9 Hz), 7.05 (1H, d, J=8.3 Hz), 6.24 (1H, dd, J=8.2, 2.1 Hz), 5.44 (1H, d, J=2.2 Hz), 3.69 (1H, d, J=9.0 Hz), 3.60 (1H, d, J=9.0 Hz), 3.52-3.58 (4H, m), 2.82 (4H, dd, J=5.6, 3.2 Hz), 2.73 (3H, s), 2.25 (3H, s), 1.45 (3H, s), 1.40 (3H, s). Mass Spectrum (ESI) m/e=422 (M+1).

Example 72

4-(3,3-Dimethyl-6-(4-morpholinyl)-2,3-dihydro-1H-indol-1-yl)-2,3-dimethyl-8-(trifluoromethyl)quinoline 2,3-Dimethyl-8-(trifluoromethyl)quinolin-4-ol

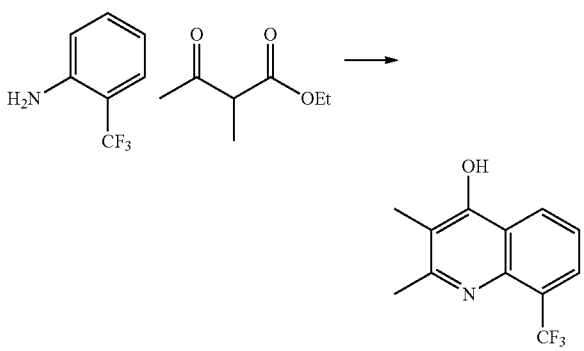

Prepared according to procedure R using 2-(trifluoromethyl)aniline (1.61 g, 10 mmol) and ethyl 2-methyl-3-oxobutanoate (2.89 g, 20 mmol) in PPA (4 g, 40 mmol). The resulting precipitate was collected by filtration, washed with water, and dried to give 2,3-dimethyl-8-(trifluoromethyl)quinolin-4-ol. Mass Spectrum (ESI) m/e=242 (M+1).

4-Chloro-2,3-dimethyl-8-(trifluoromethyl)quinoline

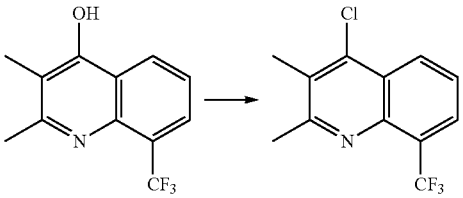 [SMILES: Cc1nc2c(C(F)(F)F)cccc2c(O)c1C ; Cc1nc2c(C(F)(F)F)cccc2c(Cl)c1C]

Prepared according to procedure S using 2,3-dimethyl-8-(trifluoromethyl)-quinolin-4-ol (1.25 g, 5.18 mmol) in POCl₃ (7 mL). The resulting precipitate was collected by filtration to give 4-chloro-2,3-dimethyl-8-(trifluoromethyl)quinoline. Mass Spectrum (ESI) m/e=260 (M+1).

4-(3,3-Dimethyl-6-(4-morpholinyl)-2,3-dihydro-1H-indol-1-yl)-2,3-dimethyl-8-(trifluoromethyl)quinoline

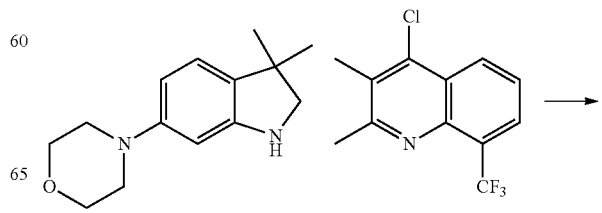

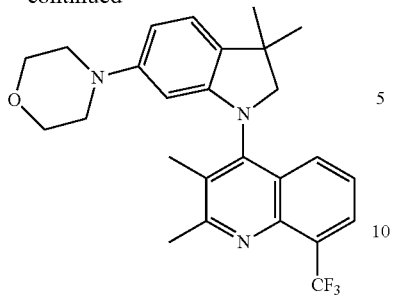

Prepared according to procedure T using 4-(3,3-dimethylindolin-6-yl)morpholine (0.116 g, 0.5 mmol), 4-chloro-2,3-dimethyl-8-(trifluoromethyl)quinoline (0.19 g, 0.73 mmol), cesium carbonate (0.326 g, 1 mmol), Pd$_2$(dba)$_3$ (0.046 g, 0.05 mmol) and (±) BINAP (0.124 g, 0.2 mmol) were added together in 1,4-dioxane (2 mL). Crude residue was purified via HPLC to give 4-(3,3-dimethyl-6-(4-morpholinyl)-2,3-dihydro-1H-indol-1-yl)-2,3-dimethyl-8-(trifluoromethyl)quinoline. 1H NMR (400 MHz, DMSO-d$_6$) δ ppm 8.06 (2H, dd, J=11.3, 8.2 Hz), 7.61 (1H, t, J=7.8 Hz), 7.05 (1H, d, J=8.2 Hz), 6.24 (1H, dd, J=8.2, 2.0 Hz), 5.48 (1H, s), 3.70 (1H, d, J=9.0 Hz), 3.51-3.62 (5H, m), 2.79-2.87 (4H, m), 2.71 (3H, s), 2.23 (3H, s), 1.44 (3H, s), 1.39 (3H, s). Mass Spectrum (ESI) m/e=456 (M+1).

Example 73

1-(6-Chloro-2,3-dimethyl-4-quinolinyl)-6-(1H-pyrazol-4-yl)-1H-indole-3-carbonitrile 6-Bromo-1H-indole-3-carbaldehyde

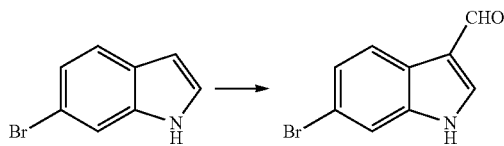 [SMILES: Brc1ccc2cc[nH]c2c1 ; O=Cc1c[nH]c2cc(Br)ccc12]

To a solution of 6-bromo-1H-indole (4 g, 20.4 mmol) in DMF (20 mL) was added Vilsmeier reagent (3.929 g, 30.6 mmol) portion-wise and the resulting mixture was stirred at rt overnight. After 45 minutes, water (100 mL) was added and the mixture was stirred at rt overnight. Water (50 mL) and 10M aqueous NaOH (10 mL) was added and the reaction was stirred at rt until a precipitate formed. The resulting solid was filtered and dried under high vacuum to give 6-bromo-1H-indole-3-carbaldehyde and used as crude for the next step. Mass Spectrum (ESI) m/e=225 (M+1).

6-Bromo-1H-indole-3-carbonitrile

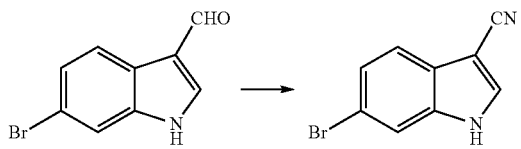 [SMILES: O=Cc1c[nH]c2cc(Br)ccc12 ; N#Cc1c[nH]c2cc(Br)ccc12]

To a solution of 6-bromo-1H-indole-3-carbaldehyde (1.2 g, 5.36 mmol) in pyridine (10 mL) was added NH$_2$OH.HCl (0.424 g, 6.11 mmol) portionwise and the resulting mixture was stirred at rt for 1.5 h. 25 mL of Ac$_2$O was added and the mixture was heated at reflux overnight. After this time the reaction mixture was cooled to rt and poured into ice. The resulting solid was filtered and the product was purified by flash column chromatography to give 6-bromo-1H-indole-3-carbonitrile slightly impure but was used for the next step. Mass Spectrum (ESI) m/e=222 (M+1).

6-Bromo-1-(6-chloro-2,3-dimethylquinolin-4-yl)-1H-indole-3-carbonitrile

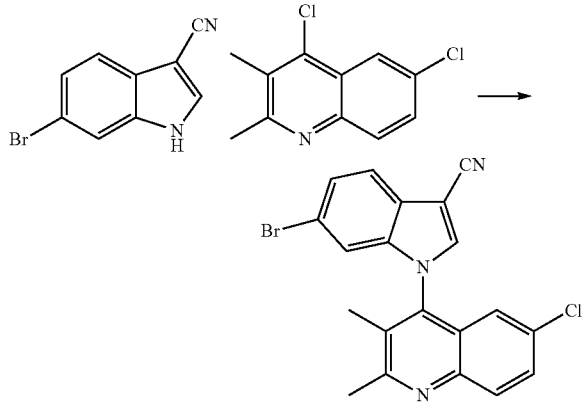

A solution of 6-bromo-1H-indole-3-carbonitrile (0.5 g, 2.26 mmol), 4,6-dichloro-2,3-dimethylquinoline (0.56 g, 2.49 mmol) and cesium carbonate (2.21 h, 6.79 mmol) in DMF (11.2 mL) was heated at 140° C. overnight. After this time the solvent was evaporated in vacuo and the residue was purified by flash column chromatography to give 6-bromo-1-(6-chloro-2,3-dimethylquinolin-4-yl)-1H-indole-3-carbonitrile as white solid. Mass Spectrum (ESI) m/e=411 (M+1).

1-(6-Chloro-2,3-dimethylquinolin-4-yl)-6-(1H-pyrazol-4-yl)-1H-indole-3-carbonitrile

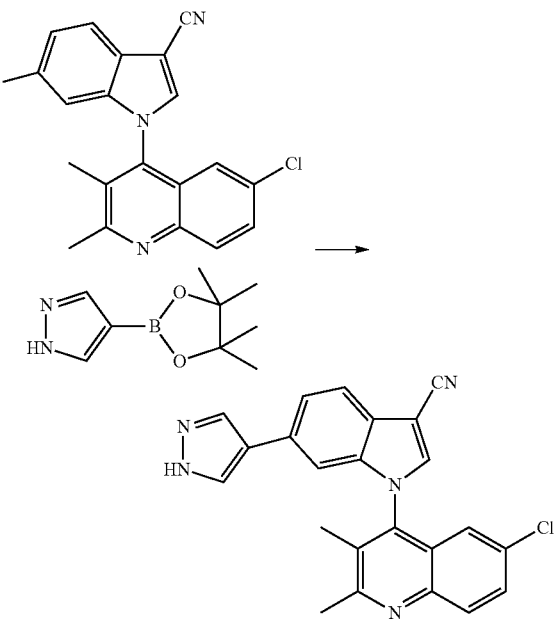

A solution of 6-bromo-1-(6-chloro-2,3-dimethylquinolin-4-yl)-1H-indole-3-carbonitrile (0.2 g, 0.49 mmol), 4-(4,4,5,5-tetramethyl-1,3,2-dioxaborolan-2-yl)-1H-pyrazole (0.188 g, 0.97 mmol), and Pd(PPh₃)₄ (0.056 g, 0.049 mmol) in a 2M aqueous solution of Na₂CO₃ (1.5 mL) and DMF (5 mL) was stirred at 100° C. overnight. After this time the reaction mixture was allowed to cool to rt and poured into ice water. The resulting precipitate was filtered and purified via flash column chromatography to give 1-(6-chloro-2,3-dimethylquinolin-4-yl)-6-(1H-pyrazol-4-yl)-1H-indole-3-carbonitrile. 1H NMR (500 MHz, chloroform-d) δ ppm 8.02 (1H, d, J=9.0 Hz), 7.82 (1H, d, J=8.3 Hz), 7.64 (2H, m), 7.58 (2H, m), 7.49 (1H, dt, J=8.3, 0.7 Hz), 6.96 (1H, d, J=2.4 Hz), 6.82 (1H, s), 2.76 (3H, s), 2.01 (3H, s). Mass Spectrum (ESI) m/e=398 (M+1).

Example 74

6-Chloro-4-(3,3-dimethyl-6-(4-morpholinyl)-2,3-dihydro-1H-indol-1-yl)-3-ethyl-2-methylquinoline

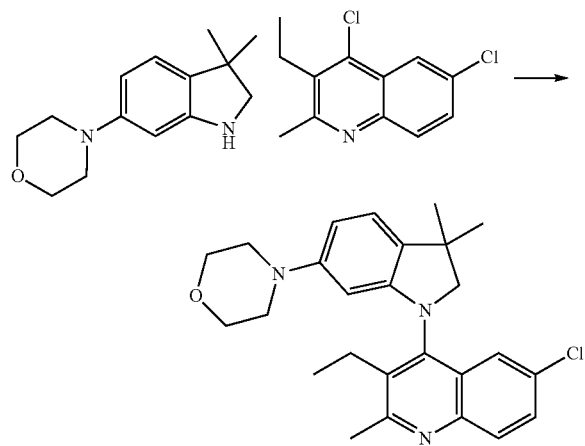

Prepared according to procedure T using 4-(3,3-dimethylindolin-6-yl)morpholine (0.033 g, 0.139 mmol), 4,6-dichloro-3-ethyl-2-methylquinoline (0.04 g, 0.167 mmol), cesium carbonate (0.091 g, 0.278 mmol), Pd₂(dba)₃ (0.013 g, 0.014 mmol) and (±) BINAP (0.013 g, 0.021 mmol) in 1,4-dioxane (1 mL). After purification by HPLC 6-chloro-4-(3,3-dimethyl-6-(4-morpholinyl)-2,3-dihydro-1H-indol-1-yl)-3-ethyl-2-methylquinoline was obtained: 1H NMR (500 MHz, chloroform-d) δ ppm 8.40 (1H, d, J=9.0 Hz), 7.72 (1H, d, J=9.0 Hz), 7.68 (1H, s), 7.13 (1H, s), 6.57 (1H, d, J=8.1 Hz), 5.73 (1H, br. s.), 3.75 (4H, m), 2.97 (6H, br. s.), 1.44 (5H, d, J=16.4 Hz), 1.19 (6H, m), 0.80 (3H, d, J=15.4 Hz). Mass Spectrum (ESI) m/e=436 (M+1).

Example 75

4-(3,3-Dimethyl-6-(4-morpholinyl)-2,3-dihydro-1H-indol-1-yl)-2,3-dimethylquinoline

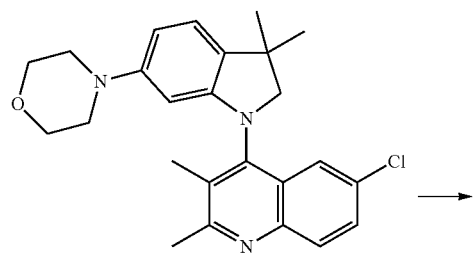

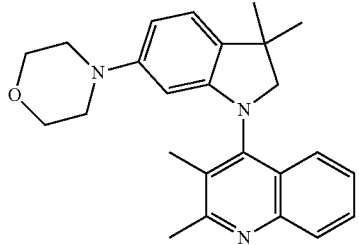

A solution of 4-(1-(6-chloro-2,3-dimethylquinolin-4-yl)-3,3-dimethylindolin-6-yl)morpholine (10 mg, 0.024 mmol) in MeOH (3 mL) was purged with N₂. After the mixture was purged a catalytical amount of triethylamine and Pd/C (0.003 g, 0.002 mmol) were added. The resulting mixture was stirred at rt for 2 h under a hydrogen atmosphere. After this time the reaction mixture was filtered through a pad of Celite™ and the solvent was evaporated in vacuo to give 4-(3,3-dimethyl-6-(4-morpholinyl)-2,3-dihydro-1H-indol-1-yl)-2,3-dimethylquinoline. 1H NMR (500 MHz, chloroform-d) δ ppm 8.06 (1H, br. s.), 7.73 (1H, d, J=8.3 Hz), 7.58 (1H, t, J=7.6 Hz), 7.33 (1H, t, J=7.6 Hz), 6.99 (1H, d, J=8.1 Hz), 6.23 (1H, d, J=7.1 Hz), 5.45 (1H, s), 3.63 (6H, m), 2.86 (4H, m), 1.43 (6H, m). Mass Spectrum (ESI) m/e=388 (M+1).

Example 76

4-(6-Chloro-7-methoxy-2,3-dimethyl-4-quinolinyl)-6-(4-morpholinyl)-3,4-dihydro-2H-1,4-benzothiazine 1,1-dioxide 6-Nitro-2H-benzo[b][1,4]thiazin-3(4H)-one

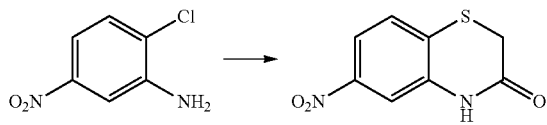 [SMILES: Nc1cc([N+](=O)[O-])ccc1Cl ; O=C1CSc2ccc([N+](=O)[O-])cc2N1]

A solution of 2.44M aqueous NaOH (24 mL, 58 mmol) was added to a stirring solution of ethyl 2-mercaptoacetate (19 mL, 174 mmol) in EtOH (150 mL). The mixture was added to the stirring solution of 2-chloro-5-nitroaniline (10 g, 58 mmol) in EtOH (68 ml). The resulting mixture was heated at reflux overnight. After this time the reaction was diluted with EtOAc and washed with water. The separated organic layer was dried over Mg₂SO₄, filtered and evaporated in vacuo. The crude residue was triturated with EtOAc to give 6-nitro-2H-benzo[b]-[1,4]thiazin-3(4H)-one. Mass Spectrum (ESI) m/e=257 (M+1).

6-Nitro-3,4-dihydro-2H-benzo[b][1,4]thiazine

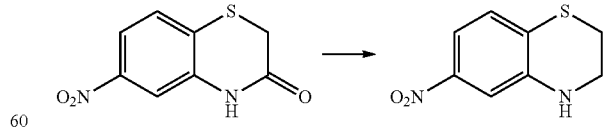

6-nitro-2H-benzo[b][1,4]thiazin-3(4H)-one (4 g, 19 mmol) was stirred in BH₃-THF (285 mL, 258 mmol) at reflux overnight. After this time the reaction mixture was cooled to rt and quenched with MeOH. The reaction was partitioned between EtOAc and water. The separated organic layer was dried over Mg₂SO₄ and evaporated in vacuo to give 6-nitro- 3,4-dihydro-2H-benzo[b][1,4]thiazine that was used without further purification in the next step. Mass Spectrum (ESI) m/e=197 (M+1).

1-(6-Nitro-2H-benzo[b][1,4]thiazin-4(3H)-yl)ethanone

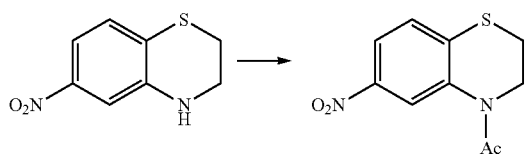 [SMILES: O=[N+]([O-])c1ccc2c(c1)NCCS2 ; CC(=O)N1CCSc2ccc([N+](=O)[O-])cc21]

A solution of 6-nitro-3,4-dihydro-2H-benzo[b][1,4] (2.92 g, 15 mmol) in EtOAc (30 mL) and Ac$_2$O (12 mL) was heated at reflux overnight. After this time the solvent was evaporated in vacuo to give 1-(6-nitro-2H-benzo[b][1,4]thiazin-4(3H)-yl)ethanone. The crude product was used without further purification in the next step. Mass Spectrum (ESI) m/e=239 (M+1).

4-Acetyl-6-nitro-3,4-dihydro-2H-1,4-benzothiazine 1,1-dioxide

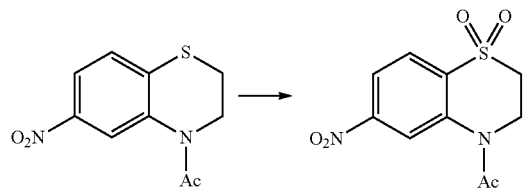 [SMILES: CC(=O)N1CCSc2ccc([N+](=O)[O-])cc21 ; CC(=O)N1CCS(=O)(=O)c2ccc([N+](=O)[O-])cc21]

To a solution of 1-(6-nitro-2H-benzo[b][1,4]thiazin-4 (3H)-yl)ethanone (3.57 g, 15 mmol) in DCM (75 mL) was added m-CPBA (13.4 g, 60 mmol) and the resulting mixture was stirred at rt overnight. After this time the reaction mixture was poured into saturated sodium bicarbonate. The separated organic layer was washed with brine, dried over Mg$_2$SO$_4$, filtered and evaporated in vacuo. The resulting white solid was triturated with EtOAc and filtered to give 4-acetyl-6-nitro-3,4-dihydro-2H-1,4-benzothiazine 1,1-dioxide. Mass Spectrum (ESI) m/e=271 (M+1).

4-Acetyl-3,4-dihydro-2H-1,4-benzothiazin-6-amine 1,1-dioxide

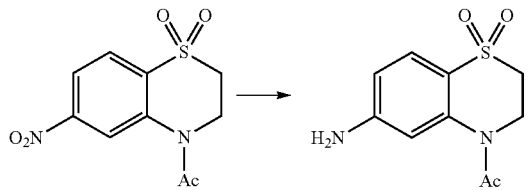 [SMILES: CC(=O)N1CCS(=O)(=O)c2ccc([N+](=O)[O-])cc21 ; CC(=O)N1CCS(=O)(=O)c2ccc(N)cc21]

To a suspension of 4-acetyl-6-nitro-3,4-dihydro-2H-1,4-benzothiazine 1,1-dioxide (1.6 g, 5.92 mmol) in EtOAc (21 mL) was added SnCl$_2$-2H$_2$O (6.68 g, 29.6 mmol) and the mixture was heated at reflux for 1.5 h. After this time the reaction mixture was cooled to rt and treated with 2N sodium bicarbonate (30 mL). The resulting solid was filtered and the aqueous layer was extracted with EtOAc. The combined organic layers were washed with brine, dried over Mg$_2$SO$_4$, filtered and evaporated in vacuo to give 4-acetyl-3,4-dihydro-2H-1,4-benzothiazin-6-amine 1,1-dioxide. Mass Spectrum (ESI) m/e=241 (M+1).

6-Morpholin-4-yl-3,4-dihydro-2H-1,4-benzothiazine 1,1-dioxide

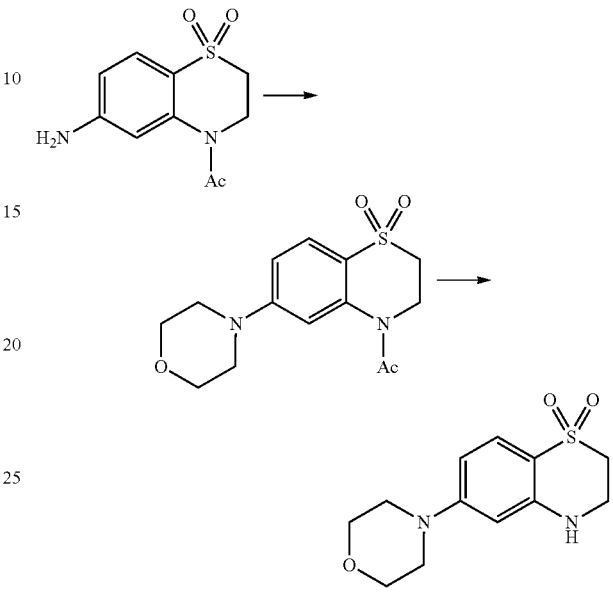

A solution of 4-acetyl-3,4-dihydro-2H-1,4-benzothiazin-6-amine 1,1-dioxide 2-bromo ethyl ether (1.276 g, 5.5 mmol) and sodium carbonate (1.06 g, 10 mmol) in MeOH (5 mL) was stirred at 150° C. for 1.5 h. After this time the reaction mixture was cooled to rt and LCMS shows intermediate 4-acetyl-6-morpholin-4-yl-3,4-dihydro-2H-1,4-benzothiazine 1,1-dioxide. The compound was suspended in 3.5 mL of water and treated with KOH (1.82 g, 32.5 mmol) and the resulting mixture was stirred at 55° C. for 1 h. After this time the reaction was cooled and the resulting precipitate was filtered to give 6-morpholin-4-yl-3,4-dihydro-2H-1,4-benzothiazine 1,1-dioxide as white solid. Mass Spectrum (ESI) m/e=269 (M+1).

4-(6-Chloro-7-methoxy-2,3-dimethyl-4-quinolinyl)-6-(4-morpholinyl)-3,4-dihydro-2H-1,4-benzothiazine 1,1-dioxide

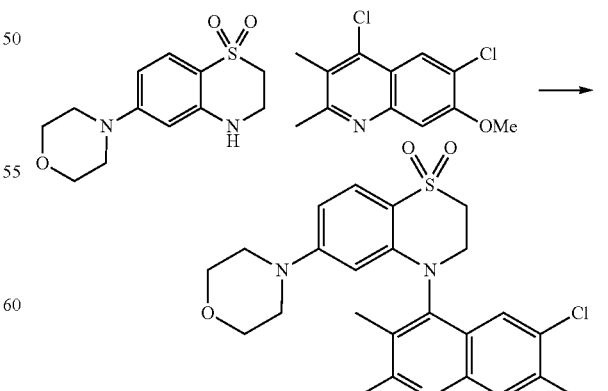

Prepared according to procedure T using 6-morpholin-4-yl-3,4-dihydro-2H-1,4-benzothiazine 1,1-dioxide (0.134 g, 0.5 mmol), 4,6-dichloro-7-methoxy-2,3-dimethylquinoline (0.256 g, 1 mmol), cesium carbonate (0.326 g, 1 mmol), Pd$_2$(dba)$_3$ (0.046 g, 0.05 mmol) and (±) BINAP (0.047 g, 0.075 mmol) in 1,4-dioxane (2 mL). After purification by HPLC 4-(6-chloro-7-methoxy-2,3-dimethyl-4-quinolinyl)-6-(4-morpholinyl)-3,4-dihydro-2H-1,4-benzothiazine 1,1-dioxide was obtained. 1H NMR (500 MHz, DMSO-d$_6$) δ ppm 8.10 (1H, s), 7.60 (1H, s), 7.48-7.54 (1H, m), 6.56 (1H, m), 5.51 (1H, dd, J=1.8, 0.9 Hz), 4.12 (2H, br. s.), 3.93 (3H, s), 3.56 (4H, dd, J=5.1, 4.6 Hz), 2.87 (4H, dd, J=5.3, 4.8 Hz), 2.72 (3H, s), 2.55 (2H, m). Mass Spectrum (ESI) m/e=489 (M+1).

Example 77

4-(5-Fluoro-2-(2-fluorophenyl)-3-methyl-4-quinolinyl)-6-(4-morpholinyl)-3,4-dihydro-2H-1,4-benzothiazine 1,1-dioxide

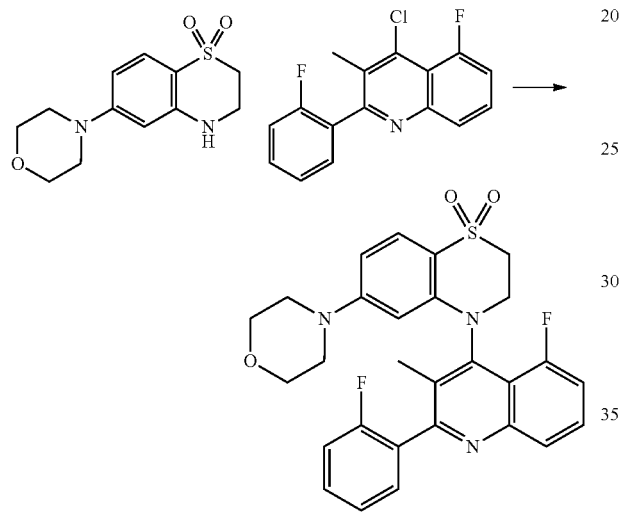

Under a N$_2$ atmosphere, 6-(4-morpholinyl)-3,4-dihydro-2H-1,4-benzothiazine 1,1-dioxide (0.0800 g, 0.298 mmol) was dissolved in DMF (2.00 mL, 26.0 mmol). Sodium hydride (0.0143 g, 0.596 mmol) was added and the reaction was allowed to stir at rt for 10 minutes. 4-Chloro-5-fluoro-2-(2-fluorophenyl)-3-methylquinoline (0.0950 g, 0.328 mmol) was added and the reaction was heated to 140° C. for 2 h. The reaction was diluted with EtOAc and washed with 2% sodium bicarbonate, then brine. The organic layer was dried (Na$_2$SO$_4$), filtered and concentrated in vacuo. The crude residue was purified by preparative reverse phase chromatography to afford 4-(5-fluoro-2-(2-fluorophenyl)-3-methyl-4-quinolinyl)-6-(4-morpholinyl)-3,4-dihydro-2H-1,4-benzothiazine 1,1-dioxide. Mass Spectrum (ESI) m/e=522.2 (M+1)

Example 78

4-(3,3-Dimethyl-6-(4-morpholinyl)-2,3-dihydro-1H-indol-1-yl)-3-methyl-2-phenylquinoline

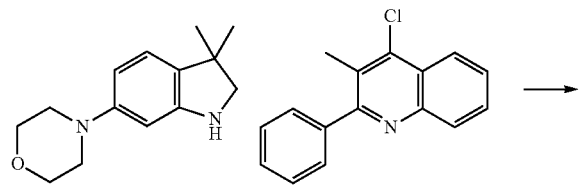

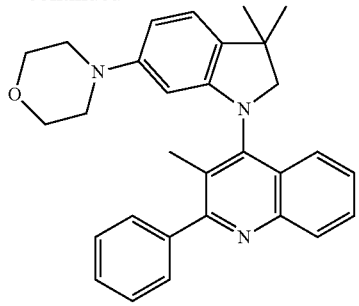

Under a N$_2$ atmosphere, 3,3-dimethyl-6-morpholinoindoline (0.100 g, 0.430 mmol) was dissolved in DMF (2.00 mL, 26.0 mmol). Sodium hydride (0.0227 g, 0.947 mmol) was added and the reaction was stirred at rt for 12 minutes. The reaction was treated with 4-chloro-3-methyl-2-phenylquinoline (0.218 g, 0.861 mmol) and placed in a preheated oil bath at 140° C. for 2 h. LCMS showed no starting quinoline remained. The reaction was diluted with EtOAc and 2% sodium bicarbonate. The organic layer was dried (Na$_2$SO$_4$), filtered and concentrated in vacuo. The crude residue was purified by flash column chromatography eluting with 20% to 50% EtOAc in hexane, and then purified again by preparative reverse phase chromatography to give 4-(3,3-dimethyl-6-(4-morpholinyl)-2,3-dihydro-1H-indol-1-yl)-3-methyl-2-phenylquinoline. Mass Spectrum (ESI) m/e=450.2 (M+1)

Example 79

1-(7-Fluoro-2-(2-fluorophenyl)-3-methyl-4-quinolinyl)-6-(4-morpholinyl)-1,2,2',3',5',6'-hexahydrospiro[indole-3,4'-pyran]

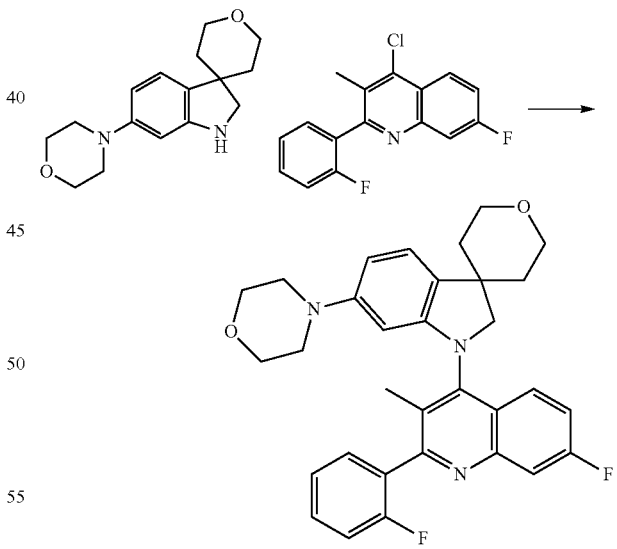

Under a N$_2$ atmosphere, 6-morpholino-2',3',5',6'-tetrahydrospiro[indoline-3,4'-pyran] (0.19 g, 0.69 mmol) was dissolved in DMF (2.00 mL, 26 mmol) and sodium hydride (0.018 g, 0.76 mmol) was added and the reaction was treated with 4-chloro-7-fluoro-2-(2-fluorophenyl)-3-methylquinoline (0.100 g, 0.35 mmol) and heated to 140° C. for 6 h. The reaction was then diluted with EtOAc and washed with 2% sodium bicarbonate then brine. The layers were separated and the organic layer was dried (Na$_2$SO$_4$), filtered and concentrated in vacuo. The reaction was then purified by flash column chromatography eluting with 40% to 60% EtOAc in hexane and then purified by preparative reverse phase HPLC to afford 1-(7-fluoro-2-(2-fluorophenyl)-3-methyl-4-quinolinyl)-6-(4-morpholinyl)-1,2,2',3',5',6'-hexahydrospiro[indole-3,4'-pyran]. Mass Spectrum (ESI) m/e=528.3 (M+1). 1H NMR (400 MHz, DMSO-d$_6$) δ ppm 7.92-7.99 (1H, m), 7.83 (1H, dd, J=10.2, 2.3 Hz), 7.50-7.62 (3H, m), 7.35-7.42 (2H, m), 7.10 (1H, d, J=8.2 Hz), 6.29 (1H, dd, J=8.2, 2.3 Hz), 5.56 (1H, d, J=2.3 Hz), 4.07 (1H, d, J=9.8 Hz), 3.80-3.91 (3H, m), 3.56-3.63 (4H, m), 3.41-3.54 (2H, m), 2.82-2.89 (4H, m), 2.05 (3H, d, J=1.2 Hz), 1.90-2.02 (2H, m), 1.81-1.88 (1H, m), 1.62-1.72 (1H, m)

Example 80

1-(3-Methyl-2-phenyl-4-quinolinyl)-6-(4-morpholinyl)-1,2,2',3',5',6'-hexahydrospiro[indole-3,4'-pyran]

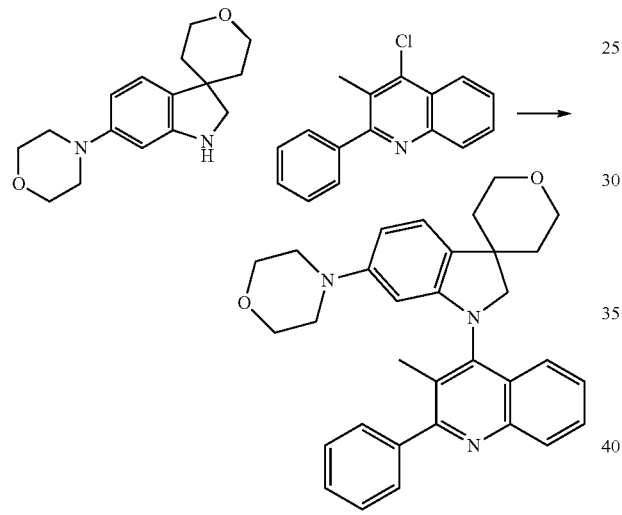

Under a N$_2$ atmosphere, 6-morpholino-2',3',5',6'-tetrahydrospiro[indoline-3,4'-pyran] (0.216 g, 0.788 mmol) was dissolved in DMF (2.00 mL, 26.0 mmol) and treated with sodium hydride (0.0208 g, 0.867 mmol). The reaction was allowed to stir at rt for 10 minutes and 4-chloro-3-methyl-2-phenylquinoline (0.100 g, 0.394 mmol) was added. The reaction was placed in a preheated oil bath at 140° C. for 6 h. LCMS showed no starting chloroquinoline remained. The reaction was diluted with EtOAc and washed with 2% sodium bicarbonate followed by brine. The organic layer was dried (Na$_2$SO$_4$), filtered and concentrated in vacuo. The crude residue was purified by flash column chromatography eluting with 40% to 60% EtOAc in hexane. The fractions that contained product were further purified by preparative reverse phase chromatography to afford 1-(3-methyl-2-phenyl-4-quinolinyl)-6-(4-morpholinyl)-1,2,2',3',5',6'-hexahydrospiro[indole-3,4'-pyran]. Mass Spectrum (ESI) m/e=492.3 (M+1) 1H NMR (500 MHz, DMSO-d$_6$) δ ppm 8.06-8.10 (1H, m), 7.80-7.84 (1H, m), 7.74 (1H, ddd, J=8.4, 6.8, 1.5 Hz), 7.64-7.69 (2H, m), 7.48-7.59 (4H, m), 7.11 (1H, d, J=8.3 Hz), 6.27 (1H, dd, J=8.3, 2.2 Hz), 5.58 (1H, d, J=2.2 Hz), 4.01 (1H, d, J=9.8 Hz), 3.83-3.97 (3H, m), 3.56-3.63 (4H, m), 3.48 (2H, tt, J=12.0, 2.1 Hz), 2.82-2.91 (4H, m), 2.22 (3H, s), 1.93-2.05 (2H, m), 1.82-1.88 (1H, m), 1.65-1.73 (1H, m)

Example 81

1-(7-Chloro-2-(2-fluorophenyl)-3-methyl-4-quinolinyl)-6-(4-morpholinyl)-1,2,2',3',5',6'-hexahydrospiro[indole-3,4'-pyran]

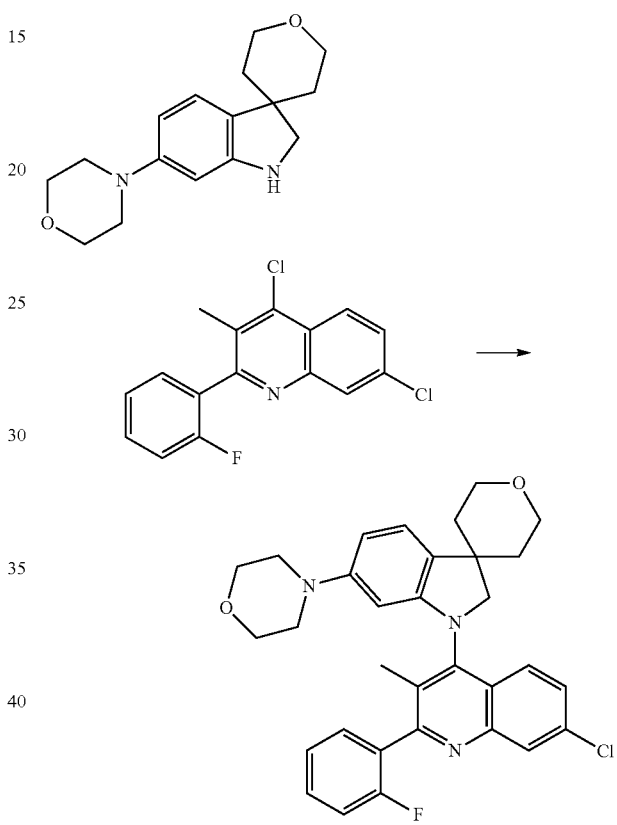

Under a N$_2$ atmosphere, 6-morpholino-2',3',5',6'-tetrahydrospiro[indoline-3,4'-pyran] (0.18 g, 0.65 mmol) was dissolved in DMF (2.00 mL, 26 mmol) and sodium hydride (0.017 g, 0.72 mmol) was added. The reaction was allowed to stir for 15 minutes at rt. 4,7-Dichloro-2-(2-fluorophenyl)-3-methylquinoline (0.100 g, 0.33 mmol) was added and the reaction was heated to 140° C. for 5 h. The reaction was diluted with EtOAc and washed with 2% sodium bicarbonate then brine. The organic layer was dried (Na$_2$SO$_4$), filtered, and concentrated in vacuo. The crude solid was purified by flash column chromatography eluting with 40% to 60% EtOAc in hexane, followed by further purification by preparative reverse phase HPLC to afford 1-(7-chloro-2-(2-fluorophenyl)-3-methyl-4-quinolinyl)-6-(4-morpholinyl)-1,2,2',3',5',6'-hexahydrospiro[indole-3,4'-pyran]. Mass Spectrum (ESI) m/e=544.3 (M+1). 1H NMR (400 MHz, DMSO-d$_6$) δ ppm 8.14 (1H, d, J=2.3 Hz), 7.90 (1H, d, J=9.0 Hz), 7.54-7.65 (3H, m), 7.35-7.42 (2H, m), 7.11 (1H, d, J=8.2 Hz), 6.30 (1H, dd, J=8.2, 2.3 Hz), 5.57 (1H, d, J=2.3 Hz), 4.06 (1H, d, J=9.4 Hz), 3.80-3.92 (3H, m), 3.56-3.63 (4H, m), 3.40-3.54 (2H, m), 2.83-2.89 (4H, m), 2.06 (3H, d, J=1.6 Hz), 1.88-2.03 (2H, m), 1.81-1.87 (1H, m), 1.66 (1H, dt, J=13.4, 1.1 Hz)

Example 82

4-(3,3-Dimethyl-6-(4-morpholinyl)-2,3-dihydro-1H-indol-1-yl)-7-fluoro-2-(2-fluorophenyl)-3-methylquinoline

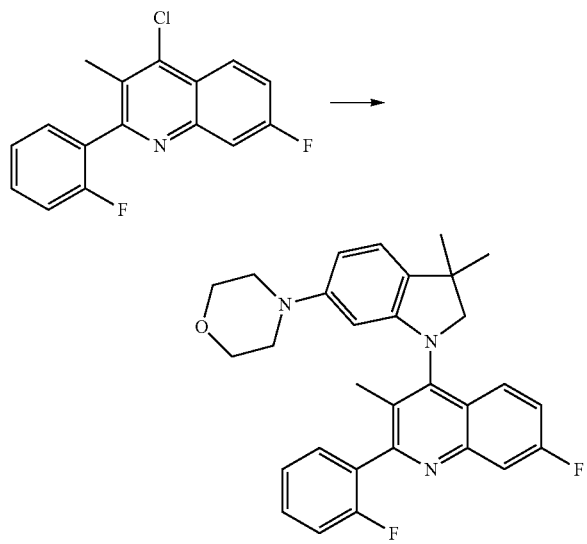

Prepared according to procedure M using 3,3-dimethyl-6-morpholinoindoline (110 mg, 473 µmol), 4-chloro-7-fluoro-2-(2-fluorophenyl)-3-methylquinoline (137 mg, 473 µmol) in DMF (2 mL), and sodium hydride (38 mg, 946 µmol) and heating at 130° C. for 7 h. After purification 4-(1-(7-fluorophenyl)-3-methylquinolin-4-yl)-3,3-dimethylindolin-4-yl)-3,3-dimethylindolin-6-yl)morpholine was obtained. 1H NMR (400 MHz, DMSO-d$_6$) δ ppm 7.94-8.03 (1H, m), 7.85 (1H, dd, J=10.0, 2.5 Hz), 7.52-7.68 (3H, m), 7.34-7.45 (2H, m) 7.14 (1H, d, J=7.8 Hz), 6.50 (1H, br s), 5.80 (1H, br s), 3.88 (1H, d, J=9.4 Hz), 3.57-3.79 (5H, m), 2.99 (4H, br s), 2.052 (3H, s), 1.46 (3H, s), 1.38 (3H, s). Mass Spectrum (ESI) m/e=486 (M+1).

Example 83

2-Benzyl-4-(3,3-dimethyl-6-(4-morpholinyl)-2,3-dihydro-1H-pyrrolo[3,2-b]pyridin-1-yl)-5,7-difluoro-3-methylquinoline 2-Benzyl-4-chloro-5,7-difluoro-3-methylquinoline

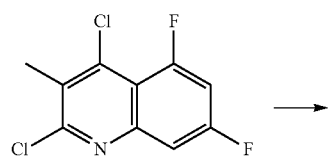

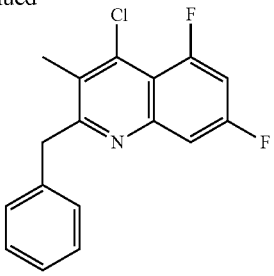

A screw cap vial was sequentially charged with 2,4-dichloro-5,7-difluoro-3-methylquinoline (250 mg, 1.00 mmol), tetrakis(triphenylphosphine)palladium(0) (116 mg, 0.10 mmol), and dry THF (2.52 mL). The mixture was then sparged with N$_2$ prior to the addition of benzylzinc(II) bromide (0.5M in THF, 2.12 mL, 1.06 mmol). The reaction was stirred under N$_2$ at 60° C. for 2 h. The reaction was then cooled to rt, slowly poured over saturated aqueous ammonium chloride and ice, and extracted with EtOAc. The organic layer was washed with water and brine, dried (MgSO$_4$), and concentrated. The crude product then was triturated with toluene to give 2-benzyl-4-chloro-5,7-difluoro-3-methylquinoline. Mass Spectrum (ESI) m/e=304.0 (M+1).

2-Benzyl-4-(3,3-dimethyl-6-(4-morpholinyl)-2,3-dihydro-1H-pyrrolo[3,2-b]pyridin-1-yl)-5,7-difluoro-3-methylquinoline

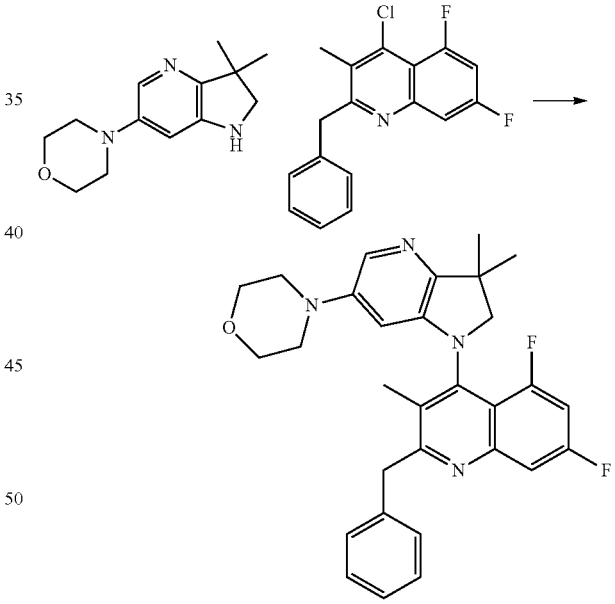

A screw cap vial was charged with 2-benzyl-4-chloro-5,7-difluoro-3-methylquinoline (37 mg, 0.122 mmol), 4-(3,3-dimethyl-2,3-dihydro-1H-pyrrolo[3,2-b]pyridin-6-yl)morpholine (36.9 mg, 0.158 mmol), Pd$_2$dba$_3$ (16.7 mg, 0.018 mmol), 2-(dicyclohexylphosphino)-2',4',6'-tri-i-propyl-1,1'-biphenyl (17.4 mg, 0.037 mmol), sodium tert-butoxide (35.1 mg, 0.365 mmol), and toluene (1.22 mL). The mixture was heated to 95° C. under N$_2$ for 18 h. The reaction was concentrated and diluted with EtOAc, then washed with saturated aqueous sodium bicarbonate solution, water, brine, and 1M NaOH. The organic layer was dried (MgSO$_4$) and concentrated. The crude product was purified by preparative HPLC (10-70% acetonitrile in water) to give 2-benzyl-4-(3,3-dimethyl-6-(4-morpholinyl)-2,3-dihydro-1H-pyrrolo[3,2-b]pyridin-1-yl)-5,7-difluoro-3-methylquinoline as a yellow solid. 1H NMR (400 MHz, chloroform-d) δ ppm 7.60-7.68 (1H, m), 7.50 (1H, d, J=2.3 Hz), 7.27-7.31 (2H, m), 7.22-7.25 (3H, m), 6.96 (1H, ddd, J=11.9, 9.0, 2.5 Hz), 5.52 (1H, d, J=2.3 Hz), 4.42 (2H, s), 3.79-3.85 (1H, m), 3.68-3.77 (4H, m), 3.56 (1H, d, J=9.0 Hz), 2.89-2.96 (4H, m), 2.19 (3H, s), 1.51 (3H, s), 1.45 (3H, s). Mass Spectrum (ESI) m/e=512.0 (M+1).

Example 84

4-(3,3-Dimethyl-6-(4-morpholinyl)-2,3-dihydro-1H-pyrrolo[3,2-b]pyridin-1-yl)-5,7-difluoro-3-methyl-2-(1-phenylethenyl)quinoline 4-Chloro-5,7-difluoro-3-methyl-2-(1-phenylvinyl)quinoline

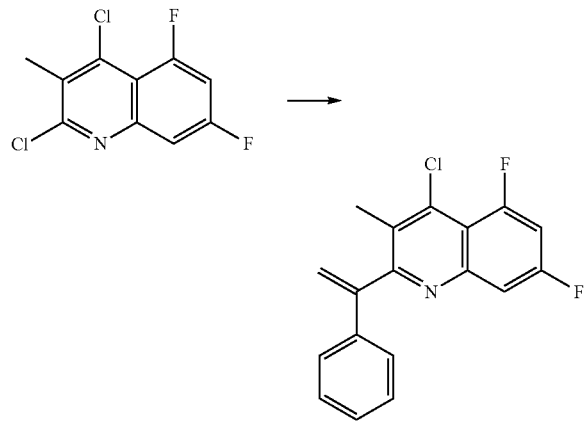

A screw cap vial was charged with 2,4-dichloro-5,7-difluoro-3-methylquinoline (99 mg, 0.398 mmol), 1-phenylvinylboronic acid pinacol ester (110 mg, 0.478 mmol), dichloro 1,1'-bis(diphenylphosphino)ferrocene palladium(II) (32.5 mg, 0.040 mmol), potassium carbonate (165 mg, 1.195 mmol), and DMF (3.98 mL), and the mixture was heated at 95° C. under a N₂ atmosphere for 18 h. The reaction was then cooled to rt, diluted with EtOAc, and washed with water and brine. The organic layer was dried (MgSO₄) and concentrated under reduced pressure. The crude product was purified by flash chromatography, eluting with a gradient of 0-10% EtOAc in hexane to give 4-chloro-5,7-difluoro-3-methyl-2-(1-phenylvinyl)-quinoline as an orange solid. Mass Spectrum (ESI) m/e=316.0 (M+1).

4-(3,3-Dimethyl-6-(4-morpholinyl)-2,3-dihydro-1H-pyrrolo[3,2-b]pyridin-1-yl)-5,7-difluoro-3-methyl-2-(1-phenylethenyl)quinoline

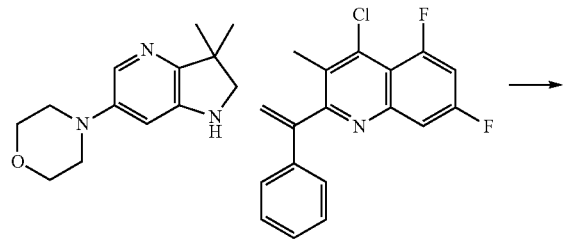

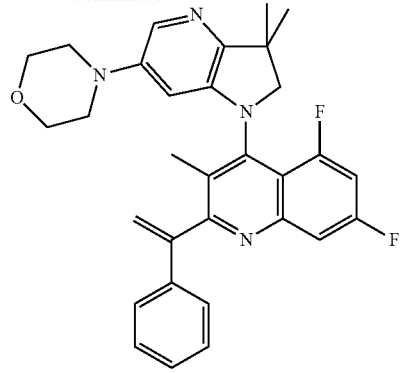

4-Chloro-5,7-difluoro-3-methyl-2-(1-phenylvinyl)quinoline (80 mg, 0.253 mmol), 4-(3,3-dimethyl-2,3-dihydro-1H-pyrrolo[3,2-b]pyridin-6-yl)morpholine (59.1 mg, 0.253 mmol), Pd₂dba₃ (23.2 mg, 0.025 mmol), 2-(dicyclohexylphosphino)-2',4',6'-tri-i-propyl-1,1'-biphenyl (24.2 mg, 0.051 mmol), sodium tert-butoxide (73.0 mg, 0.760 mmol), and toluene (2.53 mL) were stirred at 105° C. for 2 h. The reaction mixture was then concentrated and the resulting residue partitioned between EtOAc and saturated aqueous sodium bicarbonate solution. The organic layer was washed with brine and water, then dried (MgSO₄) and concentrated. Purification by flash chromatography eluting with a gradient of 0-65% hexane in EtOAc gave 4-(3,3-dimethyl-6-(4-morpholinyl)-2,3-dihydro-1H-pyrrolo[3,2-b]pyridin-1-yl)-5,7-difluoro-3-methyl-2-(1-phenylethenyl)quinoline. 1H NMR (400 MHz, chloroform-d) δ ppm 7.72 (1H, m), 7.53 (1H, m), 7.28-7.33 (5H, m), 7.01 (1H, m), 6.02 (1H, d, J=0.8 Hz), 5.63 (1H, br. s.), 5.61 (1H, d, J=1.0 Hz), 3.87 (1H, m), 3.71-3.79 (4H, m), 3.61 (1H, m), 2.96 (4H, d, J=0.8 Hz), 2.02 (3H, s), 1.55 (6H, m). Mass Spectrum (ESI) m/e=513.2 (M+1).

Example 85

4-(3,3-Dimethyl-6-(4-morpholinyl)-2,3-dihydro-1H-pyrrolo[3,2-b]pyridin-1-yl)-5,7-difluoro-3-methyl-2-(1-naphthalenyl)quinoline 4-Chloro-5,7-difluoro-3-methyl-2-(naphthalen-1-yl)quinoline

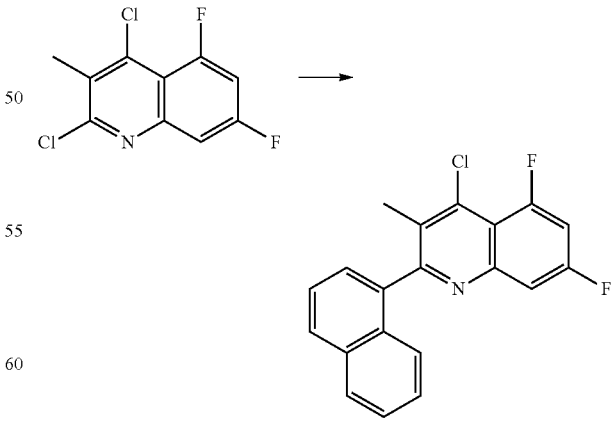

A microwave vessel was charged with 2,4-dichloro-5,7-difluoro-3-methylquinoline (250 mg, 1.008 mmol), 2-naphthylboronic acid (225 mg, 1.310 mmol), tetrakis(triphenylphosphine)palladium(0) (87 mg, 0.076 mmol), sodium carbonate (534 mg, 5.04 mmol), toluene (8.06 mL), and water (2.02 mL). The mixture was heated at 100° C. for 2 h, then cooled to rt and partitioned between EtOAc and water. The organic layer was washed with brine, dried (MgSO$_4$), and concentrated. The resulting crude material was purified by flash chromatography, eluting with a gradient of 0-6% EtOAc in hexane to give 4-chloro-5,7-difluoro-3-methyl-2-(naphthalen-1-yl)quinoline. Mass Spectrum (ESI) m/e=340.0 (M+1).

4-(3,3-Dimethyl-6-(4-morpholinyl)-2,3-dihydro-1H-pyrrolo[3,2-b]pyridin-1-yl)-5,7-difluoro-3-methyl-2-(1-naphthalenyl)quinoline 3.88 (1H, ddd, J=8.6, 1.1, 0.7 Hz), 3.71-3.83 (5H, m), 2.97-3.08 (4H, m), 2.37 (3H, s), 1.58 (3H, s), 1.51 (3H, s). Mass Spectrum (ESI) m/e=537.2 (M+1).

Example 86

4-(3,3-Dimethyl-6-(4-morpholinyl)-2,3-dihydro-1H-pyrrolo[3,2-b]pyridin-1-yl)-5,7-difluoro-3-methyl-2-(1-methyl-1H-indol-5-yl)quinoline

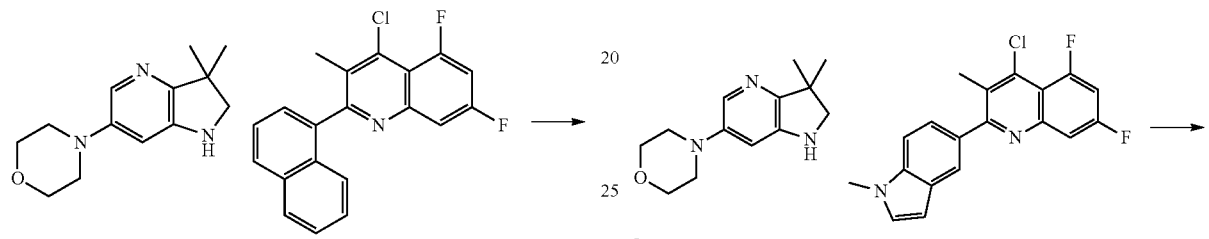

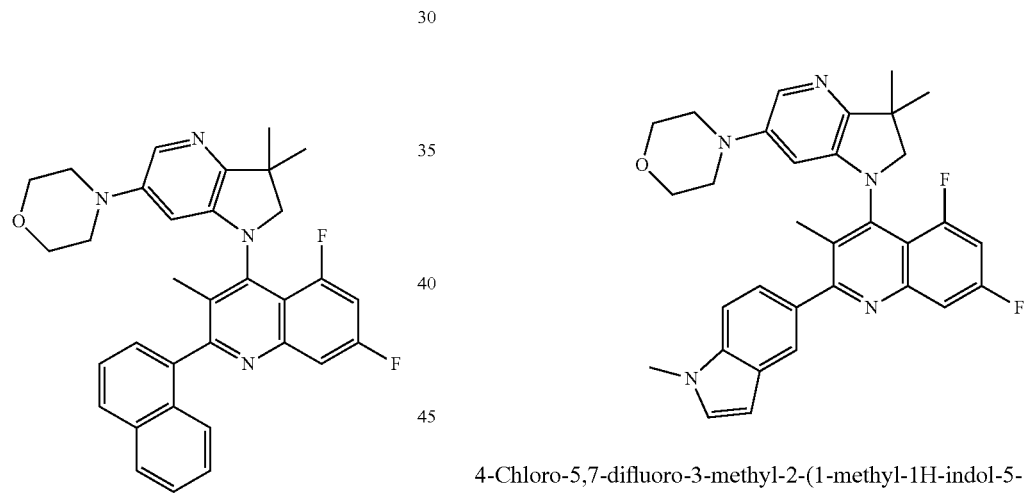

4-Chloro-5,7-difluoro-3-methyl-2-(naphthalen-1-yl) quinoline (43.7 mg, 0.129 mmol), 4-(3,3-dimethyl-2,3-dihydro-1H-pyrrolo[3,2-b]pyridin-6-yl)morpholine (30 mg, 0.129 mmol), Pd$_2$dba$_3$ (11.8 mg, 0.013 mmol), 2-(dicyclohexylphosphino)-2',4',6'-tri-i-propyl-1,1'-biphenyl (12.3 mg, 0.026 mmol), sodium tert-butoxide (37.1 mL, 0.386 mmol), and toluene (1.29 mL) were stirred at 105° C. for 2 h. The reaction mixture was then concentrated and the resulting residue partitioned between EtOAc and saturated aqueous sodium bicarbonate solution. The organic layer was washed with brine and water, then dried (MgSO$_4$) and concentrated. Purification of the crude by reverse-phase chromatography (0-70% acetonitrile in water) gave 4-(3,3-dimethyl-6-(4-morpholinyl)-2,3-dihydro-1H-pyrrolo[3,2-b]-pyridin-1-yl)-5,7-difluoro-3-methyl-2-(1-naphthalenyl)quinoline. 1H NMR (400 MHz, chloroform-d) δ ppm 8.12 (1H, dd, J=1.3, 0.7 Hz), 8.01 (1H, d, J=8.6 Hz), 7.90-7.98 (2H, m), 7.69-7.76 (2H, m), 7.58 (3H, dt, J=5.5, 2.2 Hz), 7.01 (1H, s), 5.74-5.82 (1H, m), 4-Chloro-5,7-difluoro-3-methyl-2-(1-methyl-1H-indol-5-yl)quinoline (44.1 mg, 0.129 mmol), 4-(3,3-dimethyl-2,3-dihydro-1H-pyrrolo[3,2-b]pyridin-6-yl)-morpholine (30 mg, 0.129 mmol), 2-(dicyclohexylphosphino)-2',4',6'-tri-i-propyl-1,1'-biphenyl (12.3 mg, 0.026 mmol), Pd$_2$dba$_3$ (11.8 mg, 0.013 mmol), sodium tert-butoxide (37.1 mg, 0.386 mmol), and toluene (1.29 mL) were stirred at 105° C. for 2 h. The reaction mixture was then concentrated and the resulting residue partitioned between EtOAc and saturated aqueous sodium bicarbonate solution. The organic layer was washed with brine and water, then dried (MgSO$_4$) and concentrated. Purification of the crude product by reverse-phase HPLC (0-70% acetonitrile in water) gave 4-(3,3-dimethyl-6-(4-morpholinyl)-2,3-dihydro-1H-pyrrolo[3,2-b]pyridin-1-yl)-5,7-difluoro-3-methyl-2-(1-methyl-1H-indol-5-yl)-quinoline.
1H NMR (400 MHz, chloroform-d) δ ppm 7.90 (1H, dd, J=1.6, 0.8 Hz), 7.69 (1H, ddd, J=9.6, 2.5, 1.4 Hz), 7.56 (1H, d, J=2.3 Hz), 7.43-7.53 (2H, m), 7.15 (1H, d, J=2.9 Hz), 6.95 (1H, ddd, J=11.8, 8.9, 2.6 Hz), 6.59 (1H, dd, J=3.1, 0.6 Hz), 5.77 (1H, d, J=2.3 Hz), 3.88 (3H, s), 3.84-3.86 (1H, m), 3.77

(4H, dd, J=5.1, 4.5 Hz), 3.72 (1H, d, J=9.4 Hz), 2.94-3.10 (4H, m), 2.36 (3H, s), 1.56 (3H, s), 1.50 (3H, s). Mass Spectrum (ESI) m/e=540.2 (M+1).

Example 87

4-(3,3-Dimethyl-6-(4-morpholinyl)-2,3-dihydro-1H-pyrrolo[3,2-b]pyridin-1-yl)-5,7-difluoro-2-(1H-indol-4-yl)-3-methylquinoline

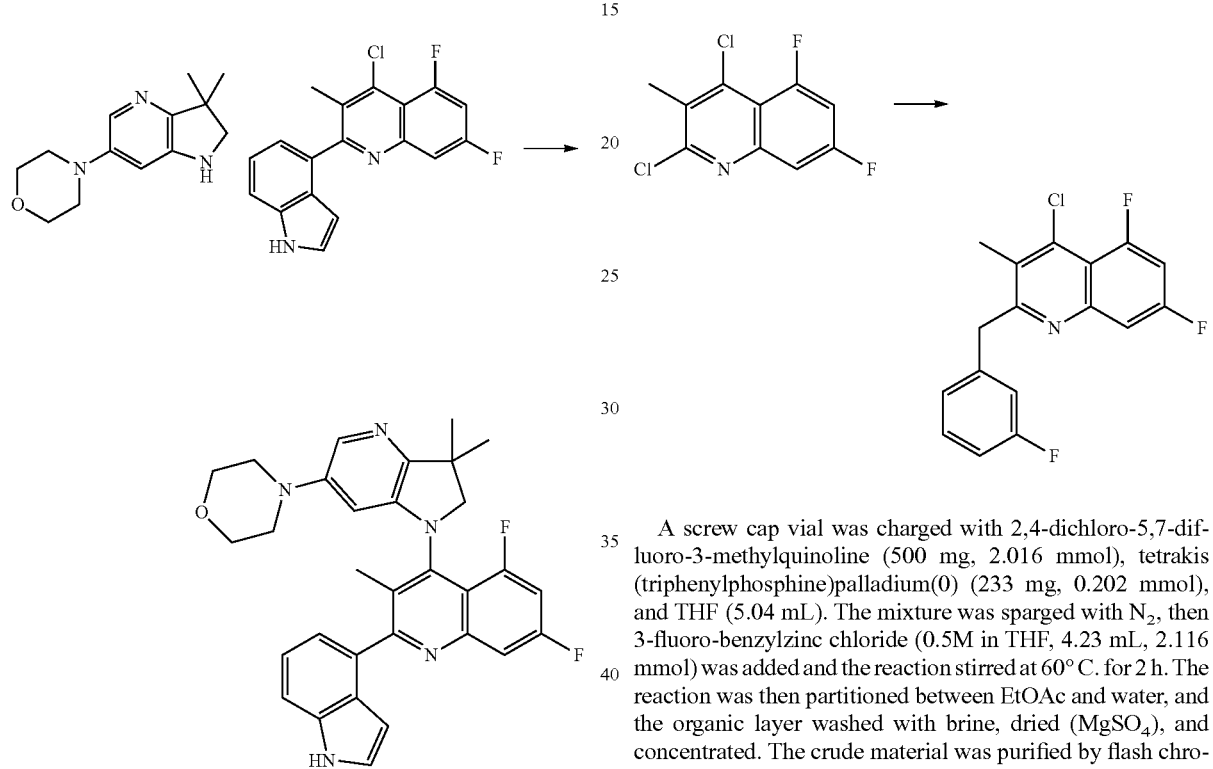

4-Chloro-5,7-difluoro-2-(1H-indol-4-yl)-3-methylquinoline (42.3 mg, 0.129 mmol), 4-(3,3-dimethyl-2,3-dihydro-1H-pyrrolo[3,2-b]pyridin-6-yl)morpholine (30 mg, 0.129 mmol), Pd$_2$dba$_3$ (11.8 mg, 0.013 mmol), 2-(dicyclohexylphosphino)-2',4',6'-tri-i-propyl-1,1'-biphenyl (12.3 mg, 0.026 mmol), sodium tert-butoxide (37.1 mg, 0.386 mmol), and toluene (1.29 mL) were stirred at 105° C. for 2 h. The reaction mixture was then concentrated and the resulting residue was partitioned between EtOAc and saturated aqueous sodium bicarbonate solution. The organic layer was washed with brine and water, then dried (MgSO$_4$) and concentrated. Purification of the crude product by reverse-phase HPLC (0-70% acetonitrile in water) gave 4-(3,3-dimethyl-6-(4-morpholinyl)-2,3-dihydro-1H-pyrrolo[3,2-b]-pyridin-1-yl)-5,7-difluoro-2-(1H-indol-4-yl)-3-methylquinoline. 1H NMR (400 MHz, chloroform-d) δ ppm 8.53 (1H, br. s.), 7.66-7.76 (1H, m), 7.50-7.58 (2H, m), 7.32-7.40 (1H, m), 7.28-7.30 (1H, m), 6.96-7.04 (1H, m), 6.35 (1H, td, J=2.2, 1.2 Hz), 5.80 (1H, t, J=2.1 Hz), 3.88-3.93 (1H, m), 3.75-3.81 (4H, m), 3.72 (1H, dd, J=8.9, 0.5 Hz), 2.99-3.08 (4H, m), 2.15-2.28 (3H, m), 1.52-1.61 (3H, m), 1.43-1.52 (3H, m). Mass Spectrum (ESI) m/e=526.1 (M+1).

Example 88

4-(3,3-Dimethyl-6-(4-morpholinyl)-2,3-dihydro-1H-pyrrolo[3,2-b]pyridin-1-yl)-5,7-difluoro-2-(3-fluorobenzyl)-3-methylquinoline 4-Chloro-5,7-difluoro-2-(3-fluorobenzyl)-3-methylquinoline A screw cap vial was charged with 2,4-dichloro-5,7-difluoro-3-methylquinoline (500 mg, 2.016 mmol), tetrakis(triphenylphosphine)palladium(0) (233 mg, 0.202 mmol), and THF (5.04 mL). The mixture was sparged with N$_2$, then 3-fluoro-benzylzinc chloride (0.5M in THF, 4.23 mL, 2.116 mmol) was added and the reaction stirred at 60° C. for 2 h. The reaction was then partitioned between EtOAc and water, and the organic layer washed with brine, dried (MgSO$_4$), and concentrated. The crude material was purified by flash chromatography, eluting with a gradient of 0-15% EtOAc in hexane to give 4-chloro-5,7-difluoro-2-(3-fluorobenzyl)-3-methylquinoline. Mass Spectrum (ESI) m/e=322.0 (M+1).

4-(3,3-Dimethyl-6-(4-morpholinyl)-2,3-dihydro-1H-pyrrolo[3,2-b]pyridin-1-yl)-5,7-difluoro-2-(3-fluorobenzyl)-3-methylquinoline

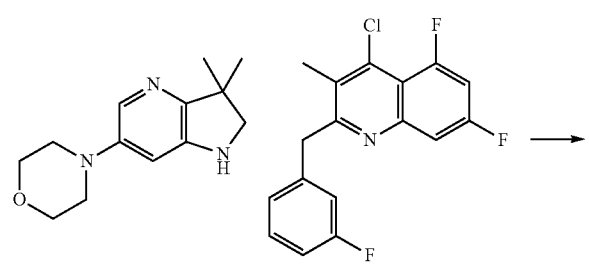

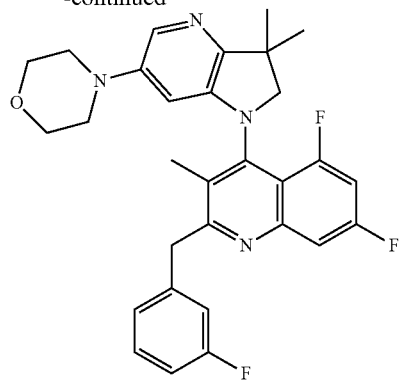

4-Chloro-5,7-difluoro-2-(3-fluorobenzyl)-3-methylquinoline (41.4 mg, 0.129 mmol), 4-(3,3-dimethyl-2,3-dihydro-1H-pyrrolo[3,2-b]pyridin-6-yl)morpholine (30 mg, 0.129 mmol), Pd$_2$dba$_3$ (11.8 mg, 0.013 mmol), 2-(dicyclohexylphosphino)-2',4',6'-tri-i-propyl-1,1'-biphenyl (12.3 mg, 0.026 mmol), sodium tert-butoxide (37.1 mg, 0.386 mmol), and toluene (1.29 mL) were stirred at 105° C. for 2 h. The reaction mixture was then concentrated and the resulting residue partitioned between EtOAc and saturated aqueous sodium bicarbonate solution. The organic layer was washed with brine and water, then dried (MgSO$_4$) and concentrated. Purification of the crude product by reverse-phase HPLC (0-70% acetonitrile in water) gave 4-(3,3-dimethyl-6-(4-morpholinyl)-2,3-dihydro-1H-pyrrolo[3,2-b]-pyridin-1-yl)-5,7-difluoro-2-(3-fluorobenzyl)-3-methylquinoline. 1H NMR (400 MHz, chloroform-d) δ ppm 7.63 (1H, ddd, J=9.4, 2.5, 1.4 Hz), 7.51-7.54 (1H, m), 7.27-7.30 (1H, m), 7.05 (1H, ddd, J=7.9, 1.3, 1.2 Hz), 6.86-7.01 (3H, m), 5.55 (1H, dd, J=2.2, 0.4 Hz), 4.42 (2H, s), 3.79-3.86 (1H, m), 3.68-3.78 (4H, m), 3.57 (1H, d, J=9.2 Hz), 2.86-2.98 (4H, m), 2.19 (3H, s), 1.52 (3H, s), 1.47 (3H, s). Mass Spectrum (ESI) m/e=519.1 (M+1).

Example 89

4-(3,3-Dimethyl-6-(4-morpholinyl)-2,3-dihydro-1H-pyrrolo[3,2-b]pyridin-1-yl)-5,7-difluoro-3-methyl-2-(2-phenylethyl)quinoline 4-Chloro-5,7-difluoro-3-methyl-2-phenethylquinoline

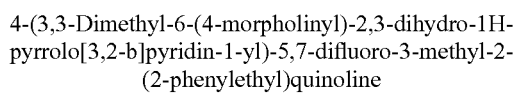

A screw cap vial was charged with 2,4-dichloro-5,7-difluoro-3-methylquinoline (500 mg, 2.016 mmol), tetrakis(triphenylphosphine)palladium(0) (233 mg, 0.202 mmol), and THF (5.04 mL). The mixture was sparged with N$_2$, then phenethyl-zinc(II) bromide (0.5 M in THF, 4.23 mL, 2.116 mmol) was added and the reaction stirred at 60° C. for 2 h. The reaction was then partitioned between EtOAc and water, and the organic layer washed with brine, dried (MgSO$_4$), and concentrated. The crude material was purified by flash chromatography, eluting with a gradient of 0-15% EtOAc in hexane to give 4-chloro-5,7-difluoro-3-methyl-2-phenethylquinoline. Mass Spectrum (ESI) m/e=318.0 (M+1).

4-(3,3-Dimethyl-6-(4-morpholinyl)-2,3-dihydro-1H-pyrrolo[3,2-b]pyridin-1-yl)-5,7-difluoro-3-methyl-2-(2-phenylethyl)quinoline

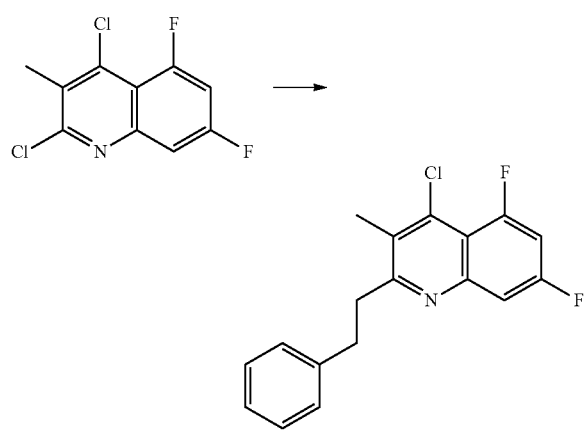

4-Chloro-5,7-difluoro-3-methyl-2-phenethylquinoline (40.9 mg, 0.129 mmol), 4-(3,3-dimethyl-2,3-dihydro-1H-pyrrolo[3,2-b]pyridin-6-yl)morpholine (30 mg, 0.129 mmol), Pd$_2$dba$_3$ (11.8 mg, 0.013 mmol), 2-(dicyclohexylphosphino)-2',4',6'-tri-i-propyl-1,1'-biphenyl (12.3 mg, 0.026 mmol), sodium tert-butoxide (37.1 mg, 0.386 mmol), and toluene (1.29 mL) were stirred at 105° C. for 2 h. The reaction mixture was then concentrated and the resulting residue partitioned between EtOAc and saturated aqueous sodium bicarbonate solution. The organic layer was washed with brine and water, then dried (MgSO$_4$) and concentrated. Purification of the crude product by reverse-phase HPLC (0-70% acetonitrile in water) gave 4-(3,3-dimethyl-6-(4-morpholinyl)-2,3-dihydro-1H-pyrrolo[3,2-b]-pyridin-1-yl)-5,7-difluoro-3-methyl-2-(2-phenylethyl)quinoline. 1H NMR (400 MHz, chloroform-d) δ ppm 7.54-7.64 (1H, m), 7.45-7.54 (1H, m), 7.27-7.32 (2H, m), 7.15-7.27 (3H, m), 6.83-6.97 (1H, m), 5.52-5.62 (1H, m), 3.65-3.85 (5H, m), 3.493.61 (1H, m), 3.12-3.35 (4H, m), 2.88-3.06 (4H, m), 2.18-2.32 (3H, m), 1.40-1.61 (6H, m). Mass Spectrum (ESI) m/e=515.2 (M+1). -

Example 90

3-((4-(3,3-dimethyl-6-(4-morpholinyl)-2,3-dihydro-1H-pyrrolo-[3,2-b]pyridin-1-yl)-5,7-difluoro-3-methyl-2-quinolinyl)methyl)benzonitrile 3-((4-Chloro-5,7-difluoro-3-methylquinolin-2-yl)methyl)benzonitrile

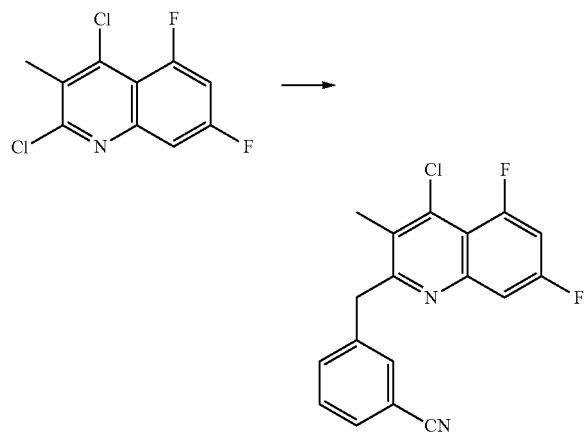

A screw cap vial was charged with 2,4-dichloro-5,7-difluoro-3-methylquinoline (500 mg, 2.016 mmol), tetrakis(triphenylphosphine)palladium(0) (233 mg, 0.202 mmol), and THF (5.04 mL). The mixture was sparged with N₂, then (3-cyanobenzyl)zinc(II) bromide (0.5M in THF, 4.23 mL, 2.116 mmol) was added and the reaction stirred at 60° C. for 2 h. The reaction was then partitioned between EtOAc and water, and the organic layer washed with brine, dried (MgSO₄), and concentrated. The crude material was purified by flash chromatography, eluting with a gradient of 0-15% EtOAc in hexane to give 3-((4-chloro-5,7-difluoro-3-methylquinolin-2-yl)methyl)benzonitrile. Mass Spectrum (ESI) m/e=329.0 (M+1).

3-((4-(3,3-Dimethyl-6-(4-morpholinyl)-2,3-dihydro-1H-pyrrolo[3,2-b]pyridin-1-yl)-5,7-difluoro-3-methyl-2-quinolinyl)methyl)benzonitrile

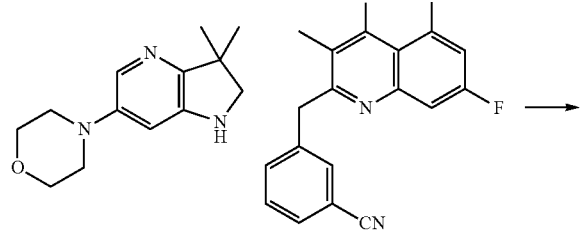

3-((4-Chloro-5,7-difluoro-3-methylquinolin-2-yl)methyl)benzonitrile (42.3 mg, 0.129 mmol), 4-(3,3-dimethyl-2,3-dihydro-1H-pyrrolo[3,2-b]pyridin-6-yl)-morpholine (30 mg, 0.129 mmol), Pd₂dba₃ (11.8 mg, 0.013 mmol), 2-(dicyclohexylphosphino)-2',4',6'-tri-i-propyl-1,1'-biphenyl (12.3 mg, 0.026 mmol), sodium tert-butoxide (37.1 mg, 0.386 mmol), and toluene (1.29 mL) were stirred at 105° C. for 2 h. The reaction mixture was then concentrated and the resulting residue partitioned between EtOAc and saturated aqueous sodium bicarbonate solution. The organic layer was washed with brine and water, then dried (MgSO₄) and concentrated. Purification of the crude product by reverse-phase HPLC (0-70% acetonitrile in water) gave 3-((4-(3,3-dimethyl-6-(4-morpholinyl)-2,3-dihydro-1H-pyrrolo[3,2-b]pyridin-1-yl)-5,7-difluoro-3-methyl-2-quinolinyl)-methyl)benzonitrile.

1H NMR (400 MHz, chloroform-d) δ ppm 7.55-7.63 (2H, m), 7.47-7.53 (2H, m), 7.38-7.46 (1H, m), 7.24 (1H, br. s.), 6.91-7.03 (1H, m), 5.53-5.59 (1H, m), 4.39-4.47 (2H, m), 3.77-3.82 (1H, m), 3.68-3.77 (4H, m), 3.58 (1H, d, J=9.0 Hz), 2.89-3.02 (4H, m), 2.19-2.26 (3H, m), 1.39-1.58 (6H, m). Mass Spectrum (ESI) m/e=526.0 (M+1).

Example 91

4-(7-Fluoro-3-methyl-2-(2-pyridinyl)-4-quinolinyl)-6-(4-morpholinyl)-3,4-dihydro-2H-1,4-benzoxazine

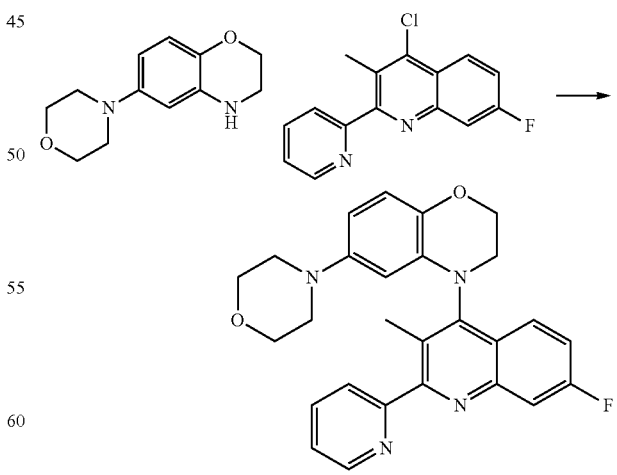

Prepared according to procedure Y by stirring 4-chloro-7-fluoro-3-methyl-2-(pyridin-2-yl)quinoline (50 mg, 0.183 mmol), 6-morpholino-3,4-dihydro-2H-benzo[b][1,4]oxazine (40.4 mg, 0.183 mmol), Pd₂dba₃ (16.8 mg, 0.018 mmol), XPhos (17.5 mg, 0.037 mmol) and sodium tert-butoxide (35.2 mg, 0.367 mmol) in toluene (2.0 mL) for 1 h at 120° C. in the microwave. Purification by reverse phase HPLC (10 to 60% acetonitrile in water) gave 4-(7-fluoro-3-methyl-2-(2-pyridinyl)-4-quinolinyl)-6-(4-morpholinyl)-3,4-dihydro-2H-1,4-benzoxazine). 1H NMR (400 MHz, chloroform-d) δ ppm 8.72-8.79 (1H, m), 7.81-7.96 (4H, m), 7.40 (1H, ddd, J=7.0, 5.0, 1.7 Hz), 7.28 (1H, ddd, J=9.2, 8.1, 2.6 Hz), 6.89 (1H, d, J=8.6 Hz), 6.29 (1H, dd, J=8.8, 2.7 Hz), 5.63 (1H, d, J=2.7 Hz), 4.40-4.51 (2H, m), 3.57-3.82 (6H, m), 2.71-2.82 (4H, m), 2.40 (3H, s). Mass Spectrum (ESI) m/e=457.0 (M+1).

Example 92

4-(6-(3,6-Dihydro-2H-pyran-4-yl)-3,3-dimethyl-2,3-dihydro-1H-pyrrolo[3,2-b]pyridin-1-yl)-7-fluoro-3-methyl-2-(2-pyridinyl)quinoline

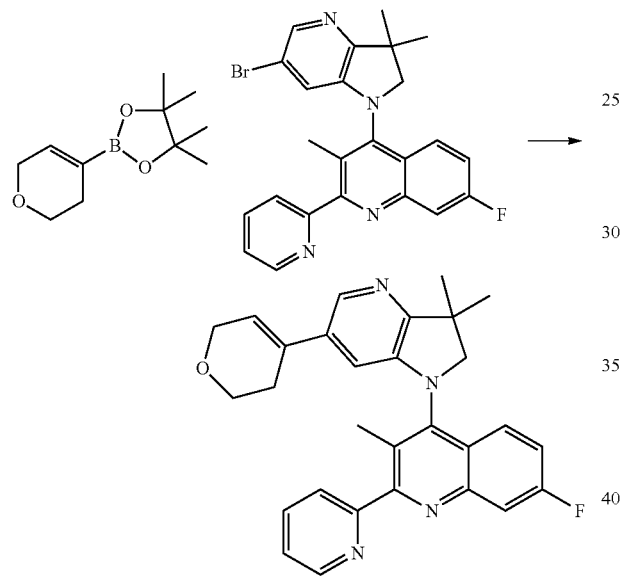

A mixture of 4-(6-bromo-3,3-dimethyl-2,3-dihydro-1H-pyrrolo[3,2-b]pyridin-1-yl)-7-fluoro-3-methyl-2-(pyridin-2-yl)quinoline (150 mg, 0.324 mmol), 2-(3,6-dihydro-2H-pyran-4-yl)-4,4,5,5-tetramethyl-1,3,2-dioxaborolane (102 mg, 0.486 mmol), potassium phosphate tribasic (206 mg, 0.971 mmol), Pd(OAc)₂ (72.7 mg, 0.324 mmol) and SPhos (26.6 mg, 0.065 mmol) in toluene (2.5 mL) was heated in the microwave for 1 h at 100° C. After this time the reaction was partitioned between EtOAc (60 mL) and water (30 mL). The separated organic layer was dried over MgSO₄, filtered and evaporated in vacuo. Column chromatography (hexanes:EtOAc, 1:0 to 0:1 as eluent) gave 4-(6-(3,6-dihydro-2H-pyran-4-yl)-3,3-dimethyl-2,3-dihydro-1H-pyrrolo[3,2-b]pyridin-1-yl)-7-fluoro-3-methyl-2-(2-pyridinyl)quinoline. 1H NMR (500 MHz, chloroform-d) δ ppm 8.71-8.77 (1H, m), 7.97 (1H, d, J=2.0 Hz), 7.83-7.94 (3H, m), 7.79 (1H, dd, J=9.3, 5.9 Hz), 7.41 (1H, ddd, J=7.3, 4.9, 1.5 Hz), 7.30 (1H, ddd, J=9.2, 8.1, 2.6 Hz), 6.20 (1H, d, J=1.7 Hz), 5.90-5.95 (1H, m), 4.18-4.27 (2H, m), 3.78-3.90 (4H, m), 2.29-2.44 (5H, m), 1.61 (3H, s), 1.55 (3H, s). Mass Spectrum (ESI) m/e=467.2 (M+1).

Example 93

4-(3,3-Dimethyl-6-(4-morpholinyl)-2,3-dihydro-1H-pyrrolo[3,2-b]pyridin-1-yl)-5,7-difluoro-3-methyl-2-((E)-2-phenylethenyl)quinoline (E)-4-chloro-5,7-difluoro-3-methyl-2-styrylquinoline

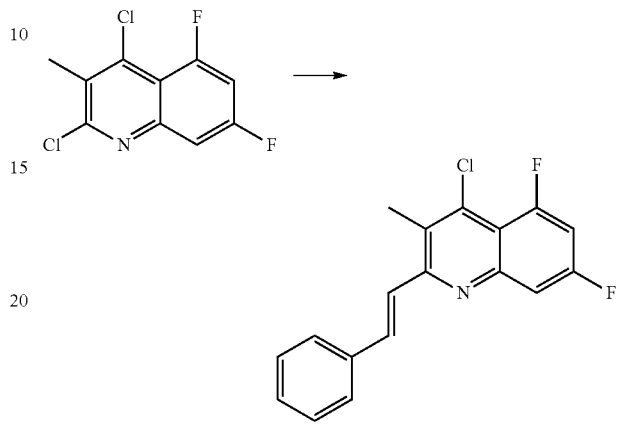

Prepared according to procedure F by stirring 2,4-dichloro-5,7-difluoro-3-methylquinoline (700 mg, 2.82 mmol), trans-2-phenylvinylboronic acid (501 mg, 3.39 mmol), Pd(PPh₃)₄ (245 mg, 0.212 mmol), sodium carbonate (0.590 mL, 14.11 mmol), toluene (23 mL), and water (6 mL) at 95° C. for 18 h. Purification by column chromatography (silica gel, 0-10% EtOAc in hexanes as eluent) gave (E)-4-chloro-5,7-difluoro-3-methyl-2-styrylquinoline. Mass Spectrum (ESI) m/e=316.0 (M+1).

4-(3,3-Dimethyl-6-(4-morpholinyl)-2,3-dihydro-1H-pyrrolo[3,2-b]pyridin-1-yl)-5,7-difluoro-3-methyl-2-((E)-2-phenylethenyl)quinoline

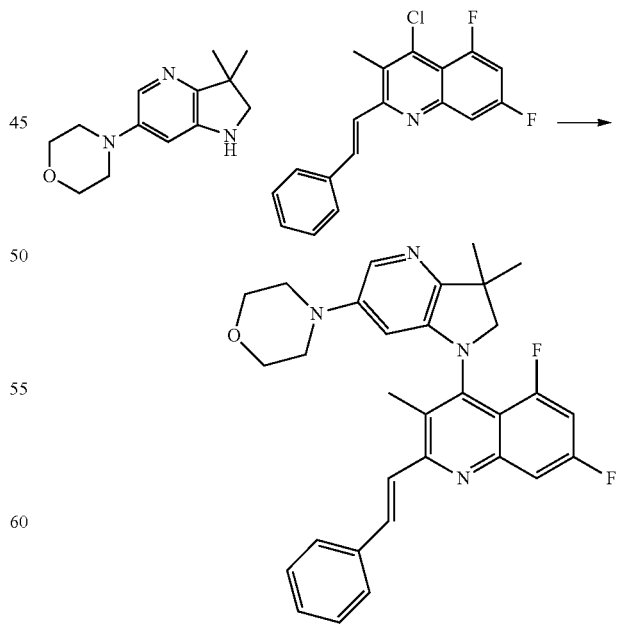

Prepared according to procedure Y by stirring (E)-4-chloro-5,7-difluoro-3-methyl-2-styrylquinoline (50 mg, 0.158 mmol), 4-(3,3-dimethyl-2,3-dihydro-1H-pyrrolo-[3,2-b]pyridin-6-yl)morpholine (37 mg, 0.158 mmol), Pd₂dba₃ (14.5 mg, 0.016 mmol), XPhos (15.1 mg, 0.032 mmol), sodium tert-butoxide (45.7 mg, 0.475 mmol), and toluene (1.6 mL) at 100° C. for 30 min. Purification by reverse-phase HPLC (0-70% acetonitrile in water) afforded 4-(3,3-dimethyl-6-(4-morpholinyl)-2,3-dihydro-1H-pyrrolo[3,2-b]pyridin-1-yl)-5,7-difluoro-3-methyl-2-((E)-2-phenylethenyl)quinoline as a yellow solid. 1H NMR (500 MHz, chloroform-d) δ ppm 8.08 (1H, d, J=15.4 Hz), 7.69 (2H, d, J=7.3 Hz), 7.61-7.66 (1H, m), 7.55 (1H, d, J=2.2 Hz), 7.52 (1H, d, J=15.4 Hz), 7.41-7.47 (2H, m), 7.39 (1H, m), 6.92 (1H, t, J=2.8 Hz), 5.67 (1H, d, J=2.2 Hz), 3.79-3.88 (1H, m), 3.70-3.79 (4H, m), 3.64 (1H, d, J=9.0 Hz), 2.95-3.07 (4H, m), 2.45 (3H, s), 1.55 (3H, s), 1.52 (3H, s). Mass Spectrum (ESI) m/e=513.2 (M+1).

Example 94

4-(3,3-Dimethyl-6-morpholino-2,3-dihydro-1H-pyrrolo[3,2-b]-pyridin-1-yl)-5,7-difluoro-3-methyl-N-(pyridin-2-yl)quinolin-2-amine 4-Chloro-5,7-difluoro-3-methyl-N-(pyridin-2-yl)quinolin-2-amine

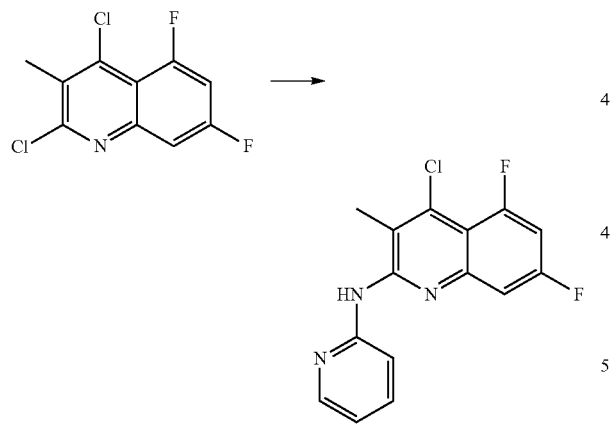

A mixture of 2,4-dichloro-5,7-difluoro-3-methylquinoline (400 mg, 1.61 mmol), 2-aminopyridine (152 mg, 1.61 mmol), Pd₂dba₃ (148 mg, 0.161 mmol), XPhos (154 mg, 0.323 mmol), sodium tert-butoxide (465 mg, 4.84 mmol) in toluene (10.8 mL) was heated at 97° C. for 18 h. Upon completion, the reaction was concentrated, diluted with EtOAc, and washed with saturated aqueous NaHCO₃, water, and brine. The organic layer was then dried over MgSO₄ and evaporated in vacuo. The resulting crude residue was purified by flash chromatography (silica gel, 0-15% EtOAc in hexanes as eluent) to give 4-chloro-5,7-difluoro-3-methyl-N-(pyridin-2-yl)quinolin-2-amine as a pale yellow solid. Mass Spectrum (ESI) m/e=306.0 (M+1).

tert-Butyl 4-chloro-5,7-difluoro-3-methylquinolin-2-yl(pyridin-2-yl)-carbamate

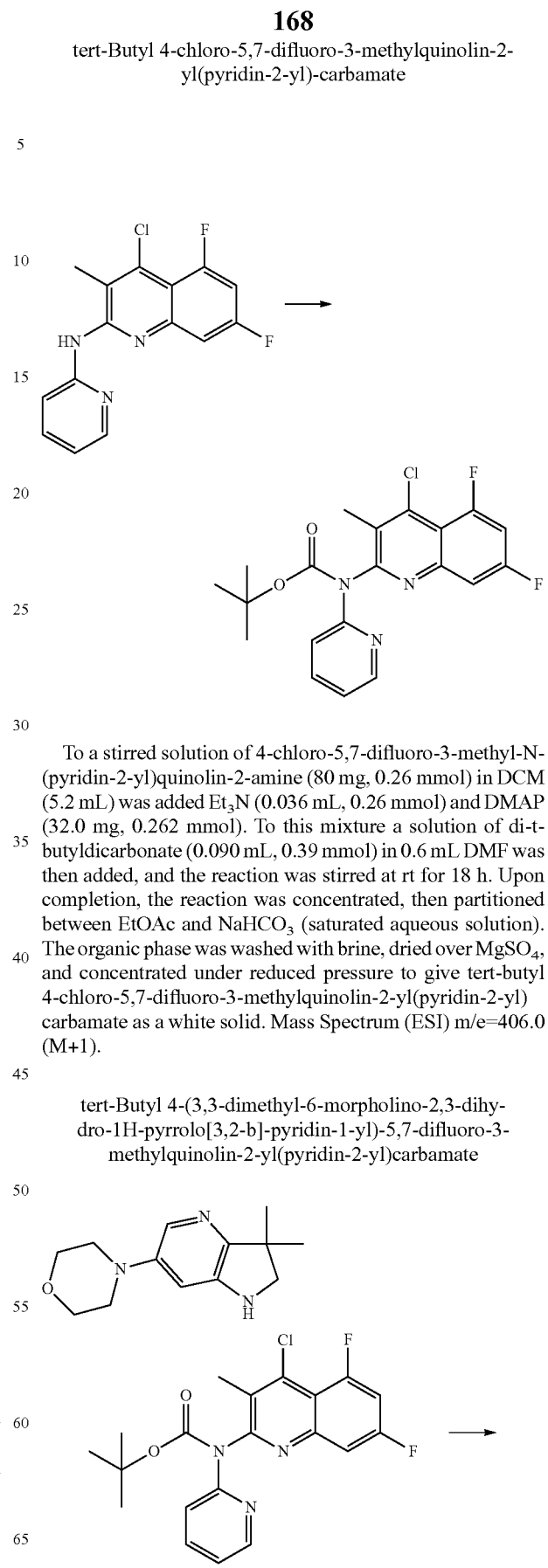

To a stirred solution of 4-chloro-5,7-difluoro-3-methyl-N-(pyridin-2-yl)quinolin-2-amine (80 mg, 0.26 mmol) in DCM (5.2 mL) was added Et₃N (0.036 mL, 0.26 mmol) and DMAP (32.0 mg, 0.262 mmol). To this mixture a solution of di-t-butyldicarbonate (0.090 mL, 0.39 mmol) in 0.6 mL DMF was then added, and the reaction was stirred at rt for 18 h. Upon completion, the reaction was concentrated, then partitioned between EtOAc and NaHCO₃ (saturated aqueous solution). The organic phase was washed with brine, dried over MgSO₄, and concentrated under reduced pressure to give tert-butyl 4-chloro-5,7-difluoro-3-methylquinolin-2-yl(pyridin-2-yl)carbamate as a white solid. Mass Spectrum (ESI) m/e=406.0 (M+1).

tert-Butyl 4-(3,3-dimethyl-6-morpholino-2,3-dihydro-1H-pyrrolo[3,2-b]-pyridin-1-yl)-5,7-difluoro-3-methylquinolin-2-yl(pyridin-2-yl)carbamate

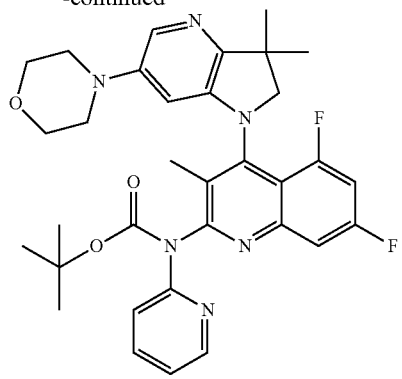

Prepared according to procedure Y by stirring tert-butyl 4-chloro-5,7-difluoro-3-methylquinolin-2-yl(pyridin-2-yl)carbamate (100 mg, 0.246 mmol), 4-(3,3-dimethyl-2,3-dihydro-1H-pyrrolo[3,2-b]pyridin-6-yl)morpholine (57.5 mg, 0.246 mmol), Pd$_2$dba$_3$ (22.6 mg, 0.025 mmol), XPhos (23.5 mg, 0.049 mmol), sodium tert-butoxide (71.0 mg, 0.739 mmol), and toluene (2.5 mL) at 100° C. for 30 min. Purification by column chromatography on silica gel (0-60% EtOAc in hexanes) gave tert-butyl 4-(3,3-dimethyl-6-morpholino-2,3-dihydro-1H-pyrrolo[3,2-b]-pyridin-1-yl)-5,7-difluoro-3-methylquinolin-2-yl(pyridin-2-yl)carbamate. Mass Spectrum (ESI) m/e=603.2 (M+1).

4-(3,3-Dimethyl-6-morpholino-2,3-dihydro-1H-pyrrolo[3,2-b]pyridin-1-yl)-5,7-difluoro-3-methyl-N-(pyridin-2-yl)quinolin-2-amine

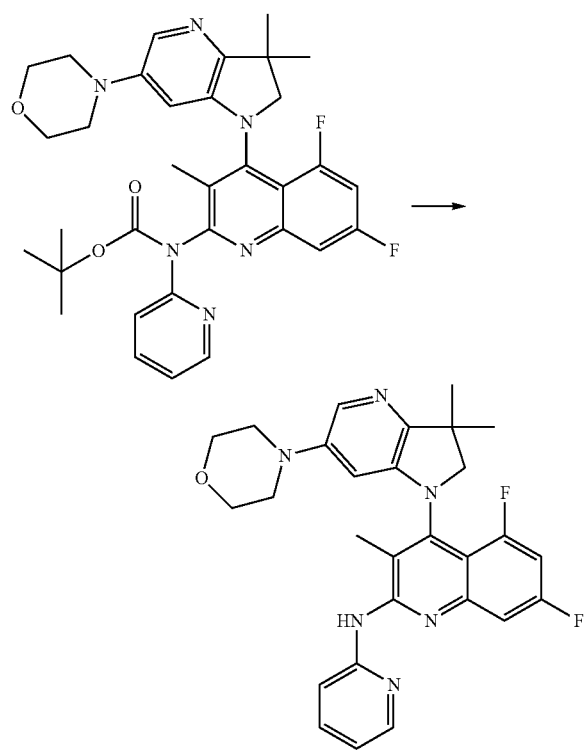

To a stirring solution of tert-butyl 4-(3,3-dimethyl-6-morpholino-2,3-dihydro-1H-pyrrolo[3,2-b]pyridin-1-yl)-5,7-difluoro-3-methylquinolin-2-yl(pyridin-2-yl)-carbamate (55.4 mg, 0.092 mmol) in DCM (1 mL) at 0° C. was added TFA (283 μL, 3.68 mmol). The solution was stirred at rt for 30 min, then concentrated and partitioned between EtOAc and saturated aqueous NaHCO$_3$. The organic layer was then dried over MgSO$_4$ and concentrated under reduced pressure to give 4-(3,3-dimethyl-6-morpholino-2,3-dihydro-1H-pyrrolo[3,2-b]pyridin-1-yl)-5,7-difluoro-3-methyl-N-(pyridin-2-yl)quinolin-2-amine as a rust-colored solid. 1H NMR (400 MHz, chloroform-d) δ ppm 8.85 (1H, d, J=8.4 Hz), 8.31-8.35 (1H, m), 7.78-7.85 (1H, m), 7.58 (1H, br. s.), 7.54 (1H, d, J=2.3 Hz), 7.39-7.45 (1H, m), 7.01-7.08 (1H, m), 6.73-6.80 (1H, m), 5.68-5.71 (1H, m), 3.81-3.86 (1H, m), 3.72-3.79 (4H, m), 3.58-3.63 (1H, m), 2.97-3.04 (4H, m), 2.34 (3H, s), 1.53 (3H, s), 1.50 (3H, s). Mass Spectrum (ESI) m/e=503.2 (M+1).

Example 95

1-(5-Fluoro-3-methyl-2-(2-pyridinyl)-4-quinolinyl)-7-(4-morpholinyl)-2,3-dihydro-1H-pyrido[2,3-b][1,4]thiazine 4,4-dioxide 7-Chloro-1H-pyrido[2,3-b][1,4]thiazin-2(3H)-one

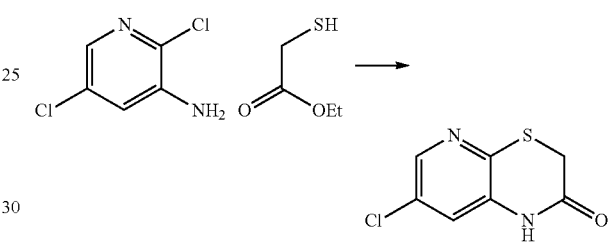

To a stirred solution of ethyl 2-mercaptoacetate (2.0 mL, 18.4 mmol) in water (5.03 mL, 12.27 mmol) was added NaOH (0.491 g, 12.27 mmol). The reaction was stirred at rt for 10 min. After this time a solution of 2,5-dichloropyridin-3-amine (2.0 g, 12.27 mmol) in EtOH (20 mL) was added and the reaction was heated at reflux for 4 days and cooled to rt. The resulting precipitate was filtered and washed with hexanes (50 mL) and MeOH (5 mL) to give 7-chloro-1H-pyrido[2,3-b][1,4]thiazin-2(3H)-one as a white solid. 1H NMR (400 MHz, DMSO-d$_6$) δ ppm 10.76 (1H, d, J=0.6 Hz), 8.15 (1H, d, J=2.2 Hz), 7.31 (1H, d, J=2.3 Hz), 3.59-3.74 (2H, m). Mass Spectrum (ESI) m/e=201.0 (M+1).

7-Chloro-2,3-dihydro-1H-pyrido[2,3-b][1,4]thiazine

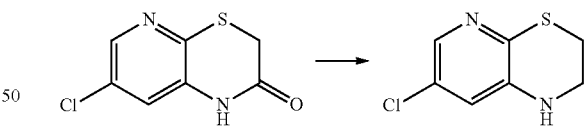

7-Chloro-1H-pyrido[2,3-b][1,4]thiazin-2(3H)-one (1.2 g, 5.98 mmol) was suspended in THF (5.0 mL), cooled to 0° C. and treated with BH$_3$-THF (47.8 mL, 47.8 mmol, 1.0M in THF). The reaction was stirred at rt for 30 min and heated at 45° C. for 2 h. At this time more BH$_3$-THF (47.8 mL, 47.8 mmol, 1.0M in THF) was added and the reaction was heated at 45° C. for 16 h. The reaction was then treated with 100 mL of MeOH and it was refluxed for 30 min. After this time the reaction was cooled to rt and acidified to pH 2 with aqueous HCl. The reaction was then basified to pH 14 with aqueous NaOH and the mixture was then extracted with EtOAc (3×80 mL). The separated organic layer was dried over MgSO$_4$, filtered and evaporated in vacuo. The resulting white solid was triturated with hot EtOAc and the mixture was allowed to cool to rt for 20 min. After filtration, the precipitate was dried over MgSO$_4$ and evaporated in vacuo to give 7-chloro-2,3- dihydro-1H-pyrido[2,3-b][1,4]thiazine as a white solid. 1H NMR (400 MHz, DMSO-d$_6$) δ ppm 7.60 (1H, d, J=2.3 Hz), 6.85 (1H, d, J=2.2 Hz), 6.52 (1H, t, J=3.0 Hz), 3.43-3.50 (2H, m), 3.04-3.15 (2H, m). Mass Spectrum (ESI) m/e=187.0 (M+1).

7-Chloro-1-(5-fluoro-3-methyl-2-(pyridin-2-yl) quinolin-4-yl)-2,3-dihydro-1H-pyrido[2,3-b][1,4]thiazine

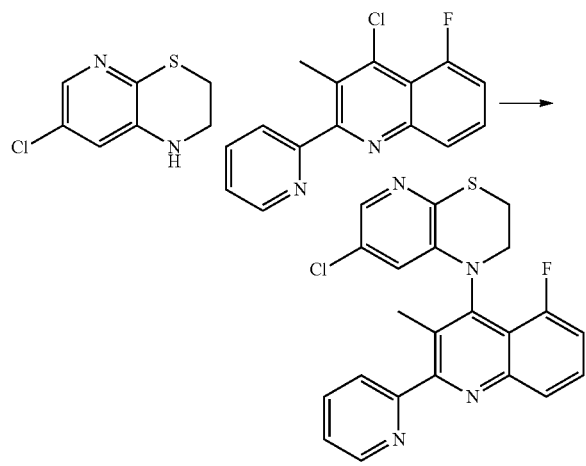

To a stirred solution of 7-chloro-2,3-dihydro-1H-pyrido[2,3-b][1,4]thiazine (100 mg, 0.536 mmol) in DMF (2.0 mL) was added sodium hydride (28.0 mg, 0.643 mmol, 55% dispersion in oil) under a N$_2$ atmosphere. The reaction was stirred at rt for 15 min. After this time 4-chloro-5-fluoro-3-methyl-2-(pyridin-2-yl)quinoline (146 mg, 0.536 mmol) in DMF (3.0 mL) was added and the reaction was heated at 60° C. for 1 h and at 100° C. overnight. After this time more NaH (28.0 mg, 0.643 mmol, 55% dispersion in oil) was added and the reaction was heated at 120° C. for 3 h. The reaction was then cooled to rt and partitioned between EtOAc and water. The separated organic layer was washed with LiCl (1.0M aqueous solution) and then it was dried over MgSO$_4$, filtered and evaporated in vacuo. Column chromatography (Hexanes: EtOAc, 1:0 to 1:1) gave 7-chloro-1-(5-fluoro-3-methyl-2-(pyridin-2-yl)quinolin-4-yl)-2,3-dihydro-1H-pyrido[2,3-b][1,4]thiazine as a yellow film. Mass Spectrum (ESI) m/e=423.0 (M+1).

7-Chloro-1-(5-fluoro-3-methyl-2-pyridin-2-ylquinolin-4-yl)-2,3-dihydro-1H-pyrido[2,3-b][1,4]thiazine 4,4-dioxide

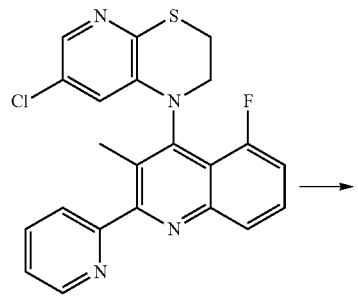

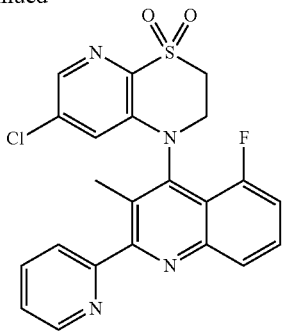

To a stirred solution of 7-chloro-1-(5-fluoro-3-methyl-2-(pyridin-2-yl)quinolin-4-yl)-2,3-dihydro-1H-pyrido[2,3-b][1,4]thiazine (30 mg, 0.071 mmol) in EtOAc (2.5 mL) was added disodium tungstate (2.08 mg, 7.09 μmol) and water (0.2 mL). The reaction was cooled at 0° C. and then H$_2$O$_2$ (36.2 μL, 0.355 mmol, 30%) was added. The reaction was allowed to warm to rt for 1 h. After this time more disodium tungstate (5 mg) was added followed by H$_2$O$_2$ (0.3 mL) and the reaction was stirred at rt overnight. After this time the reaction was diluted with EtOAc (50 mL) and treated with a saturated aqueous solution of NaHSO$_3$ (10 mL). The separated organic layer was washed with brine (10 mL), dried over MgSO$_4$, filtered and evaporated in vacuo to give 7-chloro-1-(5-fluoro-3-methyl-2-pyridin-2-ylquinolin-4-yl)-2,3-dihydro-1H-pyrido[2,3-b][1,4]thiazine 4,4-dioxide. Mass Spectrum (ESI) m/e=455.0 (M+1).

1-(5-Fluoro-3-methyl-2-(2-pyridinyl)-4-quinolinyl)-7-(4-morpholinyl)-2,3-dihydro-1H-pyrido[2,3-b][1,4]thiazine 4,4-dioxide

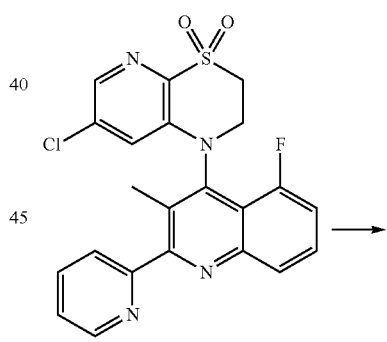

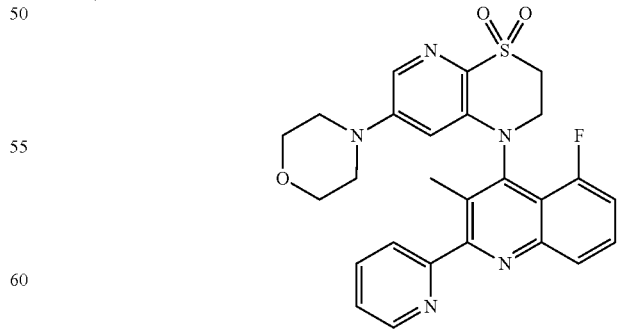

Prepared according to procedure N by heating a solution of 7-chloro-1-(5-fluoro-3-methyl-2-pyridin-2-ylquinolin-4-yl)-2,3-dihydro-1H-pyrido[2,3-b][1,4]thiazine 4,4-dioxide (34 mg, 0.075 mmol), Pd$_2$dba$_3$ (6.8 mg, 7.5 μmol), XPhos (7.13 mg, 0.015 mmol), morpholine (6.51 μL, 0.075 mmol) and sodium tert-butoxide (14.4 mg, 0.149 mmol) in toluene (2.0 mL) in the microwave for 2 h at 110° C. After this time the reaction was cooled to rt and partitioned between EtOAc (60 mL) and NaHCO$_3$ (20 mL, saturated aqueous solution). The separated organic layer was dried over MgSO$_4$, filtered and evaporated in vacuo. Purification by reverse phase HPLC (10 to 60% acetonitrile in water) gave 1-(5-fluoro-3-methyl-2-(2-pyridinyl)-4-quinolinyl)-7-(4-morpholinyl)-2,3-dihydro-1H-pyrido[2,3-b][1,4]-thiazine 4,4-dioxide. 1H NMR (400 MHz, chloroform-d) δ ppm 8.75 (1H, dt, J=4.8, 1.5 Hz), 8.05-8.12 (1H, m), 7.94 (2H, dt, J=4.6, 0.9 Hz), 7.87 (1H, d, J=2.3 Hz), 7.70 (1H, td, J=8.2, 5.4 Hz), 7.44 (1H, q, J=4.8 Hz), 7.23-7.30 (1H, m), 5.62 (1H, d, J=2.3 Hz), 4.17-4.32 (2H, m), 3.64-3.76 (5H, m), 3.49-3.60 (1H, m), 2.87-3.04 (4H, m), 2.46 (3H, s). Mass Spectrum (ESI) m/e=506.0 (M+1).

Example 96

4-(3,3-Dimethyl-6-(4-morpholinyl)-2,3-dihydro-1H-pyrrolo[3,2-b]pyridin-1-yl)-5,7-difluoro-3-methyl-2-(1-phenylcyclopropyl)quinoline

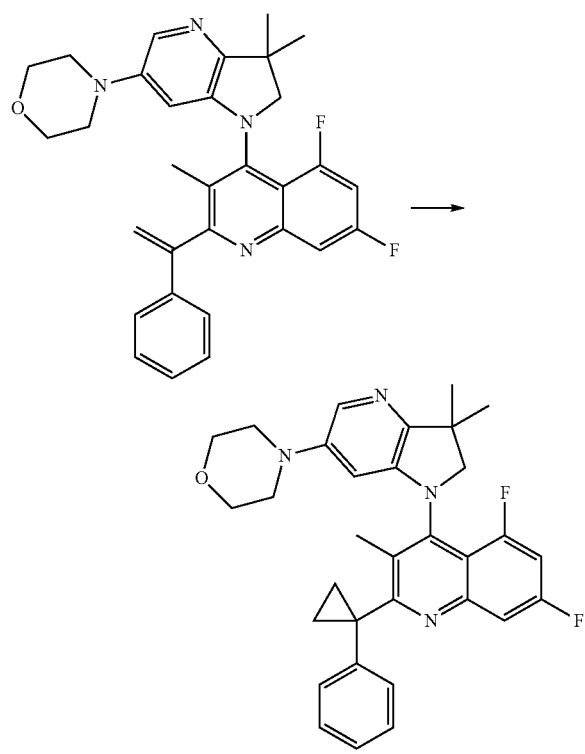

A suspension of trimethylsulfoxonium iodide (29.6 mg, 0.135 mmol) in dry DMSO (0.3 mL) was treated with potassium tert-butoxide (1.0M in THF, 0.135 mL, 0.135 mmol) at rt under a N$_2$ atmosphere. The resulting solution was stirred for 30 min. A solution of 4-(1-(5,7-difluoro-3-methyl-2-(1-phenylvinyl)quinolin-4-yl)-3,3-dimethyl-2,3-dihydro-1H-pyrrolo[3,2-b]pyridin-6-yl)morpholine (46 mg, 0.090 mmol) in dry THF (0.836 mL) was added dropwise to the stirring solution, and the reaction was stirred for 3 h. The reaction was then quenched with 1N HCl, and the product extracted twice with EtOAc. The organic phase was dried over MgSO$_4$ and concentrated under reduced pressure to give a crude residue that was purified by reverse-phase HPLC (0-80% acetonitrile in water) to give 4-(3,3-dimethyl-6-(4-morpholinyl)-2,3-dihydro-1H-pyrrolo[3,2-b]pyridin-1-yl)-5,7-difluoro-3-methyl-2-(1-phenylcyclopropyl)quinoline. 1H NMR (400 MHz, chloroform-d) δ ppm 7.62-7.73 (1H, m), 7.49-7.53 (1H, m), 7.19-7.25 (2H, m), 7.12-7.19 (1H, m), 7.03-7.11 (2H, m), 6.98 (1H, ddd, J=11.8, 8.9, 2.5 Hz), 5.51-5.55 (1H, m), 3.80-3.89 (1H, m), 3.68-3.80 (4H, m), 3.51-3.61 (1H, m), 2.86-2.97 (4H, m), 2.10-2.15 (3H, m), 1.71-1.79 (1H, m), 1.55-1.64 (2H, m), 1.49-1.54 (3H, m), 1.45-1.49 (1H, m), 1.41-1.45 (3H, m). Mass Spectrum (ESI) m/e=527.2 (M+1).

Example 97

4-(3,3-Dimethyl-6-(4-morpholinyl)-2,3-dihydro-1H-pyrrolo[3,2-b]pyridin-1-yl)-7-fluoro-3-methyl-2-(4-methyl-2-pyridinyl)quinoline 4-Chloro-7-fluoro-3-methyl-2-(4-methylpyridin-2-yl)quinoline and 4-chloro-5-fluoro-3-methyl-2-(4-methylpyridin-2-yl)quinoline

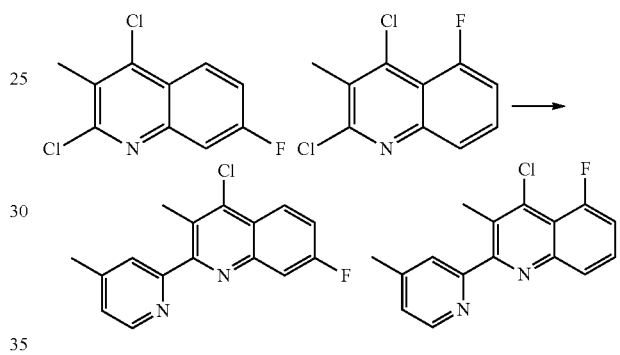

Prepared according to procedure E by heating a mixture of 2,4-dichloro-7-fluoro-3-methylquinoline, -2,4-dichloro-5-fluoro-3-methylquinoline (1.1 g, 4.78 mmol), 4-methyl-2-(tributylstannyl)pyridine (1.827 g, 4.78 mmol) and Pd(PPh$_3$)$_4$ (0.276 g, 0.239 mmol) in toluene (10 mL) at reflux for 14 h. After this time the reaction was cooled to rt and evaporated in vacuo. The resulting solid was washed with hexanes and then it was dissolved in DCM and purified by column chromatography (hexanes:EtOAc, 1:0 to 2:1) to give: 4-chloro-7-fluoro-3-methyl-2-(4-methylpyridin-2-yl)quinoline (1$^{st}$ eluted isomer). 1H NMR (400 MHz, chloroform-d) δ ppm 8.57-8.61 (1H, m), 8.28 (1H, dd, J=9.4, 5.9 Hz), 7.77 (1H, dd, J=9.8, 2.5 Hz), 7.61-7.63 (1H, m), 7.43 (1H, d, J=1.4 Hz), 7.19-7.24 (1H, m), 2.61 (3H, s), 2.48 (3H, s); and 4-chloro-5-fluoro-3-methyl-2-(4-methylpyridin-2-yl)quinoline (2$^{nd}$ eluted isomer). 1H NMR (400 MHz, chloroform-d) δ ppm 8.59 (1H, d, J=4.9 Hz), 7.95 (1H, d, J=8.6 Hz), 7.58-7.66 (2H, m), 7.28-7.33 (1H, m), 7.22 (1H, dd, J=5.1, 1.0 Hz), 2.59 (3H, s), 2.48 (3H, s).

4-(3,3-Dimethyl-6-(4-morpholinyl)-2,3-dihydro-1H-pyrrolo[3,2-b]pyridin-1-yl)-7-fluoro-3-methyl-2-(4-methyl-2-pyridinyl)quinoline

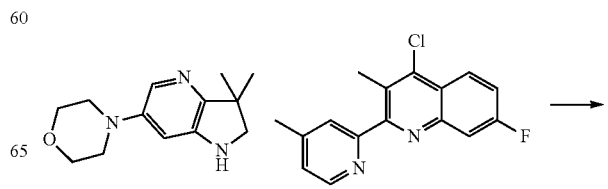

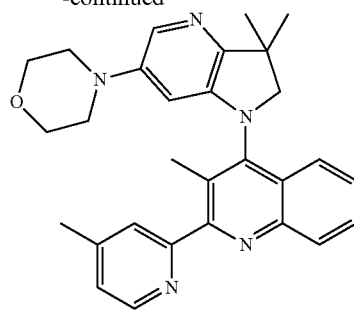

Prepared according to procedure Y by heating 4-chloro-7-fluoro-3-methyl-2-(4-methylpyridin-2-yl)quinoline (70 mg, 0.244 mmol), 4-(3,3-dimethyl-2,3-dihydro-1H-pyrrolo[3,2-b]pyridin-6-yl)morpholine (57.0 mg, 0.244 mmol), XPhos (23.3 mg, 0.049 mmol), Pd₂dba₃ (22.4 mg, 0.024 mmol) and sodium tert butoxide (46.9 mg, 0.488 mmol) in toluene (2.0 mL) at 110° C. in a microwave reactor for 2 h. After this time the reaction was partitioned between EtOAc (70 mL) and water (30 mL). The separated aqueous layer was extracted with EtOAc (30 mL) and the combined organic layers were dried over MgSO₄, filtered and evaporated in vacuo. Reverse phase HPLC (10 to 60% acetonitrile in water) gave 4-(3,3-dimethyl-6-(4-morpholinyl)-2,3-dihydro-1H-pyrrolo[3,2-b]pyridin-1-yl)-7-fluoro-3-methyl-2-(4-methyl-2-pyridinyl)quinoline. 1H NMR (500 MHz, chloroform-d) δ ppm 8.59 (1H, d, J=4.9 Hz), 7.84 (1H, dd, J=10.0, 2.7 Hz), 7.79 (1H, dd, J=9.3, 6.1 Hz), 7.66-7.70 (1H, m), 7.59 (1H, d, J=2.2 Hz), 7.27-7.32 (1H, m), 7.22 (1H, dd, J=5.0, 1.8 Hz), 5.81 (1H, d, J=2.4 Hz), 3.79-3.83 (2H, m), 3.72-3.78 (4H, m), 2.92-3.05 (4H, m), 2.47-2.52 (3H, m), 2.36 (3H, s), 1.57 (3H, s), 1.52 (3H, s). Mass Spectrum (ESI) m/e=484.2 (M+1).

Example 98

1-(4-(3,3-Dimethyl-6-(4-morpholinyl)-2,3-dihydro-1H-pyrrolo-[3,2-b]pyridin-1-yl)-5,7-difluoro-3-methyl-2-quinolinyl)-2-piperidinone 2,4-Dibromo-5,7-difluoro-3-methylquinoline

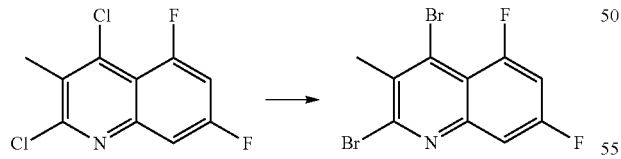

Phosphorus oxybromide (41.0 g, 140 mmol) was added to 2,4-dichloro-5,7-difluoro-3-methylquinoline (5.00 g, 20.0 mmol) and the mixture was heated at 100° C. for 3.5 h. After this time the reaction was cooled to rt and diluted with DCM (150 mL). This mixture was poured into a chilled sodium hydroxide solution (40 g of NaOH in 800 mL of ice water). The layers were separated and the aqueous layer was extracted with DCM (2×500 mL). The combined organic layers were dried over MgSO₄. The crude product was then purified by column chromatography (silica gel, 0 to 30% EtOAc:hexanes) to give 2,4-dibromo-5,7-difluoro-3-methylquinoline. Mass Spectrum (ESI) m/e=337.9 (M+1).

1-(4-Bromo-5,7-difluoro-3-methylquinolin-2-yl)piperidin-2-one

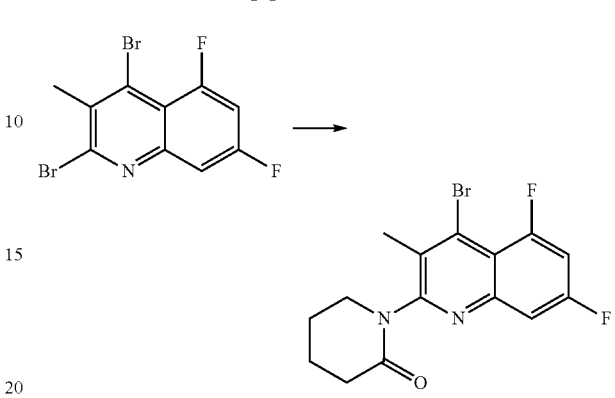

2,4-Dibromo-5,7-difluoro-3-methylquinoline (2.00 g, 5.90 mmol), piperidin-2-one (590 mg, 5.90 mmol), copper (I) iodide (57.0 mg, 0.300 mmol), (1S,2S)—N1,N2-dimethylcyclohexane-1,2-diamine (0.094 mL, 0.59 mmol) and potassium phosphate tribasic (2.50 g, 11.9 mmol) were combined in 1,4-dioxane (10 mL) and stirred in a microwave reactor for 3.5 h. The reaction was diluted with water and extracted with EtOAc (2×100 mL). The combined organic layers were washed with brine and dried over MgSO₄. The crude product was then purified by column chromatography (silica gel, 0 to 100% EtOAc:hexanes) to give 1-(4-bromo-5,7-difluoro-3-methylquinolin-2-yl)piperidin-2-one. Mass Spectrum (ESI) m/e=355.0 [(M+1) ($^{79}$Br)] and 357.1 [(M+1) ($^{81}$Br)].

1-(4-(3,3-Dimethyl-6-(4-morpholinyl)-2,3-dihydro-1H-pyrrolo[3,2-b]pyridin-1-yl)-5,7-difluoro-3-methyl-2-quinolinyl)-2-piperidinone

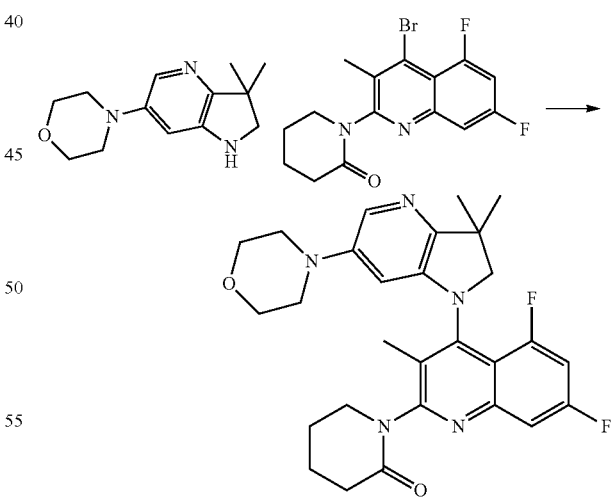

Prepared according to procedure Y using 1-(4-bromo-5,7-difluoro-3-methylquinolin-2-yl)piperidin-2-one (53.0 mg, 0.150 mmol) and 4-(3,3-dimethyl-2,3-dihydro-1H-pyrrolo[3,2-b]pyridin-6-yl)morpholine in toluene to give 1-(4-(3,3-dimethyl-6-(4-morpholinyl)-2,3-dihydro-1H-pyrrolo[3,2-b]pyridin-1-yl)-5,7-difluoro-3-methyl-2-quinolinyl)-2-piperidinone. 1H NMR (400 MHz, chloroform-d) δ ppm 7.60-7.69 (1H, m), 7.50-7.59 (1H, m), 6.89-7.09 (1H, m), 6.06 (1H, d, J=2.0 Hz), 4.21-4.36 (1H, m), 4.00 (1H, d, J=8.8 Hz), 3.68-3.92 (4H, m), 3.50-3.68 (2H, m), 3.11 (3H, dd, J=5.9, 3.7 Hz), 2.92-3.06 (2H, m), 2.52-2.70 (2H, m), 1.94-2.18 (6H, m), 1.49-1.64 (6H, m). Mass Spectrum (ESI) m/e=508.3 (M+1).

Example 99

4-(3,3-Dimethyl-6-(4-morpholinyl)-2,3-dihydro-1H-pyrrolo[3,2-b]pyridin-1-yl)-5,7-difluoro-2-(3-methoxybenzyl)-3-methylquinoline 4-Chloro-5,7-difluoro-2-(3-methoxybenzyl)-3-methylquinoline

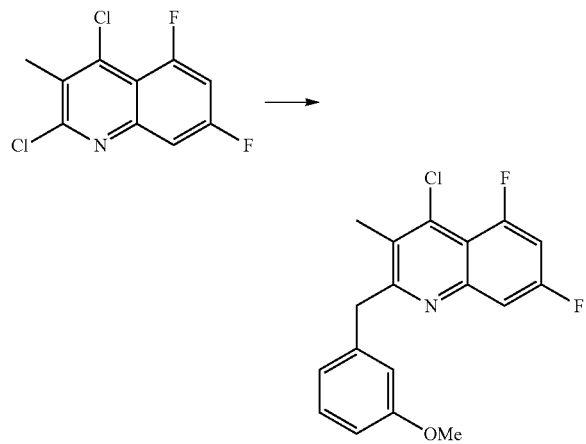

Prepared according to procedure Z using 2,4-dichloro-5,7-difluoro-3-methylquinoline (350 mg, 1.41 mmol), Pd(PPh$_3$)$_4$ (163 mg, 0.14 mmol), 3-methoxy-benzylzinc chloride (0.5M in THF, 2.96 mL, 1.48 mmol), and THF (3.5 mL). Purification by column chromatography (silica gel, 0-8% EtOAc in hexanes as eluent) gave 4-chloro-5,7-difluoro-2-(3-methoxybenzyl)-3-methylquinoline as a white solid. Mass Spectrum (ESI) m/e=334.0 (M+1).

4-(3,3-Dimethyl-6-(4-morpholinyl)-2,3-dihydro-1H-pyrrolo[3,2-b]pyridin-1-yl)-5,7-difluoro-2-(3-methoxybenzyl)-3-methylquinoline

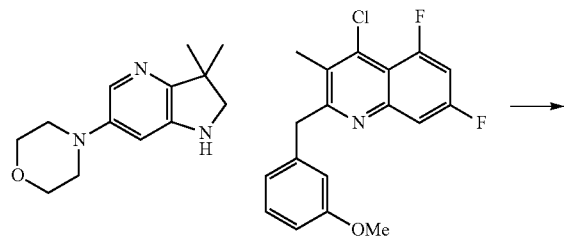

-continued

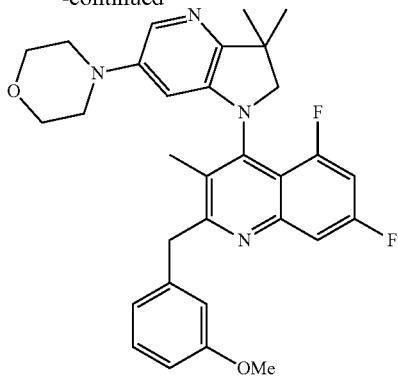

Prepared according to procedure Y by stirring 4-chloro-5,7-difluoro-2-(3-methoxybenzyl)-3-methylquinoline (50 mg, 0.150 mmol), 4-(3,3-dimethyl-2,3-dihydro-1H-pyrrolo[3,2-b]pyridin-6-yl)morpholine (35.0 mg, 0.150 mmol), Pd$_2$dba$_3$ (13.7 mg, 0.015 mmol), XPhos (14.3 mg, 0.030 mmol), sodium tert-butoxide (43 mg, 0.449 mmol), and toluene (1.5 mL) at 100° C. for 30 min. Purification by reverse-phase HPLC (0-90% acetonitrile in water) gave 4-(3,3-dimethyl-6-(4-morpholinyl)-2,3-dihydro-1H-pyrrolo[3,2-b]pyridin-1-yl)-5,7-difluoro-2-(3-methoxybenzyl)-3-methylquinoline. 1H NMR (400 MHz, chloroform-d) δ ppm 7.59-7.66 (1H, m), 7.47-7.54 (1H, m), 7.15-7.23 (1H, m), 6.91-7.00 (1H, m), 6.72-6.83 (3H, m), 5.50-5.56 (1H, m), 4.34-4.44 (2H, m), 3.78-3.83 (1H, m), 3.67-3.74 (7H, m), 3.51-3.59 (1H, m), 2.92 (4H, q, J=5.1 Hz), 2.16-2.23 (3H, m), 1.47-1.54 (3H, m), 1.40-1.47 (3H, m). Mass Spectrum (ESI) m/e=531.2 (M+1).

Example 100

4-(3,3-Dimethyl-6-(4-morpholinyl)-2,3-dihydro-1H-pyrrolo-[3,2-b]pyridin-1-yl)-5,7-difluoro-3-methyl-2-(3-(trifluoromethyl)benzyl)-quinoline 4-Chloro-5,7-difluoro-3-methyl-2-(3-(trifluoromethyl)benzyl)quinoline

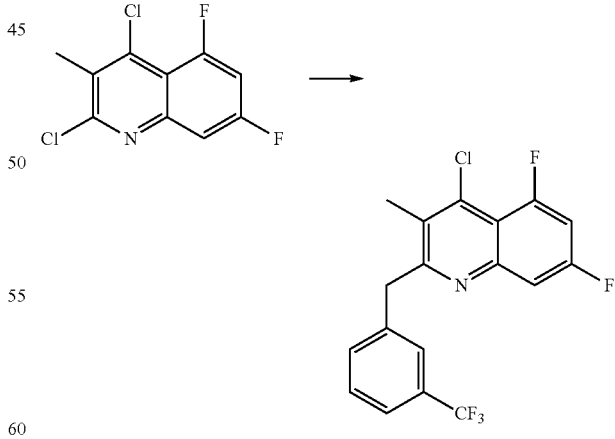

Prepared according to procedure Z using 2,4-dichloro-5,7-difluoro-3-methylquinoline (350 mg, 1.411 mmol), Pd(PPh$_3$)$_4$ (163 mg, 0.14 mmol), 3-(trifluoromethyl)benzylzinc chloride (0.5M in THF, 2.96 mL, 1.48 mmol), and THF (3.5 mL). Purification by column chromatography (silica gel, 0-8% EtOAc in hexanes) gave 4-chloro-5,7-difluoro-3-methyl-2-(3-(trifluoromethyl)benzyl)-quinoline as a white solid. Mass Spectrum (ESI) m/e=372.0 (M+1).

4-(3,3-Dimethyl-6-(4-morpholinyl)-2,3-dihydro-1H-pyrrolo[3,2-b]pyridin-1-yl)-5,7-difluoro-3-methyl-2-(3-(trifluoromethyl)benzyl)quinoline

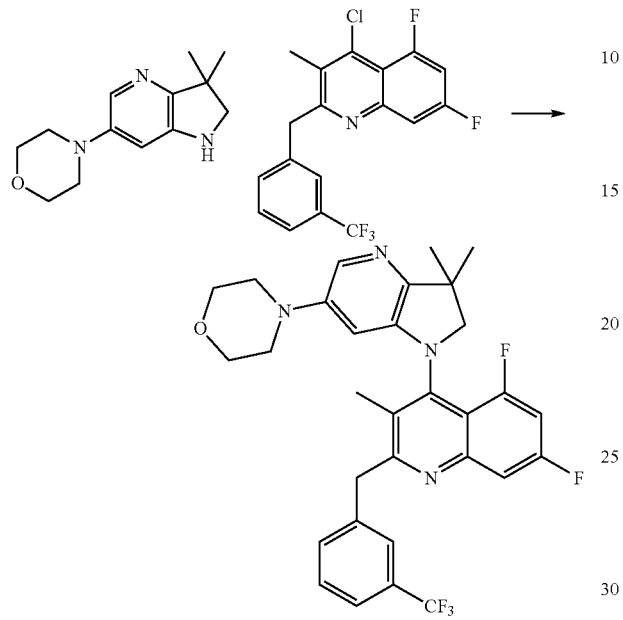

Prepared according to procedure Y by stirring 4-chloro-5,7-difluoro-3-methyl-2-(3-(trifluoromethyl)benzyl)quinoline (50 mg, 0.135 mmol), 4-(3,3-dimethyl-2,3-dihydro-1H-pyrrolo[3,2-b]pyridin-6-yl)morpholine (31.4 mg, 0.135 mmol), Pd$_2$dba$_3$ (12 mg, 0.013 mmol), XPhos (13 mg, 0.027 mmol), sodium tert-butoxide (39 mg, 0.404 mmol), and toluene (1.3 mL) at 100° C. for 30 min. Purification by reverse-phase HPLC (0-90% acetonitrile in water) gave 4-(3,3-dimethyl-6-(4-morpholinyl)-2,3-dihydro-1H-pyrrolo[3,2-b]pyridin-1-yl)-5,7-difluoro-3-methyl-2-(3-(trifluoromethyl)benzyl)quinoline. 1H NMR (400 MHz, chloroform-d) δ ppm 7.60-7.66 (1H, m), 7.40-7.55 (5H, m), 6.94-7.01 (1H, m), 5.53-5.56 (1H, m), 4.47 (2H, s), 3.78-3.85 (1H, m), 3.67-3.78 (4H, m), 3.57 (1H, d, J=8.8 Hz), 2.86-2.97 (4H, m), 2.22 (3H, s), 1.48-1.58 (3H, m), 1.46 (3H, s). Mass Spectrum (ESI) m/e=569.0 (M+1).

Example 101

4-(3,3-Dimethyl-6-(4-morpholinyl)-2,3-dihydro-1H-pyrrolo-[3,2-b]pyridin-1-yl)-5,7-difluoro-3-methyl-2-(4-methyl-2-pyridinyl)quinoline 4-Chloro-5,7-difluoro-3-methyl-2-(4-methylpyridin-2-yl)quinoline

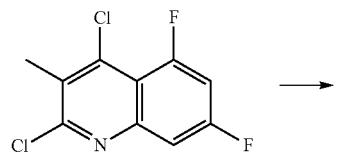

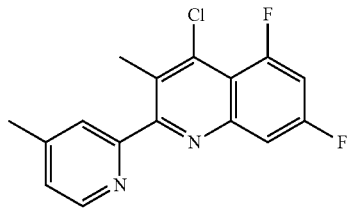

Prepared according to procedure E by stirring 2,4-dichloro-5,7-difluoro-3-methylquinoline (1.25 g, 5.04 mmol), 4-methyl-2-(tributylstannyl)pyridine (2.12 g, 5.54 mmol), Pd(PPh$_3$)$_4$ (0.58 g, 0.50 mmol), and toluene (25 mL) at 100° C. for 18 h. Purification by column chromatography (silica gel, 0-20% EtOAc in hexanes) gave 4-chloro-5,7-difluoro-3-methyl-2-(4-methylpyridin-2-yl)quinoline as a white solid. Mass Spectrum (ESI) m/e=305.0 (M+1).

4-(3,3-Dimethyl-6-(4-morpholinyl)-2,3-dihydro-1H-pyrrolo[3,2-b]pyridin-1-yl)-5,7-difluoro-3-methyl-2-(4-methyl-2-pyridinyl)quinoline

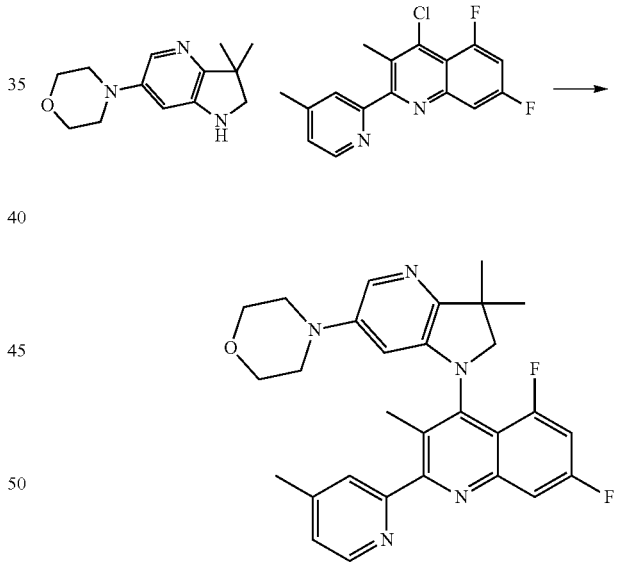

Prepared according to procedure Y by stirring 4-chloro-5,7-difluoro-3-methyl-2-(4-methylpyridin-2-yl)quinoline (65 mg, 0.213 mmol), 4-(3,3-dimethyl-2,3-dihydro-1H-pyrrolo[3,2-b]pyridin-6-yl)morpholine (54.7 mg, 0.235 mmol), Pd$_2$dba$_3$ (29.3 mg, 0.032 mmol), XPhos (30.5 mg, 0.064 mmol), sodium tert-butoxide (51 mg, 0.533 mmol), and toluene (2.1 mL) at 100° C. for 2 h. Purification by reverse-phase HPLC (0-90% acetonitrile in water) gave 4-(3,3-dimethyl-6-(4-morpholinyl)-2,3-dihydro-1H-pyrrolo[3,2-b]pyridin-1-yl)-5,7-difluoro-3-methyl-2-(4-methyl-2-pyridinyl)quinoline. 1H NMR (400 MHz, chloroform-d) δ ppm 8.59 (1H, s), 7.75 (1H, d), 7.71 (2H, m), 7.55 (1H, br. s.), 7.00 (1H, m), 5.76

(1H, s), 3.67-3.92 (6H, m), 3.00 (4H, br. s.), 2.46 (3H, s), 2.41 (3H, s), 1.57 (3H, br. s.), 1.51 (3H, br. s.). Mass Spectrum (ESI) m/e=502.2 (M+1).

Example 102

4-(3,3-Dimethyl-6-(4-morpholinyl)-2,3-dihydro-1H-pyrrolo-[3,2-b]pyridin-1-yl)-5,7-difluoro-2-(5-fluoro-3-pyridinyl)-3-methylquinoline 4-Chloro-5,7-difluoro-2-(5-fluoropyridin-3-yl)-3-methylquinoline

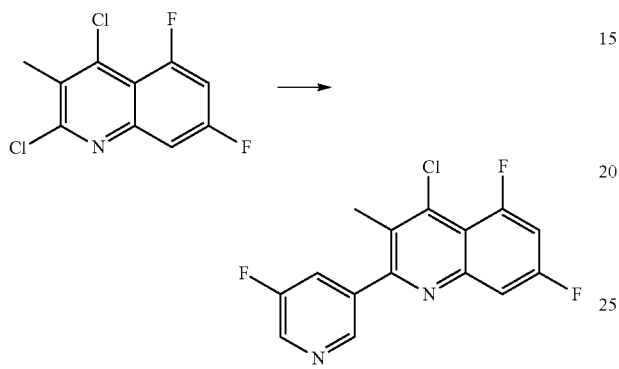

Prepared according to procedure F by stirring 2,4-dichloro-5,7-difluoro-3-methylquinoline (1 g, 4.03 mmol), 5-fluoropyridine-3-boronic acid (0.568 g, 4.03 mmol), PdCl$_2$(PPh$_3$)$_2$ (0.283 g, 0.403 mmol), sodium carbonate (0.505 mL, 12.09 mmol), 1,4-dioxane (5 mL), and water (1.25 mL) at 95° C. for 3 h. Trituration of the crude product with DCM afforded 4-chloro-5,7-difluoro-2-(5-fluoropyridin-3-yl)-3-methylquinoline. Mass Spectrum (ESI) m/e=309.0 (M+1).

4-(3,3-Dimethyl-6-(4-morpholinyl)-2,3-dihydro-1H-pyrrolo[3,2-b]pyridin-1-yl)-5,7-difluoro-2-(5-fluoro-3-pyridinyl)-3-methylquinoline

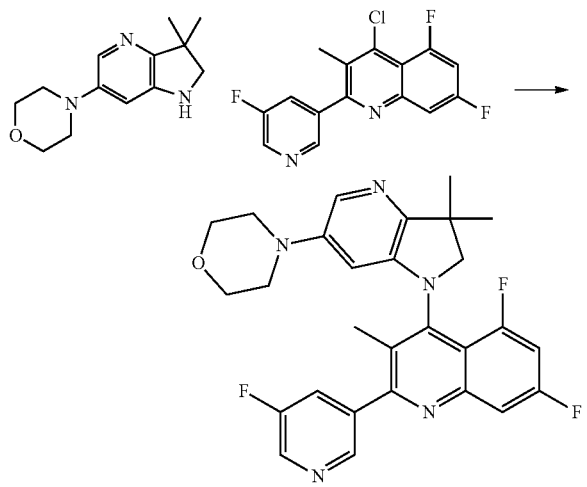

Prepared according to procedure Y by stirring 4-chloro-5,7-difluoro-2-(5-fluoropyridin-3-yl)-3-methylquinoline (50 mg, 0.162 mmol), 4-(3,3-dimethyl-2,3-dihydro-1H-pyrrolo[3,2-b]pyridin-6-yl)morpholine (37.8 mg, 0.162 mmol), Pd$_2$dba$_3$ (22.3 mg, 0.024 mmol), XPhos (23.2 mg, 0.049 mmol), sodium tert-butoxide (47 mg, 0.486 mmol), and toluene (1.6 mL) at 100° C. for 2 h. Purification by reverse-phase HPLC (0-70% acetonitrile in water) gave 4-(3,3-dimethyl-6-(4-morpholinyl)-2,3-dihydro-1H-pyrrolo[3,2-b]pyridin-1-yl)-5,7-difluoro-2-(5-fluoro-3-pyridinyl)-3-methylquinoline. 1H NMR (400 MHz, chloroform-d) δ ppm 8.69-8.76 (1H, m), 8.62 (1H, d, J=2.7 Hz), 7.74-7.80 (1H, m), 7.65-7.70 (1H, m), 7.59-7.62 (1H, m), 7.04 (1H, ddd, J=11.7, 8.9, 2.5 Hz), 5.75 (1H, d, J=2.3 Hz), 3.84-3.88 (1H, m), 3.70-3.81 (5H, m), 2.97-3.06 (4H, m), 2.36 (3H, s), 1.58 (3H, s), 1.47-1.55 (3H, m). Mass Spectrum (ESI) m/e=506.0 (M+1).

Example 103

4-(3,3-Dimethyl-6-(4-morpholinyl)-2,3-dihydro-1H-pyrrolo-[3,2-b]pyridin-1-yl)-5,7-difluoro-3-methyl-2-(5-methyl-3-pyridinyl)quinoline 4-Chloro-5,7-difluoro-3-methyl-2-(5-methylpyridin-3-yl)quinoline

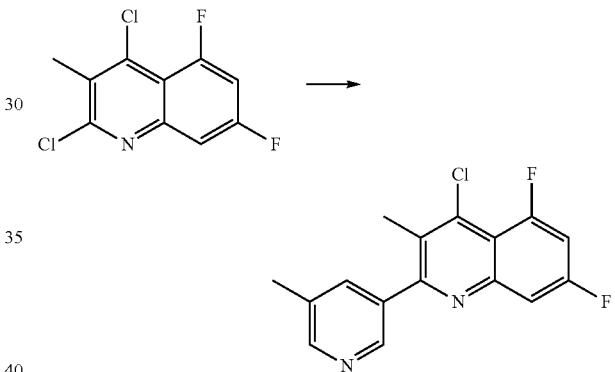

Prepared according to procedure F by stirring 2,4-dichloro-5,7-difluoro-3-methylquinoline (600 mg, 2.419 mmol), 5-methylpyridine-3-boronic acid (348 mg, 2.54 mmol), PdCl$_2$(PPh$_3$)$_2$ (170 mg, 0.242 mmol), sodium carbonate (769 mg, 7.26 mmol), 1,4-dioxane (6.5 mL), and water (1.6 mL) at 95° C. for 22 h. Purification by column chromatography (silica gel, 0-30% EtOAc in hexanes) gave 4-chloro-5,7-difluoro-3-methyl-2-(5-methylpyridin-3-yl)quinoline. Mass Spectrum (ESI) m/e=305.0 (M+1).

4-(3,3-Dimethyl-6-(4-morpholinyl)-2,3-dihydro-1H-pyrrolo[3,2-b]pyridin-1-yl)-5,7-difluoro-3-methyl-2-(5-methyl-3-pyridinyl)quinoline

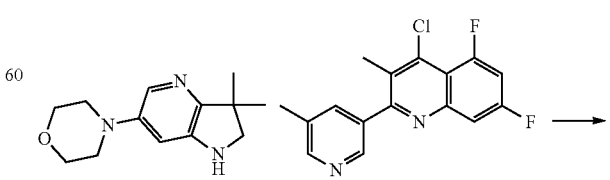

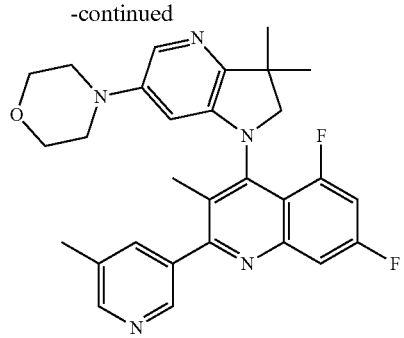

Prepared according to procedure Y by stirring 4-chloro-5,7-difluoro-3-methyl-2-(5-methylpyridin-3-yl)quinoline (40 mg, 0.131 mmol), 4-(3,3-dimethyl-2,3-dihydro-1H-pyrrolo[3,2-b]pyridin-6-yl)morpholine (30.6 mg, 0.131 mmol), Pd$_2$dba$_3$ (12.0 mg, 0.013 mmol), XPhos (12.5 mg, 0.026 mmol), sodium tert-butoxide (38 mg, 0.394 mmol), and toluene (1.3 mL) at 105° C. for 2 h. Purification by reverse-phase HPLC (0-60% acetonitrile in water) gave 4-(3,3-dimethyl-6-(4-morpholinyl)-2,3-dihydro-1H-pyrrolo[3,2-b]pyridin-1-yl)-5,7-difluoro-3-methyl-2-(5-methyl-3-pyridinyl)quinoline. 1H NMR (400 MHz, chloroform-d) δ ppm 8.65-8.72 (1H, m), 8.58-8.61 (1H, m), 7.81-7.84 (1H, m), 7.67-7.72 (1H, m), 7.54-7.57 (1H, m), 7.01-7.08 (1H, m), 5.79-5.82 (1H, m), 3.85-3.92 (1H, m), 3.69-3.82 (5H, m), 3.01-3.08 (4H, m), 2.48 (3H, s), 2.32-2.38 (3H, m), 1.67 (3H, br. s.), 1.60 (3H, br. s.). Mass Spectrum (ESI) m/e=502.2 (M+1).

Example 104

4-(3,3-Dimethyl-6-(4-morpholinyl)-2,3-dihydro-1H-pyrrolo-[3,2-b]pyridin-1-yl)-5,7-difluoro-3-methyl-2-(5-(methylsulfonyl)-3-pyridinyl)-quinoline 4-Chloro-5,7-difluoro-3-methyl-2-(5-(methylthio)pyridin-3-yl)quinoline

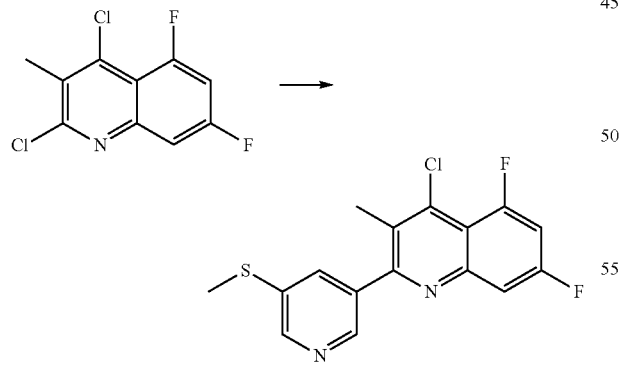

Prepared according to procedure F by stirring 2,4-dichloro-5,7-difluoro-3-methylquinoline (600 mg, 2.419 mmol), 5-(methylthio)pyridin-3-ylboronic acid (429 mg, 2.54 mmol), PdCl$_2$(PPh$_3$)$_2$ (170 mg, 0.242 mmol), sodium carbonate (769 mg, 7.26 mmol), 1,4-dioxane (6.5 mL), and water (1.6 mL) at 95° C. for 2 h. Purification by column chromatography (silica gel, 0-30% EtOAc in hexanes) gave 4-chloro-5,7-difluoro-3-methyl-2-(5-(methylthio)pyridin-3-yl)quinoline. Mass Spectrum (ESI) m/e=337.0 (M+1).

4-Chloro-5,7-difluoro-3-methyl-2-(5-(methylsulfonyl)pyridin-3-yl)quinoline

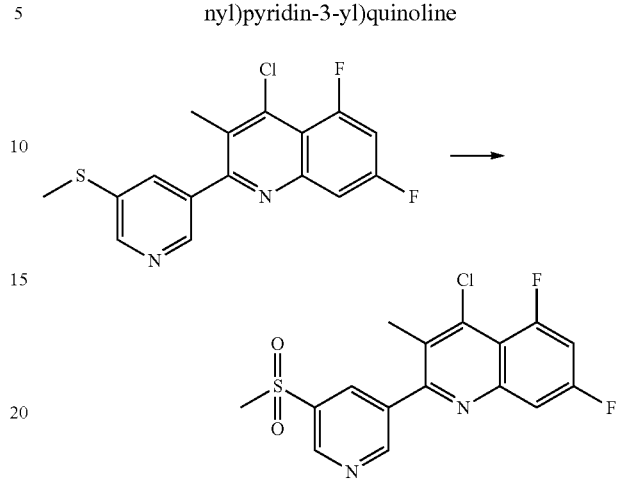

To a stirring suspension of 4-chloro-5,7-difluoro-3-methyl-2-(5-(methylthio)pyridin-3-yl)quinoline (200 mg, 0.594 mmol) in THF (4.5 mL) and water (1.5 mL) was added oxone (913 mg, 1.485 mmol). The reaction was stirred at rt for 18 h, then poured into 15 mL water and stirred for 10 min. The resulting precipitate was isolated by filtration, then dissolved in EtOAc, dried over MgSO$_4$, and concentrated under reduced pressure to give 4-chloro-5,7-difluoro-3-methyl-2-(5-(methylsulfonyl)pyridin-3-yl)quinoline. Mass Spectrum (ESI) m/e=369.0 (M+1).

4-(3,3-Dimethyl-6-(4-morpholinyl)-2,3-dihydro-1H-pyrrolo[3,2-b]pyridin-1-yl)-5,7-difluoro-3-methyl-2-(5-(methylsulfonyl)-3-pyridinyl)quinoline

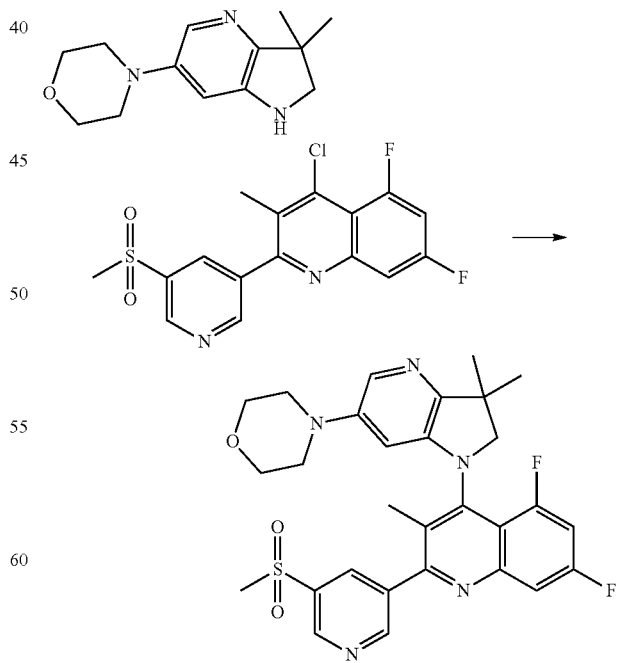

Prepared according to procedure Y by stirring 4-chloro-5,7-difluoro-3-methyl-2-(5-(methylsulfonyl)pyridin-3-yl)

quinoline (40 mg, 0.108 mmol), 4-(3,3-dimethyl-2,3-dihydro-1H-pyrrolo[3,2-b]pyridin-6-yl)morpholine (25.3 mg, 0.108 mmol), Pd₂dba₃ (10.1 mg, 10.85 μmol), X-Phos (10.3 mg, 0.022 mmol), sodium tert-butoxide (31.3 mg, 0.325 mmol), and toluene (1.1 mL) at 105° C. for 30 min. Purification by reverse-phase HPLC (0-80% acetonitrile in water) gave 4-(3,3-dimethyl-6-(4-morpholinyl)-2,3-dihydro-1H-pyrrolo[3,2-b]pyridin-1-yl)-5,7-difluoro-3-methyl-2-(5-(methylsulfonyl)-3-pyridinyl)quinoline. 1H NMR (400 MHz, chloroform-d) δ ppm 9.28 (1H, d, J=2.2 Hz), 9.17-9.20 (1H, m), 8.56-8.59 (1H, m), 7.67-7.72 (1H, m), 7.58-7.61 (1H, m), 7.06-7.13 (1H, m), 5.79-5.82 (1H, m), 3.86-3.91 (1H, m), 3.74-3.81 (5H, m), 3.23 (3H, s), 3.02-3.08 (4H, m), 2.37-2.41 (3H, m), 1.65-1.74 (3H, m), 1.57-1.65 (3H, m). Mass Spectrum (ESI) m/e=566.2 (M+1).

Example 105

1-(4-(3,3-Dimethyl-6-(4-morpholinyl)-2,3-dihydro-1H-pyrrolo[3,2-b]pyridin-1-yl)-5,7-difluoro-3-methyl-2-quinolinyl)-2-pyrrolidinone 1-(4-Bromo-5,7-difluoro-3-methylquinolin-2-yl)pyrrolidin-2-one

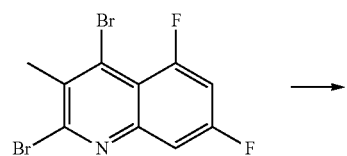

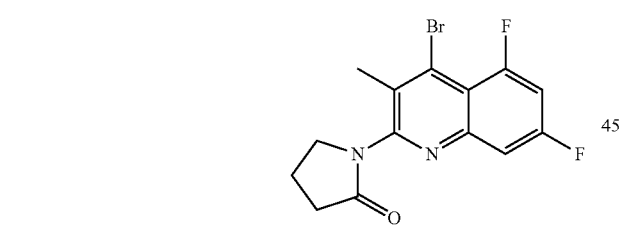

2,4-Dibromo-5,7-difluoro-3-methylquinoline (500 mg, 1.50 mmol), pyrrolidin-2-one (0.110 mL, 1.50 mmol), copper (I) iodide (14 mg, 0.074 mmol), (1S,2S)—N1,N2-dimethyl-cyclohexane-1,2-diamine (0.023 mL, 0.150 mmol) and potassium phosphate tribasic (630 mg, 3.00 mmol) were slurried in 1,4-dioxane (5 mL) and stirred in a microwave reactor at 110° C. for 2 h. The resulting slurry was partitioned between EtOAc and water. The separated aqueous layer was extracted with EtOAc and the combined organic extracts were washed with brine (1×50 mL) and dried over MgSO₄. The crude product was purified by column chromatography (silica gel, 0 to 100% EtOAc:DCM) to give 1-(4-bromo-5,7-difluoro-3-methylquinolin-2-yl)pyrrolidin-2-one. Mass Spectrum (ESI) m/e=341.0 [(M+1) (⁷⁹Br)] and 343.1 [(M+1) (⁸¹Br)].

1-(4-(3,3-Dimethyl-6-(4-morpholinyl)-2,3-dihydro-1H-pyrrolo[3,2-b]pyridin-1-yl)-5,7-difluoro-3-methyl-2-quinolinyl)-2-pyrrolidinone

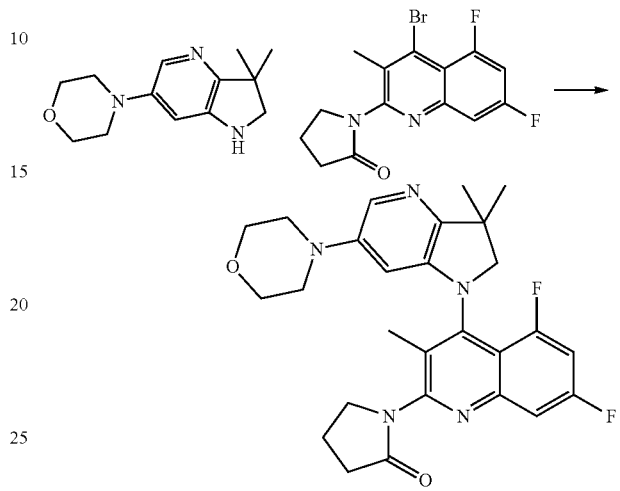

Prepared according to procedure Y using 1-(4-bromo-5,7-difluoro-3-methylquinolin-2-yl)pyrrolidin-2-one (55.0 mg, 0.160 mmol) and 4-(3,3-dimethyl-2,3-dihydro-1H-pyrrolo[3,2-b]pyridin-6-yl)morpholine in toluene to give 1-(4-(3,3-dimethyl-6-(4-morpholinyl)-2,3-dihydro-1H-pyrrolo[3,2-b]pyridin-1-yl)-5,7-difluoro-3-methyl-2-quinolinyl)-2-pyrrolidinone. 1H NMR (400 MHz, chloroform-d) δ ppm 7.67 (1H, d, J=2.3 Hz), 7.54 (1H, ddd, J=9.2, 2.4, 1.3 Hz), 7.05 (1H, ddd, J=12.3, 8.6, 2.5 Hz), 6.14 (1H, d, J=2.2 Hz), 4.26-4.41 (1H, m), 4.07-4.12 (1H, m), 4.04 (1H, d, J=9.2 Hz), 3.69-3.83 (5H, m), 3.12-3.18 (4H, m), 2.63-2.71 (2H, m), 2.27-2.40 (2H, m), 2.18 (3H, s), 1.70 (3H, s), 1.67 (3H, s). Mass Spectrum (ESI) m/e=494.2 (M+1).

Example 106

1'-(5,7-Difluoro-3-methyl-2-(4-methyl-2-pyridinyl)-4-quinolinyl)-6'-(4-morpholinyl)-1',2,2',3,5,6-hexahydrospiro[pyran-4,3'-pyrrolo[3,2-b]-pyridine]

tert-Butyl 6'-bromo-2,3,5,6-tetrahydrospiro[pyran-4,3'-pyrrolo[3,2-b]-pyridine]-1'(2'H)-carboxylate

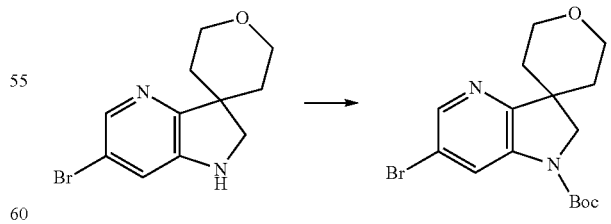

To a stirred solution of 6'-bromo-1',2,2',3,5,6-hexahydrospiro[pyran-4,3'-pyrrolo-[3,2-b]pyridine] (10.0 g, 37.2 mmol) in THF (100 mL) was added di-tert-butyl dicarbonate (9.73 g, 44.6 mmol), triethylamine (7.77 mL, 55.7 mmol) and 4-dimethylamino pyridine (0.908 g, 7.43 mmol) and the reaction was stirred at rt for 24 h. After this time more di-tert-butyl dicarbonate (2.0 g) and 4-dimethylamino pyridine (0.3 g) was added and the reaction was stirred at rt for an additional 24 hours. After this time the reaction was partitioned between EtOAc (300 mL) and saturated NaHCO₃ (60 mL). The separated organic layer was washed with brine, dried over MgSO₄ and evaporated in vacuo. Column chromatography (hexanes: EtOAc, 1:0 to 1:2 as eluent) gave tert-butyl 6'-bromo-2,3,5,6-tetrahydrospiro-[pyran-4,3'-pyrrolo[3,2-b]pyridine]-1' (2'H)-carboxylate as a white solid. Mass Spectrum (ESI) m/e=369.0 [(M+1) (⁷⁹Br)], 371.0 [(M+1) (⁸¹Br)].

tert-Butyl 6'-morpholino-2,3,5,6-tetrahydrospiro [pyran-4,3'-pyrrolo[3,2-b]-pyridine]-1'(2'H)-carboxylate

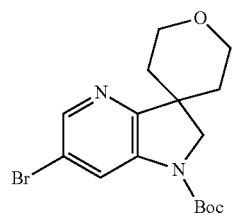

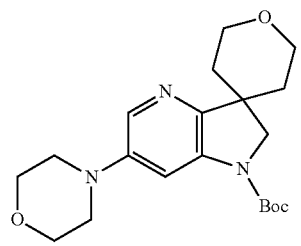

Prepared according to procedure N using tert-butyl 6'-bromo-2,3,5,6-tetrahydrospiro[pyran-4,3'-pyrrolo[3,2-b] pyridine]-1'(2'H)-carboxylate (12.0 g, 32.5 mmol), morpholine (3.11 mL, 35.7 mmol), Pd₂dba₃ (1.19 g, 1.30 mmol), XPhos (1.24 g, 0.08 mmol) and sodium tert-butoxide (6.25 g, 65.0 mmol) in toluene (200 mL) at 110° C. for 5 h. Purification by column chromatography (hexanes:EtOAC, 1:0 to 1:3 as eluent) gave tert-butyl 6'-morpholino-2,3,5,6-tetrahydrospiro[pyran-4,3'-pyrrolo[3,2-b]pyridine]-1'(2'H)-carboxylate. Mass Spectrum (ESI) m/e=376.2 (M+1).

6'-Morpholino-1',2,2',3,5,6-hexahydrospiro[pyran-4, 3'-pyrrolo[3,2-b]-pyridine]

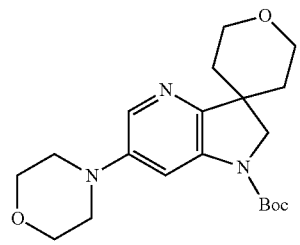

To a stirred solution of tert-butyl 6'-morpholino-2,3,5,6-tetrahydrospiro[pyran-4,3'-pyrrolo[3,2-b]pyridine]-1'(2'H)-carboxylate (5.8 g, 15.45 mmol) in DCM (30 mL) was added TFA (23.80 mL, 309 mmol) and the reaction was stirred at rt for 3 h. After this time the reaction was evaporated under reduced pressure and dried under vacuum overnight. After this time the reaction was partitioned between EtOAc (80 mL) and 1.0M aqueous HCl (200 mL). The separated aqueous layer was washed with EtOAc (40 mL). The aqueous layer was then basified to pH 14 with aqueous NaOH and extracted with EtOAc (2×200 mL) and DCM (100 mL). The combined organic layers were dried over MgSO₄, filtered and evaporated in vacuo to give 6'-morpholino-1',2,2',3,5,6-hexahydrospiro[pyran-4,3'-pyrrolo[3,2-b]pyridine] as a white solid. Mass Spectrum (ESI) m/e=276.2 (M+1)

1'-(5,7-Difluoro-3-methyl-2-(4-methyl-2-pyridinyl)-4-quinolinyl)-6'-(4-morpholinyl)-1',2,2',3,5,6-hexahydrospiro[pyran-4,3'-pyrrolo[3,2-b]pyridine]

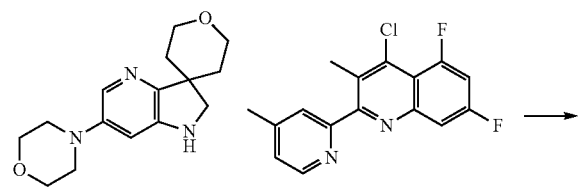

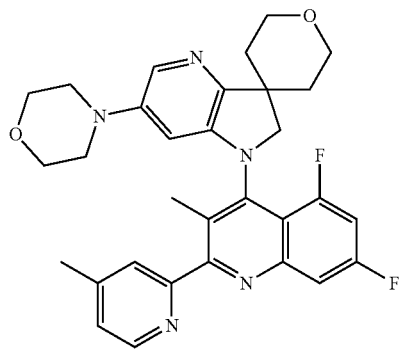

Prepared according to procedure Y by stirring 4-chloro-5,7-difluoro-3-methyl-2-(4-methylpyridin-2-yl)quinoline (45 mg, 0.148 mmol), 6'-morpholino-1',2,2',3,5,6-hexahydrospiro[pyran-4,3'-pyrrolo[3,2-b]pyridine] (48.8 mg, 0.177 mmol), XPhos precatalyst (10.9 mg, 0.015 mmol), sodium tert-butoxide (28.4 mg, 0.295 mmol), and toluene (1.6 mL) at 95° C. for 24 h. Purification by column chromatography (basic alumina, 0-30% EtOAc in hexanes) gave 1'-(5,7-difluoro-3-methyl-2-(4-methyl-2-pyridinyl)-4-quinolinyl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 8.60 (1H, d, J=5.1 Hz), 7.68-7.74 (2H, m), 7.54-7.58 (1H, m), 7.21-7.27 (1H, m), 7.02 (1H, t, J=3.1 Hz), 5.78 (1H, s), 4.14 (2H, td, J=11.6, 3.9 Hz), 3.92-4.00 (1H, m), 3.71-3.84 (5H, m), 3.49-3.62 (2H, m), 2.98-3.08 (4H, m), 2.51 (3H, s), 2.37-2.42 (3H, m), 1.83 (1H, d, J=13.9 Hz), 1.68-1.78 (1H, m), 1.28-1.34 (2H, m). Mass Spectrum (ESI) m/e=544.1 (M+1).

Example 107

1-(5,7-Difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-piperidinone

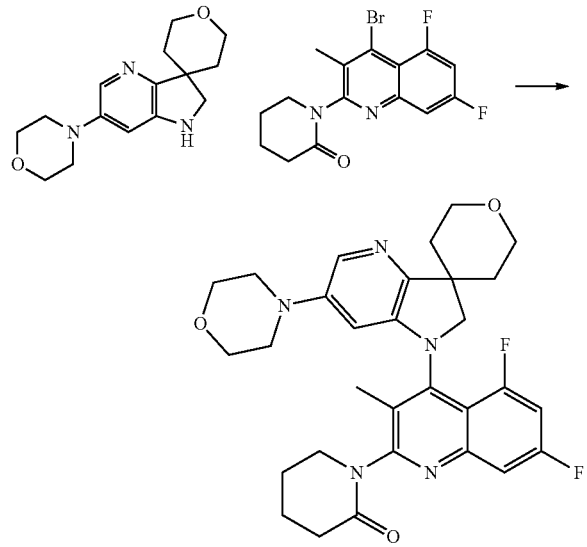

Prepared according to procedure Y using 1-(4-bromo-5,7-difluoro-3-methylquinolin-2-yl)piperidin-2-one (45.0 mg, 0.130 mmol) and 6'-morpholino-1',2,2',3,5,6-hexahydrospiro[pyran-4,3'-pyrrolo[3,2-b]pyridine] in toluene to give 1-(5,7-difluoro-3-methyl-4-(6'-(4-morpholinyl)-2,3,5,6-tetrahydrospiro[pyran-4,3'-pyrrolo-[3,2-b]pyridin]-1'(2'H)-yl)-2-quinolinyl)-2-piperidinone. 1H NMR (400 MHz, chloroform-d) δ ppm 7.58 (1H, t, J=2.3 Hz), 7.55 (1H, d, J=9.4 Hz), 6.89-7.07 (1H, m), 5.55-6.01 (1H, m), 3.98-4.39 (4H, m), 3.46-3.93 (7H, m), 2.88-3.26 (4H, m), 2.54-2.72 (2H, m), 1.92-2.47 (8H, m), 1.61-1.90 (4H, m). Mass Spectrum (ESI) m/e=550.3 (M+1).

Example 108

1'-(5,7-Difluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]

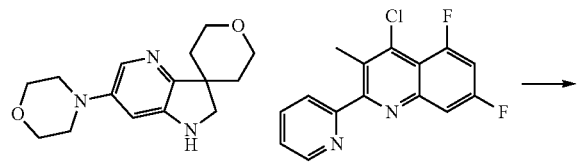

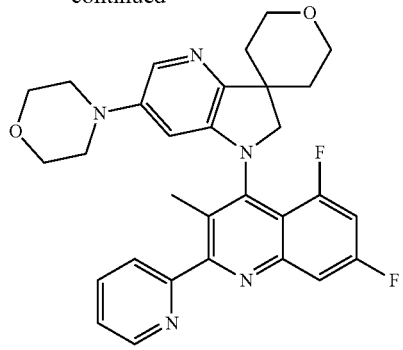

Prepared according to procedure Y by stirring 4-chloro-5,7-difluoro-3-methyl-2-(pyridin-2-yl)quinoline (58.1 mg, 0.20 mmol), 6'-morpholino-1',2,2',3,5,6-hexahydrospiro[pyran-4,3'-pyrrolo[3,2-b]pyridine] (55 mg, 0.20 mmol), XPhos pre-catalyst (14.8 mg, 0.02 mmol) and sodium tert butoxide (38.4 mg, 0.40 mmol) in toluene (4 mL) at 90° C. for 2 h. Purification by reverse phase HPLC (10 to 60% acetonitrile in water) gave 1'-(5,7-difluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]-pyridine]. 1H NMR (400 MHz, chloroform-d) δ ppm 8.75 (1H, dt, J=4.8, 1.4 Hz), 7.86-7.95 (2H, m), 7.70 (1H, ddd, J=9.3, 2.5, 1.5 Hz), 7.55-7.60 (1H, m), 7.39-7.46 (1H, m), 6.96-7.06 (1H, m), 5.70-5.85 (1H, m), 4.07-4.21 (2H, m), 3.87-4.01 (2H, m), 3.71-3.81 (4H, m), 3.50-3.63 (2H, m), 2.96-3.06 (4H, m), 2.19-2.44 (5H, m), 1.68-1.86 (2H, m). Mass Spectrum (ESI) m/e=530.0 (M+1).

Example 109

1'-(5-Fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]

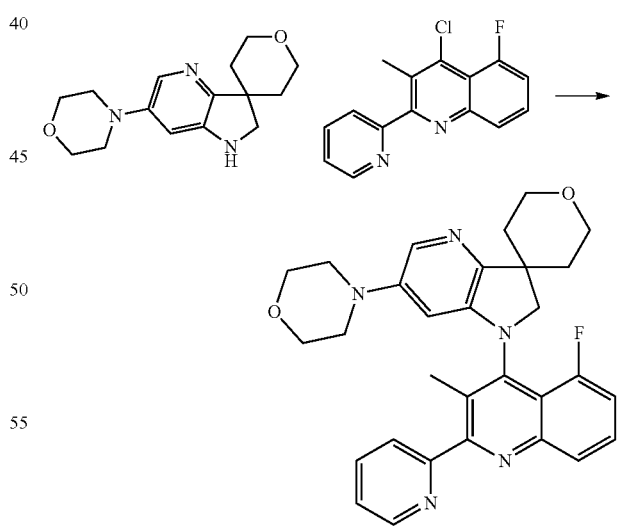

Prepared according to procedure Y by stirring 4-chloro-5-fluoro-3-methyl-2-(pyridin-2-yl)quinoline (29.7 mg, 0.11 mmol), 6'-morpholino-1',2,2',3,5,6-hexahydrospiro[pyran-4,3'-pyrrolo[3,2-b]pyridine] (30 mg, 0.11 mmol), XPhos pre-catalyst (7 mg, 0.01 mmol) and sodium tert butoxide (20.9 mg, 0.22 mmol) in toluene (3 mL) at 90° C. for 2 h. Purification by reverse phase HPLC (10 to 60% acetonitrile in water)

gave 1'-(5-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]. 1H NMR (500 MHz, chloroform-d) δ ppm 8.65-8.84 (1H, m), 8.02-8.07 (1H, m), 7.86-7.96 (2H, m), 7.64 (1H, td, J=8.1, 5.4 Hz), 7.56 (1H, d, J=2.2 Hz), 7.42 (1H, ddd, J=6.8, 4.9, 2.0 Hz), 7.14-7.21 (1H, m), 5.77 (1H, d, J=2.2 Hz), 4.08-4.18 (2H, m), 3.91-4.02 (2H, m), 3.70-3.80 (4H, m), 3.51-3.63 (2H, m), 2.95-3.05 (4H, m), 2.42-2.45 (3H, s), 2.35-2.40 (1H, m), 2.28 (1H, ddd, J=13.7, 11.5, 4.4 Hz), 1.85 (1H, ddd, J=13.6, 1.5, 1.3 Hz), 1.70-1.76 (1H, m). Mass Spectrum (ESI) m/e=512.0 (M+1).

Example 110

1'-(7-Fluoro-3-methyl-2-(2-pyridinyl)-4-quinolinyl)-6'-(1H-pyrazol-4-yl)-1',2,2',3,5,6-hexahydrospiro[pyran-4,3'-pyrrolo[3,2-b]pyridine]

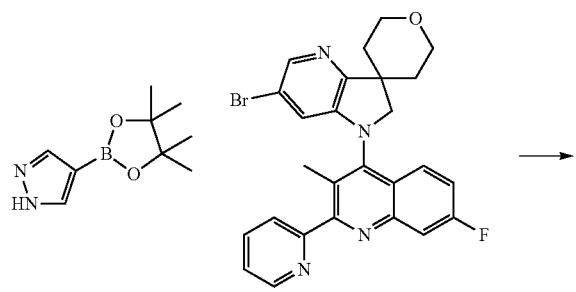

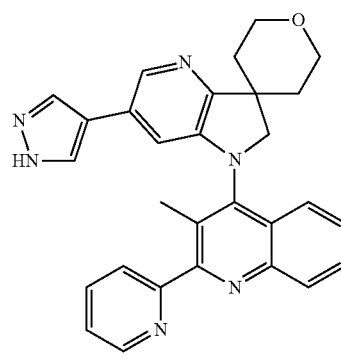

A stirred solution of 6'-bromo-1'-(7-fluoro-3-methyl-2-(pyridin-2-yl)quinolin-4-yl)-1',2,2',3,5,6-hexahydrospiro[pyran-4,3'-pyrrolo[3,2-b]pyridine] (25 mg, 0.049 mmol), 4,4,5,5-tetramethyl-2-(1H-pyrazol-4-yl)-1,3,2-dioxaborolane (9.60 mg, 0.049 mmol), PdCl$_2$(PPh$_3$)$_2$ (3.5 mg, 4.95 μmol) and Na$_2$CO$_3$ (10.5 mg, 0.099 mmol) in toluene:water (2 mL:1 mL) was heated in the microwave for 2 h at 120° C. After this time PdCl$_2$(PPh$_3$)$_2$ (5.0 mg) and 4,4,5,5-tetramethyl-2-(1H-pyrazol-4-yl)-1,3,2-dioxaborolane (9.60 mg, 0.049 mmol) was added and the reaction was heated in the microwave for 1 h at 140° C. After this time the reaction was partitioned between EtOAc (50 mL) and water (20 mL). The separated organic layer was dried with MgSO$_4$, filtered and evaporated in vacuo. Reverse phase HPLC (10 to 60% acetonitrile:water) gave 1'-(7-fluoro-3-methyl-2-(2-pyridinyl)-4-quinolinyl)-6'-(1H-pyrazol-4-yl)-1',2,2',3,5,6-hexahydrospiro[pyran-4,3'-pyrrolo[3,2-b]pyridine]. Mass Spectrum (ESI) m/e=493.0 (M+1).

Example 111

1'-(5,7-Difluoro-3-methyl-2-(2-(methylsulfonyl)phenyl)-4-quinolinyl)-6'-(4-morpholinyl)-1',2,2',3,5,6-hexahydrospiro[pyran-4,3'-pyrrolo[3,2-b]pyridine]

4-Chloro-5,7-difluoro-3-methyl-2-(2-(methylthio)phenyl)quinoline

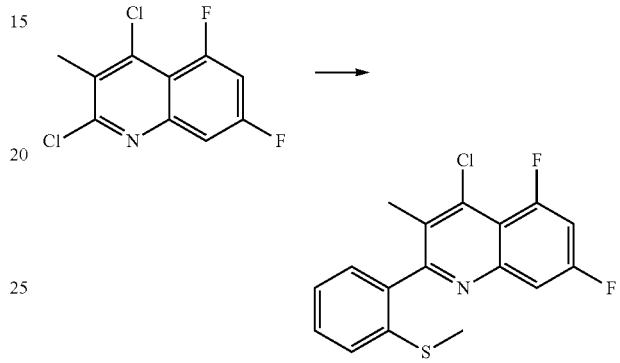

Prepared according to procedure F by stirring 2,4-dichloro-5,7-difluoro-3-methylquinoline (550 mg, 2.22 mmol), 2-(methylthio)phenylboronic acid (484 mg, 2.88 mmol), sodium carbonate (705 mg, 6.65 mmol), Pd(PPh$_3$)$_4$ (128 mg, 0.11 mmol), acetonitrile (5.2 mL), and water (1.3 mL) at 100° C. in a microwave reactor for 1 h. Purification by column chromatography (silica gel, 0-20% EtOAc in hexanes) gave 4-chloro-5,7-difluoro-3-methyl-2-(2-(methylthio)phenyl)quinoline as a white amorphous solid. Mass Spectrum (ESI) m/e=336.1 (M+1).

4-Chloro-5,7-difluoro-3-methyl-2-(2-(methylsulfonyl)phenyl)quinoline

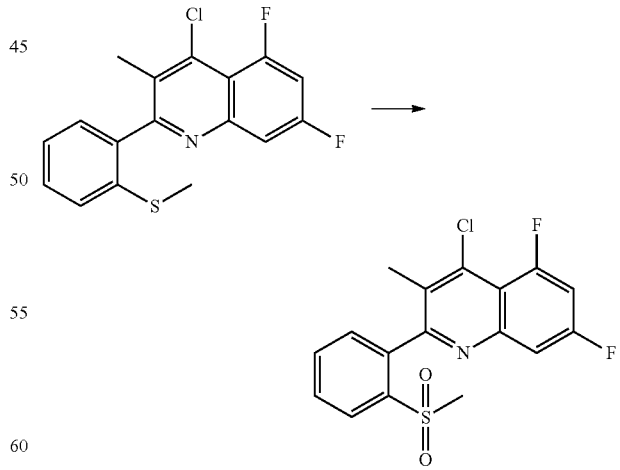

To a stirring solution of 4-chloro-5,7-difluoro-3-methyl-2-(2-(methylthio)phenyl)-quinoline (0.940 g, 2.80 mmol) in THF (20 mL) and water (6.7 mL) was added oxone (4.3 g, 7.00 mmol). The reaction was stirred at rt for 2 h, then 75 mL water was added and the mixture was stirred for 10 min. The resulting precipitate was isolated by filtration, then dissolved in EtOAc, dried over MgSO$_4$, and concentrated to give 4-chloro-5,7-difluoro-3-methyl-2-(2-(methylsulfonyl)phenyl)-quinoline. Mass Spectrum (ESI) m/e=368.0 (M+1).

Example 112

1-(5,7-Difluoro-3-methyl-4-(6-(4-morpholinyl)-2',3', 5',6'-tetrahydrospiro[indole-3,4'-pyran]-1(2H)-yl)-2-quinolinyl)-2(1H)-pyridinone 1'-(5,7-Difluoro-3-methyl-2-(2-(methylsulfonyl) phenyl)-4-quinolinyl)-6'-(4-morpholinyl)-1',2,2',3,5, 6-hexahydrospiro[pyran-4,3'-pyrrolo[3,2-b]pyridine]

1-(4-Bromo-5,7-difluoro-3-methylquinolin-2-yl) pyridin-2(1H)-one

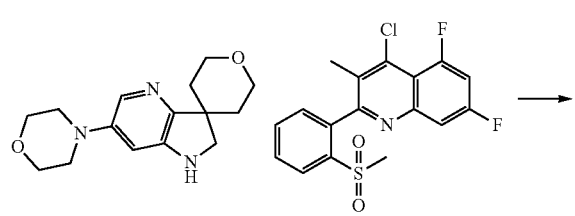

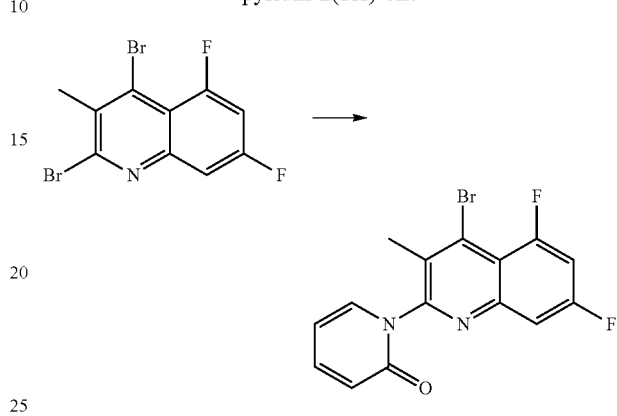

Reference: Leung, et. al.; Tetrahedron, 2005, pp. 2931. The procedure was followed as described in the above reference. The reaction mixture was refluxed for 16 h and purified by column chromatography (silica gel, 0 to 20% EtOAc:hexanes as eluent) to give 1-(4-bromo-5,7-difluoro-3-methylquinolin-2-yl)pyridin-2(1H)-one. Mass Spectrum (ESI) m/e=351.0 [(M+1) ($^{79}$Br)] and 353.0 [(M+1) ($^{81}$Br)]

1-(5,7-Difluoro-3-methyl-4-(6-(4-morpholinyl)-2',3', 5',6'-tetrahydrospiro-[indole-3,4'-pyran]-1(2H)-yl)-2-quinolinyl)-2(1H)-pyridinone

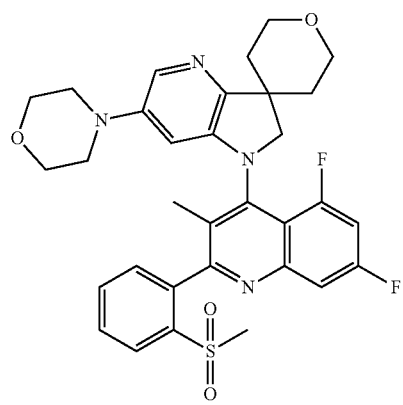

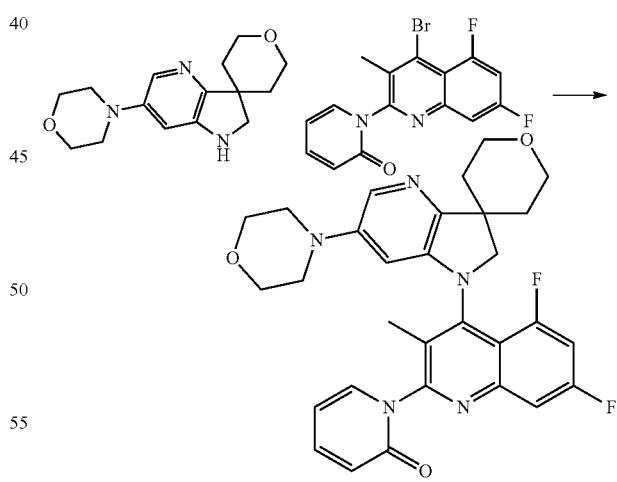

Prepared according to procedure Y by stirring 4-chloro-5, 7-difluoro-3-methyl-2-(2-(methylsulfonyl)phenyl)quinoline (50 mg, 0.14 mmol), 6'-morpholino-1',2,2',3,5,6-hexahydrospiro[pyran-4,3'-pyrrolo[3,2-b]pyridine] (44.9 mg, 0.16 mmol), XPhos precatalyst (20.1 mg, 0.027 mmol), sodium tert-butoxide (32.7 mg, 0.34 mmol), and toluene (1.5 mL) at 95° C. for 18 h. Purification by reverse-phase HPLC (0-70% acetonitrile in water) gave 1'-(5,7-difluoro-3-methyl-2-(2-(methylsulfonyl)phenyl)-4-quinolinyl)-6'-(4-morpholinyl)-1',2,2',3,5,6-hexahydrospiro-[pyran-4,3'-pyrrolo[3,2-b]pyridine]. 1H NMR (400 MHz, chloroform-d) δ ppm 7.62-7.76 (1H, m), 7.24-7.33 (1H, m), 7.13-7.23 (1H, m), 6.98-7.09 (2H, m), 6.87-6.98 (1H, m), 6.48-6.60 (1H, m), 5.42-5.51 (1H, m), 3.67-3.76 (1H, m), 3.50-3.67 (2H, m), 3.20-3.28 (4H, m), 2.94-3.14 (2H, m), 2.59-2.65 (1H, m), 2.48-2.59 (6H, m), 1.71-1.88 (2H, m), 1.50-1.55 (1H, m), 1.38-1.46 (2H, m), 1.23-1.38 (1H, m), 1.07-1.19 (1H, m), 0.70-0.75 (1H, m). Mass Spectrum (ESI) m/e=607.0 (M+1).

Prepared according to procedure Y using 1-(4-bromo-5,7-difluoro-3-methylquinolin-2-yl)pyridin-2(1H)-one (35.0 mg, 0.100 mmol) and 6'-morpholino-1',2,2',3,5,6-hexahydrospiro [pyran-4,3'-pyrrolo[3,2-b]pyridine] in toluene to give 1-(5,7-difluoro-3-methyl-4-(6-(4-morpholinyl)-2',3',5',6'-tetrahydrospiro[indole-3,4'-pyran]-1(2H)-yl)-2-quinolinyl)-2(1H)-pyridinone. 1H NMR (400 MHz, chloroform-d) δ ppm 8.41-8.47 (1H, m), 7.94-8.01 (1H, m), 7.74 (1H, d, J=2.3 Hz), 7.35

(1H, ddd, J=7.4, 5.0, 0.9 Hz), 7.27-7.32 (2H, m), 6.94 (1H, ddd, J=12.5, 8.6, 2.5 Hz), 6.03 (1H, d), 4.08-4.22 (3H, m), 4.01-4.06 (1H, m), 3.72-3.81 (4H, m), 3.37-3.57 (2H, m), 3.13 (4H, dd, J=6.2, 3.8 Hz), 2.52-2.69 (2H, m), 2.38 (3H, s), 1.72-1.93 (2H, m). Mass Spectrum (ESI) m/e=

Example 113

1'-(8-Chloro-2,3-dimethyl-4-quinolinyl)-6'-(4-morpholinyl)-1',2,2',3,5,6-hexahydrospiro[pyran-4,3'-pyrrolo[3,2-b]pyridine]

6'-Bromo-1'-(8-chloro-2,3-dimethylquinolin-4-yl)-1',2,2',3,5,6-hexahydrospiro[pyran-4,3'-pyrrolo[3,2-b]pyridine]

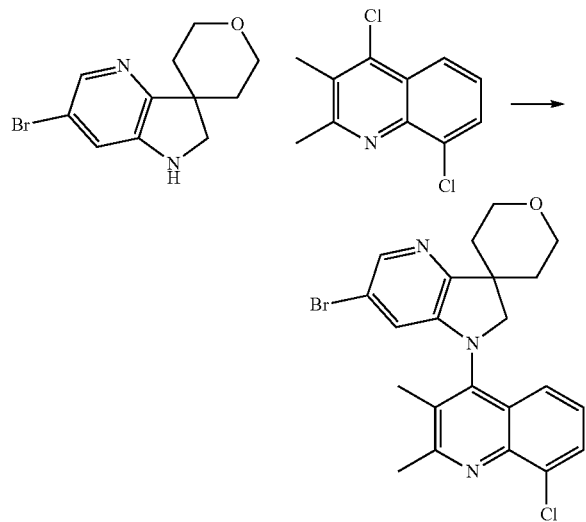

Prepared according to procedure M by using 6'-bromo-1',2,2',3,5,6-hexahydrospiro[pyran-4,3'-pyrrolo[3,2-b]pyridine] (150 mg, 0.56 mmol), 4,8-dichloro-2,3-dimethylquinoline (126 mg, 0.56 mmol) and NaH (48.6 mg, 1.11 mmol, 55% dispersion in oil) in DMF (2.5 mL) while heating the reaction at 60° C. for 14 h. Purification by reverse phase HPLC (10 to 60% acetonitrile in water) gave 6'-bromo-1'-(8-chloro-2,3-dimethylquinolin-4-yl)-1',2,2',3,5,6-hexahydrospiro-[pyran-4,3'-pyrrolo[3,2-b]pyridine]. Mass Spectrum (ESI) m/e=458.0 [(M+1) ($^{79}$Br)] and 460.0 [(M+1) ($^{81}$Br)].

1'-(8-Chloro-2,3-dimethyl-4-quinolinyl)-6'-(4-morpholinyl)-1',2,2',3,5,6-hexahydrospiro[pyran-4,3'-pyrrolo[3,2-b]pyridine]

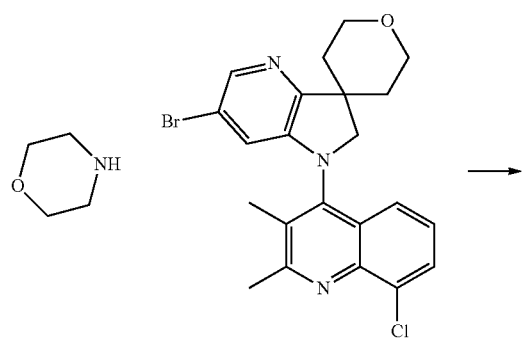

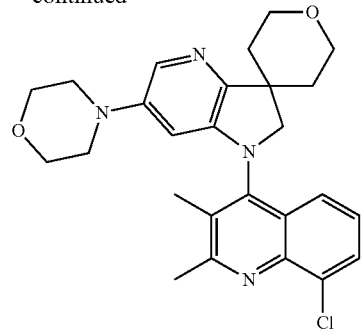

Prepared according to procedure N by stirring 6'-bromo-1'-(8-chloro-2,3-dimethylquinolin-4-yl)-1',2,2',3,5,6-hexahydrospiro[pyran-4,3'-pyrrolo[3,2-b]-pyridine] (25 mg, 0.054 mmol), morpholine (4.75 µL, 0.054 mmol), Pd$_2$dba$_3$ (5 mg, 5.4 µmol) and XPhos (5.2 mg, 10.9 µmol) in toluene (2.0 mL) at reflux for 14 h. Purification by reverse phase HPLC (10 to 60% acetonitrile in water) gave 1'-(8-chloro-2,3-dimethyl-4-quinolinyl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 7.78 (1H, dd, J=7.4, 1.4 Hz), 7.58-7.62 (2H, m), 7.32-7.36 (1H, m), 5.68 (1H, d, J=2.3 Hz), 4.11-4.20 (2H, m), 3.95-4.00 (1H, m), 3.85-3.91 (1H, m), 3.74 (4H, dd, J=5.3, 4.5 Hz), 3.52-3.62 (2H, m), 2.92-3.05 (4H, m), 2.84 (3H, s), 2.33-2.42 (2H, m), 2.31 (3H, s), 1.73-1.87 (2H, m). Mass Spectrum (ESI) m/e=465.2 (M+1).

Example 114

1-(5,7-Difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-pyrrolidinone

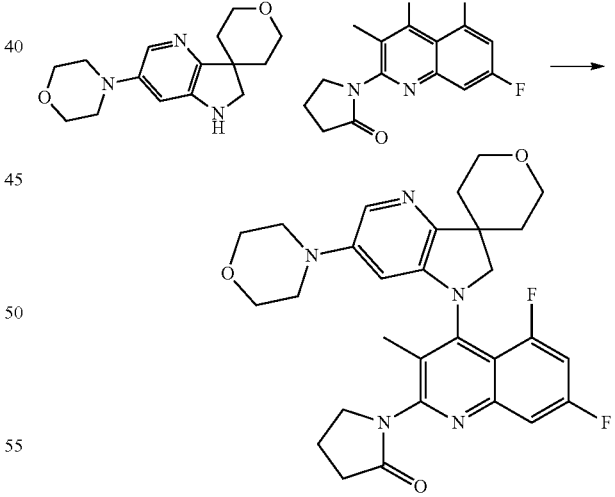

Prepared according to procedure Y using 1-(4-bromo-5,7-difluoro-3-methylquinolin-2-yl)pyrrolidin-2-one (60.0 mg, 0.180 mmol) and 6'-morpholino-1',2,2',3,5,6-hexahydrospiro[pyran-4,3'-pyrrolo[3,2-b]pyridine] in toluene to give 1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-pyrrolidinone. 1H NMR (400 MHz, chloroform-d) δ ppm 7.61 (1H, d, J=2.3 Hz), 7.49 (1H, ddd, J=9.4, 2.5, 1.4 Hz), 6.95 (1H, ddd, J=11.8, 8.9, 2.5 Hz), 5.86

(1H, d, J=2.2 Hz), 4.19-4.31 (1H, m), 4.02-4.19 (4H, m), 3.84 (1H, d, J=9.2 Hz), 3.70-3.78 (4H, m), 3.56 (2H, qd, J=11.5, 2.5 Hz), 2.94-3.12 (4H, m), 2.64 (2H, t, J=8.0 Hz), 2.24-2.40 (4H, m), 2.17 (3H, s), 1.82 (1H, d, J=13.5 Hz), 1.69 (1H, dd, J=13.9, 2.2 Hz). Mass Spectrum (ESI) m/e=536.2 (M+1).

Example 115

1-(7-Fluoro-3-methyl-4-(6'-(4-morpholinyl)-2,3,5,6-tetrahydrospiro[pyran-4,3'-pyrrolo[3,2-b]pyridin]-1' (2'H)-yl)-2-quinolinyl)-2-piperidinone 1-(4-Chloro-7-fluoro-3-methylquinolin-2-yl)piperidin-2-one

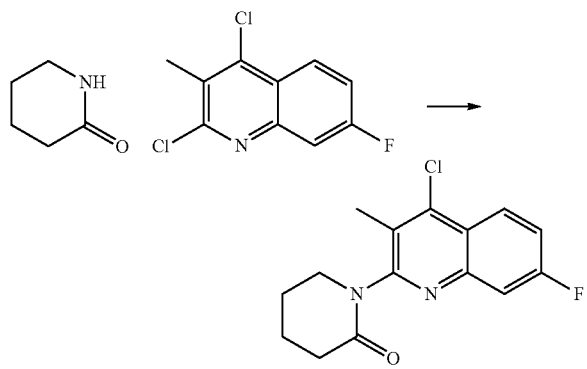

Freshly prepared powdered 3 Å molecular sieves were transferred to a round bottom flask and activated by heating under vacuum for 3 min. After this time the flask was allowed to cool to rt for 10 min. At this time, K₂CO₃ (601 mg, 4.35 mmol), 2-di-tert-butylphosphino-3,4,5,6-tetramethyl-2',4', 6'-tri-i-propylbiphenyl (209 mg, 0.435 mmol), Pd₂dba₃ (199 mg, 0.217 mmol), 2,4-dichloro-7-fluoro-3-methylquinoline (500 mg, 2.173 mmol), delta-valerolactam (215 mg, 2.173 mmol) and the previously activated molecular sieves were suspended in tBuOH (4 mL) and heated in the microwave for 1 h at 150° C. After this time the reaction was partitioned between EtOAc (70 mL) and water (40 mL). The separated aqueous layer was extracted with EtOAc (40 mL) and the combined organic extracts were washed with water (20 mL). The separated organic layer was dried over MgSO₄, filtered and evaporated in vacuo. Column chromatography (hexanes: EtOAc, 1:0 to 2:1) gave 1-(4-chloro-7-fluoro-3-methylquinolin-2-yl)piperidin-2-one. 1H NMR (400 MHz, chloroform-d) δ ppm 8.12-8.29 (1H, m), 7.63 (1H, dd, J=9.8, 2.5 Hz), 7.35-7.47 (1H, m), 4.07-4.22 (1H, m), 3.39-3.53 (1H, m), 2.54-2.70 (2H, m), 2.35-2.50 (3H, m), 1.90-2.15 (4H, m). Mass Spectrum (ESI) m/e=293.0 (M+1).

1-(7-Fluoro-3-methyl-4-(6'-(4-morpholinyl)-2,3,5,6-tetrahydrospiro[pyran-4,3'-pyrrolo[3,2-b]pyridin]-1' (2'H)-yl)-2-quinolinyl)-2-piperidinone

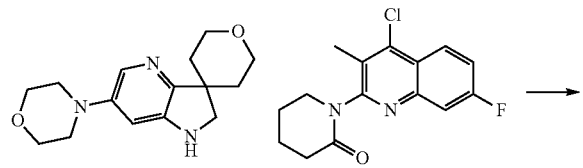

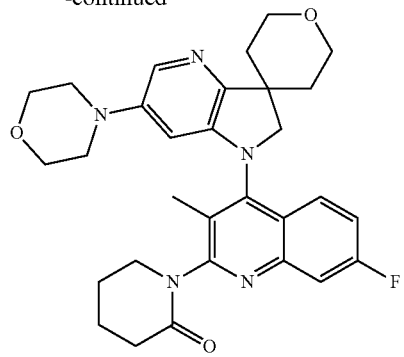

Prepared according to procedure Y by stirring 6'-morpholino-1',2,2',3,5,6-hexahydrospiro[pyran-4,3'-pyrrolo[3,2-b]pyridine] (56.4 mg, 0.20 mmol), 1-(4-chloro-7-fluoro-3-methylquinolin-2-yl)piperidin-2-one (60 mg, 0.20 mmol), sodium tert-butoxide (39.4 mg, 0.41 mmol) and XPhos precatalyst (15.1 mg, 0.020 mmol) in toluene (1.5 mL) at 130° C. for 1 h and 15 min in a microwave reactor. Purification by column chromatography (DCM: (DCM:MeOH:NH₄OH, 9:1:0.4) from 1:0 to 7:3) gave the desired product. Further purification by reverse phase HPLC (10 to 60% acetonitrile in water) gave 1-(7-fluoro-3-methyl-4-(6'-(4-morpholinyl)-2,3, 5,6-tetrahydrospiro[pyran-4,3'-pyrrolo[3,2-b]pyridin]-1' (2'H)-yl)-2-quinolinyl)-2-piperidinone. 1H NMR (500 MHz, chloroform-d) δ ppm 7.59-7.84 (3H, m), 7.20-7.33 (1H, m), 6.02-5.69 (1H, m), 4.10-4.34 (3H, m), 3.88-4.08 (1H, m), 3.71-3.82 (4H, m), 3.41-3.64 (4H, m), 2.91-3.15 (4H, m), 2.53-2.68 (2H, m), 2.28-2.41 (2H, m), 1.98-2.18 (7H, m), 1.78-1.87 (2H, m). Mass Spectrum (ESI) m/e=532.2 (M+1).

Example 116

1'-(2-(3,5-Dimethylphenyl)-7-fluoro-3-methyl-4-quinolinyl)-6'-(4-morpholinyl)-1',2,2',3,5,6-hexahydrospiro[pyran-4,3'-pyrrolo[3,2-b]-pyridine

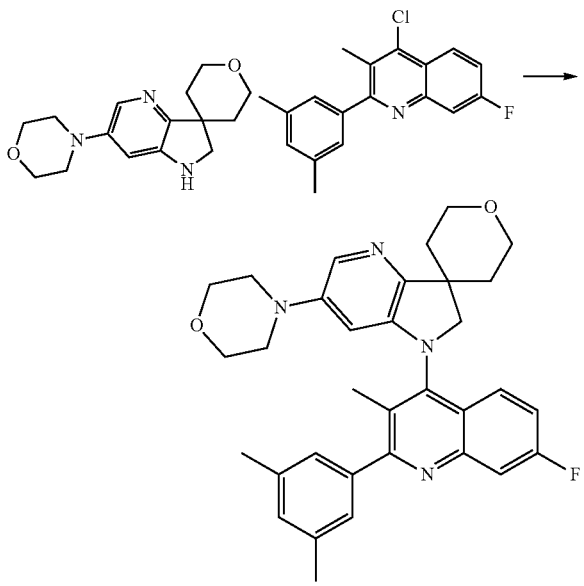

Prepared according to procedure Y by stirring 4-chloro-2-(3,5-dimethylphenyl)-7-fluoro-3-methylquinoline (100 mg, 0.33 mmol), 6'-morpholino-1',2,2',3,5,6-hexahydrospiro[pyran-4,3'-pyrrolo[3,2-b]pyridine] (92 mg, 0.33 mmol), sodium tert-butoxide (64.1 mg, 0.67 mmol) and XPhos precatalyst (24.65 mg, 0.033 mmol) in toluene (4 mL) at reflux for 2 h. Purification by reverse phase HPLC (10 to 60% acetonitrile in water) gave 1'-(2-(3,5-dimethylphenyl)-7-fluoro-3-methyl-4-quinolinyl)-6'-(4-morpholinyl)-1',2,2',3,5,6-hexahydrospiro[pyran-4,3'-pyrrolo[3,2-b]pyridine. 1H NMR (400 MHz, chloroform-d) δ ppm 7.85 (1H, dd, J=10.0, 2.5 Hz), 7.72 (1H, dd, J=9.2, 6.1 Hz), 7.63 (1H, d, J=2.3 Hz), 7.24-7.31 (1H, m), 7.18-7.22 (2H, m), 7.12 (1H, d, J=1.8 Hz), 5.80 (1H, d, J=2.5 Hz), 4.10-4.20 (2H, m), 3.99 (2H, s), 3.73-3.82 (4H, m), 3.55-3.64 (2H, m), 2.96-3.07 (4H, m), 2.32-2.48 (8H, m), 2.27 (3H, s), 1.67-1.92 (2H, m). Mass Spectrum (ESI) m/e=539.2 (M+1).

Example 117

4-(3,3-Dimethyl-6-(4-morpholinyl)-2,3-dihydro-1H-pyrrolo-[3,2-b]pyridin-1-yl)-5,7-difluoro-3-methyl-2-(5-methyl-2-(methylsulfonyl)-phenyl)quinoline (2-Bromo-4-methylphenyl)(methyl)sulfane

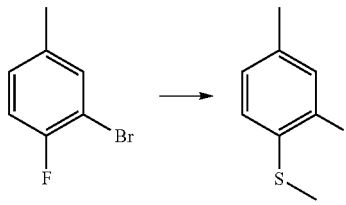

The 2-bromo-1-fluoro-4-methylbenzene (2.00 g, 11.0 mmol) was dissolved in dimethylacetamide (5.3 mL) followed by the addition of sodium thiomethoxide (0.82 g, 12.0 mmol). The reaction was heated at 125° C. for 5.5 h. The reaction was then cooled to rt and stirred overnight. The reaction was then diluted with water (200 mL) and the mixture was extracted with EtOAc (3×125 mL). The combined organic layers were washed with water (1×150 mL) and brine (1×100 mL) and dried over MgSO₄. The crude product was purified by column chromatography (silica gel, 0 to 40% EtOAc:hexanes) to give (2-bromo-4-methylphenyl)-(methyl) sulfane. 1H NMR (400 MHz, chloroform-d) δ ppm 7.38 (1H, d, J=0.8 Hz), 7.09-7.13 (1H, m), 7.06 (1H, d), 2.47 (3H, s), 2.31 (3H, s).

5-Methyl-2-(methylthio)phenylboronic acid

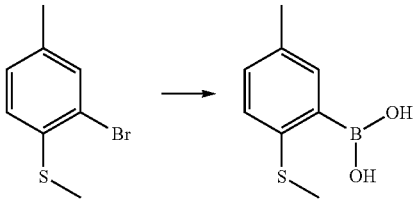

(2-Bromo-4-methylphenyl)(methyl)sulfane (700 mg, 3.20 mmol) was dissolved in THF (5.0 mL) and cooled to −78° C. To the cooled solution was added n-butyl lithium (2.2 mL, 3.60 mmol) dropwise. The reaction was stirred for 2 min at −78° C. then the triisopropyl borate (0.82 mL, 3.56 mmol) was added dropwise and the reaction mixture was allowed to warm to 0° C. over a period of approximately 90 min. The reaction was quenched by addition of 1N HCl solution and was stirred for 5 min. The mixture was then extracted with EtOAc (2×50 mL). The combined organic layers were washed with water (1×30 mL), brine (1×30 mL) and dried over MgSO₄. The crude product was then triturated with EtOAc and hexanes to give 5-methyl-2-(methylthio)phenylboronic acid. The mother liquor was purified by column chromatography (silica gel, 0 to 30% EtOAc:hexanes) to give more desired product. Mass Spectrum (ESI) m/e=183.1 (M+1).

4-Chloro-5,7-difluoro-3-methyl-2-(5-methyl-2-(methylthio)phenyl)quinoline

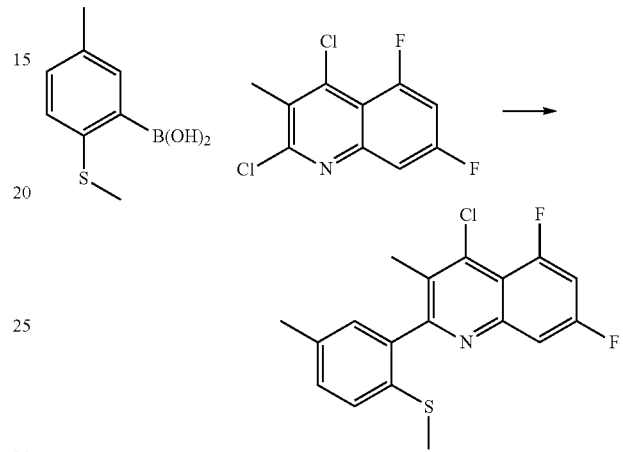

Prepared according to procedure F using 2,4-dichloro-5,7-difluoro-3-methylquinoline (130 mg, 0.51 mmol) and 5-methyl-2-(methylthio)phenylboronic acid to give 4-chloro-5,7-difluoro-3-methyl-2-(5-methyl-2-(methylthio)phenyl) quinoline. Mass Spectrum (ESI) m/e=350.0 (M+1).

4-Chloro-5,7-difluoro-3-methyl-2-(5-methyl-2-(methylsulfonyl)phenyl)-quinoline

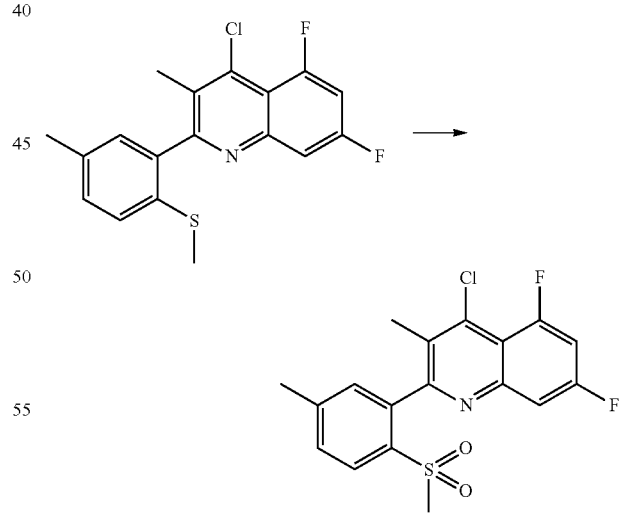

4-Chloro-5,7-difluoro-3-methyl-2-(5-methyl-2-(methylthio)phenyl)quinoline (160 mg, 0.46 mmol) was slurried in a mixture of THF (3.4 mL) and water (1.1 mL). Oxone™ (700 mg, 1.1 mmol) was added and the mixture was stirred vigorously overnight. The reaction mixture was then poured into water (25 mL) and stirred for 10 min. The mixture was then filtered and washed with water. The precipitate was dissolved in EtOAc (50 mL) and dried over MgSO$_4$. The filtrate was concentrated to give 4-chloro-5,7-difluoro-3-methyl-2-(5-methyl-2-(methylsulfonyl)phenyl)-quinoline. Mass Spectrum (ESI) m/e=382.0 (M+1).

4-(3,3-Dimethyl-6-(4-morpholinyl)-2,3-dihydro-1H-pyrrolo[3,2-b]pyridin-1-yl)-5,7-difluoro-3-methyl-2-(5-methyl-2-(methylsulfonyl)phenyl)quinoline

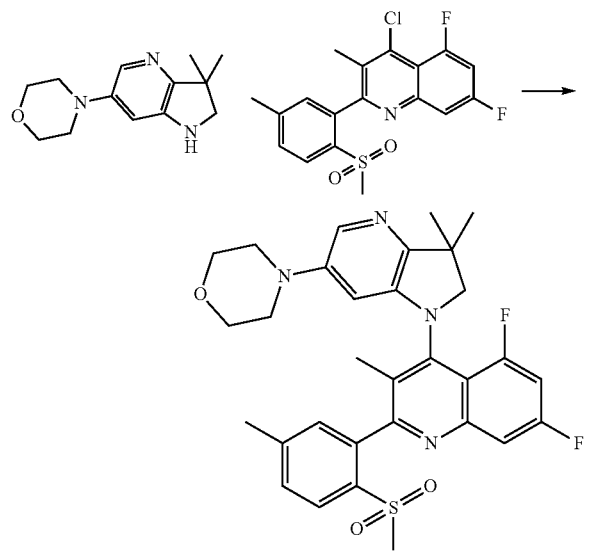

Prepared according to procedure Y using 4-chloro-5,7-difluoro-3-methyl-2-(5-methyl-2-(methylsulfonyl)phenyl)quinoline (60.0 mg, 0.160 mmol) and 4-(3,3-dimethyl-2,3-dihydro-1H-pyrrolo[3,2-b]pyridin-6-yl)morpholine in toluene to give 4-(3,3-dimethyl-6-(4-morpholinyl)-2,3-dihydro-1H-pyrrolo[3,2-b]pyridin-1-yl)-5,7-difluoro-3-methyl-2-(5-methyl-2-(methylsulfonyl)phenyl)quinoline. 1H NMR (400 MHz, chloroform-d) δ ppm 7.99-8.17 (1H, m), 7.43-7.64 (3H, m), 7.22-7.31 (1H, m), 7.07 (1H, ddd, J=11.9, 8.9, 2.4 Hz), 6.00 (1H, d, J=2.2 Hz), 4.03 (1H, d, J=9.0 Hz), 3.66-3.87 (4H, m), 3.61 (1H, d, J=8.8 Hz), 2.97-3.16 (7H, m), 2.52 (3H, s), 1.96 (3H, s), 1.42-1.60 (6H, m). Mass Spectrum (ESI) m/e=579.2 (M+1).

Example 118

1'-(7-Fluoro-3-methyl-2-(4-methyl-2-pyridinyl)-4-quinolinyl)-6'-(4-morpholinyl)-1',2,2',3,5,6-hexahydrospiro[pyran-4,3'-pyrrolo[3,2-b]pyridine]

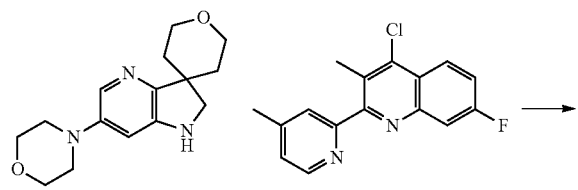

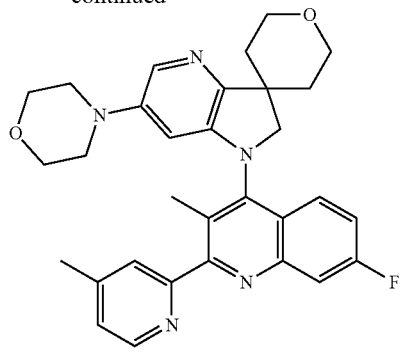

Prepared according to procedure Y by stirring 4-chloro-7-fluoro-3-methyl-2-(4-methylpyridin-2-yl)quinoline (50 mg, 0.17 mmol), 6'-morpholino-1',2,2',3,5,6-hexahydrospiro[pyran-4,3'-pyrrolo[3,2-b]pyridine] (48.0 mg, 0.17 mmol), sodium tert-butoxide (33.5 mg, 0.35 mmol), XPhos precatalyst (26 mg, 0.035 mmol), and toluene (1.7 mL) at 90° C. for 18 h. Purification by reverse-phase HPLC (0-70% acetonitrile in water) gave 1'-(7-fluoro-3-methyl-2-(4-methyl-2-pyridinyl)-4-quinolinyl)-6'-(4-morpholinyl)-1',2,2',3,5,6-hexahydrospiro[pyran-4,3'-pyrrolo-[3,2-b]pyridine] as a yellow film. 1H NMR (400 MHz, chloroform-d) δ ppm 8.60 (1H, d, J=5.1 Hz), 7.87 (1H, dd, J=9.8, 2.5 Hz), 7.69-7.75 (2H, m), 7.59-7.61 (1H, m), 7.29-7.36 (1H, m), 7.23-7.27 (1H, m), 5.89 (1H, s), 4.14-4.21 (2H, m), 4.02 (2H, s), 3.70-3.81 (4H, m), 3.50-3.62 (2H, m), 2.95-3.09 (4H, m), 2.51 (4H, s), 2.45 (1H, s), 2.38 (3H, s), 1.81-1.90 (1H, m), 1.70-1.81 (1H, m). Mass Spectrum (ESI) m/e=526.2 (M+1).

Example 119

1'-(5,7-Difluoro-2-(2-methoxy-4-pyridinyl)-3-methyl-4-quinolinyl)-6'-(4-morpholinyl)-1',2,2',3,5,6-hexahydrospiro[pyran-4,3'-pyrrolo[3,2-b]pyridine]

4-Chloro-5,7-difluoro-2-(2-methoxypyridin-4-yl)-3-methylquinoline

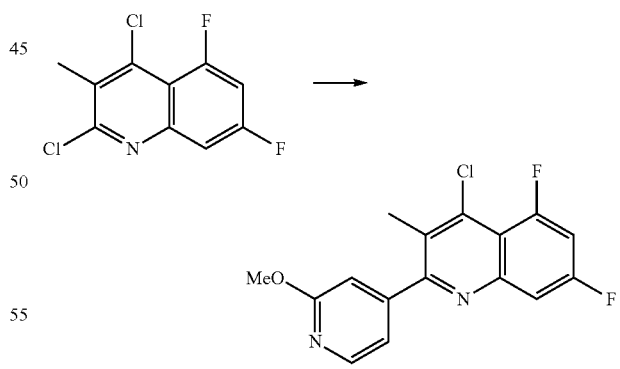

Prepared according to procedure F by stirring 2,4-dichloro-5,7-difluoro-3-methylquinoline (0.5 g, 2.02 mmol), 2-methoxypyridin-4-ylboronic acid (0.31 g, 2.02 mmol), potassium carbonate (0.56 g, 4.03 mmol), Pd(PPh$_3$)$_4$ (0.23 g, 0.20 mmol), and toluene (4 mL) at 100° C. for 18 h. Purification by column chromatography (silica gel, 0-30% EtOAc in hexanes) gave 4-chloro-5,7-difluoro-2-(2-methoxypyridin-4-yl)-3-methylquinoline as an off-white solid. Mass Spectrum (ESI) m/e=321.1 (M+1).

1'-(5,7-Difluoro-2-(2-methoxy-4-pyridinyl)-3-methyl-4-quinolinyl)-6'-(4-morpholinyl)-1',2,2',3,5,6-hexahydrospiro[pyran-4,3'-pyrrolo[3,2-b]pyridine]

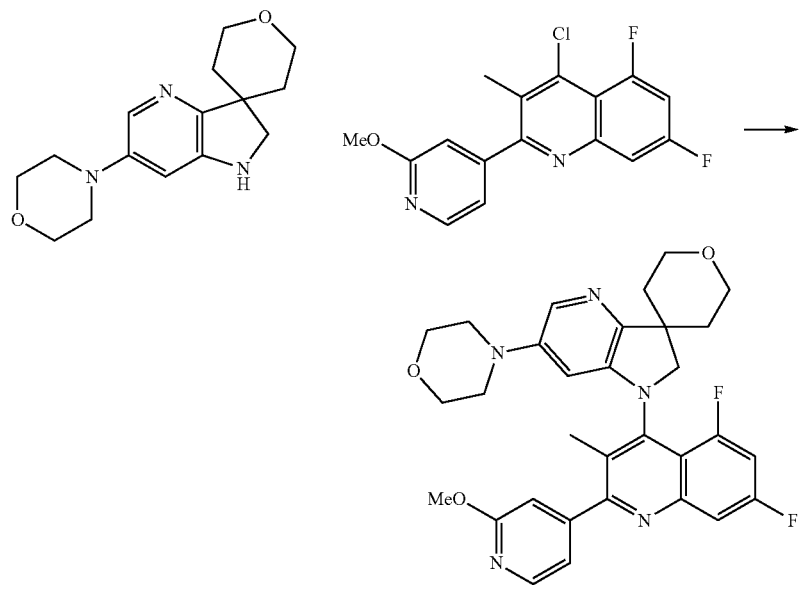

Prepared according to procedure Y by stirring 4-chloro-5,7-difluoro-2-(2-methoxypyridin-4-yl)-3-methylquinoline (50 mg, 0.16 mmol), 6'-morpholino-1',2,2',3,5,6-hexahydrospiro[pyran-4,3'-pyrrolo[3,2-b]pyridine] (42.9 mg, 0.16 mmol), sodium tert-butoxide (33.0 mg, 0.34 mmol), XPhos precatalyst (23.0 mg, 0.031 mmol), and toluene (1.7 mL) at 85° C. for 6 h. Purification by reverse-phase HPLC (0-70% acetonitrile in water) gave 1'-(5,7-difluoro-2-(2-methoxy-4-pyridinyl)-3-methyl-4-quinolinyl)-6'-(4-morpholinyl)-1',2,2',3,5,6-hexahydro-[pyran-4,3'-pyrrolo[3,2-b]pyridine] as a yellow solid. 1H NMR (400 MHz, chloroform-d) δ ppm 8.32-8.36 (1H, m), 7.66-7.71 (1H, m), 7.60 (1H, d, J=2.3 Hz), 7.09 (1H, dd, J=5.2, 1.5 Hz), 6.99-7.07 (1H, m), 6.95-6.97 (1H, m), 5.73-5.76 (1H, m), 4.14-4.20 (2H, m), 4.03 (3H, s), 3.96-4.01 (1H, m), 3.89-3.94 (1H, m), 3.74-3.81 (4H, m), 3.52-3.62 (2H, m), 2.98-3.07 (4H, m), 2.31-2.46 (2H, m), 2.27-2.30 (3H, m), 1.78-1.86 (1H, m), 1.67-1.75 (1H, m). Mass Spectrum (ESI) m/e=560.0 (M+1).

Example 120

1'-(2-(2,2-Dimethyl-4-morpholinyl)-5,7-difluoro-3-methyl-4-quinolinyl)-6'-(4-morpholinyl)-1',2,2',3,5,6-hexahydrospiro[pyran-4,3'-pyrrolo[3,2-b]pyridine]

4-(4-Chloro-5,7-difluoro-3-methylquinolin-2-yl)-2,2-dimethylmorpholine

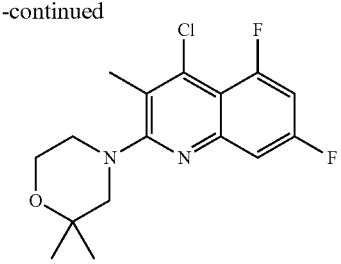

2,4-dichloro-5,7-difluoro-3-methylquinoline (1.0 g, 4.03 mmol) and 2,2-dimethylmorpholine (0.46 mL, 4.03 mmol) were slurried in 2-propanol (10 mL) and heated in a microwave reactor at 120° C. for 5 h. The reaction was then concentrated to dryness and purified by column chromatography (hexanes:EtOAc, 1:0 to 1:1) to give 4-(4-chloro-5,7-difluoro-3-methylquinolin-2-yl)-2,2-dimethylmorpholine. 1H NMR (400 MHz, chloroform-d) δ ppm 7.31 (1H, ddd, J=9.7, 2.7, 1.5 Hz), 6.89 (1H, ddd, J=12.3, 8.9, 2.5 Hz), 3.93-3.98 (2H, m), 3.23-3.28 (2H, m), 3.10 (2H, s), 2.47 (3H, s), 1.37 (6H, s). Mass Spectrum (ESI) m/e=327.2 (M+1).

1'-(2-(2,2-Dimethyl-4-morpholinyl)-5,7-difluoro-3-methyl-4-quinolinyl)-6'-(4-morpholinyl)-1',2,2',3,5,6-hexahydrospiro[pyran-4,3'-pyrrolo[3,2-b]pyridine

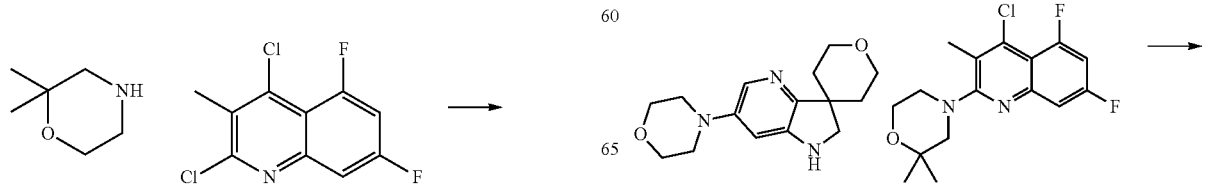

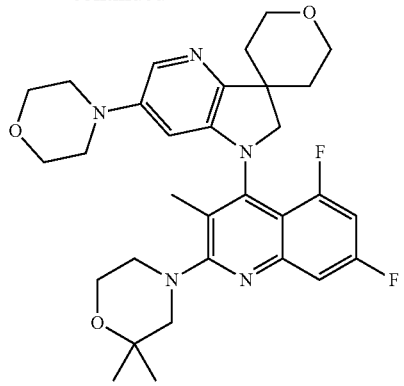

Prepared according to procedure Y by using 4-(4-chloro-5,7-difluoro-3-methylquinolin-2-yl)-2,2-dimethylmorpholine (47.5 mg, 0.14 mmol), 6'-morpholino-1',2,2',3,5,6-hexahydrospiro[pyran-4,3'-pyrrolo[3,2-b]pyridine] (40 mg, 0.14 mmol), sodium tert-butoxide and XPhos precatalyst (10.7 mg, 0.01 mmol) in toluene (4 mL) for 2 h at reflux. Purification by reverse phase HPLC (10 to 60% acetonitrile in water) gave 1'-(2-(2,2-dimethyl-4-morpholinyl)-5,7-difluoro-3-methyl-4-quinolinyl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 7.57 (1H, d, J=2.5 Hz), 7.35-7.40 (1H, m), 6.75 (1H, ddd, J=11.8, 8.9, 2.5 Hz), 5.67 (1H, d, J=2.3 Hz), 4.09-4.18 (2H, m), 3.94-4.00 (2H, m), 3.82-3.94 (2H, m), 3.72-3.80 (4H, m), 3.51-3.63 (2H, m), 3.27-3.38 (2H, m), 3.11-3.25 (2H, m), 2.95-3.02 (4H, m), 2.23-2.38 (5H, m), 1.55-1.78 (2H, m), 1.40 (3H, s), 1.37 (3H, s). Mass Spectrum (ESI) m/e=566.2 (M+1).

Example 121

2-(2,2-Dimethyl-4-morpholinyl)-4-(3,3-dimethyl-6-(4-morpholinyl)-2,3-dihydro-1H-pyrrolo[3,2-b]pyridin-1-yl)-5,7-difluoro-3-methylquinoline

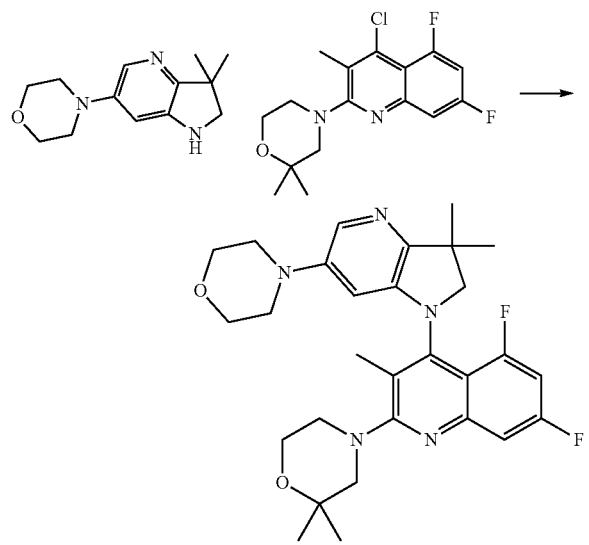

Preparing according to procedure Y by using 4-(4-chloro-5,7-difluoro-3-methylquinolin-2-yl)-2,2-dimethylmorpholine (70.0 mg, 0.21 mmol), 4-(3,3-dimethyl-2,3-dihydro-1H-pyrrolo[3,2-b]pyridin-6-yl)morpholine (50 mg, 0.21 mmol), sodium tert-butoxide (20.60 mg, 0.21 mmol) and XPhos precatalyst (16 mg, 0.02 mmol) in toluene (4 mL) at reflux for 2 h. Purification by reverse phase HPLC (10 to 60% acetonitrile in water) gave 2-(2,2-dimethyl-4-morpholinyl)-4-(3,3-dimethyl-6-(4-morpholinyl)-2,3-dihydro-1H-pyrrolo[3,2-b]pyridin-1-yl)-5,7-difluoro-3-methylquinoline. 1H NMR (400 MHz, chloroform-d) δ ppm 7.56 (1H, d, J=2.3 Hz), 7.34-7.40 (1H, m), 6.69-6.82 (1H, m), 5.67 (1H, d, J=2.3 Hz), 3.90-4.02 (2H, m), 3.77-3.81 (1H, m), 3.71-3.76 (4H, m), 3.66 (1H, d, J=9.0 Hz), 3.27-3.37 (2H, m), 3.10-3.23 (2H, m), 2.92-3.01 (4H, m), 2.28 (3H, s), 1.53 (3H, d, J=0.8 Hz), 1.49 (3H, s), 1.40 (3H, s), 1.35 (3H, s). Mass Spectrum (ESI) m/e=524.2 (M+1).

Example 122

1'-(5,7-Difluoro-3-methyl-2-(5-methyl-2-(methylsulfonyl)-phenyl)-4-quinolinyl)-6'-(4-morpholinyl)-1',2,2',3,5,6-hexahydrospiro[pyran-4,3'-pyrrolo[3,2-b]pyridine]

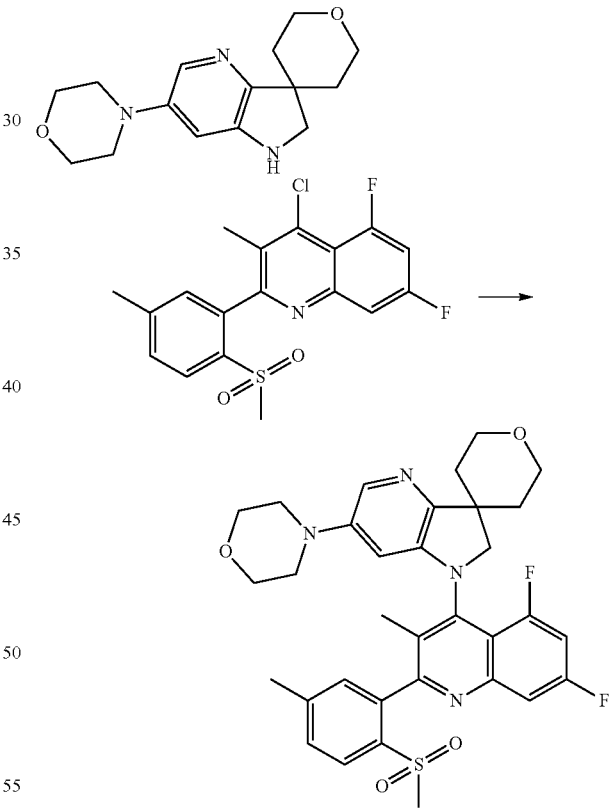

Prepared according to procedure Y using 4-chloro-5,7-difluoro-3-methyl-2-(5-methyl-2-(methylsulfonyl)phenyl)quinoline (80.0 mg, 0.210 mmol) and 6'-morpholino-1',2,2',3,5,6-hexahydrospiro[pyran-4,3'-pyrrolo[3,2-b]pyridine] in toluene to give 1'-(5,7-difluoro-3-methyl-2-(5-methyl-2-(methylsulfonyl)phenyl)-4-quinolinyl)-6'-(4-morpholinyl)-1',2,2',3,5,6-hexahydrospiro[pyran-4,3'-pyrrolo[3,2-b]pyridine]. TFA Salt: 1H NMR (400 MHz, chloroform-d) δ ppm 8.06 (1H, d, J=8.2 Hz), 7.64 (1H, ddd, J=9.0, 2.4, 1.3 Hz), 7.61 (1H, d, J=2.2 Hz), 7.54 (1H, dd, J=8.1, 1.1 Hz), 7.32 (1H, d, J=0.8 Hz), 7.18 (1H, ddd, J=12.3, 8.6, 2.5 Hz), 6.28 (1H, d, J=2.2 Hz), 4.43 (1H, d, J=9.6 Hz), 4.04-4.22 (2H, m), 3.92 (1H, d, J=9.6 Hz), 3.69-3.77 (4H, m), 3.56 (1H, td, J=12.4, 1.8 Hz), 3.42 (1H, td, J=12.3, 1.7 Hz), 3.13-3.22 (4H, m), 2.95 (3H, s), 2.57-2.69 (1H, m), 2.55 (3H, s), 2.41-2.54 (1H, m), 1.97 (3H, s), 1.72 (1H, d, J=13.3 Hz), 1.29-1.36 (1H, m). Mass Spectrum (ESI) m/e=621.3 (M+1).

Example 123

1-(7-Fluoro-3-methyl-2-(2-pyridinyl)-4-quinolinyl)-7-(4-morpholinyl)-2,3-dihydro-1H-pyrido[2,3-b][1,4]thiazine 4,4-dioxide tert-Butyl 7-chloro-2,3-dihydro-1H-pyrido[2,3-b][1,4]thiazine-1-carboxylate

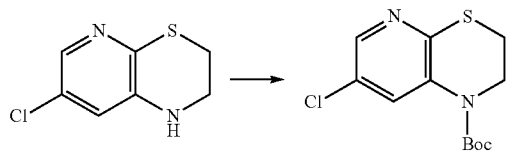 [SMILES: Clc1cnc2c(c1)NCCS2 ; CC(C)(C)OC(=O)N1CCSc2ncc(Cl)cc21]

To a stirred solution of 7-chloro-2,3-dihydro-1H-pyrido[2,3-b][1,4]thiazine (378 mg, 2.02 mmol) in THF (5 mL) was added Et₃N (0.42 mL, 3.04 mmol), di-tert-butyl dicarbonate (530 mg, 2.430 mmol) N,N-dimethylpyridin-4-amine (49.5 mg, 0.405 mmol) and stirred at rt overnight. After this time more Et₃N (1 eq), di-tert-butyl dicarbonate (0.5 eq) and N,N-dimethylpyridin-4-amine (0.1 eq) was added and the reaction stirred at rt for 24 h. After this time the reaction was partitioned between EtOAc (100 mL) and water (50 mL). The separated organic layer was dried over MgSO₄, filtered and evaporated in vacuo. Column chromatography (Hexanes:EtOAc, 1:0 to 1:1) gave tert-butyl 7-chloro-2,3-dihydro-1H-pyrido-[2,3-b][1,4]thiazine-1-carboxylate. 1H NMR (400 MHz, chloroform-d) δ ppm 8.07-8.18 (1H, m), 7.75 (1H, br. s.), 3.84-3.97 (2H, m), 3.13-3.27 (2H, m), 1.48-1.53 (9H, s). Mass Spectrum (ESI) m/e=287.0 (M+1).

tert-Butyl 7-morpholino-2,3-dihydro-1H-pyrido[2,3-b][1,4]thiazine-1-carboxylate

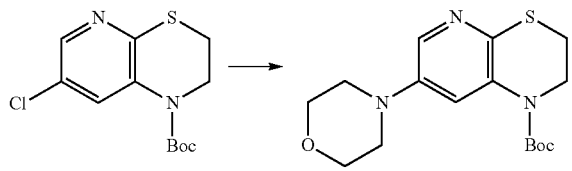 [SMILES: CC(C)(C)OC(=O)N1CCSc2ncc(Cl)cc21 ; CC(C)(C)OC(=O)N1CCSc2ncc(N3CCOCC3)cc21]

Prepared according to procedure N by using tert-butyl 7-chloro-2,3-dihydro-1H-pyrido[2,3-b][1,4]thiazine-1-carboxylate (340 mg, 1.19 mmol), Pd₂dba₃ (109 mg, 0.119 mmol), XPhos (113 mg, 0.237 mmol), sodium ter-butoxide (228 mg, 2.371 mmol), morpholine (0.13 mL, 1.54 mmol) in toluene (8 mL) at 100° C. for 14 h. Purification by column chromatography (hexanes:EtOAc, 1:0 to 1:1) gave tert-butyl 7-morpholino-2,3-dihydro-1H-pyrido[2,3-b][1,4]thiazine-1-carboxylate. Mass Spectrum (ESI) m/e=338.2 (M+1).

4-(2,3-Dihydro-1H-pyrido[2,3-b][1,4]thiazin-7-yl)morpholine

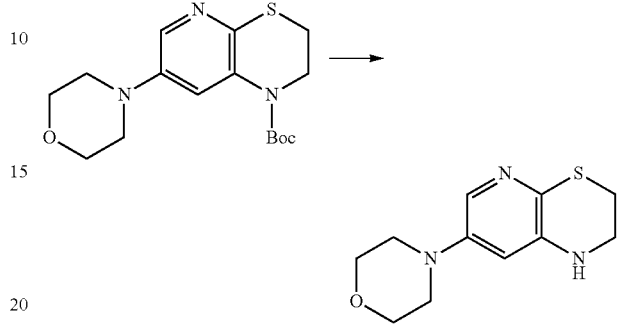

To a stirred solution of tert-butyl 7-morpholino-2,3-dihydro-1H-pyrido[2,3-b]-[1,4]thiazine-1-carboxylate (280 mg, 0.83 mmol) in DCM (2.0 mL) was added TFA (3.2 mL, 41.5 mmol). The reaction was stirred at rt for 2 h and evaporated in vacuo. The resulting residue was dissolved in DCM (40 mL) and washed with NaHCO₃ (20 mL, saturated aqueous solution). The separated organic layer was dried over MgSO₄, filtered and evaporated in vacuo to give 4-(2,3-dihydro-1H-pyrido[2,3-b][1,4]thiazin-7-yl)morpholine as a white solid. 1H NMR (400 MHz, chloroform-d) δ ppm 7.62 (1H, d, J=2.5 Hz), 6.26 (1H, d, J=2.5 Hz), 3.82-3.87 (4H, m), 3.59-3.63 (2H, m), 3.13-3.17 (2H, m), 3.06-3.10 (4H, m). Mass Spectrum (ESI) m/e=238.2 (M+1).

4-(1-(7-Fluoro-3-methyl-2-(pyridin-2-yl)quinolin-4-yl)-2,3-dihydro-1H-pyrido[2,3-b][1,4]thiazin-7-yl)morpholine

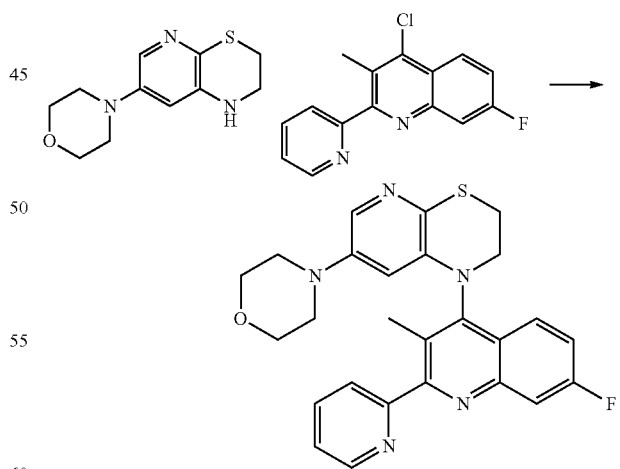

Prepared according to procedure Y by using 4-(2,3-dihydro-1H-pyrido[2,3-b]-[1,4]thiazin-7-yl)morpholine (43.5 mg, 0.18 mmol), 4-chloro-7-fluoro-3-methyl-2-(pyridin-2-yl)quinoline (50 mg, 0.183 mmol), XPhos precatalyst (13.5 mg, 0.018 mmol) and sodium tert-butoxide (35.2 mg, 0.37 mmol) with heating in toluene (5 mL) for 1 h at 110° C.

Purification by column chromatography (gradient of DCM to (DCM:MeOH:NH₄OH, 90:9:1) from 1:0 to 9:1) gave 4-(1-(7-fluoro-3-methyl-2-(pyridin-2-yl)quinolin-4-yl)-2,3-dihydro-1H-pyrido[2,3-b][1,4]thiazin-7-yl)morpholine. Mass Spectrum (ESI) m/e=474.0 (M+1).

1-(7-Fluoro-3-methyl-2-(2-pyridinyl)-4-quinolinyl)-7-(4-morpholinyl)-2,3-dihydro-1H-pyrido[2,3-b][1,4]thiazine 4,4-dioxide

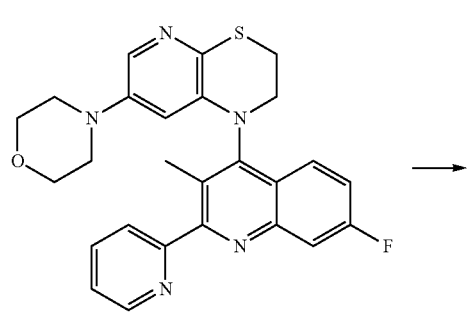

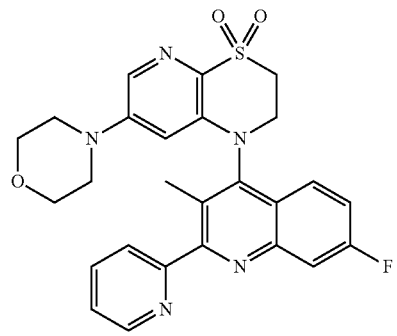

To a stirred solution of 4-(1-(7-fluoro-3-methyl-2-(pyridin-2-yl)quinolin-4-yl)-2,3-dihydro-1H-pyrido[2,3-b][1,4]thiazin-7-yl)morpholine (40 mg, 0.084 mmol) in EtOAc (2.5 mL) was added disodium tungstate (24.8 mg, 0.084 mol) and water (0.3 mL). The reaction was cooled at 0° C. and then H₂O₂ (25.9 µL, 0.84 mmol, 30%) was added. The reaction was allowed to warm to rt for 1 h. After this time more disodium tungstate (7 mg) was added followed by H₂O₂ (0.4 mL, 30%) and the reaction was stirred at rt overnight. After this time the reaction was diluted with EtOAc (50 mL) and treated with a saturated aqueous solution of NaHSO₃ (15 mL). The separated organic layer was washed with brine (15 mL), dried over MgSO₄, filtered and evaporated in vacuo to give 1-(7-fluoro-3-methyl-2-(2-pyridinyl)-4-quinolinyl)-7-(4-morpholinyl)-2,3-dihydro-1H-pyrido[2,3-b][1,4]thiazine 4,4-dioxide. 1H NMR (400 MHz, chloroform-d) δ ppm 8.64-8.81 (1H, m), 7.87-7.95 (4H, m), 7.74 (1H, dd, J=9.1, 5.8 Hz), 7.36-7.45 (2H, m), 5.59 (1H, s), 4.21-4.26 (2H, m), 3.63-3.72 (6H, m), 2.88-3.01 (4H, m), 2.46 (3H, s). Mass Spectrum (ESI) m/e=506.0 (M+1).

Example 124

1-(7-Fluoro-3-methyl-2-(4-methyl-2-pyridinyl)-4-quinolinyl)-7-(4-morpholinyl)-2,3-dihydro-1H-pyrido[2,3-b][1,4]thiazine 4,4-dioxide 4-(1-(7-Fluoro-3-methyl-2-(4-methylpyridin-2-yl)quinolin-4-yl)-2,3-dihydro-1H-pyrido[2,3-b][1,4]thiazin-7-yl)morpholine

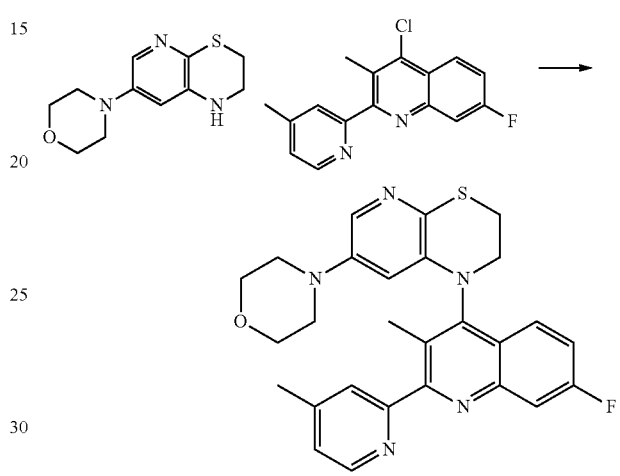

Prepared according to procedure Y by using 4-chloro-7-fluoro-3-methyl-2-(4-methylpyridin-2-yl)quinoline (54 mg, 0.19 mmol), 4-(2,3-dihydro-1H-pyrido[2,3-b][1,4]thiazin-7-yl)morpholine (45 mg, 0.19 mmol), sodium tert-butoxide (36 mg, 0.38 mmol), XPhos precatalyst (14 mg, 0.019 mmol) in toluene (4 mL) for 1 h at 110° C. Purification by column chromatography (gradient of DCM to (DCM:MeOH:NH₄OH, 90:9:1) from 1:0 to 8:2) gave 4-(1-(7-fluoro-3-methyl-2-(4-methylpyridin-2-yl)quinolin-4-yl)-2,3-dihydro-1H-pyrido[2,3-b][1,4]thiazin-7-yl)morpholine. Mass Spectrum (ESI) m/e=488.0 (M+1).

1-(7-Fluoro-3-methyl-2-(4-methyl-2-pyridinyl)-4-quinolinyl)-7-(4-morpholinyl)-2,3-dihydro-1H-pyrido[2,3-b][1,4]thiazine 4,4-dioxide

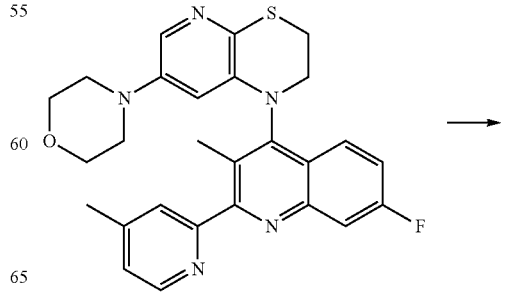

-continued

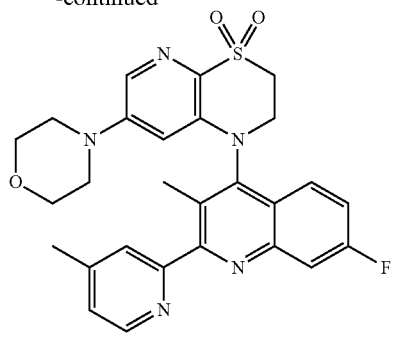

To a stirred solution of 4-(1-(7-fluoro-3-methyl-2-(4-methylpyridin-2-yl)quinolin-4-yl)-2,3-dihydro-1H-pyrido[2,3-b][1,4]thiazin-7-yl)morpholine (45 mg, 0.09 mmol) in EtOAc (2.5 mL) was added disodium tungstate (30.4 mg, 0.092 mol) and water (0.5 mL). The reaction was cooled at 0° C. and then $H_2O_2$ (56.6 μL, 1.85 mmol, 30%) was added. The reaction was allowed to warm to rt for 1 h. After this time more disodium tungstate (10 mg) was added followed by $H_2O_2$ (0.5 mL, 30%) and the reaction was stirred at rt overnight. After this time the reaction was diluted with EtOAc (50 mL) and treated with a saturated aqueous solution of $NaHSO_3$ (15 mL). The separated organic layer was washed with brine (15 mL), dried over $MgSO_4$, filtered and evaporated in vacuo to give 1-(7-fluoro-3-methyl-2-(4-methyl-2-pyridinyl)-4-quinolinyl)-7-(4-morpholinyl)-2,3-dihydro-1H-pyrido[2,3-b][1,4]thiazine 4,4-dioxide. 1H NMR (400 MHz, chloroform-d) δ ppm 8.59 (1H, d, J=4.7 Hz), 7.86-7.91 (2H, m), 7.70-7.77 (2H, m), 7.38 (1H, ddd, J=9.2, 8.0, 2.5 Hz), 7.25 (1H, dd, J=5.0, 0.9 Hz), 5.58 (1H, d, J=2.5 Hz), 4.18-4.27 (2H, m), 3.59-3.75 (6H, m), 2.84-3.02 (4H, m), 2.51 (3H, s), 2.44 (3H, s). Mass Spectrum (ESI) m/e=520.0 (M+1).

Example 125

1'-(3-Methyl-2-(2-pyridinyl)-1,8-naphthyridin-4-yl)-6'-(4-morpholinyl)-1',2,2',3,5,6-hexahydrospiro[pyran-4,3'-pyrrolo[3,2-b]pyridine]

3-Methyl-1,8-naphthyridine-2,4-diol

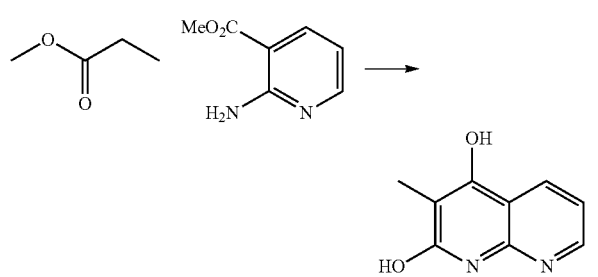

To a stirred solution of methyl 2-aminonicotinate (1.3 g, 8.54 mmol) and methyl propionate (20.08 mL, 214 mmol) in THF (20 mL) was added sodium 2-methylpropan-2-olate (2.053 g, 21.36 mmol) portionwise over 1 min. The reaction was stirred at rt for 40 min and at 100° C. for 4 h. After this time the reaction was cooled to rt and evaporated in vacuo. The resulting solid was dissolved in water (20 mL) and neutralized to pH 7 with 1.0M aqueous HCl. The resulting solid was filtered and dried under vacuum overnight to give 3-methyl-1,8-naphthyridine-2,4-diol as a tan solid. Mass Spectrum (ESI) m/e=177.2 (M+1).

2,4-Dichloro-3-methyl-1,8-naphthyridine

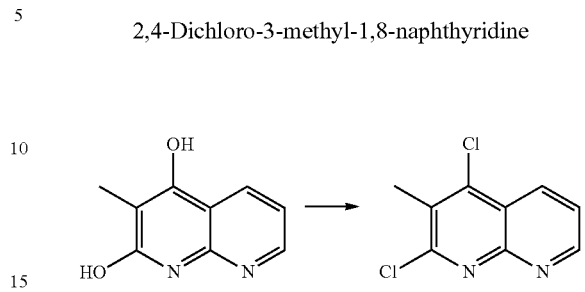

A stirred suspension of 3-methyl-1,8-naphthyridine-2,4-diol (0.82 g, 4.65 mmol) in phosphorus oxychloride (4.34 mL, 46.5 mmol) was heated at 120° C. for 3 h. After this time the reaction was allowed to cool to rt and evaporated in vacuo. The resulting residue was carefully basified to pH>10 with an aqueous solution of $Na_2CO_3$ and the resulting solid was filtered, washed with water and dried under vacuum to give 2,4-dichloro-3-methyl-1,8-naphthyridine. 1H NMR (400 MHz, chloroform-d) δ ppm 9.11 (1H, dd, J=4.3, 2.0 Hz), 8.57 (1H, dd, J=8.4, 2.0 Hz), 7.60 (1H, dd, J=8.3, 4.2 Hz), 2.72 (3H, s).

4-Chloro-3-methyl-2-(pyridin-2-yl)-1,8-naphthyridine

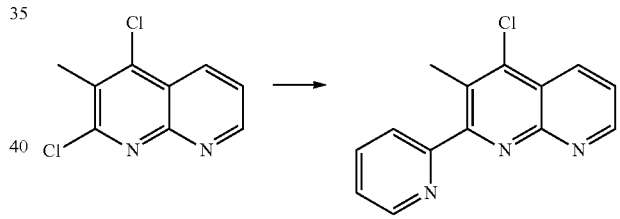

Prepared according to procedure E by using 2,4-dichloro-3-methyl-1,8-naphthyridine (540 mg, 2.53 mmol), 2-(1,1,1-tributylstannyl)pyridine (933 μL, 2.53 mmol), Pd(PPh$_3$)$_4$ (293 mg, 0.253 mmol) in toluene (10 mL) at reflux for 14 h. After this time the reaction was allowed to cool to rt and evaporated in vacuo. The resulting residue was triturated with hexanes and the solid was dried under vacuum to give 4-chloro-3-methyl-2-(pyridin-2-yl)-1,8-naphthyridine.

1'-(3-Methyl-2-(2-pyridinyl)-1,8-naphthyridin-4-yl)-6'-(4-morpholinyl)-1',2,2',3,5,6-hexahydrospiro[pyran-4,3'-pyrrolo[3,2-b]pyridine]

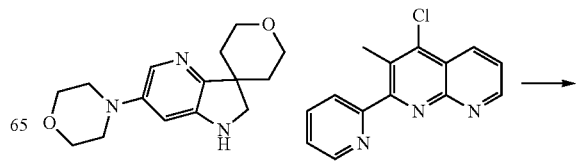

-continued

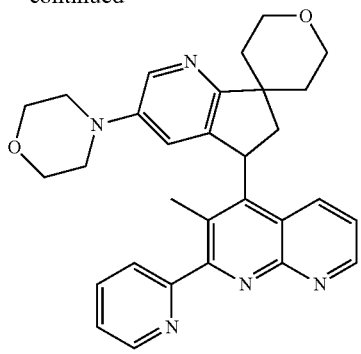

Prepared according to procedure Y by using 6'-morpholino-1',2,2',3,5,6-hexahydrospiro[pyran-4,3'-pyrrolo[3,2-b]pyridine] (70 mg, 0.254 mmol), 4-chloro-3-methyl-2-(pyridin-2-yl)-1,8-naphthyridine (65.0 mg, 0.25 mmol), sodium tert-butoxide (48.9 mg, 0.51 mmol) and XPhos precatalyst (18.7 mg, 0.025 mmol) in toluene (5 mL) for 2 h at 100° C. Purification by reverse phase HPLC (10 to 60% acetonitrile in water) gave 1'-(3-methyl-2-(pyridin-2-yl)-1,8-naphthyridin-4-yl)-6'-morpholino-1',2,2',3,5,6-hexahydrospiro[pyran-4,3'-pyrrolo[3,2-b]pyridine]. 1H NMR (400 MHz, chloroform-d) δ ppm 9.13 (1H, dd, J=4.1, 2.0 Hz), 8.72 (1H, ddd, J=4.8, 1.8, 1.0 Hz), 8.19 (1H, dt, J=7.8, 1.2 Hz), 8.13 (1H, dd, J=8.4, 2.0 Hz), 7.93 (1H, td, J=7.7, 1.8 Hz), 7.64 (1H, d, J=2.3 Hz), 7.39-7.47 (2H, m), 5.82 (1H, d, J=2.3 Hz), 4.13-4.20 (2H, m), 4.08 (1H, d, J=9.8 Hz), 3.97 (1H, d, J=9.6 Hz), 3.72-3.78 (4H, m), 3.55-3.62 (2H, m), 2.95-3.04 (4H, m), 2.51 (3H, s), 2.20-2.35 (2H, m), 1.74-1.87 (2H, m). Mass Spectrum (ESI) m/e=495.2 (M+1).

Example 126

1-(7-Fluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-pyrrolidinone 1-(4-Chloro-5-fluoro-3-methylquinolin-2-yl)pyrrolidin-2-one

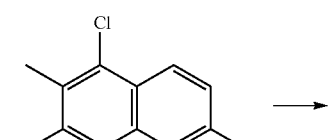

as a 4:1 mixture with the 5-F regioisomer

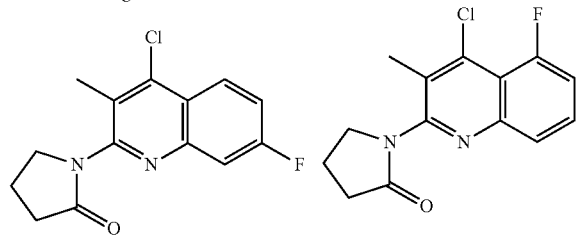

Prepared according to procedure AA using 2,4-dichloro-7-fluoro-3-methylquinoline (3 g, 13.04 mmol; contains 20% 5-F regioisomer), pyrrolidin-2-one (1.0 mL, 13.04 mmol), Pd$_2$dba$_3$ (0.597 g, 0.652 mmol), XantPhos (1.132 g, 1.956 mmol), cesium carbonate (5.95 g, 18.26 mmol), and 1,4-dioxane (35 mL). Column chromatography (silica gel, 0-50% EtOAc in hexanes) afforded (in order of elution) 1-(4-chloro-7-fluoro-3-methylquinolin-2-yl)pyrrolidin-2-one and 1-(4-chloro-5-fluoro-3-methylquinolin-2-yl)pyrrolidin-2-one as white amorphous solids. Mass Spectrum (ESI) m/e=279.0 (M+1).

1-(7-Fluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-pyrrolidinone

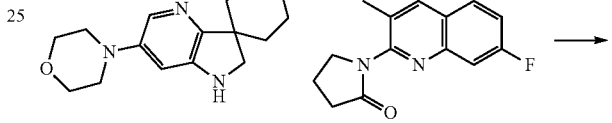

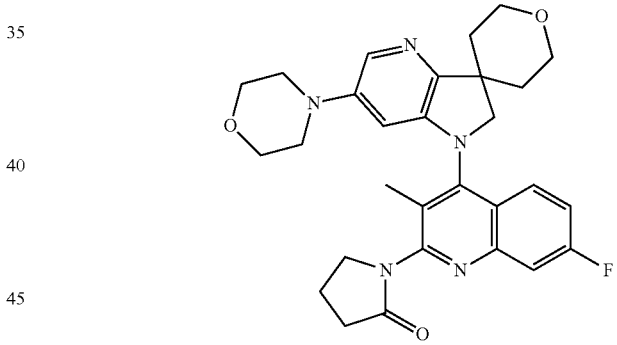

Prepared according to procedure Y by stirring 1-(4-chloro-7-fluoro-3-methylquinolin-2-yl)pyrrolidin-2-one (50 mg, 0.179 mmol), 6'-morpholino-1',2,2',3,5,6-hexahydrospiro[pyran-4,3'-pyrrolo[3,2-b]pyridine] (49.4 mg, 0.179 mmol), XPhos precatalyst (26.5 mg, 0.036 mmol), sodium tert-butoxide (34.5 mg, 0.359 mmol), and toluene (1.5 mL) at 95° C. for 2 h. Purification by reverse phase HPLC (0-70% acetonitrile in water) gave 1-(7-fluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-pyrrolidinone. 1H NMR (400 MHz, chloroform-d) δ ppm 7.76 (1H, dd, J=9.1, 6.0 Hz), 7.61-7.69 (2H, m), 7.21-7.26 (1H, m), 5.89 (1H, s), 4.13 (4H, d, J=6.8 Hz), 4.04-4.10 (1H, m), 3.93 (1H, d, J=9.6 Hz), 3.70-3.83 (4H, m), 3.51-3.66 (2H, m), 3.03 (4H, dd, J=5.7, 3.7 Hz), 2.65 (2H, t, J=8.0 Hz), 2.24-2.42 (4H, m), 2.18 (3H,

215 s), 1.83 (1H, d, J=13.7 Hz), 1.73 (1H, d, J=13.3 Hz). Mass Spectrum (ESI) m/e=518.2 (M+1).

Example 127

4-(3-Methyl-2-(2-pyridinyl)-1,8-naphthyridin-4-yl)-6-(4-morpholinyl)-3,4-dihydro-2H-1,4-benzoxazine

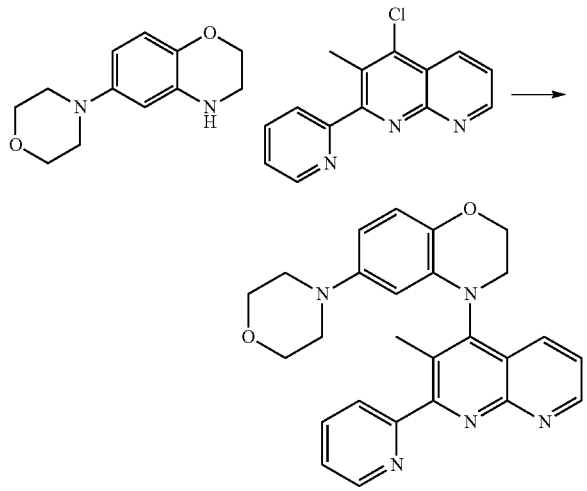

Prepared according to procedure Y by using 6-morpholino-3,4-dihydro-2H-benzo-[b][1,4]oxazine (68 mg, 0.31 mmol), 4-chloro-3-methyl-2-(pyridin-2-yl)-1,8-naphthyridine (79 mg, 0.31 mmol), XPhos precatalyst (23 mg, 0.031 mmol) in toluene (5 mL) for 2 h at 100° C. Purification by reverse phase HPLC (10 to 60% acetonitrile in water) gave 4-(3-methyl-2-(2-pyridinyl)-1,8-naphthyridin-4-yl)-6-(4-morpholinyl)-3,4-dihydro-2H-1,4-benzoxazine. 1H NMR (400 MHz, chloroform-d) δ ppm 9.10 (1H, dd, J=4.1, 2.0 Hz), 8.71 (1H, ddd, J=4.8, 1.9, 1.0 Hz), 8.16-8.24 (2H, m), 7.92 (1H, td, J=7.7, 1.8 Hz), 7.37-7.45 (2H, m), 6.89 (1H, d, J=8.8 Hz), 6.31 (1H, dd, J=8.8, 2.7 Hz), 5.60 (1H, d, J=2.7 Hz), 4.42-4.52 (2H, m), 3.80-3.87 (1H, m), 3.62-3.76 (5H, m), 2.68-2.80 (4H, m), 2.53 (3H, s). Mass Spectrum (ESI) m/e=440.0 (M+1).

Example 128

4-(3,3-Dimethyl-6-(4-morpholinyl)-2,3-dihydro-1H-pyrrolo-[3,2-b]pyridin-1-yl)-3-methyl-2-(2-pyridinyl)-1,8-naphthyridine

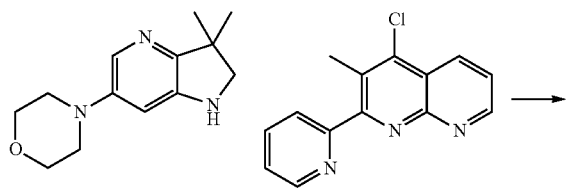

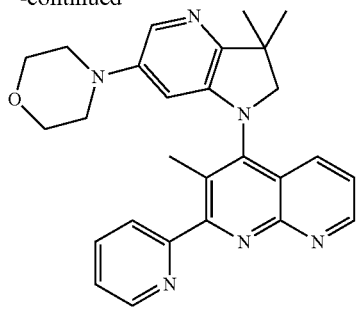

Prepared according to procedure Y by using 4-chloro-3-methyl-2-(pyridin-2-yl)-1,8-naphthyridine (40 mg, 0.156 mmol), 4-(3,3-dimethyl-2,3-dihydro-1H-pyrrolo-[3,2-b]pyridin-6-yl)morpholine (36.5 mg, 0.156 mmol), XPhos precatalyst (11.5 mg, 0.015 mmol) and sodium tert-butoxide (30 mg, 0.313 mmol) in toluene (4 mL) for 2 h at 110° C. Purification by reverse phase HPLC (10 to 50% acetonitrile in water) gave 4-(3,3-dimethyl-6-(4-morpholinyl)-2,3-dihydro-1H-pyrrolo-[3,2-b]pyridin-1-yl)-3-methyl-2-(2-pyridinyl)-1,8-naphthyridine. 1H NMR (400 MHz, chloroform-d) δ ppm 9.12 (1H, dd, J=4.1, 2.0 Hz), 8.71 (1H, ddd, J=4.8, 1.9, 1.0 Hz), 8.14-8.21 (2H, m), 7.92 (1H, td, J=7.7, 1.8 Hz), 7.62 (1H, d, J=2.3 Hz), 7.37-7.48 (2H, m), 5.82 (1H, d, J=2.3 Hz), 3.86-3.91 (1H, m), 3.69-3.82 (5H, m), 2.93-3.04 (4H, m), 2.50 (3H, s), 1.58 (3H, s), 1.53 (3H, s). Mass Spectrum (ESI) m/e=453.2 (M+1).

Example 129

1'-(3-Methyl-2-(2-pyridinyl)-1,7-naphthyridin-4-yl)-6'-(4-morpholinyl)-1',2,2',3,5,6-hexahydrospiro[pyran-4,3'-pyrrolo[3,2-b]pyridine]

3-Methyl-1,7-naphthyridine-2,4-diol

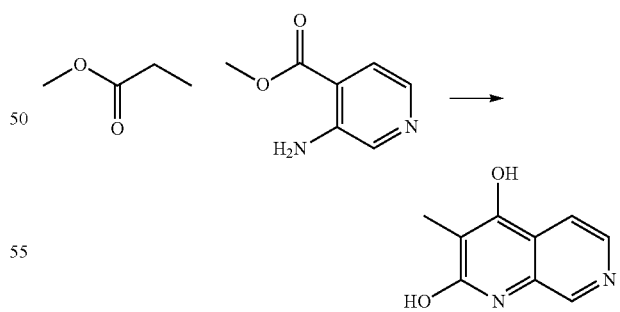

To a stirred solution of methyl 3-aminonicotinate (2.0 g, 13.14 mmol) and methyl propionate (30.9 mL, 329 mmol) in THF (30 mL) was added sodium tert-butoxide (3.16 g, 32.9 mmol) portionwise over 1 min. The reaction was stirred at rt for 40 min and at 100° C. for 4 h. After this time the reaction was cooled to rt and evaporated in vacuo. The resulting solid was dissolved in water (20 mL) and neutralized to pH 7 with 1.0M aqueous HCl. The resulting precipitate was filtered and dried under vacuum overnight to give 3-methyl-1,7-naphthyridine-2,4-diol. Mass Spectrum (ESI) m/e=177.2 (M+1).

2,4-Dichloro-3-methyl-1,7-naphthyridine

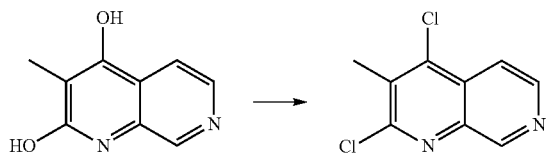

A stirred suspension of 3-methyl-1,7-naphthyridine-2,4-diol (0.5 g, 2.84 mmol) in phosphorus oxychloride (2.64 mL, 28.4 mmol) was heated at 120° C. for 3 h. After this time the reaction was allowed to cool to rt and evaporated in vacuo. The resulting residue was carefully basified to pH>10 with an aqueous solution of $Na_2CO_3$ and the resulting precipitate was filtered, washed with water and dried under vacuum to give 2,4-dichloro-3-methyl-1,7-naphthyridine. H NMR (400 MHz, chloroform-d) δ ppm 9.41 (1H, d, J=1.0 Hz), 8.72 (1H, d, J=5.9 Hz), 7.95 (1H, dd, J=5.9, 1.0 Hz), 2.73 (3H, s)

4-Chloro-3-methyl-2-(pyridin-2-yl)-1,7-naphthyridine

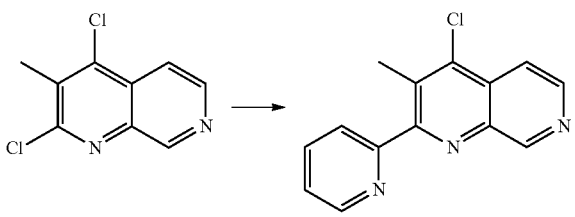 [SMILES: Cc1c(Cl)nc2cnccc2c1Cl ; Cc1c(-c2ccccn2)nc2cnccc2c1Cl]

Prepared according to procedure E using 2,4-dichloro-3-methyl-1,7-naphthyridine (200 mg, 0.94 mmol), 2-tri-n-butylstannylpyridine (0.35 mL, 0.939 mmol), Pd(PPh$_3$)$_4$ (108 mg, 0.094 mmol) with heating in toluene (10 mL) for 14 h. After purification 4-chloro-3-methyl-2-(pyridin-2-yl)-1,7-naphthyridine was obtained as a white solid.

1'-(3-Methyl-2-(2-pyridinyl)-1,7-naphthyridin-4-yl)-6'-(4-morpholinyl)-1',2,2',3,5,6-hexahydrospiro[pyran-4,3'-pyrrolo[3,2-b]pyridine]

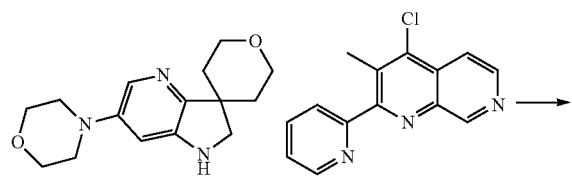

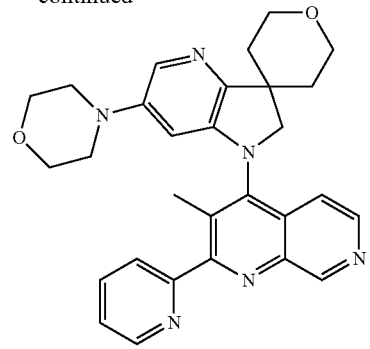

Prepared according to procedure Y by using 4-chloro-3-methyl-2-(pyridin-2-yl)-1,7-naphthyridine (70 mg, 0.274 mmol), 6'-morpholino-1',2,2',3,5,6-hexahydrospiro[pyran-4,3'-pyrrolo[3,2-b]pyridine] (75 mg, 0.274 mmol), sodium tert-butoxide (52.6 mg, 0.548 mmol) and XPhos precatalyst (20 mg, 0.027 mmol) with heating in toluene (4 mL) for 2 h at 110° C. Purification by reverse phase HPLC (to 10 50% acetonitrile water) gave 1'-(3-methyl-2-(2-pyridinyl)-1,7-naphthyridin-4-yl)-6'-(4-morpholinyl)-1',2,2',3,5,6-hexahydrospiro[pyran-4,3'-pyrrolo[3,2-b]-pyridine]. 1H NMR (400 MHz, chloroform-d) δ ppm 9.60 (1H, d, J=1.0 Hz), 8.75 (1H, dt, J=4.8, 1.5 Hz), 8.55 (1H, d, J=5.9 Hz), 7.92-8.01 (2H, m), 7.65 (1H, d, J=2.3 Hz), 7.51 (1H, dd, J=5.7, 1.0 Hz), 7.43 (1H, ddd, J=6.0, 4.8, 2.9 Hz), 5.84 (1H, d, J=2.3 Hz), 4.12-4.20 (2H, m), 3.93-4.05 (2H, m), 3.71-3.77 (4H, m), 3.52-3.62 (2H, m), 2.95-3.12 (4H, m), 2.47 (3H, s), 2.28-2.43 (2H, m), 1.69-1.88 (2H, m). Mass Spectrum (ESI) m/e=495.0 (M+1).

Example 130

1'-(2-(3,5-Difluorophenyl)-3-methyl-1,8-naphthyridin-4-yl)-6'-(4-morpholinyl)-1',2,2',3,5,6-hexahydrospiro[pyran-4,3'-pyrrolo[3,2-b]-pyridine]

4-Chloro-2-(3,5-difluorophenyl)-3-methyl-1,8-naphthyridine

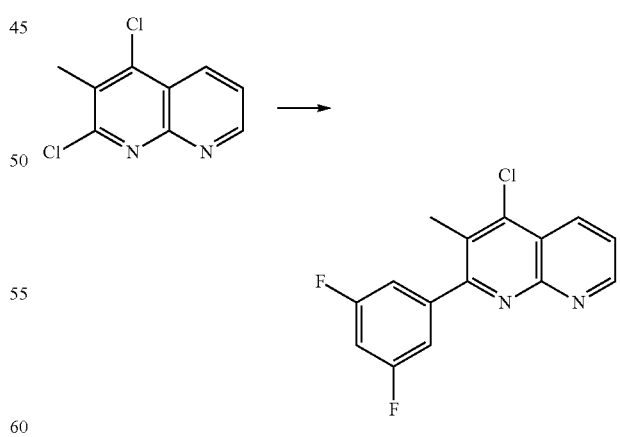

Prepared according to procedure F using 2,4-dichloro-3-methyl-1,8-naphthyridine (0.4 g, 1.877 mmol), 3,5-difluorophenylboronic acid (0.445 g, 2.82 mmol), Pd(PPh$_3$)$_4$ (0.217 g, 0.188 mmol), potassium carbonate (0.519 g, 3.75 mmol) in toluene (6 mL) at 95° C. for 18 h. Purification by column chromatography (silica gel; 0-25% EtOAc in hexanes) gave 4-chloro-2-(3,5-difluorophenyl)-3-methyl-1,8-naphthyridine as a yellow amorphous solid. Mass Spectrum (ESI) m/e=291.0 (M+1).

1'-(2-(3,5-Difluorophenyl)-3-methyl-1,8-naphthyridin-4-yl)-6'-(4-morpholinyl)-1',2,2',3,5,6-hexahydrospiro[pyran-4,3'-pyrrolo[3,2-b]pyridine]

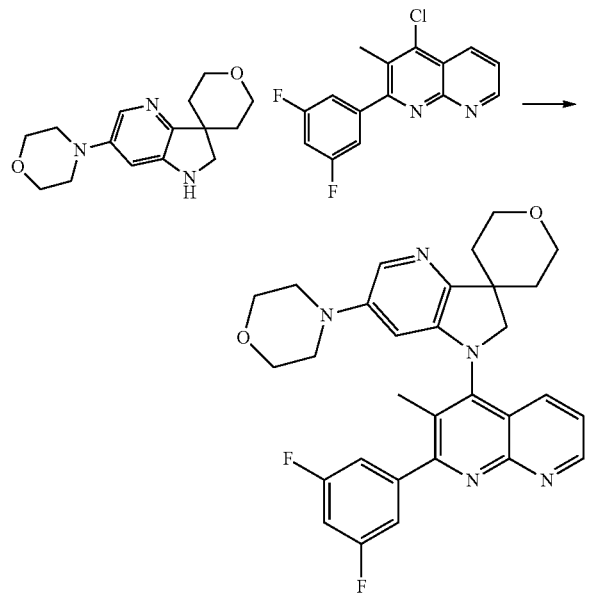

Prepared according to procedure Y using 4-chloro-2-(3,5-difluorophenyl)-3-methyl-1,8-naphthyridine (60 mg, 0.206 mmol), 6'-morpholino-1',2,2',3,5,6-hexahydrospiro[pyran-4,3'-pyrrolo[3,2-b]pyridine] (56.8 mg, 0.206 mmol), sodium tert-butoxide (39.7 mg, 0.413 mmol) and XPhos precatalyst (15 mg, 0.021 mmol). Purification by reverse phase HPLC (10 to 60% acetonitrile in water) gave 1'-(2-(3,5-difluorophenyl)-3-methyl-1,8-naphthyridin-4-yl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 9.14 (1H, dd, J=4.1, 2.0 Hz), 8.13 (1H, dd, J=8.4, 2.0 Hz), 7.67 (1H, d, J=2.3 Hz), 7.46 (1H, dd, J=8.3, 4.2 Hz), 7.21-7.33 (2H, m), 6.88-7.00 (1H, m), 5.78 (1H, d, J=2.3 Hz), 4.14-4.21 (2H, m), 3.93-4.07 (2H, m), 3.70-3.80 (4H, m), 3.52-3.66 (2H, m, J=11.3, 11.3, 2.5, 2.2 Hz), 2.91-3.07 (4H, m), 2.27-2.43 (5H, m), 1.70-1.89 (2H, m). Mass Spectrum (ESI) m/e=530.2 (M+1).

Example 131

1'-(2-(3,5-Difluorophenyl)-3-methyl-1,7-naphthyridin-4-yl)-6'-(4-morpholinyl)-1',2,2',3,5,6-hexahydrospiro[pyran-4,3'-pyrrolo[3,2-b]-pyridine]

4-Chloro-2-(3,5-difluorophenyl)-3-methyl-1,7-naphthyridine

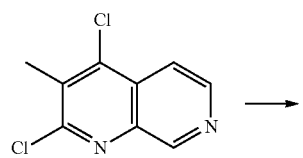

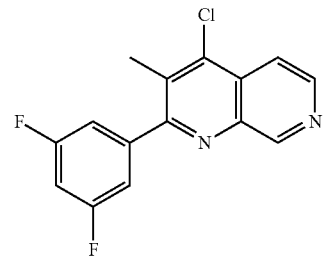

Prepared according to procedure F using 2,4-dichloro-3-methyl-1,7-naphthyridine (0.18 g, 0.845 mmol), 3,5-difluorophenylboronic acid (0.147 g, 0.929 mmol), Pd(PPh₃)₄ (0.098 g, 0.084 mmol), potassium carbonate (0.519 g, 3.75 mmol) in toluene (6 mL) at 95° C. for 18 h. Purification by column chromatography (silica gel; 0-25% EtOAc in hexanes) gave 4-chloro-2-(3,5-difluorophenyl)-3-methyl-1,7-naphthyridine as a yellow amorphous solid. Mass Spectrum (ESI) m/e=291.0 (M+1).

1'-(2-(3,5-Difluorophenyl)-3-methyl-1,7-naphthyridin-4-yl)-6'-(4-morpholinyl)-1',2,2',3,5,6-hexahydrospiro[pyran-4,3'-pyrrolo[3,2-b]pyridine]

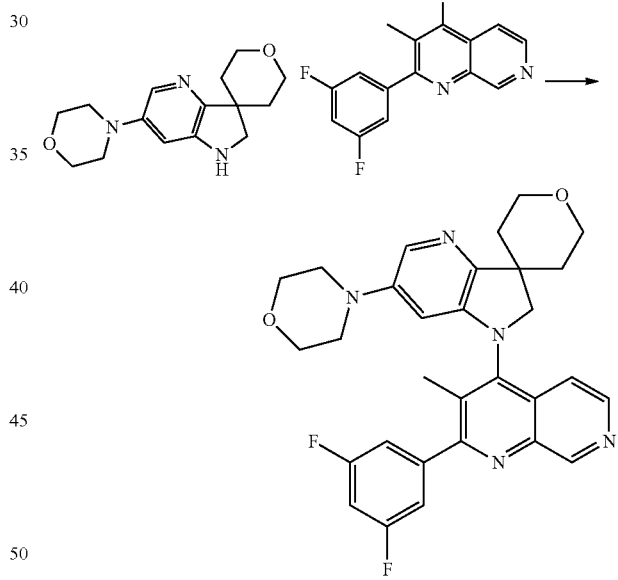

Prepared according to procedure Y using 4-chloro-2-(3,5-difluorophenyl)-3-methyl-1,7-naphthyridine (40 mg, 0.138 mmol), 6'-morpholino-1',2,2',3,5,6-hexahydrospiro[pyran-4,3'-pyrrolo[3,2-b]pyridine] (37.9 mg, 0.138 mmol), sodium tert-butoxide (26.4 mg, 0.275 mmol) and XPhos precatalyst (10.4 mg, 0.014 mmol) in toluene (4 mL) at 110° C. for 2 h. Purification by reverse phase HPLC (10 to 50% acetonitrile in water) gave 1'-(2-(3,5-difluorophenyl)-3-methyl-1,7-naphthyridin-4-yl)-6'-(4-morpholinyl)-1',2,2',3,5,6-hexahydrospiro[pyran-4,3'-pyrrolo[3,2-b]-pyridine]. 1H NMR (400 MHz, CHLOROFORM-d) δ ppm 9.59 (1H, d, J=1.0 Hz), 8.57 (1H, d, J=5.9 Hz), 7.69 (1H, d, J=2.3 Hz), 7.51 (1H, dd, J=5.9, 1.0 Hz), 7.15-7.22 (2H, m), 6.94-7.01 (1H, m), 5.82 (1H, d, J=2.3 Hz), 4.12-4.21 (2H, m), 3.94-4.05 (2H, m), 3.71-3.81 (4H, m), 3.59 (2H, tt, J=11.4, 2.8 Hz), 2.93-3.07 (4H, m), 2.28-2.45 (5H, m), 1.72-1.88 (2H, m). Mass Spectrum (ESI) m/e=530.2 (M+1).

Example 132

2-(3,5-Difluorophenyl)-4-(3,3-dimethyl-6-(4-morpholinyl)-2,3-dihydro-1H-pyrrolo[3,2-b]pyridin-1-yl)-3-methyl-1,7-naphthyridine

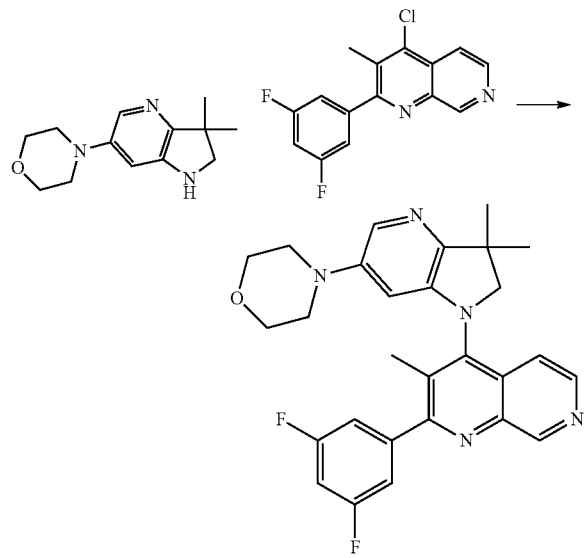

Prepared according to procedure Y using 4-chloro-2-(3,5-difluorophenyl)-3-methyl-1,7-naphthyridine (40 mg, 0.138 mmol), 4-(3,3-dimethyl-2,3-dihydro-1H-pyrrolo[3,2-b]pyridin-6-yl)morpholine (32.1 mg, 0.138 mmol), sodium tert-butoxide (26.4 mg, 0.275 mmol) and XPhos precatalyst (10.4 mg, 0.014 mmol) in toluene (4 mL) for 2 hours at 110° C. Purification by reverse phase HPLC (10 to 60% acetonitrile in water) gave 2-(3,5-difluorophenyl)-4-(3,3-dimethyl-6-(4-morpholinyl)-2,3-dihydro-1H-pyrrolo[3,2-b]pyridin-1-yl)-3-methyl-1,7-naphthyridine. 1H NMR (400 MHz, chloroform-d) δ ppm 9.59 (1H, d, J=1.0 Hz), 8.57 (1H, d, J=5.9 Hz), 7.69 (1H, d, J=2.3 Hz), 7.51 (1H, dd, J=5.9, 1.0 Hz), 7.15-7.22 (2H, m), 6.94-7.01 (1H, m), 5.82 (1H, d, J=2.3 Hz), 4.13-4.23 (2H, m), 3.71-3.81 (4H, m), 3.59 (2H, tt, J=11.4, 2.8 Hz), 2.95-3.07 (4H, m), 2.29-2.45 (5H, m), 1.71-1.92 (2H, m). Mass Spectrum (ESI) m/e=488.2 (M+1).

Example 133

4-(3,3-Dimethyl-6-(4-morpholinyl)-2,3-dihydro-1H-pyrrolo-[3,2-b]pyridin-1-yl)-3-methyl-2-(4-methyl-2-pyridinyl)-1,8-naphthyridine 4-Chloro-3-methyl-2-(4-methylpyridin-2-yl)-1,8-naphthyridine

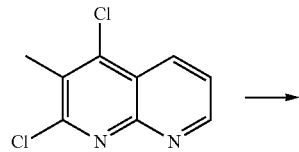

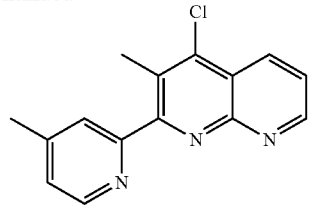

Prepared according to procedure E and using 2,4-dichloro-3-methyl-1,8-naphthyridine (500 mg, 2.347 mmol), 4-methyl-2-(tributylstannyl)pyridine (897 mg, 2.347 mmol) and Pd(PPh₃)₄ (271 mg, 0.235 mmol). Purification by column chromatography (hexanes:EtOAc, from 1:0 to 1:2) gave 4-chloro-3-methyl-2-(4-methylpyridin-2-yl)-1,8-naphthyridine. Mass Spectrum (ESI) m/e=270.0 (M+1).

4-(3,3-Dimethyl-6-(4-morpholinyl)-2,3-dihydro-1H-pyrrolo[3,2-b]pyridin-1-yl)-3-methyl-2-(4-methyl-2-pyridinyl)-1,8-naphthyridine

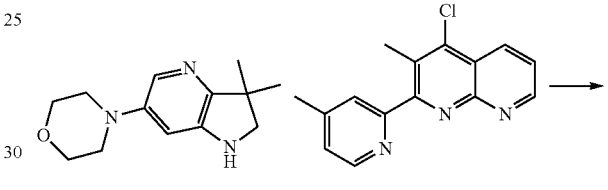

Prepared according to procedure Y using 4-(3,3-dimethyl-2,3-dihydro-1H-pyrrolo[3,2-b]pyridin-6-yl)morpholine (18 mg, 0.077 mmol), 4-chloro-3-methyl-2-(4-methylpyridin-2-yl)-1,8-naphthyridine (20.81 mg, 0.077 mmol), sodium tert-butoxide (14.86 mg, 0.154 mmol) and XPhos (7.72 mmol, 7.72 mol) in toluene (4 mL) for 2 hours at 110° C. Purification by reverse phase HPLC (10 to 60% acetonitrile in water) gave 4-(3,3-dimethyl-6-(4-morpholinyl)-2,3-dihydro-1H-pyrrolo[3,2-b]pyridin-1-yl)-3-methyl-2-(4-methyl-2-pyridinyl)-1,8-naphthyridine. 1H NMR (400 MHz, chloroform-d) δ ppm 9.12 (1H, dd, J=4.3, 2.0 Hz), 8.57 (1H, d, J=5.1 Hz), 8.17 (1H, dd, J=8.2, 2.0 Hz), 8.00-8.03 (1H, m), 7.61 (1H, d, J=2.3 Hz), 7.44 (1H, dd, J=8.3, 4.2 Hz), 7.22 (1H, ddd, J=5.1, 1.8, 0.8 Hz), 5.81 (1H, d, J=2.3 Hz), 3.86-3.90 (1H, m), 3.77-3.82 (1H, m), 3.72-3.77 (4H, m), 2.93-3.04 (4H, m), 2.50 (3H, s), 2.49 (3H, s), 1.58 (3H, s), 1.53 (3H, s). Mass Spectrum (ESI) m/e=467.2 (M+1).

Example 134

2-(3,5-Difluorophenyl)-4-(3,3-dimethyl-6-(4-morpholinyl)-2,3-dihydro-1H-pyrrolo[3,2-b]pyridin-1-yl)-3-methyl-1,8-naphthyridine

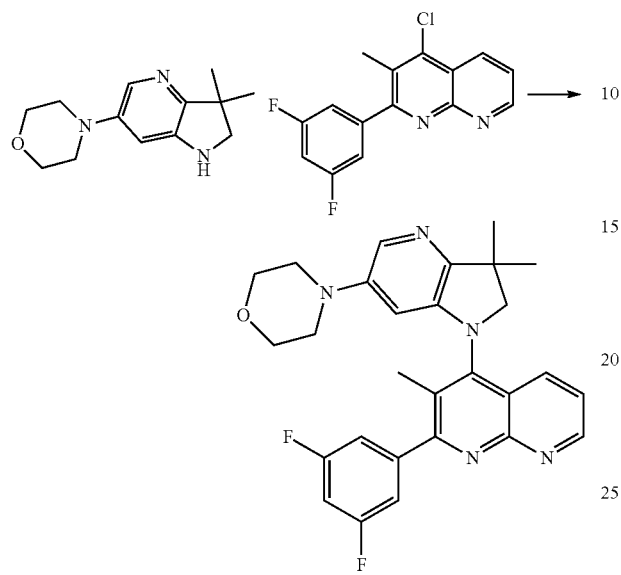

Prepared according to procedure Y using 4-chloro-2-(3,5-difluorophenyl)-3-methyl-1,8-naphthyridine (68 mg, 0.234 mmol), 4-(3,3-dimethyl-2,3-dihydro-1H-pyrrolo[3,2-b]pyridin-6-yl)morpholine (54.6 mg, 0.234 mmol), sodium tert-butoxide (45 mg, 0.468 mmol) and XPhos precatalyst (17.1 mg, 0.023 mmol) in toluene (4 mL) for 2 hours at 110° C. Purification by reverse phase HPLC (10 to 60% acetonitrile in waiter) gave 2-(3,5-difluorophenyl)-4-(3,3-dimethyl-6-(4-morpholinyl)-2,3-dihydro-1H-pyrrolo[3,2-b]pyridin-1-yl)-3-methyl-1,8-naphthyridine. 1H NMR (400 MHz, chloroform-d) δ ppm 9.13 (1H, dd, J=4.3, 2.0 Hz), 8.17 (1H, dd, J=8.2, 2.0 Hz), 7.65 (1H, d, J=2.3 Hz), 7.45 (1H, dd, J=8.3, 4.2 Hz), 7.25-7.28 (2H, m), 6.91-6.98 (1H, m), 5.78 (1H, d, J=2.5 Hz), 3.86-3.91 (1H, m), 3.79-3.84 (1H, m), 3.71-3.78 (4H, m), 2.94-3.04 (4H, m), 2.37 (3H, s), 1.58 (3H, s), 1.53 (3H, s). Mass Spectrum (ESI) m/e=488.2 (M+1).

Example 135

Methyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate 4-Chloro-5,7-difluoro-3-methyl-2-(piperazin-1-yl)quinoline 2,2,2-trifluoroacetate

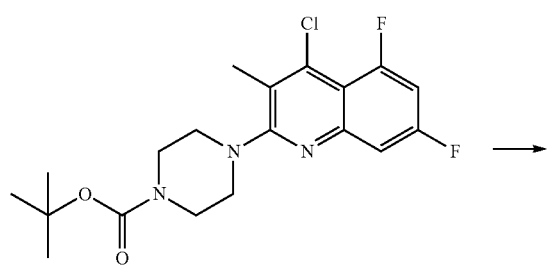

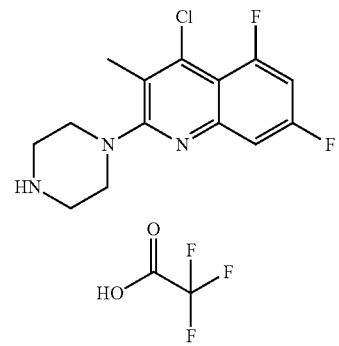

Tert-Butyl 4-(4-chloro-5,7-difluoro-3-methylquinolin-2-yl)piperazine-1-carboxylate (370 mg, 0.93 mmol) was dissolved in DCM (3.0 mL) and cooled to 0° C. TFA (0.50 mL, 6.5 mmol) was then added and the mixture was stirred for 2 h while warming to rt. The mixture was then concentrated and triturated with EtOAc. The slurry was filtered to give 4-chloro-5,7-difluoro-3-methyl-2-(piperazin-1-yl)quinoline 2,2,2-trifluoroacetate. Mass Spectrum (ESI) m/e=298.1 (M+1).

Methyl 4-(4-chloro-5,7-difluoro-3-methylquinolin-2-yl)piperazine-1-carboxylate

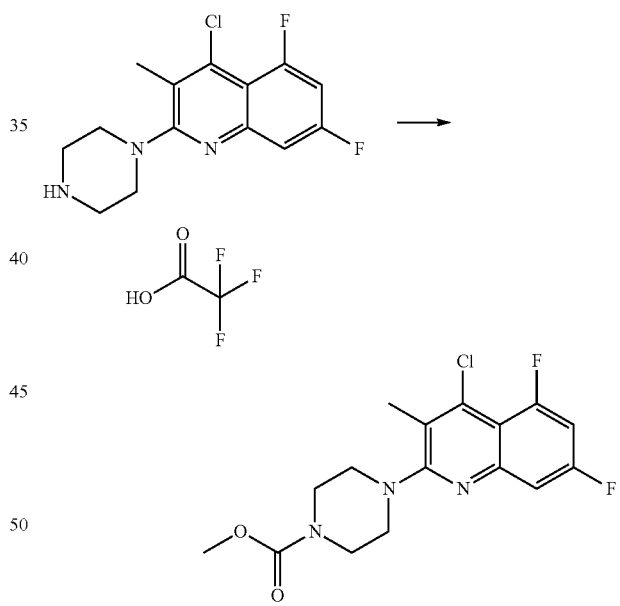

The 4-chloro-5,7-difluoro-3-methyl-2-(piperazin-1-yl)quinoline 2,2,2-trifluoroacetate (150 mg, 0.37 mmol), potassium carbonate (360 mg, 2.60 mmol) and methyl chloroformate (0.11 mL, 1.50 mmol) were added to acetone (3.0 mL). The slurry was heated in a microwave reactor at 80° C. for 3 h. The reaction mixture was concentrated and the residue was partitioned between water and EtOAc. The aqueous layer was extracted with EtOAc (2×50 mL). The combined organic layers were washed with brine (1×30 mL) and dried over MgSO$_4$ to give methyl 4-(4-chloro-5,7-difluoro-3-methylquinolin-2-yl)piperazine-1-carboxylate. Mass Spectrum (ESI) m/e=356.2 (M+1).

225

Methyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate

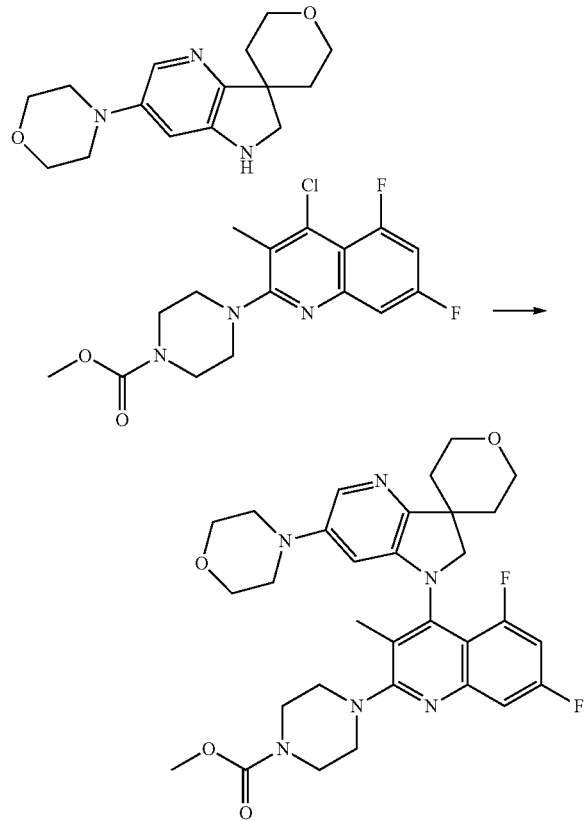

Prepared according to procedure Y using methyl 4-(4-chloro-5,7-difluoro-3-methylquinolin-2-yl)piperazine-1-carboxylate (40.0 mg, 0.110 mmol) and 6'-morpholino-1',2,2',3,5,6-hexahydrospiro[pyran-4,3'-pyrrolo[3,2-b]pyridine] in toluene to give methyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate. TFA Salt: 1H NMR (400 MHz, chloroform-d) δ ppm 9.47 (3H, br. s.), 7.70 (1H, d, J=2.2 Hz), 7.42 (1H, dt, J=9.4, 1.2 Hz), 6.77-6.91 (1H, m), 5.87 (1H, d, J=2.2 Hz), 3.98-4.20 (4H, m), 3.60-3.83 (11H, m), 3.27-3.60 (6H, m), 3.07 (4H, dd, J=6.0, 3.6 Hz), 2.46-2.65 (2H, m), 2.30 (3H, s), 1.69-1.95 (2H, m). Mass Spectrum (ESI) m/e=595.3 (M+1).

Example 136

1-(5,7-Difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-5,5-dimethyl-2-piperidinone 5,5-Dimethylpiperidin-2-one

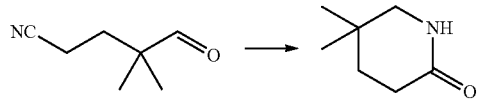

226

The procedure outlined in *J. Med. Chem.* 1977, pg. 1180 was followed using 4,4-dimethyl-5-oxopentanenitrile (4.00 g, 32.0 mmol) to obtain 5,5-dimethylpiperidin-2-one. Mass Spectrum (ESI) m/e=128.2 (M+1).

1-(4-Chloro-5,7-difluoro-3-methylquinolin-2-yl)-5,5-dimethylpiperidin-2-one

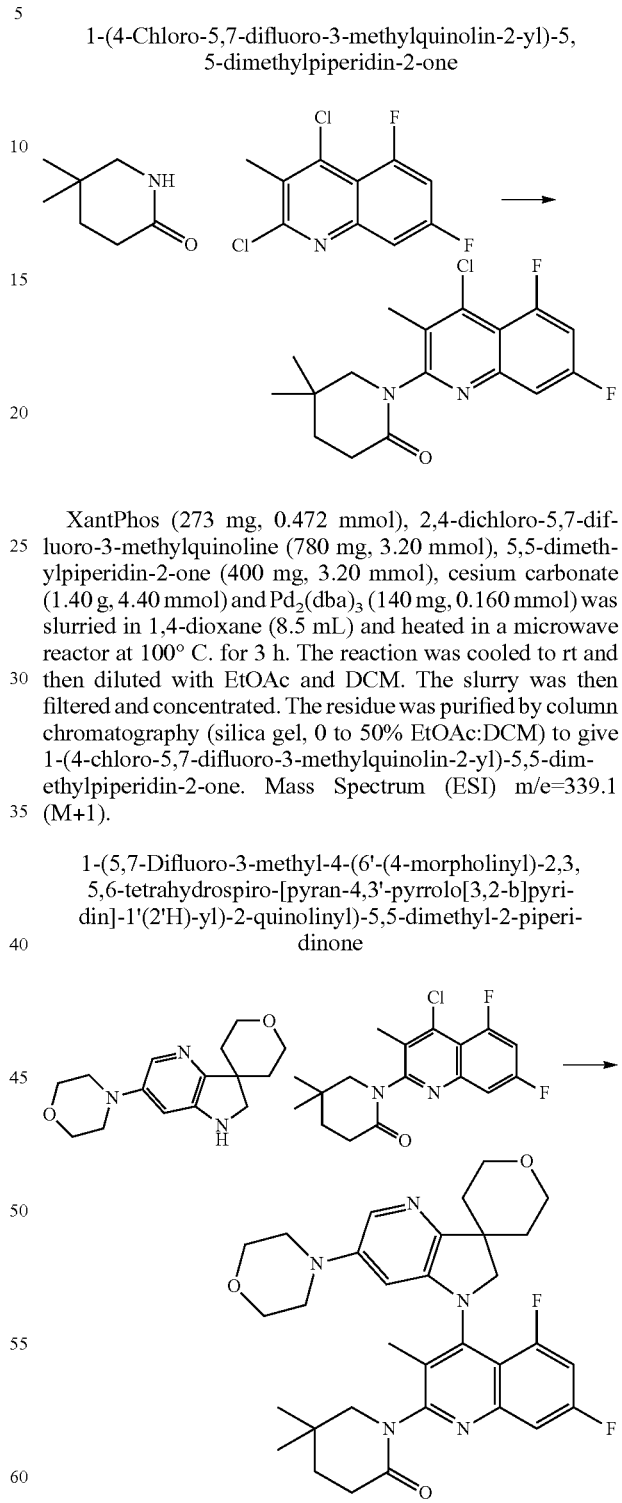

XantPhos (273 mg, 0.472 mmol), 2,4-dichloro-5,7-difluoro-3-methylquinoline (780 mg, 3.20 mmol), 5,5-dimethylpiperidin-2-one (400 mg, 3.20 mmol), cesium carbonate (1.40 g, 4.40 mmol) and Pd$_2$(dba)$_3$ (140 mg, 0.160 mmol) was slurried in 1,4-dioxane (8.5 mL) and heated in a microwave reactor at 100° C. for 3 h. The reaction was cooled to rt and then diluted with EtOAc and DCM. The slurry was then filtered and concentrated. The residue was purified by column chromatography (silica gel, 0 to 50% EtOAc:DCM) to give 1-(4-chloro-5,7-difluoro-3-methylquinolin-2-yl)-5,5-dimethylpiperidin-2-one. Mass Spectrum (ESI) m/e=339.1 (M+1).

1-(5,7-Difluoro-3-methyl-4-(6'-(4-morpholinyl)-2,3,5,6-tetrahydrospiro-[pyran-4,3'-pyrrolo[3,2-b]pyridin]-1'(2'H)-yl)-2-quinolinyl)-5,5-dimethyl-2-piperidinone Prepared according to procedure Y using 1-(4-chloro-5,7-difluoro-3-methylquinolin-2-yl)-5,5-dimethylpiperidin-2-one (24.0 mg, 0.071 mmol) and 6'-morpholino-1',2,2',3,5,6-hexahydrospiro[pyran-4,3'-pyrrolo[3,2-b]pyridine] in toluene to give 1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-5,5-dimethyl-2-piperidinone. TFA Salt: 1H NMR (400 MHz, chloroform-d) δ ppm 8.18 (1H, br. s.), 7.68-7.80 (1H, m), 7.54-7.64 (1H, m), 6.96-7.16 (1H, m), 5.76-6.28 (1H, m), 4.16-4.42 (1H, m), 4.09 (3H, dd, J=11.9, 7.8 Hz), 3.86 (1H, d, J=9.8 Hz), 3.67-3.82 (4H, m), 3.46-3.60 (1H, m), 3.35-3.46 (1H, m), 3.28 (1H, dd, J=12.1, 1.8 Hz), 3.00-3.25 (4H, m), 2.39-2.82 (4H, m), 2.14 (3H, s), 1.67-2.01 (4H, m), 1.16-1.37 (6H, m). Mass Spectrum (ESI) m/e=578.3 (M+1).

Example 137 tert-Butyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate tert-Butyl 4-(4-chloro-5,7-difluoro-3-methylquinolin-2-yl)piperazine-1-carboxylate

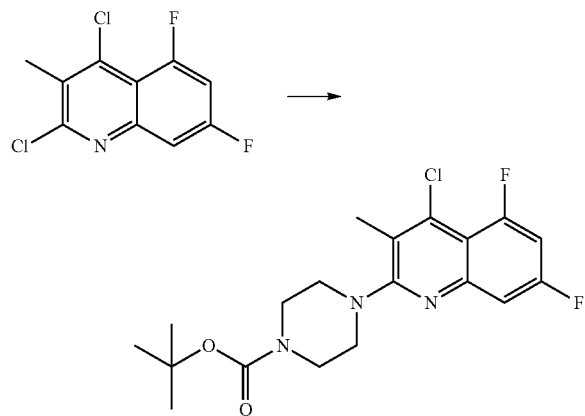

2,4-dichloro-5,7-difluoro-3-methylquinoline (4.90 g, 10.0 mmol), tert-butyl piperazine-1-carboxylate (3.70 g, 20.0 mmol) and triethylamine (2.80 mL, 20.0 mmol) were slurried in isopropyl alcohol (40 mL) and heated at 120° C. for 12 h. The reaction was then allowed to cool to rt and concentrated to dryness. The crude product was then purified by column chromatography (silica gel, 0 to 20% EtOAc:hexane) to give tert-butyl 4-(4-chloro-5,7-difluoro-3-methylquinolin-2-yl)piperazine-1-carboxylate. Mass Spectrum (ESI) m/e=398.2 (M+1).

tert-Butyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate

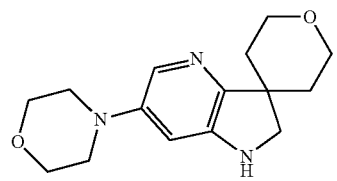

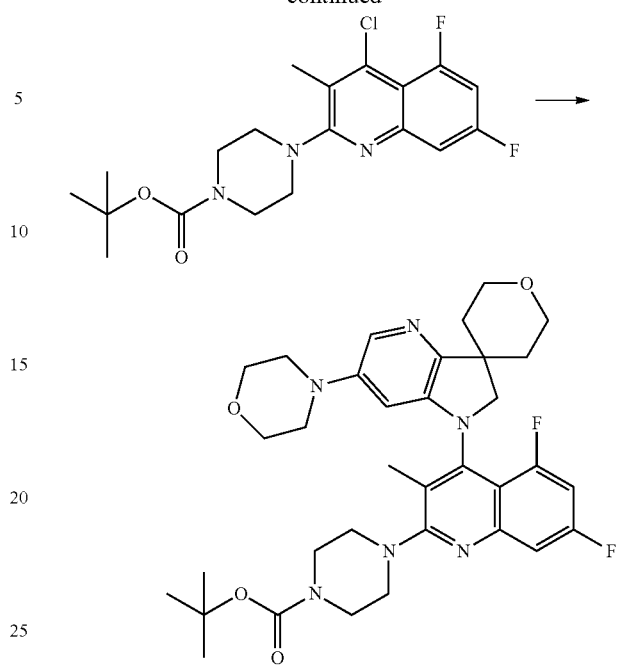

Prepared according to procedure Y using tert-butyl 4-(4-chloro-5,7-difluoro-3-methylquinolin-2-yl)piperazine-1-carboxylate (690.0 mg, 1.70 mmol) and 6'-morpholino-1',2,2',3,5,6-hexahydrospiro[pyran-4,3'-pyrrolo[3,2-b]pyridine] in toluene to give tert-butyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate. 1H NMR (400 MHz, chloroform-d) δ ppm 7.56 (1H, d, J=2.3 Hz), 7.35 (1H, ddd, J=9.8, 2.4, 1.1 Hz), 6.75 (1H, ddd, J=11.8, 8.9, 2.5 Hz), 5.66 (1H, d, J=2.3 Hz), 4.05-4.22 (2H, m), 3.80-3.98 (2H, m), 3.71-3.79 (4H, m), 3.48-3.71 (6H, m), 3.24-3.44 (4H, m), 2.89-3.06 (4H, m), 2.26-2.43 (2H, m), 2.25 (3H, s), 1.64-1.87 (3H, m), 1.51 (9H, s). Mass Spectrum (ESI) m/e=637.5 (M+1).

Example 138

1'-(5,7-Difluoro-3-methyl-2-(1-piperazinyl)-4-quinolinyl)-6'-(4-morpholinyl)-1',2,2',3,5,6-hexahydrospiro[pyran-4,3'-pyrrolo[3,2-b]pyridine]

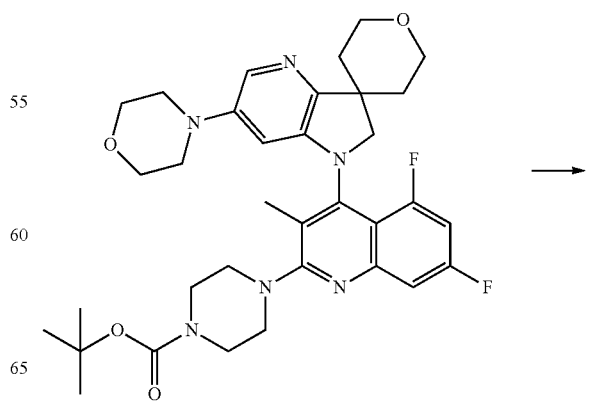

-continued

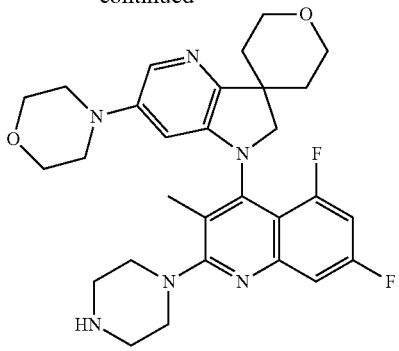

Tert-Butyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate (450 mg, 0.70 mmol) was dissolved in DCM (5.0 mL) and cooled to 0° C. TFA (5.0 mL, 65.0 mmol) was then added and the reaction mixture was allowed to warm to rt and stirred for 2.5 h. The reaction was diluted with DCM and concentrated to dryness. The residue was then converted to the free amine by eluting through an SCX column with 0 to 2M ammonia in MeOH to give 1'-(5,7-difluoro-3-methyl-2-(1-piperazinyl)-4-quinolinyl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 7.56 (1H, d, J=2.3 Hz), 7.36 (1H, ddd, J=9.9, 2.5, 1.3 Hz), 6.73 (1H, ddd, J=11.8, 9.1, 2.5 Hz), 5.66 (1H, d, J=2.3 Hz), 4.04-4.21 (2H, m), 3.80-3.97 (2H, m), 3.70-3.79 (4H, m), 3.56 (2H, qd, J=11.6, 2.4 Hz), 3.27-3.46 (4H, m), 3.02-3.18 (4H, m), 2.90-3.02 (4H, m), 2.26-2.38 (2H, m), 2.24 (3H, s), 1.97 (1H, br. s.), 1.79 (1H, d, J=13.3 Hz), 1.70 (1H, dd, J=13.6, 1.9 Hz). Mass Spectrum (ESI) m/e=537.3 (M+1).

Example 139

1-(7-Fluoro-3-methyl-2-(2-pyridinyl)-4-quinolinyl)-6-(4-morpholinyl)-1,2,2',3',5',6'-hexahydrospiro[indole-3,4'-thiopyran]1',1'-dioxide 6-Bromo-2',3',5',6'-tetrahydrospiro[indole-3,4'-thiopyran] and 4-bromo-2',3',5',6'-tetrahydrospiro[indole-3,4'-thiopyran

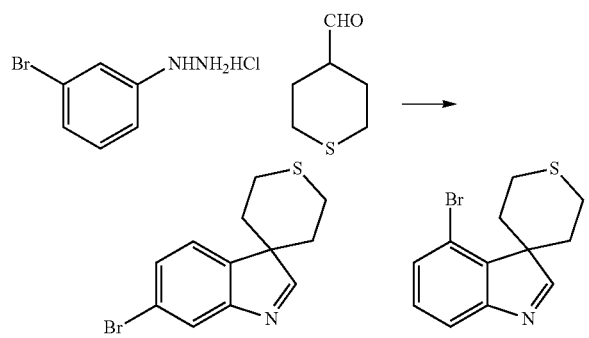

To a stirred ice cooled solution of tetrahydro-2H-thiopyran-4-carbaldehyde (2.1 g, 16.1 mmol) in DCM (30 mL) was added 3-bromophenylhydrazine hydrochloride (1.0 eq., 3.6 g) in one portion. The resulting mixture was stirred at 0° C. for 10 min before TFA (3.0 eq., 5.52 g) was added dropwise via syringe. The resulting mixture was stirred at 0° C. for 10 min and then at rt for 4 h. After this time the mixture was poured into ice and NH₃H₂O (28%) and extracted with EtOAc. The combined organic extracts were washed with brine, dried over anhydrous Na₂SO₄, and concentrated in vacuo. The residue was dissolved in benzene and evaporated in vacuo to give 6-bromo-2',3',5',6'-tetrahydrospiro[indole-3,4'-thiopyran] and 4-bromo-2',3',5',6'-tetrahydrospiro[indole-3,4'-thiopyran] in a ratio of 1 to 1.3. Mass Spectrum (ESI) m/e=282.0 [(M+1) ($^{79}$Br)] and 284.0 [(M+1) ($^{81}$Br)].

6-Bromo-1,2,2',3',5',6'-hexahydrospiro[indole-3,4'-thiopyran] and 4-bromo-1,2,2',3',5',6'-hexahydrospiro[indole-3,4'-thiopyran]

To a stirred solution of the crude mixture of 6-bromo-2',3',5',6'-tetrahydrospiro-[indole-3,4'-thiopyran] and 4-bromo-2',3',5',6'-tetrahydrospiro[indole-3,4'-thiopyran] (4.9 g, 17.5 mmol) in toluene (80 mL) at 80° C. was added dropwise via syringe Red-AL (15 mL) under a N₂ atmosphere. The resulting mixture was stirred at 80° C. for 1.5 h. After this time the mixture was cooled in an ice bath and carefully quenched with and ice cold 2 N aqueous NaOH solution. The reaction mixture was further diluted with ice-cold aqueous 2 N NaOH and extracted with EtOAc. The combined organic extracts were dried over anhydrous Na₂SO₄, concentrated in vacuo and purified by column chromatography (EtOAc:hexanes) to give: 6-bromo-1,2,2',3',5',6'-hexahydrospiro[indole-3,4'-thiopyran] (1$^{st}$ eluted isomer): 1H NMR (400 MHz, chloroform-d) δ ppm 6.89-6.94 (1H, m), 6.81-6.87 (1H, m), 6.75 (1H, d, J=1.2 Hz), 3.78 (1H, br. s.), 3.44 (2H, s), 2.69-2.83 (2H, m), 2.60 (2H, d, J=14.1 Hz), 1.87-2.07 (4H, m). Mass Spectrum (ESI) m/e=284.0 [(M+1) ($^{79}$Br)] and 286.0 [(M+1) ($^{81}$Br)]; 4-bromo-1,2,2',3',5',6'-hexahydrospiro[indole-3,4'-thiopyran] (2$^{nd}$ eluted isomer): 1H NMR (400 MHz, chloroform-d) δ ppm 6.80-6.92 (2H, m), 6.55 (1H, d, J=7.4 Hz), 4.04 (0H, br. s.), 3.51 (2H, s), 2.75-2.90 (4H, m), 2.53-2.63 (2H, m), 1.881.99 (2H, m). Mass Spectrum (ESI) m/e=284.0 [(M+1) ($^{79}$Br)] and 286.0 [(M+1) ($^{81}$Br)]. -

1-Acetyl-6-bromo-1,2,2',3',5',6'-hexahydrospiro[indole-3,4'-thiopyran]

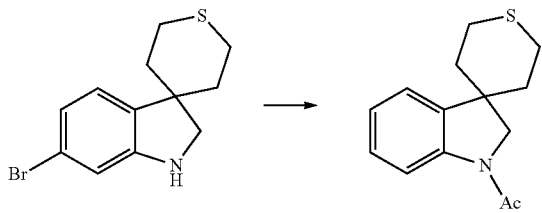 [SMILES: Brc1ccc2c(c1)NCC21CCSCC1 ; CC(=O)N1CC2(CCSCC2)c2ccccc21]

To a stirred ice-cooled solution of 6-bromo-1,2,2',3',5',6'-hexahydrospiro[indole-3,4'-thiopyran] (0.7 g, 2.46 mmol), 4-dimethylaminopyridine (0.03 g, 0.25 mmol) and Et$_3$N (0.37 g, 3.69 mmol) in DCM (25 mL) was added acetyl chloride (0.21 mL, 2.96 mmol) via syringe. The resulting mixture was stirred at 0° C. for 5 min and at rt for 1.5 h. After this time the mixture was poured into ice and 2N aqueous HCl and the mixture was extracted with EtOAc. The combined organic extracts were washed with brine, saturated aqueous NaHCO$_3$, brine, and dried over anhydrous Na$_2$SO$_4$. Purification by column chromatography (EtOAc:hexanes) gave 1-acetyl-6-bromo-1,2,2',3',5',6'-hexahydrospiro[indole-3,4'-thiopyran] as an off-white solid. Mass Spectrum (ESI) m/e=326.0 [(M+1) ($^{79}$Br)] and 328.0 [(M+1) ($^{81}$Br)].

1-Acetyl-6-bromo-1,2,2',3',5',6'-hexahydrospiro[indole-3,4'-thiopyran]1',1'-dioxide

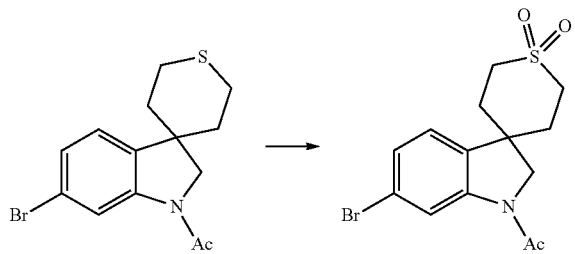 [SMILES: CC(=O)N1CC2(CCSCC2)c2ccc(Br)cc21 ; CC(=O)N1CC2(CCS(=O)(=O)CC2)c2ccc(Br)cc21]

To a stirred ice-cooled suspension of crude 1-acetyl-6-bromo-1,2,2',3',5',6'-hexahydrospiro[indole-3,4'-thiopyran] (0.68 g, 2.1 mmol) in MeOH (40 mL), H$_2$O (5 mL) and acetone (10 mL) was added oxone (2.58 g, 4.20 mmol) in H$_2$O (15 mL). The resulting mixture was stirred at rt for 20 h. After this time the mixture was poured into ice and saturated aqueous NH$_4$Cl and extracted with EtOAc. The combined organic extracts were washed with brine, dried over Na$_2$SO$_4$, and concentrated in vacuo to give 1-acetyl-6-bromo-1,2,2',3',5',6'-hexahydrospiro-[indole-3,4'-thiopyran]1',1'-dioxide as a white solid. Mass Spectrum (ESI) m/e=358.0 [(M+1) ($^{79}$Br)] and 360.0 [(M+1) ($^{81}$Br)].

6-Bromo-1,2,2',3',5',6'-hexahydrospiro[indole-3,4'-thiopyran]1',1'-dioxide

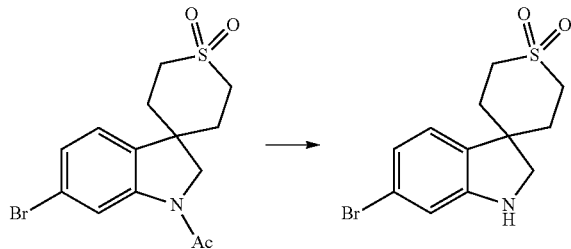 [SMILES: CC(=O)N1CC2(CCS(=O)(=O)CC2)c2ccc(Br)cc21 ; O=S1(=O)CCC2(CC1)CNc1cc(Br)ccc12]

A mixture of 1-acetyl-6-bromo-1,2,2',3',5',6'-hexahydrospiro[indole-3,4'-thiopyran]1',1'-dioxide (0.75 g, 2.1 mmol) and 5 N HCl (8 mL) in MeOH (20 mL) was heated at reflux for 3 h. After this time the solvent was removed in vacuo to give 6-bromo-1,2,2',3',5',6'-hexahydrospiro[indole-3,4'-thiopyran]1',1'-dioxide as an off-white solid. Purification by column chromatography gave 6-Bromo-1,2,2',3',5',6'-hexahydrospiro[indole-3,4'-thiopyran]1',1'-dioxide. Mass Spectrum (ESI) m/e=316.0 [(M+1) ($^{79}$Br)] and 318.0 [(M+1) ($^{81}$Br)]

tert-Butyl 6-bromo-2',3',5',6'-tetrahydrospiro[indole-3,4'-thiopyran]-1(2H)-carboxylate 1',1'-dioxide

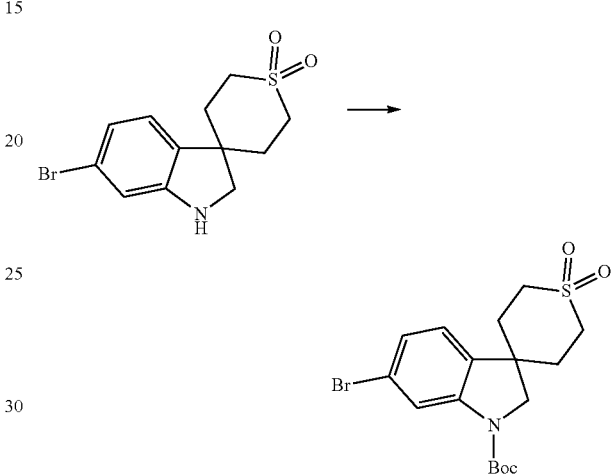

To a stirred suspension of 6-bromo-1,2,2',3',5',6'-hexahydrospiro[indole-3,4'-thiopyran]1',1'-dioxide (225 mg, 0.712 mmol) in THF:DCM (4 mL: 2 mL) was added di-tert-butyl dicarbonate (186 mg, 0.854 mmol), triethylamine (298 µL, 2.135 mmol), 4-dimethylaminopyridine (17.39 mg, 0.142 mmol) and the reaction was stirred at rt for 5 h. After this time the reaction was treated with more 4-dimethylaminopyridine (17.39 mg, 0.142 mmol) and di-tert-butyl dicarbonate (186 mg, 0.854 mmol) and it was stirred at rt overnight. At this time the reaction was partitioned between DCM (80 mL) and water (30 mL). The separated organic layer was washed with 1.0M aqueous HCl (20 mL) and NaHCO$_3$ (20 mL, saturated aqueous solution) and then it was dried over MgSO$_4$, filtered and evaporated in vacuo to give tert-butyl 6-bromo-2',3',5',6'-tetrahydrospiro[indole-3,4'-thiopyran]-1(2H)-carboxylate 1',1'-dioxide. Mass Spectrum (ESI) m/e=437.9 [(M+1) ($^{79}$Br)] and 440.0 [(M+1) ($^{81}$Br)]

tert-Butyl 6-(4-morpholinyl)-2',3',5',6'-tetrahydrospiro[indole-3,4'-thiopyran]-1(2H)-carboxylate 1',1'-dioxide

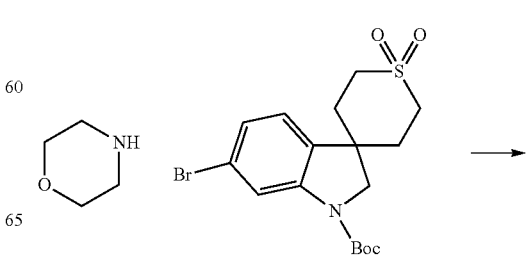

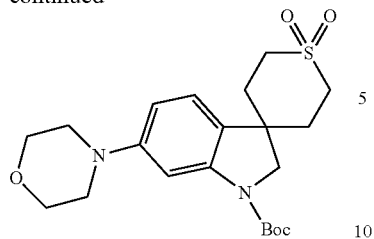

Prepared according to procedure N by stirring tert-butyl 6-bromo-2',3',5',6'-tetrahydrospiro[indole-3,4'-thiopyran]-1(2H)-carboxylate 1',1'-dioxide (200 mg, 0.48 mmol), morpholine (62.8 µL, 0.721 mmol), sodium tert-butoxide, Pd₂dba₃ (44 mg, 0.048 mmol) and XPhos (45.8 mg, 0.096 mmol) in toluene (6 mL) at 100° C. for 2 h. Purification by column chromatography (hexanes:EtOAc, 1:0 to 1:1 as eluant) gave tert-butyl 6-(4-morpholinyl)-2',3',5',6'-tetrahydrospiro[indole-3,4'-thiopyran]-1(2H)-carboxylate 1',1'-dioxide. Mass Spectrum (ESI) m/e=423.0 (M+1).

6-Morpholin-4-yl-1,2,2',3',5',6'-hexahydrospiro[indole-3,4'-thiopyran]1',1'-dioxide

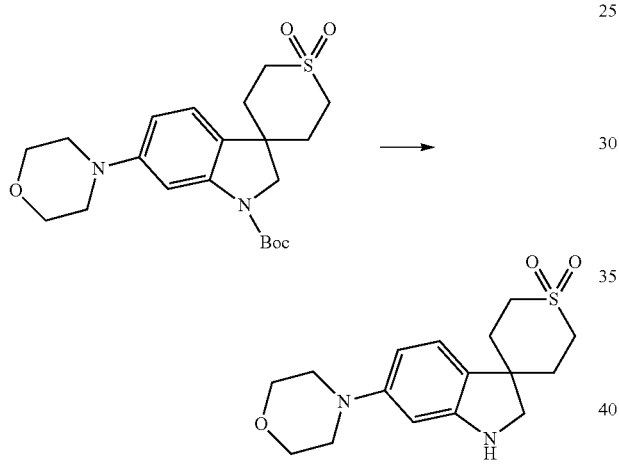

To a stirred solution of tert-butyl 6-(4-morpholinyl)-2',3',5',6'-tetrahydrospiro-[indole-3,4'-thiopyran]-1(2H)-carboxylate 1',1'-dioxide (60 mg, 0.142 mmol) in DCM (1 mL) was added TFA (438 µL, 5.68 mmol) and the reaction was stirred at rt for 1 h. After this time the reaction was evaporated in vacuo and dried on the vacuum pump overnight. The resulting residue was then partitioned between DCM (40 mL) and NaHCO₃ (10 mL, sat. aqueous solution). The separated organic layer was dried over MgSO₄, filtered and evaporated in vacuo to give 6-morpholin-4-yl-1,2,2',3',5',6'-hexahydrospiro[indole-3,4'-thiopyran]1',1'-dioxide. Mass Spectrum (ESI) m/e=323.2 (M+1).

1-(7-Fluoro-3-methyl-2-(2-pyridinyl)-4-quinolinyl)-6-(4-morpholinyl)-1,2,2',3',5',6'-hexahydrospiro[indole-3,4'-thiopyran]1',1'-dioxide

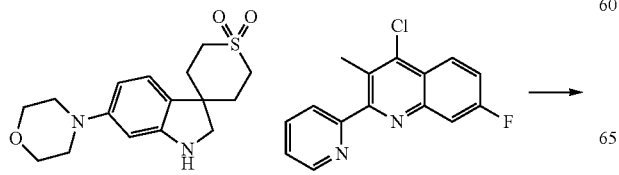

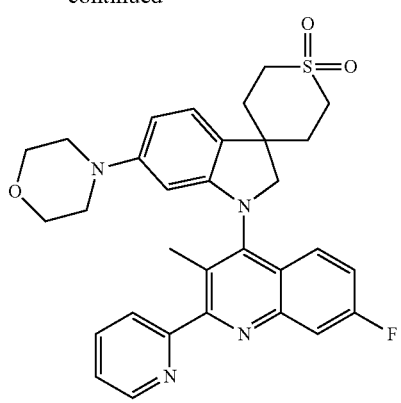

Prepared according to procedure Y using 4-chloro-7-fluoro-3-methyl-2-(pyridin-2-yl)quinoline (29.6 mg, 0.109 mmol), 6-morpholin-4-yl-1,2,2',3',5',6'-hexahydrospiro[indole-3,4'-thiopyran]1',1'-dioxide (35 mg, 0.109 mmol), sodium tert-butoxide (20.9 mg, 0.217 mmol) and XPhos precatalyst (8.02 mg, 10.86 µmol). Purification by reverse phase HPLC gave 1-(7-fluoro-3-methyl-2-(2-pyridinyl)-4-quinolinyl)-6-(4-morpholinyl)-1,2,2',3',5',6'-hexahydrospiro[indole-3,4'-thiopyran]1',1'-dioxide. 1H NMR (400 MHz, chloroform-d) δ ppm 8.74 (1H, dt, J=4.9, 1.4 Hz), 7.82-7.96 (3H, m), 7.75 (1H, dd, J=9.2, 6.1 Hz), 7.39-7.44 (1H, m), 7.24-7.29 (1H, m), 7.19 (1H, d, J=8.2 Hz), 6.35 (1H, dd, J=8.2, 2.2 Hz), 5.61 (1H, d, J=2.2 Hz), 3.94-3.99 (1H, m), 3.87-3.92 (1H, m), 3.68-3.78 (4H, m), 3.07-3.26 (4H, m), 2.91-3.03 (4H, m), 2.61-2.76 (2H, m), 2.29-2.49 (5H, m). Mass Spectrum (ESI) m/e=559.0 (M+1)

Example 140

1'-(5,7-Difluoro-3-methyl-2-(4-(methylsulfonyl)-1-piperazinyl)-4-quinolinyl)-6'-(4-morpholinyl)-1',2,2',3,5,6-hexahydrospiro[pyran-4,3'-pyrrolo[3,2-b]pyridine]

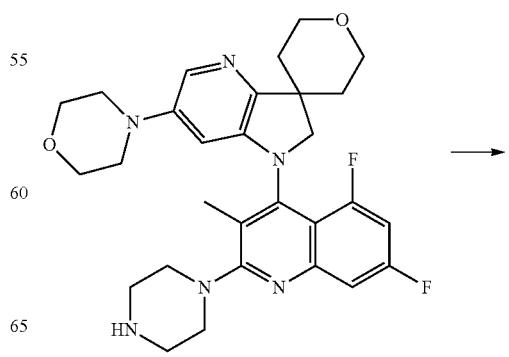

-continued

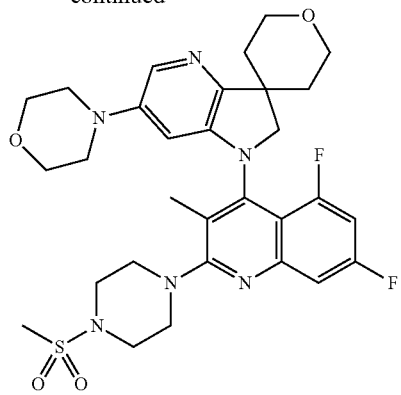

1'-(5,7-difluoro-3-methyl-2-(piperazin-1-yl)quinolin-4-yl)-6'-morpholino-1',2,2',3,5,6-hexahydrospiro[pyran-4,3'-pyrrolo[3,2-b]pyridine] (50 mg, 0.093 mmol) in DCM (5.0 mL) was treated with triethylamine (0.019 mL, 0.140 mmol) and methanesulfonyl chloride (7.3 µL, 0.093 mmol) and the reaction was stirred at rt overnight. After this time the reaction was partitioned between EtOAc and water. The separated organic layer was dried over MgSO$_4$ and evaporated in vacuo. Purification by reverse-phase HPLC (10% to 95% acetonitrile in water) gave 1'-(5,7-difluoro-3-methyl-2-(4-(methylsulfonyl)piperazin-1-yl)quinolin-4-yl)-6'-morpholino-1',2,2',3,5,6-hexahydrospiro[pyran-4,3'-pyrrolo[3,2-b]pyridine]. 1H NMR (400 MHz, chloroform-d) δ ppm 7.57 (1H, d, J=2.3 Hz), 7.37 (1H, dt, J=9.8, 1.3 Hz), 6.78 (1H, ddd, J=11.8, 9.0, 2.4 Hz), 5.65 (1H, d, J=2.3 Hz), 4.04-4.25 (2H, m), 3.83-3.97 (2H, m), 3.69-3.78 (4H, m), 3.30-3.65 (10H, m), 2.90-3.09 (4H, m), 2.86 (3H, s), 2.26-2.39 (2H, m), 2.25 (3H, s), 1.78 (1H, d, J=13.3 Hz), 1.64-1.75 (1H, m). Mass Spectrum (ESI) m/e=615.3 (M+1).

Example 141

4-(3,3-Dimethyl-6-(4-morpholinyl)-2,3-dihydro-1H-pyrrolo-[3,2-b]pyridin-1-yl)-2-(3-fluorophenyl)-3-methyl-1,8-naphthyridine 4-Chloro-2-(3-fluorophenyl)-3-methyl-1,8-naphthyridine

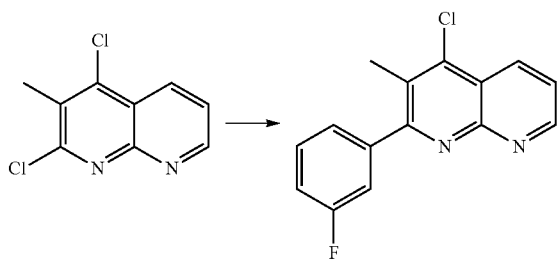 [SMILES: Cc1c(Cl)nc2ncccc2c1Cl ; Cc1c(-c2cccc(F)c2)nc2ncccc2c1Cl]

Prepared according to procedure F using 2,4-dichloro-3-methyl-1,8-naphthyridine (200 mg, 0.939 mmol), 3-fluorophenylboronic acid (131 mg, 0.939 mmol), sodium carbonate (199 mg, 1.877 mmol) and Pd(PPh$_3$)$_4$. Product used without further purification in the next step. Mass Spectrum (ESI) m/e=273.0 (M+1)

4-(3,3-Dimethyl-6-(4-morpholinyl)-2,3-dihydro-1H-pyrrolo[3,2-b]pyridin-1-yl)-2-(3-fluorophenyl)-3-methyl-1,8-naphthyridine

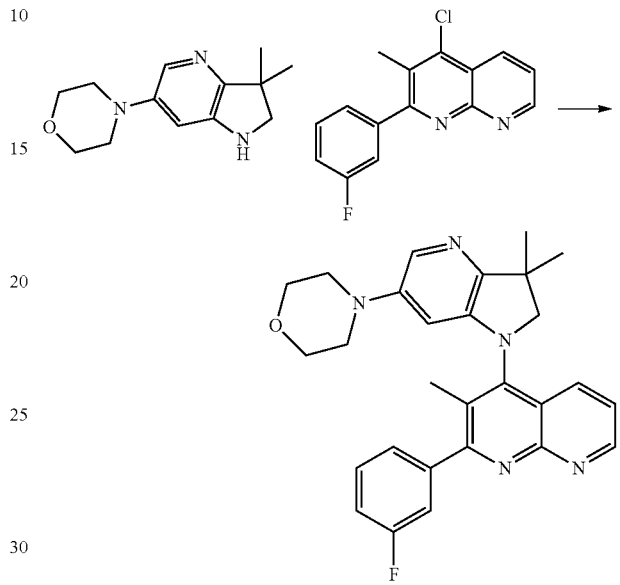

Prepared according to procedure Y using 4-chloro-2-(3-fluorophenyl)-3-methyl-1,8-naphthyridine (70.1 mg, 0.257 mmol), 4-(3,3-dimethyl-2,3-dihydro-1H-pyrrolo[3,2-b]pyridin-6-yl)morpholine (60 mg, 0.257 mmol), sodium tert-butoxide (49.4 mg, 0.514 mmol) and XPhos precatalyst (18.9 mg, 0.026 mmol) in toluene (4 mL) for 2 hours at 110° C. Purification by reverse phase HPLC (10 to 60% acetonitrile in water) gave 4-(3,3-dimethyl-6-(4-morpholinyl)-2,3-dihydro-1H-pyrrolo[3,2-b]pyridin-1-yl)-2-(3-fluorophenyl)-3-methyl-1,8-naphthyridine. 1H NMR (400 MHz, chloroform-d) δ ppm 9.12 (1H, dd, J=4.3, 2.0 Hz), 8.17 (1H, dd, J=8.4, 2.0 Hz), 7.64 (1H, d, J=2.3 Hz), 7.42-7.54 (4H, m), 7.13-7.23 (1H, m), 5.79 (1H, d, J=2.3 Hz), 3.86-3.91 (1H, m), 3.80-3.84 (1H, m), 3.72-3.79 (4H, m), 2.94-3.05 (4H, m), 2.37 (3H, s), 1.58 (3H, s), 1.53 (3H, s). Mass Spectrum (ESI) m/e=470.2 (M+1)

Example 142

1'-(2-(3-Fluorophenyl)-3-methyl-1,8-naphthyridin-4-yl)-6'-(4-morpholinyl)-1',2,2',3,5,6-hexahydrospiro[pyran-4,3'-pyrrolo[3,2-b]pyridine]

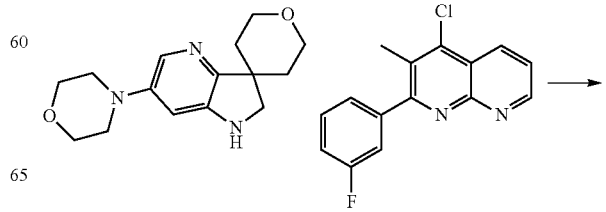

237

-continued

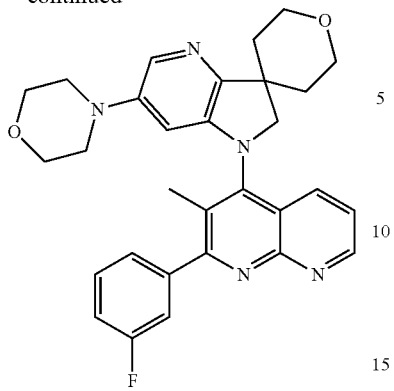

Prepared according to procedure Y using 4-chloro-2-(3-fluorophenyl)-3-methyl-1,8-naphthyridine (49.5 mg, 0.182 mmol), 6'-morpholino-1',2,2',3,5,6-hexahydrospiro[pyran-4,3'-pyrrolo[3,2-b]pyridine] (50 mg, 0.182 mmol), sodium tert-butoxide (34.9 mg, 0.363 mmol) and XPhos precatalyst (13.35 mg, 0.018 mmol) in toluene (4 mL) for 2 hours at 110° C. Purification by reverse phase HPLC (10 to 60% acetonitrile in water) gave 1'-(2-(3-fluorophenyl)-3-methyl-1,8-naphthyridin-4-yl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 9.13 (1H, dd, J=4.3, 2.0 Hz), 8.13 (1H, dd, J=8.2, 2.0 Hz), 7.66 (1H, d, J=2.3 Hz), 7.42-7.54 (4H, m), 7.15-7.23 (1H, m), 5.79 (1H, d, J=2.3 Hz), 4.14-4.21 (2H, m), 3.71-3.82 (4H, m), 3.56-3.65 (2H, m), 2.95-3.06 (4H, m), 2.30-2.43 (5H, m), 1.62-1.89 (4H, m). Mass Spectrum (ESI) m/e=512.2 (M+1).

Example 143

4-(3,3-Dimethyl-6-(4-morpholinyl)-2,3-dihydro-1H-pyrrolo-[3,2-b]pyridin-1-yl)-3-methyl-2-phenyl-1,8-naphthyridine 4-Chloro-3-methyl-2-phenyl-1,8-naphthyridine

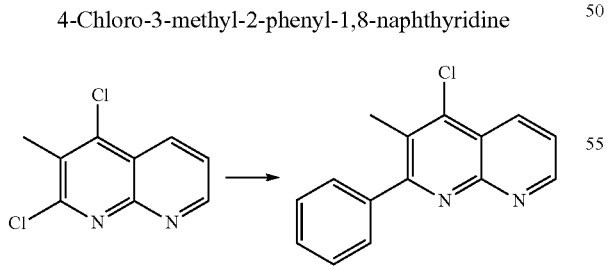

Prepared according to procedure F using 2,4-dichloro-3-methyl-1,8-naphthyridine (150 mg, 0.704 mmol), phenylboronic acid (86 mg, 0.704 mmol), sodium carbonate (149 mg, 1.408 mmol) and Pd(PPh$_3$)$_4$. Product used without further purification in the next step. Mass Spectrum (ESI) m/e=255.0 (M+1).

238

4-(3,3-Dimethyl-6-(4-morpholinyl)-2,3-dihydro-1H-pyrrolo[3,2-b]pyridin-1-yl)-3-methyl-2-phenyl-1,8-naphthyridine

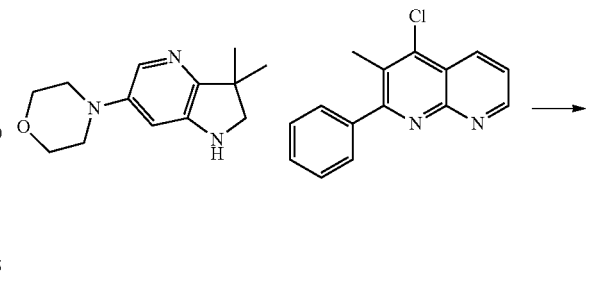

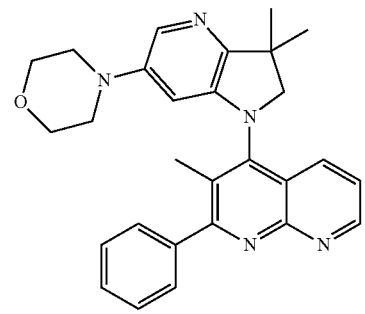

Prepared according to procedure Y using 4-chloro-3-methyl-2-phenyl-1,8-naphthyridine (60 mg, 0.236 mmol), 4-(3,3-dimethyl-2,3-dihydro-1H-pyrrolo[3,2-b]-pyridin-6-yl)morpholine (55 mg, 0.236 mmol), sodium tert-butoxide (45.3 mg, 0.471 mmol) and XPhos precatalyst (17.4 mg, 0.024 mmol). Purification by reverse phase HPLC (10 to 60% acetonitrile in water) gave 4-(3,3-dimethyl-6-(4-morpholinyl)-2,3-dihydro-1H-pyrrolo[3,2-b]pyridin-1-yl)-3-methyl-2-phenyl-1,8-naphthyridine. 1H NMR (400 MHz, chloroform-d) δ ppm 9.10 (1H, dd, J=4.1, 2.0 Hz), 8.16 (1H, dd, J=8.4, 2.0 Hz), 7.67-7.77 (2H, m), 7.62 (1H, d, J=2.3 Hz), 7.40-7.57 (4H, m), 5.80 (1H, d, J=2.3 Hz), 3.79-3.90 (2H, m), 3.70-3.77 (4H, m), 2.88-3.07 (4H, m), 2.36 (3H, s), 1.57 (3H, s), 1.52 (3H, s). Mass Spectrum (ESI) m/e=452.2 (M+1).

Example 144

1'-(3-Methyl-2-phenyl-1,8-naphthyridin-4-yl)-6'-(4-morpholinyl)-1',2,2',3,5,6-hexahydrospiro[pyran-4,3'-pyrrolo[3,2-b]pyridine]

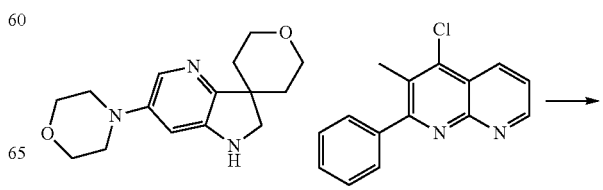

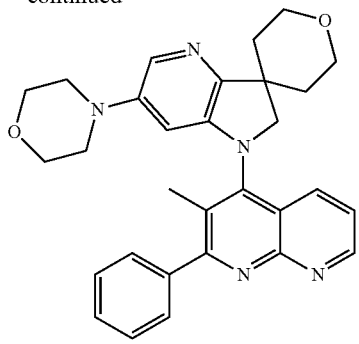

Prepared according to procedure Y using 4-chloro-3-methyl-2-phenyl-1,8-naphthyridine (46.3 mg, 0.182 mmol), 6'-morpholino-1',2,2',3,5,6-hexahydrospiro[pyran-4,3'-pyrrolo[3,2-b]pyridine] (50 mg, 0.182 mmol), sodium tert-butoxide (34.9 mg, 0.363 mmol) and XPhos precatalyst (0.0182, 13.5 mg). Purification by reverse phase HPLC (10 to 60% acetonitrile in water) gave 1'-(3-methyl-2-phenyl-1,8-naphthyridin-4-yl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 9.12 (1H, dd, J=4.1, 2.0 Hz), 8.12 (1H, dd, J=8.4, 2.0 Hz), 7.71-7.77 (2H, m), 7.65 (1H, d, J=2.3 Hz), 7.47-7.56 (3H, m), 7.43 (1H, dd, J=8.3, 4.2 Hz), 5.80 (1H, d, J=2.3 Hz), 4.12-4.21 (2H, m), 4.02 (2H, q, J=9.6 Hz), 3.71-3.80 (4H, m), 3.56-3.65 (2H, m, J=11.4, 11.4, 2.5, 2.4 Hz), 2.95-3.05 (4H, m), 2.28-2.41 (5H, m), 1.75-1.90 (2H, m). Mass Spectrum (ESI) m/e=494.2 (M+1).

Example 145

5'-Bromo-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]

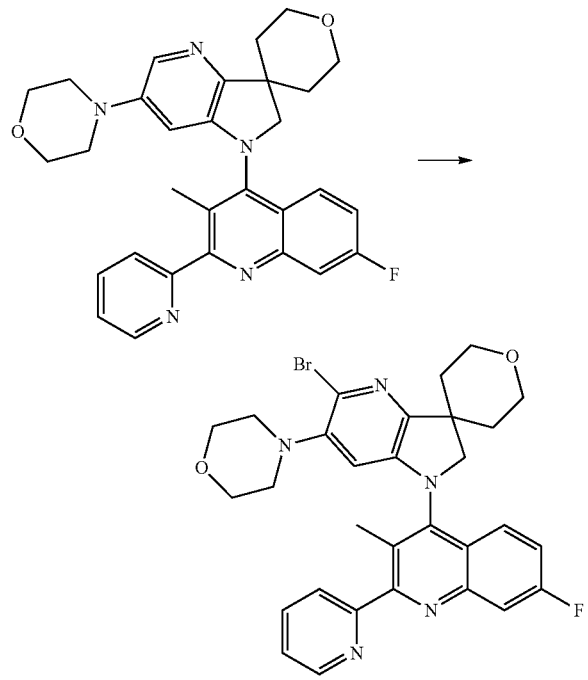

To a stirred solution of 1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] (250 mg, 0.489 mmol) in acetonitrile (6 mL) at 0° C. was added dropwise via syringe over 5 min a solution of N-bromosuccinimide (87 mg, 0.489 mmol) in acetonitrile (4 mL). The reaction was stirred at this temperature for 15 min. After this time the reaction was partitioned between EtOAc (40 mL) and water (15 mL). The separated organic layer was washed with NaHCO$_3$ (15 mL, saturated aqueous solution) and Na$_2$S$_2$O$_3$ (15 mL, saturated aqueous solution) and then it was dried over MgSO$_4$, filtered and evaporated in vacuo to give 5'-bromo-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 8.74 (1H, dt, J=4.8, 1.4 Hz), 7.83-7.99 (3H, m), 7.70 (1H, dd, J=9.2, 5.9 Hz), 7.42 (1H, ddd, J=6.8, 4.7, 2.2 Hz), 7.28-7.34 (1H, m), 5.97 (1H, s), 4.10-4.20 (2H, m), 3.94-4.06 (2H, m), 3.74-3.84 (4H, m), 3.49-3.64 (2H, m), 2.78-2.94 (4H, m), 2.28-2.46 (5H, m), 1.72-1.88 (2H, m). Mass Spectrum (ESI) m/e=590.0 [(M+1) ($^{79}$Br)] and 592.0 [(M+1) ($^{81}$Br)]

Example 146

1'-(7-Fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]-pyridine]-5'-carbonitrile

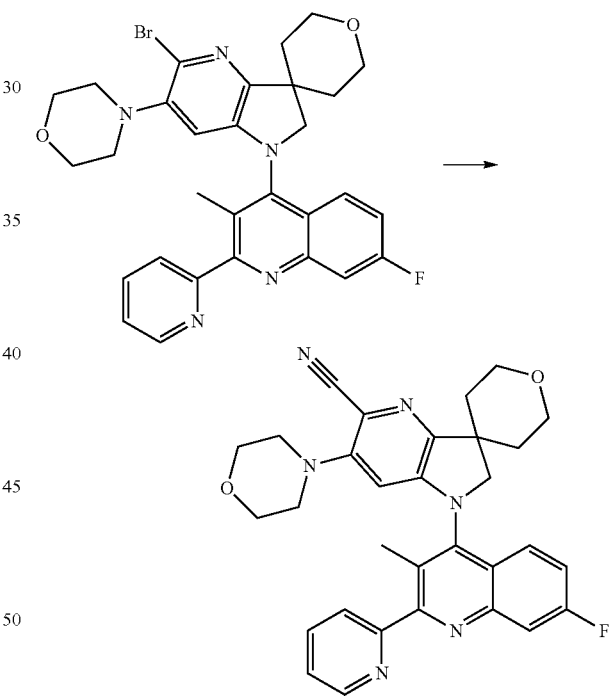

To a stirred solution of 5'-bromo-P-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] (45 mg, 0.076 mmol) in NMP (1.5 mL) was added tri-n-butyltin cyanide (24.09 mg, 0.076 mmol), sodium tert-butoxide (14.65 mg, 0.152 mmol) and XPhos precatalyst (11.2 mg, 0.015 mmol) and the reaction was heated at 140° C. for 2 h in the microwave. After this time the reaction was partitioned between EtOAc (60 mL) and water (30 mL). The separated organic layer was dried over MgSO$_4$, filtered and evaporated in vacuo. Purification by reverse phase HPLC (10 to 60% acetonitrile water) gave 1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]-5'-carbonitrile. 1H NMR (400 MHz, chloroform-d) δ ppm 8.74-8.77 (1H, m), 7.87-7.97 (3H, m), 7.63 (1H, dd, J=9.2, 5.9 Hz), 7.40-7.46 (1H, m), 7.36 (1H, ddd, J=9.2, 8.0, 2.5 Hz), 5.75 (1H, s), 4.15-4.25 (2H, m), 3.99-4.07 (2H, m), 3.80 (4H, t, J=4.7 Hz), 3.54-3.62 (2H, m), 2.95-3.11 (4H, m), 2.27-2.44 (5H, m), 1.73-1.87 (2H, m). Mass Spectrum (ESI) m/e=537.2 (M+1).

Example 147

1'-(7-Fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridin]-5'-amine

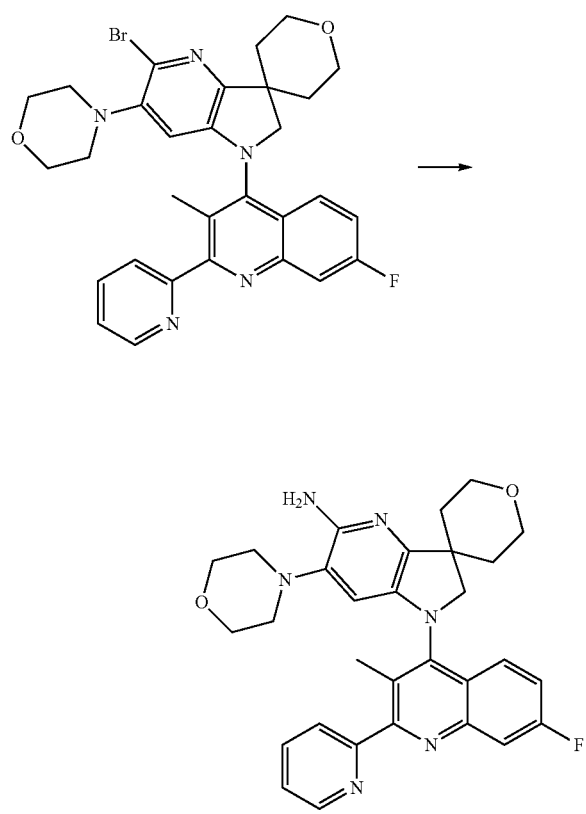

To a stirred solution of 5'-bromo-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] (60 mg, 0.102 mmol) in 1,4-dioxane (1.5 mL) was added 4-methoxybenzylamine (19.78 μL, 0.152 mmol) and sodium tert-butoxide (19.53 mg, 0.203 mmol). The reaction was heated at reflux for 2 h. After this time the reaction was partitioned between EtOAc (50 mL) and water (15 mL). The separated organic layer was dried over MgSO₄, filtered and evaporated in vacuo. The crude mixture was then dissolved in DCM (3 mL) and treated with TFA (0.5 mL) and stirred at rt for 2 h. At this time the reaction was evaporated in vacuo and partitioned between DCM (30 mL) and NaHCO₃ (10 mL, sat. aqueous solution). The separated organic layer was dried over MgSO₄, filtered and evaporated in vacuo. The resulting crude product was purified by reverse phase HPLC (10 to 60% acetonitrile water) to give 1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridin]-5'-amine. 1H NMR (400 MHz, chloroform-d) δ ppm 8.71-8.78 (1H, m), 7.77-7.94 (4H, m), 7.40 (1H, ddd, J=7.2, 4.9, 1.6 Hz), 7.18-7.26 (1H, m), 6.10-6.15 (1H, m), 4.13 (2H, q, J=7.2 Hz), 3.92-4.02 (2H, m), 3.68-3.86 (4H, m), 3.51-3.60 (2H, m), 2.67-2.82 (4H, m), 2.24-2.41 (5H, m), 1.67-1.84 (2H, m). Mass Spectrum (ESI) m/e=527.2 (M+1).

Example 148

5'-Ethenyl-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]-pyridine]

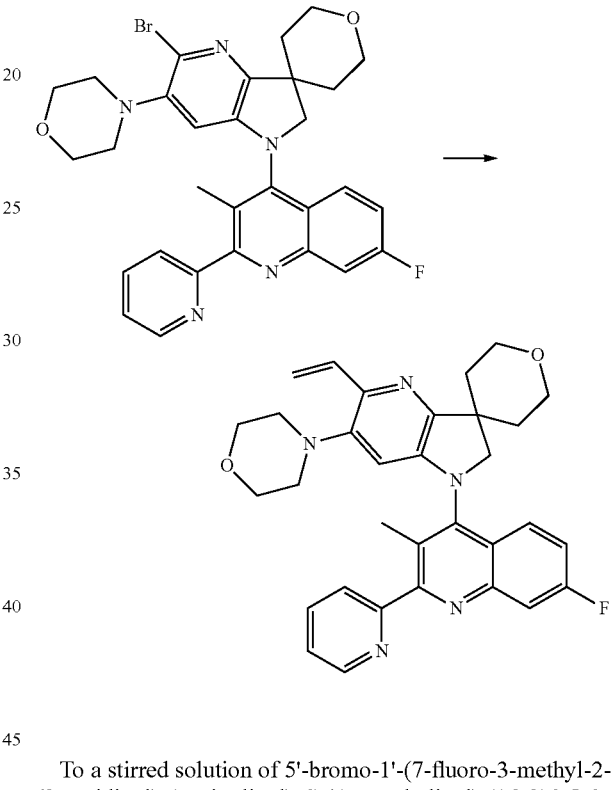

To a stirred solution of 5'-bromo-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] (140 mg, 0.237 mmol) in 1,4-dioxane (4 mL) was added bis(tri-tert-butylphosphine)palladium (0) (12.12 mg, 0.024 mmol), cesium fluoride (36 mg, 0.237 mmol) and tri-n-butyl(vinyl) tin (90 μL, 0.285 mmol) and the reaction was heated at 120° C. for 3 h in the microwave. After this time the reaction was partitioned between EtOAc (50 mL) and water (15 mL). The separated organic layer was dried over MgSO₄, filtered and evaporated in vacuo. The crude reaction was purified by column chromatography on silica gel (DCM to DCM:MeOH:—NH₄OH (9:1:0.4), 1:0 to 2:1 as eluent) to give 5'-ethenyl-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 8.66-8.80 (1H, m), 7.85-7.96 (3H, m), 7.73 (1H, dd, J=9.3, 6.0 Hz), 7.42 (1H, ddd, J=6.8, 4.8, 2.1 Hz), 7.23-7.30 (1H, m), 7.09 (1H, dd, J=17.2, 10.8 Hz), 6.30 (1H, dd, J=17.3, 2.6 Hz), 5.96 (1H, s), 5.18-5.36 (1H, m), 4.23-4.32 (2H, m), 3.93-4.03 (2H, m), 3.77 (4H, t, J=4.6 Hz), 3.61-3.69 (2H, m), 2.68-2.80 (4H, m), 2.27-2.47 (5H, m), 1.77-1.90 (2H, m). Mass Spectrum (ESI) m/e=538.2 (M+1).

Example 149

5'-Chloro-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]-pyridine]

Example 150

4-(5-Bromo-3,3-dimethyl-6-(4-morpholinyl)-2,3-dihydro-1H-pyrrolo[3,2-b]pyridin-1-yl)-7-fluoro-3-methyl-2-(2-pyridinyl)quinoline

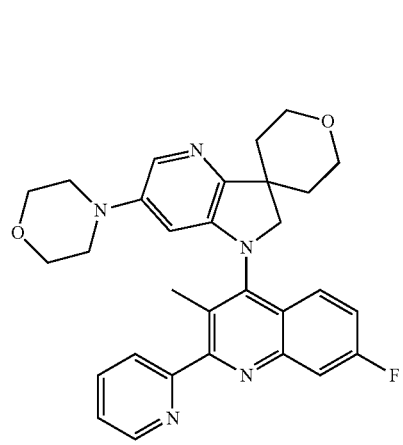

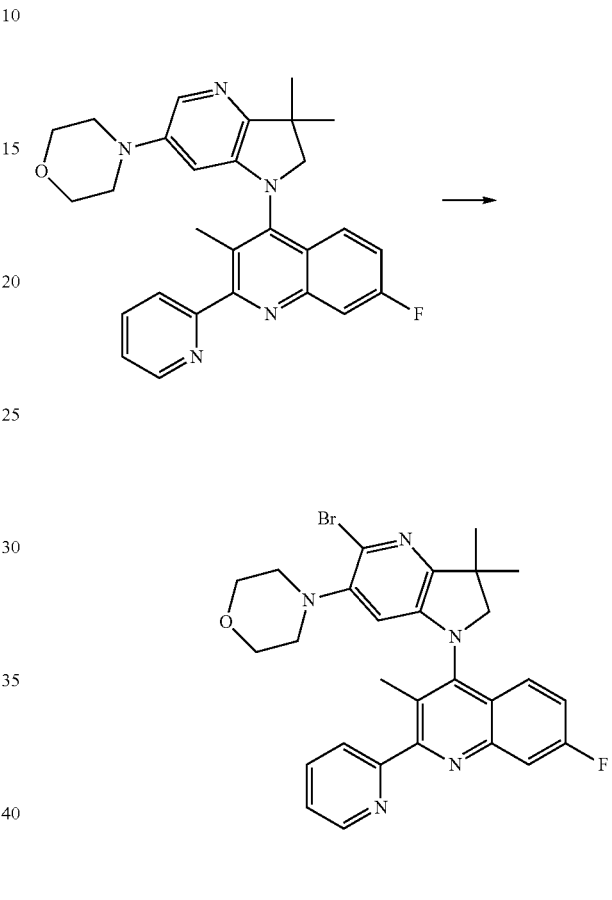

To a stirred solution of 1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] (53 mg, 0.104 mmol) in acetonitrile (4 mL) at 0° C. was added dropwise via syringe over 5 min a solution of n-chlorosuccinimide (13.83 mg, 0.104 mmol) in acetonitrile (2 mL). The reaction was stirred at this temperature for 15 min. After this time the reaction was partitioned between EtOAc (40 mL) and water (15 mL). The separated organic layer was washed with NaHCO$_3$ (15 mL, saturated aqueous solution) and Na$_2$S$_2$O$_3$ (15 mL, saturated aqueous solution) and dried over MgSO$_4$, filtered and evaporated in vacuo. Purification by reverse phase HPLC (10 to 60% acetonitrile in water) gave 5'-chloro-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]. 1H NMR (400 MHz, chloroform-d) δ ppm 8.69-8.78 (1H, m), 7.90-7.96 (2H, m), 7.86 (1H, dd, J=9.8, 2.5 Hz), 7.70 (1H, dd, J=9.2, 5.9 Hz), 7.42 (1H, ddd, J=6.8, 4.8, 2.1 Hz), 7.30 (1H, ddd, J=9.2, 8.0, 2.5 Hz), 5.98 (1H, s), 4.09-4.20 (2H, m), 3.94-4.07 (2H, m), 3.78 (4H, t, J=4.6 Hz), 3.52-3.63 (2H, m), 2.78-2.97 (4H, m), 2.30-2.49 (5H, m), 1.71-1.86 (2H, m). Mass Spectrum (ESI) m/e=546.0 (M+1).

To a stirred solution of 4-(3,3-dimethyl-6-(4-morpholinyl)-2,3-dihydro-1H-pyrrolo[3,2-b]pyridin-1-yl)-7-fluoro-3-methyl-2-(2-pyridinyl)quinoline (250 mg, 0.489 mmol) in acetonitrile (6 mL) at 0° C. was added dropwise via syringe over 5 min a solution of n-bromosuccinimide (76 mg, 0.426 mmol) in acetonitrile (4 mL). The reaction was stirred at this temperature for 15 min. After this time the reaction was partitioned between EtOAc (40 mL) and water (15 mL). The separated organic layer was washed with NaHCO$_3$ (15 mL, saturated aqueous solution) and Na$_2$S$_2$O$_3$ (15 mL, saturated aqueous solution) and dried over MgSO$_4$, filtered and evaporated in vacuo to give 4-(5-bromo-3,3-dimethyl-6-(4-morpholinyl)-2,3-dihydro-1H-pyrrolo[3,2-b]pyridin-1-yl)-7-fluoro-3-methyl-2-(2-pyridinyl)quinoline. 1H NMR (400 MHz, chloroform-d) δ ppm 8.64-8.82 (1H, m), 7.85-7.97 (3H, m), 7.75 (1H, dd, J=9.2, 5.9 Hz), 7.40-7.45 (1H, m), 7.31 (1H, ddd, J=9.3, 8.0, 2.6 Hz), 5.97 (1H, s), 3.71-3.90 (6H, m), 2.77-2.94 (4H, m), 2.38 (3H, s), 1.58 (3H, s), 1.52 (3H, s). Mass Spectrum (ESI) m/e=548.0 [(M+1) ($^{79}$Br)] and 550.0 [(M+1) ($^{81}$Br)]

Example 151

1-(7-Fluoro-3-methyl-2-(2-pyridinyl)-4-quinolinyl)-3,3-dimethyl-6-(4-morpholinyl)-2,3-dihydro-1H-pyrrolo[3,2-b]pyridine-5-carbonitrile

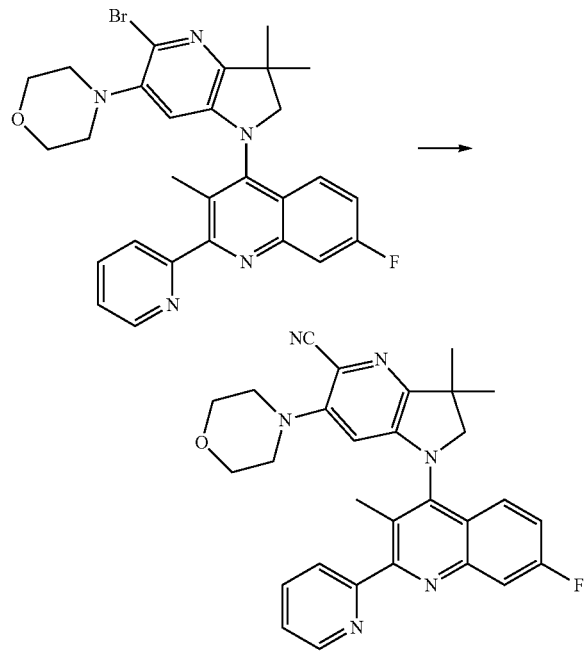

To a stirred solution of 4-(5-bromo-3,3-dimethyl-6-(4-morpholinyl)-2,3-dihydro-1H-pyrrolo[3,2-b]pyridin-1-yl)-7-fluoro-3-methyl-2-(2-pyridinyl)quinoline (61 mg, 0.111 mmol) in NMP (1.5 mL) was added tri-n-butyltin cyanide (35.2 mg, 0.111 mmol), XPhos precatalyst (16.3 mg, 0.022 mmol) and heated at 140° C. for 2 h in the microwave. After this time the reaction was partitioned between EtOAc (60 mL) and water (30 mL). The separated organic layer was dried over MgSO₄, filtered and evaporated in vacuo. Purification by reverse phase HPLC (10 to 60% acetonitrile water) gave 1-(7-fluoro-3-methyl-2-(2-pyridinyl)-4-quinolinyl)-3,3-dimethyl-6-(4-morpholinyl)-2,3-dihydro-1H-pyrrolo[3,2-b]pyridine-5-carbonitrile. 1H NMR (400 MHz, chloroform-d) δ ppm 8.68-8.80 (1H, m), 7.84-7.99 (3H, m), 7.67 (1H, dd, J=9.2, 5.9 Hz), 7.44 (1H, ddd, J=6.9, 4.9, 1.9 Hz), 7.35 (1H, ddd, J=9.2, 8.0, 2.5 Hz), 5.74 (1H, s), 3.87 (2H, s), 3.79 (4H, t, J=4.7 Hz), 2.94-3.11 (4H, m), 2.40 (3H, s), 1.59 (3H, s), 1.53 (3H, s). Mass Spectrum (ESI) m/e=495.0 (M+1).

Example 152

4-(5-Chloro-3,3-dimethyl-6-(4-morpholinyl)-2,3-dihydro-1H-pyrrolo[3,2-b]pyridin-1-yl)-3-methyl-2-(4-methyl-2-pyridinyl)-1,8-naphthyridine

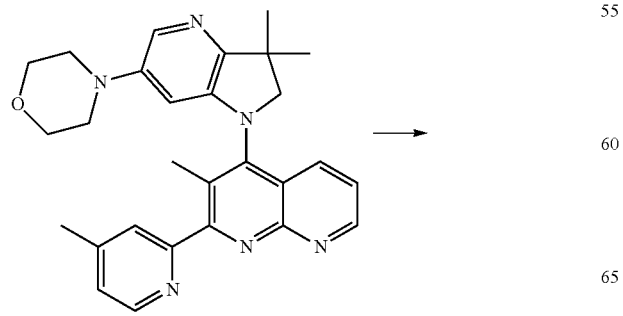

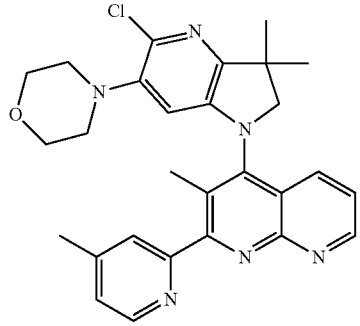

To a stirred solution of 4-(3,3-dimethyl-6-(4-morpholinyl)-2,3-dihydro-1H-pyrrolo[3,2-b]pyridin-1-yl)-3-methyl-2-(4-methyl-2-pyridinyl)-1,8-naphthyridine in acetonitrile (4 mL) at 0° C. was added dropwise via syringe over 5 min a solution of n-chlorosuccinimide (7.44 mg, 0.056 mmol) in acetonitrile (2 mL). The reaction was stirred at this temperature for 15 min. After this time the reaction was partitioned between EtOAc (40 mL) and water (15 mL). The separated organic layer was washed with NaHCO₃ (15 mL, saturated aqueous solution), Na₂S₂O₃ (15 mL, saturated aqueous solution) dried over MgSO₄, filtered and evaporated in vacuo. Purification by reverse phase HPLC (10 to 60 acetonitrile in water) gave 4-(5-chloro-3,3-dimethyl-6-(4-morpholinyl)-2,3-dihydro-1H-pyrrolo[3,2-b]pyridin-1-yl)-3-methyl-2-(4-methyl-2-pyridinyl)-1,8-naphthyridine. 1H NMR (400 MHz, chloroform-d) δ ppm 9.15 (1H, dd, J=4.1, 2.0 Hz), 8.63 (1H, d, J=5.3 Hz), 8.16 (1H, dd, J=8.4, 2.0 Hz), 8.05-8.08 (1H, m), 7.47 (1H, dd, J=8.4, 4.3 Hz), 7.31-7.36 (1H, m), 6.02 (1H, s), 3.87-3.96 (1H, m), 3.82 (1H, d, J=9.4 Hz), 3.78 (4H, t, J=4.6 Hz), 2.86-3.03 (2H, m), 2.76-2.86 (2H, m), 2.55 (3H, s), 2.50 (3H, s), 1.58 (3H, s), 1.53 (3H, s). Mass Spectrum (ESI) m/e=501.0 (M+1).

Example 153

4-(5-Chloro-3,3-dimethyl-6-(4-morpholinyl)-2,3-dihydro-1H-pyrrolo[3,2-b]pyridin-1-yl)-7-fluoro-3-methyl-2-(2-pyridinyl)quinoline

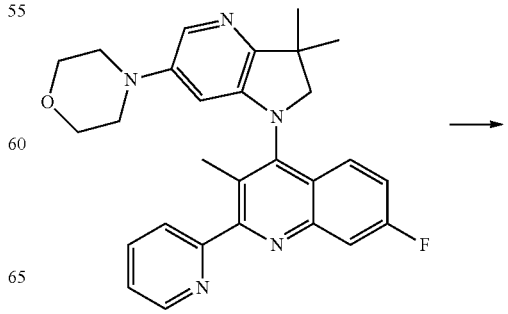

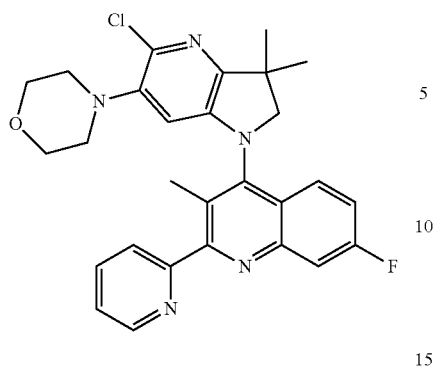

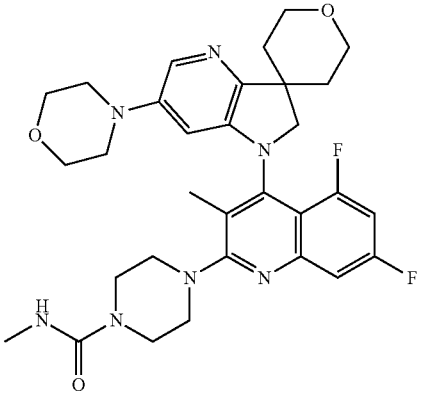

To a stirred solution of 4-(3,3-dimethyl-6-(4-morpholinyl)-2,3-dihydro-1H-pyrrolo[3,2-b]pyridin-1-yl)-7-fluoro-3-methyl-2-(2-pyridinyl)quinoline (40 mg, 0.085 mmol) in acetonitrile (4 mL) at 0° C. was added dropwise via syringe over 5 min a solution of n-chlorosuccinimide (13.65 mg, 0.102 mmol) in acetonitrile (2 mL). The reaction was stirred at this temperature for 15 min. After this time the reaction was partitioned between EtOAc (40 mL) and water (15 mL). The separated organic layer was washed with $NaHCO_3$ (15 mL, saturated aqueous solution), $Na_2S_2O_3$ (15 mL, saturated aqueous solution) dried over $MgSO_4$, filtered and evaporated in vacuo. Purification by reverse phase HPLC (10 to 60% acetonitrile in water) gave 4-(5-chloro-3,3-dimethyl-6-(4-morpholinyl)-2,3-dihydro-1H-pyrrolo[3,2-b]pyridin-1-yl)-7-fluoro-3-methyl-2-(2-pyridinyl)quinoline. 1H NMR (400 MHz, chloroform-d) δ ppm 8.77 (1H, ddd, J=4.9, 1.8, 1.1 Hz), 7.85-8.00 (3H, m), 7.76 (1H, dd, J=9.2, 5.9 Hz), 7.43-7.49 (1H, m), 7.31 (1H, ddd, J=9.2, 8.0, 2.5 Hz), 5.99 (1H, s), 3.75-3.89 (6H, m), 2.88-2.96 (2H, m), 2.78-2.86 (2H, m), 2.38 (3H, s), 1.58 (3H, s), 1.52 (3H, s). Mass Spectrum (ESI) m/e=504.0 (M+1).

1'-(5,7-difluoro-3-methyl-2-(piperazin-1-yl)quinolin-4-yl)-6'-morpholino-1',2,2',3,5,6-hexahydrospiro[pyran-4,3'-pyrrolo[3,2-b]pyridine] (50 mg, 0.093 mmol) was dissolved in DCM (5.0 mL), and treated with methylisocyanate (5.50 μL, 0.093 mmol) and the reaction was stirred at rt for 2.5 h. After this time the reaction was concentrated to dryness and the residue was purified using an SCX column (compound loaded in MeOH and using 2M ammonia in MeOH as eluent) to give 4-(5,7-difluoro-3-methyl-4-(6'-morpholino-2,3,5,6-tetrahydrospiro[pyran-4,3'-pyrrolo[3,2-b]pyridine]-1'(2'H)-yl)quinolin-2-yl)-N-methylpiperazine-1-carboxamide. 1H NMR (400 MHz, chloroform-d) δ ppm 7.55 (1H, d, J=2.3 Hz), 7.34 (1H, dt, J=9.8, 1.3 Hz), 6.75 (1H, ddd, J=11.8, 9.0, 2.4 Hz), 5.65 (1H, d, J=2.3 Hz), 4.69 (1H, q, J=4.2 Hz), 4.03-4.20 (2H, m), 3.80-3.97 (2H, m), 3.68-3.80 (4H, m), 3.48-3.67 (6H, m), 3.27-3.48 (4H, m), 2.90-3.04 (4H, m), 2.85 (3H, d, J=4.5 Hz), 2.19-2.39 (5H, m), 1.78 (1H, d, J=13.5 Hz), 1.69 (1H, d, J=13.5 Hz). Mass Spectrum (ESI) m/e=594.4 (M+1).

Example 155

1-(5,7-Difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-azetidinone Example 154

4-(5,7-Difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-N-methyl-1-piperazinecarboxamide 1-(4-Chloro-5,7-difluoro-3-methylquinolin-2-yl)azetidin-2-one

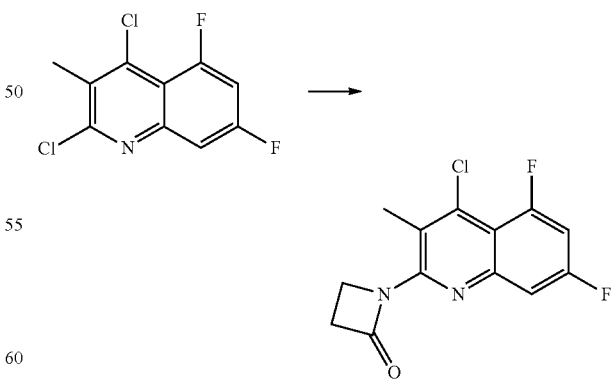

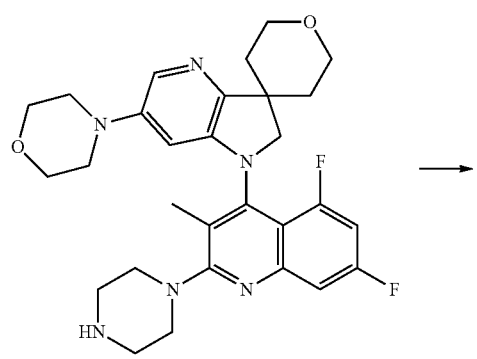

2,4-Dichloro-5,7-difluoro-3-methylquinoline (1.90 g, 7.70 mmol), XantPhos™ (670 mg, 1.20 mmol), azetidin-2-one (550 mg, 7.70 mmol), cesium carbonate (3.50 g, 11.0 mmol), 3 Å activated molecular sieves (1.0 g) and $Pd_2(dba)_3$ (350 mg, 0.39 mmol) were slurried in 1,4-dioxane (26 mL). The reaction was heated in an oil bath at 100° C. for 3 h. After this time the reaction was cooled to rt, diluted with EtOAc and filtered over a pad of Celite™. The filtrate was concentrated and the residue was purified by column chromatography (silica gel, 0 to 30% EtOAc:DCM) to give 1-(4-chloro-5,7-difluoro-3-methylquinolin-2-yl)-azetidin-2-one. Mass Spectrum (ESI) m/e=283.1 (M+1).

1-(5,7-Difluoro-3-methyl-4-(6'-(4-morpholinyl)-2,3,5,6-tetrahydrospiro-[pyran-4,3'-pyrrolo[3,2-b]pyridin]-1'(2'H)-yl)-2-quinolinyl)-2-azetidinone

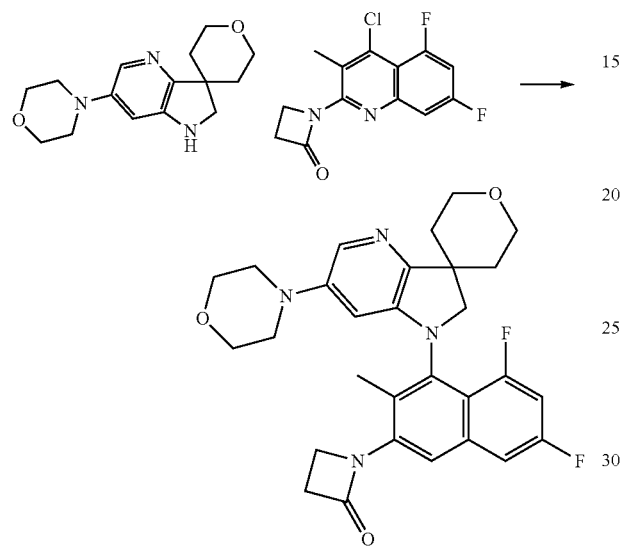

Prepared according to procedure Y using 1-(4-chloro-5,7-difluoro-3-methylquinolin-2-yl)azetidin-2-one (130 mg, 0.44 mmol) and 6'-morpholino-1',2,2',3,5,6-hexahydrospiro[pyran-4,3'-pyrrolo[3,2-b]pyridine] in toluene (except using cesium carbonate as base) to give 1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-azetidinone. 1H NMR (400 MHz, chloroform-d) δ ppm 7.59 (1H, d, J=2.3 Hz), 7.45 (1H, ddd, J=9.5, 2.4, 1.2 Hz), 6.89 (1H, ddd, J=11.8, 9.0, 2.4 Hz), 5.72 (1H, d, J=2.3 Hz), 4.13 (2H, m, J=11.6, 4.2, 4.0, 4.0 Hz), 4.00-4.09 (2H, m), 3.98 (1H, d, J=9.4 Hz), 3.85 (1H, d, J=9.4 Hz), 3.69-3.80 (4H, m), 3.57 (2H, m, J=11.7, 11.7, 2.9, 2.7 Hz), 3.16 (2H, t, J=5.0 Hz), 2.96-3.07 (4H, m), 2.39 (3H, s), 2.31 (2H, dddd, J=15.8, 8.9, 8.6, 4.5 Hz), 1.80 (1H, d, J=14.5 Hz), 1.67-1.75 (1H, m). Mass Spectrum (ESI) m/e=522.4 (M+1).

Example 156

1-(5,7-Difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-4,4-dimethyl-2-pyrrolidinone
1-(4-Chloro-5,7-difluoro-3-methylquinolin-2-yl)-4,4-dimethylpyrrolidin-2-one

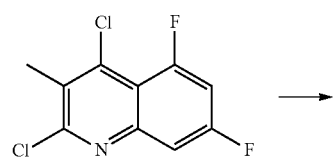

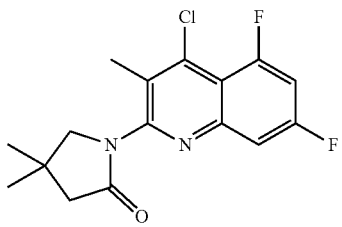

2,4-dichloro-5,7-difluoro-3-methylquinoline (1.50 g, 6.20 mmol), XantPhos (540 mg, 0.93 mmol), 4,4-dimethylpyrrolidin-2-one (700 mg, 6.20 mmol), cesium carbonate (2.80 g, 8.70 mmol), 3 A activated molecular sieves (1.0 g) and Pd$_2$(dba)$_3$ (280 mg, 0.31 mmol) were slurried in 1,4-dioxane (21 mL). The reaction was heated in an oil bath at 100° C. for 1 h. After this time the reaction was cooled to rt, diluted with EtOAc and filtered over a pad of Celite™. The filtrate was concentrated and the residue was purified by column chromatography (silica gel, 0 to 30% EtOAc:DCM as eluant) to give 1-(4-chloro-5,7-difluoro-3-methylquinolin-2-yl)-4,4-dimethylpyrrolidin-2-one. Mass Spectrum (ESI) m/e=325.1 (M+1).

1-(5,7-Difluoro-3-methyl-4-(6'-(4-morpholinyl)-2,3,5,6-tetrahydrospiro-[pyran-4,3'-pyrrolo[3,2-b]pyridin]-1'(2'H)-yl)-2-quinolinyl)-4,4-dimethyl-2-pyrrolidinone

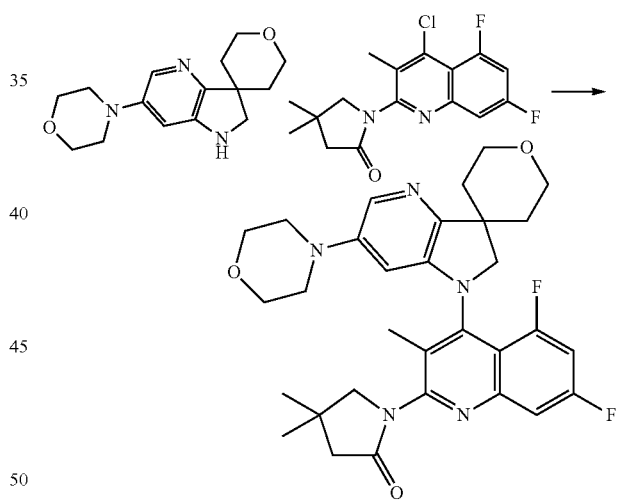

Prepared according to procedure Y using 1-(4-chloro-5,7-difluoro-3-methylquinolin-2-yl)-4,4-dimethylpyrrolidin-2-one (130 mg, 0.39 mmol) and 6'-morpholino-1',2,2',3,5,6-hexahydrospiro[pyran-4,3'-pyrrolo[3,2-b]pyridine] in toluene to give 1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-4,4-dimethyl-2-pyrrolidinone. TFA Salt: 1H NMR (400 MHz, chloroform-d) δ ppm 10.57 (3H, br. s.), 7.70 (1H, d, J=2.2 Hz), 7.54 (1H, ddd, J=9.2, 2.4, 1.3 Hz), 7.05 (1H, ddd, J=12.3, 8.6, 2.5 Hz), 6.15 (1H, d, J=2.0 Hz), 4.27 (1H, d, J=9.8 Hz), 4.05-4.18 (3H, m), 3.96 (1H, d, J=9.8 Hz), 3.70-3.84 (5H, m), 3.37-3.57 (2H, m), 3.08-3.25 (4H, m), 2.51-2.63 (2H, m), 2.50 (3H, s), 2.19 (3H,

Example 157

4-(3,3-Dimethyl-6-(4-morpholinyl)-2,3-dihydro-1H-pyrrolo-[3,2-b]pyridin-1-yl)-2-(5-fluoro-3-pyridinyl)-3-methyl-1,8-naphthyridine 4-Chloro-2-(5-fluoropyridin-3-yl)-3-methyl-1,8-naphthyridine

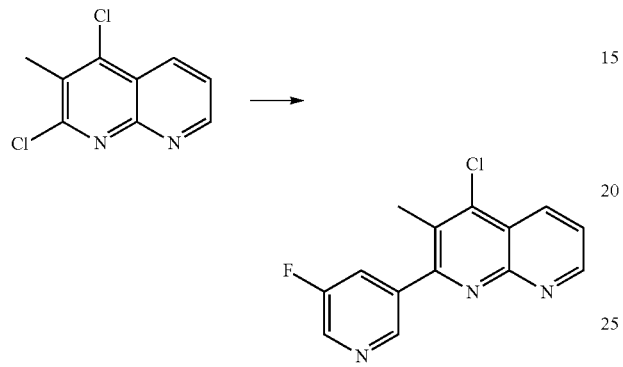

Prepared according to procedure F using 2,4-dichloro-3-methyl-1,8-naphthyridine (165 mg, 0.774 mmol), 5-fluoropyridine-3-boronic acid (109 mg, 0.774 mmol), sodium carbonate (144 mg, 1.75 mmol) and Pd(PPh$_3$)$_4$ (89 mg, 0.077 mmol). Purification by column chromatography (hexanes: EtOAc, 1:0 to 1:1 as eluant) gave 4-chloro-2-(5-fluoropyridin-3-yl)-3-methyl-1,8-naphthyridine. Mass Spectrum (ESI) m/e=274.0 (M+1).

4-(3,3-Dimethyl-6-(4-morpholinyl)-2,3-dihydro-1H-pyrrolo[3,2-b]pyridin-1-yl)-2-(5-fluoro-3-pyridinyl)-3-methyl-1,8-naphthyridine

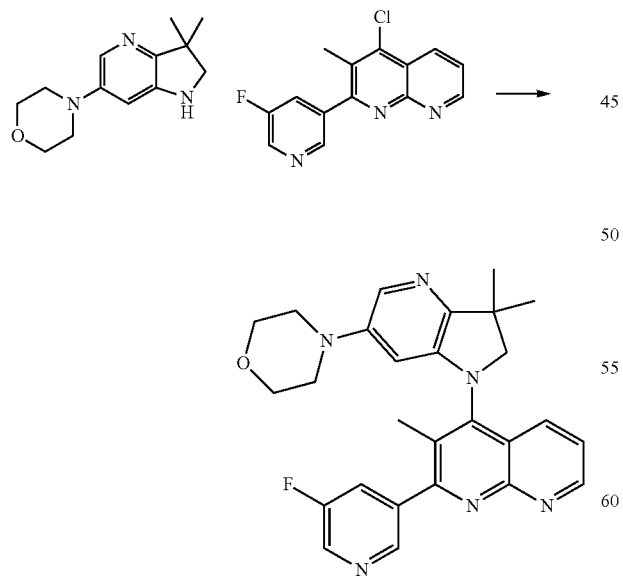

Prepared according to procedure Y using 4-chloro-2-(5-fluoropyridin-3-yl)-3-methyl-1,8-naphthyridine (15 mg, 0.055 mmol), 4-(3,3-dimethyl-2,3-dihydro-1H-pyrrolo[3,2-b]pyridin-6-yl)morpholine (12.79 mg, 0.055 mmol), sodium tert-butoxide (10.53 mg, 0.110 mmol) and XPhos precatalyst (4.03 mg, 5.48 μmol) in toluene (4 mL) at 110° C. for 2 h. Purification by reverse phase HPLC gave 4-(3,3-dimethyl-6-(4-morpholinyl)-2,3-dihydro-1H-pyrrolo[3,2-b]pyridin-1-yl)-2-(5-fluoro-3-pyridinyl)-3-methyl-1,8-naphthyridine. 1H NMR (400 MHz, chloroform-d) δ ppm 9.17 (1H, dd, J=4.1, 2.0 Hz), 8.78 (1H, t, J=1.7 Hz), 8.61 (1H, d, J=2.7 Hz), 8.18 (1H, dd, J=8.4, 2.0 Hz), 7.91 (1H, ddd, J=9.0, 2.9, 1.8 Hz), 7.68 (1H, d, J=2.3 Hz), 7.50 (1H, dd, J=8.4, 4.3 Hz), 5.84 (1H, d, J=2.3 Hz), 3.84-3.94 (2H, m), 3.73-3.80 (4H, m), 3.01 (4H, td, J=4.9, 2.3 Hz), 2.41 (3H, s), 1.63 (3H, s), 1.58 (3H, s). Mass Spectrum (ESI) m/e=471.2 (M+1).

Example 158

4-(3,3-Dimethyl-6-(4-morpholinyl)-2,3-dihydro-1H-pyrrolo-[3,2-b]pyridin-1-yl)-3-methyl-2-(4-methyl-2-pyridinyl)-1,7-naphthyridine 4-Chloro-3-methyl-2-(4-methylpyridin-2-yl)-1,7-naphthyridine

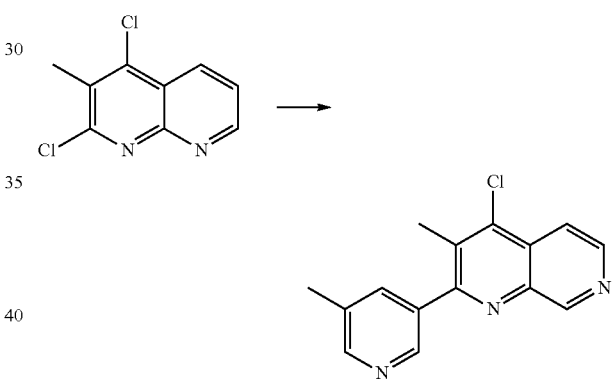

Prepared according to procedure E using 2,4-dichloro-3-methyl-1,7-naphthyridine (100 mg, 0.469 mmol), 4-methyl-2-(tributylstannyl)pyridine (215 mg, 0.563 mmol) and Pd(PPh$_3$)$_4$ (54.2 mg, 0.047 mmol). After purification 4-chloro-3-methyl-2-(4-methylpyridin-2-yl)-1,7-naphthyridine was obtained as a white solid. Mass Spectrum (ESI) m/e=270.0 (M+1).

4-(3,3-Dimethyl-6-(4-morpholinyl)-2,3-dihydro-1H-pyrrolo[3,2-b]pyridin-1-yl)-3-methyl-2-(4-methyl-2-pyridinyl)-1,7-naphthyridine

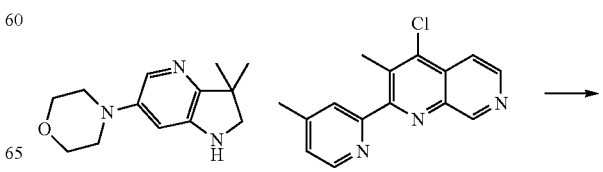

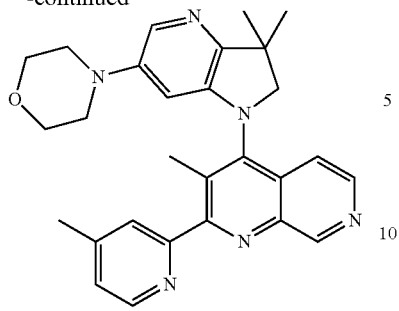

Prepared according to procedure Y using 4-chloro-3-methyl-2-(4-methylpyridin-2-yl)-1,7-naphthyridine (41 mg, 0.174 mmol), 4-chloro-3-methyl-2-(4-methylpyridin-2-yl)-1,7-naphthyridine (47 mg, 0.174 mmol), sodium tert-butoxide (33.5 mg, 0.348 mmol) and XPhos precatalyst (12.8 mg, 0.017 mmol) in toluene (4 mL) at 110° C. for 2 h. Purification by reverse phase HPLC gave 4-(3,3-dimethyl-6-(4-morpholinyl)-2,3-dihydro-1H-pyrrolo[3,2-b]pyridin-1-yl)-3-methyl-2-(4-methyl-2-pyridinyl)-1,7-naphthyridine. 1H NMR (400 MHz, chloroform-d) δ ppm 9.60 (1H, d, J=1.0 Hz), 8.53-8.62 (2H, m), 7.72-7.78 (1H, m), 7.63 (1H, d, J=2.3 Hz), 7.54 (1H, dd, J=5.9, 1.0 Hz), 7.22-7.29 (1H, m), 5.84 (1H, d, J=2.3 Hz), 3.78-3.87 (2H, m), 3.70-3.77 (4H, m), 2.90-3.04 (4H, m), 2.51 (3H, s), 2.44 (3H, s), 1.58 (3H, s), 1.52 (3H, s). Mass Spectrum (ESI) m/e=467.2 (M+1).

Example 159

4-(3,3-Dimethyl-6-(4-morpholinyl)-2,3-dihydro-1H-pyrrolo-[3,2-b]pyridin-1-yl)-2-(5-fluoro-3-pyridinyl)-3-methyl-1,7-naphthyridine 4-Chloro-2-(5-fluoropyridin-3-yl)-3-methyl-1,7-naphthyridine

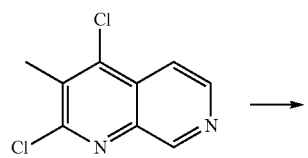

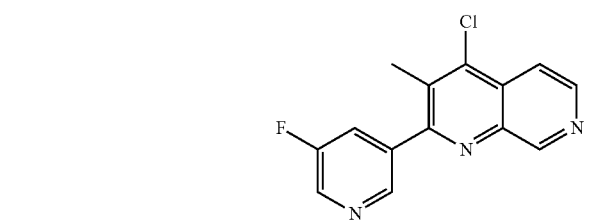

Prepared according to procedure F using 2,4-dichloro-3-methyl-1,7-naphthyridine (100 mg, 0.469 mmol), 5-fluoropyridine-3-boronic acid (66.1 mg, 0.469 mmol), sodium carbonate (87 mg, 0.821 mmol) and Pd(PPh$_3$)$_4$ (54.2 mg, 0.047 mmol). Product used without further purification in the next step. Mass Spectrum (ESI) m/e=274.0 (M+1).

4-(3,3-Dimethyl-6-(4-morpholinyl)-2,3-dihydro-1H-pyrrolo[3,2-b]pyridin-1-yl)-2-(5-fluoro-3-pyridinyl)-3-methyl-1,7-naphthyridine

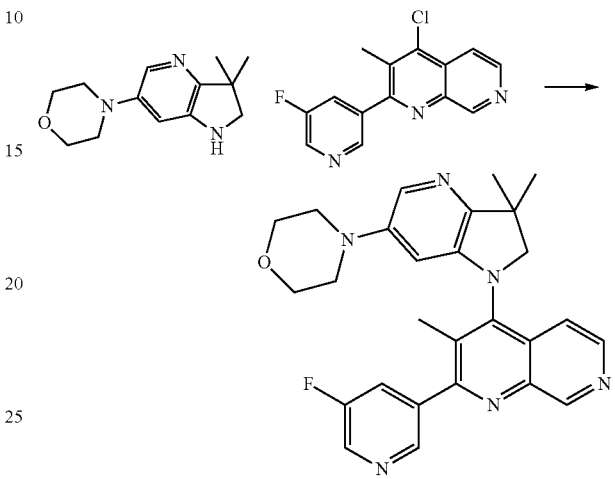

Prepared according to procedure Y using 4-chloro-2-(5-fluoropyridin-3-yl)-3-methyl-1,7-naphthyridine (100 mg, 0.365 mmol), 4-(3,3-dimethyl-2,3-dihydro-1H-pyrrolo[3,2-b]pyridin-6-yl)morpholine (85 mg, 0.365 mmol), sodium tert-butoxide (70.2 mg, 0.731 mmol) and XPhos precatalyst (26.9 mg, 0.037 mmol) in toluene (4 mL) at 110° C. for 2 h. Purification by reverse phase HPLC (10 to 60% acetonitrile in water) gave 4-(3,3-dimethyl-6-(4-morpholinyl)-2,3-dihydro-1H-pyrrolo[3,2-b]pyridin-1-yl)-2-(5-fluoro-3-pyridinyl)-3-methyl-1,7-naphthyridine. 1H NMR (400 MHz, chloroform-d) δ ppm 9.52-9.64 (1H, m), 8.74 (1H, t, J=1.8 Hz), 8.63 (1H, d, J=2.7 Hz), 8.59 (1H, d, J=5.9 Hz), 7.76-7.82 (1H, m), 7.67 (1H, d, J=2.3 Hz), 7.55-7.59 (1H, m), 5.84 (1H, d, J=2.3 Hz), 3.81-3.93 (2H, m), 3.70-3.79 (4H, m), 2.95-3.07 (4H, m), 2.40 (3H, s), 1.60 (3H, s), 1.54 (3H, s). Mass Spectrum (ESI) m/e=471.2 (M+1).

Example 160

1-(7-Fluoro-3-methyl-2-(2-pyridinyl)-4-quinolinyl)-6-(4-morpholinyl)-1,2-dihydrospiro[indole-3,3'-thietane]1',1'-dioxide tert-Butyl 6-bromo-2-oxoindoline-1-carboxylate

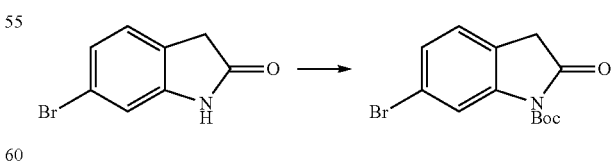

To a solution of 6-bromooxindole (4.91 g, 23.16 mmol) and di-tert-butyl dicarbonate (13.4 mL, 57.9 mmol) in THF (129 mL) was added NaHCO$_3$ (19.4 g, 232 mmol). After stirring at 80° C. for 2 h, the solution was poured into water and extracted with DCM. The organic extracts were purified by column chromatography (eluting with a gradient of 2-10% EtOAc in hexanes) to give tert-butyl 6-bromo-2-oxoindoline- 1-carboxylate as an off-white solid. Mass Spectrum (ESI) m/e=334.0 [(M+Na$^+$) ($^{79}$Br)] and 336.0 [(M+Na$^+$) ($^{81}$Br)].

tert-Butyl 6-bromo-3,3-bis(hydroxymethyl)-2-oxoindoline-1-carboxylate

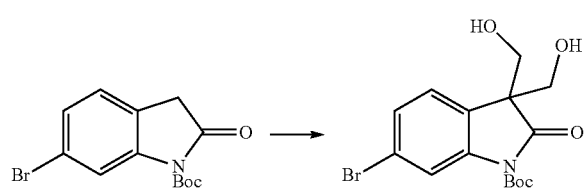 [SMILES: CC(C)(C)OC(=O)N1C(=O)Cc2ccc(Br)cc21 ; CC(C)(C)OC(=O)N1C(=O)C(CO)(CO)c2ccc(Br)cc21]

To a solution of tert-butyl 6-bromo-2-oxoindoline-1-carboxylate (5.20 g, 16.7 mmol) in THF (100 mL) was added potassium carbonate (6.91 g, 50.0 mmol) followed by paraformaldehyde (12.00 g, 400 mmol). The resulting suspension was stirred at rt for 90 min. The suspension was cooled and poured into saturated aqueous NaHCO$_3$ and extracted with DCM. Organic extracts were purified by column chromatography (eluting with a gradient of 0-10% MeOH in DCM) to give tert-butyl 6-bromo-3,3-bis(hydroxymethyl)-2-oxoindoline-1-carboxylate as a white solid. 1H NMR (400 MHz, DMSO-d$_6$) δ ppm 7.90 (1H, s), 7.41 (2H, br. s.), 4.97 (2H, t, J=5.18 Hz), 3.63-3.76 (4H, m), 1.57 (s, 9H).

tert-Butyl 6-bromo-3,3-bis((methylsulfonyloxy)methyl)-2-oxoindoline-1-carboxylate

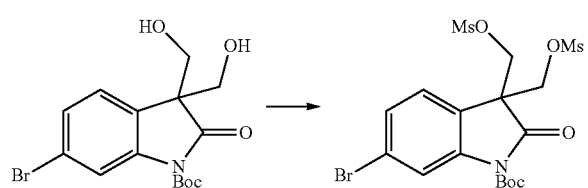 [SMILES: CC(C)(C)OC(=O)N1C(=O)C(CO)(CO)c2ccc(Br)cc21 ; CC(C)(C)OC(=O)N1C(=O)C(COS(C)(=O)=O)(COS(C)(=O)=O)c2ccc(Br)cc21]

To an ice-cooled solution of tert-butyl 6-bromo-3,3-bis(hydroxymethyl)-2-oxoindoline-1-carboxylate (5.27 g, 14.16 mmol) in DCM (94 mL) was added triethylamine (7.89 mL, 56.6 mmol) followed by methanesulfonyl chloride (2.21 mL, 28.3 mmol). The solution was stirred for 1 h and then it was concentrated under reduced pressure. Purification by column chromatography (eluting with a gradient of 10-60% EtOAc in hexanes) gave tert-butyl 6-bromo-3,3-bis((methylsulfonyloxy)methyl)-2-oxoindoline-1-carboxylate as a white foam. Mass Spectrum (ESI) m/e=550.0 [(M+Na$^+$) ($^{79}$Br)] and 552.0 [(M+Na$^+$) ($^{81}$Br)].

6-Bromospiro[indoline-3,3'-thietan]-2-one

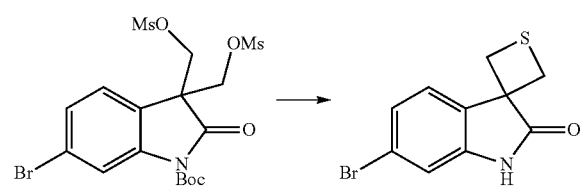 [SMILES: CC(C)(C)OC(=O)N1C(=O)C(COS(C)(=O)=O)(COS(C)(=O)=O)c2ccc(Br)cc21 ; O=C1Nc2cc(Br)ccc2C12CSC2]

To a solution of tert-butyl 6-bromo-3,3-bis((methylsulfonyloxy)methyl)-2-oxoindoline-1-carboxylate (3.70 g, 7.0 mmol) in anhydrous DMF (33 mL, deoxygenated with argon for 10 min) was added sodium sulfide nonahydrate (1.01 g, 4.20 mmol) under an argon atmosphere. The solution was stirred at 110° C. for 3 h, poured into saturated aqueous ammonium chloride solution and extracted with EtOAc. The combined organic extracts were dried over MgSO$_4$, filtered and evaporated in vacuo. Purification by column chromatography (eluting with a gradient of 10-50% EtOAc in hexanes) gave 6-bromospiro[indoline-3,3'-thietan]-2-one as a yellow solid. Mass Spectrum (ESI) m/e=270.0 [(M+1) ($^{79}$Br)] and 271.9 [(M+1) ($^{81}$Br)].

6-Bromo-1,2-dihydrospiro[indole-3,3'-thietane]

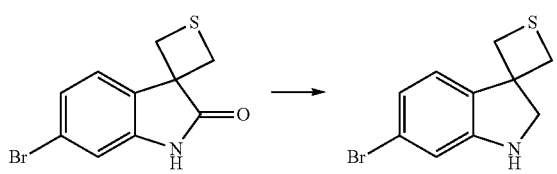 [SMILES: O=C1Nc2cc(Br)ccc2C12CSC2 ; Brc1ccc2c(c1)NCC21CSC1]

To a solution of 6-bromospiro[indoline-3,3'-thietan]-2-one (0.260 g, 0.962 mmol) in toluene (39 mL) was added sodium bis(2-methoxyethoxy)aluminium hydride (60% in toluene, 1.47 mL, 4.81 mmol) dropwise under an atmosphere of argon gas. The solution was stirred at 80° C. for 40 min, cooled in an ice bath, quenched with aqueous 2N NaOH and treated with EtOAc. The combined organic extracts were dried over MgSO$_4$ and concentrated in vacuo to give 6-bromo-1,2-dihydrospiro[indole-3,3'-thietane] as a tan solid. Mass Spectrum (ESI) m/e=256.0 [(M+1) ($^{79}$Br)] and 258.0 [(M+1) ($^{81}$Br)].

1-Acetyl-6-bromo-1,2-dihydrospiro[indole-3,3'-thietane]

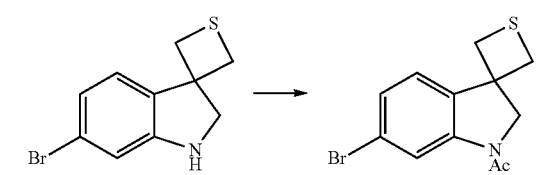

To an ice cooled solution of 6-bromo-1,2-dihydrospiro[indole-3,3'-thietane] (0.25 g, 0.96 mmol), 4-dimethylaminopyridine (5.89 mg, 0.048 mmol), and triethylamine (0.269 mL, 1.928 mmol) in DCM (9.64 mL) was added acetyl chloride (0.137 mL, 1.928 mmol). The solution was stirred for 5 min at this temperature, the ice bath was removed and the solution was stirred at rt for 3 h. The reaction was poured into 2N HCl aqueous solution and extracted with EtOAc. The combined organic extracts were dried over MgSO$_4$ and concentrated under reduced pressure to give 1-acetyl-6-bromo- 1,2-dihydrospiro[indole-3,3'-thietane] as a yellow solid. Mass Spectrum (ESI) m/e=297.9 [(M+1) ($^{79}$Br)] and 300.0 [(M+1) ($^{81}$Br)].

1-Acetyl-6-bromo-1,2-dihydrospiro[indole-3,3'thietane]1',1'-dioxide

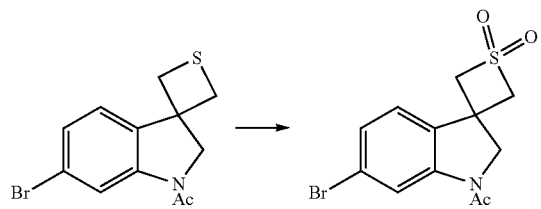

To a stirred ice-cooled solution of 1-acetyl-6-bromo-1,2-dihydrospiro[indole-3,3'-thietane] (0.288 g, 0.97 mmol) in a mixture water (2.4 mL), MeOH (18.9 mL), and acetone (4.7 mL) was added a solution of oxone (1.19 g, 1.93 mmol) in water (1.8 mL). The ice bath was removed and the solution was stirred at rt for 4 h. The mixture was poured into saturated aqueous ammonium chloride and extracted with EtOAc. The combined organic extracts were dried over MgSO$_4$, filtered and evaporated in vacuo to give 1-acetyl-6-bromo-1,2-dihydrospiro[indole-3,3'thietane]1',1'-dioxide as a tan solid. Mass Spectrum (ESI) m/e=330.0 [(M+1) ($^{79}$Br)] and 332.0 [(M+1) ($^{81}$Br)].

1-Acetyl-6-(4-morpholinyl)-1,2-dihydrospiro[indole-3,3'-thietane]1',1'-dioxide

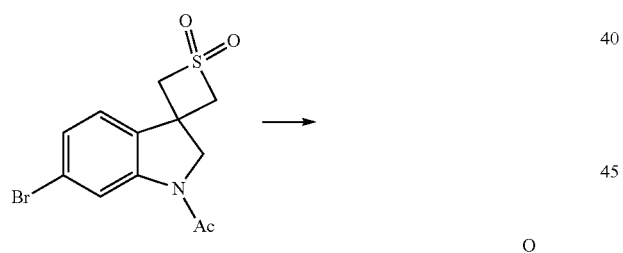

To a microwave vessel was added sodium tert-butoxide (0.045 g, 0.466 mmol), morpholine (0.030 mL, 0.350 mmol), XPhos, Pd$_2$(dba)$_3$ (0.021 g, 0.023 mmol), and 1-acetyl-6-bromo-1,2-dihydrospiro[indole-3,3'thietane]1',1'-dioxide (0.077 g, 0.233 mmol) in 1,4-dioxane (2.3 mL). The suspension was deoxygenated with argon for 5 min and stirred at 110° C. for 90 min under microwave irradiation. The crude mixture was loaded directly onto a silica gel column (eluting with a gradient of 0-10% MeOH in DCM) to give 1-acetyl-6-(4-morpholinyl)-1,2-dihydrospiro[indole-3,3'-thietane]1',1'-dioxide as a tan oil. Mass Spectrum (ESI) m/e=337.1 (M+1).

6-(4-Morpholinyl)-1,2-dihydrospiro[indole-3,3'-thietane]1',1'-dioxide

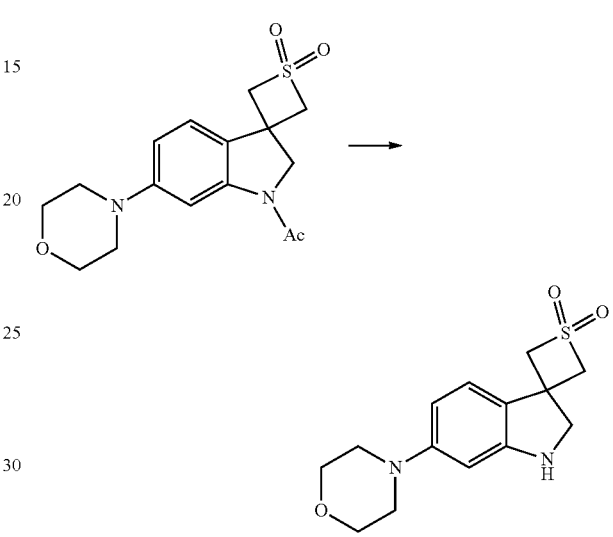

To a solution of 1-acetyl-6-(4-morpholinyl)-1,2-dihydrospiro[indole-3,3'-thietane]1',1'-dioxide (0.046 g, 0.137 mmol) in MeOH (1.367 mL) was added 5.0N HCl solution (0.27 mL, 1.37 mmol). The solution was stirred at 60° C. for 3 h and then it was cooled to rt and poured into saturated aqueous NaHCO$_3$ and extracted with DCM. The organic extracts were dried over MgSO$_4$ and evaporated in vacuo to give 6-(4-morpholinyl)-1,2-dihydrospiro[indole-3,3'-thietane]1',1'-dioxide as a brown solid. Mass Spectrum (ESI) m/e=295.1 (M+1).

1-(7-Fluoro-3-methyl-2-(2-pyridinyl)-4-quinolinyl)-6-(4-morpholinyl)-1,2-dihydrospiro[indole-3,3'-thietane]1',1'-dioxide -continued

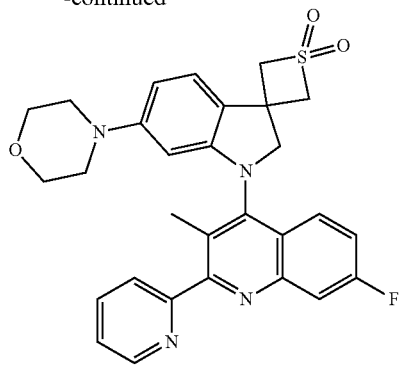

To a microwave vial was added sodium tert-butoxide (0.017 g, 0.177 mmol), ruphos (4.12 mg, 8.83 μmol), 4-chloro-7-fluoro-3-methyl-2-(pyridin-2-yl)-quinoline (0.025 g, 0.093 mmol), 6-(4-morpholinyl)-1,2-dihydrospiro[indole-3,3'-thietane]1',1'-dioxide (0.026 g, 0.088 mmol), and XPhos pre-catalyst (6.5 mg, 8.8 mmol) in toluene (0.6 mL). The suspension was deoxygenated with argon for 5 min then stirred at 100° C. for 1 h under microwave irradiation. Purification by column chromatography (eluting with a gradient of 0-10% MeOH in DCM) gave a yellow solid that was repurified by reverse phase HPLC (10-60% acetonitrile in water) to give 1-(7-fluoro-3-methyl-2-(2-pyridinyl)-4-quinolinyl)-6-(4-morpholinyl)-1,2-dihydrospiro[indole-3,3'-thietane]1',1'-dioxide as a yellow solid. 1H NMR (500 MHz, DMSO-d$_6$) δ ppm 8.71 (1H, d, J=4.89 Hz), 7.99-8.05 (1H, m), 7.83-7.94 (3H, m), 7.50-7.56 (2H, m), 7.49 (1H, d, J=8.31 Hz, 6.40 (1H, dd, J=8.44, 2.08 Hz), 5.58 (1H, d, J=1.96 Hz), 4.72 (1H, dd, J=13.57, 2.32 Hz), 4.55-4.63 (3H, m), 4.35 (1H, d, J=10.03 Hz), 4.25 (1H, d, J=10.03 Hz), 3.58 (4H, t, J=4.89 Hz), 2.82-2.93 (4H, m), 2.24 (3H, s). Mass Spectrum (ESI) m/e=531.2 (M+1).

Example 161

(1-(7-Fluoro-3-methyl-2-(2-pyridinyl)-4-quinolinyl)-6-(4-morpholinyl)-2,3-dihydro-1H-indole-3,3-diyl)dimethanol tert-Butyl 6'-bromo-2,2-dimethyl-2'-oxospiro[[1,3]dioxane-5,3'-indoline]-1'-carboxylate

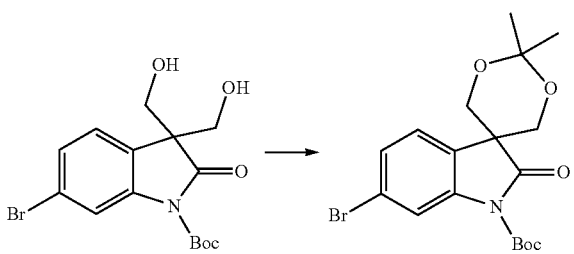 [SMILES: CC(C)(C)OC(=O)N1C(=O)C(CO)(CO)c2ccc(Br)cc21 ; CC(C)(C)OC(=O)N1C(=O)C2(COC(C)(C)OC2)c2ccc(Br)cc21]

To a solution or tert-butyl 6-bromo-3,3-bis(hydroxymethyl)-2-oxoindoline-1-carboxylate (1.00 g, 2.69 mmol) and 4-methylbenzenesulfonic acid hydrate (0.026 g, 0.134 mmol) in DMF (27 mL) was added 2,2-dimethoxypropane (0.49 mL, 4.03 mmol). The solution was stirred at rt overnight followed by the addition of additional 2,2-dimethoxypropane (0.49 mL, 4.03 mmol) and 4-methylbenzenesulfonic acid hydrate (0.026 g, 0.134 mmol). After stirring at 60° C. for 5 h, the solution was poured into saturated aqueous NaHCO$_3$ and extracted with DCM. The combined organic extracts were purified by column chromatography (eluting with a gradient of 0-30% EtOAc in hexanes) to give tert-butyl 6'-bromo-2,2-dimethyl-2'-oxospiro[[1,3]dioxane-5,3'-indoline]-1'-carboxylate as a white solid. Mass Spectrum (ESI) m/e=434.0 [(M+Na$^+$) ($^{79}$Br)] and 436.0 [(M+Na$^+$) ($^{81}$Br)].

2,2-Dimethyl-6'-morpholinospiro[[1,3]dioxane-5,3'-indolin]-2'-one

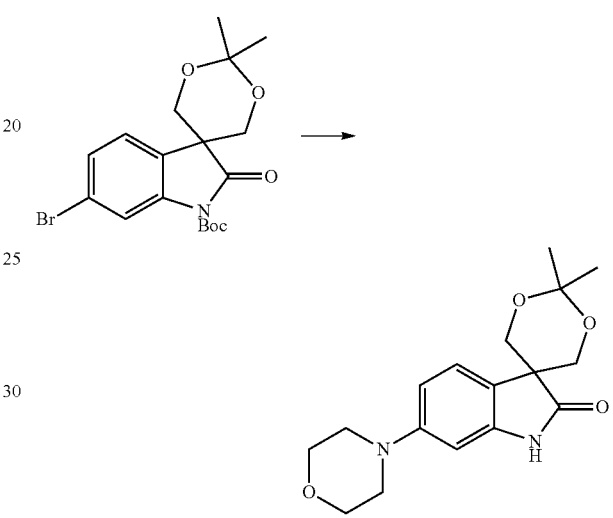

To a microwave vessel was added sodium tert-butoxide (0.19 g, 1.99 mmol), morpholine (0.13 mL, 1.49 mmol), XPhos (0.095 g, 0.20 mmol), Pd$_2$(dba)$_3$ (0.091 g, 0.099 mmol), and tert-butyl 6'-bromo-2,2-dimethyl-2'-oxospiro[[1,3]dioxane-5,3'-indoline]-1'-carboxylate (0.41 g, 0.99 mmol) in 1,4-dioxane (9.9 mL). The mixture was deoxygenated with argon for 5 min and stirred at 110° C. for 90 min under microwave irradiation. The resulting mixture was purified by column chromatography (eluting with a gradient of 10-70% EtOAc in hexanes) to give 2,2-dimethyl-6'-morpholinospiro[[1,3]dioxane-5,3'-indolin]-2'-one as a white solid. Mass Spectrum (ESI) m/e=319.2 (M+1).

2,2-Dimethyl-6'-morpholinospiro[[1,3]dioxane-5,3'-indoline]

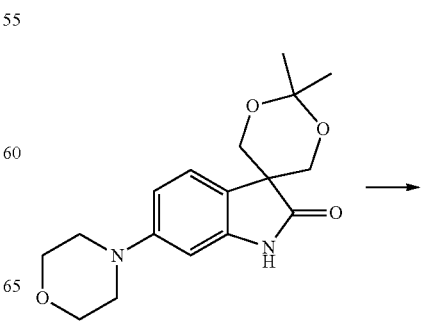

-continued

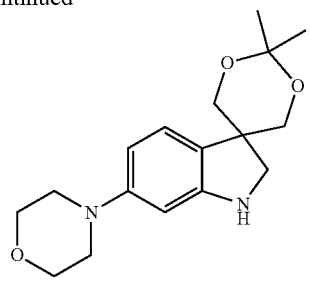

To a solution of 2,2-dimethyl-6'-morpholinospiro[[1,3]dioxane-5,3'-indolin]-2'-one (0.11 g, 0.35 mmol) in toluene (14 mL) was added sodium bis(2-methoxyethoxy)aluminium hydride (60% in toluene, 0.53 mL, 1.74 mmol). After stirring at 80° C. for 40 min, the solution was poured into a mixture of ice and 2N NaOH. The product was extracted with DCM and the combined organic extracts were dried over $MgSO_4$, filtered and evaporated in vacuo. Purification by column chromatography (eluting with a gradient of 5-60% EtOAc in hexanes) gave 2,2-dimethyl-6'-morpholinospiro[[1,3]dioxane-5, 3'-indoline] as a white solid. Mass Spectrum (ESI) m/e=305.2 (M+1).

1'-(7-Fluoro-3-methyl-2-(pyridin-2-yl)quinolin-4-yl)-2,2-dimethyl-6'-morpholinospiro[[1,3]dioxane-5, 3'-indoline]

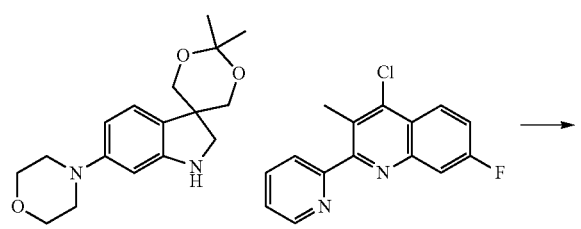

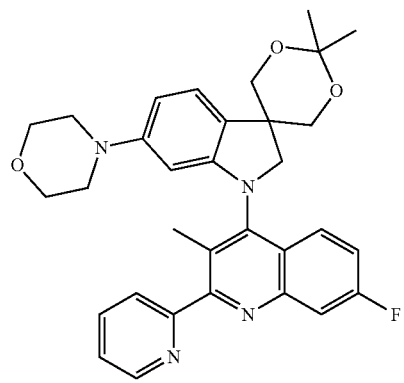

To a microwave vial was added sodium tert-butoxide (0.035 g, 0.37 mmol), ruphos (8.6 mg, 0.018 mmol), 4-chloro-7-fluoro-3-methyl-2-(pyridin-2-yl)-quinoline (0.053 g, 0.19 mmol), 2,2-dimethyl-6'-morpholinospiro[[1,3]dioxane-5,3'-indoline] (0.056 g, 0.18 mmol), and XPhos pre-catalyst (0.014 g, 0.018 mmol) in toluene (1.2 mL). The suspension was deoxygenated with argon for 5 min and stirred at 100° C. for 90 min under microwave irradiation. Purification by column chromatography (eluting with a gradient of 10-60% EtOAc in hexanes) gave 1'-(7-fluoro-3-methyl-2-(pyridin-2-yl)quinolin-4-yl)-2,2-dimethyl-6'-morpholinospiro[[1,3]dioxane-5,3'-indoline] as a yellow solid. Mass Spectrum (ESI) m/e=541.3 (M+1).

(1-(7-Fluoro-3-methyl-2-(2-pyridinyl)-4-quinolinyl)-6-(4-morpholinyl)-2,3-dihydro-1H-indole-3,3-diyl)dimethanol

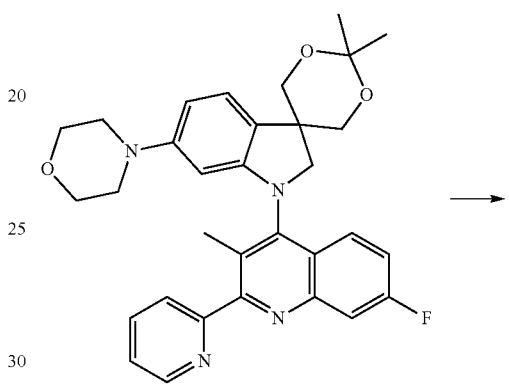

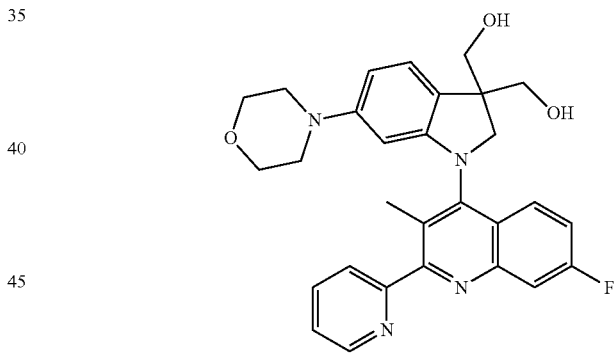

To a solution of 1'-(7-fluoro-3-methyl-2-(pyridin-2-yl)quinolin-4-yl)-2,2-dimethyl-6'-morpholinospiro[[1,3]dioxane-5,3'-indoline] (0.057 g, 0.105 mmol) in THF (1 mL) was added 1.0 N HCl (1.05 mL, 1.05 mmol). After stirring at rt for 1 h, the solution was purified by column chromatography (eluting with a gradient of 0-10% MeOH in DCM) to give (1-(7-fluoro-3-methyl-2-(pyridin-2-yl)quinolin-4-yl)-6-morpholinoindoline-3,3-diyl)dimethanol as a yellow solid. 1H NMR (500 MHz, DMSO-$d_6$) δ ppm 8.72 (1H, d, J=4.89 Hz), 8.03 (1H, td, J=7.70, 1.71 Hz), 7.97 (1H, dd, J=9.29, 6.11 Hz) 7.92 (1H, d, J=7.83 Hz), 7.84 (1H, dd, J=10.15, 2.57 Hz), 7.47-7.57 (2H, m), 7.06 (1H, d, J=8.07 Hz), 6.21 (1H, dd, J=8.19, 2.08 Hz), 5.45 (1H, d, J=1.96 Hz), 4.91 (1H, t, J=5.26 Hz), 4.84 (1H, t, J=5.26 Hz), 3.79-3.91 (2H, m), 3.72 (2H, d, J=5.38 Hz), 3.65 (2H, dd, J=5.38, 1.22 Hz), 3.58 (4H, t, J=4.89 Hz), 2.76-2.89 (4H, m), 2.29 (s, 3H). Mass Spectrum (ESI) m/e=501.2 (M+1).

Example 162

2-Cyclopropyl-4-(3,3-dimethyl-6-(4-morpholinyl)-2,3-dihydro-1H-pyrrolo[3,2-b]pyridin-1-yl)-3-methyl-1,8-naphthyridine

4-Chloro-2-cyclopropyl-3-methyl-1,8-naphthyridine

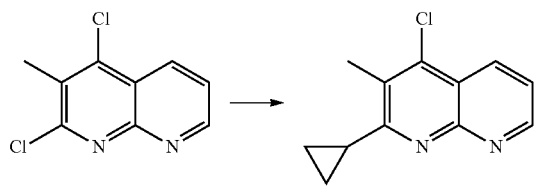

To a stirred solution of 2,4-dichloro-3-methyl-1,8-naphthyridine (210 mg, 0.986 mmol) in toluene (5 mL) was added dichloro 1,1'-bis(diphenylphosphino)-ferrocene palladium (II) (161 mg, 0.197 mmol), cyclopropylzinc bromide solution 0.5 m in THF (3.94 mL, 1.971 mmol). The reaction was heated at 100° C. for 2 h. After this time the reaction was cooled to rt and partitioned between EtOAc (60 mL) and water (20 mL). The separated organic layer was dried over MgSO$_4$, filtered and evaporated in vacuo. Column chromatography (DCM/DCM:—MeOH:NH$_4$OH (9:1:0.4), 1:0 to 7:3 as eluent) gave 4-chloro-2-cyclopropyl-3-methyl-1,8-naphthyridine. Mass Spectrum (ESI) m/e=219.2.

2-Cyclopropyl-4-(3,3-dimethyl-6-(4-morpholinyl)-2,3-dihydro-1H-pyrrolo[3,2-b]pyridin-1-yl)-3-methyl-1,8-naphthyridine

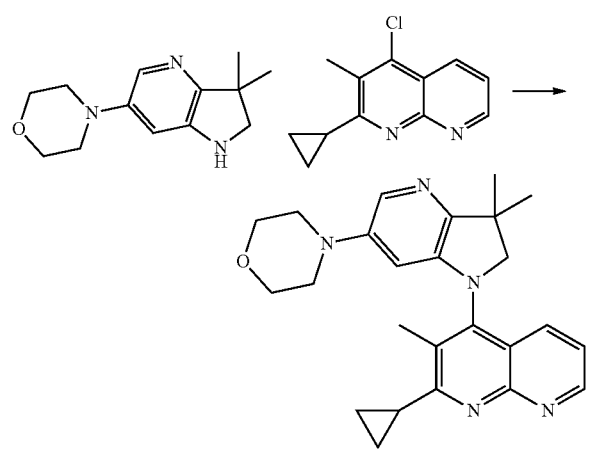

Prepared according to procedure Y using 4-chloro-2-cyclopropyl-3-methyl-1,8-naphthyridine (40 mg, 0.183 mmol), 4-(3,3-dimethyl-2,3-dihydro-1H-pyrrolo[3,2-b]pyridin-6-yl)morpholine (42.7 mg, 0.183 mmol), XPhos precatalyst (13.52 mg, 0.018 mmol) and sodium tert-butoxide (35.2 mg, 0.366 mmol) by heating in toluene (4 mL) for 2 hours at 110° C. Purification by reverse phase HPLC (10 to 60% acetonitrile in water) gave 2-cyclopropyl-4-(3,3-dimethyl-6-(4-morpholinyl)-2,3-dihydro-1H-pyrrolo[3,2-b]pyridin-1-yl)-3-methyl-1,8-naphthyridine. 1H NMR (400 MHz, chloroform-d) δ ppm 8.98 (1H, dd, J=4.1, 2.0 Hz), 8.05 (1H, dd, J=8.2, 2.0 Hz), 7.59 (1H, d, J=2.3 Hz), 7.31 (1H, dd, J=8.3, 4.2 Hz), 5.69-5.74 (1H, m), 3.70-3.78 (6H, m), 2.90-3.03 (4H, m), 2.43-2.48 (3H, m), 2.30-2.40 (1H, m), 1.54-1.59 (4H, m), 1.45-1.53 (4H, m), 1.12-1.17 (2H, m). Mass Spectrum (ESI) m/e=416.2 (M+1).

Biological Assays

Recombinant Expression of PI3Ks

Full length p110 subunits of PI3k α, β and δ, N-terminally labeled with polyHis tag, were coexpressed with p85 with Baculo virus expression vectors in sf9 insect cells. P110/p85 heterodimers were purified by sequential Ni-NTA, Q-HP, Superdex-100 chromatography. Purified α, β and δ isozymes were stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with polyHis tag, was expressed with Baculo virus in Hi5 insect cells. The γ isozyme was purified by sequential Ni-NTA, Superdex-200, Q-HP chromatography. The γ isozyme was stored frozen at −80° C. in NaH$_2$PO$_4$, pH 8, 0.2M NaCl, 1% ethylene glycol, 2 mM β-mercaptoethanol.

|           | Alpha  | Beta   | Delta  | gamma  |
|-----------|--------|--------|--------|--------|
| 50 mM Tris | pH 8  | pH 7.5 | pH 7.5 | pH 8   |
| MgCl2     | 15 mM  | 10 mM  | 10 mM  | 15 mM  |
| Na cholate | 2 mM  | 1 mM   | 0.5 mM | 2 mM   |
| DTT       | 2 mM   | 1 mM   | 1 mM   | 2 mM   |
| ATP       | 1 uM   | 0.5 uM | 0.5 uM | 1 uM   |
| PIP2      | none   | 2.5 uM | 2.5 uM | none   |
| time      | 1 h    | 2 h    | 2 h    | 1 h    |
| [Enzyme]  | 15 nM  | 40 nM  | 15 nM  | 50 nM  |

In Vitro PI3K Enzyme Assays

A PI3K Alphascreen® assay (PerkinElmer, Waltham, Mass.) was used to measure the activity of a panel of four phosphoinositide 3-kinases: PI3Kα, PI3Kβ, PI3Kγ, and PI3Kδ. Enzyme reaction buffer was prepared using sterile water (Baxter, Deerfield, Ill.) and 50 mM Tris HCl pH 7, 14 mM MgCl$_2$, 2 mM sodium cholate, and 100 mM NaCl. 2 mM DTT was added fresh the day of the experiment. The Alphascreen buffer was made using sterile water and 10 mM Tris HCl pH 7.5, 150 mM NaCl, 0.10% Tween 20, and 30 mM EDTA. 1 mM DTT was added fresh the day of the experiment. Compound source plates used for this assay were 384-well Greiner clear polypropylene plates containing test compounds at 5 mM and diluted 1:2 over 22 concentrations. Columns 23 and 24 contained only DMSO as these wells comprised the positive and negative controls, respectively. Source plates were replicated by transferring 0.5 uL per well into 384-well Optiplates (PerkinElmer, Waltham, Mass.).

Each PI3K isoform was diluted in enzyme reaction buffer to 2× working stocks. PI3Kα was diluted to 1.6 nM, PI3Kβ was diluted to 0.8 nM, PI3Kγ was diluted to 15 nM, and PI3Kδ was diluted to 1.6 nM. PI(4,5)P2 (Echelon Biosciences, Salt Lake City, Utah) was diluted to 10 μM and ATP was diluted to 20 μM. This 2× stock was used in the assays for PI3Kα and PI3Kβ. For assay of PI3Kγ and PI3Kδ, PI(4,5)P2 was diluted to 10 μM and ATP was diluted to 8 μM to prepare a similar 2× working stock. Alphascreen reaction solutions were made using beads from the anti-GST Alphascreen kit (PerkinElmer, Waltham, Mass.). Two 4× working stocks of the Alphascreen reagents were made in Alphascreen reaction buffer. In one stock, biotinylated-IP$_4$ (Echelon Biosciences, Salt Lake City, Utah) was diluted to 40 nM and streptavadin-donor beads were diluted to 80 μg/mL. In the second stock, PIP$_3$-binding protein (Echelon Biosciences, Salt Lake City, Utah) was diluted to 40 nM and anti-GST-acceptor beads were diluted to 80 μg/mL. As a negative control, a reference inhibitor at a concentration>>Ki (40 uM) was included in column 24 as a negative (100% inhibition) control.

Using a 384-well Multidrop (Titertek, Huntsville, Ala.), 10 µL/well of 2× enzyme stock was added to columns 1-24 of the assay plates for each isoform. 10 µL/well of the appropriate substrate 2× stock (containing 20 µM ATP for the PI3Kα and β assays and containing 8 µM ATP for the PI3Kγ and δ assays) was then added to Columns 1-24 of all plates. Plates were then incubated at room temperature for 20 minutes. In the dark, 10 µL/well of the donor bead solution was added to columns 1-24 of the plates to quench the enzyme reaction. The plates were incubated at room temperature for 30 minutes. Still in the dark, 10 µL/well of the acceptor bead solution was added to columns 1-24 of the plates. The plates were then incubated in the dark for 1.5 hours. The plates were read on an Envision multimode Plate Reader (PerkinElmer, Waltham, Mass.) using a 680 nm excitation filter and a 520-620 nm emission filter.

Alternative In Vitro Enzyme Assays.

Assays were performed in 25 µL with the above final concentrations of components in white polypropylene plates (Costar 3355). Phosphatidyl inositol phosphoacceptor, PtdIns(4,5)P2 P4508, was from Echelon Biosciences. The ATPase activity of the alpha and gamma isozymes was not greatly stimulated by PtdIns(4,5)P2 under these conditions and was therefore omitted from the assay of these isozymes. Test compounds were dissolved in dimethyl sulfoxide and diluted with three-fold serial dilutions. The compound in DMSO (1 µL) was added per test well, and the inhibition relative to reactions containing no compound, with and without enzyme was determined. After assay incubation at rt, the reaction was stopped and residual ATP determined by addition of an equal volume of a commercial ATP bioluminescence kit (Perkin Elmer EasyLite) according to the manufacturer's instructions, and detected using a AnalystGT luminometer.

Human B Cells Proliferation Stimulate by Anti-IgM
Isolate Human B Cells:

Isolate PBMCs from Leukopac or from human fresh blood. Isolate human B cells by using Miltenyi protocol and B cell isolation kit II. —human B cells were Purified by using AutoMacs.column.

Activation of Human B Cells

Use 96 well Flat bottom plate, plate 50000/well purified B cells in B cell proliferation medium (DMEM+5% FCS, 10 mM Hepes, 50 µM 2-mercaptoethanol); 150 µL medium contain 250 ng/mL CD40L-LZ recombinant protein (Amgen) and 2 µg/mL anti-Human IgM antibody (Jackson ImmunoReseach Lab.#109-006-129), mixed with 50 µL B cell medium containing PI3K inhibitors and incubate 72 h at 37° C. incubator. After 72 h, pulse labeling B cells with 0.5-1 uCi/well $^3$H thymidine for overnight ~18 h, and harvest cell using TOM harvester.

Human B Cells Proliferation Stimulate by IL-4
Isolate Human B Cells:

Isolate human PBMCs from Leukopac or from human fresh blood. Isolate human B cells using Miltenyi protocol-B cell isolation kit. Human B cells were Purified by AutoMacs.column.

Activation of Human B Cells

Use 96-well flat bottom plate, plate 50000/well purified B cells in B cell proliferation medium (DMEM+5% FCS, 50 µM 2-mercaptoethanol, 10 mM Hepes). The medium (150 µL) contain 250 ng/mL CD40L-LZ recombinant protein (Amgen) and 10 ng/mL IL-4 (R&D system #204-IL-025), mixed with 50 150 µL B cell medium containing compounds and incubate 72 h at 37° C. incubator. After 72 h, pulse labeling B cells with 0.5-1 uCi/well 3H thymidine for overnight ~18 h, and harvest cell using TOM harvester.

Specific T Antigen (Tetanus Toxoid) Induced Human PBMC Proliferation Assays

Human PBMC are prepared from frozen stocks or they are purified from fresh human blood using a Ficoll gradient. Use 96 well round-bottom plate and plate $2 \times 10^5$ PBMC/well with culture medium (RPMI1640+10% FCS, 50 uM 2-Mercaptoethanol, 10 mM Hepes). For $IC_{50}$ determinations, PI3K inhibitors was tested from 10 µM to 0.001 µM, in half log increments and in triplicate. Tetanus toxoid, T cell specific antigen (University of Massachusetts Lab) was added at 1 µg/mL and incubated 6 days at 37° C. incubator. Supernatants are collected after 6 days for IL2 ELISA assay, then cells are pulsed with $^3$H-thymidine for ~18 h to measure proliferation.

GFP Assays for Detecting Inhibition of Class Ia and Class III PI3K

AKT1 (PKBa) is regulated by Class Ia PI3K activated by mitogenic factors (IGF-1, PDGF, insulin, thrombin, NGF, etc.). In response to mitogenic stimuli, AKT1 translocates from the cytosol to the plasma membrane Forkhead (FKHRL1) is a substrate for AKT1. It is cytoplasmic when phosphorylated by AKT (survival/growth). Inhibition of AKT (stasis/apoptosis)-forkhead translocation to the nucleus FYVE domains bind to PI(3)P. the majority is generated by constitutive action of PI3K Class III AKT Membrane Ruffling Assay (CHO-IR-AKT1-EGFP Cells/GE Healthcare)

Wash cells with assay buffer. Treat with compounds in assay buffer 1 h. Add 10 ng/mL insulin. Fix after 10 minutes at rt and image Forkhead Translocation Assay (MDA MB468 Forkhead-DiversaGFP Cells)

Treat cells with compound in growth medium 1 h. Fix and image.

Class III PI(3)P Assay (U2OS EGFP-2×FYVE Cells/GE Healthcare)

Wash cells with assay buffer. Treat with compounds in assay buffer 1 h. Fix and image.

Control for all 3 Assays is 10 uM Wortmannin:
AKT is cytoplasmic
Forkhead is nuclear
PI(3)P depleted from endosomes
Biomarker Assay: B-Cell Receptor Stimulation of CD69 or B7.2 (CD86) Expression Heparinized human whole blood was stimulated with 10 µg/mL anti-IgD (Southern Biotech, #9030-01). 90 µL of the stimulated blood was then aliquoted per well of a 96-well plate and treated with 10 µL of various concentrations of blocking compound (from 10-0.0003 µM) diluted in IMDM+10% FBS (Gibco). Samples were incubated together for 4 h (for CD69 expression) to 6 h (for B7.2 expression) at 37° C. Treated blood (50 µL) was transferred to a 96-well, deep well plate (Nunc) for antibody staining with 10 µL each of CD45-PerCP (BD Biosciences, #347464), CD19-FITC (BD Biosciences, #340719), and CD69-PE (BD Biosciences, #341652). The second 50 µL of the treated blood was transferred to a second 96-well, deep well plate for antibody staining with 10 µL each of CD19-FITC (BD Biosciences, #340719) and CD86-PeCy5 (BD Biosciences, #555666). All stains were performed for 15-30 minutes in the dark at rt. The blood was then lysed and fixed using 450 µL of FACS lysing solution (BD Biosciences, #349202) for 15 minutes at rt. Samples were then washed 2× in PBS+2% FBS before FACS analysis. Samples were gated on either CD45/CD19 double positive cells for CD69 staining, or CD19 positive cells for CD86 staining.

Gamma Counterscreen Stimulation of Human Monocytes for Phospho-AKT Expression

A human monocyte cell line, THP-1, was maintained in RPMI+10% FBS (Gibco). One day before stimulation, cells were counted using trypan blue exclusion on a hemocytometer and suspended at a concentration of $1 \times 10^6$ cells per mL of media. 100 µL of cells plus media ($1 \times 10^5$ cells) was then aliquoted per well of 4-96-well, deep well dishes (Nunc) to test eight different compounds. Cells were rested overnight before treatment with various concentrations (from 10-0.0003 µM) of blocking compound. The compound diluted in media (12 µL) was added to the cells for 10 minutes at 37° C. Human MCP-1 (12 µL, R&D Diagnostics, #279-MC) was diluted in media and added to each well at a final concentration of 50 ng/mL. Stimulation lasted for 2 minutes at rt. Pre-warmed FACS Phosflow Lyse/Fix buffer (1 mL of 37° C.) (BD Biosciences, #558049) was added to each well. Plates were then incubated at 37° C. for an additional 10-15 minutes. Plates were spun at 1500 rpm for 10 minutes, supernatant was aspirated off, and 1 mL of ice cold 90% MeOH was added to each well with vigorous shaking Plates were then incubated either overnight at −70° C. or on ice for 30 minutes before antibody staining Plates were spun and washed 2× in PBS+2% FBS (Gibco). Wash was aspirated and cells were suspended in remaining buffer. Rabbit pAKT (50 µL, Cell Signaling, #4058L) at 1:100, was added to each sample for 1 h at rt with shaking Cells were washed and spun at 1500 rpm for 10 minutes. Supernatant was aspirated and cells were suspended in remaining buffer. Secondary antibody, goat anti-rabbit Alexa 647 (50 µL, Invitrogen, #A21245) at 1:500, was added for 30 minutes at rt with shaking Cells were then washed 1× in buffer and suspended in 150 µL of buffer for FACS analysis. Cells need to be dispersed very well by pipetting before running on flow cytometer. Cells were run on an LSR II (Becton Dickinson) and gated on forward and side scatter to determine expression levels of pAKT in the monocyte population.

Gamma Counterscreen: Stimulation of Monocytes for Phospho-AKT Expression in Mouse Bone Marrow Mouse femurs were dissected from five female BALB/c mice (Charles River Labs.) and collected into RPMI+10% FBS media (Gibco). Mouse bone marrow was removed by cutting the ends of the femur and by flushing with 1 mL of media using a 25 gauge needle. Bone marrow was then dispersed in media using a 21 gauge needle. Media volume was increased to 20 mL and cells were counted using trypan blue exclusion on a hemocytometer. The cell suspension was then increased to $7.5 \times 10^6$ cells per 1 mL of media and 100 µL ($7.5 \times 10^5$ cells) was aliquoted per well into 4-96-well, deep well dishes (Nunc) to test eight different compounds. Cells were rested at 37° C. for 2 h before treatment with various concentrations (from 10-0.0003 µM) of blocking compound. Compound diluted in media (12 µL) was added to bone marrow cells for 10 minutes at 37° C. Mouse MCP-1 (12 µL, R&D Diagnostics, #479-JE) was diluted in media and added to each well at a final concentration of 50 ng/mL. Stimulation lasted for 2 minutes at rt. 1 mL of 37° C. pre-warmed FACS Phosflow Lyse/Fix buffer (BD Biosciences, #558049) was added to each well. Plates were then incubated at 37° C. for an additional 10-15 minutes. Plates were spun at 1500 rpm for 10 minutes. Supernatant was aspirated off and 1 mL of ice cold 90% MeOH was added to each well with vigorous shaking Plates were then incubated either overnight at −70° C. or on ice for 30 minutes before antibody staining Plates were spun and washed 2× in PBS+2% FBS (Gibco). Wash was aspirated and cells were suspended in remaining buffer. Fc block (2 µL, BD Pharmingen, #553140) was then added per well for 10 minutes at rt. After block, 50 µL of primary antibodies diluted in buffer; CD11b-Alexa488 (BD Biosciences, #557672) at 1:50, CD64-PE (BD Biosciences, #558455) at 1:50, and rabbit pAKT (Cell Signaling, #4058L) at 1:100, were added to each sample for 1 h at RT with shaking Wash buffer was added to cells and spun at 1500 rpm for 10 minutes. Supernatant was aspirated and cells were suspended in remaining buffer. Secondary antibody; goat anti-rabbit Alexa 647 (50 µL, Invitrogen, #A21245) at 1:500, was added for 30 minutes at rt with shaking Cells were then washed 1× in buffer and suspended in 100 µL of buffer for FACS analysis. Cells were run on an LSR II (Becton Dickinson) and gated on CD11b/CD64 double positive cells to determine expression levels of pAKT in the monocyte population.

pAKT In Vivo Assay

Vehicle and compounds are administered p.o. (0.2 mL) by gavage (Oral Gavage Needles Popper & Sons, New Hyde Park, N.Y.) to mice (Transgenic Line 3751, female, 10-12 wks Amgen Inc, Thousand Oaks, Calif.) 15 minutes prior to the injection i.v (0.2 mLs) of anti-IgM FITC (50 ug/mouse) (Jackson Immuno Research, West Grove, Pa.). After 45 minutes the mice are sacrificed within a $CO_2$ chamber. Blood is drawn via cardiac puncture (0.3 mL) (1 cc 25 g Syringes, Sherwood, St. Louis, Mo.) and transferred into a 15 mL conical vial (Nalge/Nunc International, Denmark). Blood is immediately fixed with 6.0 mL of BD Phosflow Lyse/Fix Buffer (BD Bioscience, San Jose, Calif.), inverted 3×'s and placed in 37° C. water bath. Half of the spleen is removed and transferred to an eppendorf tube containing 0.5 mL of PBS (Invitrogen Corp, Grand Island, N.Y.). The spleen is crushed using a tissue grinder (Pellet Pestle, Kimble/Kontes, Vineland, N.J.) and immediately fixed with 6.0 mL of BD Phosflow Lyse/Fix buffer, inverted 3×'s and placed in 37° C. water bath. Once tissues have been collected the mouse is cervically-dislocated and carcass to disposed. After 15 minutes, the 15 mL conical vials are removed from the 37° C. water bath and placed on ice until tissues are further processed. Crushed spleens are filtered through a 70 µm cell strainer (BD Bioscience, Bedford, Mass.) into another 15 mL conical vial and washed with 9 mL of PBS. Splenocytes and blood are spun @ 2,000 rpms for 10 minutes (cold) and buffer is aspirated. Cells are resuspended in 2.0 mL of cold (−20° C.) 90% MeOH (Mallinckrodt Chemicals, Phillipsburg, N.J.). MeOH is slowly added while conical vial is rapidly vortexed. Tissues are then stored at −20° C. until cells can be stained for FACS analysis.

Multi-Dose TNP Immunization

Blood was collected by retro-orbital eye bleeds from 7-8 week old BALB/c female mice (Charles River Labs.) at day 0 before immunization. Blood was allowed to clot for 30 minutes and spun at 10,000 rpm in serum microtainer tubes (Becton Dickinson) for 10 minutes. Sera were collected, aliquoted in Matrix tubes (Matrix Tech. Corp.) and stored at −70° C. until ELISA was performed. Mice were given compound orally before immunization and at subsequent time periods based on the life of the molecule. Mice were then immunized with either 50 µg of TNP-LPS (Biosearch Tech., #T-5065), 50 µg of TNP-Ficoll (Biosearch Tech., #F-1300), or 100 µg of TNP-KLH (Biosearch Tech., #T-5060) plus 1% alum (Brenntag, #3501) in PBS. TNP-KLH plus alum solution was prepared by gently inverting the mixture 3-5 times every 10 minutes for 1 h before immunization. On day 5, post-last treatment, mice were $CO_2$ sacrificed and cardiac punctured. Blood was allowed to clot for 30 minutes and spun at 10,000 rpm in serum microtainer tubes for 10 minutes. Sera were collected, aliquoted in Matrix tubes, and stored at −70° C. until further analysis was performed. TNP-specific IgG1, IgG2a, IgG3 and IgM levels in the sera were then measured via ELISA. TNP-BSA (Biosearch Tech., #T-5050) was used to capture the TNP-specific antibodies. TNP-BSA (10 µg/mL) was used to coat 384-well ELISA plates (Corning Costar) overnight. Plates were then washed and blocked for 1 h using 10% BSA ELISA Block solution (KPL). After blocking, ELISA plates were washed and sera samples/standards were serially diluted and allowed to bind to the plates for 1 h. Plates were washed and Ig-HRP conjugated secondary antibodies (goat anti-mouse IgG1, Southern Biotech #1070-05, goat anti-mouse IgG2a, Southern Biotech #1080-05, goat anti-mouse IgM, Southern Biotech #1020-05, goat anti-mouse IgG3, Southern Biotech #1100-05) were diluted at 1:5000 and incubated on the plates for 1 h. TMB peroxidase solution (SureBlue Reserve TMB from KPL) was used to visualize the antibodies. Plates were washed and samples were allowed to develop in the TMB solution approximately 5-20 minutes depending on the Ig analyzed. The reaction was stopped with 2M sulfuric acid and plates were read at an OD of 450 nm.

Data from the PI3Kδ Alphascreen® assay:

| Compound | Ki(µM) |
| --- | --- |
| 4-(3,3-dimethyl-6-(4-morpholinyl)-2,3-dihydro-1H-indol-1-yl)-7-fluoro-3-methyl-2-(2-pyridinyl)quinoline | 0.030169 |
| 4-(3,3-dimethyl-6-(4-morpholinyl)-2,3-dihydro-1H-indol-1-yl)-5-fluoro-3-methyl-2-(2-pyridinyl)quinoline | 0.155901 |
| 1-(7-fluoro-3-methyl-2-(2-pyridinyl)-4-quinolinyl)-6-(4-morpholinyl)-1,2,2',3',5',6'-hexahydrospiro[indole-3,4'-pyran] | 0.018244 |
| 4-(3,3-dimethyl-6-(4-morpholinyl)-2,3-dihydro-1H-indol-1-yl)-7-fluoro-3-methyl-2-(3-pyridinyl)quinoline | 0.026813 |
| 3-(4-(3,3-dimethyl-6-(4-morpholinyl)-2,3-dihydro-1H-indol-1-yl)-7-fluoro-3-methyl-2-quinolinyl)benzonitrile | 0.154127 |
| 4-(3,3-dimethyl-6-(4-morpholinyl)-2,3-dihydro-1H-indol-1-yl)-8-fluoro-3-methyl-2-(2-pyridinyl)quinoline | 0.093683 |
| 1-(7-fluoro-3-methyl-2-(4-pyridinyl)-4-quinolinyl)-6-(4-morpholinyl)-1,2,2',3',5',6'-hexahydrospiro[indole-3,4'-pyran] | 0.233974 |
| 1-(7-fluoro-3-methyl-2-(3-pyridinyl)-4-quinolinyl)-6-(4-morpholinyl)-1,2,2',3',5',6'-hexahydrospiro[indole-3,4'-pyran] | 0.047496 |
| 4-(3,3-dimethyl-6-(4-morpholinyl)-2,3-dihydro-1H-pyrrolo[3,2-b]pyridin-1-yl)-7-fluoro-3-methyl-2-(2-pyridinyl)quinoline | 0.006759 |
| 4-(1-(7-fluoro-3-methyl-2-(2-pyridinyl)-4-quinolinyl)-3,3-dimethyl-2,3-dihydro-1H-indol-6-yl)-2-pyrimidinamine | 0.009774 |
| 4-(1-(7-fluoro-3-methyl-2-(2-pyridinyl)-4-quinolinyl)-3,3-dimethyl-2,3-dihydro-1H-pyrrolo[3,2-b]pyridin-6-yl)-2-pyrimidinamine | 0.003323 |
| 4-(3,3-dimethyl-6-(4-morpholinyl)-2,3-dihydro-1H-pyrrolo[3,2-b]pyridin-1-yl)-7-fluoro-3-(1-methylethyl)-2-(2-pyridinyl)quinoline | 0.005868 |
| 1'-(7-fluoro-3-methyl-2-(2-pyridinyl)-4-quinolinyl)-6'-(4-morpholinyl)-1,2,2',3,5,6-hexahydrospiro[pyran-4,3'-pyrrolo[3,2-b]pyridine] | 0.009877 |
| 1-(7-fluoro-3-methyl-2-(2-methyl-3-pyridinyl)-4-quinolinyl)-6-(4-morpholinyl)-1,2,2',3',5',6'-hexahydrospiro[indole-3,4'-pyran] | 0.01452 |
| 4-(3,3-dimethyl-6-(4-morpholinyl)-2,3-dihydro-1H-pyrrolo[3,2-b]pyridin-1-yl)-7-fluoro-3-methyl-2-(2-methyl-3-pyridinyl)quinoline | 0.004071 |
| 1-(7-fluoro-3-methyl-2-(2-pyridinyl)-4-quinolinyl)-N-(2-methoxyethyl)-N,3,3-trimethyl-2,3-dihydro-1H-pyrrolo[3,2-b]pyridin-6-amine | 0.055835 |
| 4-(3,3-dimethyl-6-(1H-pyrazol-4-yl)-2,3-dihydro-1H-pyrrolo[3,2-b]pyridin-1-yl)-7-fluoro-3-methyl-2-(2-pyridinyl)quinoline | 0.095175 |
| 4-(3,3-dimethyl-6-(9H-purin-6-yl)-2,3-dihydro-1H-pyrrolo[3,2-b]pyridin-1-yl)-7-fluoro-3-methyl-2-(2-pyridinyl)quinoline | 0.02901 |
| 1-(7-fluoro-3-methyl-2-(2-pyridinyl)-4-quinolinyl)-3,3-dimethyl-2,3-dihydro-1H-pyrrolo[3,2-b]pyridine-6-carboxamide | 0.4948 |
| 4-(3,3-dimethyl-6-(4-morpholinyl)-2,3-dihydro-1H-pyrrolo[3,2-b]pyridin-1-yl)-2-(3,5-dimethylphenyl)-7-fluoro-3-methylquinoline | 0.01564 |
| 4-(1-(7-fluoro-3-methyl-2-(2-pyridinyl)-4-quinolinyl)-3,3-dimethyl-2,3-dihydro-1H-indol-6-yl)-6-methyl-2-pyrimidinamine | 0.44915 |
| 5-chloro-4-(1-(7-fluoro-3-methyl-2-(2-pyridinyl)-4-quinolinyl)-3,3-dimethyl-2,3-dihydro-1H-indol-6-yl)-2-pyrimidinamine | 1.427 |
| 1-(7-fluoro-3-methyl-2-(2-(methylsulfonyl)phenyl)-4-quinolinyl)-6-(4-morpholinyl)-1,2,2',3',5',6'-hexahydrospiro[indole-3,4'-pyran] | 0.010219 |
| 4-(3,3-dimethyl-6-(4-morpholinyl)-2,3-dihydro-1H-indol-1-yl)-7-fluoro-3-methyl-2-(2-(methylsulfonyl)phenyl)quinoline | 0.004434 |
| 4-(1-(7-fluoro-3-methyl-2-(2-(methylsulfonyl)phenyl)-4-quinolinyl)-3,3-dimethyl-2,3-dihydro-1H-pyrrolo[3,2-b]pyridin-6-yl)-2-pyrimidinamine | 0.002437 |
| 6-(7-fluoro-3-methyl-4-(6-(4-morpholinyl)-2',3',5',6'-tetrahydrospiro[indole-3,4'-pyran]-1(2H)-yl)-2-quinolinyl)-2-pyridinol | 0.1553 |
| 4-(3,3-dimethyl-6-(4-morpholinyl)-2,3-dihydro-1H-pyrrolo[3,2-b]pyridin-1-yl)-7-fluoro-3-methyl-2-(2-(methylsulfonyl)phenyl)quinoline | 0.007801 |
| 6-(4-(3,3-dimethyl-6-(4-morpholinyl)-2,3-dihydro-1H-pyrrolo[3,2-b]pyridin-1-yl)-7-fluoro-3-methyl-2-quinolinyl)-2(1H)-pyridinone | 0.01474 |

-continued

| Compound | Ki(μM) |
|---|---|
| 1-(7-fluoro-2-(6-methoxy-2-pyridinyl)-3-methyl-4-quinolinyl)-6-(4-morpholinyl)-1,2,2',3',5',6'-hexahydrospiro[indole-3,4'-pyran] | 0.068845 |
| 1-(7-fluoro-3-methyl-2-(3-(methylsulfonyl)phenyl)-4-quinolinyl)-6-(4-morpholinyl)-1,2,2',3',5',6'-hexahydrospiro[indole-3,4'-pyran] | 0.12715 |
| 1-(5,7-difluoro-3-methyl-2-(2-pyridinyl)-4-quinolinyl)-6-(4-morpholinyl)-1,2,2',3',5',6'-hexahydrospiro[indole-3,4'-pyran] | 0.021095 |
| 4-(3,3-dimethyl-6-(4-morpholinyl)-2,3-dihydro-1H-pyrrolo[3,2-b]pyridin-1-yl)-5-fluoro-3-methyl-2-(2-pyridinyl)quinoline | 0.003327 |
| 2-(2,5-difluorophenyl)-4-(3,3-dimethyl-6-(4-morpholinyl)-2,3-dihydro-1H-indol-1-yl)-7-fluoro-3-methylquinoline | 0.020305 |
| 2-(3,5-bis(trifluoromethyl)phenyl)-4-(3,3-dimethyl-6-(4-morpholinyl)-2,3-dihydro-1H-indol-1-yl)-7-fluoro-3-methylquinoline | 3.0785 |
| 2-(3,5-bis(trifluoromethyl)phenyl)-4-(3,3-dimethyl-6-(4-morpholinyl)-2,3-dihydro-1H-indol-1-yl)-5-fluoro-3-methylquinoline | 3.779 |
| 5-chloro-4-(3,3-dimethyl-6-(4-morpholinyl)-2,3-dihydro-1H-indol-1-yl)-2-(2-fluorophenyl)-3-methylquinoline | 0.8904 |
| 4-(3,3-dimethyl-6-(4-morpholinyl)-2,3-dihydro-1H-pyrrolo[3,2-b]pyridin-1-yl)-5-fluoro-3,8-dimethyl-2-(2-pyridinyl)quinoline | 0.004072 |
| 4-(3,3-dimethyl-6-(4-morpholinyl)-2,3-dihydro-1H-pyrrolo[3,2-b]pyridin-1-yl)-7-fluoro-2-(2-pyridinyl)-3-quinolinecarbonitrile | 0.4371 |
| 4-(3,3-dimethyl-6-(4-morpholinyl)-2,3-dihydro-1H-indol-1-yl)-5,7-difluoro-3-methyl-2-(1-piperidinyl)quinoline | 0.0737 |
| 6-chloro-4-(3,3-dimethyl-6-(4-morpholinyl)-2,3-dihydro-1H-indol-1-yl)-7-methoxy-2,3-dimethylquinoline | 0.196 |
| 4-(3,3-dimethyl-6-(4-morpholinyl)-2,3-dihydro-1H-indol-1-yl)-7-methoxy-2,3,6-trimethylquinoline | 0.622 |
| 8-chloro-4-(3,3-dimethyl-6-(4-morpholinyl)-2,3-dihydro-1H-indol-1-yl)-2,3,6-trimethylquinoline | 3.179 |
| 4-(3,3-dimethyl-6-(4-morpholinyl)-2,3-dihydro-1H-indol-1-yl)-6,8-dimethoxy-2,3-dimethylquinoline | 3.969 |
| 6-chloro-4-(3,3-dimethyl-6-(4-morpholinyl)-2,3-dihydro-1H-indol-1-yl)-2-(2-methoxyphenyl)quinoline | 5.563 |
| 6-chloro-4-(3,3-dimethyl-6-(4-pyridinyl)-2,3-dihydro-1H-indol-1-yl)-2,3-dimethylquinoline | 1.703 |
| 6-chloro-4-(3,3-dimethyl-6-(1H-pyrazol-4-yl)-2,3-dihydro-1H-indol-1-yl)-2,3-dimethylquinoline | 9.533 |
| 6-chloro-4-(3,3-dimethyl-6-(4-morpholinyl)-2,3-dihydro-1H-indol-1-yl)-2,3-dimethylquinoline | 0.626 |
| 4-(6-chloro-2,3-dimethyl-4-quinolinyl)-6-(4-morpholinyl)-3,4-dihydro-2H-1,4-benzoxazine | 1.258 |
| 6-chloro-4-(4-methoxy-6-(4-pyridinyl)-1H-indol-1-yl)-2,3-dimethylquinoline | 1.439 |
| 6-chloro-4-(4-methoxy-6-(1H-pyrazol-4-yl)-1H-indol-1-yl)-2,3-dimethylquinoline | 2.054 |
| 1-(6-chloro-2,3-dimethyl-4-quinolinyl)-6-(1H-pyrazol-4-yl)-1H-indol-4-ol | 4.11 |
| 1-(6-chloro-2,3-dimethyl-4-quinolinyl)-6-(4-pyridinyl)-1H-indole-4-carbonitrile | 1.481 |
| 1-(6-chloro-2,3-dimethyl-4-quinolinyl)-6-(1H-pyrazol-4-yl)-1H-indole-4-carbonitrile | 1.083 |
| 6-chloro-4-(3,3-dimethyl-6-(4-morpholinyl)-2,3-dihydro-1H-indol-1-yl)-3-methyl-2-(trifluoromethyl)quinoline | 0.985 |
| 6-chloro-4-(4-methoxy-6-(4-morpholinyl)-1H-indol-1-yl)-2,3-dimethylquinoline | 3.71 |
| 1-(6-chloro-2,3-dimethyl-4-quinolinyl)-6-(4-morpholinyl)-1H-indole-4-carbonitrile | 0.153 |
| 1-(6-chloro-2,3-dimethyl-4-quinolinyl)-6-(4-morpholinyl)-1,2,2',3',5',6'-hexahydrospiro[indole-3,4'-pyran] | 0.073 |
| 1-(2,3-dimethyl-4-quinolinyl)-6-(4-morpholinyl)-1,2,2',3',5',6'-hexahydrospiro[indole-3,4'-pyran] | 0.45 |
| 6-bromo-1-(6-chloro-7-methoxy-2,3-dimethyl-4-quinolinyl)-1,2,2',3',5',6'-hexahydrospiro[indole-3,4'-pyran] | 0.571 |
| 1-(6-chloro-7-methoxy-2,3-dimethyl-4-quinolinyl)-1,2,2',3',5',6'-hexahydrospiro[indole-3,4'-pyran]-6-carbonitrile | 7.5 |
| 6-(4-morpholinyl)-1-(2,3,8-trimethyl-4-quinolinyl)-1,2,2',3',5',6'-hexahydrospiro[indole-3,4'-pyran] | 0.121 |
| 6-chloro-7-methoxy-2,3-dimethyl-4-(3,3,7-trimethyl-6-(4-morpholinyl)-2,3-dihydro-1H-indol-1-yl)quinoline | 3.961 |
| 7-chloro-9-(3,3-dimethyl-6-(4-morpholinyl)-2,3-dihydro-1H-indol-1-yl)-2,3-dihydro-1H-cyclopenta[b]quinoline | 0.772 |
| 7-chloro-9-(3,3-dimethyl-6-(4-morpholinyl)-2,3-dihydro-1H-indol-1-yl)-1,2,3,4-tetrahydroacridine | 2.624 |
| 7-chloro-9-(3,3-dimethyl-6-(4-morpholinyl)-2,3-dihydro-1H-indol-1-yl)-3,3-dimethyl-2,3-dihydro-1H-cyclopenta[b]quinoline | 0.111 |
| 4-(3,3-dimethyl-6-(4-morpholinyl)-2,3-dihydro-1H-indol-1-yl)-3-methylquinoline | 0.654368 |

-continued

| Compound | Ki(μM) |
|---|---|
| 4-(3,3-dimethyl-6-(4-pyridinyl)-2,3-dihydro-1H-indol-1-yl)-7-fluoro-3-methyl-2-(2-pyridinyl)quinoline | 5.029498 |
| 6-chloro-4-(3,3-dimethyl-6-(4-morpholinyl)-2,3-dihydro-1H-indol-1-yl)-2,3,8-trimethylquinoline | 0.618 |
| 4-(3,3-dimethyl-6-(4-morpholinyl)-2,3-dihydro-1H-indol-1-yl)-2-(2-fluorophenyl)-3-methylquinoline | 0.047 |
| 4-(3,3-dimethyl-6-(4-morpholinyl)-2,3-dihydro-1H-indol-1-yl)-2,3,8-trimethylquinoline | 0.044 |
| 8-chloro-4-(3,3-dimethyl-6-(4-morpholinyl)-2,3-dihydro-1H-indol-1-yl)-2,3-dimethylquinoline | 0.05 |
| 4-(3,3-dimethyl-6-(4-morpholinyl)-2,3-dihydro-1H-indol-1-yl)-2,3-dimethyl-8-(trifluoromethyl)quinoline | 0.516 |
| 1-(6-chloro-2,3-dimethyl-4-quinolinyl)-6-(1H-pyrazol-4-yl)-1H-indole-3-carbonitrile | 2.11 |
| 6-chloro-4-(3,3-dimethyl-6-(4-morpholinyl)-2,3-dihydro-1H-indol-1-yl)-3-ethyl-2-methylquinoline | 1.134 |
| 4-(3,3-dimethyl-6-(4-morpholinyl)-2,3-dihydro-1H-indol-1-yl)-2,3-dimethylquinoline | 0.362 |
| 4-(6-chloro-7-methoxy-2,3-dimethyl-4-quinolinyl)-6-(4-morpholinyl)-3,4-dihydro-2H-1,4-benzothiazine 1,1-dioxide | 0.028 |
| 4-(5-fluoro-2-(2-fluorophenyl)-3-methyl-4-quinolinyl)-6-(4-morpholinyl)-3,4-dihydro-2H-1,4-benzothiazine 1,1-dioxide | 0.023473 |
| 4-(3,3-dimethyl-6-(4-morpholinyl)-2,3-dihydro-1H-indol-1-yl)-3-methyl-2-phenylquinoline | 0.085363 |
| 1-(7-fluoro-2-(2-fluorophenyl)-3-methyl-4-quinolinyl)-6-(4-morpholinyl)-1,2,2',3',5',6'-hexahydrospiro[indole-3,4'-pyran] | 0.025382 |
| 1-(3-methyl-2-phenyl-4-quinolinyl)-6-(4-morpholinyl)-1,2,2',3',5',6'-hexahydrospiro[indole-3,4'-pyran] | 0.091283 |
| 1-(7-chloro-2-(2-fluorophenyl)-3-methyl-4-quinolinyl)-6-(4-morpholinyl)-1,2,2',3',5',6'-hexahydrospiro[indole-3,4'-pyran] | 0.569997 |
| 4-(3,3-dimethyl-6-(4-morpholinyl)-2,3-dihydro-1H-indol-1-yl)-7-fluoro-2-(2-fluorophenyl)-3-methylquinoline | 0.196985 |
| 2-benzyl-4-(3,3-dimethyl-6-(4-morpholinyl)-2,3-dihydro-1H-pyrrolo[3,2-b]pyridin-1-yl)-5,7-difluoro-3-methylquinoline | 0.0032 |
| 4-(3,3-dimethyl-6-(4-morpholinyl)-2,3-dihydro-1H-pyrrolo[3,2-b]pyridin-1-yl)-5,7-difluoro-3-methyl-2-(1-phenylethenyl)quinoline | 0.0029 |
| 4-(3,3-dimethyl-6-(4-morpholinyl)-2,3-dihydro-1H-pyrrolo[3,2-b]pyridin-1-yl)-5,7-difluoro-3-methyl-2-(1-naphthalenyl)quinoline | 0.23 |
| 4-(3,3-dimethyl-6-(4-morpholinyl)-2,3-dihydro-1H-pyrrolo[3,2-b]pyridin-1-yl)-5,7-difluoro-3-methyl-2-(1-methyl-1H-indol-5-yl)quinoline | 0.1948 |
| 4-(3,3-dimethyl-6-(4-morpholinyl)-2,3-dihydro-1H-pyrrolo[3,2-b]pyridin-1-yl)-5,7-difluoro-2-(1H-indol-4-yl)-3-methylquinoline | 0.002766 |
| 4-(3,3-dimethyl-6-(4-morpholinyl)-2,3-dihydro-1H-pyrrolo[3,2-b]pyridin-1-yl)-5,7-difluoro-2-(3-fluorobenzyl)-3-methylquinoline | 0.002874 |
| 4-(3,3-dimethyl-6-(4-morpholinyl)-2,3-dihydro-1H-pyrrolo[3,2-b]pyridin-1-yl)-5,7-difluoro-3-methyl-2-(2-phenylethyl)quinoline | 0.008121 |
| 3-((4-(3,3-dimethyl-6-(4-morpholinyl)-2,3-dihydro-1H-pyrrolo[3,2-b]pyridin-1-yl)-5,7-difluoro-3-methyl-2-quinolinyl)methyl)benzonitrile | 0.002676 |
| 4-(7-fluoro-3-methyl-2-(2-pyridinyl)-4-quinolinyl)-6-(4-morpholinyl)-3,4-dihydro-2H-1,4-benzoxazine | 0.351 |
| 4-(6-(3,6-dihydro-2H-pyran-4-yl)-3,3-dimethyl-2,3-dihydro-1H-pyrrolo[3,2-b]pyridin-1-yl)-7-fluoro-3-methyl-2-(2-pyridinyl)quinoline | 0.00647 |
| 4-(3,3-dimethyl-6-(4-morpholinyl)-2,3-dihydro-1H-pyrrolo[3,2-b]pyridin-1-yl)-5,7-difluoro-3-methyl-2-((E)-2-phenylethenyl)quinoline | 0.0883 |
| 4-(3,3-dimethyl-6-morpholino-2,3-dihydro-1H-pyrrolo[3,2-b]pyridin-1-yl)-5,7-difluoro-3-methyl-N-(pyridin-2-yl)quinolin-2-amine | 0.0171 |
| 1-(5-fluoro-3-methyl-2-(2-pyridinyl)-4-quinolinyl)-7-(4-morpholinyl)-2,3-dihydro-1H-pyrido[2,3-b][1,4]thiazine 4,4-dioxide | 0.0129 |
| 4-(3,3-dimethyl-6-(4-morpholinyl)-2,3-dihydro-1H-pyrrolo[3,2-b]pyridin-1-yl)-5,7-difluoro-3-methyl-2-(1-phenylcyclopropyl)quinoline | 0.0218 |
| 4-(3,3-dimethyl-6-(4-morpholinyl)-2,3-dihydro-1H-pyrrolo[3,2-b]pyridin-1-yl)-7-fluoro-3-methyl-2-(4-methyl-2-pyridinyl)quinoline | 0.00417 |
| 1-(4-(3,3-dimethyl-6-(4-morpholinyl)-2,3-dihydro-1H-pyrrolo[3,2-b]pyridin-1-yl)-5,7-difluoro-3-methyl-2-quinolinyl)-2-piperidinone | 0.00314 |
| 4-(3,3-dimethyl-6-(4-morpholinyl)-2,3-dihydro-1H-pyrrolo[3,2-b]pyridin-1-yl)-5,7-difluoro-2-(3-methoxybenzyl)-3-methylquinoline | 0.00234 |

-continued

| Compound | Ki(μM) |
|---|---|
| 4-(3,3-dimethyl-6-(4-morpholinyl)-2,3-dihydro-1H-pyrrolo[3,2-b]pyridin-1-yl)-5,7-difluoro-3-methyl-2-(3-(trifluoromethyl)benzyl)quinoline | 0.0173 |
| 4-(3,3-dimethyl-6-(4-morpholinyl)-2,3-dihydro-1H-pyrrolo[3,2-b]pyridin-1-yl)-5,7-difluoro-3-methyl-2-(4-methyl-2-pyridinyl)quinoline | 0.0184 |
| 4-(3,3-dimethyl-6-(4-morpholinyl)-2,3-dihydro-1H-pyrrolo[3,2-b]pyridin-1-yl)-5,7-difluoro-2-(5-fluoro-3-pyridinyl)-3-methylquinoline | 0.00521 |
| 4-(3,3-dimethyl-6-(4-morpholinyl)-2,3-dihydro-1H-pyrrolo[3,2-b]pyridin-1-yl)-5,7-difluoro-3-methyl-2-(5-methyl-3-pyridinyl)quinoline | 0.003 |
| 4-(3,3-dimethyl-6-(4-morpholinyl)-2,3-dihydro-1H-pyrrolo[3,2-b]pyridin-1-yl)-5,7-difluoro-3-methyl-2-(5-(methylsulfonyl)-3-pyridinyl)quinoline | 0.0167 |
| 1-(4-(3,3-dimethyl-6-(4-morpholinyl)-2,3-dihydro-1H-pyrrolo[3,2-b]pyridin-1-yl)-5,7-difluoro-3-methyl-2-quinolinyl)-2-pyrrolidinone | 0.00154 |
| 1'-(5,7-difluoro-3-methyl-2-(4-methyl-2-pyridinyl)-4-quinolinyl)-6'-(4-morpholinyl)-1',2,2',3,5,6-hexahydrospiro[pyran-4,3'-pyrrolo[3,2-b]pyridine] | 0.00882 |
| 1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-piperidinone | 0.00551 |
| 1'-(5,7-difluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] | 0.00944 |
| 1'-(5-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] | 0.00648 |
| 1'-(7-fluoro-3-methyl-2-(2-pyridinyl)-4-quinolinyl)-6'-(1H-pyrazol-4-yl)-1',2,2',3,5,6-hexahydrospiro[pyran-4,3'-pyrrolo[3,2-b]pyridine] | 0.32 |
| 1'-(5,7-difluoro-3-methyl-2-(2-(methylsulfonyl)phenyl)-4-quinolinyl)-6'-(4-morpholinyl)-1',2,2',3,5,6-hexahydrospiro[pyran-4,3'-pyrrolo[3,2-b]pyridine] | 0.00451 |
| 1-(5,7-difluoro-3-methyl-4-(6-(4-morpholinyl)-2',3',5',6'-tetrahydrospiro[indole-3,4'-pyran]-1(2H)-yl)-2-quinolinyl)-2(1H)-pyridinone | 0.00464 |
| 1'-(8-chloro-2,3-dimethyl-4-quinolinyl)-6'-(4-morpholinyl)-1',2,2',3,5,6-hexahydrospiro[pyran-4,3'-pyrrolo[3,2-b]pyridine] | 0.00268 |
| 1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-pyrrolidinone | 0.00236 |
| 1-(7-fluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-piperidinone | 0.00162 |
| 1'-(2-(3,5-dimethylphenyl)-7-fluoro-3-methyl-4-quinolinyl)-6'-(4-morpholinyl)-1',2,2',3,5,6-hexahydrospiro[pyran-4,3'-pyrrolo[3,2-b]pyridine] | 0.0121 |
| 4-(3,3-dimethyl-6-(4-morpholinyl)-2,3-dihydro-1H-pyrrolo[3,2-b]pyridin-1-yl)-5,7-difluoro-3-methyl-2-(5-methyl-2-(methylsulfonyl)phenyl)quinoline | 0.00105 |
| 1'-(7-fluoro-3-methyl-2-(4-methyl-2-pyridinyl)-4-quinolinyl)-6'-(4-morpholinyl)-1',2,2',3,5,6-hexahydrospiro[pyran-4,3'-pyrrolo[3,2-b]pyridine] | 0.00519 |
| 1'-(5,7-difluoro-2-(2-methoxy-4-pyridinyl)-3-methyl-4-quinolinyl)-6'-(4-morpholinyl)-1',2,2',3,5,6-hexahydrospiro[pyran-4,3'-pyrrolo[3,2-b]pyridine] | 0.00689 |
| 1'-(2-(2,2-dimethyl-4-morpholinyl)-5,7-difluoro-3-methyl-4-quinolinyl)-6'-(4-morpholinyl)-1',2,2',3,5,6-hexahydrospiro[pyran-4,3'-pyrrolo[3,2-b]pyridine] | 0.0054 |
| 2-(2,2-dimethyl-4-morpholinyl)-4-(3,3-dimethyl-6-(4-morpholinyl)-2,3-dihydro-1H-pyrrolo[3,2-b]pyridin-1-yl)-5,7-difluoro-3-methylquinoline | 0.00152 |
| 1'-(5,7-difluoro-3-methyl-2-(5-methyl-2-(methylsulfonyl)phenyl)-4-quinolinyl)-6'-(4-morpholinyl)-1',2,2',3,5,6-hexahydrospiro[pyran-4,3'-pyrrolo[3,2-b]pyridine] | 0.00151 |
| 1-(7-fluoro-3-methyl-2-(2-pyridinyl)-4-quinolinyl)-7-(4-morpholinyl)-2,3-dihydro-1H-pyrido[2,3-b][1,4]thiazine 4,4-dioxide | 0.00222 |
| 1-(7-fluoro-3-methyl-2-(4-methyl-2-pyridinyl)-4-quinolinyl)-7-(4-morpholinyl)-2,3-dihydro-1H-pyrido[2,3-b][1,4]thiazine 4,4-dioxide | 0.00196 |
| 1'-(3-methyl-2-(2-pyridinyl)-1,8-naphthyridin-4-yl)-6'-(4-morpholinyl)-1',2,2',3,5,6-hexahydrospiro[pyran-4,3'-pyrrolo[3,2-b]pyridine] | 0.0659 |

-continued

| Compound | Ki(μM) |
|---|---|
| 1-(7-fluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-pyrrolidinone | 0.00764 |
| 4-(3-methyl-2-(2-pyridinyl)-1,8-naphthyridin-4-yl)-6-(4-morpholinyl)-3,4-dihydro-2H-1,4-benzoxazine | 0.883 |
| 4-(3,3-dimethyl-6-(4-morpholinyl)-2,3-dihydro-1H-pyrrolo[3,2-b]pyridin-1-yl)-3-methyl-2-(2-pyridinyl)-1,8-naphthyridine | 0.0125 |
| 1'-(3-methyl-2-(2-pyridinyl)-1,7-naphthyridin-4-yl)-6'-(4-morpholinyl)-1',2,2',3,5,6-hexahydrospiro[pyran-4,3'-pyrrolo[3,2-b]pyridine] | 0.0307 |
| 1'-(2-(3,5-difluorophenyl)-3-methyl-1,8-naphthyridin-4-yl)-6'-(4-morpholinyl)-1',2,2',3,5,6-hexahydrospiro[pyran-4,3'-pyrrolo[3,2-b]pyridine] | 0.0282 |
| 1'-(2-(3,5-difluorophenyl)-3-methyl-1,7-naphthyridin-4-yl)-6'-(4-morpholinyl)-1',2,2',3,5,6-hexahydrospiro[pyran-4,3'-pyrrolo[3,2-b]pyridine] | 0.0134 |
| 2-(3,5-difluorophenyl)-4-(3,3-dimethyl-6-(4-morpholinyl)-2,3-dihydro-1H-pyrrolo[3,2-b]pyridin-1-yl)-3-methyl-1,7-naphthyridine | 0.00236 |
| 4-(3,3-dimethyl-6-(4-morpholinyl)-2,3-dihydro-1H-pyrrolo[3,2-b]pyridin-1-yl)-3-methyl-2-(4-methyl-2-pyridinyl)-1,8-naphthyridine | 0.01 |
| 2-(3,5-difluorophenyl)-4-(3,3-dimethyl-6-(4-morpholinyl)-2,3-dihydro-1H-pyrrolo[3,2-b]pyridin-1-yl)-3-methyl-1,8-naphthyridine | 0.00311 |
| methyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate | 0.00149 |
| 1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-5,5-dimethyl-2-piperidinone | 0.0027 |
| tert-butyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate | 0.0124 |
| 1'-(5,7-difluoro-3-methyl-2-(1-piperazinyl)-4-quinolinyl)-6'-(4-morpholinyl)-1',2,2',3,5,6-hexahydrospiro[pyran-4,3'-pyrrolo[3,2-b]pyridine] | 0.00137 |
| 1-(7-fluoro-3-methyl-2-(2-pyridinyl)-4-quinolinyl)-6-(4-morpholinyl)-1,2,2',3',5',6'-hexahydrospiro[indole-3,4'-thiopyran]-1',1'-dioxide | 0.0644 |
| 1'-(5,7-difluoro-3-methyl-2-(4-(methylsulfonyl)-1-piperazinyl)-4-quinolinyl)-6'-(4-morpholinyl)-1',2,2',3,5,6-hexahydrospiro[pyran-4,3'-pyrrolo[3,2-b]pyridine] | 0.0023 |
| 4-(3,3-dimethyl-6-(4-morpholinyl)-2,3-dihydro-1H-pyrrolo[3,2-b]pyridin-1-yl)-2-(3-fluorophenyl)-3-methyl-1,8-naphthyridine | 0.00538 |
| 1'-(2-(3-fluorophenyl)-3-methyl-1,8-naphthyridin-4-yl)-6'-(4-morpholinyl)-1',2,2',3,5,6-hexahydrospiro[pyran-4,3'-pyrrolo[3,2-b]pyridine] | 0.0278 |
| 4-(3,3-dimethyl-6-(4-morpholinyl)-2,3-dihydro-1H-pyrrolo[3,2-b]pyridin-1-yl)-3-methyl-2-phenyl-1,8-naphthyridine | 0.00436 |
| 1'-(3-methyl-2-phenyl-1,8-naphthyridin-4-yl)-6'-(4-morpholinyl)-1',2,2',3,5,6-hexahydrospiro[pyran-4,3'-pyrrolo[3,2-b]pyridine] | 0.0226 |
| 5'-bromo-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] | 0.0416 |
| 1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]-5'-carbonitrile | 0.219 |
| 1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridin]-5'-amine | 0.029 |
| 5'-ethenyl-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] | 0.0941 |
| 5'-chloro-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine] | 0.0133 |
| 4-(5-bromo-3,3-dimethyl-6-(4-morpholinyl)-2,3-dihydro-1H-pyrrolo[3,2-b]pyridin-1-yl)-7-fluoro-3-methyl-2-(2-pyridinyl)quinoline | 0.0333 |
| 1-(7-fluoro-3-methyl-2-(2-pyridinyl)-4-quinolinyl)-3,3-dimethyl-6-(4-morpholinyl)-2,3-dihydro-1H-pyrrolo[3,2-b]pyridine-5-carbonitrile | 0.0495 |
| 4-(5-chloro-3,3-dimethyl-6-(4-morpholinyl)-2,3-dihydro-1H-pyrrolo[3,2-b]pyridin-1-yl)-3-methyl-2-(4-methyl-2-pyridinyl)-1,8-naphthyridine | 0.0687 |

-continued

| Compound | Ki(μM) |
|---|---|
| 4-(5-chloro-3,3-dimethyl-6-(4-morpholinyl)-2,3-dihydro-1H-pyrrolo[3,2-b]pyridin-1-yl)-7-fluoro-3-methyl-2-(2-pyridinyl)quinoline | 0.00316 |
| 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-N-methyl-1-piperazinecarboxamide | 0.00127 |
| 1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-azetidinone | 0.0023 |
| 1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-4,4-dimethyl-2-pyrrolidinone | 0.00224 |
| 4-(3,3-dimethyl-6-(4-morpholinyl)-2,3-dihydro-1H-pyrrolo[3,2-b]pyridin-1-yl)-2-(5-fluoro-3-pyridinyl)-3-methyl-1,8-naphthyridine | 0.053 |
| 4-(3,3-dimethyl-6-(4-morpholinyl)-2,3-dihydro-1H-pyrrolo[3,2-b]pyridin-1-yl)-3-methyl-2-(4-methyl-2-pyridinyl)-1,7-naphthyridine | 0.00537 |
| 4-(3,3-dimethyl-6-(4-morpholinyl)-2,3-dihydro-1H-pyrrolo[3,2-b]pyridin-1-yl)-2-(5-fluoro-3-pyridinyl)-3-methyl-1,7-naphthyridine | 0.00775 |
| 1-(7-fluoro-3-methyl-2-(2-pyridinyl)-4-quinolinyl)-6-(4-morpholinyl)-1,2-dihydrospiro[indole-3,3'-thietane] 1',1'-dioxide | 0.0805 |
| (1-(7-fluoro-3-methyl-2-(2-pyridinyl)-4-quinolinyl)-6-(4-morpholinyl)-2,3-dihydro-1H-indole-3,3-diyl)dimethanol | 0.154 |
| 2-cyclopropyl-4-(3,3-dimethyl-6-(4-morpholinyl)-2,3-dihydro-1H-pyrrolo[3,2-b]pyridin-1-yl)-3-methyl-1,8-naphthyridine | 0.032 |

For the treatment of PI3Kδ-mediated-diseases, such as rheumatoid arthritis, ankylosing spondylitis, osteoarthritis, psoriatic arthritis, psoriasis, inflammatory diseases, and autoimmune diseases, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, rheumatoid arthritis, ankylosing spondylitis, osteoarthritis, psoriatic arthritis, psoriasis, inflammatory diseases, and autoimmune diseases and the like.

The dosage regimen for treating PI3Kδ-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$-$C_4$)-alkyloxy)ethyl, for example, methoxyethyl, ethoxyethyl, propoxyethyl, isopropoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethylformamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:

1. A compound having the structure:

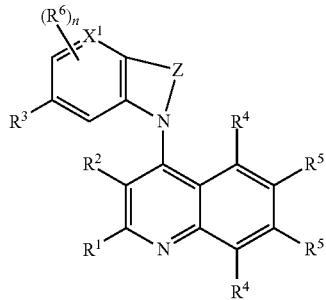

or any pharmaceutically-acceptable salt thereof, wherein:
$X^1$ is C or N;

Z is —C=C—, —C—C—, —O—C=C—, —C=O—C—, —C=C—O—, —C=N—, —N=C—, —C—N—, —N—C—, —S(=O)$_2$—C=C—, —C—S(=O)$_2$—C—, —C—C—S(=O)$_2$—, —S(=O)$_2$—N=C—, —N=S(=O)$_2$—C—, —C—S(=O)$_2$—N—, —C—N—S(=O)$_2$—, —C=C—C(=O)— and —C(=O)—C=C—; any of which are substituted by 0, 1, 2, 3 or 4 substituents selected from halo, nitro, cyano, $C_{1-4}$alk, $OC_{1-4}$alk, $OC_{1-4}$haloalk, $NHC_{1-4}$alk, $N(C_{1-4}alk)C_{1-4}$alk and $C_{1-4}$haloalk; and additionally substituted by 0 or 1 saturated or partially saturated 3-, 4-, 5- or 6-membered spiro rings containing 0, 1 or 2 heteroatoms selected from N, O and S, the spiro ring being substituted by 0, 1, 2 or 3 substituents independently selected from halo, $C_{1-6}$alk and $C_{1-4}$haloalk;

n is 0, 1, 2 or 3;

$R^1$ is a saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)$OR^a$, —C(=O)$NR^aR^a$, —C(=$NR^a$)$NR^aR^a$, —$OR^a$, —OC(=O)$R^a$, —OC(=O)$NR^aR^a$, —OC(=O)N($R^a$)S(=O)$_2R^a$, —$OC_{2-6}$alkNR$^a$R$^a$, —$OC_{2-6}$alkOR$^a$, —$SR^a$, —S(=O)$R^a$, —S(=O)$_2R^a$, —S(=O)$_2$NR$^a$R$^a$, —S(=O)$_2$N(R$^a$)C(=O)$R^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2R^a$, —N(R$^a$)S(=O)$_2$ NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups;

$R^2$ is selected from H, halo, $C_{1-6}$alk, $C_{1-4}$haloalk, cyano, nitro, —C(=O)$R^a$, —C(=O)$OR^a$, —C(=O)$NR^aR^a$, —C(=NR$^a$)NR$^a$R$^a$, —OR$^a$, —OC(=O)R$^a$, —OC(=O)NR$^a$R$^a$, —OC(=O)N(R$^a$)S(=O$_2$)R$^a$, —OC$_{2-6}$alkNR$^a$R$^a$, —OC$_{2-6}$alkOR$^a$, —SR$^a$—S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2R^a$, —N(R$^a$)S(=O)$_2$ NR$^a$R$^a$, —NR$^a$C$_{2-6}$alkNR$^a$R$^a$ and —NR$^a$C$_{2-6}$alkOR$^a$;

$R^3$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$alk, $C_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2R^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$; or $R^3$ is selected from halo, $C_{1-6}$alk, $C_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^4$ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk, C$_{1-4}$haloalk, or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —OC$_{1-4}$alk, —NH$_2$, —NHC$_{1-4}$alk, —N(C$_{1-4}$alk)C$_{1-4}$alk;

R$^5$ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk or $C_{1-4}$haloalk; R$^6$ is selected from halo, cyano, OH, OC$_{1-4}$alk, C$_{1-4}$alk, C$_{1-3}$haloalk, OC$_{1-4}$alk, NH$_2$, NHC$_{1-4}$alk, N(C$_{1-4}$alk)C$_{1-4}$alk;

R$^a$ is independently, at each instance, H or R$^b$; and

R$^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OC$_{1-4}$alk, —NH$_2$, —NHC$_{1-4}$alk, —N(C$_{1-4}$alk)C$_{1-4}$alk.

2. A compound according to claim 1, wherein the compound is:

4-(3,3-dimethyl-6-(4-morpholinyl)-2,3-dihydro-1H-indol-1-yl)-7-fluoro-3-methyl-2-(2-pyridinyl)quinoline;

4-(3,3-dimethyl-6-(4-morpholinyl)-2,3-dihydro-1H-indol-1-yl)-5-fluoro-3-methyl-2-(2-pyridinyl)quinoline;

1-(7-fluoro-3-methyl-2-(2-pyridinyl)-4-quinolinyl)-6-(4-morpholinyl)-1,2,2',3',5',6'-hexahydrospiro[indole-3,4'-pyran];

4-(3,3-dimethyl-6-(4-morpholinyl)-2,3-dihydro-1H-indol-1-yl)-7-fluoro-3-methyl-2-(3-pyridinyl)quinoline;

3-(4-(3,3-dimethyl-6-(4-morpholinyl)-2,3-dihydro-1H-indol-1-yl)-7-fluoro-3-methyl-2-quinolinyl)benzonitrile;

4-(3,3-dimethyl-6-(4-morpholinyl)-2,3-dihydro-1H-indol-1-yl)-8-fluoro-3-methyl-2-(2-pyridinyl)quinoline;

1-(7-fluoro-3-methyl-2-(4-pyridinyl)-4-quinolinyl)-6-(4-morpholinyl)-1,2,2',3',5',6'-hexahydrospiro[indole-3,4'-pyran];

1-(7-fluoro-3-methyl-2-(3-pyridinyl)-4-quinolinyl)-6-(4-morpholinyl)-1,2,2',3',5',6'-hexahydrospiro[indole-3,4'-pyran];

4-(3,3-dimethyl-6-(4-morpholinyl)-2,3-dihydro-1H-pyrrolo[3,2-b]pyridin-1-yl)-7-fluoro-3-methyl-2-(2-pyridinyl)quinoline;

4-(1-(7-fluoro-3-methyl-2-(2-pyridinyl)-4-quinolinyl)-3,3-dimethyl-2,3-dihydro-1H-indol-6-yl)-2-pyrimidinamine;

4-(1-(7-fluoro-3-methyl-2-(2-pyridinyl)-4-quinolinyl)-3,3-dimethyl-2,3-dihydro-1H-pyrrolo[3,2-b]pyridin-6-yl)-2-pyrimidinamine;

4-(3,3-dimethyl-6-(4-morpholinyl)-2,3-dihydro-1H-pyrrolo[3,2-b]pyridin-1-yl)-7-fluoro-3-(1-methylethyl)-2-(2-pyridinyl)quinoline;

1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine];

1-(7-fluoro-3-methyl-2-(2-methyl-3-pyridinyl)-4-quinolinyl)-6-(4-morpholinyl)-1,2,2',3',5',6'-hexahydrospiro[indole-3,4'-pyran];

4-(3,3-dimethyl-6-(4-morpholinyl)-2,3-dihydro-1H-pyrrolo[3,2-b]pyridin-1-yl)-7-fluoro-3-methyl-2-(2-methyl-3-pyridinyl)quinoline;

1-(7-fluoro-3-methyl-2-(2-pyridinyl)-4-quinolinyl)-N-(2-methoxyethyl)-N,3,3-trimethyl-2,3-dihydro-1H-pyrrolo[3,2-b]pyridin-6-amine;

4-(3,3-dimethyl-6-(1H-pyrazol-4-yl)-2,3-dihydro-1H-pyrrolo[3,2-b]pyridin-1-yl)-7-fluoro-3-methyl-2-(2-pyridinyl)quinoline;

4-(3,3-dimethyl-6-(9H-purin-6-yl)-2,3-dihydro-1H-pyrrolo[3,2-b]pyridin-1-yl)-7-fluoro-3-methyl-2-(2-pyridinyl)quinoline;

1-(7-fluoro-3-methyl-2-(2-pyridinyl)-4-quinolinyl)-3,3-dimethyl-2,3-dihydro-1H-pyrrolo[3,2-b]pyridine-6-carboxamide;

4-(3,3-dimethyl-6-(4-morpholinyl)-2,3-dihydro-1H-pyrrolo[3,2-b]pyridin-1-yl)-2-(3,5-dimethylphenyl)-7-fluoro-3-methylquinoline;

4-(1-(7-fluoro-3-methyl-2-(2-pyridinyl)-4-quinolinyl)-3,3-dimethyl-2,3-dihydro-1H-indol-6-yl)-6-methyl-2-pyrimidinamine;

5-chloro-4-(1-(7-fluoro-3-methyl-2-(2-pyridinyl)-4-quinolinyl)-3,3-dimethyl-2,3-dihydro-1H-indol-6-yl)-2-pyrimidinamine;

1-(7-fluoro-3-methyl-2-(2-(methylsulfonyl)phenyl)-4-quinolinyl)-6-(4-morpholinyl)-1,2,2',3',5',6'-hexahydrospiro[indole-3,4'-pyran];

4-(3,3-dimethyl-6-(4-morpholinyl)-2,3-dihydro-1H-indol-1-yl)-7-fluoro-3-methyl-2-(2-(methylsulfonyl)phenyl)quinoline;

4-(1-(7-fluoro-3-methyl-2-(2-(methylsulfonyl)phenyl)-4-quinolinyl)-3,3-dimethyl-2,3-dihydro-1H-pyrrolo[3,2-b]pyridin-6-yl)-2-pyrimidinamine;

6-(7-fluoro-3-methyl-4-(6-(4-morpholinyl)-2',3',5',6'-tetrahydrospiro[indole-3,4'-pyran]-1(2H)-yl)-2-quinolinyl)-2-pyridinol;

4-(3,3-dimethyl-6-(4-morpholinyl)-2,3-dihydro-1H-pyrrolo[3,2-b]pyridin-1-yl)-7-fluoro-3-methyl-2-(2-(methylsulfonyl)phenyl)quinoline;

6-(4-(3,3-dimethyl-6-(4-morpholinyl)-2,3-dihydro-1H-pyrrolo[3,2-b]pyridin-1-yl)-7-fluoro-3-methyl-2-quinolinyl)-2(1H)-pyridinone;

1-(7-fluoro-2-(6-methoxy-2-pyridinyl)-3-methyl-4-quinolinyl)-6-(4-morpholinyl)-1,2,2',3',5',6'-hexahydrospiro[indole-3,4'-pyran];

1-(7-fluoro-3-methyl-2-(3-(methylsulfonyl)phenyl)-4-quinolinyl)-6-(4-morpholinyl)-1,2,2',3',5',6'-hexahydrospiro[indole-3,4'-pyran];

1-(5,7-difluoro-3-methyl-2-(2-pyridinyl)-4-quinolinyl)-6-(4-morpholinyl)-1,2,2',3',5',6'-hexahydrospiro[indole-3,4'-pyran];

4-(3,3-dimethyl-6-(4-morpholinyl)-2,3-dihydro-1H-pyrrolo[3,2-b]pyridin-1-yl)-5-fluoro-3-methyl-2-(2-pyridinyl)quinoline;

2-(2,5-difluorophenyl)-4-(3,3-dimethyl-6-(4-morpholinyl)-2,3-dihydro-1H-indol-1-yl)-7-fluoro-3-methylquinoline;

2-(3,5-bis(trifluoromethyl)phenyl)-4-(3,3-dimethyl-6-(4-morpholinyl)-2,3-dihydro-1H-indol-1-yl)-7-fluoro-3-methylquinoline;

2-(3,5-bis(trifluoromethyl)phenyl)-4-(3,3-dimethyl-6-(4-morpholinyl)-2,3-dihydro-1H-indol-1-yl)-5-fluoro-3-methylquinoline;

5-chloro-4-(3,3-dimethyl-6-(4-morpholinyl)-2,3-dihydro-1H-indol-1-yl)-2-(2-fluorophenyl)-3-methylquinoline;

4-(3,3-dimethyl-6-(4-morpholinyl)-2,3-dihydro-1H-pyrrolo[3,2-b]pyridin-1-yl)-5-fluoro-3,8-dimethyl-2-(2-pyridinyl)quinoline;

4-(3,3-dimethyl-6-(4-morpholinyl)-2,3-dihydro-1H-pyrrolo[3,2-b]pyridin-1-yl)-7-fluoro-2-(2-pyridinyl)-3-quinolinecarbonitrile;

4-(3,3-dimethyl-6-(4-morpholinyl)-2,3-dihydro-1H-indol-1-yl)-5,7-difluoro-3-methyl-2-(1-piperidinyl)quinoline;

6-chloro-4-(3,3-dimethyl-6-(4-morpholinyl)-2,3-dihydro-1H-indol-1-yl)-7-methoxy-2,3-dimethylquinoline;

4-(3,3-dimethyl-6-(4-morpholinyl)-2,3-dihydro-1H-indol-1-yl)-7-methoxy-2,3,6-trimethylquinoline;

8-chloro-4-(3,3-dimethyl-6-(4-morpholinyl)-2,3-dihydro-1H-indol-1-yl)-2,3,6-trimethylquinoline;

4-(3,3-dimethyl-6-(4-morpholinyl)-2,3-dihydro-1H-indol-1-yl)-6,8-dimethoxy-2,3-dimethylquinoline;

6-chloro-4-(3,3-dimethyl-6-(4-morpholinyl)-2,3-dihydro-1H-indol-1-yl)-2-(2-methoxyphenyl)quinoline;

6-chloro-4-(3,3-dimethyl-6-(4-pyridinyl)-2,3-dihydro-1H-indol-1-yl)-2,3-dimethylquinoline;

6-chloro-4-(3,3-dimethyl-6-(1H-pyrazol-4-yl)-2,3-dihydro-1H-indol-1-yl)-2,3-dimethylquinoline;

6-chloro-4-(3,3-dimethyl-6-(4-morpholinyl)-2,3-dihydro-1H-indol-1-yl)-2,3-dimethylquinoline;

4-(6-chloro-2,3-dimethyl-4-quinolinyl)-6-(4-morpholinyl)-3,4-dihydro-2H-1,4-benzoxazine;

6-chloro-4-(4-methoxy-6-(4-pyridinyl)-1H-indol-1-yl)-2,3-dimethylquinoline;

6-chloro-4-(4-methoxy-6-(1H-pyrazol-4-yl)-1H-indol-1-yl)-2,3-dimethylquinoline;

1-(6-chloro-2,3-dimethyl-4-quinolinyl)-6-(1H-pyrazol-4-yl)-1H-indol-4-ol;

1-(6-chloro-2,3-dimethyl-4-quinolinyl)-6-(4-pyridinyl)-1H-indole-4-carbonitrile;

1-(6-chloro-2,3-dimethyl-4-quinolinyl)-6-(1H-pyrazol-4-yl)-1H-indole-4-carbonitrile;

6-chloro-4-(3,3-dimethyl-6-(4-morpholinyl)-2,3-dihydro-1H-indol-1-yl)-3-methyl-2-(trifluoromethyl)quinoline;

6-chloro-4-(4-methoxy-6-(4-morpholinyl)-1H-indol-1-yl)-2,3-dimethylquinoline;

1-(6-chloro-2,3-dimethyl-4-quinolinyl)-6-(4-morpholinyl)-1H-indole-4-carbonitrile;

1-(6-chloro-2,3-dimethyl-4-quinolinyl)-6-(4-morpholinyl)-1,2,2',3',5',6'-hexahydrospiro[indole-3,4'-pyran];

1-(2,3-dimethyl-4-quinolinyl)-6-(4-morpholinyl)-1,2,2',3',5',6'-hexahydrospiro[indole-3,4'-pyran];

6-bromo-1-(6-chloro-7-methoxy-2,3-dimethyl-4-quinolinyl)-1,2,2',3',5',6'-hexahydrospiro[indole-3,4'-pyran];

1-(6-chloro-7-methoxy-2,3-dimethyl-4-quinolinyl)-1,2,2',3',5',6'-hexahydrospiro[indole-3,4'-pyran]-6-carbonitrile;

6-(4-morpholinyl)-1-(2,3,8-trimethyl-4-quinolinyl)-1,2,2',3',5',6'-hexahydrospiro[indole-3,4'-pyran];

6-chloro-7-methoxy-2,3-dimethyl-4-(3,3,7-trimethyl-6-(4-morpholinyl)-2,3-dihydro-1H-indol-1-yl)quinoline;

7-chloro-9-(3,3-dimethyl-6-(4-morpholinyl)-2,3-dihydro-1H-indol-1-yl)-2,3-dihydro-1H-cyclopenta[b]quinoline;

7-chloro-9-(3,3-dimethyl-6-(4-morpholinyl)-2,3-dihydro-1H-indol-1-yl)-1,2,3,4-tetrahydroacridine;

7-chloro-9-(3,3-dimethyl-6-(4-morpholinyl)-2,3-dihydro-1H-indol-1-yl)-3,3-dimethyl-2,3-dihydro-1H-cyclopenta[b]quinoline;

4-(3,3-dimethyl-6-(4-morpholinyl)-2,3-dihydro-1H-indol-1-yl)-3-methylquinoline;

4-(3,3-dimethyl-6-(4-pyridinyl)-2,3-dihydro-1H-indol-1-yl)-7-fluoro-3-methyl-2-(2-pyridinyl)quinoline;

6-chloro-4-(3,3-dimethyl-6-(4-morpholinyl)-2,3-dihydro-1H-indol-1-yl)-2,3,8-trimethylquinoline;

4-(3,3-dimethyl-6-(4-morpholinyl)-2,3-dihydro-1H-indol-1-yl)-2-(2-fluorophenyl)-3-methylquinoline;

4-(3,3-dimethyl-6-(4-morpholinyl)-2,3-dihydro-1H-indol-1-yl)-2,3,8-trimethylquinoline;

8-chloro-4-(3,3-dimethyl-6-(4-morpholinyl)-2,3-dihydro-1H-indol-1-yl)-2,3-dimethylquinoline;

4-(3,3-dimethyl-6-(4-morpholinyl)-2,3-dihydro-1H-indol-1-yl)-2,3-dimethyl-8-(trifluoromethyl)quinoline;

1-(6-chloro-2,3-dimethyl-4-quinolinyl)-6-(1H-pyrazol-4-yl)-1H-indole-3-carbonitrile;

6-chloro-4-(3,3-dimethyl-6-(4-morpholinyl)-2,3-dihydro-1H-indol-1-yl)-3-ethyl-2-methylquinoline;

4-(3,3-dimethyl-6-(4-morpholinyl)-2,3-dihydro-1H-indol-1-yl)-2,3-dimethylquinoline;

4-(6-chloro-7-methoxy-2,3-dimethyl-4-quinolinyl)-6-(4-morpholinyl)-3,4-dihydro-2H-1,4-benzothiazine 1,1-dioxide;

4-(5-fluoro-2-(2-fluorophenyl)-3-methyl-4-quinolinyl)-6-(4-morpholinyl)-3,4-dihydro-2H-1,4-benzothiazine 1,1-dioxide;

4-(3,3-dimethyl-6-(4-morpholinyl)-2,3-dihydro-1H-indol-1-yl)-3-methyl-2-phenylquinoline;

1-(7-fluoro-2-(2-fluorophenyl)-3-methyl-4-quinolinyl)-6-(4-morpholinyl)-1,2,2',3',5',6'-hexahydrospiro[indole-3,4'-pyran];

1-(3-methyl-2-phenyl-4-quinolinyl)-6-(4-morpholinyl)-1,2,2',3',5',6'-hexahydrospiro[indole-3,4'-pyran];

1-(7-chloro-2-(2-fluorophenyl)-3-methyl-4-quinolinyl)-6-(4-morpholinyl)-1,2,2',3',5',6'-hexahydrospiro[indole-3,4'-pyran];

4-(3,3-dimethyl-6-(4-morpholinyl)-2,3-dihydro-1H-indol-1-yl)-7-fluoro-2-(2-fluorophenyl)-3-methylquinoline;

2-benzyl-4-(3,3-dimethyl-6-(4-morpholinyl)-2,3-dihydro-1H-pyrrolo[3,2-b]pyridin-1-yl)-5,7-difluoro-3-methylquinoline;

4-(3,3-dimethyl-6-(4-morpholinyl)-2,3-dihydro-1H-pyrrolo[3,2-b]pyridin-1-yl)-5,7-difluoro-3-methyl-2-(1-phenylethenyl)quinoline;

4-(3,3-dimethyl-6-(4-morpholinyl)-2,3-dihydro-1H-pyrrolo[3,2-b]pyridin-1-yl)-5,7-difluoro-3-methyl-2-(1-naphthalenyl)quinoline;

4-(3,3-dimethyl-6-(4-morpholinyl)-2,3-dihydro-1H-pyrrolo[3,2-b]pyridin-1-yl)-5,7-difluoro-3-methyl-2-(1-methyl-1H-indol-5-yl)quinoline;

4-(3,3-dimethyl-6-(4-morpholinyl)-2,3-dihydro-1H-pyrrolo[3,2-b]pyridin-1-yl)-5,7-difluoro-2-(1H-indol-4-yl)-3-methylquinoline;

4-(3,3-dimethyl-6-(4-morpholinyl)-2,3-dihydro-1H-pyrrolo[3,2-b]pyridin-1-yl)-5,7-difluoro-2-(3-fluorobenzyl)-3-methylquinoline;

4-(3,3-dimethyl-6-(4-morpholinyl)-2,3-dihydro-1H-pyrrolo[3,2-b]pyridin-1-yl)-5,7-difluoro-3-methyl-2-(2-phenylethyl)quinoline;

3-((4-(3,3-dimethyl-6-(4-morpholinyl)-2,3-dihydro-1H-pyrrolo[3,2-b]pyridin-1-yl)-5,7-difluoro-3-methyl-2-quinolinyl)methyl)benzonitrile;

4-(7-fluoro-3-methyl-2-(2-pyridinyl)-4-quinolinyl)-6-(4-morpholinyl)-3,4-dihydro-2H-1,4-benzoxazine;

4-(6-(3,6-dihydro-2H-pyran-4-yl)-3,3-dimethyl-2,3-dihydro-1H-pyrrolo[3,2-b]pyridin-1-yl)-7-fluoro-3-methyl-2-(2-pyridinyl)quinoline;

4-(3,3-dimethyl-6-(4-morpholinyl)-2,3-dihydro-1H-pyrrolo[3,2-b]pyridin-1-yl)-5,7-difluoro-3-methyl-2-((E)-2-phenylethenyl)quinoline;

4-(3,3-dimethyl-6-morpholino-2,3-dihydro-1H-pyrrolo[3,2-b]pyridin-1-yl)-5,7-difluoro-3-methyl-N-(pyridin-2-yl)quinolin-2-amine;

1-(5-fluoro-3-methyl-2-(2-pyridinyl)-4-quinolinyl)-7-(4-morpholinyl)-2,3-dihydro-1H-pyrido[2,3-b][1,4]thiazine 4,4-dioxide;

4-(3,3-dimethyl-6-(4-morpholinyl)-2,3-dihydro-1H-pyrrolo[3,2-b]pyridin-1-yl)-5,7-difluoro-3-methyl-2-(1-phenylcyclopropyl)quinoline;

4-(3,3-dimethyl-6-(4-morpholinyl)-2,3-dihydro-1H-pyrrolo[3,2-b]pyridin-1-yl)-7-fluoro-3-methyl-2-(4-methyl-2-pyridinyl)quinoline;

1-(4-(3,3-dimethyl-6-(4-morpholinyl)-2,3-dihydro-1H-pyrrolo[3,2-b]pyridin-1-yl)-5,7-difluoro-3-methyl-2-quinolinyl)-2-piperidinone;

4-(3,3-dimethyl-6-(4-morpholinyl)-2,3-dihydro-1H-pyrrolo[3,2-b]pyridin-1-yl)-5,7-difluoro-2-(3-methoxybenzyl)-3-methylquinoline;

4-(3,3-dimethyl-6-(4-morpholinyl)-2,3-dihydro-1H-pyrrolo[3,2-b]pyridin-1-yl)-5,7-difluoro-3-methyl-2-(3-(trifluoromethyl)benzyl)quinoline;

4-(3,3-dimethyl-6-(4-morpholinyl)-2,3-dihydro-1H-pyrrolo[3,2-b]pyridin-1-yl)-5,7-difluoro-3-methyl-2-(4-methyl-2-pyridinyl)quinoline;

4-(3,3-dimethyl-6-(4-morpholinyl)-2,3-dihydro-1H-pyrrolo[3,2-b]pyridin-1-yl)-5,7-difluoro-2-(5-fluoro-3-pyridinyl)-3-methylquinoline;

4-(3,3-dimethyl-6-(4-morpholinyl)-2,3-dihydro-1H-pyrrolo[3,2-b]pyridin-1-yl)-5,7-difluoro-3-methyl-2-(5-methyl-3-pyridinyl)quinoline;

4-(3,3-dimethyl-6-(4-morpholinyl)-2,3-dihydro-1H-pyrrolo[3,2-b]pyridin-1-yl)-5,7-difluoro-3-methyl-2-(5-(methylsulfonyl)-3-pyridinyl)quinoline;

1-(4-(3,3-dimethyl-6-(4-morpholinyl)-2,3-dihydro-1H-pyrrolo[3,2-b]pyridin-1-yl)-5,7-difluoro-3-methyl-2-quinolinyl)-2-pyrrolidinone;

1'-(5,7-difluoro-3-methyl-2-(4-methyl-2-pyridinyl)-4-quinolinyl)-6'-(4-morpholinyl)-1',2,2',3,5,6-hexahydrospiro[pyran-4,3'-pyrrolo[3,2-b]pyridine];

1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-piperidinone;

1'-(5,7-difluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine];

1'-(5-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine];

1'-(7-fluoro-3-methyl-2-(2-pyridinyl)-4-quinolinyl)-6'-(1H-pyrazol-4-yl)-1',2,2',3,5,6-hexahydrospiro[pyran-4,3'-pyrrolo[3,2-b]pyridine];

1'-(5,7-difluoro-3-methyl-2-(2-(methylsulfonyl)phenyl)-4-quinolinyl)-6'-(4-morpholinyl)-1',2,2',3,5,6-hexahydrospiro[pyran-4,3'-pyrrolo[3,2-b]pyridine];

1-(5,7-difluoro-3-methyl-4-(6-(4-morpholinyl)-2',3',5',6'-tetrahydrospiro[indole-3,4'-pyran]-1(2H)-yl)-2-quinolinyl)-2(1H)-pyridinone;

1'-(8-chloro-2,3-dimethyl-4-quinolinyl)-6'-(4-morpholinyl)-1',2,2',3,5,6-hexahydrospiro[pyran-4,3'-pyrrolo[3,2-b]pyridine];

1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-pyrrolidinone;

1-(7-fluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-piperidinone;

1'-(2-(3,5-dimethylphenyl)-7-fluoro-3-methyl-4-quinolinyl)-6'-(4-morpholinyl)-1',2,2',3,5,6-hexahydrospiro[pyran-4,3'-pyrrolo[3,2-b]pyridine];

4-(3,3-dimethyl-6-(4-morpholinyl)-2,3-dihydro-1H-pyrrolo[3,2-b]pyridin-1-yl)-5,7-difluoro-3-methyl-2-(5-methyl-2-(methylsulfonyl)phenyl)quinoline;

1'-(7-fluoro-3-methyl-2-(4-methyl-2-pyridinyl)-4-quinolinyl)-6'-(4-morpholinyl)-1',2,2',3,5,6-hexahydrospiro[pyran-4,3'-pyrrolo[3,2-b]pyridine];

1'-(5,7-difluoro-2-(2-methoxy-4-pyridinyl)-3-methyl-4-quinolinyl)-6'-(4-morpholinyl)-1',2,2',3,5,6-hexahydrospiro[pyran-4,3'-pyrrolo[3,2-b]pyridine];

1'-(2-(2,2-dimethyl-4-morpholinyl)-5,7-difluoro-3-methyl-4-quinolinyl)-6'-(4-morpholinyl)-1',2,2',3,5,6-hexahydrospiro[pyran-4,3'-pyrrolo[3,2-b]pyridine];

2-(2,2-dimethyl-4-morpholinyl)-4-(3,3-dimethyl-6-(4-morpholinyl)-2,3-dihydro-1H-pyrrolo[3,2-b]pyridin-1-yl)-5,7-difluoro-3-methylquinoline;

1'-(5,7-difluoro-3-methyl-2-(5-methyl-2-(methylsulfonyl)phenyl)-4-quinolinyl)-6'-(4-morpholinyl)-1',2,2',3,5,6-hexahydrospiro[pyran-4,3'-pyrrolo[3,2-b]pyridine];

1-(7-fluoro-3-methyl-2-(2-pyridinyl)-4-quinolinyl)-7-(4-morpholinyl)-2,3-dihydro-1H-pyrido[2,3-b][1,4]thiazine 4,4-dioxide;

1-(7-fluoro-3-methyl-2-(4-methyl-2-pyridinyl)-4-quinolinyl)-7-(4-morpholinyl)-2,3-dihydro-1H-pyrido[2,3-b][1,4]thiazine 4,4-dioxide;

1'-(3-methyl-2-(2-pyridinyl)-1,8-naphthyridin-4-yl)-6'-(4-morpholinyl)-1',2,2',3,5,6-hexahydrospiro[pyran-4,3'-pyrrolo[3,2-b]pyridine];

1-(7-fluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-pyrrolidinone;

4-(3-methyl-2-(2-pyridinyl)-1,8-naphthyridin-4-yl)-6-(4-morpholinyl)-3,4-dihydro-2H-1,4-benzoxazine;

4-(3,3-dimethyl-6-(4-morpholinyl)-2,3-dihydro-1H-pyrrolo[3,2-b]pyridin-1-yl)-3-methyl-2-(2-pyridinyl)-1,8-naphthyridine;

1'-(3-methyl-2-(2-pyridinyl)-1,7-naphthyridin-4-yl)-6'-(4-morpholinyl)-1',2,2',3,5,6-hexahydrospiro[pyran-4,3'-pyrrolo[3,2-b]pyridine];

1'-(2-(3,5-difluorophenyl)-3-methyl-1,8-naphthyridin-4-yl)-6'-(4-morpholinyl)-1',2,2',3,5,6-hexahydrospiro[pyran-4,3'-pyrrolo[3,2-b]pyridine];

1'-(2-(3,5-difluorophenyl)-3-methyl-1,7-naphthyridin-4-yl)-6'-(4-morpholinyl)-1',2,2',3,5,6-hexahydrospiro[pyran-4,3'-pyrrolo[3,2-b]pyridine];

2-(3,5-difluorophenyl)-4-(3,3-dimethyl-6-(4-morpholinyl)-2,3-dihydro-1H-pyrrolo[3,2-b]pyridin-1-yl)-3-methyl-1,7-naphthyridine;

4-(3,3-dimethyl-6-(4-morpholinyl)-2,3-dihydro-1H-pyrrolo[3,2-b]pyridin-1-yl)-3-methyl-2-(4-methyl-2-pyridinyl)-1,8-naphthyridine;

2-(3,5-difluorophenyl)-4-(3,3-dimethyl-6-(4-morpholinyl)-2,3-dihydro-1H-pyrrolo[3,2-b]pyridin-1-yl)-3-methyl-1,8-naphthyridine;

methyl 4-(5,7-difluoro-3-methyl-4-(6'-(4-morpholinyl)-2,3,5,6-tetrahydrospiro[pyran-4,3'-pyrrolo[3,2-b]pyridin-1'(2'H)-yl)-2-quinolinyl)-1-piperazinecarboxylate;

1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-5,5-dimethyl-2-piperidinone;

tert-butyl 4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-1-piperazinecarboxylate;

1'-(5,7-difluoro-3-methyl-2-(1-piperazinyl)-4-quinolinyl)-6'-(4-morpholinyl)-1',2,2',3,5,6-hexahydrospiro[pyran-4,3'-pyrrolo[3,2-b]pyridine];

1-(7-fluoro-3-methyl-2-(2-pyridinyl)-4-quinolinyl)-6-(4-morpholinyl)-1,2,2',3',5',6'-hexahydrospiro[indole-3,4'-thiopyran]1',1'-dioxide;

1'-(5,7-difluoro-3-methyl-2-(4-(methylsulfonyl)-1-piperazinyl)-4-quinolinyl)-6'-(4-morpholinyl)-1',2,2',3,5,6-hexahydrospiro[pyran-4,3'-pyrrolo[3,2-b]pyridine];

4-(3,3-dimethyl-6-(4-morpholinyl)-2,3-dihydro-1H-pyrrolo[3,2-b]pyridin-1-yl)-2-(3-fluorophenyl)-3-methyl-1,8-naphthyridine;

1'-(2-(3-fluorophenyl)-3-methyl-1,8-naphthyridin-4-yl)-6'-(4-morpholinyl)-1',2,2',3,5,6-hexahydrospiro[pyran-4,3'-pyrrolo[3,2-b]pyridine];

4-(3,3-dimethyl-6-(4-morpholinyl)-2,3-dihydro-1H-pyrrolo[3,2-b]pyridin-1-yl)-3-methyl-2-phenyl-1,8-naphthyridine;

1'-(3-methyl-2-phenyl-1,8-naphthyridin-4-yl)-6'-(4-morpholinyl)-1',2,2',3,5,6-hexahydrospiro[pyran-4,3'-pyrrolo[3,2-b]pyridine];

5'-bromo-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine];

1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine]-5'-carbonitrile;

1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridin]-5'-amine;

5'-ethenyl-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine];

5'-chloro-1'-(7-fluoro-3-methyl-2-(2-pyridinyl)-4-quinolinyl)-6'-(4-morpholinyl)-1',2,2',3,5,6-hexahydrospiro[pyran-4,3'-pyrrolo[3,2-b]pyridine];

4-(5-bromo-3,3-dimethyl-6-(4-morpholinyl)-2,3-dihydro-1H-pyrrolo[3,2-b]pyridin-1-yl)-7-fluoro-3-methyl-2-(2-pyridinyl)quinoline;

1-(7-fluoro-3-methyl-2-(2-pyridinyl)-4-quinolinyl)-3,3-dimethyl-6-(4-morpholinyl)-2,3-dihydro-1H-pyrrolo[3,2-b]pyridine-5-carbonitrile;

4-(5-chloro-3,3-dimethyl-6-(4-morpholinyl)-2,3-dihydro-1H-pyrrolo[3,2-b]pyridin-1-yl)-3-methyl-2-(4-methyl-2-pyridinyl)-1,8-naphthyridine;

4-(5-chloro-3,3-dimethyl-6-(4-morpholinyl)-2,3-dihydro-1H-pyrrolo[3,2-b]pyridin-1-yl)-7-fluoro-3-methyl-2-(2-pyridinyl)quinoline;

4-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-N-methyl-1-piperazinecarboxamide;

1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-2-azetidinone;

1-(5,7-difluoro-3-methyl-4-(6'-(4-morpholinyl)-2,3,5,6-tetrahydrospiro[pyran-4,3'-pyrrolo[3,2-b]pyridin]-1'(2'H)-yl)-2-quinolinyl)-4,4-dimethyl-2-pyrrolidinone;

4-(3,3-dimethyl-6-(4-morpholinyl)-2,3-dihydro-1H-pyrrolo[3,2-b]pyridin-1-yl)-2-(5-fluoro-3-pyridinyl)-3-methyl-1,8-naphthyridine;

4-(3,3-dimethyl-6-(4-morpholinyl)-2,3-dihydro-1H-pyrrolo[3,2-b]pyridin-1-yl)-3-methyl-2-(4-methyl-2-pyridinyl)-1,7-naphthyridine;

4-(3,3-dimethyl-6-(4-morpholinyl)-2,3-dihydro-1H-pyrrolo[3,2-b]pyridin-1-yl)-2-(5-fluoro-3-pyridinyl)-3-methyl-1,7-naphthyridine;

1-(7-fluoro-3-methyl-2-(2-pyridinyl)-4-quinolinyl)-6-(4-morpholinyl)-1,2-dihydrospiro[indole-3,3'-thietane]1',1'-dioxide;

(1-(7-fluoro-3-methyl-2-(2-pyridinyl)-4-quinolinyl)-6-(4-morpholinyl)-2,3-dihydro-1H-indole-3,3-diyl)dimethanol; or 2-cyclopropyl-4-(3,3-dimethyl-6-(4-morpholinyl)-2,3-dihydro-1H-pyrrolo[3,2-b]pyridin-1-yl)-3-methyl-1,8-naphthyridine; or a pharmaceutically-acceptable salt thereof.

3. A pharmaceutical composition comprising a compound according to claim 1 and a pharmaceutically-acceptable diluent or carrier.

4. A compound having the structure:

or any pharmaceutically-acceptable salt thereof, wherein:

$X^1$ is N;

Z is —C—C—, —S(=O)$_2$—C—C— or —C—C—S(=O)$_2$—; any of which are substituted by 0, 1, 2, 3 or 4 substituents selected from halo, nitro, cyano, $C_{1-4}$alk, $OC_{1-4}$alk, $OC_{1-4}$haloalk, $NHC_{1-4}$alk, $N(C_{1-4}$alk$)C_{1-4}$alk and $C_{1-4}$haloalk; and additionally substituted by 0 or 1 saturated or partially saturated 3-, 4-, 5- or 6-membered spiro rings containing 0, 1 or 2 heteroatoms selected from N, O and S, the spiro ring being substituted by 0, 1, 2 or 3 substituents independently selected from halo, $C_{1-6}$alk and $C_{1-4}$haloalk;

n is 0, 1, 2 or 3;

$R^1$ is selected from H, halo, $C_{1-6}$alk, $C_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$ NR$^a$R$^a$, —NR$^a$C$_{2-6}$alkNR$^a$R$^a$ and —NR$^a$C$_{2-6}$alkOR$^a$; or R$^1$ is a direct-bonded, $C_{1-4}$alk-linked, $OC_{1-2}$alk-linked, $C_{1-2}$alkO-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups;

$R^2$ is selected from H, halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$ N$R^aR^a$, —N$R^aC_{2-6}$alkN$R^aR^a$ and —N$R^aC_{2-6}$alkO$R^a$;

$R^3$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; or $R^3$ is selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$ alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$ N$R^aR^a$, —N$R^aC_{2-6}$alkN$R^aR^a$ and —N$R^aC_{2-6}$alkO$R^a$;

$R^4$ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk, $C_{1-4}$haloalk, or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from $C_{1-4}$alk, $C_{1-3}$haloalk, —OC$_{1-4}$alk, —NH$_2$, —NHC$_{1-4}$alk, —N(C$_{1-4}$alk)C$_{1-4}$alk;

$R^5$ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk or $C_{1-4}$haloalk; $R^6$ is selected from halo, cyano, OH, OC$_{1-4}$alk, $C_{1-4}$alk, $C_{1-3}$haloalk, OC$_{1-4}$alk, NH$_2$, NHC$_{1-4}$alk, N(C$_{1-4}$alk)C$_{1-4}$alk;

$R^a$ is independently, at each instance, H or $R^b$; and $R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OC$_{1-4}$alk, —NH$_2$, —NHC$_{1-4}$alk, —N(C$_{1-4}$alk)C$_{1-4}$alk.

5. A compound having the structure:

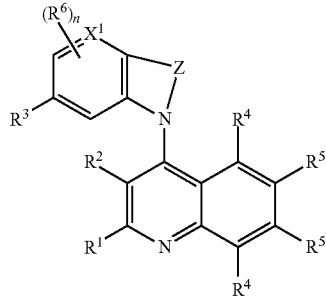

or any pharmaceutically-acceptable salt thereof, wherein:

$X^1$ is C or N;

Z is —C=C— substituted by 0, 1 or 2 substituents selected from halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk and $C_{1-4}$haloalk; and additionally substituted by 0 or 1 saturated or partially saturated 3-, 4-, 5- or 6-membered spiro rings containing 0, 1 or 2 heteroatoms selected from N, O and S, the spiro ring being substituted by 0, 1, 2 or 3 substituents independently selected from halo, $C_{1-6}$alk and $C_{1-4}$haloalk; n is 0, 1, 2 or 3;

$R^1$ is selected from H, halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$ N$R^aR^a$, —N$R^aC_{2-6}$alkN$R^aR^a$ and —N$R^aC_{2-6}$alkO$R^a$; or $R^1$ is a direct-bonded, $C_{1-4}$alk-linked, OC$_{1-2}$alk-linked, $C_{1-2}$alkO-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups;

$R^2$ is selected from H, halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$ N$R^aR^a$, —N$R^aC_{2-6}$alkN$R^aR^a$ and —N$R^aC_{2-6}$alkO$R^a$;

$R^3$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; or $R^3$ is selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$;

$R^4$ is, independently, in each instance, H, halo, nitro, cyano, $C_{1-4}$alk, O$C_{1-4}$alk, O$C_{1-4}$haloalk, NH$C_{1-4}$alk, N($C_{1-4}$alk)$C_{1-4}$alk, $C_{1-4}$haloalk, or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —O$C_{1-4}$alk, —NH$_2$, —NH$C_{1-4}$alk, —N($C_{1-4}$alk)$C_{1-4}$alk;

$R^5$ is, independently, in each instance, H, halo, nitro, cyano, $C_{1-4}$alk, O$C_{1-4}$alk, O$C_{1-4}$haloalk, NH$C_{1-4}$alk, N($C_{1-4}$alk)$C_{1-4}$alk or $C_{1-4}$haloalk; $R^6$ is selected from halo, cyano, OH, O$C_{1-4}$alk, $C_{1-4}$alk, $C_{1-3}$haloalk, O$C_{1-4}$alk, NH$_2$, NH$C_{1-4}$alk, N($C_{1-4}$alk)$C_{1-4}$alk;

$R^a$ is independently, at each instance, H or $R^b$; and $R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —O$C_{1-4}$alk, —NH$_2$, —NH$C_{1-4}$alk, —N($C_{1-4}$alk)$C_{1-4}$alk.

* * * * *